United States Patent [19]

Yamamoto et al.

[11] Patent Number: 4,881,965

[45] Date of Patent: Nov. 21, 1989

[54] WHEAT GROWING PROCESS UTILIZING SELECTIVE HEREBICIDE

[75] Inventors: Susumu Yamamoto; Takuya Kakuta; Toshiaki Sato; Katsushi Morimoto, all of Funabashi; Eiichi Oya, Narashino; Takashi Ikai, Tokyo; Tsutomu Nawamaki, Yono, all of Japan

[73] Assignee: Nissan Chemical Industries, Ltd., Tokyo, Japan

[21] Appl. No.: 147,651

[22] Filed: Jan. 25, 1988

Related U.S. Application Data

[62] Division of Ser. No. 814,568, Dec. 30, 1985, abandoned.

[30] Foreign Application Priority Data

| | | | |
|---|---|---|---|
| Jan. 18, 1985 | [JP] | Japan | 60-6800 |
| Apr. 13, 1985 | [JP] | Japan | 60-78784 |
| Oct. 22, 1985 | [JP] | Japan | 60-236780 |

[51] Int. Cl.[4] .................... A01N 43/54; C07D 401/14

[52] U.S. Cl. .................... 71/92; 544/320; 544/321; 544/324; 544/331

[58] Field of Search .................... 71/92; 544/320, 321, 544/324, 331

[56] References Cited

U.S. PATENT DOCUMENTS

| | | | |
|---|---|---|---|
| 4,534,790 | 8/1985 | Wolf | 71/93 |
| 4,705,558 | 11/1987 | Hartzell | 71/92 |

FOREIGN PATENT DOCUMENTS

| | | | |
|---|---|---|---|
| 83-3850 | 5/1983 | South Africa | 71/90 |

*Primary Examiner*—John M. Ford
*Attorney, Agent, or Firm*—Frishauf, Holtz, Goodman & Woodward

[57] ABSTRACT

A process for growing wheat and selectively preventing or controlling the growth of wild oats in the same site in which the wheat is being cultivated which comprises applying to said site an amount of an active compound sufficient to control the growth of wild oats without adversely affecting the growth of the wheat, said active compound being N-[(4,6-dimethylpyrimidin-2-yl)aminocarbonyl]-4-methoxycarbonyl-3-methyl-1-(2-pyridyl)pyrazole-5-sulfonamide or N-[(4,6-dimethylpyrimidin-2-yl)aminocarbonyl]-4-methoxycarbonyl-1-(2-pyridyl)pyrazole-5-sulfonamide.

6 Claims, No Drawings

WHEAT GROWING PROCESS UTILIZING SELECTIVE HEREBICIDE

This application is a division of application Ser. No. 814,568, filed Dec. 30, 1985, now abandoned.

BACKGROUND OF THE INVENTION

This invention relates to a novel pyrazolesulfonamide derivative, a process for preparing the compound and a herbicide cotaining the compounds as an active component. In order to protect important crops such as rice plants, wheat, cotton and sugar beets from damges by weeds to achieve an increased yield, it is indispensable to use a herbicide. In recent years in particular, a herbicide having selectivity (or discriminativity) is saught after as it can kill only weeds selectively (or discriminatively) without damages to crops by agricultural chemicals even when a foliage treatment is applied simultaneously on crops and weeds in a cultivated land wherein useful crops and weeds are grown together. Also, from viewpoints of the prevention of environmental pollution, the transportion, and the economical cost reduction in application of chemicals, studies and researches have been made over many years on such compounds that may achieve a higher herbicidal activity with use of chemcicals in a lower amount. Some of the compounds having such a property are presently used as the herbicide having selectivity. Still, however, there are further demands for new compounds having such a property.

Conventionally, a number of compounds having sulfonylurea structure has been known. Any of these, however, show very strong activities to sugar beets. For example, sugar beets have extremely high sensibility to chlorsulfuron which is known as a herbicide for wheat, and accordingly the sugar beets which are cultured as second crops of wheat are known to be seriously suffered from damages by agricultural chemicals even after two years, because of a trace amount of the acvtive component remaining in the soil. Also, other sulfonylurea compounds than the chlorsulfuron are also considered to have very particularly strong effect to sugar beets, and, of the sulfonylurea type compounds, the compound which may have the selectivity on sugar beets have been hitherto almost unknown.

As a prior technique, European Patent Publication No. 87,780 discloses a pyrazolesulfonylurea which may have the sturcture similar to the compound of this invention. However, there has been nothing disclosing the compound wherein a heterocyclic ring is substituted on a pyrazole ring as this invention discloses.

SUMMARY OF THE INVENTION

The present inventors have made researches over many years to develop herbicides having the selectivity on important crops, and have examined herbicidal properties of a number of compounds to create compounds having a higher herbicidal effect and the selectivity. As a result, it was found that a pyrazolesulfonamide derivative of Formula (I) shown below (hereinafter often referred to as "the compound of this invention") has a strong herbicidal effect to various weeds while retaining high safety to the important crops in either case of the soil treatment or the foliage treatment.

According to the invention, there is provided a pyrazolesulfonamide derivative represented by Formula (I):

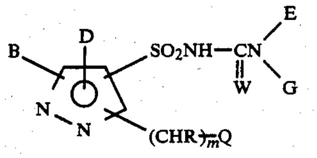

(I)

wherein Q represents a group of;

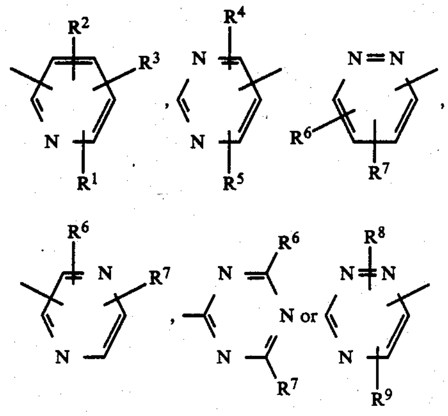

wherein $R^1$, $R^2$ and $R^3$ each independently represent a hydrogen atom, a halogen atom, a nitro group, a $C_1$–$C_8$ alkyl group, a halogenated $C_1$–$C_8$ alkyl group, a group of $COOR^{10}$, a group of $S(O)_nR^{11}$, a group of $NR^{12}R^{13}$, a $C_1$–$C_8$ alkoxy group, a group of $SO_2NR^8R^9$, a group of $SO_2OR^{11}$ or an unsubstituted phenyl group or a phenyl group substituted with a halogen atom, a nitro group, a group of $COOR^{10}$, a $C_1$–$C_8$ alkoxy group or a $C_1$–$C_8$ alkyl group;

$R^4$ and $R^5$ each independently represent a hydrogen atom, a halogen atom, a $C_1$–$C_8$ alkyl group, a halogenated $C_1$–$C_8$ alkyl group, a nitro group, a group of $COOR^{10}$, a group of $S(O)_nR^{11}$, a $C_1$–$C_8$ alkoxy group or an unsubstituted phenyl group or a phenyl group substituted with a halogen atom, a group of $COOR^{10}$, a nitro group, a $C_1$–$C_8$ alkoxy group or a $C_1$–$C_8$ alkyl group;

$R^6$ and $R^7$ each independently represent a hydrogen atom, a halogen atom, a $C_1$–$C_8$ alkyl group or a $C_1$–$C_8$ alkoxy group;

$R^8$ and $R^9$ each independently represent a hydrogen atom, a $C_1$–$C_8$ alkyl group or a phenyl group;

$R^{10}$ represents a hydrogen atom or a $C_1$–$C_8$ alkyl group;

$R^{11}$ represents a $C_1$–$C_8$ alkyl group and n is an integer of 0, 1 or 2;

$R^{12}$ and $R^{13}$ each independently represent a hydrogen atom or a $C_1$–$C_8$ alkyl group;

m represents an integer of 0, 1 or 2, and R represents a hydrogen atom or a $C_1$–$C_8$ alkyl group;

B and D each independently represent a hydrogen atom, a halogen atom, a nitro group, a $C_1$–$C_8$ alkyl group, an arylalkyl group, a $C_1$–$C_8$ alkoxy group, a halogenated $C_1$–$C_8$ alkyl group, a group of $COOR^{14}$, a group of $CONR^{15}R^{16}$, a group of $S(O)_nR^{17}$, a cyano group, a group of $NR^{18}R^{19}$, a group of $SO_2NR^{20}R^{21}$, a group of OH, an unsubstituted benzoyl group or a benzoyl group substituted with a halogen atom or a $C_1$–$C_8$ alkyl group, or an unsubstituted phenyl group or a phenyl group substituted with a halogen atom, a nitro group, a group of $COOR^{10}$ or a $C_1$–$C_8$ alkyl group;

$R^{14}$ represents a hydrogen atom, an unsubstituted $C_1$–$C_8$ alkyl group (or a $C_1$–$C_8$ alkyl group substituted with an unsubstituted $C_1$–$C_8$ alkoxy group or a $C_1$–$C_8$ alkoxy group substituted with a group of $R^{10}O$, a halogenated $C_1$–$C_8$ alkoxy group, a cyano group, a phenoxy group, a $c_1$–$C_8$ alkoxycarbonyl group, a group of $R^{10}R^{11}N$, a $C_3$–$C_7$ cycloalkyl group, a $C_1$–$C_8$ alkylthio group or a $C_1$–$C_8$ alkylcarbonyl group), an unsubstituted $C_1$–$C_8$ alkenyl group or a $C_1$–$C_8$ alkenyl group substituted with a halogen atom, an unsubstituted $C_1$–$C_8$ alkynyl group or a $C_1$–$C_8$ alkynyl group substituted with a halogen atom, a halogenated $C_1$–$C_8$ alkyl group, a $C_3$–$C_7$ cycloalkyl group or a benzyl group;

$R^{15}$ represents a hydrogen atom, a $C_1$–$C_8$ alkyl group or a phenyl group, and $R^{16}$ represents a hydrogen atom, a $C_1$–$C_8$ alkyl group or a $C_1$–$C_8$ alkoxy group;

$R^{17}$ represents a $C_1$–$C_8$ alkyl group, a $C_1$–$C_8$ alkoxy group, a phenyl group, a halogenated $C_1$–$C_8$ alkyl group, a $C_1$–$C_8$ alkenyloxy group or a $C_1$–$C_8$ alkynyloxy group, and n represents an integer of 0, 1 or 2;

$R^{18}$ and $R^{19}$ each independently represent a hydrogen atom, a $C_1$–$C_8$ alkyl group, a $C_1$–$C_8$ alkylcarbonyl group or a $C_1$–$C_8$ alkylsulfonyl group;

$R^{20}$ and $R^{21}$ each independently represent a hydrogen atom, a $C_1$–$C_8$ alkyl group, a $C_1$–$C_8$ alkenyl group or a $C_1$–$C_8$ alkynyl group;

$R^{10}$ is as defined above;

E represents a hydroge atom, a $C_1$–$C_8$ alkyl group, a $C_1$–$C_8$ alkenyl group, a $C_1$–$C_8$ alkynyl group, or a $C_1$–$C_8$ alkoxy group;

W represents an oxygen atom, a sulfur atom or a group of N—$R^{16}$, wherein $R^{16}$ is as defined above;

G represents a group of;

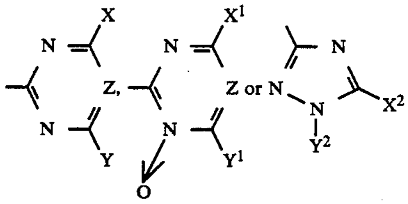

wherein

X and Y each independently represent a hydrogen atom, a halogen group, a $C_1$–$C_8$ alkyl group, a $C_1$–$C_8$ alkoxy group, a $C_1$–$C_8$ alkoxyalkyl group, a halogenated $C_1$–$C_8$ alkyl group, or a halogenated $C_1$–$C_8$ alkoxy group, a group of $NR^{22}R^{23}$, a group of $OCH(R^{10})COOR^{10}$, a group of $COOR^{10}$, a cyclopropyl group, a group of $CH(OR^{24})_2$, a $C_1$–$C_8$ alkylthio group or a halogenated $C_1$–$C_8$ alkylthio group;

$R^{22}$ and $R^{23}$ each independently represent a hydrogen atom, a $C_1$–$C_8$ alkyl group or a $C_1$–$C_8$ alkoxy group;

$R^{24}$ represents a $C_1$–$C_8$ alkyl group;

$R^{10}$ is as defined above;

$X^1$ and $Y^1$ each independently represent a hydrogen atom, a halogen group, a $C_1$–$C_8$ alkyl group or a $C_1$–$C_8$ alkoxy group;

$X^2$ represents a $C_1$–$C_8$ alkyl group, a $C_1$–$C_8$ alkylthio group or a $C_1$–$C_8$ alkoxy group, and $Y^2$ represents a $C_1$–$C_8$ alkyl group;

Z represents a nitrogen atom or a group of C—$R^{25}$;

$R^{25}$ represents a hydrogen atom, a $C_1$–$C_8$ alkyl group or a halogenated $C_1$–$C_8$ alkyl group, a halogen atom, a $C_1$–$C_8$ alkoxy group or a 5-membered ring containing an oxygen atom together with Y or $Y^1$;

with the proviso that the group:

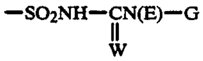

in Formula (I) is not substituted on the nitrogen atom in the pyrazole ring, and, when the group of —(CHR)$_m$—Q is not substituted on the nitrogen atom in the pyrazole ring, the substituent for B or D on the nitrogen atom is selected from a hydrogen atom, a $C_1$–$C_8$ alkyl group, a $C_1$–$C_8$ alkenyl group, a $C_1$–$C_8$ alkynyl group, a group of $CH_2CN$, a $C_1$–$C_8$ alkoxyalkyl group, a $C_1$–$C_8$ alkylthioalkyl group, a group of $—CH_2COOR^{10}$, a group of $—COR^{10}$, a group of $SO_2R^{24}$, a group of $SO_2NR^{10}R^{24}$ or an unsubstituted phenyl group or a phenyl group substituted with a halogen atom, a nitro group, a group of $COOR^{10}$ or a $C_1$–$C_8$ alkyl group; $R^{10}$ and $R^{24}$ is as defined above.

The above compound can be obtained by a process for preparing a pyrazolesulfonamide derivative represented by Formula (I)':

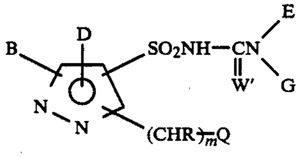
(I)' wherein

Q, m, R, B, D, E and G are as defined above, and

W' represents an oxygen atom or a sulfur atom;

which comprises allowing a pyrazolesulfonyl(thio)isocyanate derivative represented by Formula (II):

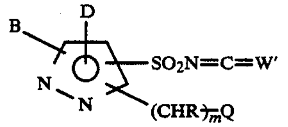
(II)

wherein

Q, m, R, B, D and W' are as defined above; with the proviso that the group $—SO_2N{=}C{=}W'$ in Formula (II) is not substituted on the nitrogen atom in the pyrazole ring, and, when the group of —(CHR)$_m$—Q is not substituted on the nitrogen atom in the pyrazole ring, the substituent for B or D on the nitrogen atom is selected from a hydrogen atom, a $C_1$–$C_8$ alkyl group, a $C_1$–$C_8$ alkenyl group, a $C_1$–$C_8$ alkynyl group, a group of $CH_2CN$, a $C_1$–$C_8$ alkoxyalkyl group, a $C_1$–$C_8$ alkylthioalkyl group, a group of $—CH_2COOR^{10}$, a group of $—COR^{10}$, a group of $SO_2R^{24}$, a group of $SO_2NR^{10}R^{24}$ or an unsubstituted phenyl group or a phenyl group substituted with a halogen atom, a nitro group, a group of $COOR^{10}$ or a $C_1$–$C_8$ alkyl group;

$R^{10}$ and $R^{24}$ is as defined above;

to react with an aminopyrimidine, aminotriazine or aminotriazole derivative represented by Formula (III):

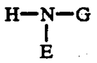
(III)

wherein G and E are as defined above; in an inert solvent, or allowing a pyrazolesulfonyl(thio)carbamate derivative represented by Formula (IV):

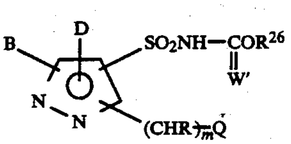
(IV)

wherein

Q, m, R, B, D and W' are as defined above; with the proviso that the group $—SO_2N═C═W'$ in Formula (II) is not substituted on the nitrogen atom in the pyrazole ring, and, when the group of $—(CHR)_m—Q$ is not substituted in the nitrogen atom in the pyrazole ring, the substituent for B or D on the nitrogen atom is selected from a hydrogen atom, a $C_1$–$C_8$ alkyl group, a $C_1$–$C_8$ alkenyl group, a $C_1$–$C_8$ alkynyl group, a group of $CH_2CN$, a $C_1$–$C_8$ alkoxyalkyl group, a $C_1$–$C_8$ alkylthioalkyl group, a group of $—CH_2COOR^{10}$, a group of $—COR^{10}$, a group of $SO_2R^{24}$, a group of $SO_2NR^{10}R^{24}$ or an unsubstituted phenyl group or a phenyl group substituted with a halogen atom, a nitro group, a group of $COOR^{10}$ or a $C_1$–$C_8$ alkyl group;

$R^{10}$ and $R^{24}$ is as defined above;

to react with an aminopyrimidine, aminotriazine or aminotriazole derivative represented by Formula (III):

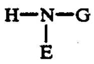
(III)

wherein G and E are as defined above; in an inert solvent.

Certain compounds of the above compounds show very high selectivity on beets. Also, certain compounds of the compound of this invention have the selectivity not only to beets but also to wheat, cotton. corn, etc. The certain compounds of the compound of this invention, having the selectivity on wheat, are suited for selectivity controlling wild oats. Wild oats are known to be improtant weeds growing with the culture of wheat. However, since wheat and wild oats belong to a plant species which is akin to each other, the known sulfonylurea type herbicides (the above-mentioned chlorosulfuron, for example) having the selectivity on wheat have also no effect to the wild oats, and thus it has been difficult to control them. The compound of this invention, on the other hand, shows a high herbicidal activity in a very low amount of the active component as compared with the conventional herbicides, and accordingly it is useful also as a herbicide for orchards and uncultivated lands.

DESCRIPTION OF THE PREFERRED EMBODIMENTS

The compound of this invention, represented by Formula (I) can be readily prepared by selecting either one of the procedures shown by the following reaction schemes.

Reaction Scheme I

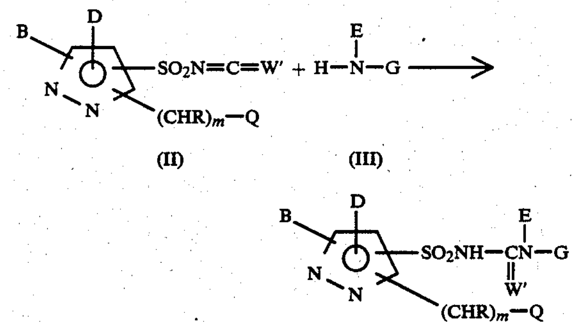
(II) (III) (I)' wherein B, D, Q, m, R, E, W' and G are as defined above.

Namely, a pyarazolesulfonyl(thio)isocyanate derivative (II) is dissolved in an inert solvent of sufficiently dried dioxane, acetonitrile, etc., to which a pyrimidine, triazine or triazole derivative shown by Formula (III) is added to carry out stirring, whereupon a compound of Formula (I)' which is a part of the compound of this invention is obtained by generally swift reaction. When the reaction proceeds with difficulty, a suitable base or bases such as triethylamine, triethylenediamine, pyridine, sodium alkoxide and sodium hydride may be added to allow the reaction to proceed readily.

Reaction Scheme 2

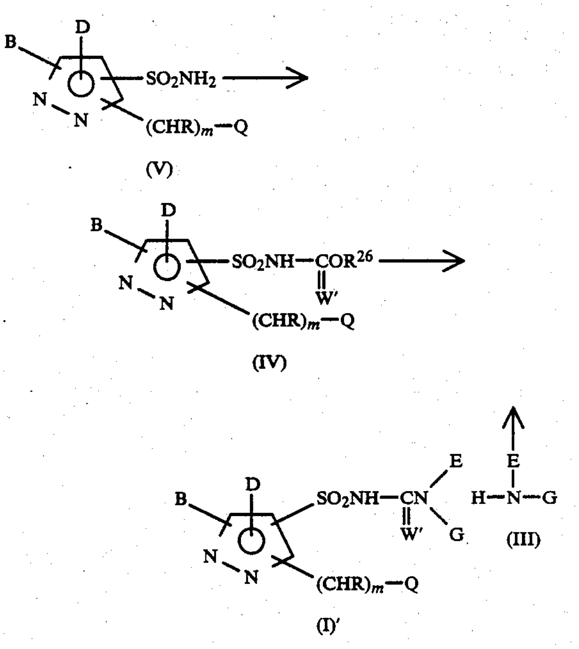
(V) (IV) (III) (I)' wherein B, D, Q, m, R, E, W', G and $R^{26}$ are as defined above.

Namely, a pyrazolesulfonamide derivative (V) is reacted with chloro(thio)formate or (thio)carbonate in a solvent such as acetone, methyl ethyl ketone and acetonitrile and in the presence of a base or bases such as potassium carbonate to form a compound (IV), followed by heating together with a compound (III) to obtain a compound (I)' which is a part of the compound of this invention.

Reaction Scheme 3

(1)

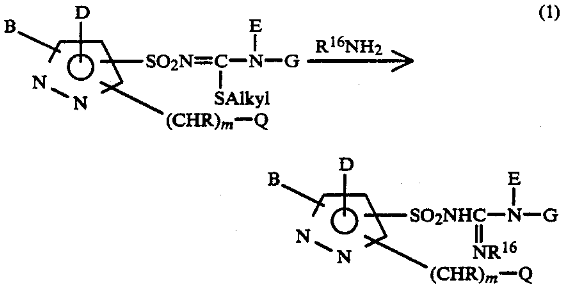

(2)

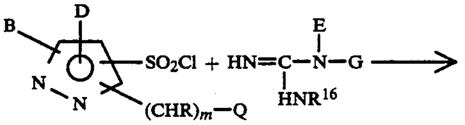

-continued

Reaction Scheme 3

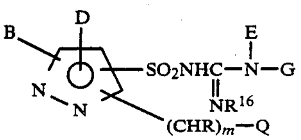

wherein B, D, Q, m, R, E, W', G and $R^{16}$ are as defined above.

Namely, the above sulfonylguanidine type compound which is a part of the compound of this invention can be synthesized in accordance with the process disclosed in Japanese Unexamined Patent Publications No. 167570/1984, No. 6654/1985 and No. 36467/1985.

The starting pyrazolesulfonyl(thio)isocyanate (II) or pyrazolesulfonyl(thio)carbamate derivative (IV) used in the reactions in Reaction Scheme 1 and Raction Scheme 2 can be synthesized by first synthesizing a pyrazolesulfonamide (V) by selecting a suitable process as mentioned below, and further making reference to the process disclosed in European Patent Publication No. 87,780 and Japanese Unexamined Patent Publication No. 13266/1980.

This pyrazolesulfonamide which is an intermediate used in this invention is also a novel compound, and may be obtained by selecting a suitable process from the processes shown in Reaction Schemes 4 to 9 below.

Reaction Scheme 4

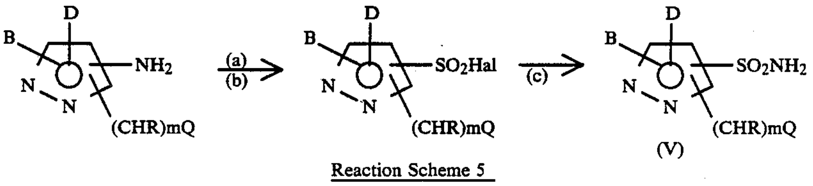

(V)

Reaction Scheme 5

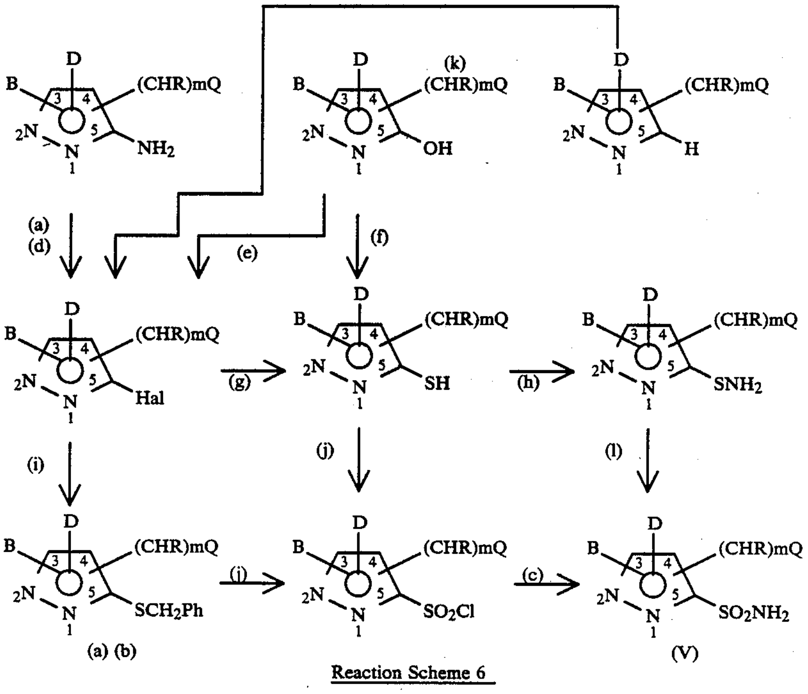

(a) (b)

(V)

Reaction Scheme 6

-continued

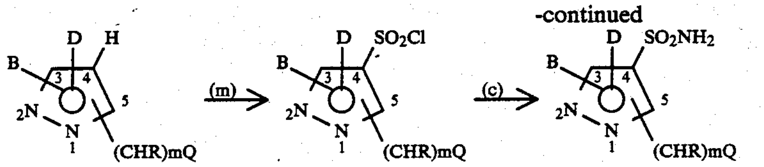

(V)

Reaction Scheme 7

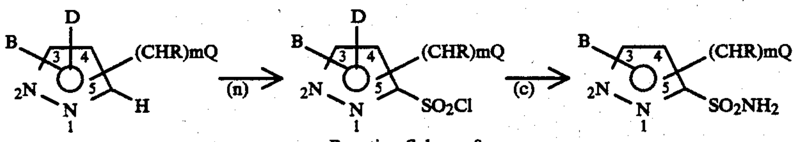

Reaction Scheme 8

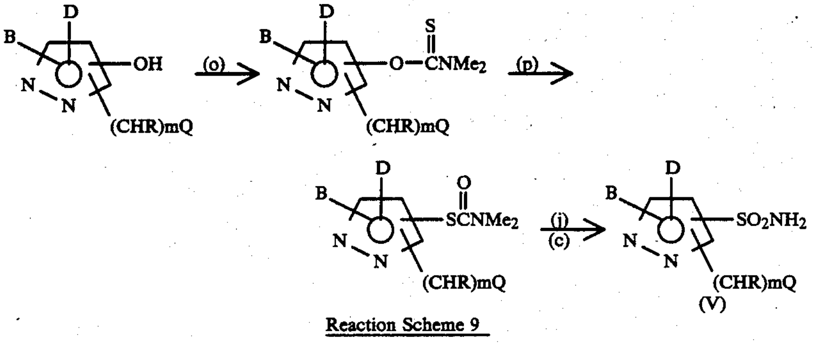

(V)

Reaction Scheme 9

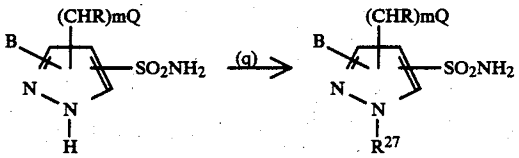

(V')

In the above;

(a): $NaNO_2.HCl$ or $NaNO_2.HBr$
(b): $SO_2$.Cu salt
(c): $NH_4OH$ or ammonium carbonate
(d): Cu salt
(e): $POCl_3$ or $POBr_3$
(f): $P_2S_5$
(g): NaSH
(h): $NaOH.NH_4OH.NaOCl$
(i): $NaSCH_2Ph$
(j): $Cl_2/CH_3COOH.H_2O$
(k): BuLi or $LiN(i\text{-}Pr)_2$, followed by $Cl_2$ or $Br_2$
(l): an oxidant
(m): (1) $ClSO_3H$, (2) $SOCl_2$ or $PCl_5$
(n): (1) BuLi or $LiN(i\text{-}Pr)_2$, (2) $SO_2$, (3) N-chlorosuccinimide
(o): $ClC(=S)NMe_2$/base
(p): heating
(q): $R^{27}$Hal/base In the above formulae, B, D, Q, m, R, E, W and G are as defined above; and $R^{27}$ is $C_1$–$C_8$ alkyl group, a $C_1$–$C_8$ alkenyl group, a $C_1$–$C_8$ alkynyl group, a group of $CH_2CN$, a $C_1$–$C_8$ alkoxyalkyl group, a $C_1$–$C_8$ alkylthioalkyl group, a group of $CH_2COOR^{10}$, a group of $COR^{24}$, a group of $SO_2R^{24}$ or a group of $SO_2NR^{10}R^{24}$; $R^{10}$ and $R^{24}$ are as defined above.

Usually, pyrazolesulfonamide (V) is obtained by reacting a corresponding pyrazolesulfonylchloride with ammonia water or ammonium carbonate. In order to introduce a sulfonyl group into pyrazole, the following methods may be used:

(i) An amino group is subjected to diazonium decomposition in the presence of sulfur dioxide to obtain pyrazolesulfonylchloride.

(ii) Hydroxypyrazole is formed into o-pyrazolethiocarbamate, and thereafter a sulfur atom is introduced into pyrazole ring by a rearrangement reaction, followed further by oxidation to obtain pyrazolesulfonylchloride.

(iii) A sulfur atom is introduced into pyrazole by a nucleophilic substitution with a halogen atom, etc., followed further by oxidation, if necessary, to obtain pyrazolesulfonylchloride.

(iv) Carbanion of pyrazole is formed by use of a base, on which sulfur dioxide is acted, followed by halogenation to obtain pyrazolesulfonylchloride.

(v) Pyrazolesulfonylchloride is directly obtained by sulfuryl chloride.

(vi) A pyrazole derivative obtained by any of the above methods is modified with other functional group by utilizing an attribute of pyrazole.

More specifically;

(i) Taking the procedures of Reaction Scheme 4, aminopyrazole is formed into a diazonium salt with use of sodium nitrite, etc. in hydrochloric acid or hydrobromic acid, and then sulfur dioxide is acted on it in the presence of a catalyst such as copper salt usually used for the diazonium decomposition, to obtain the corresponding pyrazolesulfonylchloride. By allowing ammonia water to act on it, the desired pyrazolesulfonamide (V) can be obtained.

(ii) Taking the procedures of Reaction Scheme 8, hydroxypyrazole is used as a starting material to obtain o-pyrazolethiocarbamate, which is then heated for its transition to s-pyrazolethiolcarbamate, followed by oxidation with use of chlorine in a solvent such as acetic acid to obtain pyrazolesulfonylchloride. Similar to Reaction Scheme 3, the desired pyrazolesulfonamide can be obtained by allowing ammonia water to act on the pyrazolesulfonylchloride.

Both of these Reaction Schemes 4 and 8 are not affected by the position of substituent.

(iii) A nucleophilic substitution against pyrazole usually takes place most readily at the 5-position, and, in the next place, at 3-position it may sometimes takes place when an electron attractive group is substituted on the 4-position. Taking the procedures of Reaction Scheme 5 by utilizing this tendency, a sulfur atom is introduced into the 5-position by treating halogenated pyrazole with use of sodium hydrosulfide, sodium salt of benzylmercaptan, etc., followed by oxidation with use of chlorine in a solvent such as acetic acid to obtain pyrazolesulfonlchloride. Similar to Reaction Scheme 4, the desired pyrazolesulfonamide (V) can be obtained by allowing ammonia water to act on it. It is also possible to obtain the desired pyrazolesulfonamide (V) by forming an intermediate 5-mercaptopyrazole into sulfenamide, followed by oxidation thereof. The starting 5-position halogenated pyrazole can be obtained by diazo decomposition of aminopyrazole, a reaction of hydroxypyrazole with phosphorous oxychloride or phosphorous oxybromide, or by formation of a 5-position anion with use of a strong base such as butyl lithium and lithium diisopropylamide, followed by halogenation.

(iv) When a substituent is at the 1-position, the hydrogen at the 5-position of a pyrazole ring generally has relatively strong acidity. Taking the procedures of Reaction Scheme 7, an anion can be formed with use of a strong base such as butyl lithium and lithium diisopropylamide, thereafter treating it with sulfur dioxide and N-halogenosuccinimide to form pyrazolesulfonylchloride, and then treating it with ammonia water to obtain the desired pyrazolesulfonamide (V).

(v) As compared with the nucleophilic substitution, an electrophilic substitution against a pyrazole ring tends to take palce at the 4-position. Taking the procedures of Reaction Scheme 6, pyrazole-4-sulfonylchloride can be directly obtained with use of chlorosulfonic acid.

(vi) Taking the procedures of Reaction Scheme 9, alkylation, acylation or sulfonylation of pyrazolesulfonamide having no substituent at the 1-position results in alkylation, acylation or sulfonylation at the 1-position or the 2-position. According to this procedures, it is somethimes possible to obtain two kinds of compounds as a mixture wherein the substituents at the 3-position and the 5-position have been replaced with each other, but it is possible to separate these compounds by column chromatography, recrystallization, etc. for use as an intermediate for the compound of this invention.

It is also possible by utilizing an attribute of pyrazole to obtain various types of pyrazolesulfonamide (V) by newly intorducing a substituent into pyrazolesulfonamide, or by modifying a substituent having been introduced in it.

Pyrazoles used as starting materials in the above reactions can be synthesized in most cases by making reference to A. N. Kost and I. I. Groundberg, Advan. Heterocyclic Chem., Vol. 6, p. 347, 1966; T. L. Yacobs, Heterocyclic Compounds, R. C. Elderfield, Vol. 5, p. 45, Wiley, New York, 1957; or K. Shofield, M. R. Grimmett and B. R. T. Keene, Heterocyclic Nitrogen Compounds The Azóles, Cambridge University Press, London, Newyork, Melbourne, 1976; Kevin T. Potts, Comprehensive Heterocyclic Chemistry, Vol. 5, p. 167, Pergamon Press, 1984. When the group of $(CHR)_m$—Q is substituted on the 1-position of a pyrazole ring, it can be obtained by using $(CHR)_m$—$QNHNH_2$ in place of hydrazine, methylhydrazine, phenylhydrazine, etc. in the above publications.

Usually, it is possible for one skilled in the art to obtain an intermediate of the compound of this invention by studying experimental conditions on the basis of the descriptions hereinabove and the known arts in the above publications. In the following, synthesis examples for synthesizing the compound of this invention and the intermediate pyrazolesulfonamide will be described concretely as Exampels and Reference Examples, by which, however, by no means the invention is limited.

REFERENCE EXAMPLE 1

Synthesis of 4-ethoxycarbonyl-1-(2-pyridyl)pyrazole-5-sulfonamide (1) Synthesis of ethyl 5-chloro-1-(2-pyridyl)pyrazole-4-carboxylate:

14 g of ethyl 5-amino-1-(2-pyridyl)pyrazole-4-carboxylate was dissolved in 50 ml of conc. hydrochloric acid, and the solution obtained was cooled to −5° C., to which 5.5 g of sodium nitrite dissolved in 10 ml of water was added cropwise, and thereafter, stirred for 10 minutes, followed by addition of 0.6 g of urea. The solution thus obtained was added dropwise at 5° C. to a solution obtained by adding 2 g of sulfur dioxide and 0.6 g of cuprous chloride to 50 ml of 1,2-dichloroethane. After stirring at room temperature for 1 hour, 200 ml of ice water was added thereto, followed by extraction with chloroform. Seperation of the layer of chloroform, washing with water, drying and concentration were then carried out to obtain 13.1 g of the title compound. m.p.: 38° to 42° C.

(2) Synthesis of ethyl 5-mercapto-1-(2-pyridyl)-pyrazole-4-carboxylate:

12 g of ethyl 5-chloro-1-(2-pyridyl)pyrazole-4-carboxylate was dissolved in 60 ml of dimethylformamide, to which 9.5 g of 70% sodium hydrosulfide was added and then heated at 90° to 100° C. for 5 hours. After the reaction was completed, ice water was added to make the reaction mixture acidic with use of conc. hydrochloric acid, followed by extraction with chloroform. Separation of the layer of chloroform, washing with water, drying and concentration were then carried out to obtain 11.4 g of the title compound. m.p.: 73° to 76° C.

(3) Synthesis of 4-ethoxycarbonyl-1-(2-pyridyl)-pyrazole-5-sulfonamide:

5.8 g of ethyl 5-mercapto-1-(2-pyridyl)pyrazole-4-carboxylate was dissolved in 50 ml of 80% acetic acid, into which chlorine was brown at 5° to 15° C. until it is saturated. After the reaction was completed, 200 ml of ice water was added, followed by extraction with 1,2-dichloroethane. Separation of the layer of 1,2-dichloroethane, washing with water, drying and concentration were then carried out to obtain 4-ethoxycarbonyl-1-(2-pyridyl)pyrazole-5-sulfonylchloride. The sulfonylchloride obtained was dissolved in 50 ml of 1,2-dichloroethan, followed by addition of 4 g of ammonium carbonate (containing 30% of ammonia) and stirring at room temperature for 3 hours. After filtration of inorganic salt, solvent was evaporated to obtain 5.7 g of the title compound. The amount obtained after purification by use of a silica gel column chromatography was 3.9 g. m.p.: 134° to 135° C.

REFERENCE EXAMPLE 2

Synthesis of 4-ethoxycarbonyl-3-methyl-1-(2-pyridyl)pyrazole-5-sulfonamide

Synthesis was carried out following Reference Example 1. m.p.: 166° to 167° C.

Each of the intermediates had the following property.

Ethyl 5-amino-3-methyl-1-(2-pyridyl)pyrazole-4-carboxylate, obtained by heating 2-hydrazinopyridine and ethyl β-ethyl-α-cyanochlotonate in n-butyl alcohol. m.p.: 80° to 81° C.

Ethyl 5-chloro-3-methyl-1-(2-pyridyl)pyrazole-4-carboxylate, m.p.: 49° to 52° C.

Ethyl 5-mercapto-3-methyl-1-(2-pyridyl)pyrazole-4-carboxylate, m.p.: 99° to 101° C.

REFERENCE EXAMPLE 3

Synthesis of 4-methoxycarbonyl-1-(2-pyridyl)pyrazole-5-sulfonamide

Synthesis was carried out following Reference Examples 1 and 2. m.p.: 151° to 153° C.

Each of the intermediates had the following property.

Methyl 5-chloro-1-(2-pyridyl)pyrazole-4-carboxylate, m.p.: 86° to 88° C.

Methyl 5-mercapto-1-(2-pyridyl)pyrazole-4-carboxylate, m.p.: 120° to 121° C.

REFERENCE EXAMPLE 4

Synthesis of 1-(3,5-dichloropyridin-2-yl)-4-ethoxycarbonylpyrazole-5-sulfonamide Synthesis was carried out following Reference Examples 1 and 2. m.p.: 161° C.

Each of the intermediates had the following property.

Ethyl 5-chloro-1-(3,5-dichloropyridin-2-yl)pyrazole-4-carboxylate, m.p.: 81° to 82° C.

REFERENCE EXAMPLE 5

Synthesis of 4-ethoxycarbonyl-1-(3-methylpyridin-2-yl)pyrazole-5-sulfonamide Synthesis was carried out following Reference Examples 1 and 2. m.p.: 165° to 170° C.

Each of the intermediates had the following property.

Ethyl 5-amino-1-(3-methylpyridin-2-yl)pyrazole-4-carboxylate, an oily substance.

Ethyl 5-chloro-1-(3-methylpyridin-2-yl)pyrazole-4-carboxylate, an oily substance.

Ethyl 5-mercapto-1-(3-methylpyridin-2-yl)pyrazole-4-carboxylate, an oily substance.

REFERENCE EXAMPLE 6

Synthesis of 4-ethoxycarbonyl-1-(2-pyrimidyl)pyrazole-5-sulfonamide

Synthesis was carried out following Reference Examples 1 and 2. m.p.: 175° C.

Each of the intermediates had the following property.

Ethyl 5-amino-1-(2-pyrimidyl)pyrazole-4-carboxylate, m.p.: 190° to 191° C.

Ethyl 5-chloro-1-(2-pyrimidyl)pyrazole-4-carboxylate, m.p.: 80° to 84° C.

Ethyl 5-mercapto-1-(2-pyrimidyl)pyrazole-4-carboxylate, m.p.: 131° to 133° C.

REFERENCE EXAMPLE 7

Synthesis of 3,5-dimethyl-1-(2-pyridyl)pyrazole-4-sulfonamide (1) Synthesis of 3,5-dimethyl-1-(2-pyridyl)pyrazole:

10 g of acetylacetone was added to 20 ml of ethanol, to which 10.9 g of 2-hydrazinopyridine was further added little by little under ice cooling. After stirring overnight at room temperature, distillation was carried out under reduced pressure. b.p.: 85° to 90° C./0.8 mmHg. Amount obtained: 14.5 g.

(2) Synthesis of 3,5-dimethyl-1-(2-pyridyl)pyrazole-4-sulfonamide:

10.4 g of 3,5-dimethyl-1-(2-pyridyl)pyrazole dissolved in 12.5 ml of chloroform under ice-cooling was added dropwise to a mixed solution of 18 ml of chlorosulfonic acid and 18 ml of chloroform. The mixture was stirred at room temperature for 1 hour and then heated under reflux for 4.5 hours. Next, after chloroform was evaporated under reduced pressure, 25.1 g of phosphorous pentachloride was added little by little, followed by heating at 90° to 100° C. for 1 hour while elevating the temperature gradually. After cooling, ice water was added to the reaction mixture, which was then extracted with benzene. After benzene was evaporated under reduced pressure, 18 g of 28% ammonia water was added dropwise thereto. After stirring overnight at room temperature, solvent was evaporated under reduced pressure to obtain 12.6 g of the title compound as crystals. m.p.: 160° to 163° C.

REFERENCE EXAMPLE 8

Synthesis of 4-bromo-1-(2-pyridyl)pyrazole-3-sulfonamide (1) Synthesis of 2-(3-amino-2-pyrazolin-1-yl)pyridine:

The compound was synthesized from 2-hydrazinopyridine and acrylonitrile following the procedures disclosed in U.S. Pat. No. 4,347,251. m.p.: 169° to 171° C.

(2) Synthesis of 3-amino-1-(2-pyridyl)pyrazole:

10 g of 2-(3-amino-2-pyrazolin-1-yl)pyridine was added to a 500 ml acetone suspensison of 50 g of active manganese dioxide ground into powder. After stirring at room temperature for 2 hours, insolubles were filtered off and acetone was evaporated under reduced pressure to obtain 6.4 g of the deisred product as crystals. m.p.: 98° to 101° C.

(3) Synthesis of 3-amino-4-bromo-1-(2-pyridyl)-pyrazole:

5.6 g of 3-amino-1-(2-pyridyl)pyrazole was added to 35 ml of acetic acid, to which 5.8 g of bromine was further added dropwise at room temperature. After stirring at room temperature for 20 minutes, crystals precipitated were collected by filtration and dissolved in 50 ml of diluted hydrochloric acid. To this hydrochloric acid solution, added was an aqueous solution of 30% potassium hydroxide for neutralization to obtain 5.3 g of the title compound as crystals. m.p.: 145° to 146° C.

(4) Synthesis of 4-bromo-1-(2-pyridyl)pyrazole-3-sulfonamide:

3 g of 3-amino-4-bromo-1-(2-pyridyl)pyrazole was suspended in 60 ml of hydrochloric acid, to which 2.5 ml of an aqueous solution containing 1.2 g of sodium nitrite was added dropwise at −10° to −5° C. to prepare a solution of diazonium salt. This solution of diazonium salt was added dropwise at 5° C. to 30 ml of acetic acid saturated with sulfur dioxide containing 0.5 g of cuprous chloride. After stirring at room temperature for 20 minutes, 100 ml of water and 300 ml of 1,2-dichloroethane were added and stirred to separate an organic layer. To the organic layer, added was 10 ml of 28% ammonia water, followed by vigorous stirring at room temperature for 1 hour. Thereafter, solvent was evaporated under reduced pressure and 200 ml of ethyl acetate was added. After further stirring, insolubles were filtered off and ethyl acetate was evaporated to obtain 2.2 g of the title compound as a crude product. This crude product was purified by a silica gel column chromatography (developed with ethyl acetate) to obtain 0.5 g of the title compound as a pure product. m.p.: 201° to 203° C.

REFERENCE EXAMPLE 9

Synthesis of 1-methyl-4-(2-pyridyl)pyrazole-5-sulfonamide (1) Synthesis of α-ethoxymethylene-2-pyridineacetonitrile:

A mixture of 25 g of 2-pyridineacetonitrile, 63 g of ethyl orthoformate and 11 g of acetate anhydride was stirred at 120° to 130° C. for 3 hours, and thereafter 30 g of ethyl orthoformate and 11 g of acetic anhydride were further added, followed by stirring at 120° to 130° C. for 2 hours while evaporating the low boiling compound. After cooling, distillation was carried out under reduced pressure to obtain 22.7 g of distillates having b.p. of 100° to 130° C./0.1 mmHg (principal distillates: 110° C./0.1 mmHg). To the distillates obtained, added was diisopropyl ether, and then insoluble solids were filtered off and the filtrate was concentrated to obtain 20.7 g of the title compound.

(2) Synthesis of 5-amino-1-methyl-4-(2-pyridyl)-pyrazole:

10 g of α-ethoxymethylene-2-pyridineacetonitrile was dissolved in 100 ml of ethanol, to which 3.1 g of methylhydrazine was added at room temperature. After heating under reflux for 4 hours, concentration under reduced pressure was carried out to obtain 10 g of the title compound. m.p.: 113° to 114° C.

(3) Synthesis of 1-methyl-4-(2-pyridyl)pyrazole:

10 g of 5-aminio-1-methyl-4-(2-pyridyl)pyrazole was dissolved in a solution of 10 ml of conc. sulfuric acid, 30 ml of phosphorous acid and 50 ml of water, to which 15 ml of an aqueous solution containing 5.1 g of sodium nitrite was added dropwise at −10° to −5° C. to prepare a soution of diazonium salt. This solution of diazonium salt was added to 100 ml of 50% hypophosphorous acid containing 0.5 g of cupric oxide, followed by stirring at room temperature, and further stirring at 40° C. for 1 hour. After the reacton was completed, the reaction mixture was made alkaline under ice-cooling with use of 28% ammonia water, followed by extraction with chloroform by adding an excess amount of water. After the liquid extracted with chloroform was dried with use of anhydrous sodium sulfate, solvent was evaporated under reduced pressure to obtain an oily product. The oily product was purified by a silica gel column chromatograpghy to obtain 5.9 g of the title compound as an oily product.

(4) Synthesis of 1-methyl-4-(2-pyridyl)pyrazole-5-sulfonamide:

A 200 ml solution of anhydrous diethyl ether containing 5.9 g of 1-methyl-4-(2-pyridyl)pyrazole was cooled to −70° C., to which was added dropwise a lithium diisopropylamide solution separately prepared (prepared by use of 3.9 g of diisopropylamine and a hexane solution of 15% n-butyllithium). After stirring of the mixture at the same temperature for 1 hour, sulfur dioxide gas was blown into it, followed by further stirring for 1 hour. Filtration was carried out at the stage a cooler was removed and the temperature of the reaction mixture was returned to room temperature, to obtain 10 g of solid lithium sulfinate. 10 g of the lithium sulfinate obtained was added at 5° to 10° C. to 6 g of a suspension comprising 100 ml of water, 100 ml of methylene chloride and 6 g of N-chlorosuccinimide. After vigorous stirring at 5° C. for 20 minutes, 100 ml of 28% ammonia water was added dropwise thereto, followed by further stirring at room temperature for 1 hour. After separation of organic layer, aqueous layer was extracted with dichloromethane and the extract was combined with the organic layer, followed by drying with use of anhydrous sodium sulfate, and then solvent was evaporated under reduced pressure. Crystals precipitated from 3.4 g of an oily crude product were collected by filtration and washed with methanol to obtain 0.9 g of the title compound. m.p.: 195° to 197° C.

Reference Example 9-2

Synthesis of 1-methyl-4-(2-pyridyl)pyrazole-5-sulfonamide: (another procedures)

The above can be also obtained by the process of Reference Example 1. Each of the intermediates had the following property.

5-Chloro-1-methyl-4-(2-pyridyl)pyrazole, m.p.: 81° to 82° C.

5-Mercapto-1-methyl-4-(2-pyridyl)pyrazole, m.p.: 223° to 228° C.

REFERENCE EXAMPLE 10

Synthesis of 4-ethoxycarbonyl-1-(3-pyridazinyl)pyrazole-5-sulfonamide

Synthesis was carried out following Reference Examples 1 to 6. m.p.: 189° to 191° C.

Each of the intermediates had the following property.

Ethyl 5-amino-1-(3-pyridazinyl)pyrazole-4-carboxylate, m.p.: 136° to 137° C.

Ethyl 5-chloro-1-(3-pyridazinyl)pyrazole-4-carboxylate, m.p.: 100° to 107° C.

Ethyl 5-mercapto-1-(3-pyridazinyl)pyrazole-4-carboxylate, m.p.: 155° to 159° C.

REFERENCE EXAMPLE 11

Synthesis of 4-methoxycarbonyl-3-methyl-1-(2-pyridyl)pyrazole-5-sulfonamide

Synthesis was carried out following Examples 1 to 6. m.p.: 196° to 198° C.

REFERENCE EXAMPLE 12

Synthesis of 1-(3-chloropyridin-2-yl)-4-ethoxycarbonylpyrazole-5-sulfonamide

Synthesis was carried out following Reference Examples 1 to 6. m.p.: 178° to 179° C.

Each of the intermediates had the following property.

Ethyl 5-amino-1-(3-chloropyridin-2-yl)pyrazole-4-carboxylate, m.p.: 65° to 66° C.

Ethyl 5-chloro-1-(3-chloropyridin-2-yl)pyrazole-4-carboxylate, m.p.: 114° to 115° C.

Ethyl 1-(3-chloropyridin-2-yl)-5-mercaptopyrazole-4-carboxylate, m.p.: 62° to 65° C.

REFERENCE EXAMPLE 13

Synthesis of 1-(5-chloropyridin-2-yl)-4-ethoxycarbonylpyrazole-5-sulfonamide

Synthesis was carried out following the above Reference Example. m.p.: 114° to 115° C.

Each of the intermediates had the following property.

Ethyl 5-amino-1-(5-chloropyridin-2-yl)pyrazole-4-carboxylate, m.p.: 132° to 133° C.

Ethyl 5-chloro-1-(5-chloropyridin-2-yl)pyrazole-4-carboxylate, m.p.: 109° to 114° C.

Ethyl 1-(5-chloropyridin-2-yl)-5-mercaptopyrazole-4-carboxylate, m.p.: 138° to 139° C.

REFERENCE EXAMPLE 14

Synthesis of 1-(6-chloropyridin-2-yl)-4-methoxycarbonylpyrazole-5-sulfonamide

Synthesis was carried out following the above Reference Example. m.p.: 143° to 145° C.

Each of the intermediates had the following property. Methyl 5-amino-1-(6-chloropyridin-2-yl)pyrazole-4-carboxylate, m.p.: 140° C.

Methyl 1-(6-chloropyridin-2-yl)-5-mercaptopyrazole-4-carboxylate, m.p.: 118° to 120° C.

REFERENCE EXAMPLE 15

Synthesis of 1-(6-chloropyridin-2-yl)-4-ethoxycarbonylpyrazole-5-sulfonamide 1 g of sulfonamide obtained in Reference Example 14 and 0.3 g of sodium hydroxide were refluxed with stirring for 1 hour in a mixed solvent of ethanol and water. After solvent was evaporated, water was added, followed by neutralization with use of hydrochloric acid. Crystals precipitated were collected by filtration and washed with water to obtain 0.8 g of 1-(6-chloropyridin-2-yl)-4-carboxypyrazole-5-sulfonamide. m.p.: 179° to 182° C.

Next, the above sulfonamide was introduced in ethanol saturated with hydrogen chloride, and, while stirring, heated under reflux for 7 hours. After solvent was evaporated, water was added, followed by extraction with chloroform. Extract liquid was evaporated to dryness to obtain 0.62 g of the title compound. m.p.: 125° to 128° C.

REFERENCE EXAMPLE 16

Synthesis of 4-ethoxycarbonyl-1-(4-methylpyridyn-2-yl)pyrazole-5-sulfonamide

Synthesis was carried out following Reference Examples 1 to 6. m.p.: 135° to 137° C.

The intermediate had the following property.

Ethyl 5-amino-1-(4-methylpyridyn-2-yl)pyrazole-4-carboxylate, m.p.: 99° to 100° C.

REFERENCE EXAMPLE 17

Synthesis of 4-ethoxycarbonyl-1-(6-methylpyridyn-2-yl)pyrazole-5-sulfonamide

Synthesis was carried out following Reference Examples 1 to 6. m.p.: 131° to 133° C.

REFERENCE EXAMPLE 18

Synthesis of 4-methoxycarbonyl-1-(pyrimidin-2-yl)pyrazole-5-sulfonamide

Synthesis was carried out following Reference Examples 1 to 6. m.p.: 263° to 265° C.

Each of the intermediates had the following property.

Methyl 5-amino-1-(pyrimidin-2yl)pyrazole-4-carboxylate, m.p.: 176° to 179° C.

Methyl 5-chloro-1-(pyrimidin-2-yl)pyrazole-4-carboxylate, m.p.: 153° to 156° C.

Methyl 5-mercapto-1-(pyrimidin-2-yl)pyrazole-4-carboxylate, m.p.: 185° to 186° C.

REFERENCE EXAMPLE 19

Synthesis of 4-n-propyloxycarbonyl-1-(2-pyridyl)pyrazole-5-sulfonamide

Sulfonamide obtained in Reference Example 1 was hydrolyzed following the procedures in Reference Example 15 to obtain 4-carboxy-1-(2-pyridyl)pyrazole-5-sulfonamide (m.p.: 270° to 271° C.), followed by esterification with use of n-propyl alcohol to obtain the title compound. m.p.: 153° to 154° C.

REFERENCE EXAMPLE 20

Synthesis of 4-i-propyloxycarbonyl-1-(2-pyridyl)pyrazole-5-sulfonamide

Synthesis was carried out following Reference Example 19 except that the reaction was carried out for 72 hours for the esterification using i-propyl alcohol. m.p.: 123° to 124° C.

REFERENCE EXAMPLE 21

Synthesis of 1-(6-chloropyridin-2-yl)-4-methoxycarbonyl-3-methylpyrazole-5-sulfonamide Synthesis was carried out following Reference Examples 1 to 6, 14 and 15. m.p.: 119° to 120° C.

Each of the intermediates had the following property.

Methyl 5-amino-1-(6-chloropyridin-2-yl)-3-methylpyrazole-4-carboxylate, m.p.: 185° to 187° C.

Methyl 1-(6-chloropyridin-2-yl)-5-mercapto-3-methylpyrazole-4-carboxylate, m.p.: 142° to 144° C.

REFERENCE EXAMPLE 22

Synthesis of 4-ethoxycarbonyl-1-(3-fluoropyridin-2-yl)pyrazole-5-sulfonamide

Synthesis was carried out following Examples 1 to 6. m.p.: 177° to 178° C.

Each of the intermediates had the following property.

Ethyl 5-amino-1-(3-fluoropyridin-2-yl)pyrazole-4-carboxylate, m.p.: 136° to 138° C.

Ethyl 5-chloro-1-(3-fluoropyridin-2-yl)pyrazole-4-carboxylate, m.p.: 73° to 76° C.

Ethyl 5-mercapto-1-(3-fluoropyridin-2-yl)pyrazole-4-carboxylate, m.p.: 71° to 74° C.

REFERENCE EXAMPLE 23

Synthesis of 4-ethoxycarbonyl-1-(pyrazin-2-yl)pyrazole-5-sulfonamide

Synthesis was carried out following Reference Examples 1 to 6. m.p.: 189° to 191° C.

Each of the intermediates had the following property.

Ethyl 5-amino-1-(pyrazin-2-yl)pyrazole-4-carboxylate, m.p.: 138° to 140° C.

Ethyl 5-chloro-1-(pyrazin-2-yl)pyrazole-4-carboxylate, m.p.: 107° to 114° C.

Ethyl 5-mercapto-1-(pyrazin-2-yl)pyrazole-4-carboxylate,m.p.: 130° to 137° C.

4-Ethoxycarbonyl-1-(pyrazin-2-yl)pyrazole-5-sulfonylchloride, m.p.: 105° to 106° C.

REFERENCE EXAMPLE 24

Synthesis of 4-methoxycarbonyl-1-(4-methylpyrimidin-2-yl)pyrazole-5-sulfonamide

Synthesis was carried out following Reference Examples 1 to 6. m.p.: 165° to 168° C.

Each of the intermediate had the following property.

Methyl 5-amino-1-(4-methylpyrimidin-2-yl)pyrazole-4-carboxylate, m.p.: 163° to 165° C.

Methyl 5-chloro-1-(4-methylpyrimidin-2-yl)pyrazole-4-carboxylate, m.p.: 85° to 87° C.

Methyl 5-mercapto-1-(4-methylpyrimidin-2-yl)pyrazole-4-carboxylate, m.p.: 127° to 130° C.

REFERENCE EXAMPLE 25

Synthesis of 5-methoxycarbonyl-3-methyl-1-(2-pyridyl)pyrazole-4-sulfonamide (1) Synthesis of 3-methyl-1-(2-pyridyl)pyrazole:

54.7 g of acetylacetoaldehyde dimethylacetal (purity: 90%) was dissolved in 350 ml of ethanol, to which was added dropwise at room temperature 40.7 g of 2-hydrazinopyridine dissolved in 200 ml of ethanol. After stirring at room temperature for 2 hours, the reaction mixture was heated under reflux, and 40 ml of conc. hydrochloric acid was added thereto after cooling. After stirring at 60° C. for 30 minutes, the reaction mixture was concentrated, followed by addition of ice water, was made alkaline with use of ammonia water, and thereafter extracted with chloroform. After drying of organiclayer, solvent was evaporated under reduced pressure to obtain 59.2 g of an oily product. The oily product obtained was distilled under reduced pressure to obtain 52.9 g of the title compound as an oily product. b.p.: 115° to 120° C./10 mmHg.

(2) Synthesis of N-t-butyl-[3-methyl-1-(2-pyridyl)-]pyrazole-4-sulfonamide:

To 30 ml of chlorosulfonic acid contained in 60 ml of chloroform, 30 g of 3-methyl-1-(2-pyridyl)pyrazole was added dropwise under ice-cooling, followed by stirring at 60° C. for 3 hours. To a residue obtained by evaporating chloroform under reduced pressure, 30 ml of thionyl chloride was added dropwise at about 60° C. over a period of 1 hour. After the addition, the reaction mixture was stirred at 95° C. for 30 minutes while heating under reflux. After cooling, it was poured into ice water and extracted with chloroform, organic layer was washed with water and dried, and thereafter solvent was evaporated under reduced pressure to obtain 49 g of crude 3-methyl-1-(2-pyridyl)pyrazole-4-sulfonylchloride as an oily product. The sulfonylchloride obtained was dissolved in 50 ml of tetrahydrofuran, and then was added dropwise at 0° to 10° C. to 41.4 g of t-butylamine contained in 100 ml of tetrahydrofuran. After stirring at room temperature for 1.5 hour, filtration was carried out, and filtrate obtained was concentrated to give a residue, to which ethyl acetate was added, followed by washing with diluted hydrochloric acid and drying, and then solvent was evaporated to give crystals. Crystals obtained was washed with ether to obtain 48.6 g of the title compound. m.p.: 174° to 175° C.

(3) Synthesis of N-t-butyl-[5-carboxy-3-methyl-1-(2-pyridyl)]pyrazole-4-sulfonamide:

15 g of N-t-butyl-[3-methyl-1-(2-pyridyl)]pyrazole-4-sulfonamide was dissolved in 300 ml of tetrahydrofuran, to which a lithium diisopropylamine solution (obtained by adding dropwise 75 ml of a 15% n-butyllithium-hexane solution to 11.3 g of diisopropylamine contained in 50 ml of tetrahydrofuran, at −60° to −50° C.) was added dropwise at −70° to −65° C. over a period of 20 minutes. After stirring at the same temperature for 1 hour, carbonic acid gas was blown into the reaction mixture for 30 minutes and further for 30 minutes while the temperature thereof was returned to room temperature. The reaction mixture thus treated was poured into ice water to make it acidic with use of conc. hydrochloric acid, and then extracted with ethyl acetate. Organic layer was dried, and solvent was evaporated under reduced pressure to give crystals, which were then washed with ether to obtain 11.8 g of the title compound. m.p.: 170° to 172° C.

(4) Synthesis of 5-methoxycarbonyl-3-methyl-1-(2-pyridyl)pyrazole-4-sulfonamide:

11 g of N-t-butyl-[5-carboxy-3-methyl-1-(2-pyridyl)-]pyrazole-4-sulfonamide was added to 50 ml of trifluoroacetic acid, and the mixture was stirred at room temperature for 6 hours, followed by concentration under reduced pressure to obtain crude 5-carboxy-3-methyl-1-(2-pyridyl)pyrazole-4-sulfonamide. Subsequently, 250 ml of methanol were added to the residue, which was then saturated with hydrogen chloride and heated under reflux for 20 hours with stirring. The reaction mixture was concentrated under reduced pressure, followed by addition of ice water, and extracted with ethyl acetate. Organic layer was washed with water and, after drying, solvent was evaporated under reduced pressure to give crystals, which were then washed with ether to obtain the title compound as crystals. m.p.: 175° to 177° C.

REFERENCE EXAMPLE 26

Synthesis of 1-(3-chloro-6-methoxypyridin-2-yl)-4-methoxycarbonylpyrazole-5-sulfonamide Following the above Reference Examples 1 to 6, methyl 5-mercapto-1-(6-methoxypyridin-2yl)pyrazole-4-carboxylate was synthesized from methyl 5-amino-1-(6-methoxypyridin-2-yl)pyrazole-4-carboxylate (m.p.: 131° to 132° C.), and then derived to sulfonamide. The sulfonamide formed was a 1:1 mixture (white solids) of 1-(3-chloro-6-methoxypyridin-2-yl)-4-methoxycarbonylpyrazole-5-sulfonamide and 4-methoxycarbonyl-1-(6-methoxypyridin-2-yl)pyrazole-5-sulfonamide.

Subsequently, following the procedures in Example 1, the sulfonamide was reacted with methyl chloroformate, and the product was formed by toluene recrystallization to give N-[4-methoxycarbonyl-1-(3-chloro-6-methoxypyridin-2-yl)pyrazole-5-sulfonyl]methylcarbamate. m.p.: 131° to 132° C.

REFERENCE EXAMPLE 27

Synthesis of 4-methoxycarbonyl-1-(3-trifluoromethylpyridin-2-yl)pyrazole-5-sulfonamide Synthesis was carried out following Reference Examples 1 to 6. m.p.: 194° to 195° C.

Each of the intermediates had the following property.

Methyl 5-amino-1-(3-trifluoromethylpyridin-2-yl)pyrazole-4-carboxylate, m.p.: 107° to 110° C.

Methyl 5-chloro-1-(3-trifluoromethylpyridin-2-yl)pyrazole-4-carboxylate, m.p.: 72° to 73° C.

Methyl 5-mercapto-1-(3-trifluoromethylpyridin-2-yl)pyrazole-4-carboxylate, m.p.: 88° to 91° C.

REFERENCE EXAMPLE 28

Synthesis of 4-methoxycarbonyl-1-(6-methylpyridin-2-yl)pyrazole-5-sulfonamide Synthesis was carried out following Reference Example 15. m.p.: 125° to 129° C.

The intermediate had the following property.

1-(6-methylpyridin-2-yl)-4-carboxypyrazole-5-sulfonamide, m.p.: 201° to 202° C.

REFERENCE EXAMPLE 29

Synthesis of 4-ethoxycarbonyl-1-(6-methylpyridin-2-yl)-3-methylpyrazole-5-sulfonamide Synthesis was carried out following Reference Examples 1 to 6. m.p.: 162° to 163° C.

Each of the intermediates had the following property.

Ethyl 5-amino-3-methyl-1-(6-methylpyridin-2-yl)pyrazole-4-carboxylate, m.p.: 108° to 109° C.

Ethyl 5-chloro-3-methyl-1-(6-methylpyridin-2-yl)pyrazole-4-carboxylate, an oily product.

Ethyl 3-methyl-1-(6-methylpyridin-2-yl)-5-mercaptopyrazole-4-carboxylate, m.p.: 100° to 101° C.

REFERENCE EXAMPLE 30

Synthesis of 4-methoxycarbonyl-1-(6-methylpyridin-2-yl)-3-methylpyrazole-5-sulfonamide Synthesis was carried out following Reference Examples 15 and 19. m.p.: 155° to 159° C.

The intermediate had the following property.

3-Methyl-1-(6-methylpyridin-2-yl)-4-carboxypyrazole-5-sulfonamide, m.p.: 196° to 198° C.

REFERENCE EXAMPLE 31

Synthesis of 4-ethoxycarbonyl-1-(6-ethylpyridin-2-yl)pyrazole-5-sulfonamide

Synthesis was carried out following Reference Examples 1 to 6. m.p.: 87° to 88° C.

Each of the intermediates had the following property.

Ethyl 5-amino-1-(6-ethylpyridin-2-yl)pyrazole-4-carboxylate, m.p.: 116° to 117° C.

Ethyl 5-chloro-1-(6-ethylpyridin-2-yl)pyrazole-4-carboxylate, an oily product.

Ethyl 1-(6-ethylpyridin-2-yl)-5-mercaptopyrazole-4-carboxylate, m.p.: 79° to 80° C.

REFERENCE EXAMPLE 32

Synthesis of 4-ethoxycarbonyl-1-(6-fluoropyridin-2-yl)pyrazole-5-sulfonamide Synthesis was carried out following Reference Example 22. m.p.: 114° to 116° C.

Each of the intermediates had the following property.

Ethyl 5-amino-1-(6-fluoropyridin-2-yl)pyrazole-4-carboxylate, m.p.: 86° to 88° C.

Ethyl 5-chloro-1-(6-fluoropyridin-2-yl)pyrazole-4-carboxylate, m.p.: 57° to 60° C.

Ethyl 1-(6-fluoropyridin-2-yl)-5-mercaptopyrazole-4-carboxylate, m.p.: 105° to 107° C.

REFERENCE EXAMPLE 33

Synthesis of 1-(6-bromopyridin-2-yl)-4-ethoxycarbonylpyrazole-5-sulfonamide

Synthesis was carried out following Reference Examples 1 to 6. m.p.: 142° to 144° C.

Each of the intermediates had the following property.

Ethyl 5-amino-1-(6-bromopyridin-2-yl)pyrazole-4-carboxylate, m.p.: 135° to 137° C.

Ethyl 1-(6-bromopyridin-2-yl)-5-chloropyrazole-4-carboxylate, m.p.: 91° to 94° C.

Synthesis of ethyl 5-benzylthio-1-(6-bromopyridin-2-yl)pyrazole-4-carboxylate In 30 ml of dimethylformamide was dissolved 8 g of the above ethyl 1-(6-bromopyridin-2-yl)-5-chloropyrazole-4-carboxylate, to which added were 3 g of benzylmercaptan and 3.5 g of anhydrous potassium carbonate, followed by stirring overnight at room temperature. After the reaction, water was added to the reaction mixture, which was extracted with benzene, followed by washing with water and drying, and then solvent was evaporated to obtain the above carboxylate. This compound was further reacted following the procedures in Reference Example 1 to obtain 4 g of the title sulfonamide.

REFERENCE EXAMPLE 34

Synthesis of 4-ethoxycarbonyl-1-(4-pyrimidyl)pyrazole-5-sulfonamide

Synthesis was carried out following Reference Examples 1 to 6. m.p.: 238° to 239° C.

Each of the intermediates had the following property.

Ethyl 5-amino-1-(4-pyrimidyl)pyrazole-4-carboxylate, m.p.: 135° to 136° C.

Ethyl 5-chloro-1-(4-pyrimidyl)pyrazole-4-carboxylate, m.p.: 139° to 142° C.

Ethyl 5-mercapto-1-(4-pyrimidyl)pyrazole-4-carboxylate, m.p.: 143° to 147° C.

REFERENCE EXAMPLE 35

Synthesis of 4-cyano-1-(4-pyridyl)pyrazole-5-sulfonamide

Synthesis was carried out following Reference Examples 1 to 6. m.p.: 211° to 213° C.

Each of the intermediates had the following property.

5-Amino-4-cyano-1-(2-pyridyl)pyrazole, obtained by heating 2-hydrazinopyridine and ethoxymethylenemalononitrile in n-butyl alcohol, m.p.: 197° to 200° C.

5-Chloro-4-cyano-1-(2-pyridyl)pyrazole, m.p.: 130° to 133° C.

4-Cyano-5-mercapto-1-(2-pyridyl)pyrazole, m.p.: 206° to 210° C.

5-Benzylthio-4-cyano-1-(2-pyridyl)pyrazole, obtained by reacting 5-chloro-4-cyano-1-(2-pyridyl)-pyrazole with benzylmercaptan and sodium ethylate at room temperature in dimethylformamide. m.p.: 110° to 115° C.

REFERENCE EXAMPLE 36

Synthesis of 4-ethoxycarbonyl-1-(4-pyridyl)pyrazole-5-sulfonamide

Synthesis was carried out following Reference Examples 1 to 6. m.p.: 288° to 289° C.

Each of the intermediates had the following property.

Ethyl 5-amino-1-(4-pyridyl)pyrazole-4-carboxylate, m.p.: 140° to 141° C.

Ethyl 5-chloro-1-(4-pyridyl)pyrazole-4-carboxylate, taken out by extraction with chloroform, after the reaction and after nutralized with use of potassium carbonate.

Ethyl 5-mercapto-1-(4-pyridyl)pyrazole-4-carboxylate, m.p.: 195° to 198° C.

Subsequently, 5.3 g of ethyl 5-mercapto-1-(4-pyridyl)pyrazole-4-carboxylate was suspended in 150 ml of water, and chlorine was passed to the suspension for 15 minutes under ice-cooling. Thereafter, 50 ml of tetrahydrofuran and 30 ml of ammonia water was added thereto, followed by stirring at room temperature for 30 minutes. The reaction mixture was concentrated to collect by filtration white solids formed, which were then washed with water and dried to obtain 3.0 g of the title compound.

REFERENCE EXAMPLE 37

Synthesis of 1-(6-dimethylaminopyridin-2-yl)-4-ethoxycarbonyl-pyrazole-5-sulfonamide The sulfonamide obtained in Reference Example 32 was dissolved in dimethylformamide, to which were added dimethylamine and anhydrous potassium carbonate, followed by stirring overnight at room temperature to obtain the title compound. m.p.: 157° to 160° C.

REFERENCE EXAMPLE 38

Synthesis of 4-methoxycarbonyl-1-(5-methylpyridin-2-yl)pyrazole-5-sulfonamide

Synthesis was carried out following Reference Examples 1 to 6. m.p.: 145° to 147° C.

Each of the intermediates had the following property.

5-Amino-4-methoxycarbonyl-1-(5-methylpyridin-2-yl)pyrazole, m.p.: 136° to 138° C.

5-Chloro-4-methoxycarbonyl-1-(5-methylpyridin-2-yl)pyrazole, m.p.: 101° to 102° C.

5-Mercapto-4-methoxycarbonyl-1-(5-methylpyridin-2-yl)pyrazole, m.p.: 144° to 147° C.

REFERENCE EXAMPLE 39

Synthesis of 1-(6-fluoropyridin-2-yl)-4-methoxycarbonylpyrazole-5-sulfonamide

Synthesis was carried out following Reference Examples 1 to 6 and Reference Example 22. m.p.: 174° to 175° C.

Each of the intermediates had the following property.

Methyl 5-amino-1-(6-fluoropyridin-2-yl)pyrazole-4-carboxylate, m.p.: 143° to 145° C.

Methyl 5-chloro-1-(6-fluoropyridin-2-yl)pyrazole-4-carboxylate, m.p.: 112° to 115° C.

Methyl 1-(6-fluoropyridin-2-yl)-5-mercaptopyrazole-4-carboxylate, m.p.: 120° to 122° C.

REFERENCE EXAMPLE 40

Synthesis of 1,3-dimethyl-5-(2-pyridyl)pyrazole-4-sulfonamide m.p.: 188° to 190° C.

(1) Synthesis of 1,3-dimethyl-5-(2-pyridyl)pyrazole:

5.9 g of picolinoylacetone was added to 20 ml of ethanol, to which 1.7 g of methylhydrazine was added dropwise little by little under ice-cooling. After stirring overnight at room temperature, the reaction mixture was heated under reflux for 5 hours, followed by concentration to obtain 6.1 g of an oily product.

(2) Synthesis of 1,3-dimethyl-5-(2-pyridyl)pyrazole-4-sulfonamide:

To a mixed solution of 4.2 g of chlorosulfonic acid and 10 ml of chloroform, 5.7 g of 1,3-dimethyl-5-(2-pyridyl)pyrazole dissolved in 5 ml of chloroform was added dropwise under ice-cooling. After stirring at room temperature for 1 hour, the reaction mixture was heated under reflux for 3 hours. Subsequently, chloroform was evaporated under reduced pressure, followed by addition of 30 ml of thionyl chloride and heating under reflux for 6 hours. After the thionyl chloride was evaporated under reduced pressure, 50 ml of tetrahydrofuran was added to the reaction mixture, to which 20 ml of 28% ammonia water was further added dropwise under ice-cooling. After stirring at room temperature for 3 hours, solvent was evaporated, followed by washing with water to obtain 3.5 g of crude product, which was washed with hot benzene to obtain 2.9 g of the title compound. m.p.: 188° to 190° C.

REFERENCE EXAMPLE 41

Synthesis of 4-ethoxycarbonyl-1-(5-nitropyridin-2-yl)pyrazole-3-sulfonamide m.p.: 245° to 247° C.

Synthesis of the intermediate was carried out in the following manner.

3-benzylthio-4-ethoxycarbonyl-1-(5-nitropyridin-2-yl)pyrazole:

To 50 ml of dimethylformamide, 2.0 g of 5(3)-benzylthio-4-ethoxycarbonylpyrazole, 1.33 g of 2-chloro-5-nitropyridine and 1.5 g of anhydrous potassium carbonate were added, followed by heating at room temperature for 1 hour and further at a temperature of 60° to 70° C. for 1 hour. After cooling, water was added to the reaction mixture, which was then extracted with chloroform. The layer of chloroform was separated, and after washing with water and drying, solvent was evaporated to obtain 2.5 g of the title compound. m.p.: 164.5° to 165.5° C.

Subsequently, the derivation of the desired product may be carried out following the procedures in Reference Examples 1 to 6.

REFERENCE EXAMPLE 42

Synthesis of 4-methoxycarbonyl-3-methyl-1-(2-pyridyl)pyrazole-5-sulfonamide: (procedures other than Reference Example 11)

Properties of intermediates:

Methyl 5-amino-3-methyl-1-(2-pyridyl)pyrazole-4-carboxylate, m.p.: 115° to 116° C.

Methyl 5-chloro-3-methyl-1-(2-pyridyl)pyrazole-4-carboxylate, m.p.: 111° to 112° C.

Methyl 3-methyl-5-mercapto-1-(2-pyridyl)pyrazole-4-carboxylate, m.p.: 102° to 105° C.

Synthesis of 4-methoxycarbonyl-3-methyl-1-(2-pyridyl)pyrazole-5-sulfonamide

In 200 ml of methylene chloride, 20.4 g of methyl 3-methyl-5-mercapto-1-(2-pyridyl)pyrazole-4-carboxylate was dissolved, and thereafter 200 ml of water was added. While maintaining the mixture at not higher than 5° C., 64 ml of conc. hydrochloric acid was added thereto, to which 250 ml of an aqueous solution of sodium hypochlorite (effective chlorine concentration: 6%) was added dropwise at −5° C., followed by stirring at −5° C. for 10 minutes. After separation of organic layer, extraction was carried out by adding 100 ml of methylene chloride to the aqueous layer. Organic layer was combined with the previous organic layer, followed by washing with an aqueous solution of sodium bisulfite, and then 40 ml of 28% ammonia water was added at 10° C. or lower. After stirring at room temperature for 10 minutes, solvent was evaporated. Crystals precipitated were filtered, washed with water, further washed with ether and dried to obtain 18.3 g of the title compound. m.p.: 196° to 198° C.

REFERENCE EXAMPLE 43

Synthesis of 1-(6-fluoropyridin-2-yl)-4-methoxycarbonylpyrazole-5-sulfonamide

Synthesis was carried out following Reference Examples 1 to 6. m.p.: 174° to 175° C.

Each of the intermediates had the following property.

Methyl 5-amino-1-(6-fluoropyridin-2-yl)pyrazole-4-carboxylate, m.p.: 143° to 145° C.

Methyl 5-chloro-1-(6-fluoropyridin-2-yl)pyrazole-4-carboxylate, m.p.: 112° to 115° C.

Methyl 1-(6-fluoropyridin-2-yl)-5-mercaptopyrazole-4-carboxylate, m.p.: 120° to 122° C.

REFERENCE EXAMPLE 44

Synthesis of 1-(6-dimethylsulfamoylpyridin-2-yl)-4-ethoxycarbonylpyrazole-5-sulfonamide (1) Synthesis of 2-chloro-6-dimethylsulfamoylpyridine:

To 50 ml of dimethylformamide were added 10 g of 2,6-dichloropyridine, 8.4 g of benzylmercaptan and 10 g of potassium carbonate, which was then stirred at room temperature for 1 hour, followed by heating to 60° to 70° C. After cooling, water was added to the reaction mixture to carry out extraction with chloroform. Extract was subjected to evaporation under reduced pressure, and thereafter, crystals obtained were dissolved in 200 ml of an aqueous solution of 90% acetic acid. Chlorine gas was blown into the reaction mixture over a period of 10 minutes under ice-cooling. Thereafter, water was added to the reaction mixture, which was then extracted with about 150 ml of chloroform. After the extraction was completed, washing with water was carried out several times, and then 12 g of an aqueous solution of 50% dimethylamine was added dropwise with stirring at about 10° C. After stirring for 1 hour, the layer of chloroform was evaporated under reduced pressure to obtain 12.4 g of 2-chloro-6-dimethylsulfamoylpyridine. m.p.: 53° to 55° C.

(2) Synthesis of 6-dimethylsulfamoyl-2-hydrazinopyridine:

To 12 g of 2-chloro-6-dimethylsulfamoylpyridine were added 30 ml of n-butanol and 4 g of hydrazine hydrate. The mixture was stirred at room temperature for 30 minutes, followed by heating under reflux for 18 hours. After cooling, crystals obtained were filtered and washed with water to obtain 6.1 g of 6-dimethylsulfamoyl-2-hydrazinopyridine. m.p.: 117° to 120° C.

(3) Ethyl 5-amino-1-(6-dimethylsulfamoylpyridin-2-yl)pyrazole-4-carboxylate was synthesized following Reference Example 2. m.p.: 197° to 198° C.

(4) Ethyl 5-chloro-1-(6-dimethylsulfamoylpyridin-2-yl)pyrazole-4-carboxylate was synthesized following Reference Example 1. m.p.: 117° to 120° C.

(5) Ethyl 5-benzylthio-1-(6-dimethylsulfamoylpyridin-2-yl)pyrazole-4-carboxylate:

To 50 ml of dried dimethylformamide, added were 4.2 g of ethyl 5-chloro-1-(6-dimethylsulfamoylpyridin-2-yl)pyrazole-4-carboxylate and 1.46 g of benzylmercaptan and 3.2 g of potassium carbonate, followed by stirring at room temperature for 24 hours in the atmosphere of $N_2$. After the reaction, inorganic salt was filtered off and dimethylformamide was evaporated from the filtrate to obtain 4.4 g of the title compound as an oily product.

(6) 1-(6-dimethylsulfamoylpyridin-2-yl)-4-ethoxycarbonylpyrazole-5-sulfonamide was synthesized following Reference Example 1. m.p.: 102° to 104° C.

REFERENCE EXAMPLE 45

Synthesis of
4-allylcarbonyl-1-(2-pyridyl)pyrazole-5-sulfonamide

To a mixture of 2.2 of 4-carboxy-1-(2-pyridyl)-pyrazole-5-sulfonamide and 20 ml of allyl alcohol, 1 ml of methanesulfonic acid was added, followed by stirring at 110° C. for 18 hours. The reaction mixture was concentrated under reduced pressure, and purified by silica gel chromatography to obtain 0.7 g of the title compound. m.p.: 140° to 142° C.

REFERENCE EXAMPLE 46

4-Propargyloxycarbonyl-1-(2-pyridyl)pyrazole-5-sulfonamide

Synthesis was carried out following Reference Example 45. m.p.: 106° to 108° C.

REFERENCE EXAMPLE 47

4-(2-chloroethyl)oxycarbonyl-1-(2-pyridyl)pyrazole-5-sulfonamide

Synthesis was carried out following Reference Example 45. m.p.: 119° to 121° C.

REFERENCE EXAMPLE 48

Synthesis of
1-(4,6-dimethylpyrimidin-2-yl)-4-ethoxycarbonyl-pyrazole-5-sulfonmamide Synthesis was carried out following Reference Examples 1 to 6 and Reference Example 35. m.p.: 164° to 165° C.

Each of the intermediates had the following property.

Ethyl 5-amino-1-(4,6-dimethylpyrimidin-2-yl)pyrazole-4-carboxylate, m.p.: 184° to 186° C.

Ethyl 5-chloro-1-(4,6-dimethylpyrimidin-2-yl)pyrazole-4-carboxylate, m.p.: 88° to 89° C.

Ethyl 5-benzylmercapto-1-(4,6-dimethylpyrimidin-2-yl)pyrazole-4-carboxylate, m.p.: 84° to 85° C.

EXAMPLE 1

Synthesis of
N-[(4,6-dimethoxypyrimidin-2-yl)aminocarbonyl]-4-ethoxycarbonyl-1-(2-pyridyl)pyrazole-5-sulfonamide
(Compound No. 49)

2.0 g of 4-ethoxycarbonyl-1-(2-pyridyl)pyrazole-5-sulfonamide, 0.82 g of methyl chloroformate and 1.4 g of anhydrous potassium carbonate were heated under reflux in 50 ml of anhydrous acetonitrile for 4 hours. After the reaction was completed, solvent was evaporated under reduced pressure. After dilution with ice water, insolubles were filtered off, and the filtrate was precipitated with use of diluted hydrochloric acid. Crystals precipitated were filtered, washed with water and dried to obtain 2.2 g of N-[4-ethoxycarbonyl-1-(2-pyridyl)pyrazole-5-sulfonyl]methylcarbamate. m.p.: 127° to 129° C.

0.95 g of N-[4-ethoxycarbonyl-1-(2-pyridyl)pyrazole-5-sulfonyl]methylcarbamate and 0.41 g of 2-amino-4,6-dimethoxypyrimidine were heated under reflux in 30 ml of toluene for 6 hours while allowing the toluene to evaporate little by little. Toluene having been decreased was occasionally supplemented. After the reaction was completed, toluene was evaporated under reduced pressure. Isopropyl ether was added to the residue, which was then stirred to obtain 1.1 g of the title compound as crystals. m.p.: 140° to 142° C.

EXAMPLE 2

Synthesis of
N-[(4-methoxy-6-methyltriazin-2-yl)aminocarbonyl]-4-ethoxycarbonyl-1-(2-pyridyl)pyrazole-5-sulfonamide
(Compound No. 51)

To a 70 ml acetone mixture of 8.5 g of 4-ethoxycarbonyl-1-(2-pyridyl)pyrazole-5-sulfonamide and 6.0 g of anhydrous potassium carbonate, added was 3.3 g of n-butylisocyanate at room temperature, followed by heating under reflux for 3 hours. After the reaction was completed, acetone was evaporated under reduced pressure, and then the residue was emptied into ice water to filter insolbles off, and then the filtrate was precipitated with hydrochloric acid. Crystals precipitated was filtered, washed with water and dried to obtain 10.8 g of N-(n-butylcarbamoyl)-4-ethoxycarbonyl-1-(2-pyridyl)pyrazole-5-sulfonamide. m.p.: 180° to 181° C.

Subsequently, the above compound was added to 100 ml of dried toluene, into which 7.5 g of phosgene was blown while heating under reflux, and thereafter the reaction mixture was further heated under reflux for 1.5 hours. After the reaction was completed, solvent was evaporated under reduced pressure to obtain 8.4 g of crude 4-ethoxycarbonyl-1-(2-pyridyl)pyrazole-5-sulfonylisocyanate. 1.3 g of this crude suflonylisocyanate was added to a 30 ml solution of dried acetonitrile, containing 0.42 g of 2-amino-4-methoxy-6-methyltriazine, followed by stirring at room temperature. After the reaction mixture was concentrated, ether was added thereto, followed by stirring at room temperature, and crystals formed were filtered, washed with ether and dried to obtain 1.2 g of the title compound. m.p.: 133° to 136° C.

EXAMPLE 3

Synthesis of
N-[(4,6-dimethoxypyrimidin-2-yl)aminocarbonyl]-4-ethoxycarbonyl-1-[(2-pyridyl)methyl]pyrazole-3-sulfonamide (Compound No. 6218)

0.7 g of N-[(4,6-dimethoxypyrimidin-2-yl)aminocarbonyl]-4-ethoxycarbonylpyrazole-5(3)-sulfonamide was dissolved in 10 ml of tetrahydrofuran, to which 0.6 g of potassium t-butylate and 0.29 g of 2-chloromethylpyridine hydrochloride were added, and the mixture was refluxed for 5 hours. Tetrahydrofuran was evaporated under reduced pressure, and then 20 ml of ice water was added and insolbles were filtered off. To the aqueous layer obtained, added was 35% hydrochloric acid to make it acidic, followed by addition of chloroform to carry out extraction. Organic layer was washed with water and dried, and then solvent was evaporated to obtain 0.3 g of an oily product. This oily product was dissolved in a small amount of acetonitrile, to which a small amount of diisopropylether was added, whereupon the title compound in a pure form was crystalized, and was collected by filtration. Amount obtained was 0.18 g. m.p.: 95° to 96° C.

In the following, examples of specific compounds included in the compound of this invention are shown in Table 1 to Table 14 in addition to the compounds synthesized in the above Examples 1 to 3, by which, however, this invention is not limited.

The compounds shown in Table 1 to Table 14 can be synthesized following the procedures in Examples 1 and 2. Properties of some of these compounds are shown in Table 15. In Table 15, the compound number correspond to the compound number in Table 1 to Table 14.

TABLE 1

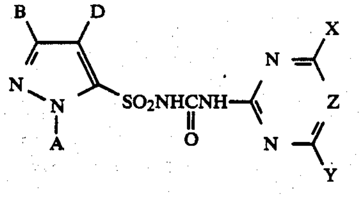

| No. | A | B | D | X | Y | Z |
|---|---|---|---|---|---|---|
| 1 | $Q_1$ | H | COOMe | Me | Me | CH |
| 2 | $Q_1$ | H | COOMe | Me | OMe | CH |
| 3 | $Q_1$ | H | COOMe | OMe | OMe | CH |
| 4 | $Q_1$ | H | COOMe | Me | Me | N |
| 5 | $Q_1$ | H | COOMe | Me | OMe | N |
| 6 | $Q_1$ | H | COOMe | OMe | OMe | N |
| 7 | $Q_1$ | H | COOMe | Me | Cl | CH |
| 8 | $Q_1$ | H | COOMe | Me | OEt | CH |
| 9 | $Q_1$ | H | COOMe | Me | H | CH |
| 10 | $Q_1$ | H | COOMe | Me | $CH_2OMe$ | CH |
| 11 | $Q_1$ | H | COOMe | Me | $CF_3$ | CH |
| 12 | $Q_1$ | H | COOMe | Me | $OCH_2CF_3$ | CH |
| 13 | $Q_1$ | H | COOMe | Me | $OCH_2COOMe$ | CH |
| 14 | $Q_1$ | H | COOMe | Cl | Cl | CH |
| 15 | $Q_1$ | H | COOMe | Br | Br | CH |
| 16 | $Q_1$ | H | COOMe | Me | Cl | N |
| 17 | $Q_1$ | H | COOMe | Cl | $NMe_2$ | N |
| 18 | $Q_1$ | H | COOMe | OMe | $NMe_2$ | N |
| 19 | $Q_1$ | H | COOMe | Me | OEt | N |
| 20 | $Q_1$ | H | COOMe | Me | NHEt | N |
| 21 | $Q_1$ | H | COOMe | Me | $CH_2OMe$ | N |
| 22 | $Q_1$ | H | COOMe | Me | OCH(Me)COOH | N |
| 23 | $Q_1$ | H | COOMe | Me | COOMe | CH |
| 24 | $Q_1$ | H | COOMe | Me | COOEt | CH |
| 25 | $Q_1$ | H | COOMe | OMe | COOMe | CH |
| 26 | $Q_1$ | H | COOMe | Cl | COOMe | CH |
| 27 | $Q_1$ | H | COOMe | Me | 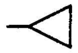 | CH |
| 28 | $Q_1$ | H | COOMe | Me | $OCHF_2$ | CH |
| 29 | $Q_1$ | H | COOMe | $OCHF_2$ | $OCHF_2$ | CH |
| 30 | $Q_1$ | H | COOMe | Cl | $OCHF_2$ | CH |
| 31 | $Q_1$ | H | COOMe | Cl | OMe | CH |
| 32 | $Q_1$ | H | COOMe | Cl | $NH_2$ | CH |
| 33 | $Q_1$ | H | COOMe | Me | Me | CMe |
| 34 | $Q_1$ | H | COOMe | Me | Me | CCl |
| 35 | $Q_1$ | H | COOMe | Me | OMe | CCl |
| 36 | $Q_1$ | H | COOMe | OMe | OMe | CF |
| 37 | $Q_1$ | H | COOMe | Me | Me | COMe |
| 38 | $Q_1$ | H | COOMe | OMe | OMe | $CCF_3$ |
| 39 | $Q_1$ | H | COOMe | Me | N(Me)OMe | CH |
| 40 | $Q_1$ | H | COOMe | Me | SMe | CH |
| 41 | $Q_1$ | H | COOMe | Me | $CH(OMe)_2$ | CH |
| 42 | $Q_1$ | H | COOMe | OMe | $CH(OEt)_2$ | N |
| 43 | $Q_1$ | H | COOMe | OMe | 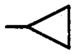 | N |
| 44 | $Q_1$ | H | COOMe | Me | $SCHF_2$ | CH |
| 45 | $Q_1$ | H | COOMe | Me | $SCHF_2$ | N |
| 46 | $Q_1$ | H | COOMe | Me | $OCF_2CF_2H$ | CH |
| 47 | $Q_1$ | H | COOEt | Me | Me | CH |
| 48 | $Q_1$ | H | COOEt | Me | OMe | CH |
| 49 | $Q_1$ | H | COOEt | OMe | OMe | CH |
| 50 | $Q_1$ | H | COOEt | Me | Me | N |
| 51 | $Q_1$ | H | COOEt | Me | OMe | N |
| 52 | $Q_1$ | H | COOEt | OMe | OMe | N |
| 53 | $Q_1$ | H | COOEt | Me | Cl | CH |
| 54 | $Q_1$ | H | COOEt | Me | OEt | CH |
| 55 | $Q_1$ | H | COOEt | Me | H | CH |
| 56 | $Q_1$ | H | COOEt | Me | $CH_2OMe$ | CH |
| 57 | $Q_1$ | H | COOEt | Me | $CF_3$ | CH |
| 58 | $Q_1$ | H | COOEt | Me | $OCH_2CF_3$ | CH |

TABLE 1-continued

| | | | | | | |
|---|---|---|---|---|---|---|
| 59 | $Q_1$ | H | COOEt | Me | $OCH_2COOMe$ | CH |
| 60 | $Q_1$ | H | COOEt | Cl | Cl | CH |
| 61 | $Q_1$ | H | COOEt | Br | Br | CH |
| 62 | $Q_1$ | H | COOEt | Me | Cl | N |
| 63 | $Q_1$ | H | COOEt | Cl | $NMe_2$ | N |
| 64 | $Q_1$ | H | COOEt | OMe | $NMe_2$ | N |
| 65 | $Q_1$ | H | COOEt | Me | OEt | N |
| 66 | $Q_1$ | H | COOEt | Me | NHEt | N |
| 67 | $Q_1$ | H | COOEt | Me | $CH_2OMe$ | N |
| 68 | $Q_1$ | H | COOEt | Me | OCH(Me)COOH | N |
| 69 | $Q_1$ | H | COOEt | Me | COOMe | CH |
| 70 | $Q_1$ | H | COOEt | Me | COOEt | CH |
| 71 | $Q_1$ | H | COOEt | OMe | COOMe | CH |
| 72 | $Q_1$ | H | COOEt | Cl | COOMe | CH |
| 73 | $Q_1$ | H | COOEt | Me | 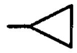 | CH |
| 74 | $Q_1$ | H | COOEt | Me | $OCHF_2$ | CH |
| 75 | $Q_1$ | H | COOEt | $OCHF_2$ | $OCHF_2$ | CH |
| 76 | $Q_1$ | H | COOEt | Cl | $OCHF_2$ | CH |
| 77 | $Q_1$ | H | COOEt | Cl | OMe | CH |
| 78 | $Q_1$ | H | COOEt | Cl | $NH_2$ | CH |
| 79 | $Q_1$ | H | COOEt | Me | Me | CMe |
| 80 | $Q_1$ | H | COOEt | Me | Me | CCl |
| 81 | $Q_1$ | H | COOEt | Me | OMe | CCl |
| 82 | $Q_1$ | H | COOEt | OMe | OMe | CF |
| 83 | $Q_1$ | H | COOEt | Me | Me | COMe |
| 84 | $Q_1$ | H | COOEt | OMe | OMe | $CCF_3$ |
| 85 | $Q_1$ | H | COOEt | Me | N(Me)OMe | CH |
| 86 | $Q_1$ | H | COOEt | Me | SMe | CH |
| 87 | $Q_1$ | H | COOEt | Me | $CH(OMe)_2$ | CH |
| 88 | $Q_1$ | H | COOEt | OMe | $CH(OEt)_2$ | N |
| 89 | $Q_1$ | H | COOEt | OMe | 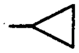 | N |
| 90 | $Q_1$ | H | COOEt | Me | $SCHF_2$ | CH |
| 91 | $Q_1$ | H | COOEt | Me | $SCHF_2$ | N |
| 92 | $Q_1$ | H | COOEt | Me | $OCF_2CF_2H$ | CH |
| 93 | $Q_1$ | H | COOH | Me | Me | CH |
| 94 | $Q_1$ | H | COOH | Me | OMe | CH |
| 95 | $Q_1$ | H | COOH | OMe | OMe | CH |
| 96 | $Q_1$ | H | COOH | Me | OMe | N |
| 97 | $Q_1$ | H | COOH | OMe | OMe | N |
| 98 | $Q_1$ | H | COOPr—n | Me | Me | CH |
| 99 | $Q_1$ | H | COOPr—n | Me | OMe | CH |
| 100 | $Q_1$ | H | COOPr—n | OMe | OMe | CH |
| 101 | $Q_1$ | H | COOPr—n | Me | OMe | N |
| 102 | $Q_1$ | H | COOPr—n | OMe | OMe | N |
| 103 | $Q_1$ | H | COOPr—i | Me | Me | CH |
| 104 | $Q_1$ | H | COOPr—i | Me | OMe | CH |
| 105 | $Q_1$ | H | COOPr—i | OMe | OMe | CH |
| 106 | $Q_1$ | H | COOPr—i | Me | OMe | N |
| 107 | $Q_1$ | H | COOPr—i | OMe | OMe | N |
| 108 | $Q_1$ | H | $COOCH_2CH_2Cl$ | Me | Me | CH |
| 109 | $Q_1$ | H | $COOCH_2CH_2Cl$ | Me | OMe | CH |
| 110 | $Q_1$ | H | $COOCH_2CH_2Cl$ | OMe | OMe | CH |
| 111 | $Q_1$ | H | $COOCH_2CH_2Cl$ | Me | OMe | N |
| 112 | $Q_1$ | H | $COOCH_2CH_2Cl$ | OMe | OMe | N |
| 113 | $Q_1$ | H | $COOCH_2CF_3$ | Me | OMe | CH |
| 114 | $Q_1$ | H | $COOCH_2CF_3$ | OMe | OMe | CH |
| 115 | $Q_1$ | H | $COOCH_2CF_3$ | Me | OMe | N |
| 116 | $Q_1$ | H | COOBu—n | Me | OMe | CH |
| 117 | $Q_1$ | H | COOBu—n | OMe | OMe | CH |
| 118 | $Q_1$ | H | COOBu—n | Me | OMe | N |
| 119 | $Q_1$ | H | $COOCH_2CH{=}CH_2$ | Me | Me | CH |
| 120 | $Q_1$ | H | $COOCH_2CH{=}CH_2$ | Me | OMe | CH |
| 121 | $Q_1$ | H | $COOCH_2CH{=}CH_2$ | OMe | OMe | CH |
| 122 | $Q_1$ | H | $COOCH_2CH{=}CH_2$ | Me | OMe | N |
| 123 | $Q_1$ | H | $COOCH_2CH{=}CH_2$ | OMe | OMe | N |
| 124 | $Q_1$ | H | $COOCH_2C{\equiv}CH$ | Me | Me | CH |
| 125 | $Q_1$ | H | $COOCH_2C{\equiv}CH$ | Me | OMe | CH |
| 126 | $Q_1$ | H | $COOCH_2C{\equiv}CH$ | OMe | OMe | CH |
| 127 | $Q_1$ | H | $COOCH_2C{\equiv}CH$ | Me | OMe | N |
| 128 | $Q_1$ | H | $COOCH_2C{\equiv}CH$ | OMe | OMe | N |
| 129 | $Q_1$ | H | $COOCH_2CH_2OMe$ | Me | OMe | CH |
| 130 | $Q_1$ | H | $COOCH_2CH_2OMe$ | OMe | OMe | CH |
| 131 | $Q_1$ | H | $COOCH_2CH_2OMe$ | Me | OMe | N |
| 132 | $Q_1$ | Me | COOMe | Me | Me | CH |

TABLE 1-continued

| | | | | | | |
|---|---|---|---|---|---|---|
| 133 | $Q_1$ | Me | COOMe | Me | OMe | CH |
| 134 | $Q_1$ | Me | COOMe | OMe | OMe | CH |
| 135 | $Q_1$ | Me | COOMe | Me | OMe | N |
| 136 | $Q_1$ | Me | COOMe | OMe | OMe | N |
| 137 | $Q_1$ | Me | COOEt | Me | Me | CH |
| 138 | $Q_1$ | Me | COOEt | Me | OMe | CH |
| 139 | $Q_1$ | Me | COOEt | OMe | OMe | CH |
| 140 | $Q_1$ | Me | COOEt | Me | OMe | N |
| 141 | $Q_1$ | Me | COOEt | OMe | OMe | N |
| 142 | $Q_1$ | Et | COOMe | Me | OMe | CH |
| 143 | $Q_1$ | Et | COOMe | OMe | OMe | CH |
| 144 | $Q_1$ | Et | COOMe | Me | OMe | N |
| 145 | $Q_1$ | Et | COOEt | Me | OMe | CH |
| 146 | $Q_1$ | Et | COOEt | OMe | OMe | CH |
| 147 | $Q_1$ | Et | COOEt | Me | OMe | N |
| 148 | $Q_1$ | Cl | COOMe | Me | Me | CH |
| 149 | $Q_1$ | Cl | COOMe | Me | OMe | CH |
| 150 | $Q_1$ | Cl | COOMe | OMe | OMe | CH |
| 151 | $Q_1$ | Cl | COOMe | Me | OMe | N |
| 152 | $Q_1$ | Cl | COOMe | OMe | OMe | N |
| 153 | $Q_1$ | Cl | COOEt | Me | Me | CH |
| 154 | $Q_1$ | Cl | COOEt | Me | OMe | CH |
| 155 | $Q_1$ | Cl | COOEt | OMe | OMe | CH |
| 156 | $Q_1$ | Cl | COOEt | Me | OMe | N |
| 157 | $Q_1$ | Cl | COOEt | OMe | OMe | N |
| 158 | $Q_1$ | F | COOMe | Me | Me | CH |
| 159 | $Q_1$ | F | COOMe | Me | OMe | CH |
| 160 | $Q_1$ | F | COOMe | OMe | OMe | CH |
| 161 | $Q_1$ | F | COOMe | Me | OMe | N |
| 162 | $Q_1$ | F | COOMe | OMe | OMe | N |
| 163 | $Q_1$ | Br | COOMe | Me | Me | CH |
| 164 | $Q_1$ | Br | COOMe | Me | OMe | CH |
| 165 | $Q_1$ | Br | COOMe | OMe | OMe | CH |
| 166 | $Q_1$ | Br | COOMe | Me | OMe | N |
| 167 | $Q_1$ | Br | COOMe | OMe | OMe | N |
| 168 | $Q_1$ | OMe | COOMe | Me | Me | CH |
| 169 | $Q_1$ | OMe | COOMe | Me | OMe | CH |
| 170 | $Q_1$ | OMe | COOMe | OMe | OMe | CH |
| 171 | $Q_1$ | OMe | COOMe | Me | OMe | N |
| 172 | $Q_1$ | OMe | COOMe | OMe | OMe | N |
| 173 | $Q_1$ | OMe | COOEt | Me | Me | CH |
| 174 | $Q_1$ | OMe | COOEt | Me | OMe | CH |
| 175 | $Q_1$ | OMe | COOEt | OMe | OMe | CH |
| 176 | $Q_1$ | OMe | COOEt | Me | OMe | N |
| 177 | $Q_1$ | OMe | COOEt | OMe | OMe | N |
| 178 | $Q_1$ | OEt | COOMe | Me | Me | CH |
| 179 | $Q_1$ | OEt | COOMe | Me | OMe | CH |
| 180 | $Q_1$ | OEt | COOMe | OMe | OMe | CH |
| 181 | $Q_1$ | OEt | COOMe | OMe | OMe | N |
| 182 | $Q_1$ | $CF_3$ | COOMe | Me | OMe | CH |
| 183 | $Q_1$ | $CF_3$ | COOMe | OMe | OMe | CH |
| 184 | $Q_1$ | $CF_3$ | COOMe | Me | OMe | N |
| 185 | $Q_1$ | SMe | COOMe | Me | OMe | CH |
| 186 | $Q_1$ | SMe | COOMe | OMe | OMe | CH |
| 187 | $Q_1$ | SMe | COOMe | Me | OMe | N |
| 188 | $Q_1$ | $SO_2Me$ | COOMe | Me | OMe | CH |
| 189 | $Q_1$ | $SO_2Me$ | COOMe | OMe | OMe | CH |
| 190 | $Q_1$ | $SO_2Me$ | COOMe | Me | OMe | N |
| 191 | $Q_1$ | $CO_2Me$ | COOMe | Me | OMe | CH |
| 192 | $Q_1$ | $CO_2Me$ | COOMe | OMe | OMe | CH |
| 193 | $Q_1$ | $CO_2Me$ | COOMe | Me | OMe | N |
| 194 | $Q_1$ | $CH_2OMe$ | COOMe | Me | Me | CH |
| 195 | $Q_1$ | $CH_2OMe$ | COOMe | Me | OMe | CH |
| 196 | $Q_1$ | $CH_2OMe$ | COOMe | OMe | OMe | CH |
| 197 | $Q_1$ | $CH_2OMe$ | COOMe | Me | OMe | N |
| 198 | $Q_1$ | $CH_2OMe$ | COOMe | OMe | OMe | N |
| 199 | $Q_1$ | $NO_2$ | COOMe | Me | Me | CH |
| 200 | $Q_1$ | $NO_2$ | COOMe | Me | OMe | CH |
| 201 | $Q_1$ | $NO_2$ | COOMe | OMe | OMe | CH |
| 202 | $Q_1$ | $NO_2$ | COOMe | Me | OMe | N |
| 203 | $Q_1$ | $NO_2$ | COOMe | OMe | OMe | N |
| 204 | $Q_1$ | OH | COOMe | Me | OMe | CH |
| 205 | $Q_1$ | OH | COOMe | OMe | OMe | CH |
| 206 | $Q_1$ | OH | COOMe | Me | OMe | N |
| 207 | $Q_1$ | H | Cl | Me | Me | CH |
| 208 | $Q_1$ | H | Cl | Me | OMe | CH |
| 209 | $Q_1$ | H | Cl | OMe | OMe | CH |
| 210 | $Q_1$ | H | Cl | Me | OMe | N |
| 211 | $Q_1$ | H | Cl | OMe | OMe | N |
| 212 | $Q_1$ | H | Br | Me | OMe | CH |
| 213 | $Q_1$ | H | Br | OMe | OMe | CH |
| 214 | $Q_1$ | H | Br | OMe | OMe | N |

TABLE 1-continued

| | | | | | | |
|---|---|---|---|---|---|---|
| 215 | $Q_1$ | H | Br | Me | OMe | N |
| 216 | $Q_1$ | Me | Cl | Me | Me | CH |
| 217 | $Q_1$ | Me | Cl | Me | OMe | CH |
| 218 | $Q_1$ | Me | Cl | OMe | OMe | CH |
| 219 | $Q_1$ | Me | Cl | Me | OMe | N |
| 220 | $Q_1$ | Me | Cl | OMe | OMe | N |
| 221 | $Q_1$ | H | $NO_2$ | Me | Me | N |
| 222 | $Q_1$ | H | $NO_2$ | Me | Me | CH |
| 223 | $Q_1$ | H | $NO_2$ | Me | OMe | CH |
| 224 | $Q_1$ | H | $NO_2$ | OMe | OMe | CH |
| 225 | $Q_1$ | H | $NO_2$ | Me | OMe | N |
| 226 | $Q_1$ | H | $NO_2$ | OMe | OMe | N |
| 227 | $Q_1$ | Me | $NO_2$ | Me | OMe | CH |
| 228 | $Q_1$ | Me | $NO_2$ | OMe | OMe | CH |
| 229 | $Q_1$ | Me | $NO_2$ | Me | OMe | N |
| 230 | $Q_1$ | H | OMe | Me | OMe | CH |
| 231 | $Q_1$ | H | OMe | OMe | OMe | CH |
| 232 | $Q_1$ | H | OMe | Me | OMe | N |
| 233 | $Q_1$ | H | OEt | Me | OMe | CH |
| 234 | $Q_1$ | H | OEt | OMe | OMe | CH |
| 235 | $Q_1$ | H | OEt | Me | OMe | N |
| 236 | $Q_1$ | Me | OMe | Me | OMe | CH |
| 237 | $Q_1$ | Me | OMe | OMe | OMe | CH |
| 238 | $Q_1$ | Me | OMe | Me | OMe | N |
| 239 | $Q_1$ | H | $CONMe_2$ | Me | OMe | CH |
| 240 | $Q_1$ | H | $CONMe_2$ | OMe | OMe | CH |
| 241 | $Q_1$ | H | $CONMe_2$ | Me | OMe | N |
| 242 | $Q_1$ | H | $CONEt_2$ | Me | OMe | CH |
| 243 | $Q_1$ | H | $CONEt_2$ | OMe | OMe | CH |
| 244 | $Q_1$ | H | $CONEt_2$ | Me | OMe | N |
| 245 | $Q_1$ | H | CONHMe | Me | OMe | CH |
| 246 | $Q_1$ | H | CONHMe | OMe | OMe | CH |
| 247 | $Q_1$ | H | CONHMe | Me | OMe | N |
| 248 | $Q_1$ | H | CONHPh | Me | OMe | CH |
| 249 | $Q_1$ | H | CONHPh | OMe | OMe | CH |
| 250 | $Q_1$ | H | CONHPh | Me | OMe | N |
| 251 | $Q_1$ | H | CON(Me)OMe | Me | OMe | CH |
| 252 | $Q_1$ | H | CON(Me)OMe | OMe | OMe | CH |
| 253 | $Q_1$ | H | CON(Me)OMe | Me | OMe | N |
| 254 | $Q_1$ | H | SMe | Me | OMe | CH |
| 255 | $Q_1$ | H | SMe | OMe | OMe | CH |
| 256 | $Q_1$ | H | SMe | Me | OMe | N |
| 257 | $Q_1$ | H | $SO_2Me$ | Me | OMe | CH |
| 258 | $Q_1$ | H | $SO_2Me$ | OMe | OMe | CH |
| 259 | $Q_1$ | H | $SO_2Me$ | Me | OMe | N |
| 260 | $Q_1$ | H | $SO_2Et$ | Me | OMe | CH |
| 261 | $Q_1$ | H | $SO_2Et$ | OMe | OMe | CH |
| 262 | $Q_1$ | H | $SO_2Et$ | Me | OMe | N |
| 263 | $Q_1$ | H | $SO_3Me$ | Me | OMe | CH |
| 264 | $Q_1$ | H | $SO_3Me$ | OMe | OMe | CH |
| 265 | $Q_1$ | H | $SO_3Me$ | Me | OMe | N |
| 266 | $Q_1$ | H | $SO_2Ph$ | Me | OMe | CH |
| 267 | $Q_1$ | H | $SO_2Ph$ | OMe | OMe | CH |
| 268 | $Q_1$ | H | $SO_2Ph$ | Me | OMe | N |
| 269 | $Q_1$ | H | $SO_2NMe_2$ | Me | Me | CH |
| 270 | $Q_1$ | H | $SO_2NMe_2$ | Me | OMe | CH |
| 271 | $Q_1$ | H | $SO_2NMe_2$ | OMe | OMe | CH |
| 272 | $Q_1$ | H | $SO_2NMe_2$ | Me | OMe | N |
| 273 | $Q_1$ | H | $SO_2NMe_2$ | OMe | OMe | N |
| 274 | $Q_1$ | H | $SO_2NEt_2$ | Me | OMe | CH |
| 275 | $Q_1$ | H | $SO_2NEt_2$ | OMe | OMe | CH |
| 276 | $Q_1$ | H | $SO_2NEt_2$ | Me | OMe | N |
| 277 | $Q_1$ | H | $SO_2NHMe$ | Me | OMe | CH |
| 278 | $Q_1$ | H | $SO_2NHMe$ | OMe | OMe | CH |
| 279 | $Q_1$ | H | $SO_2NHMe$ | Me | OMe | N |
| 280 | $Q_1$ | H | $SO_2NHPh$ | Me | OMe | CH |
| 281 | $Q_1$ | H | $SO_2NHPh$ | OMe | OMe | CH |
| 282 | $Q_1$ | H | $SO_2NHPh$ | Me | OMe | N |
| 283 | $Q_1$ | Me | $SO_2NMe_2$ | Me | OMe | CH |
| 284 | $Q_1$ | Me | $SO_2NMe_2$ | OMe | OMe | CH |
| 285 | $Q_1$ | Me | $SO_2NMe_2$ | Me | OMe | N |
| 286 | $Q_1$ | H | CN | Me | Me | CH |
| 287 | $Q_1$ | H | CN | Me | OMe | CH |
| 288 | $Q_1$ | H | CN | OMe | OMe | CH |
| 289 | $Q_1$ | H | CN | Me | OMe | N |
| 290 | $Q_1$ | H | CN | OMe | OMe | N |
| 291 | $Q_1$ | Me | CN | Me | Me | CH |
| 292 | $Q_1$ | Me | CN | Me | OMe | CH |
| 293 | $Q_1$ | Me | CN | OMe | OMe | CH |
| 294 | $Q_1$ | Me | CN | Me | OMe | N |
| 295 | $Q_1$ | Me | CN | OMe | OMe | N |
| 296 | $Q_1$ | H | $NMe_2$ | Me | Me | CH |

TABLE 1-continued

| | | | | | | |
|---|---|---|---|---|---|---|
| 297 | $Q_1$ | H | $NMe_2$ | Me | OMe | CH |
| 298 | $Q_1$ | H | $NMe_2$ | OMe | OMe | CH |
| 299 | $Q_1$ | H | $NMe_2$ | Me | OMe | N |
| 300 | $Q_1$ | H | $NMe_2$ | OMe | OMe | N |
| 301 | $Q_1$ | H | NHCOMe | Me | OMe | CH |
| 302 | $Q_1$ | H | NHCOMe | OMe | OMe | CH |
| 303 | $Q_1$ | H | NHCOMe | Me | OMe | N |
| 304 | $Q_1$ | H | Me | Me | Me | CH |
| 305 | $Q_1$ | H | Me | Me | OMe | CH |
| 306 | $Q_1$ | H | Me | OMe | OMe | CH |
| 307 | $Q_1$ | H | Me | Me | OMe | N |
| 308 | $Q_1$ | H | Me | OMe | OMe | N |
| 309 | $Q_1$ | H | Et | Me | Me | CH |
| 310 | $Q_1$ | H | Et | Me | OMe | CH |
| 311 | $Q_1$ | H | Et | OMe | OMe | CH |
| 312 | $Q_1$ | H | Et | Me | OMe | N |
| 313 | $Q_1$ | H | Et | OMe | OMe | N |
| 314 | $Q_1$ | H | Pr—n | Me | OMe | CH |
| 315 | $Q_1$ | H | Pr—n | OMe | OMe | CH |
| 316 | $Q_1$ | H | Pr—n | Me | OMe | N |
| 317 | $Q_1$ | Me | H | Me | Me | CH |
| 318 | $Q_1$ | Me | H | Me | OMe | CH |
| 319 | $Q_1$ | Me | H | OMe | OMe | CH |
| 320 | $Q_1$ | Me | H | Me | OMe | N |
| 321 | $Q_1$ | Me | H | OMe | OMe | N |
| 322 | $Q_1$ | H | H | Me | Me | CH |
| 323 | $Q_1$ | H | H | Me | OMe | CH |
| 324 | $Q_1$ | H | H | OMe | OMe | CH |
| 325 | $Q_1$ | H | H | Me | OMe | N |
| 326 | $Q_1$ | H | H | OMe | OMe | N |
| 327 | $Q_1$ | H | COPh | Me | Me | CH |
| 328 | $Q_1$ | H | COPh | Me | OMe | CH |
| 329 | $Q_1$ | H | COPh | OMe | OMe | CH |
| 330 | $Q_1$ | H | COPh | Me | OMe | N |
| 331 | $Q_1$ | H | COPh | OMe | OMe | N |
| 332 | $Q_1$ | Me | COPh | Me | Me | CH |
| 333 | $Q_1$ | Me | COPh | Me | OMe | CH |
| 334 | $Q_1$ | Me | COPh | OMe | OMe | CH |
| 335 | $Q_1$ | Me | COPh | Me | OMe | N |
| 336 | $Q_1$ | Me | COPh | OMe | OMe | N |
| 337 | $Q_1$ | H | COPh—2,4$Cl_2$ | Me | OMe | CH |
| 338 | $Q_1$ | H | COPh—2,4$Cl_2$ | OMe | OMe | CH |
| 339 | $Q_1$ | H | COPh—2,4$Cl_2$ | Me | OMe | N |
| 340 | $Q_1$ | H | COPh—2Me | Me | OMe | CH |
| 341 | $Q_1$ | H | COPh—2Me | OMe | OMe | CH |
| 342 | $Q_1$ | H | COPh—2Me | Me | OMe | N |
| 343 | H | $Q_1$ | H | Me | Me | CH |
| 344 | H | $Q_1$ | H | Me | OMe | CH |
| 345 | H | $Q_1$ | H | OMe | OMe | CH |
| 346 | H | $Q_1$ | H | Me | OMe | N |
| 347 | H | $Q_1$ | H | OMe | OMe | N |
| 348 | Me | $Q_1$ | H | Me | Me | CH |
| 349 | Me | $Q_1$ | H | Me | OMe | CH |
| 350 | Me | $Q_1$ | H | OMe | OMe | CH |
| 351 | Me | $Q_1$ | H | Me | OMe | N |
| 352 | Me | $Q_1$ | H | OMe | OMe | N |
| 353 | H | $Q_1$ | Me | Me | Me | CH |
| 354 | H | $Q_1$ | Me | Me | OMe | CH |
| 355 | H | $Q_1$ | Me | OMe | OMe | CH |
| 356 | H | $Q_1$ | Me | Me | OMe | N |
| 357 | H | $Q_1$ | Me | OMe | OMe | N |
| 358 | Me | $Q_1$ | Me | Me | Me | CH |
| 359 | Me | $Q_1$ | Me | Me | OMe | CH |
| 360 | Me | $Q_1$ | Me | OMe | OMe | CH |
| 361 | Me | $Q_1$ | Me | Me | OMe | N |
| 362 | Me | $Q_1$ | Me | OMe | OMe | N |
| 363 | H | $Q_1$ | COOMe | Me | Me | CH |
| 364 | H | $Q_1$ | COOMe | Me | OMe | CH |
| 365 | H | $Q_1$ | COOMe | OMe | OMe | CH |
| 366 | H | $Q_1$ | COOMe | Me | OMe | N |
| 367 | H | $Q_1$ | COOMe | OMe | OMe | N |
| 368 | H | $Q_1$ | COOEt | Me | Me | CH |
| 369 | H | $Q_1$ | COOEt | Me | OMe | CH |
| 370 | H | $Q_1$ | COOEt | OMe | OMe | CH |
| 371 | H | $Q_1$ | COOEt | Me | OMe | N |
| 372 | H | $Q_1$ | COOEt | OMe | OMe | N |
| 373 | Me | $Q_1$ | COOMe | Me | Me | CH |
| 374 | Me | $Q_1$ | COOMe | Me | OMe | CH |
| 375 | Me | $Q_1$ | COOMe | OMe | OMe | CH |
| 376 | Me | $Q_1$ | COOMe | Me | OMe | N |
| 377 | Me | $Q_1$ | COOMe | OMe | OMe | N |
| 378 | Me | $Q_1$ | COOEt | Me | Me | CH |

TABLE 1-continued

| | | | | | | |
|---|---|---|---|---|---|---|
| 379 | Me | $Q_1$ | COOEt | Me | OMe | CH |
| 380 | Me | $Q_1$ | COOEt | OMe | OMe | CH |
| 381 | Me | $Q_1$ | COOEt | Me | OMe | N |
| 382 | Me | $Q_1$ | COOEt | OMe | OMe | N |
| 383 | $CH_2OCH_3$ | $Q_1$ | COOMe | Me | OMe | CH |
| 384 | $CH_2OCH_3$ | $Q_1$ | COOMe | OMe | OMe | CH |
| 385 | $CH_2OCH_3$ | $Q_1$ | COOMe | Me | OMe | N |
| 386 | $CH_2SCH_3$ | $Q_1$ | COOMe | Me | OMe | CH |
| 387 | $CH_2SCH_3$ | $Q_1$ | COOMe | OMe | OMe | CH |
| 388 | $CH_2SCH_3$ | $Q_1$ | COOMe | Me | OMe | N |
| 389 | Me | $Q_1$ | $SO_2NMe_2$ | Me | OMe | CH |
| 390 | Me | $Q_1$ | $SO_2NMe_2$ | OMe | OMe | CH |
| 391 | Me | $Q_1$ | $SO_2NMe_2$ | Me | OMe | N |
| 392 | Me | $Q_1$ | $NO_2$ | Me | OMe | CH |
| 393 | Me | $Q_1$ | $NO_2$ | OMe | OMe | CH |
| 394 | Me | $Q_1$ | $NO_2$ | Me | OMe | N |
| 395 | Me | $Q_1$ | OMe | Me | OMe | CH |
| 396 | Me | $Q_1$ | OMe | OMe | OMe | CH |
| 397 | Me | $Q_1$ | OMe | Me | OMe | N |
| 398 | Me | $Q_1$ | CN | Me | OMe | CH |
| 399 | Me | $Q_1$ | CN | OMe | OMe | CH |
| 400 | Me | $Q_1$ | CN | Me | OMe | N |
| 401 | H | H | $Q_1$ | Me | Me | CH |
| 402 | H | H | $Q_1$ | Me | OMe | CH |
| 403 | H | H | $Q_1$ | OMe | OMe | CH |
| 404 | H | H | $Q_1$ | Me | OMe | N |
| 405 | H | H | $Q_1$ | OMe | OMe | N |
| 406 | Me | H | $Q_1$ | Me | Me | CH |
| 407 | Me | H | $Q_1$ | Me | OMe | CH |
| 408 | Me | H | $Q_1$ | OMe | OMe | CH |
| 409 | Me | H | $Q_1$ | Me | OMe | N |
| 410 | Me | H | $Q_1$ | OMe | OMe | N |
| 411 | Et | H | $Q_1$ | Me | OMe | CH |
| 412 | Et | H | $Q_1$ | OMe | OMe | CH |
| 413 | Et | H | $Q_1$ | Me | OMe | N |
| 414 | $CH_2CH{=}CH_2$ | H | $Q_1$ | Me | OMe | CH |
| 415 | $CH_2CH{=}CH_2$ | H | $Q_1$ | OMe | OMe | CH |
| 416 | $CH_2CH{=}CH_2$ | H | $Q_1$ | Me | OMe | N |
| 417 | $CH_2C{\equiv}CH$ | H | $Q_1$ | Me | OMe | CH |
| 418 | $CH_2C{\equiv}CH$ | H | $Q_1$ | OMe | OMe | CH |
| 419 | $CH_2C{\equiv}CH$ | H | $Q_1$ | Me | OMe | N |
| 420 | $CH_2CN$ | H | $Q_1$ | Me | OMe | CH |
| 421 | $CH_2CN$ | H | $Q_1$ | OMe | OMe | CH |
| 422 | $CH_2CN$ | H | $Q_1$ | Me | OMe | N |
| 423 | $CH_2COOMe$ | H | $Q_1$ | Me | OMe | CH |
| 424 | $CH_2COOMe$ | H | $Q_1$ | OMe | OMe | CH |
| 425 | $CH_2COOMe$ | H | $Q_1$ | Me | OMe | N |
| 426 | $CH_2COOEt$ | H | $Q_1$ | Me | Me | CH |
| 427 | $CH_2COOEt$ | H | $Q_1$ | Me | OMe | CH |
| 428 | $CH_2COOEt$ | H | $Q_1$ | OMe | OMe | CH |
| 429 | $CH_2COOEt$ | H | $Q_1$ | Me | OMe | N |
| 430 | $CH_2COOEt$ | H | $Q_1$ | OMe | OMe | N |
| 431 | $CH_2OMe$ | H | $Q_1$ | Me | Me | CH |
| 432 | $CH_2OMe$ | H | $Q_1$ | Me | OMe | CH |
| 433 | $CH_2OMe$ | H | $Q_1$ | OMe | OMe | CH |
| 434 | $CH_2OMe$ | H | $Q_1$ | Me | OMe | N |
| 435 | $CH_2OMe$ | H | $Q_1$ | OMe | OMe | N |
| 436 | $CH_2SMe$ | H | $Q_1$ | Me | Me | CH |
| 437 | $CH_2SMe$ | H | $Q_1$ | Me | OMe | CH |
| 438 | $CH_2SMe$ | H | $Q_1$ | OMe | OMe | CH |
| 439 | $CH_2SMe$ | H | $Q_1$ | Me | OMe | N |
| 440 | $CH_2SMe$ | H | $Q_1$ | OMe | OMe | N |
| 441 | $SO_2NMe_2$ | H | $Q_1$ | Me | Me | CH |
| 442 | $SO_2NMe_2$ | H | $Q_1$ | Me | OMe | CH |
| 443 | $SO_2NMe_2$ | H | $Q_1$ | OMe | OMe | CH |
| 444 | $SO_2NMe_2$ | H | $Q_1$ | Me | OMe | N |
| 445 | $SO_2NMe_2$ | H | $Q_1$ | OMe | OMe | N |
| 446 | $SO_2Me$ | H | $Q_1$ | Me | Me | CH |
| 447 | $SO_2Me$ | H | $Q_1$ | Me | OMe | CH |
| 448 | $SO_2Me$ | H | $Q_1$ | OMe | OMe | CH |
| 449 | $SO_2Me$ | H | $Q_1$ | Me | OMe | N |
| 450 | $SO_2Me$ | H | $Q_1$ | OMe | OMe | N |
| 451 | Ph | H | $Q_1$ | Me | Me | CH |
| 452 | Ph | H | $Q_1$ | Me | OMe | CH |
| 453 | Ph | H | $Q_1$ | OMe | OMe | CH |
| 454 | Ph | H | $Q_1$ | Me | OMe | N |
| 455 | Ph | H | $Q_1$ | OMe | OMe | N |
| 456 | Ph—2-Cl | H | $Q_1$ | Me | OMe | CH |
| 457 | Ph—2-Cl | H | $Q_1$ | OMe | OMe | CH |
| 458 | Ph—2-Cl | H | $Q_1$ | Me | OMe | N |
| 459 | Ph—2-Me | H | $Q_1$ | Me | OMe | CH |
| 460 | Ph—2-Me | H | $Q_1$ | OMe | OMe | CH |

TABLE 1-continued

| | | | | | | |
|---|---|---|---|---|---|---|
| 461 | Ph—2-Me | H | $Q_1$ | Me | OMe | N |
| 462 | Ph—2-COOMe | H | $Q_1$ | Me | OMe | CH |
| 463 | Ph—2-COOMe | H | $Q_1$ | OMe | OMe | CH |
| 464 | Ph—2-COOMe | H | $Q_1$ | Me | OMe | N |
| 465 | H | Me | $Q_1$ | Me | Me | CH |
| 466 | H | Me | $Q_1$ | Me | OMe | CH |
| 467 | H | Me | $Q_1$ | OMe | OMe | CH |
| 468 | H | Me | $Q_1$ | Me | OMe | N |
| 469 | H | Me | $Q_1$ | OMe | OMe | N |
| 470 | Me | Me | $Q_1$ | Me | Me | CH |
| 471 | Me | Me | $Q_1$ | Me | OMe | CH |
| 472 | Me | Me | $Q_1$ | OMe | OMe | CH |
| 473 | Me | Me | $Q_1$ | Me | OMe | N |
| 474 | Me | Me | $Q_1$ | OMe | OMe | N |
| 475 | Ph | Me | $Q_1$ | Me | Me | CH |
| 476 | Ph | Me | $Q_1$ | Me | OMe | CH |
| 477 | Ph | Me | $Q_1$ | OMe | OMe | CH |
| 478 | Ph | Me | $Q_1$ | Me | OMe | N |
| 479 | Ph | Me | $Q_1$ | OMe | OMe | N |
| 480 | $Q_1$ | H | COOMe | Me | $-OCH_2CH_2C-$ | |
| 481 | $Q_1$ | H | COOEt | Me | $-OCH_2CH_2C-$ | |
| 482 | $Q_2$ | H | COOMe | Me | Me | CH |
| 483 | $Q_2$ | H | COOMe | Me | OMe | CH |
| 484 | $Q_2$ | H | COOMe | OMe | OMe | CH |
| 485 | $Q_2$ | H | COOMe | Me | Me | N |
| 486 | $Q_2$ | H | COOMe | Me | OMe | N |
| 487 | $Q_2$ | H | COOMe | OMe | OMe | N |
| 488 | $Q_2$ | H | COOMe | Me | $OCHF_2$ | CH |
| 489 | $Q_2$ | H | COOMe | Cl | OMe | CH |
| 490 | $Q_2$ | H | COOEt | Me | Me | CH |
| 491 | $Q_2$ | H | COOEt | Me | OMe | CH |
| 492 | $Q_2$ | H | COOEt | OMe | OMe | CH |
| 493 | $Q_2$ | H | COOEt | Me | Me | N |
| 494 | $Q_2$ | H | COOEt | Me | OMe | N |
| 495 | $Q_2$ | H | COOEt | OMe | OMe | N |
| 496 | $Q_2$ | H | COOEt | Me | $OCHF_2$ | CH |
| 497 | $Q_2$ | H | COOEt | Cl | OMe | CH |
| 498 | $Q_2$ | H | COOPr—n | Me | OMe | CH |
| 499 | $Q_2$ | H | COOPr—n | OMe | OMe | CH |
| 500 | $Q_2$ | H | COOPr—n | Me | OMe | N |
| 501 | $Q_2$ | H | COOPr—i | Me | OMe | CH |
| 502 | $Q_2$ | H | COOPr—i | OMe | OMe | CH |
| 503 | $Q_2$ | H | COOPr—i | Me | OMe | N |
| 504 | $Q_2$ | H | $COOCH_2CH_2Cl$ | Me | OMe | CH |
| 505 | $Q_2$ | H | $COOCH_2CH_2Cl$ | OMe | OMe | CH |
| 506 | $Q_2$ | H | $COOCH_2CH_2Cl$ | Me | OMe | N |
| 507 | $Q_2$ | H | $COOCH_2CH{=}CH_2$ | Me | OMe | CH |
| 508 | $Q_2$ | H | $COOCH_2CH{=}CH_2$ | OMe | OMe | CH |
| 509 | $Q_2$ | H | $COOCH_2CH{=}CH_2$ | Me | OMe | N |
| 510 | $Q_2$ | H | $COOCH_2C{\equiv}CH$ | Me | OMe | CH |
| 511 | $Q_2$ | H | $COOCH_2C{\equiv}CH$ | OMe | OMe | CH |
| 512 | $Q_2$ | H | $COOCH_2C{\equiv}CH$ | Me | OMe | N |
| 513 | $Q_2$ | Me | COOMe | Me | Me | CH |
| 514 | $Q_2$ | Me | COOMe | Me | OMe | CH |
| 515 | $Q_2$ | Me | COOMe | OMe | OMe | CH |
| 516 | $Q_2$ | Me | COOMe | Me | OMe | N |
| 517 | $Q_2$ | Me | COOMe | OMe | OMe | N |
| 518 | $Q_2$ | Me | COOEt | Me | Me | CH |
| 519 | $Q_2$ | Me | COOEt | Me | OMe | CH |
| 520 | $Q_2$ | Me | COOEt | OMe | OMe | CH |
| 521 | $Q_2$ | Me | COOEt | Me | OMe | N |
| 522 | $Q_2$ | Me | COOEt | OMe | OMe | N |
| 523 | $Q_2$ | Cl | COOMe | Me | OMe | CH |
| 524 | $Q_2$ | Cl | COOMe | OMe | OMe | CH |
| 525 | $Q_2$ | Cl | COOMe | Me | OMe | N |
| 526 | $Q_2$ | Cl | COOEt | Me | OMe | CH |
| 527 | $Q_2$ | Cl | COOEt | OMe | OMe | CH |
| 528 | $Q_2$ | Cl | COOEt | Me | OMe | N |
| 529 | $Q_2$ | OMe | COOMe | Me | OMe | CH |
| 530 | $Q_2$ | OMe | COOMe | OMe | OMe | CH |
| 531 | $Q_2$ | OMe | COOMe | Me | OMe | N |
| 532 | $Q_2$ | OMe | COOEt | Me | OMe | CH |
| 533 | $Q_2$ | OMe | COOEt | OMe | OMe | CH |
| 534 | $Q_2$ | OMe | COOEt | Me | OMe | N |
| 535 | $Q_2$ | H | Cl | Me | OMe | CH |
| 536 | $Q_2$ | H | Cl | OMe | OMe | CH |
| 537 | $Q_2$ | H | Cl | Me | OMe | N |
| 538 | $Q_2$ | H | $NO_2$ | Me | OMe | CH |
| 539 | $Q_2$ | H | $NO_2$ | OMe | OMe | CH |
| 540 | $Q_2$ | H | $NO_2$ | Me | OMe | N |
| 541 | $Q_2$ | H | $SO_2NMe_2$ | Me | OMe | CH |
| 542 | $Q_2$ | H | $SO_2NMe_2$ | OMe | OMe | CH |

TABLE 1-continued

| | | | | | | |
|---|---|---|---|---|---|---|
| 543 | $Q_2$ | H | $SO_2NMe_2$ | Me | OMe | N |
| 544 | $Q_2$ | H | CN | Me | OMe | CH |
| 545 | $Q_2$ | H | CN | OMe | OMe | CH |
| 546 | $Q_2$ | H | CN | Me | OMe | N |
| 547 | $Q_2$ | Me | CN | Me | OMe | CH |
| 548 | $Q_2$ | Me | CN | OMe | OMe | CH |
| 549 | $Q_2$ | Me | CN | Me | OMe | N |
| 550 | $Q_2$ | H | Me | Me | OMe | CH |
| 551 | $Q_2$ | H | Me | OMe | OMe | CH |
| 552 | $Q_2$ | H | Me | Me | OMe | N |
| 553 | $Q_2$ | H | Et | Me | OMe | CH |
| 554 | $Q_2$ | H | Et | OMe | OMe | CH |
| 555 | $Q_2$ | H | Et | Me | OMe | N |
| 556 | $Q_2$ | H | H | Me | OMe | CH |
| 557 | $Q_2$ | H | H | OMe | OMe | CH |
| 558 | $Q_2$ | H | H | Me | OMe | N |
| 559 | $Q_2$ | H | COPh | Me | OMe | CH |
| 560 | $Q_2$ | H | COPh | OMe | OMe | CH |
| 561 | $Q_2$ | H | COPh | Me | OMe | N |
| 562 | Me | $Q_2$ | COOMe | Me | OMe | CH |
| 563 | Me | $Q_2$ | COOMe | OMe | OMe | CH |
| 564 | Me | $Q_2$ | COOMe | Me | OMe | N |
| 565 | H | H | $Q_2$ | Me | OMe | CH |
| 566 | H | H | $Q_2$ | OMe | OMe | CH |
| 567 | H | H | $Q_2$ | Me | OMe | N |
| 568 | Me | H | $Q_2$ | Me | Me | CH |
| 569 | Me | H | $Q_2$ | Me | OMe | CH |
| 570 | Me | H | $Q_2$ | OMe | OMe | CH |
| 571 | Me | H | $Q_2$ | Me | OMe | N |
| 572 | Me | H | $Q_2$ | OMe | OMe | N |
| 573 | Me | Me | $Q_2$ | Me | OMe | CH |
| 574 | Me | Me | $Q_2$ | OMe | OMe | CH |
| 575 | Me | Me | $Q_2$ | Me | OMe | N |
| 576 | $Q_3$ | H | COOMe | Me | Me | CH |
| 577 | $Q_3$ | H | COOMe | Me | OMe | CH |
| 578 | $Q_3$ | H | COOMe | OMe | OMe | CH |
| 579 | $Q_3$ | H | COOMe | Me | OMe | N |
| 580 | $Q_3$ | H | COOMe | OMe | OMe | N |
| 581 | $Q_3$ | H | COOEt | Me | Me | CH |
| 582 | $Q_3$ | H | COOEt | Me | OMe | CH |
| 583 | $Q_3$ | H | COOEt | OMe | OMe | CH |
| 584 | $Q_3$ | H | COOEt | Me | OMe | N |
| 585 | $Q_3$ | H | COOEt | OMe | OMe | N |
| 586 | $Q_3$ | Me | COOMe | Me | OMe | CH |
| 587 | $Q_3$ | Me | COOMe | OMe | OMe | CH |
| 588 | $Q_3$ | Me | COOMe | Me | OMe | N |
| 589 | $Q_3$ | Me | COOEt | Me | OMe | CH |
| 590 | $Q_3$ | Me | COOEt | OMe | OMe | CH |
| 591 | $Q_3$ | Me | COOEt | Me | OMe | N |
| 592 | $Q_3$ | H | CN | Me | OMe | CH |
| 593 | $Q_3$ | H | CN | OMe | OMe | CH |
| 594 | $Q_3$ | H | CN | Me | OMe | N |
| 595 | $Q_3$ | H | H | Me | OMe | CH |
| 596 | $Q_3$ | H | H | OMe | OMe | CH |
| 597 | $Q_3$ | H | H | Me | OMe | N |
| 598 | Me | H | $Q_3$ | Me | Me | CH |
| 599 | Me | H | $Q_3$ | Me | OMe | CH |
| 600 | Me | H | $Q_3$ | OMe | OMe | CH |
| 601 | Me | H | $Q_3$ | Me | OMe | N |
| 602 | Me | H | $Q_3$ | OMe | OMe | N |
| 603 | $Q_4$ | H | COOMe | Me | Me | CH |
| 604 | $Q_4$ | H | COOMe | Me | OMe | CH |
| 605 | $Q_4$ | H | COOMe | OMe | OMe | CH |
| 606 | $Q_4$ | H | COOMe | Me | OMe | N |
| 607 | $Q_4$ | H | COOMe | OMe | OMe | N |
| 608 | $Q_4$ | H | COOEt | Me | Me | CH |
| 609 | $Q_4$ | H | COOEt | Me | OMe | CH |
| 610 | $Q_4$ | H | COOEt | OMe | OMe | CH |
| 611 | $Q_4$ | H | COOEt | Me | OMe | N |
| 612 | $Q_4$ | H | COOEt | OMe | OMe | N |
| 613 | $Q_4$ | Me | COOMe | Me | OMe | CH |
| 614 | $Q_4$ | Me | COOMe | OMe | OMe | CH |
| 615 | $Q_4$ | Me | COOMe | Me | OMe | N |
| 616 | $Q_4$ | Me | COOEt | Me | OMe | CH |
| 617 | $Q_4$ | Me | COOEt | OMe | OMe | CH |
| 618 | $Q_4$ | Me | COOEt | Me | OMe | N |
| 619 | $Q_4$ | H | CN | Me | OMe | CH |
| 620 | $Q_4$ | H | CN | OMe | OMe | CH |
| 621 | $Q_4$ | H | CN | Me | OMe | N |
| 622 | $Q_4$ | H | H | Me | OMe | CH |
| 623 | $Q_4$ | H | H | OMe | OMe | CH |
| 624 | $Q_4$ | H | H | Me | OMe | N |

TABLE 1-continued

| | | | | | | |
|---|---|---|---|---|---|---|
| 625 | Me | H | $Q_4$ | Me | Me | CH |
| 626 | Me | H | $Q_4$ | Me | OMe | CH |
| 627 | Me | H | $Q_4$ | OMe | OMe | CH |
| 628 | Me | H | $Q_4$ | Me | OMe | N |
| 629 | Me | H | $Q_4$ | OMe | OMe | N |
| 630 | $Q_5$ | H | COOMe | Me | Me | CH |
| 631 | $Q_5$ | H | COOMe | Me | OMe | CH |
| 632 | $Q_5$ | H | COOMe | OMe | OMe | CH |
| 633 | $Q_5$ | H | COOMe | Me | Me | N |
| 634 | $Q_5$ | H | COOMe | Me | OMe | N |
| 635 | $Q_5$ | H | COOMe | OMe | OMe | N |
| 636 | $Q_5$ | H | COOMe | Me | $OCHF_2$ | CH |
| 637 | $Q_5$ | H | COOMe | Cl | OMe | CH |
| 638 | $Q_5$ | H | COOEt | Me | Me | CH |
| 639 | $Q_5$ | H | COOEt | Me | OMe | CH |
| 640 | $Q_5$ | H | COOEt | OMe | OMe | CH |
| 641 | $Q_5$ | H | COOEt | Me | Me | N |
| 642 | $Q_5$ | H | COOEt | Me | OMe | N |
| 643 | $Q_5$ | H | COOEt | OMe | OMe | N |
| 644 | $Q_5$ | H | COOEt | Me | $OCHF_2$ | CH |
| 645 | $Q_5$ | H | COOEt | Cl | OMe | CH |
| 646 | $Q_5$ | H | COOPr—n | Me | OMe | CH |
| 647 | $Q_5$ | H | COOPr—n | OMe | OMe | CH |
| 648 | $Q_5$ | H | COOPr—n | Me | OMe | N |
| 649 | $Q_5$ | H | COOPr—i | Me | OMe | CH |
| 650 | $Q_5$ | H | COOPr—i | OMe | OMe | CH |
| 651 | $Q_5$ | H | COOPr—i | Me | OMe | N |
| 652 | $Q_5$ | H | $COOCH_2CH_2Cl$ | Me | OMe | CH |
| 653 | $Q_5$ | H | $COOCH_2CH_2Cl$ | OMe | OMe | CH |
| 654 | $Q_5$ | H | $COOCH_2CH_2Cl$ | Me | OMe | N |
| 655 | $Q_5$ | H | $COOCH_2CH{=}CH_2$ | Me | OMe | CH |
| 656 | $Q_5$ | H | $COOCH_2CH{=}CH_2$ | OMe | OMe | CH |
| 657 | $Q_5$ | H | $COOCH_2CH{=}CH_2$ | Me | OMe | N |
| 658 | $Q_5$ | H | $COOCH_2C{\equiv}CH$ | Me | OMe | CH |
| 659 | $Q_5$ | H | $COOCH_2C{\equiv}CH$ | OMe | OMe | CH |
| 660 | $Q_5$ | H | $COOCH_2C{\equiv}CH$ | Me | OMe | N |
| 661 | $Q_5$ | Me | COOMe | Me | Me | CH |
| 662 | $Q_5$ | Me | COOMe | Me | OMe | CH |
| 663 | $Q_5$ | Me | COOMe | OMe | OMe | CH |
| 664 | $Q_5$ | Me | COOMe | Me | OMe | N |
| 665 | $Q_5$ | Me | COOMe | OMe | OMe | N |
| 666 | $Q_5$ | Me | COOEt | Me | Me | CH |
| 667 | $Q_5$ | Me | COOEt | Me | OMe | CH |
| 668 | $Q_5$ | Me | COOEt | OMe | OMe | CH |
| 669 | $Q_5$ | Me | COOEt | Me | OMe | N |
| 670 | $Q_5$ | Me | COOEt | OMe | OMe | N |
| 671 | $Q_5$ | Cl | COOMe | Me | OMe | CH |
| 672 | $Q_5$ | Cl | COOMe | OMe | OMe | CH |
| 673 | $Q_5$ | Cl | COOMe | Me | OMe | N |
| 674 | $Q_5$ | Cl | COOEt | Me | OMe | CH |
| 675 | $Q_5$ | Cl | COOEt | OMe | OMe | CH |
| 676 | $Q_5$ | Cl | COOEt | Me | OMe | N |
| 677 | $Q_5$ | OMe | COOMe | Me | OMe | CH |
| 678 | $Q_5$ | OMe | COOMe | OMe | OMe | CH |
| 679 | $Q_5$ | OMe | COOMe | Me | OMe | N |
| 680 | $Q_5$ | OMe | COOEt | Me | OMe | CH |
| 681 | $Q_5$ | OMe | COOEt | OMe | OMe | CH |
| 682 | $Q_5$ | OMe | COOEt | Me | OMe | N |
| 683 | $Q_5$ | H | Cl | Me | OMe | CH |
| 684 | $Q_5$ | H | Cl | OMe | OMe | CH |
| 685 | $Q_5$ | H | Cl | Me | OMe | N |
| 686 | $Q_5$ | H | $NO_2$ | Me | OMe | CH |
| 687 | $Q_5$ | H | $NO_2$ | OMe | OMe | CH |
| 688 | $Q_5$ | H | $NO_2$ | Me | OMe | N |
| 689 | $Q_5$ | H | $SO_2NMe_2$ | Me | OMe | CH |
| 690 | $Q_5$ | H | $SO_2NMe_2$ | OMe | OMe | CH |
| 691 | $Q_5$ | H | $SO_2NMe_2$ | Me | OMe | N |
| 692 | $Q_5$ | H | CN | Me | OMe | CH |
| 693 | $Q_5$ | H | CN | OMe | OMe | CH |
| 694 | $Q_5$ | H | CN | Me | OMe | N |
| 695 | $Q_5$ | Me | CN | Me | OMe | CH |
| 696 | $Q_5$ | Me | CN | OMe | OMe | CH |
| 697 | $Q_5$ | Me | CN | Me | OMe | N |
| 698 | $Q_5$ | H | Me | Me | OMe | CH |
| 699 | $Q_5$ | H | Me | OMe | OMe | CH |
| 700 | $Q_5$ | H | Me | Me | OMe | N |
| 701 | $Q_5$ | H | Et | Me | OMe | CH |
| 702 | $Q_5$ | H | Et | OMe | OMe | CH |
| 703 | $Q_5$ | H | Et | Me | OMe | N |
| 704 | $Q_5$ | H | H | Me | OMe | CH |
| 705 | $Q_5$ | H | H | OMe | OMe | CH |
| 706 | $Q_5$ | H | H | Me | OMe | N |

TABLE 1-continued

| | | | | | | |
|---|---|---|---|---|---|---|
| 707 | $Q_5$ | H | COPh | Me | OMe | CH |
| 708 | $Q_5$ | H | COPh | OMe | OMe | CH |
| 709 | $Q_5$ | H | COPh | Me | OMe | N |
| 710 | Me | $Q_5$ | COOMe | Me | OMe | CH |
| 711 | Me | $Q_5$ | COOMe | OMe | OMe | CH |
| 712 | Me | $Q_5$ | COOMe | Me | OMe | N |
| 713 | H | H | $Q_5$ | Me | OMe | CH |
| 714 | H | H | $Q_5$ | OMe | OMe | CH |
| 715 | H | H | $Q_5$ | Me | OMe | N |
| 716 | Me | H | $Q_5$ | Me | Me | CH |
| 717 | Me | H | $Q_5$ | Me | OMe | CH |
| 718 | Me | H | $Q_5$ | OMe | OMe | CH |
| 719 | Me | H | $Q_5$ | Me | OMe | N |
| 720 | Me | H | $Q_5$ | OMe | OMe | N |
| 721 | Me | Me | $Q_5$ | Me | OMe | CH |
| 722 | Me | Me | $Q_5$ | OMe | OMe | CH |
| 723 | Me | Me | $Q_5$ | Me | OMe | N |
| 724 | $Q_6$ | H | COOMe | Me | Me | CH |
| 725 | $Q_6$ | H | COOMe | Me | OMe | CH |
| 726 | $Q_6$ | H | COOMe | OMe | OMe | CH |
| 727 | $Q_6$ | H | COOMe | Me | OMe | N |
| 728 | $Q_6$ | H | COOMe | OMe | OMe | N |
| 729 | $Q_6$ | H | COOEt | Me | Me | CH |
| 730 | $Q_6$ | H | COOEt | Me | OMe | CH |
| 731 | $Q_6$ | H | COOEt | OMe | OMe | CH |
| 732 | $Q_6$ | H | COOEt | Me | OMe | N |
| 733 | $Q_6$ | H | COOEt | OMe | OMe | N |
| 734 | $Q_6$ | Me | COOMe | Me | OMe | CH |
| 735 | $Q_6$ | Me | COOMe | OMe | OMe | CH |
| 736 | $Q_6$ | Me | COOMe | Me | OMe | N |
| 737 | $Q_6$ | Me | COOEt | Me | OMe | CH |
| 738 | $Q_6$ | Me | COOEt | OMe | OMe | CH |
| 739 | $Q_6$ | Me | COOEt | Me | OMe | N |
| 740 | $Q_6$ | H | CN | Me | OMe | CH |
| 741 | $Q_6$ | H | CN | OMe | OMe | CH |
| 742 | $Q_6$ | H | CN | Me | OMe | N |
| 743 | $Q_6$ | H | H | Me | OMe | CH |
| 744 | $Q_6$ | H | H | OMe | OMe | CH |
| 745 | $Q_6$ | H | H | Me | OMe | N |
| 746 | Me | H | $Q_6$ | Me | Me | CH |
| 747 | Me | H | $Q_6$ | Me | OMe | CH |
| 748 | Me | H | $Q_6$ | OMe | OMe | CH |
| 749 | Me | H | $Q_6$ | Me | OMe | N |
| 750 | Me | H | $Q_6$ | OMe | OMe | N |
| 751 | $Q_7$ | H | COOMe | Me | OMe | CH |
| 752 | $Q_7$ | H | COOMe | OMe | OMe | CH |
| 753 | $Q_7$ | H | COOEt | Me | OMe | CH |
| 754 | $Q_7$ | H | COOEt | OMe | OMe | CH |
| 755 | $Q_7$ | Me | COOMe | Me | OMe | CH |
| 756 | $Q_7$ | Me | COOMe | OMe | OMe | CH |
| 757 | $Q_7$ | Me | COOEt | Me | OMe | CH |
| 758 | $Q_7$ | Me | COOEt | OMe | OMe | CH |
| 759 | $Q_7$ | H | H | Me | OMe | CH |
| 760 | $Q_7$ | H | H | OMe | OMe | CH |
| 761 | Me | H | $Q_7$ | Me | OMe | CH |
| 762 | Me | H | $Q_7$ | OMe | OMe | CH |
| 763 | $Q_8$ | H | COOMe | Me | Me | CH |
| 764 | $Q_8$ | H | COOMe | Me | OMe | CH |
| 765 | $Q_8$ | H | COOMe | OMe | OMe | CH |
| 766 | $Q_8$ | H | COOMe | Me | Me | N |
| 767 | $Q_8$ | H | COOMe | Me | OMe | N |
| 768 | $Q_8$ | H | COOMe | OMe | OMe | N |
| 769 | $Q_8$ | H | COOMe | Me | $OCHF_2$ | CH |
| 770 | $Q_8$ | H | COOMe | Cl | OMe | CH |
| 771 | $Q_8$ | H | COOEt | Me | Me | CH |
| 772 | $Q_8$ | H | COOEt | Me | OMe | CH |
| 773 | $Q_8$ | H | COOEt | OMe | OMe | CH |
| 774 | $Q_8$ | H | COOEt | Me | Me | N |
| 775 | $Q_8$ | H | COOEt | Me | OMe | N |
| 776 | $Q_8$ | H | COOEt | OMe | OMe | N |
| 777 | $Q_8$ | H | COOEt | Me | $OCHF_2$ | CH |
| 778 | $Q_8$ | H | COOEt | Cl | OMe | CH |
| 779 | $Q_8$ | H | COOPr—n | Me | OMe | CH |
| 780 | $Q_8$ | H | COOPr—n | OMe | OMe | CH |
| 781 | $Q_8$ | H | COOPr—n | Me | OMe | N |
| 782 | $Q_8$ | H | COOPr—i | Me | OMe | CH |
| 783 | $Q_8$ | H | COOPr—i | OMe | OMe | CH |
| 784 | $Q_8$ | H | COOPr—i | Me | OMe | N |
| 785 | $Q_8$ | H | $COOCH_2CH_2Cl$ | Me | OMe | CH |
| 786 | $Q_8$ | H | $COOCH_2CH_2Cl$ | OMe | OMe | CH |
| 787 | $Q_8$ | H | $COOCH_2CH_2Cl$ | Me | OMe | N |
| 788 | $Q_8$ | H | $COOCH_2CH{=}CH_2$ | Me | OMe | CH |

TABLE 1-continued

| | | | | | | |
|---|---|---|---|---|---|---|
| 789 | $Q_8$ | H | $COOCH_2CH{=}CH_2$ | OMe | OMe | CH |
| 790 | $Q_8$ | H | $COOCH_2CH{=}CH_2$ | Me | OMe | N |
| 791 | $Q_8$ | H | $COOCH_2C{\equiv}CH$ | Me | OMe | CH |
| 792 | $Q_8$ | H | $COOCH_2C{\equiv}CH$ | OMe | OMe | CH |
| 793 | $Q_8$ | H | $COOCH_2C{\equiv}CH$ | Me | OMe | N |
| 794 | $Q_8$ | Me | COOMe | Me | Me | CH |
| 795 | $Q_8$ | Me | COOMe | Me | OMe | CH |
| 796 | $Q_8$ | Me | COOMe | OMe | OMe | CH |
| 797 | $Q_8$ | Me | COOMe | Me | OMe | N |
| 798 | $Q_8$ | Me | COOMe | OMe | OMe | N |
| 799 | $Q_8$ | Me | COOEt | Me | Me | CH |
| 800 | $Q_8$ | Me | COOEt | Me | OMe | CH |
| 801 | $Q_8$ | Me | COOEt | OMe | OMe | CH |
| 802 | $Q_8$ | Me | COOEt | Me | OMe | N |
| 803 | $Q_8$ | Me | COOEt | OMe | OMe | N |
| 804 | $Q_8$ | Cl | COOMe | Me | OMe | CH |
| 805 | $Q_8$ | Cl | COOMe | OMe | OMe | CH |
| 806 | $Q_8$ | Cl | COOMe | Me | OMe | N |
| 807 | $Q_8$ | Cl | COOEt | Me | OMe | CH |
| 808 | $Q_8$ | Cl | COOEt | OMe | OMe | CH |
| 809 | $Q_8$ | Cl | COOEt | Me | OMe | N |
| 810 | $Q_8$ | OMe | COOMe | Me | OMe | CH |
| 811 | $Q_8$ | OMe | COOMe | OMe | OMe | CH |
| 812 | $Q_8$ | OMe | COOMe | Me | OMe | N |
| 813 | $Q_8$ | OMe | COOEt | Me | OMe | CH |
| 814 | $Q_8$ | OMe | COOEt | OMe | OMe | CH |
| 815 | $Q_8$ | OMe | COOEt | Me | OMe | N |
| 816 | $Q_8$ | H | Cl | Me | OMe | CH |
| 817 | $Q_8$ | H | Cl | OMe | OMe | CH |
| 818 | $Q_8$ | H | Cl | Me | OMe | N |
| 819 | $Q_8$ | H | $NO_2$ | Me | OMe | CH |
| 820 | $Q_8$ | H | $NO_2$ | OMe | OMe | CH |
| 821 | $Q_8$ | H | $NO_2$ | Me | OMe | N |
| 822 | $Q_8$ | H | $SO_2NMe_2$ | Me | OMe | CH |
| 823 | $Q_8$ | H | $SO_2NMe_2$ | OMe | OMe | CH |
| 824 | $Q_8$ | H | $SO_2NMe_2$ | Me | OMe | N |
| 825 | $Q_8$ | H | CN | Me | OMe | CH |
| 826 | $Q_8$ | H | CN | OMe | OMe | CH |
| 827 | $Q_8$ | H | CN | Me | OMe | N |
| 828 | $Q_8$ | Me | CN | Me | OMe | CH |
| 829 | $Q_8$ | Me | CN | OMe | OMe | CH |
| 830 | $Q_8$ | Me | CN | Me | OMe | N |
| 831 | $Q_8$ | H | Me | Me | OMe | CH |
| 832 | $Q_8$ | H | Me | OMe | OMe | CH |
| 833 | $Q_8$ | H | Me | Me | OMe | N |
| 834 | $Q_8$ | H | Et | Me | OMe | CH |
| 835 | $Q_8$ | H | Et | OMe | OMe | CH |
| 836 | $Q_8$ | H | Et | Me | OMe | N |
| 837 | $Q_8$ | H | H | Me | OMe | CH |
| 838 | $Q_8$ | H | H | OMe | OMe | CH |
| 839 | $Q_8$ | H | H | Me | OMe | N |
| 840 | $Q_8$ | H | COPh | Me | OMe | CH |
| 841 | $Q_8$ | H | COPh | OMe | OMe | CH |
| 842 | $Q_8$ | H | COPh | Me | OMe | N |
| 843 | Me | $Q_8$ | COOMe | Me | OMe | CH |
| 844 | Me | $Q_8$ | COOMe | OMe | OMe | CH |
| 845 | Me | $Q_8$ | COOMe | Me | OMe | N |
| 846 | H | H | $Q_8$ | Me | OMe | CH |
| 847 | H | H | $Q_8$ | OMe | OMe | CH |
| 848 | H | H | $Q_8$ | Me | OMe | N |
| 849 | Me | H | $Q_8$ | Me | Me | CH |
| 850 | Me | H | $Q_8$ | Me | OMe | CH |
| 851 | Me | H | $Q_8$ | OMe | OMe | CH |
| 852 | Me | H | $Q_8$ | Me | OMe | N |
| 853 | Me | H | $Q_8$ | OMe | OMe | N |
| 854 | Me | Me | $Q_8$ | Me | OMe | CH |
| 855 | Me | Me | $Q_8$ | OMe | OMe | CH |
| 856 | Me | Me | $Q_8$ | Me | OMe | N |
| 857 | $Q_9$ | H | COOMe | Me | Me | CH |
| 858 | $Q_9$ | H | COOMe | Me | OMe | CH |
| 859 | $Q_9$ | H | COOMe | OMe | OMe | CH |
| 860 | $Q_9$ | H | COOMe | Me | OMe | N |
| 861 | $Q_9$ | H | COOMe | OMe | OMe | N |
| 862 | $Q_9$ | H | COOEt | Me | Me | CH |
| 863 | $Q_9$ | H | COOEt | Me | OMe | CH |
| 864 | $Q_9$ | H | COOEt | OMe | OMe | CH |
| 865 | $Q_9$ | H | COOEt | Me | OMe | N |
| 866 | $Q_9$ | H | COOEt | OMe | OMe | N |

-continued

| | | | | | | |
|---|---|---|---|---|---|---|
| 867 | $Q_9$ | Me | COOMe | Me | OMe | CH |
| 868 | $Q_9$ | Me | COOMe | OMe | OMe | CH |
| 869 | $Q_9$ | Me | COOMe | Me | OMe | N |
| 870 | $Q_9$ | Me | COOEt | Me | OMe | CH |
| 871 | $Q_9$ | Me | COOEt | OMe | OMe | CH |
| 872 | $Q_9$ | Me | COOEt | Me | OMe | N |
| 873 | $Q_9$ | H | CN | Me | OMe | CH |
| 874 | $Q_9$ | H | CN | OMe | OMe | CH |
| 875 | $Q_9$ | H | CN | Me | OMe | N |
| 876 | $Q_9$ | H | H | Me | OMe | CH |
| 877 | $Q_9$ | H | H | OMe | OMe | CH |
| 878 | $Q_9$ | H | H | Me | OMe | N |
| 879 | Me | H | $Q_9$ | Me | Me | CH |
| 880 | Me | H | $Q_9$ | Me | OMe | CH |
| 881 | Me | H | $Q_9$ | OMe | OMe | CH |
| 882 | Me | H | $Q_9$ | Me | OMe | N |
| 883 | Me | H | $Q_9$ | OMe | OMe | N |
| 884 | Me | Me | $Q_9$ | Me | OMe | N |
| 885 | $Q_{10}$ | H | COOMe | Me | Me | CH |
| 886 | $Q_{10}$ | H | COOMe | Me | OMe | CH |
| 887 | $Q_{10}$ | H | COOMe | OMe | OMe | CH |
| 888 | $Q_{10}$ | H | COOMe | Me | OMe | N |
| 889 | $Q_{10}$ | H | COOMe | OMe | OMe | N |
| 890 | $Q_{10}$ | H | COOEt | Me | Me | CH |
| 891 | $Q_{10}$ | H | COOEt | Me | OMe | CH |
| 892 | $Q_{10}$ | H | COOEt | OMe | OMe | CH |
| 893 | $Q_{10}$ | H | COOEt | Me | OMe | N |
| 894 | $Q_{10}$ | H | COOEt | OMe | OMe | N |
| 895 | $Q_{10}$ | Me | COOMe | Me | OMe | CH |
| 895 | $Q_{10}$ | Me | COOMe | Me | OMe | CH |
| 896 | $Q_{10}$ | Me | COOMe | OMe | OMe | CH |
| 897 | $Q_{10}$ | Me | COOMe | Me | OMe | N |
| 898 | $Q_{10}$ | Me | COOEt | Me | OMe | CH |
| 899 | $Q_{10}$ | Me | COOEt | OMe | OMe | CH |
| 900 | $Q_{10}$ | Me | COOEt | Me | OMe | N |
| 901 | $Q_{10}$ | H | CN | Me | OMe | CH |
| 902 | $Q_{10}$ | H | CN | OMe | OMe | CH |
| 903 | $Q_{10}$ | H | CN | Me | OMe | N |
| 904 | $Q_{10}$ | H | H | Me | OMe | CH |
| 905 | $Q_{10}$ | H | H | OMe | OMe | CH |
| 906 | $Q_{10}$ | H | H | Me | OMe | N |
| 907 | Me | H | $Q_{10}$ | Me | Me | CH |
| 908 | Me | H | $Q_{10}$ | Me | OMe | CH |
| 909 | Me | H | $Q_{10}$ | OMe | OMe | CH |
| 910 | Me | H | $Q_{10}$ | Me | OMe | N |
| 911 | Me | H | $Q_{10}$ | OMe | OMe | N |
| 912 | $Q_{11}$ | H | COOMe | Me | Me | CH |
| 913 | $Q_{11}$ | H | COOMe | Me | OMe | CH |
| 914 | $Q_{11}$ | H | COOMe | OMe | OMe | CH |
| 915 | $Q_{11}$ | H | COOMe | Me | OMe | N |
| 916 | $Q_{11}$ | H | COOMe | OMe | OMe | N |
| 917 | $Q_{11}$ | H | COOEt | Me | Me | CH |
| 918 | $Q_{11}$ | H | COOEt | Me | OMe | CH |
| 919 | $Q_{11}$ | H | COOEt | OMe | OMe | CH |
| 920 | $Q_{11}$ | H | COOEt | Me | OMe | N |
| 921 | $Q_{11}$ | H | COOEt | OMe | OMe | N |
| 922 | $Q_{11}$ | Me | COOMe | Me | OMe | CH |
| 923 | $Q_{11}$ | Me | COOMe | OMe | OMe | CH |
| 924 | $Q_{11}$ | Me | COOMe | Me | OMe | N |
| 925 | $Q_{11}$ | Me | COOEt | Me | OMe | CH |
| 926 | $Q_{11}$ | Me | COOEt | OMe | OMe | CH |
| 927 | $Q_{11}$ | Me | COOEt | Me | OMe | N |
| 928 | $Q_{11}$ | H | CN | Me | OMe | CH |
| 929 | $Q_{11}$ | H | CN | OMe | OMe | CH |
| 930 | $Q_{11}$ | H | CN | Me | OMe | N |
| 931 | $Q_{11}$ | H | H | Me | OMe | CH |
| 932 | $Q_{11}$ | H | H | OMe | OMe | CH |
| 933 | $Q_{11}$ | H | H | Me | OMe | N |
| 934 | Me | H | $Q_{11}$ | Me | Me | CH |
| 935 | Me | H | $Q_{11}$ | Me | OMe | CH |
| 936 | Me | H | $Q_{11}$ | OMe | OMe | CH |
| 937 | Me | H | $Q_{11}$ | Me | OMe | N |
| 938 | Me | H | $Q_{11}$ | OMe | OMe | N |
| 939 | $Q_{12}$ | H | COOMe | Me | Me | CH |
| 940 | $Q_{12}$ | H | COOMe | Me | OMe | CH |
| 941 | $Q_{12}$ | H | COOMe | OMe | OMe | CH |
| 942 | $Q_{12}$ | H | COOMe | Me | OMe | N |
| 943 | $Q_{12}$ | H | COOMe | OMe | OMe | N |
| 944 | $Q_{12}$ | H | COOEt | Me | Me | CH |
| 945 | $Q_{12}$ | H | COOEt | Me | OMe | CH |
| 946 | $Q_{12}$ | H | COOEt | OMe | OMe | CH |
| 947 | $Q_{12}$ | H | COOEt | Me | OMe | N |

-continued

| | | | | | | |
|---|---|---|---|---|---|---|
| 948 | $Q_{12}$ | H | COOEt | OMe | OMe | N |
| 949 | $Q_{12}$ | Me | COOMe | Me | OMe | CH |
| 950 | $Q_{12}$ | Me | COOMe | OMe | OMe | CH |
| 951 | $Q_{12}$ | Me | COOMe | Me | OMe | N |
| 952 | $Q_{12}$ | Me | COOEt | Me | OMe | CH |
| 953 | $Q_{12}$ | Me | COOEt | OMe | OMe | CH |
| 954 | $Q_{12}$ | Me | COOEt | Me | OMe | N |
| 955 | $Q_{12}$ | H | CN | Me | OMe | CH |
| 956 | $Q_{12}$ | H | CN | OMe | OMe | CH |
| 957 | $Q_{12}$ | H | CN | Me | OMe | N |
| 958 | $Q_{12}$ | H | H | Me | OMe | CH |
| 959 | $Q_{12}$ | H | H | OMe | OMe | CH |
| 960 | $Q_{12}$ | H | H | Me | OMe | N |
| 961 | Me | H | $Q_{12}$ | Me | Me | CH |
| 962 | Me | H | $Q_{12}$ | Me | OMe | CH |
| 963 | Me | H | $Q_{12}$ | OMe | OMe | CH |
| 964 | Me | H | $Q_{12}$ | Me | OMe | N |
| 965 | Me | H | $Q_{12}$ | OMe | OMe | N |
| 966 | $Q_{13}$ | H | COOMe | Me | OMe | CH |
| 967 | $Q_{13}$ | H | COOMe | OMe | OMe | CH |
| 968 | $Q_{13}$ | H | COOEt | Me | OMe | CH |
| 969 | $Q_{13}$ | H | COOEt | OMe | OMe | CH |
| 970 | $Q_{13}$ | Me | COOMe | Me | OMe | CH |
| 971 | $Q_{13}$ | Me | COOMe | OMe | OMe | CH |
| 972 | $Q_{13}$ | Me | COOEt | Me | OMe | CH |
| 973 | $Q_{13}$ | Me | COOEt | OMe | OMe | CH |
| 974 | $Q_{13}$ | H | H | Me | OMe | CH |
| 975 | $Q_{13}$ | H | H | OMe | OMe | CH |
| 976 | Me | H | $Q_{13}$ | Me | OMe | CH |
| 977 | Me | H | $Q_{13}$ | OMe | OMe | CH |
| 978 | $Q_{14}$ | H | COOMe | Me | Me | CH |
| 979 | $Q_{14}$ | H | COOMe | Me | OMe | CH |
| 980 | $Q_{14}$ | H | COOMe | OMe | OMe | CH |
| 981 | $Q_{14}$ | H | COOMe | Me | OMe | N |
| 982 | $Q_{14}$ | H | COOMe | OMe | OMe | N |
| 983 | $Q_{14}$ | H | COOEt | Me | Me | CH |
| 984 | $Q_{14}$ | H | COOEt | Me | OMe | CH |
| 985 | $Q_{14}$ | H | COOEt | OMe | OMe | CH |
| 986 | $Q_{14}$ | H | COOEt | Me | OMe | N |
| 987 | $Q_{14}$ | H | COOEt | OMe | OMe | N |
| 988 | $Q_{14}$ | Me | COOMe | Me | OMe | CH |
| 989 | $Q_{14}$ | Me | COOMe | OMe | OMe | CH |
| 990 | $Q_{14}$ | Me | COOMe | Me | OMe | N |
| 991 | $Q_{14}$ | Me | COOEt | Me | OMe | CH |
| 992 | $Q_{14}$ | Me | COOEt | OMe | OMe | CH |
| 993 | $Q_{14}$ | Me | COOEt | Me | OMe | N |
| 994 | $Q_{14}$ | H | CN | Me | OMe | CH |
| 995 | $Q_{14}$ | H | CN | OMe | OMe | CH |
| 996 | $Q_{14}$ | H | CN | Me | OMe | N |
| 997 | $Q_{14}$ | H | H | Me | OMe | CH |
| 998 | $Q_{14}$ | H | H | OMe | OMe | CH |
| 999 | $Q_{14}$ | H | H | Me | OMe | N |
| 1000 | Me | H | $Q_{14}$ | Me | Me | CH |
| 1001 | Me | H | $Q_{14}$ | Me | OMe | CH |
| 1002 | Me | H | $Q_{14}$ | OMe | OMe | CH |
| 1003 | Me | H | $Q_{14}$ | Me | OMe | N |
| 1004 | Me | H | $Q_{14}$ | OMe | OMe | N |
| 1005 | $Q_{15}$ | H | COOMe | Me | Me | CH |
| 1006 | $Q_{15}$ | H | COOMe | Me | OMe | CH |
| 1007 | $Q_{15}$ | H | COOMe | OMe | OMe | CH |
| 1008 | $Q_{15}$ | H | COOMe | Me | OMe | N |
| 1009 | $Q_{15}$ | H | COOMe | OMe | OMe | N |
| 1010 | $Q_{15}$ | H | COOEt | Me | Me | CH |
| 1011 | $Q_{15}$ | H | COOEt | Me | OMe | CH |
| 1012 | $Q_{15}$ | H | COOEt | OMe | OMe | CH |
| 1013 | $Q_{15}$ | H | COOEt | Me | OMe | N |
| 1014 | $Q_{15}$ | H | COOEt | OMe | OMe | N |
| 1015 | $Q_{15}$ | Me | COOMe | Me | OMe | CH |
| 1016 | $Q_{15}$ | Me | COOMe | OMe | OMe | CH |
| 1017 | $Q_{15}$ | Me | COOMe | Me | OMe | N |
| 1018 | $Q_{15}$ | Me | COOEt | Me | OMe | CH |
| 1019 | $Q_{15}$ | Me | COOEt | OMe | OMe | CH |
| 1020 | $Q_{15}$ | Me | COOEt | Me | OMe | N |
| 1021 | $Q_{15}$ | H | CN | Me | OMe | CH |
| 1022 | $Q_{15}$ | H | CN | OMe | OMe | CH |
| 1023 | $Q_{15}$ | H | CN | Me | OMe | N |
| 1024 | $Q_{15}$ | H | H | Me | OMe | CH |
| 1025 | $Q_{15}$ | H | H | OMe | OMe | CH |
| 1026 | $Q_{15}$ | H | H | Me | OMe | N |
| 1027 | Me | H | $Q_{15}$ | Me | Me | CH |
| 1028 | Me | H | $Q_{15}$ | Me | OMe | CH |
| 1029 | Me | H | $Q_{15}$ | OMe | OMe | CH |

-continued

| | | | | | | |
|---|---|---|---|---|---|---|
| 1030 | Me | H | $Q_{15}$ | Me | OMe | N |
| 1031 | Me | H | $Q_{15}$ | OMe | OMe | N |
| 1032 | $Q_{16}$ | H | COOMe | Me | Me | CH |
| 1033 | $Q_{16}$ | H | COOMe | Me | OMe | CH |
| 1034 | $Q_{16}$ | H | COOMe | OMe | OMe | CH |
| 1035 | $Q_{16}$ | H | COOMe | Me | OMe | N |
| 1036 | $Q_{16}$ | H | COOMe | OMe | OMe | N |
| 1037 | $Q_{16}$ | H | COOEt | Me | Me | CH |
| 1038 | $Q_{16}$ | H | COOEt | Me | OMe | CH |
| 1039 | $Q_{16}$ | H | COOEt | OMe | OMe | CH |
| 1040 | $Q_{16}$ | H | COOEt | Me | OMe | N |
| 1041 | $Q_{16}$ | H | COOEt | OMe | OMe | N |
| 1042 | $Q_{16}$ | Me | COOMe | Me | OMe | CH |
| 1043 | $Q_{16}$ | Me | COOMe | OMe | OMe | CH |
| 1044 | $Q_{16}$ | Me | COOMe | Me | OMe | N |
| 1045 | $Q_{16}$ | Me | COOEt | Me | OMe | CH |
| 1046 | $Q_{16}$ | Me | COOEt | OMe | OMe | CH |
| 1047 | $Q_{16}$ | Me | COOEt | Me | OMe | N |
| 1048 | $Q_{16}$ | H | CN | Me | OMe | CH |
| 1049 | $Q_{16}$ | H | CN | OMe | OMe | CH |
| 1050 | $Q_{16}$ | H | CN | Me | OMe | N |
| 1051 | $Q_{16}$ | H | H | Me | OMe | CH |
| 1052 | $Q_{16}$ | H | H | OMe | OMe | CH |
| 1053 | $Q_{16}$ | H | H | Me | OMe | N |
| 1054 | Me | H | $Q_{16}$ | Me | Me | CH |
| 1055 | Me | H | $Q_{16}$ | Me | OMe | CH |
| 1056 | Me | H | $Q_{16}$ | OMe | OMe | CH |
| 1057 | Me | H | $Q_{16}$ | Me | OMe | N |
| 1058 | Me | H | $Q_{16}$ | OMe | OMe | N |
| 1059 | $Q_{17}$ | H | COOMe | Me | OMe | CH |
| 1060 | $Q_{17}$ | H | COOMe | OMe | OMe | CH |
| 1061 | $Q_{17}$ | H | COOEt | Me | OMe | CH |
| 1062 | $Q_{17}$ | H | COOEt | OMe | OMe | CH |
| 1063 | $Q_{17}$ | Me | COOMe | Me | OMe | CH |
| 1064 | $Q_{17}$ | Me | COOMe | OMe | OMe | CH |
| 1065 | $Q_{17}$ | Me | COOEt | Me | OMe | CH |
| 1066 | $Q_{17}$ | Me | COOEt | OMe | OMe | CH |
| 1067 | $Q_{17}$ | H | H | Me | OMe | CH |
| 1068 | $Q_{17}$ | H | H | OMe | OMe | CH |
| 1069 | Me | H | $Q_{17}$ | Me | OMe | CH |
| 1070 | Me | H | $Q_{17}$ | OMe | OMe | CH |
| 1071 | $Q_{18}$ | H | COOMe | Me | Me | CH |
| 1072 | $Q_{18}$ | H | COOMe | Me | OMe | CH |
| 1073 | $Q_{18}$ | H | COOMe | OMe | OMe | CH |
| 1074 | $Q_{18}$ | H | COOMe | Me | OMe | N |
| 1075 | $Q_{18}$ | H | COOMe | OMe | OMe | N |
| 1076 | $Q_{18}$ | H | COOEt | Me | Me | CH |
| 1077 | $Q_{18}$ | H | COOEt | Me | OMe | CH |
| 1078 | $Q_{18}$ | H | COOEt | OMe | OMe | CH |
| 1079 | $Q_{18}$ | H | COOEt | Me | OMe | N |
| 1080 | $Q_{18}$ | H | COOEt | OMe | OMe | N |
| 1081 | $Q_{18}$ | Me | COOMe | Me | OMe | CH |
| 1082 | $Q_{18}$ | Me | COOMe | OMe | OMe | CH |
| 1083 | $Q_{18}$ | Me | COOMe | Me | OMe | N |
| 1084 | $Q_{18}$ | Me | COOEt | Me | OMe | CH |
| 1085 | $Q_{18}$ | Me | COOEt | OMe | OMe | CH |
| 1086 | $Q_{18}$ | Me | COOEt | Me | OMe | N |
| 1087 | $Q_{18}$ | H | CN | Me | OMe | CH |
| 1088 | $Q_{18}$ | H | CN | OMe | OMe | CH |
| 1089 | $Q_{18}$ | H | CN | Me | OMe | N |
| 1090 | $Q_{18}$ | H | H | Me | OMe | CH |
| 1091 | $Q_{18}$ | H | H | OMe | OMe | CH |
| 1092 | $Q_{18}$ | H | H | Me | OMe | N |
| 1093 | Me | H | $Q_{18}$ | Me | Me | CH |
| 1094 | Me | H | $Q_{18}$ | Me | OMe | CH |
| 1095 | Me | H | $Q_{18}$ | OMe | OMe | CH |
| 1096 | Me | H | $Q_{18}$ | Me | OMe | N |
| 1097 | Me | H | $Q_{18}$ | OMe | OMe | N |
| 1098 | $Q_{19}$ | H | COOMe | Me | Me | CH |
| 1099 | $Q_{19}$ | H | COOMe | Me | OMe | CH |
| 1100 | $Q_{19}$ | H | COOMe | OMe | OMe | CH |
| 1101 | $Q_{19}$ | H | COOMe | Me | OMe | N |
| 1102 | $Q_{19}$ | H | COOMe | OMe | OMe | N |
| 1103 | $Q_{19}$ | H | COOEt | Me | Me | CH |
| 1104 | $Q_{19}$ | H | COOEt | Me | OMe | CH |
| 1105 | $Q_{19}$ | H | COOEt | OMe | OMe | CH |
| 1106 | $Q_{19}$ | H | COOEt | Me | OMe | N |
| 1107 | $Q_{19}$ | H | COOEt | OMe | OMe | N |
| 1108 | $Q_{19}$ | Me | COOMe | Me | OMe | CH |
| 1109 | $Q_{19}$ | Me | COOMe | OMe | OMe | CH |
| 1110 | $Q_{19}$ | Me | COOMe | Me | OMe | N |
| 1111 | $Q_{19}$ | Me | COOEt | Me | OMe | CH |

-continued

| | | | | | | |
|---|---|---|---|---|---|---|
| 1112 | $Q_{19}$ | Me | COOEt | OMe | OMe | CH |
| 1113 | $Q_{19}$ | Me | COOEt | Me | OMe | N |
| 1114 | $Q_{19}$ | H | CN | Me | OMe | CH |
| 1115 | $Q_{19}$ | H | CN | OMe | OMe | CH |
| 1116 | $Q_{19}$ | H | CN | Me | OMe | N |
| 1117 | $Q_{19}$ | H | H | Me | OMe | CH |
| 1118 | $Q_{19}$ | H | H | OMe | OMe | CH |
| 1119 | $Q_{19}$ | H | H | Me | OMe | N |
| 1120 | Me | H | $Q_{19}$ | Me | Me | CH |
| 1121 | Me | H | $Q_{19}$ | Me | OMe | CH |
| 1122 | Me | H | $Q_{19}$ | OMe | OMe | CH |
| 1123 | Me | H | $Q_{19}$ | Me | OMe | N |
| 1124 | Me | H | $Q_{19}$ | OMe | OMe | N |
| 1125 | $Q_{20}$ | H | COOMe | Me | Me | CH |
| 1126 | $Q_{20}$ | H | COOMe | Me | OMe | CH |
| 1127 | $Q_{20}$ | H | COOMe | OMe | OMe | CH |
| 1128 | $Q_{20}$ | H | COOMe | Me | OMe | N |
| 1129 | $Q_{20}$ | H | COOMe | OMe | OMe | N |
| 1130 | $Q_{20}$ | H | COOEt | Me | Me | CH |
| 1131 | $Q_{20}$ | H | COOEt | Me | OMe | CH |
| 1132 | $Q_{20}$ | H | COOEt | OMe | OMe | CH |
| 1133 | $Q_{20}$ | H | COOEt | Me | OMe | N |
| 1134 | $Q_{20}$ | H | COOEt | OMe | OMe | N |
| 1135 | $Q_{20}$ | Me | COOMe | Me | OMe | CH |
| 1136 | $Q_{20}$ | Me | COOMe | OMe | OMe | CH |
| 1137 | $Q_{20}$ | Me | COOMe | Me | OMe | N |
| 1138 | $Q_{20}$ | Me | COOEt | Me | OMe | CH |
| 1139 | $Q_{20}$ | Me | COOEt | OMe | OMe | CH |
| 1140 | $Q_{20}$ | Me | COOEt | Me | OMe | N |
| 1141 | $Q_{20}$ | H | CN | Me | OMe | CH |
| 1142 | $Q_{20}$ | H | CN | OMe | OMe | CH |
| 1143 | $Q_{20}$ | H | CN | Me | OMe | N |
| 1144 | $Q_{20}$ | H | H | Me | OMe | CH |
| 1145 | $Q_{20}$ | H | H | OMe | OMe | CH |
| 1146 | $Q_{20}$ | H | H | Me | OMe | N |
| 1147 | Me | H | $Q_{20}$ | Me | Me | CH |
| 1148 | Me | H | $Q_{20}$ | Me | OMe | CH |
| 1149 | Me | H | $Q_{20}$ | OMe | OMe | CH |
| 1150 | Me | H | $Q_{20}$ | Me | OMe | N |
| 1151 | Me | H | $Q_{20}$ | OMe | OMe | N |
| 1152 | $Q_{21}$ | H | COOMe | Me | Me | CH |
| 1153 | $Q_{21}$ | H | COOMe | Me | OMe | CH |
| 1154 | $Q_{21}$ | H | COOMe | OMe | OMe | CH |
| 1155 | $Q_{21}$ | H | COOMe | Me | OMe | N |
| 1156 | $Q_{21}$ | H | COOMe | OMe | OMe | N |
| 1157 | $Q_{21}$ | H | COOEt | Me | Me | CH |
| 1158 | $Q_{21}$ | H | COOEt | Me | OMe | CH |
| 1159 | $Q_{21}$ | H | COOEt | OMe | OMe | CH |
| 1160 | $Q_{21}$ | H | COOEt | Me | OMe | N |
| 1161 | $Q_{21}$ | H | COOEt | OMe | OMe | N |
| 1162 | $Q_{21}$ | Me | COOMe | Me | OMe | CH |
| 1163 | $Q_{21}$ | Me | COOMe | OMe | OMe | CH |
| 1164 | $Q_{21}$ | Me | COOMe | Me | OMe | N |
| 1165 | $Q_{21}$ | Me | COOEt | Me | OMe | CH |
| 1166 | $Q_{21}$ | Me | COOEt | OMe | OMe | CH |
| 1167 | $Q_{21}$ | Me | COOEt | Me | OMe | N |
| 1168 | $Q_{21}$ | H | CN | Me | OMe | CH |
| 1169 | $Q_{21}$ | H | CN | OMe | OMe | CH |
| 1170 | $Q_{21}$ | H | CN | Me | OMe | N |
| 1171 | $Q_{21}$ | H | H | Me | OMe | CH |
| 1172 | $Q_{21}$ | H | H | OMe | OMe | CH |
| 1173 | $Q_{21}$ | H | H | Me | OMe | N |
| 1174 | Me | H | $Q_{21}$ | Me | Me | CH |
| 1175 | Me | H | $Q_{21}$ | Me | OMe | CH |
| 1176 | Me | H | $Q_{21}$ | OMe | OMe | CH |
| 1177 | Me | H | $Q_{21}$ | Me | OMe | N |
| 1178 | Me | H | $Q_{21}$ | OMe | OMe | N |
| 1179 | $Q_{22}$ | H | COOMe | Me | Me | CH |
| 1180 | $Q_{22}$ | H | COOMe | Me | OMe | CH |
| 1181 | $Q_{22}$ | H | COOMe | OMe | OMe | CH |
| 1182 | $Q_{22}$ | H | COOMe | Me | OMe | N |
| 1183 | $Q_{22}$ | H | COOMe | OMe | OMe | N |
| 1184 | $Q_{22}$ | H | COOEt | Me | Me | CH |
| 1185 | $Q_{22}$ | H | COOEt | Me | OMe | CH |
| 1186 | $Q_{22}$ | H | COOEt | OMe | OMe | CH |
| 1187 | $Q_{22}$ | H | COOEt | Me | OMe | N |
| 1188 | $Q_{22}$ | H | COOEt | OMe | OMe | N |
| 1189 | $Q_{22}$ | Me | COOMe | Me | OMe | CH |
| 1190 | $Q_{22}$ | Me | COOMe | OMe | OMe | CH |
| 1191 | $Q_{22}$ | Me | COOMe | Me | OMe | N |
| 1192 | $Q_{22}$ | Me | COOEt | Me | OMe | CH |
| 1193 | $Q_{22}$ | Me | COOEt | OMe | OMe | CH |

-continued

| | | | | | | |
|---|---|---|---|---|---|---|
| 1194 | $Q_{22}$ | Me | COOEt | Me | OMe | N |
| 1195 | $Q_{22}$ | H | CN | Me | OMe | CH |
| 1196 | $Q_{22}$ | H | CN | OMe | OMe | CH |
| 1197 | $Q_{22}$ | H | CN | Me | OMe | N |
| 1198 | $Q_{22}$ | H | H | Me | OMe | CH |
| 1199 | $Q_{22}$ | H | H | OMe | OMe | CH |
| 1200 | $Q_{22}$ | H | H | Me | OMe | N |
| 1201 | Me | H | $Q_{22}$ | Me | Me | CH |
| 1202 | Me | H | $Q_{22}$ | Me | OMe | CH |
| 1203 | Me | H | $Q_{22}$ | OMe | OMe | CH |
| 1204 | Me | H | $Q_{22}$ | Me | OMe | N |
| 1205 | Me | H | $Q_{22}$ | OMe | OMe | N |
| 1206 | $Q_{23}$ | H | COOMe | Me | OMe | CH |
| 1207 | $Q_{23}$ | H | COOMe | OMe | OMe | CH |
| 1208 | $Q_{23}$ | H | COOEt | Me | OMe | CH |
| 1209 | $Q_{23}$ | H | COOEt | OMe | OMe | CH |
| 1210 | $Q_{23}$ | Me | COOMe | Me | OMe | CH |
| 1211 | $Q_{23}$ | Me | COOMe | OMe | OMe | CH |
| 1212 | $Q_{23}$ | Me | COOEt | Me | OMe | CH |
| 1213 | $Q_{23}$ | Me | COOEt | OMe | OMe | CH |
| 1214 | $Q_{23}$ | H | H | Me | OMe | CH |
| 1215 | $Q_{23}$ | H | H | OMe | OMe | CH |
| 1216 | Me | H | $Q_{23}$ | Me | OMe | CH |
| 1217 | Me | H | $Q_{23}$ | OMe | OMe | CH |
| 1218 | $Q_{24}$ | H | COOMe | Me | Me | CH |
| 1219 | $Q_{24}$ | H | COOMe | Me | OMe | CH |
| 1220 | $Q_{24}$ | H | COOMe | OMe | OMe | CH |
| 1221 | $Q_{24}$ | H | COOMe | Me | OMe | N |
| 1222 | $Q_{24}$ | H | COOMe | OMe | OMe | N |
| 1223 | $Q_{24}$ | H | COOEt | Me | Me | CH |
| 1224 | $Q_{24}$ | H | COOEt | Me | OMe | CH |
| 1225 | $Q_{24}$ | H | COOEt | OMe | OMe | CH |
| 1226 | $Q_{24}$ | H | COOEt | Me | OMe | N |
| 1227 | $Q_{24}$ | H | COOEt | OMe | OMe | N |
| 1228 | $Q_{24}$ | Me | COOMe | Me | OMe | CH |
| 1229 | $Q_{24}$ | Me | COOMe | OMe | OMe | CH |
| 1230 | $Q_{24}$ | Me | COOMe | Me | OMe | N |
| 1231 | $Q_{24}$ | Me | COOEt | Me | OMe | CH |
| 1232 | $Q_{24}$ | Me | COOEt | OMe | OMe | CH |
| 1233 | $Q_{24}$ | Me | COOEt | Me | OMe | N |
| 1234 | $Q_{24}$ | H | CN | Me | OMe | CH |
| 1235 | $Q_{24}$ | H | CN | OMe | OMe | CH |
| 1236 | $Q_{24}$ | H | CN | Me | OMe | N |
| 1237 | $Q_{24}$ | H | H | Me | OMe | CH |
| 1238 | $Q_{24}$ | H | H | OMe | OMe | CH |
| 1239 | $Q_{24}$ | H | H | Me | OMe | N |
| 1240 | Me | H | $Q_{24}$ | Me | Me | CH |
| 1241 | Me | H | $Q_{24}$ | Me | OMe | CH |
| 1242 | Me | H | $Q_{24}$ | OMe | OMe | CH |
| 1243 | Me | H | $Q_{24}$ | Me | OMe | N |
| 1244 | Me | H | $Q_{24}$ | OMe | OMe | N |
| 1245 | $Q_{25}$ | H | COOMe | Me | Me | CH |
| 1246 | $Q_{25}$ | H | COOMe | Me | OMe | CH |
| 1247 | $Q_{25}$ | H | COOMe | OMe | OMe | CH |
| 1248 | $Q_{25}$ | H | COOMe | Me | OMe | N |
| 1249 | $Q_{25}$ | H | COOMe | OMe | OMe | N |
| 1250 | $Q_{25}$ | H | COOEt | Me | Me | CH |
| 1251 | $Q_{25}$ | H | COOEt | Me | OMe | CH |
| 1252 | $Q_{25}$ | H | COOEt | OMe | OMe | CH |
| 1253 | $Q_{25}$ | H | COOEt | Me | OMe | N |
| 1254 | $Q_{25}$ | H | COOEt | OMe | OMe | N |
| 1255 | $Q_{25}$ | Me | COOMe | Me | OMe | CH |
| 1256 | $Q_{25}$ | Me | COOMe | OMe | OMe | CH |
| 1257 | $Q_{25}$ | Me | COOMe | Me | OMe | N |
| 1258 | $Q_{25}$ | Me | COOEt | Me | OMe | CH |
| 1259 | $Q_{25}$ | Me | COOEt | OMe | OMe | CH |
| 1260 | $Q_{25}$ | Me | COOEt | Me | OMe | N |
| 1261 | $Q_{25}$ | H | CN | Me | OMe | CH |
| 1262 | $Q_{25}$ | H | CN | OMe | OMe | CH |
| 1263 | $Q_{25}$ | H | CN | Me | OMe | N |
| 1264 | $Q_{25}$ | H | H | Me | OMe | CH |
| 1265 | $Q_{25}$ | H | H | OMe | OMe | CH |
| 1266 | $Q_{25}$ | H | H | Me | OMe | N |
| 1267 | Me | H | $Q_{25}$ | Me | Me | CH |
| 1268 | Me | H | $Q_{25}$ | Me | OMe | CH |
| 1269 | Me | H | $Q_{25}$ | OMe | OMe | CH |
| 1270 | Me | H | $Q_{25}$ | Me | OMe | N |
| 1271 | Me | H | $Q_{25}$ | OMe | OMe | N |
| 1272 | $Q_{26}$ | H | COOMe | Me | OMe | CH |
| 1273 | $Q_{26}$ | H | COOMe | OMe | OMe | CH |
| 1274 | $Q_{26}$ | H | COOEt | Me | OMe | CH |
| 1275 | $Q_{26}$ | H | COOEt | OMe | OMe | CH |

-continued

| | | | | | | |
|---|---|---|---|---|---|---|
| 1276 | $Q_{26}$ | Me | COOMe | Me | OMe | CH |
| 1277 | $Q_{26}$ | Me | COOMe | OMe | OMe | CH |
| 1278 | $Q_{26}$ | Me | COOEt | Me | OMe | CH |
| 1279 | $Q_{26}$ | Me | COOEt | OMe | OMe | CH |
| 1280 | $Q_{26}$ | H | H | Me | OMe | CH |
| 1281 | $Q_{26}$ | H | H | OMe | OMe | CH |
| 1282 | Me | H | $Q_{26}$ | Me | OMe | CH |
| 1283 | Me | H | $Q_{26}$ | OMe | OMe | CH |
| 1284 | $Q_{27}$ | H | COOMe | Me | OMe | CH |
| 1285 | $Q_{27}$ | H | COOMe | OMe | OMe | CH |
| 1286 | $Q_{27}$ | H | COOEt | Me | OMe | CH |
| 1287 | $Q_{27}$ | H | COOEt | OMe | OMe | CH |
| 1288 | $Q_{27}$ | Me | COOMe | Me | OMe | CH |
| 1289 | $Q_{27}$ | Me | COOMe | OMe | OMe | CH |
| 1290 | $Q_{27}$ | Me | COOEt | Me | OMe | CH |
| 1291 | $Q_{27}$ | Me | COOEt | OMe | OMe | CH |
| 1292 | $Q_{27}$ | H | H | Me | OMe | CH |
| 1293 | $Q_{27}$ | H | H | OMe | OMe | CH |
| 1294 | Me | H | $Q_{27}$ | Me | OMe | CH |
| 1295 | Me | H | $Q_{27}$ | OMe | OMe | CH |
| 1296 | $Q_{28}$ | H | COOMe | Me | Me | CH |
| 1297 | $Q_{28}$ | H | COOMe | Me | OMe | CH |
| 1298 | $Q_{28}$ | H | COOMe | OMe | OMe | CH |
| 1299 | $Q_{28}$ | H | COOMe | Me | OMe | N |
| 1300 | $Q_{28}$ | H | COOMe | OMe | OMe | N |
| 1301 | $Q_{28}$ | H | COOEt | Me | Me | CH |
| 1302 | $Q_{28}$ | H | COOEt | Me | OMe | CH |
| 1303 | $Q_{28}$ | H | COOEt | OMe | OMe | CH |
| 1304 | $Q_{28}$ | H | COOEt | Me | OMe | N |
| 1305 | $Q_{28}$ | H | COOEt | OMe | OMe | N |
| 1306 | $Q_{28}$ | Me | COOMe | Me | OMe | CH |
| 1307 | $Q_{28}$ | Me | COOMe | OMe | OMe | CH |
| 1308 | $Q_{28}$ | Me | COOMe | Me | OMe | N |
| 1309 | $Q_{28}$ | Me | COOEt | Me | OMe | CH |
| 1310 | $Q_{28}$ | Me | COOEt | OMe | OMe | CH |
| 1311 | $Q_{28}$ | Me | COOEt | Me | OMe | N |
| 1312 | $Q_{28}$ | H | CN | Me | OMe | CH |
| 1313 | $Q_{28}$ | H | CN | OMe | OMe | CH |
| 1314 | $Q_{28}$ | H | CN | Me | OMe | N |
| 1315 | $Q_{28}$ | H | H | Me | OMe | CH |
| 1316 | $Q_{28}$ | H | H | OMe | OMe | CH |
| 1317 | $Q_{28}$ | H | H | Me | OMe | N |
| 1318 | Me | H | $Q_{28}$ | Me | Me | CH |
| 1319 | Me | H | $Q_{28}$ | Me | OMe | CH |
| 1320 | Me | H | $Q_{28}$ | OMe | OMe | CH |
| 1321 | Me | H | $Q_{28}$ | Me | OMe | N |
| 1322 | Me | H | $Q_{28}$ | OMe | OMe | N |
| 1323 | $Q_{29}$ | H | COOMe | Me | OMe | CH |
| 1324 | $Q_{29}$ | H | COOMe | OMe | OMe | CH |
| 1325 | $Q_{29}$ | H | COOEt | Me | OMe | CH |
| 1326 | $Q_{29}$ | H | COOEt | OMe | OMe | CH |
| 1327 | $Q_{29}$ | Me | COOMe | Me | OMe | CH |
| 1328 | $Q_{29}$ | Me | COOMe | OMe | OMe | CH |
| 1329 | $Q_{29}$ | Me | COOEt | Me | OMe | CH |
| 1330 | $Q_{29}$ | Me | COOEt | OMe | OMe | CH |
| 1331 | $Q_{29}$ | H | H | Me | OMe | CH |
| 1332 | $Q_{29}$ | H | H | OMe | OMe | CH |
| 1333 | Me | H | $Q_{29}$ | Me | OMe | CH |
| 1334 | Me | H | $Q_{29}$ | OMe | OMe | CH |
| 1335 | $Q_{30}$ | H | COOMe | Me | OMe | CH |
| 1336 | $Q_{30}$ | H | COOMe | OMe | OMe | CH |
| 1337 | $Q_{30}$ | H | COOEt | Me | OMe | CH |
| 1338 | $Q_{30}$ | H | COOEt | OMe | OMe | CH |
| 1339 | $Q_{30}$ | Me | COOMe | Me | OMe | CH |
| 1340 | $Q_{30}$ | Me | COOMe | OMe | OMe | CH |
| 1341 | $Q_{30}$ | Me | COOEt | Me | OMe | CH |
| 1342 | $Q_{30}$ | Me | COOEt | OMe | OMe | CH |
| 1343 | $Q_{30}$ | H | H | Me | OMe | CH |
| 1344 | $Q_{30}$ | H | H | OMe | OMe | CH |
| 1345 | Me | H | $Q_{30}$ | Me | OMe | CH |
| 1346 | Me | H | $Q_{30}$ | OMe | OMe | CH |
| 1347 | $Q_{31}$ | H | COOMe | Me | OMe | CH |
| 1348 | $Q_{31}$ | H | COOMe | OMe | OMe | CH |
| 1349 | $Q_{31}$ | H | COOEt | Me | OMe | CH |
| 1350 | $Q_{31}$ | H | COOEt | OMe | OMe | CH |
| 1351 | $Q_{31}$ | Me | COOMe | Me | OMe | CH |
| 1352 | $Q_{31}$ | Me | COOMe | OMe | OMe | CH |
| 1353 | $Q_{31}$ | Me | COOEt | Me | OMe | CH |
| 1354 | $Q_{31}$ | Me | COOEt | OMe | OMe | CH |
| 1355 | $Q_{31}$ | H | H | Me | OMe | CH |
| 1356 | $Q_{31}$ | H | H | OMe | OMe | CH |
| 1357 | Me | H | $Q_{31}$ | Me | OMe | CH |

-continued

| | | | | | | |
|---|---|---|---|---|---|---|
| 1358 | Me | H | $Q_{31}$ | OMe | OMe | CH |
| 1359 | $Q_{32}$ | H | COOMe | Me | Me | CH |
| 1360 | $Q_{32}$ | H | COOMe | Me | OMe | CH |
| 1361 | $Q_{32}$ | H | COOMe | OMe | OMe | CH |
| 1362 | $Q_{32}$ | H | COOMe | Me | Me | N |
| 1363 | $Q_{32}$ | H | COOMe | Me | OMe | N |
| 1364 | $Q_{32}$ | H | COOMe | OMe | OMe | N |
| 1365 | $Q_{32}$ | H | COOMe | Me | $OCHF_2$ | CH |
| 1366 | $Q_{32}$ | H | COOMe | Cl | OMe | CH |
| 1367 | $Q_{32}$ | H | COOEt | Me | Me | CH |
| 1368 | $Q_{32}$ | H | COOEt | Me | OMe | CH |
| 1369 | $Q_{32}$ | H | COOEt | OMe | OMe | CH |
| 1370 | $Q_{32}$ | H | COOEt | Me | Me | N |
| 1371 | $Q_{32}$ | H | COOEt | Me | OMe | N |
| 1372 | $Q_{32}$ | H | COOEt | OMe | OMe | N |
| 1373 | $Q_{32}$ | H | COOEt | Me | $OCHF_2$ | CH |
| 1374 | $Q_{32}$ | H | COOEt | Cl | OMe | CH |
| 1375 | $Q_{32}$ | H | COOPr—n | Me | OMe | CH |
| 1376 | $Q_{32}$ | H | COOPr—n | OMe | OMe | CH |
| 1377 | $Q_{32}$ | H | COOPr—n | Me | OMe | N |
| 1378 | $Q_{32}$ | H | COOPr—i | Me | OMe | CH |
| 1379 | $Q_{32}$ | H | COOPr—i | OMe | OMe | CH |
| 1380 | $Q_{32}$ | H | COOPr—i | Me | OMe | N |
| 1381 | $Q_{32}$ | H | $COOCH_2CH_2Cl$ | Me | OMe | CH |
| 1382 | $Q_{32}$ | H | $COOCH_2CH_2Cl$ | OMe | OMe | CH |
| 1383 | $Q_{32}$ | H | $COOCH_2CH_2Cl$ | Me | OMe | N |
| 1384 | $Q_{32}$ | H | $COOCH_2CH{=}CH_2$ | Me | OMe | CH |
| 1385 | $Q_{32}$ | H | $COOCH_2CH{=}CH_2$ | OMe | OMe | CH |
| 1386 | $Q_{32}$ | H | $COOCH_2CH{=}CH_2$ | Me | OMe | N |
| 1387 | $Q_{32}$ | H | $COOCH_2C{\equiv}CH$ | Me | OMe | CH |
| 1388 | $Q_{32}$ | H | $COOCH_2C{\equiv}CH$ | OMe | OMe | CH |
| 1389 | $Q_{32}$ | H | $COOCH_2C{\equiv}CH$ | Me | OMe | N |
| 1390 | $Q_{32}$ | Me | COOMe | Me | Me | CH |
| 1391 | $Q_{32}$ | Me | COOMe | Me | OMe | CH |
| 1392 | $Q_{32}$ | Me | COOMe | OMe | OMe | CH |
| 1393 | $Q_{32}$ | Me | COOMe | Me | OMe | N |
| 1394 | $Q_{32}$ | Me | COOMe | OMe | OMe | N |
| 1395 | $Q_{32}$ | Me | COOEt | Me | Me | CH |
| 1396 | $Q_{32}$ | Me | COOEt | Me | OMe | CH |
| 1397 | $Q_{32}$ | Me | COOEt | OMe | OMe | CH |
| 1398 | $Q_{32}$ | Me | COOEt | Me | OMe | N |
| 1399 | $Q_{32}$ | Me | COOEt | OMe | OMe | N |
| 1400 | $Q_{32}$ | Cl | COOMe | Me | OMe | CH |
| 1401 | $Q_{32}$ | Cl | COOMe | OMe | OMe | CH |
| 1402 | $Q_{32}$ | Cl | COOMe | Me | OMe | N |
| 1403 | $Q_{32}$ | Cl | COOEt | Me | OMe | CH |
| 1404 | $Q_{32}$ | Cl | COOEt | OMe | OMe | CH |
| 1405 | $Q_{32}$ | Cl | COOEt | Me | OMe | N |
| 1406 | $Q_{32}$ | OMe | COOMe | Me | OMe | CH |
| 1407 | $Q_{32}$ | OMe | COOMe | OMe | OMe | CH |
| 1408 | $Q_{32}$ | OMe | COOMe | Me | OMe | N |
| 1409 | $Q_{32}$ | OMe | COOEt | Me | OMe | CH |
| 1410 | $Q_{32}$ | OMe | COOEt | OMe | OMe | CH |
| 1411 | $Q_{32}$ | OMe | COOEt | Me | OMe | N |
| 1412 | $Q_{32}$ | H | Cl | Me | OMe | CH |
| 1413 | $Q_{32}$ | H | Cl | OMe | OMe | CH |
| 1414 | $Q_{32}$ | H | Cl | Me | OMe | N |
| 1415 | $Q_{32}$ | H | $NO_2$ | Me | OMe | CH |
| 1416 | $Q_{32}$ | H | $NO_2$ | OMe | OMe | CH |
| 1417 | $Q_{32}$ | H | $NO_2$ | Me | OMe | N |
| 1418 | $Q_{32}$ | H | $SO_2NMe_2$ | Me | OMe | CH |
| 1419 | $Q_{32}$ | H | $SO_2NMe_2$ | OMe | OMe | CH |
| 1420 | $Q_{32}$ | H | $SO_2NMe_2$ | Me | OMe | N |
| 1421 | $Q_{32}$ | H | CN | Me | OMe | CH |
| 1422 | $Q_{32}$ | H | CN | OMe | OMe | CH |
| 1423 | $Q_{32}$ | H | CN | Me | OMe | N |
| 1424 | $Q_{32}$ | Me | CN | Me | OMe | CH |
| 1425 | $Q_{32}$ | Me | CN | OMe | OMe | CH |
| 1426 | $Q_{32}$ | Me | CN | Me | OMe | N |
| 1427 | $Q_{32}$ | H | Me | Me | OMe | CH |
| 1428 | $Q_{32}$ | H | Me | OMe | OMe | CH |
| 1429 | $Q_{32}$ | H | Me | Me | OMe | N |
| 1430 | $Q_{32}$ | H | Et | Me | OMe | CH |
| 1431 | $Q_{32}$ | H | Et | OMe | OMe | CH |
| 1432 | $Q_{32}$ | H | Et | Me | OMe | N |
| 1433 | $Q_{32}$ | H | H | Me | OMe | CH |
| 1434 | $Q_{32}$ | H | H | OMe | OMe | CH |
| 1435 | $Q_{32}$ | H | H | Me | OMe | N |
| 1436 | $Q_{32}$ | H | COPh | Me | OMe | CH |
| 1437 | $Q_{32}$ | H | COPh | OMe | OMe | CH |
| 1438 | $Q_{32}$ | H | COPh | Me | OMe | N |
| 1439 | Me | $Q_{32}$ | COOMe | Me | OMe | CH |

-continued

| | | | | | | |
|---|---|---|---|---|---|---|
| 1440 | Me | $Q_{32}$ | COOMe | OMe | OMe | CH |
| 1441 | Me | $Q_{32}$ | COOMe | Me | OMe | N |
| 1442 | H | H | $Q_{32}$ | Me | OMe | CH |
| 1443 | H | H | $Q_{32}$ | OMe | OMe | CH |
| 1444 | H | H | $Q_{32}$ | Me | OMe | N |
| 1445 | Me | H | $Q_{32}$ | Me | Me | CH |
| 1446 | Me | H | $Q_{32}$ | Me | OMe | CH |
| 1447 | Me | H | $Q_{32}$ | OMe | OMe | CH |
| 1448 | Me | H | $Q_{32}$ | Me | OMe | N |
| 1449 | Me | H | $Q_{32}$ | OMe | OMe | N |
| 1450 | Me | Me | $Q_{32}$ | Me | OMe | CH |
| 1451 | Me | Me | $Q_{32}$ | OMe | OMe | CH |
| 1452 | Me | Me | $Q_{32}$ | Me | OMe | N |
| 1453 | $Q_{33}$ | H | COOMe | Me | Me | CH |
| 1454 | $Q_{33}$ | H | COOMe | Me | OMe | CH |
| 1455 | $Q_{33}$ | H | COOMe | OMe | OMe | CH |
| 1456 | $Q_{33}$ | H | COOMe | Me | OMe | N |
| 1457 | $Q_{33}$ | H | COOMe | OMe | OMe | N |
| 1458 | $Q_{33}$ | H | COOEt | Me | Me | CH |
| 1459 | $Q_{33}$ | H | COOEt | Me | OMe | CH |
| 1460 | $Q_{33}$ | H | COOEt | OMe | OMe | CH |
| 1461 | $Q_{33}$ | H | COOEt | Me | OMe | N |
| 1462 | $Q_{33}$ | H | COOEt | OMe | OMe | N |
| 1463 | $Q_{33}$ | Me | COOMe | Me | OMe | CH |
| 1464 | $Q_{33}$ | Me | COOMe | OMe | OMe | CH |
| 1465 | $Q_{33}$ | Me | COOMe | Me | OMe | N |
| 1466 | $Q_{33}$ | Me | COOEt | Me | OMe | CH |
| 1467 | $Q_{33}$ | Me | COOEt | OMe | OMe | CH |
| 1468 | $Q_{33}$ | Me | COOEt | Me | OMe | N |
| 1469 | $Q_{33}$ | H | CN | Me | OMe | CH |
| 1470 | $Q_{33}$ | H | CN | OMe | OMe | CH |
| 1471 | $Q_{33}$ | H | CN | Me | OMe | N |
| 1472 | $Q_{33}$ | H | H | Me | OMe | CH |
| 1473 | $Q_{33}$ | H | H | OMe | OMe | CH |
| 1474 | $Q_{33}$ | H | H | Me | OMe | N |
| 1475 | Me | H | $Q_{33}$ | Me | Me | CH |
| 1476 | Me | H | $Q_{33}$ | Me | OMe | CH |
| 1477 | Me | H | $Q_{33}$ | OMe | OMe | CH |
| 1478 | Me | H | $Q_{33}$ | Me | OMe | N |
| 1479 | Me | H | $Q_{33}$ | OMe | OMe | N |
| 1480 | $Q_{34}$ | H | COOMe | Me | Me | CH |
| 1481 | $Q_{34}$ | H | COOMe | Me | OMe | CH |
| 1482 | $Q_{34}$ | H | COOMe | OMe | OMe | CH |
| 1483 | $Q_{34}$ | H | COOMe | Me | OMe | N |
| 1484 | $Q_{34}$ | H | COOMe | OMe | OMe | N |
| 1485 | $Q_{34}$ | H | COOEt | Me | Me | CH |
| 1486 | $Q_{34}$ | H | COOEt | Me | OMe | CH |
| 1487 | $Q_{34}$ | H | COOEt | OMe | OMe | CH |
| 1488 | $Q_{34}$ | H | COOEt | Me | OMe | N |
| 1489 | $Q_{34}$ | H | COOEt | OMe | OMe | N |
| 1490 | $Q_{34}$ | Me | COOMe | Me | OMe | CH |
| 1491 | $Q_{34}$ | Me | COOMe | OMe | OMe | CH |
| 1492 | $Q_{34}$ | Me | COOMe | Me | OMe | N |
| 1493 | $Q_{34}$ | Me | COOEt | Me | OMe | CH |
| 1494 | $Q_{34}$ | Me | COOEt | OMe | OMe | CH |
| 1495 | $Q_{34}$ | Me | COOEt | Me | OMe | N |
| 1496 | $Q_{34}$ | H | CN | Me | OMe | CH |
| 1497 | $Q_{34}$ | H | CN | OMe | OMe | CH |
| 1498 | $Q_{34}$ | H | CN | Me | OMe | N |
| 1499 | $Q_{34}$ | H | H | Me | OMe | CH |
| 1500 | $Q_{34}$ | H | H | OMe | OMe | CH |
| 1501 | $Q_{34}$ | H | H | Me | OMe | N |
| 1502 | Me | H | $Q_{34}$ | Me | Me | CH |
| 1503 | Me | H | $Q_{34}$ | Me | OMe | CH |
| 1504 | Me | H | $Q_{34}$ | OMe | OMe | CH |
| 1505 | Me | H | $Q_{34}$ | Me | OMe | N |
| 1506 | Me | H | $Q_{34}$ | OMe | OMe | N |
| 1507 | $Q_{35}$ | H | COOMe | Me | Me | CH |
| 1508 | $Q_{35}$ | H | COOMe | Me | OMe | CH |
| 1509 | $Q_{35}$ | H | COOMe | OMe | OMe | CH |
| 1510 | $Q_{35}$ | H | COOMe | Me | OMe | N |
| 1511 | $Q_{35}$ | H | COOMe | OMe | OMe | N |
| 1512 | $Q_{35}$ | H | COOEt | Me | Me | CH |
| 1513 | $Q_{35}$ | H | COOEt | Me | OMe | CH |
| 1514 | $Q_{35}$ | H | COOEt | OMe | OMe | CH |
| 1515 | $Q_{35}$ | H | COOEt | Me | OMe | N |
| 1516 | $Q_{35}$ | H | COOEt | OMe | OMe | N |
| 1517 | $Q_{35}$ | Me | COOMe | Me | OMe | CH |
| 1518 | $Q_{35}$ | Me | COOMe | OMe | OMe | CH |
| 1519 | $Q_{35}$ | Me | COOMe | Me | OMe | N |
| 1520 | $Q_{35}$ | Me | COOEt | Me | OMe | CH |
| 1521 | $Q_{35}$ | Me | COOEt | OMe | OMe | CH |

-continued

| | | | | | | |
|---|---|---|---|---|---|---|
| 1522 | $Q_{35}$ | Me | COOEt | Me | OMe | N |
| 1523 | $Q_{35}$ | H | CN | Me | OMe | CH |
| 1524 | $Q_{35}$ | H | CN | OMe | OMe | CH |
| 1525 | $Q_{35}$ | H | CN | Me | OMe | N |
| 1526 | $Q_{35}$ | H | H | Me | OMe | CH |
| 1527 | $Q_{35}$ | H | H | OMe | OMe | CH |
| 1528 | $Q_{35}$ | H | H | Me | OMe | N |
| 1529 | Me | H | $Q_{35}$ | Me | Me | CH |
| 1530 | Me | H | $Q_{35}$ | Me | OMe | CH |
| 1531 | Me | H | $Q_{35}$ | OMe | OMe | CH |
| 1532 | Me | H | $Q_{35}$ | Me | OMe | N |
| 1533 | Me | H | $Q_{35}$ | OMe | OMe | N |
| 1534 | $Q_{36}$ | H | COOMe | Me | OMe | CH |
| 1535 | $Q_{36}$ | H | COOMe | OMe | OMe | CH |
| 1536 | $Q_{36}$ | H | COOEt | Me | OMe | CH |
| 1537 | $Q_{36}$ | H | COOEt | OMe | OMe | CH |
| 1538 | $Q_{36}$ | Me | COOMe | Me | OMe | CH |
| 1539 | $Q_{36}$ | Me | COOMe | OMe | OMe | CH |
| 1540 | $Q_{36}$ | Me | COOEt | Me | OMe | CH |
| 1541 | $Q_{36}$ | Me | COOEt | OMe | OMe | CH |
| 1542 | $Q_{36}$ | H | H | Me | OMe | CH |
| 1543 | $Q_{36}$ | H | H | OMe | OMe | CH |
| 1544 | Me | H | $Q_{36}$ | Me | OMe | CH |
| 1545 | Me | H | $Q_{36}$ | OMe | OMe | CH |
| 1546 | $Q_{37}$ | H | COOMe | Me | Me | CH |
| 1547 | $Q_{37}$ | H | COOMe | Me | OMe | CH |
| 1548 | $Q_{37}$ | H | COOMe | OMe | OMe | CH |
| 1549 | $Q_{37}$ | H | COOMe | Me | OMe | N |
| 1550 | $Q_{37}$ | H | COOMe | OMe | OMe | N |
| 1551 | $Q_{37}$ | H | COOEt | Me | Me | CH |
| 1552 | $Q_{37}$ | H | COOEt | Me | OMe | CH |
| 1553 | $Q_{37}$ | H | COOEt | OMe | OMe | CH |
| 1554 | $Q_{37}$ | H | COOEt | Me | OMe | N |
| 1555 | $Q_{37}$ | H | COOEt | OMe | OMe | N |
| 1556 | $Q_{37}$ | Me | COOMe | Me | OMe | CH |
| 1557 | $Q_{37}$ | Me | COOMe | OMe | OMe | CH |
| 1558 | $Q_{37}$ | Me | COOMe | Me | OMe | N |
| 1559 | $Q_{37}$ | Me | COOEt | Me | OMe | CH |
| 1560 | $Q_{37}$ | Me | COOEt | OMe | OMe | CH |
| 1561 | $Q_{37}$ | Me | COOEt | Me | OMe | N |
| 1562 | $Q_{37}$ | H | CN | Me | OMe | CH |
| 1563 | $Q_{37}$ | H | CN | OMe | OMe | CH |
| 1564 | $Q_{37}$ | H | CN | Me | OMe | N |
| 1565 | $Q_{37}$ | H | H | Me | OMe | CH |
| 1566 | $Q_{37}$ | H | H | OMe | OMe | CH |
| 1567 | $Q_{37}$ | H | H | Me | OMe | N |
| 1568 | Me | H | $Q_{37}$ | Me | Me | CH |
| 1569 | Me | H | $Q_{37}$ | Me | OMe | CH |
| 1570 | Me | H | $Q_{37}$ | OMe | OMe | CH |
| 1571 | Me | H | $Q_{37}$ | Me | OMe | N |
| 1572 | Me | H | $Q_{37}$ | OMe | OMe | N |
| 1573 | $Q_{38}$ | H | COOMe | Me | Me | CH |
| 1574 | $Q_{38}$ | H | COOMe | Me | OMe | CH |
| 1575 | $Q_{38}$ | H | COOMe | OMe | OMe | CH |
| 1576 | $Q_{38}$ | H | COOMe | Me | OMe | N |
| 1577 | $Q_{38}$ | H | COOMe | OMe | OMe | N |
| 1578 | $Q_{38}$ | H | COOEt | Me | Me | CH |
| 1579 | $Q_{38}$ | H | COOEt | Me | OMe | CH |
| 1580 | $Q_{38}$ | H | COOEt | OMe | OMe | CH |
| 1581 | $Q_{38}$ | H | COOEt | Me | OMe | N |
| 1582 | $Q_{38}$ | H | COOEt | OMe | OMe | N |
| 1583 | $Q_{38}$ | Me | COOMe | Me | OMe | CH |
| 1584 | $Q_{38}$ | Me | COOMe | OMe | OMe | CH |
| 1585 | $Q_{38}$ | Me | COOMe | Me | OMe | N |
| 1586 | $Q_{38}$ | Me | COOEt | Me | OMe | CH |
| 1587 | $Q_{38}$ | Me | COOEt | OMe | OMe | CH |
| 1588 | $Q_{38}$ | Me | COOEt | Me | OMe | N |
| 1589 | $Q_{38}$ | H | CN | Me | OMe | CH |
| 1590 | $Q_{38}$ | H | CN | OMe | OMe | CH |
| 1591 | $Q_{38}$ | H | CN | Me | OMe | N |
| 1592 | $Q_{38}$ | H | H | Me | OMe | CH |
| 1593 | $Q_{38}$ | H | H | OMe | OMe | CH |
| 1594 | $Q_{38}$ | H | H | Me | OMe | N |
| 1595 | Me | H | $Q_{38}$ | Me | Me | CH |
| 1596 | Me | H | $Q_{38}$ | Me | OMe | CH |
| 1597 | Me | H | $Q_{38}$ | OMe | OMe | CH |
| 1598 | Me | H | $Q_{38}$ | Me | OMe | N |
| 1599 | Me | H | $Q_{38}$ | OMe | OMe | N |
| 1600 | $Q_{39}$ | H | COOMe | Me | Me | CH |
| 1601 | $Q_{39}$ | H | COOMe | Me | OMe | CH |
| 1602 | $Q_{39}$ | H | COOMe | OMe | OMe | CH |
| 1603 | $Q_{39}$ | H | COOMe | Me | OMe | N |

-continued

| | | | | | | |
|---|---|---|---|---|---|---|
| 1604 | $Q_{39}$ | H | COOMe | OMe | OMe | N |
| 1605 | $Q_{39}$ | H | COOEt | Me | Me | CH |
| 1606 | $Q_{39}$ | H | COOEt | Me | OMe | CH |
| 1607 | $Q_{39}$ | H | COOEt | OMe | OMe | CH |
| 1608 | $Q_{39}$ | H | COOEt | Me | OMe | N |
| 1609 | $Q_{39}$ | H | COOEt | OMe | OMe | N |
| 1610 | $Q_{39}$ | Me | COOMe | Me | OMe | CH |
| 1611 | $Q_{39}$ | Me | COOMe | OMe | OMe | CH |
| 1612 | $Q_{39}$ | Me | COOMe | Me | OMe | N |
| 1613 | $Q_{39}$ | Me | COOEt | Me | OMe | CH |
| 1614 | $Q_{39}$ | Me | COOEt | OMe | OMe | CH |
| 1615 | $Q_{39}$ | Me | COOEt | Me | OMe | N |
| 1616 | $Q_{39}$ | H | CN | Me | OMe | CH |
| 1617 | $Q_{39}$ | H | CN | OMe | OMe | CH |
| 1618 | $Q_{39}$ | H | CN | Me | OMe | N |
| 1619 | $Q_{39}$ | H | H | Me | OMe | CH |
| 1620 | $Q_{39}$ | H | H | OMe | OMe | CH |
| 1621 | $Q_{39}$ | H | H | Me | OMe | N |
| 1622 | Me | H | $Q_{39}$ | Me | Me | CH |
| 1623 | Me | H | $Q_{39}$ | Me | OMe | CH |
| 1624 | Me | H | $Q_{39}$ | OMe | OMe | CH |
| 1625 | Me | H | $Q_{39}$ | Me | OMe | N |
| 1626 | Me | H | $Q_{39}$ | OMe | OMe | N |
| 1627 | $Q_{40}$ | H | COOMe | Me | OMe | CH |
| 1628 | $Q_{40}$ | H | COOMe | OMe | OMe | CH |
| 1629 | $Q_{40}$ | H | COOEt | Me | OMe | CH |
| 1630 | $Q_{40}$ | H | COOEt | OMe | OMe | CH |
| 1631 | $Q_{40}$ | Me | COOMe | Me | OMe | CH |
| 1632 | $Q_{40}$ | Me | COOMe | OMe | OMe | CH |
| 1633 | $Q_{40}$ | Me | COOEt | Me | OMe | CH |
| 1634 | $Q_{40}$ | Me | COOEt | OMe | OMe | CH |
| 1635 | $Q_{40}$ | H | H | Me | OMe | CH |
| 1636 | $Q_{40}$ | H | H | OMe | OMe | CH |
| 1637 | Me | H | $Q_{40}$ | Me | OMe | CH |
| 1638 | Me | H | $Q_{40}$ | OMe | OMe | CH |
| 1639 | $Q_{41}$ | H | COOMe | Me | Me | CH |
| 1640 | $Q_{41}$ | H | COOMe | Me | OMe | CH |
| 1641 | $Q_{41}$ | H | COOMe | OMe | OMe | CH |
| 1642 | $Q_{41}$ | H | COOMe | Me | OMe | N |
| 1643 | $Q_{41}$ | H | COOMe | OMe | OMe | N |
| 1644 | $Q_{41}$ | H | COOEt | Me | Me | CH |
| 1645 | $Q_{41}$ | H | COOEt | Me | OMe | CH |
| 1646 | $Q_{41}$ | H | COOEt | OMe | OMe | CH |
| 1647 | $Q_{41}$ | H | COOEt | Me | OMe | N |
| 1648 | $Q_{41}$ | H | COOEt | OMe | OMe | N |
| 1649 | $Q_{41}$ | Me | COOMe | Me | OMe | CH |
| 1650 | $Q_{41}$ | Me | COOMe | OMe | OMe | CH |
| 1651 | $Q_{41}$ | Me | COOMe | Me | OMe | N |
| 1652 | $Q_{41}$ | Me | COOEt | Me | OMe | CH |
| 1653 | $Q_{41}$ | Me | COOEt | OMe | OMe | CH |
| 1654 | $Q_{41}$ | Me | COOEt | Me | OMe | N |
| 1655 | $Q_{41}$ | H | CN | Me | OMe | CH |
| 1656 | $Q_{41}$ | H | CN | OMe | OMe | CH |
| 1657 | $Q_{41}$ | H | CN | Me | OMe | N |
| 1658 | $Q_{41}$ | H | H | Me | OMe | CH |
| 1659 | $Q_{41}$ | H | H | OMe | OMe | CH |
| 1660 | $Q_{41}$ | H | H | Me | OMe | N |
| 1661 | Me | H | $Q_{41}$ | Me | Me | CH |
| 1662 | Me | H | $Q_{41}$ | Me | OMe | CH |
| 1663 | Me | H | $Q_{41}$ | OMe | OMe | CH |
| 1664 | Me | H | $Q_{41}$ | Me | OMe | N |
| 1665 | Me | H | $Q_{41}$ | OMe | OMe | N |
| 1666 | $Q_{42}$ | H | COOMe | Me | Me | CH |
| 1667 | $Q_{42}$ | H | COOMe | Me | OMe | CH |
| 1668 | $Q_{42}$ | H | COOMe | OMe | OMe | CH |
| 1669 | $Q_{42}$ | H | COOMe | Me | OMe | N |
| 1670 | $Q_{42}$ | H | COOMe | OMe | OMe | N |
| 1671 | $Q_{42}$ | H | COOEt | Me | Me | CH |
| 1672 | $Q_{42}$ | H | COOEt | Me | OMe | CH |
| 1673 | $Q_{42}$ | H | COOEt | OMe | OMe | CH |
| 1674 | $Q_{42}$ | H | COOEt | Me | OMe | N |
| 1675 | $Q_{42}$ | H | COOEt | OMe | OMe | N |
| 1676 | $Q_{42}$ | Me | COOMe | Me | OMe | CH |
| 1677 | $Q_{42}$ | Me | COOMe | OMe | OMe | CH |
| 1678 | $Q_{42}$ | Me | COOMe | Me | OMe | N |
| 1679 | $Q_{42}$ | Me | COOEt | Me | OMe | CH |
| 1680 | $Q_{42}$ | Me | COOEt | OMe | OMe | CH |
| 1681 | $Q_{42}$ | Me | COOEt | Me | OMe | N |
| 1682 | $Q_{42}$ | H | CN | Me | OMe | CH |
| 1683 | $Q_{42}$ | H | CN | OMe | OMe | CH |
| 1684 | $Q_{42}$ | H | CN | Me | OMe | N |
| 1685 | $Q_{42}$ | H | H | Me | OMe | CH |

-continued

| | | | | | | |
|---|---|---|---|---|---|---|
| 1686 | $Q_{42}$ | H | H | OMe | OMe | CH |
| 1687 | $Q_{42}$ | H | H | Me | OMe | N |
| 1688 | Me | H | $Q_{42}$ | Me | Me | CH |
| 1689 | Me | H | $Q_{42}$ | Me | OMe | CH |
| 1690 | Me | H | $Q_{42}$ | OMe | OMe | CH |
| 1691 | Me | H | $Q_{42}$ | Me | OMe | N |
| 1692 | Me | H | $Q_{42}$ | OMe | OMe | N |
| 1693 | $Q_{43}$ | H | COOMe | Me | Me | CH |
| 1694 | $Q_{43}$ | H | COOMe | Me | OMe | CH |
| 1695 | $Q_{43}$ | H | COOMe | OMe | OMe | CH |
| 1696 | $Q_{43}$ | H | COOMe | Me | OMe | N |
| 1697 | $Q_{43}$ | H | COOMe | OMe | OMe | N |
| 1698 | $Q_{43}$ | H | COOEt | Me | Me | CH |
| 1699 | $Q_{43}$ | H | COOEt | Me | OMe | CH |
| 1700 | $Q_{43}$ | H | COOEt | OMe | OMe | CH |
| 1701 | $Q_{43}$ | H | COOEt | Me | OMe | N |
| 1702 | $Q_{43}$ | H | COOEt | OMe | OMe | N |
| 1703 | $Q_{43}$ | Me | COOMe | Me | OMe | CH |
| 1704 | $Q_{43}$ | Me | COOMe | OMe | OMe | CH |
| 1705 | $Q_{43}$ | Me | COOMe | Me | OMe | N |
| 1706 | $Q_{43}$ | Me | COOEt | Me | OMe | CH |
| 1707 | $Q_{43}$ | Me | COOEt | OMe | OMe | CH |
| 1708 | $Q_{43}$ | Me | COOEt | Me | OMe | N |
| 1709 | $Q_{43}$ | H | CN | Me | OMe | CH |
| 1710 | $Q_{43}$ | H | CN | OMe | OMe | CH |
| 1711 | $Q_{43}$ | H | CN | Me | OMe | N |
| 1712 | $Q_{42}$ | H | H | Me | OMe | CH |
| 1713 | $Q_{43}$ | H | H | OMe | OMe | CH |
| 1714 | $Q_{43}$ | H | H | Me | OMe | N |
| 1715 | Me | H | $Q_{43}$ | Me | Me | CH |
| 1716 | Me | H | $Q_{43}$ | Me | OMe | CH |
| 1717 | Me | H | $Q_{43}$ | OMe | OMe | CH |
| 1718 | Me | H | $Q_{43}$ | Me | OMe | N |
| 1719 | Me | H | $Q_{43}$ | OMe | OMe | N |
| 1720 | $Q_{44}$ | H | COOMe | Me | OMe | CH |
| 1721 | $Q_{44}$ | H | COOMe | OMe | OMe | CH |
| 1722 | $Q_{44}$ | H | COOEt | Me | OMe | CH |
| 1723 | $Q_{44}$ | H | COOEt | OMe | OMe | CH |
| 1724 | $Q_{44}$ | Me | COOMe | Me | OMe | CH |
| 1725 | $Q_{44}$ | Me | COOMe | OMe | OMe | CH |
| 1726 | $Q_{44}$ | Me | COOEt | Me | OMe | CH |
| 1727 | $Q_{44}$ | Me | COOEt | OMe | OMe | CH |
| 1728 | $Q_{44}$ | H | H | Me | OMe | CH |
| 1729 | $Q_{44}$ | H | H | OMe | OMe | CH |
| 1730 | Me | H | $Q_{44}$ | Me | OMe | CH |
| 1731 | Me | H | $Q_{44}$ | OMe | OMe | CH |
| 1732 | $Q_{45}$ | H | COOMe | Me | Me | CH |
| 1733 | $Q_{45}$ | H | COOMe | Me | OMe | CH |
| 1734 | $Q_{45}$ | H | COOMe | OMe | OMe | CH |
| 1735 | $Q_{45}$ | H | COOMe | Me | Me | N |
| 1736 | $Q_{45}$ | H | COOMe | Me | OMe | N |
| 1737 | $Q_{45}$ | H | COOMe | OMe | OMe | N |
| 1738 | $Q_{45}$ | H | COOMe | Me | $OCHF_2$ | CH |
| 1739 | $Q_{45}$ | H | COOMe | Cl | OMe | CH |
| 1740 | $Q_{45}$ | H | COOEt | Me | Me | CH |
| 1741 | $Q_{45}$ | H | COOEt | Me | OMe | CH |
| 1742 | $Q_{45}$ | H | COOEt | OMe | OMe | CH |
| 1743 | $Q_{45}$ | H | COOEt | Me | Me | N |
| 1744 | $Q_{45}$ | H | COOEt | Me | OMe | N |
| 1745 | $Q_{45}$ | H | COOEt | OMe | OMe | N |
| 1746 | $Q_{45}$ | H | COOEt | Me | $OCHF_2$ | CH |
| 1747 | $Q_{45}$ | H | COOEt | Cl | OMe | CH |
| 1748 | $Q_{45}$ | H | COOPr—n | Me | OMe | CH |
| 1749 | $Q_{45}$ | H | COOPr—n | OMe | OMe | CH |
| 1750 | $Q_{45}$ | H | COOPr—n | Me | OMe | N |
| 1751 | $Q_{45}$ | H | COOPr—i | Me | OMe | CH |
| 1752 | $Q_{45}$ | H | COOPr—i | OMe | OMe | CH |
| 1753 | $Q_{45}$ | H | COOPr—i | Me | OMe | N |
| 1754 | $Q_{45}$ | H | $COOCH_2CH_2Cl$ | Me | OMe | CH |
| 1755 | $Q_{45}$ | H | $COOCH_2CH_2Cl$ | OMe | OMe | CH |
| 1756 | $Q_{45}$ | H | $COOCH_2CH_2Cl$ | Me | OMe | N |
| 1757 | $Q_{45}$ | H | $COOCH_2CH{=}CH_2$ | Me | OMe | CH |
| 1758 | $Q_{45}$ | H | $COOCH_2CH{=}CH_2$ | OMe | OMe | CH |
| 1759 | $Q_{45}$ | H | $COOCH_2CH{=}CH_2$ | Me | OMe | N |
| 1760 | $Q_{45}$ | H | $COOCH_2C{\equiv}CH$ | Me | OMe | CH |
| 1761 | $Q_{45}$ | H | $COOCH_2C{\equiv}CH$ | OMe | OMe | CH |
| 1762 | $Q_{45}$ | H | $COOCH_2C{\equiv}CH$ | Me | OMe | N |
| 1763 | $Q_{45}$ | Me | COOMe | Me | Me | CH |
| 1764 | $Q_{45}$ | Me | COOMe | Me | OMe | CH |
| 1765 | $Q_{45}$ | Me | COOMe | OMe | OMe | CH |
| 1766 | $Q_{45}$ | Me | COOMe | Me | OMe | N |
| 1767 | $Q_{45}$ | Me | COOMe | OMe | OMe | N |

-continued

| | | | | | | |
|---|---|---|---|---|---|---|
| 1768 | $Q_{45}$ | Me | COOEt | Me | Me | CH |
| 1769 | $Q_{45}$ | Me | COOEt | Me | OMe | CH |
| 1770 | $Q_{45}$ | Me | COOEt | OMe | OMe | CH |
| 1771 | $Q_{45}$ | Me | COOEt | Me | OMe | N |
| 1772 | $Q_{45}$ | Me | COOEt | OMe | OMe | N |
| 1773 | $Q_{45}$ | Cl | COOMe | Me | OMe | CH |
| 1774 | $Q_{45}$ | Cl | COOMe | OMe | OMe | CH |
| 1775 | $Q_{45}$ | Cl | COOMe | Me | OMe | N |

| | | | | | | |
|---|---|---|---|---|---|---|
| 1776 | $Q_{45}$ | Cl | COOEt | Me | OMe | CH |
| 1777 | $Q_{45}$ | Cl | COOEt | OMe | OMe | CH |
| 1778 | $Q_{45}$ | Cl | COOEt | Me | OMe | N |
| 1779 | $Q_{45}$ | OMe | COOMe | Me | OMe | CH |
| 1780 | $Q_{45}$ | OMe | COOMe | OMe | OMe | CH |
| 1781 | $Q_{45}$ | OMe | COOMe | Me | OMe | N |
| 1782 | $Q_{45}$ | OMe | COOEt | Me | OMe | CH |
| 1783 | $Q_{45}$ | OMe | COOEt | OMe | OMe | CH |
| 1784 | $Q_{45}$ | OMe | COOEt | Me | OMe | N |
| 1785 | $Q_{45}$ | H | Cl | Me | OMe | CH |
| 1786 | $Q_{45}$ | H | Cl | OMe | OMe | CH |
| 1787 | $Q_{45}$ | H | Cl | Me | OMe | N |
| 1788 | $Q_{45}$ | H | $NO_2$ | Me | OMe | CH |
| 1789 | $Q_{45}$ | H | $NO_2$ | OMe | OMe | CH |
| 1790 | $Q_{45}$ | H | $NO_2$ | Me | OMe | N |
| 1791 | $Q_{45}$ | H | $SO_2NMe_2$ | Me | OMe | CH |
| 1792 | $Q_{45}$ | H | $SO_2NMe_2$ | OMe | OMe | CH |
| 1793 | $Q_{45}$ | H | $SO_2NMe_2$ | Me | OMe | N |
| 1794 | $Q_{45}$ | H | CN | Me | OMe | CH |
| 1795 | $Q_{45}$ | H | CN | OMe | OMe | CH |
| 1796 | $Q_{45}$ | H | CN | Me | OMe | N |
| 1797 | $Q_{45}$ | Me | CN | Me | OMe | CH |
| 1798 | $Q_{45}$ | Me | CN | OMe | OMe | CH |
| 1799 | $Q_{45}$ | Me | CN | Me | OMe | N |
| 1800 | $Q_{45}$ | H | Me | Me | OMe | CH |
| 1801 | $Q_{45}$ | H | Me | OMe | OMe | CH |
| 1802 | $Q_{45}$ | H | Me | Me | OMe | N |
| 1803 | $Q_{45}$ | H | Et | Me | OMe | CH |
| 1804 | $Q_{45}$ | H | Et | OMe | OMe | CH |
| 1805 | $Q_{45}$ | H | Et | Me | OMe | N |
| 1806 | $Q_{45}$ | H | H | Me | OMe | CH |
| 1807 | $Q_{45}$ | H | H | OMe | OMe | CH |
| 1808 | $Q_{45}$ | H | H | Me | OMe | N |
| 1809 | $Q_{45}$ | H | COPh | Me | OMe | CH |
| 1810 | $Q_{45}$ | H | COPh | OMe | OMe | CH |
| 1811 | $Q_{45}$ | H | COPh | Me | OMe | N |
| 1812 | Me | $Q_{45}$ | COOMe | Me | OMe | CH |
| 1813 | Me | $Q_{45}$ | COOMe | OMe | OMe | CH |
| 1814 | Me | $Q_{45}$ | COOMe | Me | OMe | N |
| 1815 | H | H | $Q_{45}$ | Me | OMe | CH |
| 1816 | H | H | $Q_{45}$ | OMe | OMe | CH |
| 1817 | H | H | $Q_{45}$ | Me | OMe | N |
| 1818 | Me | H | $Q_{45}$ | Me | Me | CH |
| 1819 | Me | H | $Q_{45}$ | Me | OMe | CH |
| 1820 | Me | H | $Q_{45}$ | OMe | OMe | CH |
| 1821 | Me | H | $Q_{45}$ | Me | OMe | N |
| 1822 | Me | H | $Q_{45}$ | OMe | OMe | N |
| 1823 | Me | Me | $Q_{45}$ | Me | OMe | CH |
| 1824 | Me | Me | $Q_{45}$ | OMe | OMe | CH |
| 1825 | Me | Me | $Q_{45}$ | Me | OMe | N |
| 1826 | $Q_{46}$ | H | COOMe | Me | Me | CH |
| 1827 | $Q_{46}$ | H | COOMe | Me | OMe | CH |
| 1828 | $Q_{46}$ | H | COOMe | OMe | OMe | CH |
| 1829 | $Q_{46}$ | H | COOMe | Me | OMe | N |
| 1830 | $Q_{46}$ | H | COOMe | OMe | OMe | N |
| 1831 | $Q_{46}$ | H | COOEt | Me | Me | CH |
| 1832 | $Q_{46}$ | H | COOEt | Me | OMe | CH |
| 1833 | $Q_{46}$ | H | COOEt | OMe | OMe | CH |
| 1834 | $Q_{46}$ | H | COOEt | Me | OMe | N |
| 1835 | $Q_{46}$ | H | COOEt | OMe | OMe | N |
| 1836 | $Q_{46}$ | Me | COOMe | Me | OMe | CH |
| 1837 | $Q_{46}$ | Me | COOMe | OMe | OMe | CH |
| 1838 | $Q_{46}$ | Me | COOMe | Me | OMe | N |
| 1839 | $Q_{46}$ | Me | COOEt | Me | OMe | CH |
| 1840 | $Q_{46}$ | Me | COOEt | OMe | OMe | CH |
| 1841 | $Q_{46}$ | Me | COOEt | Me | OMe | N |
| 1842 | $Q_{46}$ | H | CN | Me | OMe | CH |
| 1843 | $Q_{46}$ | H | CN | OMe | OMe | CH |
| 1844 | $Q_{46}$ | H | CN | Me | OMe | N |
| 1845 | $Q_{46}$ | H | H | Me | OMe | CH |

-continued

| | | | | | | |
|---|---|---|---|---|---|---|
| 1846 | $Q_{46}$ | H | H | OMe | OMe | CH |
| 1847 | $Q_{46}$ | H | H | Me | OMe | N |
| 1848 | Me | H | $Q_{46}$ | Me | Me | CH |
| 1849 | Me | H | $Q_{46}$ | Me | OMe | CH |
| 1850 | Me | H | $Q_{46}$ | OMe | OMe | CH |
| 1851 | Me | H | $Q_{46}$ | Me | OMe | N |
| 1852 | Me | H | $Q_{46}$ | OMe | OMe | N |
| 1853 | $Q_{47}$ | H | COOMe | Me | Me | CH |
| 1854 | $Q_{47}$ | H | COOMe | Me | OMe | CH |
| 1855 | $Q_{47}$ | H | COOMe | OMe | OMe | CH |
| 1856 | $Q_{47}$ | H | COOMe | Me | OMe | N |
| 1857 | $Q_{47}$ | H | COOMe | OMe | OMe | N |
| 1858 | $Q_{47}$ | H | COOEt | Me | Me | CH |
| 1859 | $Q_{47}$ | H | COOEt | Me | OMe | CH |
| 1860 | $Q_{47}$ | H | COOEt | OMe | OMe | CH |
| 1861 | $Q_{47}$ | H | COOEt | Me | OMe | N |
| 1862 | $Q_{47}$ | H | COOEt | OMe | OMe | N |
| 1863 | $Q_{47}$ | Me | COOMe. | Me | OMe | CH |
| 1864 | $Q_{47}$ | Me | COOMe | OMe | OMe | CH |
| 1865 | $Q_{47}$ | Me | COOMe | Me | OMe | N |
| 1866 | $Q_{47}$ | Me | COOEt | Me | OMe | CH |
| 1867 | $Q_{47}$ | Me | COOEt | OMe | OMe | CH |
| 1868 | $Q_{47}$ | Me | COOEt | Me | OMe | N |
| 1869 | $Q_{47}$ | H | CN | Me | OMe | CH |
| 1870 | $Q_{47}$ | H | CN | OMe | OMe | CH |
| 1871 | $Q_{47}$ | H | CN | Me | OMe | N |
| 1872 | $Q_{47}$ | H | H | Me | OMe | CH |
| 1873 | $Q_{47}$ | H | H | OMe | OMe | CH |
| 1874 | $Q_{47}$ | H | H | Me | OMe | N |
| 1875 | Me | H | $Q_{47}$ | Me | Me | CH |
| 1876 | Me | H | $Q_{47}$ | Me | OMe | CH |
| 1877 | Me | H | $Q_{47}$ | OMe | OMe | CH |
| 1878 | Me | H | $Q_{47}$ | Me | OMe | N |
| 1879 | Me | H | $Q_{47}$ | OMe | OMe | N |
| 1880 | $Q_{48}$ | H | COOMe | Me | Me | CH |
| 1881 | $Q_{48}$ | H | COOMe | Me | OMe | CH |
| 1882 | $Q_{48}$ | H | COOMe | OMe | OMe | CH |
| 1883 | $Q_{48}$ | H | COOMe | Me | OMe | N |
| 1884 | $Q_{48}$ | H | COOMe | OMe | OMe | N |
| 1885 | $Q_{48}$ | H | COOEt | Me | Me | CH |
| 1886 | $Q_{48}$ | H | COOEt | Me | OMe | CH |
| 1887 | $Q_{48}$ | H | COOEt | OMe | OMe | CH |
| 1888 | $Q_{48}$ | H | COOEt | Me | OMe | N |
| 1889 | $Q_{48}$ | H | COOEt | OMe | OMe | N |
| 1890 | $Q_{48}$ | Me | COOMe | Me | OMe | CH |
| 1891 | $Q_{48}$ | Me | COOMe | OMe | OMe | CH |
| 1892 | $Q_{48}$ | Me | COOMe | Me | OMe | N |
| 1893 | $Q_{48}$ | Me | COOEt | Me | OMe | CH |
| 1894 | $Q_{48}$ | Me | COOEt | OMe | OMe | CH |
| 1895 | $Q_{48}$ | Me | COOEt | Me | OMe | N |
| 1896 | $Q_{48}$ | H | CN | Me | OMe | CH |
| 1897 | $Q_{48}$ | H | CN | OMe | OMe | CH |
| 1898 | $Q_{48}$ | H | CN | Me | OMe | N |
| 1899 | $Q_{48}$ | H | H | Me | OMe | CH |
| 1900 | $Q_{48}$ | H | H | OMe | OMe | CH |
| 1901 | $Q_{48}$ | H | H | Me | OMe | N |
| 1902 | Me | H | $Q_{48}$ | Me | Me | CH |
| 1903 | Me | H | $Q_{48}$ | Me | OMe | CH |
| 1904 | Me | H | $Q_{48}$ | OMe | OMe | CH |
| 1905 | Me | H | $Q_{48}$ | Me | OMe | N |
| 1906 | Me | H | $Q_{48}$ | OMe | OMe | N |
| 1907 | $Q_{49}$ | H | COOMe | Me | Me | CH |
| 1908 | $Q_{49}$ | H | COOMe | Me | OMe | CH |
| 1909 | $Q_{49}$ | H | COOMe | OMe | OMe | CH |
| 1910 | $Q_{49}$ | H | COOMe | Me | OMe | N |
| 1911 | $Q_{49}$ | H | COOMe | OMe | OMe | N |
| 1912 | $Q_{49}$ | H | COOEt | Me | Me | CH |
| 1913 | $Q_{49}$ | H | COOEt | Me | OMe | CH |
| 1914 | Q49 | H | COOEt | OMe | OMe | CH |
| 1915 | $Q_{49}$ | H | COOEt | Me | OMe | N |
| 1916 | $Q_{49}$ | H | COOEt | OMe | OMe | N |
| 1917 | $Q_{49}$ | Me | COOMe | Me | OMe | CH |
| 1918 | $Q_{49}$ | Me | COOMe | OMe | OMe | CH |
| 1919 | $Q_{49}$ | Me | COOMe | Me | OMe | N |
| 1920 | $Q_{49}$ | Me | COOEt | Me | OMe | CH |
| 1921 | $Q_{49}$ | Me | COOEt | OMe | OMe | CH |
| 1922 | $Q_{49}$ | Me | COOEt | Me | OMe | N |
| 1923 | $Q_{49}$ | H | CN | Me | OMe | CH |
| 1924 | $Q_{49}$ | H | CN | OMe | OMe | CH |
| 1925 | $Q_{49}$ | H | CN | Me | OMe | N |
| 1926 | $Q_{49}$ | H | H | Me | OMe | CH |
| 1927 | $Q_{49}$ | H | H | OMe | OMe | CH |

-continued

| | | | | | | |
|---|---|---|---|---|---|---|
| 1928 | $Q_{49}$ | H | H | Me | OMe | N |
| 1929 | Me | H | $Q_{49}$ | Me | Me | CH |
| 1930 | Me | H | $Q_{49}$ | Me | OMe | CH |
| 1931 | Me | H | $Q_{49}$ | OMe | OMe | CH |
| 1932 | Me | H | $Q_{49}$ | Me | OMe | N |
| 1933 | Me | H | $Q_{49}$ | OMe | OMe | N |
| 1934 | $Q_{50}$ | H | COOMe | Me | Me | CH |
| 1935 | $Q_{50}$ | H | COOMe | Me | OMe | CH |
| 1936 | $Q_{50}$ | H | COOMe | OMe | OMe | CH |
| 1937 | $Q_{50}$ | H | COOMe | Me | OMe | N |
| 1938 | $Q_{50}$ | H | COOMe | OMe | OMe | N |
| 1939 | $Q_{50}$ | H | COOEt | Me | Me | CH |
| 1940 | $Q_{50}$ | H | COOEt | Me | OMe | CH |
| 1941 | $Q_{50}$ | H | COOEt | OMe | OMe | CH |
| 1942 | $Q_{50}$ | H | COOEt | Me | OMe | N |
| 1943 | $Q_{50}$ | H | COOEt | OMe | OMe | N |
| 1944 | $Q_{50}$ | Me | COOMe | Me | OMe | CH |
| 1945 | $Q_{50}$ | Me | COOMe | OMe | OMe | CH |
| 1946 | $Q_{50}$ | Me | COOMe | Me | OMe | N |
| 1947 | $Q_{50}$ | Me | COOEt | Me | OMe | CH |
| 1948 | $Q_{50}$ | Me | COOEt | OMe | OMe | CH |
| 1949 | $Q_{50}$ | Me | COOEt | Me | OMe | N |
| 1950 | $Q_{50}$ | H | CN | Me | OMe | CH |
| 1951 | $Q_{50}$ | H | CN | OMe | OMe | CH |
| 1952 | $Q_{50}$ | H | CN | Me | OMe | N |
| 1953 | $Q_{50}$ | H | H | Me | OMe | CH |
| 1954 | $Q_{50}$ | H | H | OMe | OMe | CH |
| 1955 | $Q_{50}$ | H | H | Me | OMe | N |
| 1956 | Me | H | $Q_{50}$ | Me | Me | CH |
| 1957 | Me | H | $Q_{50}$ | Me | OMe | CH |
| 1958 | Me | H | $Q_{50}$ | OMe | OMe | CH |
| 1959 | Me | H | $Q_{50}$ | Me | OMe | N |
| 1960 | Me | H | $Q_{50}$ | OMe | OMe | N |
| 1961 | $Q_{51}$ | H | COOMe | Me | Me | CH |
| 1962 | $Q_{51}$ | H | COOMe | Me | OMe | CH |
| 1963 | $Q_{51}$ | H | COOMe | OMe | OMe | CH |
| 1964 | $Q_{51}$ | H | COOMe | Me | OMe | N |
| 1965 | $Q_{51}$ | H | COOMe | OMe | OMe | N |
| 1966 | $Q_{51}$ | H | COOEt | Me | Me | CH |
| 1967 | $Q_{51}$ | H | COOEt | Me | OMe | CH |
| 1968 | $Q_{51}$ | H | COOEt | OMe | OMe | CH |
| 1969 | $Q_{51}$ | H | COOEt | Me | OMe | N |
| 1970 | $Q_{51}$ | H | COOEt | OMe | OMe | N |
| 1971 | $Q_{51}$ | Me | COOMe | Me | OMe | CH |
| 1972 | $Q_{51}$ | Me | COOMe | OMe | OMe | CH |
| 1973 | $Q_{51}$ | Me | COOMe | Me | OMe | N |
| 1974 | $Q_{51}$ | Me | COOEt | Me | OMe | CH |
| 1975 | $Q_{51}$ | Me | COOEt | OMe | OMe | CH |
| 1976 | $Q_{51}$ | Me | COOEt | Me | OMe | N |
| 1977 | $Q_{51}$ | H | CN | Me | OMe | CH |
| 1978 | $Q_{51}$ | H | CN | OMe | OMe | CH |
| 1979 | $Q_{51}$ | H | CN | Me | OMe | N |
| 1980 | $Q_{51}$ | H | H | Me | OMe | CH |
| 1981 | $Q_{51}$ | H | H | OMe | OMe | CH |
| 1982 | $Q_{51}$ | H | H | Me | OMe | N |
| 1983 | Me | H | $Q_{51}$ | Me | Me | CH |
| 1984 | Me | H | $Q_{51}$ | Me | OMe | CH |
| 1985 | Me | H | $Q_{51}$ | OMe | OMe | CH |
| 1986 | Me | H | $Q_{51}$ | Me | OMe | N |
| 1987 | Me | H | $Q_{51}$ | OMe | OMe | N |
| 1988 | $Q_{52}$ | H | COOMe | Me | OMe | CH |
| 1989 | $Q_{52}$ | H | COOMe | OMe | OMe | CH |
| 1990 | $Q_{52}$ | H | COOEt | Me | OMe | CH |
| 1991 | $Q_{52}$ | H | COOEt | OMe | OMe | CH |
| 1992 | $Q_{52}$ | Me | COOMe | Me | OMe | CH |
| 1993 | $Q_{52}$ | Me | COOMe | OMe | OMe | CH |
| 1994 | $Q_{52}$ | Me | COOEt | Me | OMe | CH |
| 1995 | $Q_{52}$ | Me | COOEt | OMe | OMe | CH |
| 1996 | $Q_{52}$ | H | H | Me | OMe | CH |
| 1997 | $Q_{52}$ | H | H | OMe | OMe | CH |
| 1998 | Me | H | $Q_{52}$ | Me | OMe | CH |
| 1999 | Me | H | $Q_{52}$ | OMe | OMe | CH |
| 2000 | $Q_{53}$ | H | COOMe | Me | OMe | CH |
| 2001 | $Q_{53}$ | H | COOMe | OMe | OMe | CH |
| 2002 | $Q_{53}$ | H | COOEt | Me | OMe | CH |
| 2003 | $Q_{53}$ | H | COOEt | OMe | OMe | CH |
| 2004 | $Q_{53}$ | Me | COOMe | Me | OMe | CH |
| 2005 | $Q_{53}$ | Me | COOMe | OMe | OMe | CH |
| 2006 | $Q_{53}$ | Me | COOEt | Me | OMe | CH |
| 2007 | $Q_{53}$ | Me | COOEt | OMe | OMe | CH |
| 2008 | $Q_{53}$ | H | H | Me | OMe | CH |
| 2009 | $Q_{53}$ | H | H | OMe | OMe | CH |

-continued

| | | | | | | |
|---|---|---|---|---|---|---|
| 2010 | Me | H | $Q_{53}$ | Me | OMe | CH |
| 2011 | Me | H | $Q_{53}$ | OMe | OMe | CH |
| 2012 | $Q_{54}$ | H | COOMe | Me | Me | CH |
| 2013 | $Q_{54}$ | H | COOMe | Me | OMe | CH |
| 2014 | $Q_{54}$ | H | COOMe | OMe | OMe | CH |
| 2015 | $Q_{54}$ | H | COOMe | Me | OMe | N |
| 2016 | $Q_{54}$ | H | COOMe | OMe | OMe | N |
| 2017 | $Q_{54}$ | H | COOEt | Me | Me | CH |
| 2018 | $Q_{54}$ | H | COOEt | Me | OMe | CH |
| 2019 | $Q_{54}$ | H | COOEt | OMe | OMe | CH |
| 2020 | $Q_{54}$ | H | COOEt | Me | OMe | N |
| 2021 | $Q_{54}$ | H | COOEt | OMe | OMe | N |
| 2022 | $Q_{54}$ | Me | COOMe | Me | OMe | CH |
| 2023 | $Q_{54}$ | Me | COOMe | OMe | OMe | CH |
| 2024 | $Q_{54}$ | Me | COOMe | Me | OMe | N |
| 2025 | $Q_{54}$ | Me | COOEt | Me | OMe | CH |
| 2026 | $Q_{54}$ | Me | COOEt | OMe | OMe | CH |
| 2027 | $Q_{54}$ | Me | COOEt | Me | OMe | N |
| 2028 | $Q_{54}$ | H | CN | Me | OMe | CH |
| 2029 | $Q_{54}$ | H | CN | OMe | OMe | CH |
| 2030 | $Q_{54}$ | H | CN | Me | OMe | N |
| 2031 | $Q_{54}$ | H | H | Me | OMe | CH |
| 2032 | $Q_{54}$ | H | H | OMe | OMe | CH |
| 2033 | $Q_{54}$ | H | H | Me | OMe | N |
| 2034 | Me | H | $Q_{54}$ | Me | Me | CH |
| 2035 | Me | H | $Q_{54}$ | Me | OMe | CH |
| 2036 | Me | H | $Q_{54}$ | OMe | OMe | CH |
| 2037 | Me | H | $Q_{54}$ | Me | OMe | N |
| 2038 | Me | H | $Q_{54}$ | OMe | OMe | N |
| 2039 | $Q_{55}$ | H | COOMe | Me | Me | CH |
| 2040 | $Q_{55}$ | H | COOMe | Me | OMe | CH |
| 2041 | $Q_{55}$ | H | COOMe | OMe | OMe | CH |
| 2042 | $Q_{55}$ | H | COOMe | Me | OMe | N |
| 2043 | $Q_{55}$ | H | COOMe | OMe | OMe | N |
| 2044 | $Q_{55}$ | H | COOEt | Me | Me | CH |
| 2045 | $Q_{55}$ | H | COOEt | Me | OMe | CH |
| 2046 | $Q_{55}$ | H | COOEt | OMe | OMe | CH |
| 2047 | $Q_{55}$ | H | COOEt | Me | OMe | N |
| 2048 | $Q_{55}$ | H | COOEt | OMe | OMe | N |
| 2049 | $Q_{55}$ | Me | COOMe | Me | OMe | CH |
| 2050 | $Q_{55}$ | Me | COOMe | OMe | OMe | CH |
| 2051 | $Q_{55}$ | Me | COOMe | Me | OMe | N |
| 2052 | $Q_{55}$ | Me | COOEt | Me | OMe | CH |
| 2053 | $Q_{55}$ | Me | COOEt | OMe | OMe | CH |
| 2054 | $Q_{55}$ | Me | COOEt | Me | OMe | N |
| 2055 | $Q_{55}$ | H | CN | Me | OMe | CH |
| 2056 | $Q_{55}$ | H | CN | OMe | OMe | CH |
| 2057 | $Q_{55}$ | H | CN | Me | OMe | N |
| 2058 | $Q_{55}$ | H | H | Me | OMe | CH |
| 2059 | $Q_{55}$ | H | H | OMe | OMe | CH |
| 2060 | $Q_{55}$ | H | H | Me | OMe | N |
| 2061 | Me | H | $Q_{55}$ | Me | Me | CH |
| 2062 | Me | H | $Q_{55}$ | Me | OMe | CH |
| 2063 | Me | H | $Q_{55}$ | OMe | OMe | CH |
| 2064 | Me | H | $Q_{55}$ | Me | OMe | N |
| 2065 | Me | H | $Q_{55}$ | OMe | OMe | N |
| 2066 | $Q_{56}$ | H | COOMe | Me | Me | CH |
| 2067 | $Q_{56}$ | H | COOMe | Me | OMe | CH |
| 2068 | $Q_{56}$ | H | COOMe | OMe | OMe | CH |
| 2069 | $Q_{56}$ | H | COOMe | Me | OMe | N |
| 2070 | $Q_{56}$ | H | COOMe | OMe | OMe | N |
| 2071 | $Q_{56}$ | H | COOEt | Me | Me | CH |
| 2072 | $Q_{56}$ | H | COOEt | Me | OMe | CH |
| 2073 | $Q_{56}$ | H | COOEt | OMe | OMe | CH |
| 2074 | $Q_{56}$ | H | COOEt | Me | OMe | N |
| 2075 | $Q_{56}$ | H | COOEt | OMe | OMe | N |
| 2076 | $Q_{56}$ | Me | COOMe | Me | OMe | CH |
| 2077 | $Q_{56}$ | Me | COOMe | OMe | OMe | CH |
| 2078 | $Q_{56}$ | Me | COOMe | Me | OMe | N |
| 2079 | $Q_{56}$ | Me | COOEt | Me | OMe | CH |
| 2080 | $Q_{56}$ | Me | COOEt | OMe | OMe | CH |
| 2081 | $Q_{56}$ | Me | COOEt | Me | OMe | N |
| 2082 | $Q_{56}$ | H | CN | Me | OMe | CH |
| 2083 | $Q_{56}$ | H | CN | OMe | OMe | CH |
| 2084 | $Q_{56}$ | H | CN | Me | OMe | N |
| 2085 | $Q_{56}$ | H | H | Me | OMe | CH |
| 2086 | $Q_{56}$ | H | H | OMe | OMe | CH |
| 2087 | $Q_{56}$ | H | H | Me | OMe | N |
| 2088 | Me | H | $Q_{56}$ | Me | Me | CH |
| 2089 | Me | H | $Q_{56}$ | Me | OMe | CH |
| 2090 | Me | H | $Q_{56}$ | OMe | OMe | CH |
| 2091 | Me | H | $Q_{56}$ | Me | OMe | N |

-continued

| | | | | | | |
|---|---|---|---|---|---|---|
| 2092 | Me | H | $Q_{56}$ | OMe | OMe | N |
| 2093 | $Q_{57}$ | H | COOMe | Me | OMe | CH |
| 2094 | $Q_{57}$ | H | COOMe | OMe | OMe | CH |
| 2095 | $Q_{57}$ | H | COOEt | Me | OMe | CH |
| 2096 | $Q_{57}$ | H | COOEt | OMe | OMe | CH |
| 2097 | $Q_{57}$ | Me | COOMe | Me | OMe | CH |
| 2098 | $Q_{57}$ | Me | COOMe | OMe | OMe | CH |
| 2099 | $Q_{57}$ | Me | COOEt | Me | OMe | CH |
| 2100 | $Q_{57}$ | Me | COOEt | OMe | OMe | CH |
| 2101 | $Q_{57}$ | H | H | Me | OMe | CH |
| 2102 | $Q_{57}$ | H | H | OMe | OMe | CH |
| 2103 | Me | H | $Q_{57}$ | Me | OMe | CH |
| 2104 | Me | H | $Q_{57}$ | OMe | OMe | CH |
| 2105 | $Q_{58}$ | H | COOMe | Me | OMe | CH |
| 2106 | $Q_{58}$ | H | COOMe | OMe | OMe | CH |
| 2107 | $Q_{58}$ | H | COOEt | Me | OMe | CH |
| 2108 | $Q_{58}$ | H | COOEt | OMe | OMe | CH |
| 2109 | $Q_{58}$ | Me | COOMe | Me | OMe | CH |
| 2110 | $Q_{58}$ | Me | COOMe | OMe | OMe | CH |
| 2111 | $Q_{58}$ | Me | COOEt | Me | OMe | CH |
| 2112 | $Q_{58}$ | Me | COOEt | OMe | OMe | CH |
| 2113 | $Q_{58}$ | H | H | Me | OMe | CH |
| 2114 | $Q_{58}$ | H | H | OMe | OMe | CH |
| 2115 | Me | H | $Q_{58}$ | Me | OMe | CH |
| 2116 | Me | H | $Q_{58}$ | OMe | OMe | CH |
| 2117 | $Q_{59}$ | H | COOMe | Me | Me | CH |
| 2118 | $Q_{59}$ | H | COOMe | Me | OMe | CH |
| 2119 | $Q_{59}$ | H | COOMe | OMe | OMe | CH |
| 2120 | $Q_{59}$ | H | COOMe | Me | Me | N |
| 2121 | $Q_{59}$ | H | COOMe | Me | OMe | N |
| 2122 | $Q_{59}$ | H | COOMe | OMe | OMe | N |
| 2123 | $Q_{59}$ | H | COOMe | Me | $OCHF_2$ | CH |
| 2124 | $Q_{59}$ | H | COOMe | Cl | OMe | CH |
| 2125 | $Q_{59}$ | H | COOEt | Me | Me | CH |
| 2126 | $Q_{59}$ | H | COOEt | Me | OMe | CH |
| 2127 | $Q_{59}$ | H | COOEt | OMe | OMe | CH |
| 2128 | $Q_{59}$ | H | COOEt | Me | Me | N |
| 2129 | $Q_{59}$ | H | COOEt | Me | OMe | N |
| 2130 | $Q_{59}$ | H | COOEt | OMe | OMe | N |
| 2131 | $Q_{59}$ | H | COOEt | Me | $OCHF_2$ | CH |
| 2132 | $Q_{59}$ | H | COOEt | Cl | OMe | CH |
| 2133 | $Q_{59}$ | H | COOPr—n | Me | OMe | CH |
| 2134 | $Q_{59}$ | H | COOPr—n | OMe | OMe | CH |
| 2135 | $Q_{59}$ | H | COOPr—n | Me | OMe | N |
| 2136 | $Q_{59}$ | H | COOPr—i | Me | OMe | CH |
| 2137 | $Q_{59}$ | H | COOPr—i | OMe | OMe | CH |
| 2138 | $Q_{59}$ | H | COOPr—i | Me | OMe | N |
| 2139 | $Q_{59}$ | H | $COOCH_2CH_2Cl$ | Me | OMe | CH |
| 2140 | $Q_{59}$ | H | $COOCH_2CH_2Cl$ | OMe | OMe | CH |
| 2141 | $Q_{59}$ | H | $COOCH_2CH_2Cl$ | Me | OMe | N |
| 2142 | $Q_{59}$ | H | $COOCH_2CH=CH_2$ | Me | OMe | CH |
| 2143 | $Q_{59}$ | H | $COOCH_2CH=CH_2$ | OMe | OMe | CH |
| 2144 | $Q_{59}$ | H | $COOCH_2CH=CH_2$ | Me | OMe | N |
| 2145 | $Q_{59}$ | H | $COOCH_2C\equiv CH$ | Me | OMe | CH |
| 2146 | $Q_{59}$ | H | $COOCH_2C\equiv CH$ | OMe | OMe | CH |
| 2147 | $Q_{59}$ | H | $COOCH_2C\equiv CH$ | Me | OMe | N |
| 2148 | $Q_{59}$ | Me | COOMe | Me | Me | CH |
| 2149 | $Q_{59}$ | Me | COOMe | Me | OMe | CH |
| 2150 | $Q_{59}$ | Me | COOMe | OMe | OMe | CH |
| 2151 | $Q_{59}$ | Me | COOMe | Me | OMe | N |
| 2152 | $Q_{59}$ | Me | COOMe | OMe | OMe | N |
| 2153 | $Q_{59}$ | Me | COOEt | Me | Me | CH |
| 2154 | $Q_{59}$ | Me | COOEt | Me | OMe | CH |
| 2155 | $Q_{59}$ | Me | COOEt | OMe | OMe | CH |
| 2156 | $Q_{59}$ | Me | COOEt | Me | OMe | N |
| 2157 | $Q_{59}$ | Me | COOEt | OMe | OMe | N |
| 2158 | $Q_{59}$ | Cl | COOMe | Me | OMe | CH |
| 2159 | $Q_{59}$ | Cl | COOMe | OMe | OMe | CH |
| 2160 | $Q_{59}$ | Cl | COOMe | Me | OMe | N |
| 2161 | $Q_{59}$ | Cl | COOEt | Me | OMe | CH |
| 2162 | $Q_{59}$ | Cl | COOEt | OMe | OMe | CH |
| 2163 | $Q_{59}$ | Cl | COOEt | Me | OMe | N |
| 2164 | $Q_{59}$ | OMe | COOMe | Me | OMe | CH |
| 2165 | $Q_{59}$ | OMe | COOMe | OMe | OMe | CH |
| 2166 | $Q_{59}$ | OMe | COOMe | Me | OMe | N |
| 2167 | $Q_{59}$ | OMe | COOEt | Me | OMe | CH |
| 2168 | $Q_{59}$ | OMe | COOEt | OMe | OMe | CH |
| 2169 | $Q_{59}$ | OMe | COOEt | Me | OMe | N |
| 2170 | $Q_{59}$ | H | Cl | Me | OMe | CH |
| 2171 | $Q_{59}$ | H | Cl | OMe | OMe | CH |
| 2172 | $Q_{59}$ | H | Cl | Me | OMe | N |
| 2173 | $Q_{59}$ | H | $NO_2$ | Me | OMe | CH |

-continued

| | | | | | | |
|---|---|---|---|---|---|---|
| 2174 | $Q_{59}$ | H | $NO_2$ | OMe | OMe | CH |
| 2175 | $Q_{59}$ | H | $NO_2$ | Me | OMe | N |
| 2176 | $Q_{59}$ | H | $SO_2NMe_2$ | Me | OMe | CH |
| 2177 | $Q_{59}$ | H | $SO_2NMe_2$ | OMe | OMe | CH |
| 2178 | $Q_{59}$ | H | $SO_2NMe_2$ | Me | OMe | N |
| 2179 | $Q_{59}$ | H | CN | Me | OMe | CH |
| 2180 | $Q_{59}$ | H | CN | OMe | OMe | CH |
| 2181 | $Q_{59}$ | H | CN | Me | OMe | N |
| 2182 | $Q_{59}$ | Me | CN | Me | OMe | CH |
| 2183 | $Q_{59}$ | Me | CN | OMe | OMe | CH |
| 2184 | $Q_{59}$ | Me | CN | Me | OMe | N |
| 2185 | $Q_{59}$ | H | Me | Me | OMe | CH |
| 2186 | $Q_{59}$ | H | Me | OMe | OMe | CH |
| 2187 | $Q_{59}$ | H | Me | Me | OMe | N |
| 2188 | $Q_{59}$ | H | Et | Me | OMe | CH |
| 2189 | $Q_{59}$ | H | Et | OMe | OMe | CH |
| 2190 | $Q_{59}$ | H | Et | Me | OMe | N |
| 2191 | $Q_{59}$ | H | H | Me | OMe | CH |
| 2192 | $Q_{59}$ | H | H | OMe | OMe | CH |
| 2193 | $Q_{59}$ | H | H | Me | OMe | N |
| 2194 | $Q_{59}$ | H | COPh | Me | OMe | CH |
| 2195 | $Q_{59}$ | H | COPh | OMe | OMe | CH |
| 2196 | $Q_{59}$ | H | COPh | Me | OMe | N |
| 2197 | Me | $Q_{59}$ | COOMe | Me | OMe | CH |
| 2198 | Me | $Q_{59}$ | COOMe | OMe | OMe | CH |
| 2199 | Me | $Q_{59}$ | COOMe | Me | OMe | N |
| 2200 | H | H | $Q_{59}$ | Me | OMe | CH |
| 2201 | H | H | $Q_{59}$ | OMe | OMe | CH |
| 2202 | H | H | $Q_{59}$ | Me | OMe | N |
| 2203 | Me | H | $Q_{59}$ | Me | Me | CH |
| 2204 | Me | H | $Q_{59}$ | Me | OMe | CH |
| 2205 | Me | H | $Q_{59}$ | OMe | OMe | CH |
| 2206 | Me | H | $Q_{59}$ | Me | OMe | N |
| 2207 | Me | H | $Q_{59}$ | OMe | OMe | N |
| 2208 | Me | Me | $Q_{59}$ | Me | OMe | CH |
| 2209 | Me | Me | $Q_{59}$ | OMe | OMe | CH |
| 2210 | Me | Me | $Q_{59}$ | Me | OMe | N |
| 2211 | $Q_{60}$ | H | COOMe | Me | Me | CH |
| 2212 | $Q_{60}$ | H | COOMe | Me | OMe | CH |
| 2213 | $Q_{60}$ | H | COOMe | OMe | OMe | CH |
| 2214 | $Q_{60}$ | H | COOMe | Me | OMe | N |
| 2215 | $Q_{60}$ | H | COOMe | OMe | OMe | N |
| 2216 | $Q_{60}$ | H | COOEt | Me | Me | CH |
| 2217 | $Q_{60}$ | H | COOEt | Me | OMe | CH |
| 2218 | $Q_{60}$ | H | COOEt | OMe | OMe | CH |
| 2219 | $Q_{60}$ | H | COOEt | Me | OMe | N |
| 2220 | $Q_{60}$ | H | COOEt | OMe | OMe | N |
| 2221 | $Q_{60}$ | Me | COOMe | Me | OMe | CH |
| 2222 | $Q_{60}$ | Me | COOMe | OMe | OMe | CH |
| 2223 | $Q_{60}$ | Me | COOMe | Me | OMe | N |
| 2224 | $Q_{60}$ | Me | COOEt | Me | OMe | CH |
| 2225 | $Q_{60}$ | Me | COOEt | OMe | OMe | CH |
| 2226 | $Q_{60}$ | Me | COOEt | Me | OMe | N |
| 2227 | $Q_{60}$ | H | CN | Me | OMe | CH |
| 2228 | $Q_{60}$ | H | CN | OMe | OMe | CH |
| 2229 | $Q_{60}$ | H | CN | Me | OMe | N |
| 2230 | $Q_{60}$ | H | H | Me | OMe | CH |
| 2231 | $Q_{60}$ | H | H | OMe | OMe | CH |
| 2232 | $Q_{60}$ | H | H | Me | OMe | N |
| 2233 | Me | H | $Q_{60}$ | Me | Me | CH |
| 2234 | Me | H | $Q_{60}$ | Me | OMe | CH |
| 2235 | Me | H | $Q_{60}$ | OMe | OMe | CH |
| 2236 | Me | H | $Q_{60}$ | Me | OMe | N |
| 2237 | Me | H | $Q_{60}$ | OMe | OMe | N |
| 2238 | $Q_{61}$ | H | COOMe | Me | Me | CH |
| 2239 | $Q_{61}$ | H | COOMe | Me | OMe | CH |
| 2240 | $Q_{61}$ | H | COOMe | OMe | OMe | CH |
| 2241 | $Q_{61}$ | H | COOMe | Me | OMe | N |
| 2242 | $Q_{61}$ | H | COOMe | OMe | OMe | N |
| 2243 | $Q_{61}$ | H | COOEt | Me | Me | CH |
| 2244 | $Q_{61}$ | H | COOEt | Me | OMe | CH |
| 2245 | $Q_{61}$ | H | COOEt | OMe | OMe | CH |
| 2246 | $Q_{61}$ | H | COOEt | Me | OMe | N |
| 2247 | $Q_{61}$ | H | COOEt | OMe | OMe | N |
| 2248 | $Q_{61}$ | Me | COOMe | Me | OMe | CH |
| 2249 | $Q_{61}$ | Me | COOMe | OMe | OMe | CH |
| 2250 | $Q_{61}$ | Me | COOMe | Me | OMe | N |
| 2251 | $Q_{61}$ | Me | COOEt | Me | OMe | CH |
| 2252 | $Q_{61}$ | Me | COOEt | OMe | OMe | CH |
| 2253 | $Q_{61}$ | Me | COOEt | Me | OMe | N |
| 2254 | $Q_{61}$ | H | CN | Me | OMe | CH |
| 2255 | $Q_{61}$ | H | CN | OMe | OMe | CH |

-continued

| | | | | | | |
|---|---|---|---|---|---|---|
| 2256 | $Q_{61}$ | H | CN | Me | OMe | N |
| 2257 | $Q_{61}$ | H | H | Me | OMe | CH |
| 2258 | $Q_{61}$ | H | H | OMe | OMe | CH |
| 2259 | $Q_{61}$ | H | H | Me | OMe | N |
| 2260 | Me | H | $Q_{61}$ | Me | Me | CH |
| 2261 | Me | H | $Q_{61}$ | Me | OMe | CH |
| 2262 | Me | H | $Q_{61}$ | OMe | OMe | CH |
| 2263 | Me | H | $Q_{61}$ | Me | OMe | N |
| 2264 | Me | H | $Q_{61}$ | OMe | OMe | N |
| 2265 | $Q_{62}$ | H | COOMe | Me | Me | CH |
| 2266 | $Q_{62}$ | H | COOMe | Me | OMe | CH |
| 2267 | $Q_{62}$ | H | COOMe | OMe | OMe | CH |
| 2268 | $Q_{62}$ | H | COOMe | Me | OMe | N |
| 2269 | $Q_{62}$ | H | COOMe | OMe | OMe | N |
| 2270 | $Q_{62}$ | H | COOEt | Me | Me | CH |
| 2271 | $Q_{62}$ | H | COOEt | Me | OMe | CH |
| 2272 | $Q_{62}$ | H | COOEt | OMe | OMe | CH |
| 2273 | $Q_{62}$ | H | COOEt | Me | OMe | N |
| 2274 | $Q_{62}$ | H | COOEt | OMe | OMe | N |
| 2275 | $Q_{62}$ | Me | COOMe | Me | OMe | CH |
| 2276 | $Q_{62}$ | Me | COOMe | OMe | OMe | CH |
| 2277 | $Q_{62}$ | Me | COOMe | Me | OMe | N |
| 2278 | $Q_{62}$ | Me | COOEt | Me | OMe | CH |
| 2279 | $Q_{62}$ | Me | COOEt | OMe | OMe | CH |
| 2280 | $Q_{62}$ | Me | COOEt | Me | OMe | N |
| 2281 | $Q_{62}$ | H | CN | Me | OMe | CH |
| 2282 | $Q_{62}$ | H | CN | OMe | OMe | CH |
| 2283 | $Q_{62}$ | H | CN | Me | OMe | N |
| 2284 | $Q_{62}$ | H | H | Me | OMe | CH |
| 2285 | $Q_{62}$ | H | H | OMe | OMe | CH |
| 2286 | $Q_{62}$ | H | H | Me | OMe | N |
| 2287 | Me | H | $Q_{62}$ | Me | Me | CH |
| 2288 | Me | H | $Q_{62}$ | Me | OMe | CH |
| 2289 | Me | H | $Q_{62}$ | OMe | OMe | CH |
| 2290 | Me | H | $Q_{62}$ | Me | OMe | N |
| 2291 | Me | H | $Q_{62}$ | OMe | OMe | N |
| 2292 | $Q_{63}$ | H | COOMe | Me | OMe | CH |
| 2293 | $Q_{63}$ | H | COOMe | OMe | OMe | CH |
| 2294 | $Q_{63}$ | H | COOEt | Me | OMe | CH |
| 2295 | $Q_{63}$ | H | COOEt | OMe | OMe | CH |
| 2296 | $Q_{63}$ | Me | COOMe | Me | OMe | CH |
| 2297 | $Q_{63}$ | Me | COOMe | OMe | OMe | CH |
| 2298 | $Q_{63}$ | Me | COOEt | Me | OMe | CH |
| 2299 | $Q_{63}$ | Me | COOEt | OMe | OMe | CH |
| 2300 | $Q_{63}$ | H | H | Me | OMe | CH |
| 2301 | $Q_{63}$ | H | H | OMe | OMe | CH |
| 2302 | Me | H | $Q_{63}$ | Me | OMe | CH |
| 2303 | Me | H | $Q_{63}$ | OMe | OMe | CH |
| 2304 | $Q_{64}$ | H | COOMe | Me | OMe | CH |
| 2305 | $Q_{64}$ | H | COOMe | OMe | OMe | CH |
| 2306 | $Q_{64}$ | H | COOEt | Me | OMe | CH |
| 2307 | $Q_{64}$ | H | COOEt | OMe | OMe | CH |
| 2308 | $Q_{64}$ | Me | COOMe | Me | OMe | CH |
| 2309 | $Q_{64}$ | Me | COOMe | OMe | OMe | CH |
| 2310 | $Q_{64}$ | Me | COOEt | Me | OMe | CH |
| 2311 | $Q_{64}$ | Me | COOEt | OMe | OMe | CH |
| 2312 | $Q_{64}$ | H | H | Me | OMe | CH |
| 2313 | $Q_{64}$ | H | H | OMe | OMe | CH |
| 2314 | Me | H | $Q_{64}$ | Me | OMe | CH |
| 2315 | Me | H | $Q_{64}$ | OMe | OMe | CH |
| 2316 | $Q_{65}$ | H | COOMe | Me | Me | CH |
| 2317 | $Q_{65}$ | H | COOMe | Me | OMe | CH |
| 2318 | $Q_{65}$ | H | COOMe | OMe | OMe | CH |
| 2319 | $Q_{65}$ | H | COOMe | Me | OMe | N |
| 2320 | $Q_{65}$ | H | COOMe | OMe | OMe | N |
| 2321 | $Q_{65}$ | H | COOEt | Me | Me | CH |
| 2322 | $Q_{65}$ | H | COOEt | Me | OMe | CH |
| 2323 | $Q_{65}$ | H | COOEt | OMe | OMe | CH |
| 2324 | $Q_{65}$ | H | COOEt | Me | OMe | N |
| 2325 | $Q_{65}$ | H | COOEt | OMe | OMe | N |
| 2326 | $Q_{65}$ | Me | COOMe | Me | OMe | CH |
| 2327 | $Q_{65}$ | Me | COOMe | OMe | OMe | CH |
| 2328 | $Q_{65}$ | Me | COOMe | Me | OMe | N |
| 2329 | $Q_{65}$ | Me | COOEt | Me | OMe | CH |
| 2330 | $Q_{65}$ | Me | COOEt | OMe | OMe | CH |
| 2331 | $Q_{65}$ | Me | COOEt | Me | OMe | N |
| 2332 | $Q_{65}$ | H | CN | Me | OMe | CH |
| 2333 | $Q_{65}$ | H | CN | OMe | OMe | CH |
| 2334 | $Q_{65}$ | H | CN | Me | OMe | N |
| 2335 | $Q_{65}$ | H | H | Me | OMe | CH |
| 2336 | $Q_{65}$ | H | H | OMe | OMe | CH |
| 2337 | $Q_{65}$ | H | H | Me | OMe | N |

-continued

| | | | | | | |
|---|---|---|---|---|---|---|
| 2338 | Me | H | $Q_{65}$ | Me | Me | CH |
| 2339 | Me | H | $Q_{65}$ | Me | OMe | CH |
| 2340 | Me | H | $Q_{65}$ | OMe | OMe | CH |
| 2341 | Me | H | $Q_{65}$ | Me | OMe | N |
| 2342 | Me | H | $Q_{65}$ | OMe | OMe | N |
| 2343 | $Q_{66}$ | H | COOMe | Me | OMe | CH |
| 2344 | $Q_{66}$ | H | COOMe | OMe | OMe | CH |
| 2345 | $Q_{66}$ | H | COOEt | Me | OMe | CH |
| 2346 | $Q_{66}$ | H | COOEt | OMe | OMe | CH |
| 2347 | $Q_{66}$ | Me | COOMe | Me | OMe | CH |
| 2348 | $Q_{66}$ | Me | COOMe | OMe | OMe | CH |
| 2349 | $Q_{66}$ | Me | COOEt | Me | OMe | CH |
| 2350 | $Q_{66}$ | Me | COOEt | OMe | OMe | CH |
| 2351 | $Q_{66}$ | H | H | Me | OMe | CH |
| 2352 | $Q_{66}$ | H | H | OMe | OMe | CH |
| 2353 | Me | H | $Q_{66}$ | Me | OMe | CH |
| 2354 | Me | H | $Q_{66}$ | OMe | OMe | CH |
| 2355 | $Q_{67}$ | H | COOMe | Me | OMe | CH |
| 2356 | $Q_{67}$ | H | COOMe | OMe | OMe | CH |
| 2357 | $Q_{67}$ | H | COOEt | Me | OMe | CH |
| 2358 | $Q_{67}$ | H | COOEt | OMe | OMe | CH |
| 2359 | $Q_{67}$ | Me | COOMe | Me | OMe | CH |
| 2360 | $Q_{67}$ | Me | COOMe | OMe | OMe | CH |
| 2361 | $Q_{67}$ | Me | COOEt | Me | OMe | CH |
| 2362 | $Q_{67}$ | Me | COOEt | OMe | OMe | CH |
| 2363 | $Q_{67}$ | H | H | Me | OMe | CH |
| 2364 | $Q_{67}$ | H | H | OMe | OMe | CH |
| 2365 | Me | H | $Q_{67}$ | Me | OMe | CH |
| 2366 | Me | H | $Q_{67}$ | OMe | OMe | CH |
| 2367 | $Q_{68}$ | H | COOMe | Me | OMe | CH |
| 2368 | $Q_{68}$ | H | COOMe | OMe | OMe | CH |
| 2369 | $Q_{68}$ | H | COOEt | Me | OMe | CH |
| 2370 | $Q_{68}$ | H | COOEt | OMe | OMe | CH |
| 2371 | $Q_{68}$ | Me | COOMe | Me | OMe | CH |
| 2372 | $Q_{68}$ | Me | COOMe | OMe | OMe | CH |
| 2373 | $Q_{68}$ | Me | COOEt | Me | OMe | CH |
| 2374 | $Q_{68}$ | Me | COOEt | OMe | OMe | CH |
| 2375 | $Q_{68}$ | H | H | Me | OMe | CH |
| 2376 | $Q_{68}$ | H | H | OMe | OMe | CH |
| 2377 | Me | H | $Q_{68}$ | Me | OMe | CH |
| 2378 | Me | H | $Q_{68}$ | Me | OMe | CH |
| 2379 | $Q_{69}$ | H | COOMe | Me | OMe | CH |
| 2380 | $Q_{69}$ | H | COOMe | OMe | OMe | CH |
| 2381 | $Q_{69}$ | H | COOEt | Me | OMe | CH |
| 2382 | $Q_{69}$ | H | COOEt | OMe | OMe | CH |
| 2383 | $Q_{69}$ | Me | COOMe | Me | OMe | CH |
| 2384 | $Q_{69}$ | Me | COOMe | OMe | OMe | CH |
| 2385 | $Q_{69}$ | Me | COOEt | Me | OMe | CH |
| 2386 | $Q_{69}$ | Me | COOEt | OMe | OMe | CH |
| 2387 | $Q_{69}$ | H | H | Me | OMe | CH |
| 2388 | $Q_{69}$ | H | H | OMe | OMe | CH |
| 2389 | Me | H | $Q_{69}$ | Me | OMe | CH |
| 2390 | Me | H | $Q_{69}$ | OMe | OMe | CH |
| 2391 | $Q_{70}$ | H | COOMe | Me | Me | CH |
| 2392 | $Q_{70}$ | H | COOMe | Me | OMe | CH |
| 2393 | $Q_{70}$ | H | COOMe | OMe | OMe | CH |
| 2394 | $Q_{70}$ | H | COOMe | Me | OMe | N |
| 2395 | $Q_{70}$ | H | COOMe | OMe | OMe | N |
| 2396 | $Q_{70}$ | H | COOEt | Me | Me | CH |
| 2397 | $Q_{70}$ | H | COOEt | Me | OMe | CH |
| 2398 | $Q_{70}$ | H | COOEt | OMe | OMe | CH |
| 2399 | $Q_{70}$ | H | COOEt | Me | OMe | N |
| 2400 | $Q_{70}$ | H | COOEt | OMe | OMe | N |
| 2401 | $Q_{70}$ | Me | COOMe | Me | OMe | CH |
| 2402 | $Q_{70}$ | Me | COOMe | OMe | OMe | CH |
| 2403 | $Q_{70}$ | Me | COOMe | Me | OMe | N |
| 2404 | $Q_{70}$ | Me | COOEt | Me | OMe | CH |
| 2405 | $Q_{70}$ | Me | COOEt | OMe | OMe | CH |
| 2406 | $Q_{70}$ | Me | COOEt | Me | OMe | N |
| 2407 | $Q_{70}$ | H | CN | Me | OMe | CH |
| 2408 | $Q_{70}$ | H | CN | OMe | OMe | CH |
| 2409 | $Q_{70}$ | H | CN | Me | OMe | N |
| 2410 | $Q_{70}$ | H | H | Me | OMe | CH |
| 2411 | $Q_{70}$ | H | H | OMe | OMe | CH |
| 2412 | $Q_{70}$ | H | H | Me | OMe | N |
| 2413 | Me | H | $Q_{70}$ | Me | Me | CH |
| 2414 | Me | H | $Q_{70}$ | Me | OMe | CH |
| 2415 | Me | H | $Q_{70}$ | OMe | OMe | CH |
| 2416 | Me | H | $Q_{70}$ | Me | OMe | N |
| 2417 | Me | H | $Q_{70}$ | OMe | OMe | N |
| 2418 | $Q_{71}$ | H | COOMe | Me | OMe | CH |
| 2419 | $Q_{71}$ | H | COOMe | OMe | OMe | CH |

-continued

| | | | | | | |
|---|---|---|---|---|---|---|
| 2420 | $Q_{71}$ | H | COOEt | Me | OMe | CH |
| 2421 | $Q_{71}$ | H | COOEt | OMe | OMe | CH |
| 2422 | $Q_{71}$ | Me | COOMe | Me | OMe | CH |
| 2423 | $Q_{71}$ | Me | COOMe | OMe | OMe | CH |
| 2424 | $Q_{71}$ | Me | COOEt | Me | OMe | CH |
| 2425 | $Q_{71}$ | Me | COOEt | OMe | OMe | CH |
| 2426 | $Q_{71}$ | H | H | Me | OMe | CH |
| 2427 | $Q_{71}$ | H | H | OMe | OMe | CH |
| 2428 | Me | H | $Q_{71}$ | Me | OMe | CH |
| 2429 | Me | H | $Q_{71}$ | OMe | OMe | CH |
| 2430 | $Q_{72}$ | H | COOMe | Me | OMe | CH |
| 2431 | $Q_{72}$ | H | COOMe | OMe | OMe | CH |
| 2432 | $Q_{72}$ | H | COOEt | Me | OMe | CH |
| 2433 | $Q_{72}$ | H | COOEt | OMe | OMe | CH |
| 2434 | $Q_{72}$ | Me | COOMe | Me | OMe | CH |
| 2435 | $Q_{72}$ | Me | COOMe | OMe | OMe | CH |
| 2436 | $Q_{72}$ | Me | COOEt | Me | OMe | CH |
| 2437 | $Q_{72}$ | Me | COOEt | OMe | OMe | CH |
| 2438 | $Q_{72}$ | H | H | Me | OMe | CH |
| 2439 | $Q_{72}$ | H | H | OMe | OMe | CH |
| 2440 | Me | H | $Q_{72}$ | Me | OMe | CH |
| 2441 | Me | H | $Q_{72}$ | OMe | OMe | CH |
| 2442 | $Q_{73}$ | H | COOMe | Me | OMe | CH |
| 2443 | $Q_{73}$ | H | COOMe | OMe | OMe | CH |
| 2444 | $Q_{73}$ | H | COOEt | Me | OMe | CH |
| 2445 | $Q_{73}$ | H | COOEt | OMe | OMe | CH |
| 2446 | $Q_{73}$ | Me | COOMe | Me | OMe | CH |
| 2447 | $Q_{73}$ | Me | COOMe | OMe | OMe | CH |
| 2448 | $Q_{73}$ | Me | COOEt | Me | OMe | CH |
| 2449 | $Q_{73}$ | Me | COOEt | OMe | OMe | CH |
| 2450 | $Q_{73}$ | H | H | Me | OMe | CH |
| 2451 | $Q_{73}$ | H | H | OMe | OMe | CH |
| 2452 | Me | H | $Q_{73}$ | Me | OMe | CH |
| 2453 | Me | H | $Q_{73}$ | OMe | OMe | CH |
| 2454 | $Q_{74}$ | H | COOMe | Me | OMe | CH |
| 2455 | $Q_{74}$ | H | COOMe | OMe | OMe | CH |
| 2456 | $Q_{74}$ | H | COOEt | Me | OMe | CH |
| 2457 | $Q_{74}$ | H | COOEt | OMe | OMe | CH |
| 2458 | $Q_{74}$ | Me | COOMe | Me | OMe | CH |
| 2459 | $Q_{74}$ | Me | COOMe | OMe | OMe | CH |
| 2460 | $Q_{74}$ | Me | COOEt | Me | OMe | CH |
| 2461 | $Q_{74}$ | Me | COOEt | OMe | OMe | CH |
| 2462 | $Q_{74}$ | H | H | Me | OMe | CH |
| 2463 | $Q_{74}$ | H | H | OMe | OMe | CH |
| 2464 | Me | H | $Q_{74}$ | Me | OMe | CH |
| 2465 | Me | H | $Q_{74}$ | OMe | OMe | CH |
| 2466 | $Q_{75}$ | H | COOMe | Me | OMe | CH |
| 2467 | $Q_{75}$ | H | COOMe | OMe | OMe | CH |
| 2468 | $Q_{75}$ | H | COOEt | Me | OMe | CH |
| 2469 | $Q_{75}$ | H | COOEt | OMe | OMe | CH |
| 2470 | $Q_{75}$ | Me | COOMe | Me | OMe | CH |
| 2471 | $Q_{75}$ | Me | COOMe | OMe | OMe | CH |
| 2472 | $Q_{75}$ | Me | COOEt | Me | OMe | CH |
| 2473 | $Q_{75}$ | Me | COOEt | OMe | OMe | CH |
| 2474 | $Q_{75}$ | H | H | Me | OMe | CH |
| 2475 | $Q_{75}$ | H | H | OMe | OMe | CH |
| 2476 | Me | H | $Q_{75}$ | Me | OMe | CH |
| 2477 | Me | H | $Q_{75}$ | OMe | OMe | CH |
| 2478 | $Q_{76}$ | H | COOMe | Me | OMe | CH |
| 2479 | $Q_{76}$ | H | COOMe | OMe | OMe | CH |
| 2480 | $Q_{76}$ | H | COOEt | Me | OMe | CH |
| 2481 | $Q_{76}$ | H | COOEt | OMe | OMe | CH |
| 2482 | $Q_{76}$ | Me | COOMe | Me | OMe | CH |
| 2483 | $Q_{76}$ | Me | COOMe | OMe | OMe | CH |
| 2484 | $Q_{76}$ | Me | COOEt | Me | OMe | CH |
| 2485 | $Q_{76}$ | Me | COOEt | OMe | OMe | CH |
| 2486 | $Q_{76}$ | H | H | Me | OMe | CH |
| 2487 | $Q_{76}$ | H | H | OMe | OMe | CH |
| 2488 | Me | H | $Q_{76}$ | Me | OMe | CH |
| 2489 | Me | H | $Q_{76}$ | OMe | OMe | CH |
| 5347 | $Q_{10}$ | Me | COOMe | Me | Me | CH |
| 5348 | $Q_{77}$ | H | COOMe | Me | OMe | CH |
| 5349 | $Q_{77}$ | H | COOMe | OMe | OMe | CH |
| 5350 | $Q_{77}$ | H | COOEt | Me | OMe | CH |
| 5351 | $Q_{77}$ | H | COOEt | OMe | OMe | CH |
| 5352 | $Q_{77}$ | Me | COOMe | Me | OMe | CH |
| 5353 | $Q_{77}$ | Me | COOMe | OMe | OMe | CH |
| 5354 | $Q_{77}$ | Me | COOEt | Me | OMe | CH |
| 5355 | $Q_{77}$ | Me | COOEt | OMe | OMe | CH |
| 5356 | $Q_{77}$ | H | H | Me | OMe | CH |
| 5357 | $Q_{77}$ | H | H | OMe | OMe | CH |
| 5358 | Me | H | $Q_{77}$ | Me | OMe | CH |

-continued

| | | | | | | |
|---|---|---|---|---|---|---|
| 5359 | Me | H | $Q_{77}$ | OMe | OMe | CH |
| 5360 | $Q_{78}$ | H | COOMe | Me | Me | CH |
| 5361 | $Q_{78}$ | H | COOMe | Me | OMe | CH |
| 5362 | $Q_{78}$ | H | COOMe | OMe | OMe | CH |
| 5363 | $Q_{78}$ | H | COOMe | Me | Me | N |
| 5364 | $Q_{78}$ | H | COOMe | Me | OMe | N |
| 5365 | $Q_{78}$ | H | COOMe | OMe | OMe | N |
| 5366 | $Q_{78}$ | H | COOMe | Me | $OCHF_2$ | CH |
| 5367 | $Q_{78}$ | H | COOMe | Cl | OMe | CH |
| 5368 | $Q_{78}$ | H | COOEt | Me | Me | CH |
| 5369 | $Q_{78}$ | H | COOEt | Me | OMe | CH |
| 5370 | $Q_{78}$ | H | COOEt | OMe | OMe | CH |
| 5371 | $Q_{78}$ | H | COOEt | Me | Me | N |
| 5372 | $Q_{78}$ | H | COOEt | Me | OMe | N |
| 5373 | $Q_{78}$ | H | COOEt | OMe | OMe | N |
| 5374 | $Q_{78}$ | H | COOEt | Me | $OCHF_2$ | CH |
| 5375 | $Q_{78}$ | H | COOEt | Cl | OMe | CH |
| 5376 | $Q_{78}$ | H | COOPr—n | Me | OMe | CH |
| 5377 | $Q_{78}$ | H | COOPr—n | OMe | OMe | CH |
| 5378 | $Q_{78}$ | H | COOPr—n | Me | OMe | N |
| 5379 | $Q_{78}$ | H | COOPr—i | Me | OMe | CH |
| 5380 | $Q_{78}$ | H | COOPr—i | OMe | OMe | CH |
| 5381 | $Q_{78}$ | H | COOPr—i | Me | OMe | N |
| 5382 | $Q_{78}$ | H | $COOCH_2CH_2Cl$ | Me | OMe | CH |
| 5383 | $Q_{78}$ | H | $COOCH_2CH_2Cl$ | OMe | OMe | CH |
| 5384 | $Q_{78}$ | H | $COOCH_2CH_2Cl$ | Me | OMe | N |
| 5385 | $Q_{78}$ | H | $COOCH_2CH{=}CH_2$ | Me | OMe | CH |
| 5386 | $Q_{78}$ | H | $COOCH_2CH{=}CH_2$ | OMe | OMe | CH |
| 5387 | $Q_{78}$ | H | $COOCH_2CH{=}CH_2$ | Me | OMe | N |
| 5388 | $Q_{78}$ | H | $COOCH_2C{\equiv}CH$ | Me | OMe | CH |
| 5389 | $Q_{78}$ | H | $COOCH_2C{\equiv}CH$ | OMe | OMe | CH |
| 5390 | $Q_{78}$ | H | $COOCH_2C{\equiv}CH$ | Me | OMe | N |
| 5391 | $Q_{78}$ | Me | COOMe | Me | Me | CH |
| 5392 | $Q_{78}$ | Me | COOMe | Me | OMe | CH |
| 5393 | $Q_{78}$ | Me | COOMe | OMe | OMe | CH |
| 5394 | $Q_{78}$ | Me | COOMe | Me | OMe | N |
| 5395 | $Q_{78}$ | Me | COOMe | OMe | OMe | N |
| 5396 | $Q_{78}$ | Me | COOEt | Me | Me | CH |
| 5397 | $Q_{78}$ | Me | COOEt | Me | OMe | CH |
| 5398 | $Q_{78}$ | Me | COOEt | OMe | OMe | CH |
| 5399 | $Q_{78}$ | Me | COOEt | Me | OMe | N |
| 5400 | $Q_{78}$ | Me | COOEt | OMe | OMe | N |
| 5401 | $Q_{78}$ | Cl | COOMe | Me | OMe | CH |
| 5402 | $Q_{78}$ | Cl | COOMe | OMe | OMe | CH |
| 5403 | $Q_{78}$ | Cl | COOMe | Me | OMe | N |
| 5404 | $Q_{78}$ | Cl | COOEt | Me | OMe | CH |
| 5405 | $Q_{78}$ | Cl | COOEt | OMe | OMe | CH |
| 5406 | $Q_{78}$ | Cl | COOEt | Me | OMe | N |
| 5407 | $Q_{78}$ | OMe | COOMe | Me | OMe | CH |
| 5408 | $Q_{78}$ | OMe | COOMe | OMe | OMe | CH |
| 5409 | $Q_{78}$ | OMe | COOMe | Me | OMe | N |
| 5410 | $Q_{78}$ | OMe | COOEt | Me | OMe | CH |
| 5411 | $Q_{78}$ | OMe | COOEt | OMe | OMe | CH |
| 5412 | $Q_{78}$ | OMe | COOEt | Me | OMe | N |
| 5413 | $Q_{78}$ | H | Cl | Me | OMe | CH |
| 5414 | $Q_{78}$ | H | Cl | OMe | OMe | CH |
| 5415 | $Q_{78}$ | H | Cl | Me | OMe | N |
| 5416 | $Q_{78}$ | H | $NO_2$ | Me | OMe | CH |
| 5417 | $Q_{78}$ | H | $NO_2$ | OMe | OMe | CH |
| 5418 | $Q_{78}$ | H | $NO_2$ | Me | OMe | N |
| 5419 | $Q_{78}$ | H | $SO_2NMe_2$ | Me | OMe | CH |
| 5420 | $Q_{78}$ | H | $SO_2NMe_2$ | OMe | OMe | CH |
| 5421 | $Q_{78}$ | H | $SO_2NMe_2$ | Me | OMe | N |
| 5422 | $Q_{78}$ | H | CN | Me | OMe | CH |
| 5423 | $Q_{78}$ | H | CN | OMe | OMe | CH |
| 5424 | $Q_{78}$ | H | CN | Me | OMe | N |
| 5425 | $Q_{78}$ | Me | CN | Me | OMe | CH |
| 5426 | $Q_{78}$ | Me | CN | OMe | OMe | CH |
| 5427 | $Q_{78}$ | Me | CN | Me | OMe | N |
| 5428 | $Q_{78}$ | H | Me | Me | OMe | CH |
| 5429 | $Q_{78}$ | H | Me | OMe | OMe | CH |
| 5430 | $Q_{78}$ | H | Me | Me | OMe | N |
| 5431 | $Q_{78}$ | H | Et | Me | OMe | CH |
| 5432 | $Q_{78}$ | H | Et | OMe | OMe | CH |
| 5433 | $Q_{78}$ | H | Et | Me | OMe | N |
| 5434 | $Q_{78}$ | H | H | Me | OMe | CH |
| 5435 | $Q_{78}$ | H | H | OMe | OMe | CH |
| 5436 | $Q_{78}$ | H | H | Me | OMe | N |
| 5437 | $Q_{78}$ | H | COPh | Me | OMe | CH |
| 5438 | $Q_{78}$ | H | COPh | OMe | OMe | CH |
| 5439 | $Q_{78}$ | H | COPh | Me | OMe | N |
| 5440 | Me | $Q_{78}$ | COOMe | Me | OMe | CH |

-continued

| | | | | | | |
|---|---|---|---|---|---|---|
| 5441 | Me | $Q_{78}$ | COOMe | OMe | OMe | CH |
| 5442 | Me | $Q_{78}$ | COOMe | Me | OMe | N |
| 5443 | H | H | $Q_{78}$ | Me | OMe | CH |
| 5444 | H | H | $Q_{78}$ | OMe | OMe | CH |
| 5445 | H | H | $Q_{78}$ | Me | OMe | N |
| 5446 | Me | H | $Q_{78}$ | Me | Me | CH |
| 5447 | Me | H | $Q_{78}$ | Me | OMe | CH |
| 5448 | Me | H | $Q_{78}$ | OMe | OMe | CH |
| 5449 | Me | H | $Q_{78}$ | Me | OMe | N |
| 5450 | Me | H | $Q_{78}$ | OMe | OMe | N |
| 5451 | Me | Me | $Q_{78}$ | Me | OMe | CH |
| 5452 | Me | Me | $Q_{78}$ | OMe | OMe | CH |
| 5453 | Me | Me | $Q_{78}$ | Me | OMe | N |
| 5454 | $Q_{79}$ | H | COOMe | Me | Me | CH |
| 5455 | $Q_{79}$ | H | COOMe | Me | OMe | CH |
| 5456 | $Q_{79}$ | H | COOMe | OMe | OMe | CH |
| 5457 | $Q_{79}$ | H | COOMe | Me | Me | N |
| 5458 | $Q_{79}$ | H | COOMe | Me | OMe | N |
| 5459 | $Q_{79}$ | H | COOMe | OMe | OMe | N |
| 5460 | $Q_{79}$ | H | COOMe | Me | $OCHF_2$ | CH |
| 5461 | $Q_{79}$ | H | COOMe | Cl | OMe | CH |
| 5462 | $Q_{79}$ | H | COOEt | Me | Me | CH |
| 5463 | $Q_{79}$ | H | COOEt | Me | OMe | CH |
| 5464 | $Q_{79}$ | H | COOEt | OMe | OMe | CH |
| 5465 | $Q_{79}$ | H | COOEt | Me | Me | N |
| 5466 | $Q_{79}$ | H | COOEt | Me | OMe | N |
| 5467 | $Q_{79}$ | H | COOEt | OMe | OMe | N |
| 5468 | $Q_{79}$ | H | COOEt | Me | $OCHF_2$ | CH |
| 5469 | $Q_{79}$ | H | COOEt | Cl | OMe | CH |
| 5470 | $Q_{79}$ | H | COOPr—n | Me | OMe | CH |
| 5471 | $Q_{79}$ | H | COOPr—n | OMe | OMe | CH |
| 5472 | $Q_{79}$ | H | COOPr—n | Me | OMe | N |
| 5473 | $Q_{79}$ | H | COOPr—i | Me | OMe | CH |
| 5474 | $Q_{79}$ | H | COOPr—i | OMe | OMe | CH |
| 5475 | $Q_{79}$ | H | COOPr—i | Me | OMe | N |
| 5476 | $Q_{79}$ | H | $COOCH_2CH_2Cl$ | Me | OMe | CH |
| 5477 | $Q_{79}$ | H | $COOCH_2CH_2Cl$ | OMe | OMe | CH |
| 5478 | $Q_{79}$ | H | $COOCH_2CH_2Cl$ | Me | OMe | N |
| 5479 | $Q_{79}$ | H | $COOCH_2CH{=}CH_2$ | Me | OMe | CH |
| 5480 | $Q_{79}$ | H | $COOCH_2CH{=}CH_2$ | OMe | OMe | CH |
| 5481 | $Q_{79}$ | H | $COOCH_2CH{=}CH_2$ | Me | OMe | N |
| 5482 | $Q_{79}$ | H | $COOCH_2C{\equiv}CH$ | Me | OMe | CH |
| 5483 | $Q_{79}$ | H | $COOCH_2C{\equiv}CH$ | OMe | OMe | CH |
| 5484 | $Q_{79}$ | H | $COOCH_2C{\equiv}CH$ | Me | OMe | N |
| 5485 | $Q_{79}$ | Me | COOMe | Me | Me | CH |
| 5486 | $Q_{79}$ | Me | COOMe | Me | OMe | CH |
| 5487 | $Q_{79}$ | Me | COOMe | OMe | OMe | CH |
| 5488 | $Q_{79}$ | Me | COOMe | Me | OMe | N |
| 5489 | $Q_{79}$ | Me | COOMe | OMe | OMe | N |
| 5490 | $Q_{79}$ | Me | COOEt | Me | Me | CH |
| 5491 | $Q_{79}$ | Me | COOEt | Me | OMe | CH |
| 5492 | $Q_{79}$ | Me | COOEt | OMe | OMe | CH |
| 5493 | $Q_{79}$ | Me | COOEt | Me | OMe | N |
| 5494 | $Q_{79}$ | Me | COOEt | OMe | OMe | N |
| 5495 | $Q_{79}$ | Cl | COOMe | Me | OMe | CH |
| 5496 | $Q_{79}$ | Cl | COOMe | OMe | OMe | CH |
| 5497 | $Q_{79}$ | Cl | COOMe | Me | OMe | N |
| 5498 | $Q_{79}$ | Cl | COOEt | Me | OMe | CH |
| 5499 | $Q_{79}$ | Cl | COOEt | OMe | OMe | CH |
| 5500 | $Q_{79}$ | Cl | COOEt | Me | OMe | N |
| 5501 | $Q_{79}$ | OMe | COOMe | Me | OMe | CH |
| 5502 | $Q_{79}$ | OMe | COOMe | OMe | OMe | CH |
| 5503 | $Q_{79}$ | OMe | COOMe | Me | OMe | N |
| 5504 | $Q_{79}$ | OMe | COOEt | Me | OMe | CH |
| 5505 | $Q_{79}$ | OMe | COOEt | OMe | OMe | CH |
| 5506 | $Q_{79}$ | OMe | COOEt | Me | OMe | N |
| 5507 | $Q_{79}$ | H | Cl | Me | OMe | CH |
| 5508 | $Q_{79}$ | H | Cl | OMe | OMe | CH |
| 5509 | $Q_{79}$ | H | Cl | Me | OMe | N |
| 5510 | $Q_{79}$ | H | $NO_2$ | Me | OMe | CH |
| 5511 | $Q_{79}$ | H | $NO_2$ | OMe | OMe | CH |
| 5512 | $Q_{79}$ | H | $NO_2$ | Me | OMe | N |
| 5513 | $Q_{79}$ | H | $SO_2NMe_2$ | Me | OMe | CH |
| 5514 | $Q_{79}$ | H | $SO_2NMe_2$ | OMe | OMe | CH |
| 5515 | $Q_{79}$ | H | $SO_2NMe_2$ | Me | OMe | N |
| 5516 | $Q_{79}$ | H | CN | Me | OMe | CH |
| 5517 | $Q_{79}$ | H | CN | OMe | OMe | CH |
| 5518 | $Q_{79}$ | H | CN | Me | OMe | N |
| 5519 | $Q_{79}$ | Me | CN | Me | OMe | CH |
| 5520 | $Q_{79}$ | Me | CN | OMe | OMe | CH |
| 5521 | $Q_{79}$ | Me | CN | Me | OMe | N |
| 5522 | $Q_{79}$ | H | Me | Me | OMe | CH |

-continued

| | | | | | | |
|---|---|---|---|---|---|---|
| 5523 | $Q_{79}$ | H | Me | OMe | OMe | CH |
| 5524 | $Q_{79}$ | H | Me | Me | OMe | N |
| 5525 | $Q_{79}$ | H | Et | Me | OMe | CH |
| 5526 | $Q_{79}$ | H | Et | OMe | OMe | CH |
| 5527 | $Q_{79}$ | H | Et | Me | OMe | N |
| 5528 | $Q_{79}$ | H | H | Me | OMe | CH |
| 5529 | $Q_{79}$ | H | H | OMe | OMe | CH |
| 5530 | $Q_{79}$ | H | H | Me | OMe | N |
| 5531 | $Q_{79}$ | H | COPh | Me | OMe | CH |
| 5532 | $Q_{79}$ | H | COPh | OMe | OMe | CH |
| 5533 | $Q_{79}$ | H | COPh | Me | OMe | N |
| 5534 | Me | $Q_{79}$ | COOMe | Me | OMe | CH |
| 5535 | Me | $Q_{79}$ | COOMe | OMe | OMe | CH |
| 5536 | Me | $Q_{79}$ | COOMe | Me | OMe | N |
| 5537 | H | H | $Q_{79}$ | Me | OMe | CH |
| 5538 | H | H | $Q_{79}$ | OMe | OMe | CH |
| 5539 | H | H | $Q_{79}$ | Me | OMe | N |
| 5540 | Me | H | $Q_{79}$ | Me | Me | CH |
| 5541 | Me | H | $Q_{79}$ | Me | OMe | CH |
| 5542 | Me | H | $Q_{79}$ | OMe | OMe | CH |
| 5543 | Me | H | $Q_{79}$ | Me | OMe | N |
| 5544 | Me | H | $Q_{79}$ | OMe | OMe | N |
| 5545 | Me | Me | $Q_{79}$ | Me | OMe | CH |
| 5546 | Me | Me | $Q_{79}$ | OMe | OMe | CH |
| 5547 | Me | Me | $Q_{79}$ | Me | OMe | N |
| 5548 | $Q_{80}$ | H | COOMe | Me | Me | CH |
| 5549 | $Q_{80}$ | H | COOMe | Me | OMe | CH |
| 5550 | $Q_{80}$ | H | COOMe | OMe | OMe | CH |
| 5551 | $Q_{80}$ | H | COOMe | Me | OMe | N |
| 5552 | $Q_{80}$ | H | COOMe | OMe | OMe | N |
| 5553 | $Q_{80}$ | H | COOEt | Me | Me | CH |
| 5554 | $Q_{80}$ | H | COOEt | Me | OMe | CH |
| 5555 | $Q_{80}$ | H | COOEt | OMe | OMe | CH |
| 5556 | $Q_{80}$ | H | COOEt | Me | OMe | N |
| 5557 | $Q_{80}$ | H | COOEt | OMe | OMe | N |
| 5558 | $Q_{80}$ | Me | COOMe | Me | OMe | CH |
| 5559 | $Q_{80}$ | Me | COOMe | OMe | OMe | CH |
| 5560 | $Q_{80}$ | Me | COOMe | Me | OMe | N |
| 5561 | $Q_{80}$ | Me | COOEt | Me | OMe | CH |
| 5562 | $Q_{80}$ | Me | COOEt | OMe | OMe | CH |
| 5563 | $Q_{80}$ | Me | COOEt | Me | OMe | N |
| 5564 | $Q_{80}$ | H | CN | Me | OMe | CH |
| 5565 | $Q_{80}$ | H | CN | OMe | OMe | CH |
| 5566 | $Q_{80}$ | H | CN | Me | OMe | N |
| 5567 | $Q_{80}$ | H | H | Me | OMe | CH |
| 5568 | $Q_{80}$ | H | H | OMe | OMe | CH |
| 5569 | $Q_{80}$ | H | H | Me | OMe | N |
| 5570 | Me | H | $Q_{80}$ | Me | Me | CH |
| 5571 | Me | H | $Q_{80}$ | Me | OMe | CH |
| 5572 | Me | H | $Q_{80}$ | OMe | OMe | CH |
| 5573 | Me | H | $Q_{80}$ | Me | OMe | N |
| 5574 | Me | H | $Q_{80}$ | OMe | OMe | N |
| 5575 | $Q_{81}$ | H | COOMe | Me | OMe | CH |
| 5576 | $Q_{81}$ | H | COOMe | OMe | OMe | CH |
| 5577 | $Q_{81}$ | H | COOEt | Me | OMe | CH |
| 5578 | $Q_{81}$ | H | COOEt | OMe | OMe | CH |
| 5579 | $Q_{81}$ | Me | COOMe | Me | OMe | CH |
| 5580 | $Q_{81}$ | Me | COOMe | OMe | OMe | CH |
| 5581 | $Q_{81}$ | Me | COOEt | Me | OMe | CH |
| 5582 | $Q_{81}$ | Me | COOEt | OMe | OMe | CH |
| 5583 | $Q_{81}$ | H | H | Me | OMe | CH |
| 5584 | $Q_{81}$ | H | H | OMe | OMe | CH |
| 5585 | Me | H | $Q_{81}$ | Me | OMe | CH |
| 5586 | Me | H | $Q_{81}$ | OMe | OMe | CH |
| 5587 | $Q_{82}$ | H | COOMe | Me | OMe | CH |
| 5588 | $Q_{82}$ | H | COOMe | OMe | OMe | CH |
| 5589 | $Q_{82}$ | H | COOEt | Me | OMe | CH |
| 5590 | $Q_{82}$ | H | COOEt | OMe | OMe | CH |
| 5591 | $Q_{82}$ | Me | COOMe | Me | OMe | CH |
| 5592 | $Q_{82}$ | Me | COOMe | OMe | OMe | CH |
| 5593 | $Q_{82}$ | Me | COOEt | Me | OMe | CH |
| 5594 | $Q_{82}$ | Me | COOEt | OMe | OMe | CH |
| 5595 | $Q_{82}$ | H | H | Me | OMe | CH |
| 5596 | $Q_{82}$ | H | H | OMe | OMe | CH |
| 5597 | Me | H | $Q_{82}$ | Me | OMe | CH |
| 5598 | Me | H | $Q_{82}$ | OMe | OMe | CH |
| 5599 | $Q_{83}$ | H | COOMe | Me | OMe | CH |
| 5600 | $Q_{83}$ | H | COOMe | OMe | OMe | CH |
| 5601 | $Q_{83}$ | H | COOEt | Me | OMe | CH |
| 5602 | $Q_{83}$ | H | COOEt | OMe | OMe | CH |
| 5603 | $Q_{83}$ | Me | COOMe | Me | OMe | CH |
| 5604 | $Q_{83}$ | Me | COOMe | OMe | OMe | CH |

-continued

| | | | | | | |
|---|---|---|---|---|---|---|
| 5605 | $Q_{83}$ | Me | COOEt | Me | OMe | CH |
| 5606 | $Q_{83}$ | Me | COOEt | OMe | OMe | CH |
| 5607 | $Q_{83}$ | H | H | Me | OMe | CH |
| 5608 | $Q_{83}$ | H | H | OMe | OMe | CH |
| 5609 | Me | H | $Q_{83}$ | Me | OMe | CH |
| 5610 | Me | H | $Q_{83}$ | OMe | OMe | CH |

| | | | | | | |
|---|---|---|---|---|---|---|
| 1776 | $Q_{45}$ | Cl | COOEt | Me | OMe | CH |
| 1777 | $Q_{45}$ | Cl | COOEt | OMe | OMe | CH |
| 1778 | $Q_{45}$ | Cl | COOEt | Me | OMe | N |
| 1779 | $Q_{45}$ | OMe | COOMe | Me | OMe | CH |
| 1780 | $Q_{45}$ | OMe | COOMe | OMe | OMe | CH |
| 1781 | $Q_{45}$ | OMe | COOMe | Me | OMe | N |
| 1782 | $Q_{45}$ | OMe | COOEt | Me | OMe | CH |
| 1783 | $Q_{45}$ | OMe | COOEt | OMe | OMe | CH |
| 1784 | $Q_{45}$ | OMe | COOEt | Me | OMe | N |
| 1785 | $Q_{45}$ | H | Cl | Me | OMe | CH |
| 1786 | $Q_{45}$ | H | Cl | OMe | OMe | CH |
| 1787 | $Q_{45}$ | H | Cl | Me | OMe | N |
| 1788 | $Q_{45}$ | H | $NO_2$ | Me | OMe | CH |
| 1789 | $Q_{45}$ | H | $NO_2$ | OMe | OMe | CH |
| 1790 | $Q_{45}$ | H | $NO_2$ | Me | OMe | N |
| 1791 | $Q_{45}$ | H | $SO_2NMe_2$ | Me | OMe | CH |
| 1792 | $Q_{45}$ | H | $SO_2NMe_2$ | OMe | OMe | CH |
| 1793 | $Q_{45}$ | H | $SO_2NMe_2$ | Me | OMe | N |
| 1794 | $Q_{45}$ | H | CN | Me | OMe | CH |
| 1795 | $Q_{45}$ | H | CN | OMe | OMe | CH |
| 1796 | $Q_{45}$ | H | CN | Me | OMe | N |
| 1797 | $Q_{45}$ | Me | CN | Me | OMe | CH |
| 1798 | $Q_{45}$ | Me | CN | OMe | OMe | CH |
| 1799 | $Q_{45}$ | Me | CN | Me | OMe | N |
| 1800 | $Q_{45}$ | H | Me | Me | OMe | CH |
| 1801 | $Q_{45}$ | H | Me | OMe | OMe | CH |
| 1802 | $Q_{45}$ | H | Me | Me | OMe | N |
| 1803 | $Q_{45}$ | H | Et | Me | OMe | CH |
| 1804 | $Q_{45}$ | H | Et | OMe | OMe | CH |
| 1805 | $Q_{45}$ | H | Et | Me | OMe | N |
| 1806 | $Q_{45}$ | H | H | Me | OMe | CH |
| 1807 | $Q_{45}$ | H | H | OMe | OMe | CH |
| 1808 | $Q_{45}$ | H | H | Me | OMe | N |
| 1809 | $Q_{45}$ | H | COPh | Me | OMe | CH |
| 1810 | $Q_{45}$ | H | COPh | OMe | OMe | CH |
| 1811 | $Q_{45}$ | H | COPh | Me | OMe | N |
| 1812 | Me | $Q_{45}$ | COOMe | Me | OMe | CH |
| 1813 | Me | $Q_{45}$ | COOMe | OMe | OMe | CH |
| 1814 | Me | $Q_{45}$ | COOMe | Me | OMe | N |
| 1815 | H | H | $Q_{45}$ | Me | OMe | CH |
| 1816 | H | H | $Q_{45}$ | OMe | OMe | CH |
| 1817 | H | H | $Q_{45}$ | Me | OMe | N |
| 1818 | Me | H | $Q_{45}$ | Me | Me | CH |
| 1819 | Me | H | $Q_{45}$ | Me | OMe | CH |
| 1820 | Me | H | $Q_{45}$ | OMe | OMe | CH |
| 1821 | Me | H | $Q_{45}$ | Me | OMe | N |
| 1822 | Me | H | $Q_{45}$ | OMe | OMe | N |
| 1823 | Me | Me | $Q_{45}$ | Me | OMe | CH |
| 1824 | Me | Me | $Q_{45}$ | OMe | OMe | CH |
| 1825 | Me | Me | $Q_{45}$ | Me | OMe | N |
| 1826 | $Q_{46}$ | H | COOMe | Me | Me | CH |
| 1827 | $Q_{46}$ | H | COOMe | Me | OMe | CH |
| 1828 | $Q_{46}$ | H | COOMe | OMe | OMe | CH |
| 1829 | $Q_{46}$ | H | COOMe | Me | OMe | N |
| 1830 | $Q_{46}$ | H | COOMe | OMe | OMe | N |
| 1831 | $Q_{46}$ | H | COOEt | Me | Me | CH |
| 1832 | $Q_{46}$ | H | COOEt | Me | OMe | CH |
| 1833 | $Q_{46}$ | H | COOEt | OMe | OMe | CH |
| 1834 | $Q_{46}$ | H | COOEt | Me | OMe | N |
| 1835 | $Q_{46}$ | H | COOEt | OMe | OMe | N |
| 1836 | $Q_{46}$ | Me | COOMe | Me | OMe | CH |
| 1837 | $Q_{46}$ | Me | COOMe | OMe | OMe | CH |
| 1838 | $Q_{46}$ | Me | COOMe | Me | OMe | N |
| 1839 | $Q_{46}$ | Me | COOEt | Me | OMe | CH |
| 1840 | $Q_{46}$ | Me | COOEt | OMe | OMe | CH |
| 1841 | $Q_{46}$ | Me | COOEt | Me | OMe | N |
| 1842 | $Q_{46}$ | H | CN | Me | OMe | CH |
| 1843 | $Q_{46}$ | H | CN | OMe | OMe | CH |
| 1844 | $Q_{46}$ | H | CN | Me | OMe | N |
| 1845 | $Q_{46}$ | H | H | Me | OMe | CH |
| 1846 | $Q_{46}$ | H | H | OMe | OMe | CH |
| 1847 | $Q_{46}$ | H | H | Me | OMe | N |

-continued

| | | | | | | |
|---|---|---|---|---|---|---|
| 1848 | Me | H | $Q_{46}$ | Me | Me | CH |
| 1849 | Me | H | $Q_{46}$ | Me | OMe | CH |
| 1850 | Me | H | $Q_{46}$ | OMe | OMe | CH |
| 1851 | Me | H | $Q_{46}$ | Me | OMe | N |
| 1852 | Me | H | $Q_{46}$ | OMe | OMe | N |
| 1853 | $Q_{47}$ | H | COOMe | Me | Me | CH |
| 1854 | $Q_{47}$ | H | COOMe | Me | OMe | CH |
| 1855 | $Q_{47}$ | H | COOMe | OMe | OMe | CH |
| 1856 | $Q_{47}$ | H | COOMe | Me | OMe | N |
| 1857 | $Q_{47}$ | H | COOMe | OMe | OMe | N |
| 1858 | $Q_{47}$ | H | COOEt | Me | Me | CH |
| 1859 | $Q_{47}$ | H | COOEt | Me | OMe | CH |
| 1860 | $Q_{47}$ | H | COOEt | OMe | OMe | CH |
| 1861 | $Q_{47}$ | H | COOEt | Me | OMe | N |
| 1862 | $Q_{47}$ | H | COOEt | OMe | OMe | N |
| 1863 | $Q_{47}$ | Me | COOMe | Me | OMe | CH |
| 1864 | $Q_{47}$ | Me | COOMe | OMe | OMe | CH |
| 1865 | $Q_{47}$ | Me | COOMe | Me | OMe | N |
| 1866 | $Q_{47}$ | Me | COOEt | Me | OMe | CH |
| 1867 | $Q_{47}$ | Me | COOEt | OMe | OMe | CH |
| 1868 | $Q_{47}$ | Me | COOEt | Me | OMe | N |
| 1869 | $Q_{47}$ | H | CN | Me | OMe | CH |
| 1870 | $Q_{47}$ | H | CN | OMe | OMe | CH |
| 1871 | $Q_{47}$ | H | CN | Me | OMe | N |
| 1872 | $Q_{47}$ | H | H | Me | OMe | CH |
| 1873 | $Q_{47}$ | H | H | OMe | OMe | CH |
| 1874 | $Q_{47}$ | H | H | Me | OMe | N |
| 1875 | Me | H | $Q_{47}$ | Me | Me | CH |
| 1876 | Me | H | $Q_{47}$ | Me | OMe | CH |
| 1877 | Me | H | $Q_{47}$ | OMe | OMe | CH |
| 1878 | Me | H | $Q_{47}$ | Me | OMe | N |
| 1879 | Me | H | $Q_{47}$ | OMe | OMe | N |
| 1880 | $Q_{48}$ | H | COOMe | Me | Me | CH |
| 1881 | $Q_{48}$ | H | COOMe | Me | OMe | CH |
| 1882 | $Q_{48}$ | H | COOMe | OMe | OMe | CH |
| 1883 | $Q_{48}$ | H | COOMe | Me | OMe | N |
| 1884 | $Q_{48}$ | H | COOMe | OMe | OMe | N |
| 1885 | $Q_{48}$ | H | COOEt | Me | Me | CH |
| 1886 | $Q_{48}$ | H | COOEt | Me | OMe | CH |
| 1887 | $Q_{48}$ | H | COOEt | OMe | OMe | CH |
| 1888 | $Q_{48}$ | H | COOEt | Me | OMe | N |
| 1889 | $Q_{48}$ | H | COOEt | OMe | OMe | N |
| 1890 | $Q_{48}$ | Me | COOMe | Me | OMe | CH |
| 1891 | $Q_{48}$ | Me | COOMe | OMe | OMe | CH |
| 1892 | $Q_{48}$ | Me | COOMe | Me | OMe | N |
| 1893 | $Q_{48}$ | Me | COOEt | Me | OMe | CH |
| 1894 | $Q_{48}$ | Me | COOEt | OMe | OMe | CH |
| 1895 | $Q_{48}$ | Me | COOEt | Me | OMe | N |
| 1896 | $Q_{48}$ | H | CN | Me | OMe | CH |
| 1897 | $Q_{48}$ | H | CN | OMe | OMe | CH |
| 1898 | $Q_{48}$ | H | CN | Me | OMe | N |
| 1899 | $Q_{48}$ | H | H | Me | OMe | CH |
| 1900 | $Q_{48}$ | H | H | OMe | OMe | CH |
| 1901 | $Q_{48}$ | H | H | Me | OMe | N |
| 1902 | Me | H | $Q_{48}$ | Me | Me | CH |
| 1903 | Me | H | $Q_{48}$ | Me | OMe | CH |
| 1904 | Me | H | $Q_{48}$ | OMe | OMe | CH |
| 1905 | Me | H | $Q_{48}$ | Me | OMe | N |
| 1906 | Me | H | $Q_{48}$ | OMe | OMe | N |
| 1907 | $Q_{49}$ | H | COOMe | Me | Me | CH |
| 1908 | $Q_{49}$ | H | COOMe | Me | OMe | CH |
| 1909 | $Q_{49}$ | H | COOMe | OMe | OMe | CH |
| 1910 | $Q_{49}$ | H | COOMe | Me | OMe | N |
| 1911 | $Q_{49}$ | H | COOMe | OMe | OMe | N |
| 1912 | $Q_{49}$ | H | COOEt | Me | Me | CH |
| 1913 | $Q_{49}$ | H | COOEt | Me | OMe | CH |
| 1914 | Q49 | H | COOEt | OMe | OMe | CH |
| 1915 | $Q_{49}$ | H | COOEt | Me | OMe | N |
| 1916 | $Q_{49}$ | H | COOEt | OMe | OMe | N |
| 1917 | $Q_{49}$ | Me | COOMe | Me | OMe | CH |
| 1918 | $Q_{49}$ | Me | COOMe | OMe | OMe | CH |
| 1919 | $Q_{49}$ | Me | COOMe | Me | OMe | N |
| 1920 | $Q_{49}$ | Me | COOEt | Me | OMe | CH |
| 1921 | $Q_{49}$ | Me | COOEt | OMe | OMe | CH |
| 1922 | $Q_{49}$ | Me | COOEt | Me | OMe | N |
| 1923 | $Q_{49}$ | H | CN | Me | OMe | CH |
| 1924 | $Q_{49}$ | H | CN | OMe | OMe | CH |
| 1925 | $Q_{49}$ | H | CN | Me | OMe | N |
| 1926 | $Q_{49}$ | H | H | Me | OMe | CH |
| 1927 | $Q_{49}$ | H | H | OMe | OMe | CH |
| 1928 | $Q_{49}$ | H | H | Me | OMe | N |
| 1929 | Me | H | $Q_{49}$ | Me | Me | CH |

-continued

| | | | | | | |
|---|---|---|---|---|---|---|
| 1930 | Me | H | $Q_{49}$ | Me | OMe | CH |
| 1931 | Me | H | $Q_{49}$ | OMe | OMe | CH |
| 1932 | Me | H | $Q_{49}$ | Me | OMe | N |
| 1933 | Me | H | $Q_{49}$ | OMe | OMe | N |
| 1934 | $Q_{50}$ | H | COOMe | Me | Me | CH |
| 1935 | $Q_{50}$ | H | COOMe | Me | OMe | CH |
| 1936 | $Q_{50}$ | H | COOMe | OMe | OMe | CH |
| 1937 | $Q_{50}$ | H | COOMe | Me | OMe | N |
| 1938 | $Q_{50}$ | H | COOMe | OMe | OMe | N |
| 1939 | $Q_{50}$ | H | COOEt | Me | Me | CH |
| 1940 | $Q_{50}$ | H | COOEt | Me | OMe | CH |
| 1941 | $Q_{50}$ | H | COOEt | OMe | OMe | CH |
| 1942 | $Q_{50}$ | H | COOEt | Me | OMe | N |
| 1943 | $Q_{50}$ | H | COOEt | OMe | OMe | N |
| 1944 | $Q_{50}$ | Me | COOMe | Me | OMe | CH |
| 1945 | $Q_{50}$ | Me | COOMe | OMe | OMe | CH |
| 1946 | $Q_{50}$ | Me | COOMe | Me | OMe | N |
| 1947 | $Q_{50}$ | Me | COOEt | Me | OMe | CH |
| 1948 | $Q_{50}$ | Me | COOEt | OMe | OMe | CH |
| 1949 | $Q_{50}$ | Me | COOEt | Me | OMe | N |
| 1950 | $Q_{50}$ | H | CN | Me | OMe | CH |
| 1951 | $Q_{50}$ | H | CN | OMe | OMe | CH |
| 1952 | $Q_{50}$ | H | CN | Me | OMe | N |
| 1953 | $Q_{50}$ | H | H | Me | OMe | CH |
| 1954 | $Q_{50}$ | H | H | OMe | OMe | CH |
| 1955 | $Q_{50}$ | H | H | Me | OMe | N |
| 1956 | Me | H | $Q_{50}$ | Me | Me | CH |
| 1957 | Me | H | $Q_{50}$ | Me | OMe | CH |
| 1958 | Me | H | $Q_{50}$ | OMe | OMe | CH |
| 1959 | Me | H | $Q_{50}$ | Me | OMe | N |
| 1960 | Me | H | $Q_{50}$ | OMe | OMe | N |
| 1961 | $Q_{51}$ | H | COOMe | Me | Me | CH |
| 1962 | $Q_{51}$ | H | COOMe | Me | OMe | CH |
| 1963 | $Q_{51}$ | H | COOMe | OMe | OMe | CH |
| 1964 | $Q_{51}$ | H | COOMe | Me | OMe | N |
| 1965 | $Q_{51}$ | H | COOMe | OMe | OMe | N |
| 1966 | $Q_{51}$ | H | COOEt | Me | Me | CH |
| 1967 | $Q_{51}$ | H | COOEt | Me | OMe | CH |
| 1968 | $Q_{51}$ | H | COOEt | OMe | OMe | CH |
| 1969 | $Q_{51}$ | H | COOEt | Me | OMe | N |
| 1970 | $Q_{51}$ | H | COOEt | OMe | OMe | N |
| 1971 | $Q_{51}$ | Me | COOMe | Me | OMe | CH |
| 1972 | $Q_{51}$ | Me | COOMe | OMe | OMe | CH |
| 1973 | $Q_{51}$ | Me | COOMe | Me | OMe | N |
| 1974 | $Q_{51}$ | Me | COOEt | Me | OMe | CH |
| 1975 | $Q_{51}$ | Me | COOEt | OMe | OMe | CH |
| 1976 | $Q_{51}$ | Me | COOEt | Me | OMe | N |
| 1977 | $Q_{51}$ | H | CN | Me | OMe | CH |
| 1978 | $Q_{51}$ | H | CN | OMe | OMe | CH |
| 1979 | $Q_{51}$ | H | CN | Me | OMe | N |
| 1980 | $Q_{51}$ | H | H | Me | OMe | CH |
| 1981 | $Q_{51}$ | H | H | OMe | OMe | CH |
| 1982 | $Q_{51}$ | H | H | Me | OMe | N |
| 1983 | Me | H | $Q_{51}$ | Me | Me | CH |
| 1984 | Me | H | $Q_{51}$ | Me | OMe | CH |
| 1985 | Me | H | $Q_{51}$ | OMe | OMe | CH |
| 1986 | Me | H | $Q_{51}$ | Me | OMe | N |
| 1987 | Me | H | $Q_{51}$ | OMe | OMe | N |
| 1988 | $Q_{52}$ | H | COOMe | Me | OMe | CH |
| 1989 | $Q_{52}$ | H | COOMe | OMe | OMe | CH |
| 1990 | $Q_{52}$ | H | COOEt | Me | OMe | CH |
| 1991 | $Q_{52}$ | H | COOEt | OMe | OMe | CH |
| 1992 | $Q_{52}$ | Me | COOMe | Me | OMe | CH |
| 1993 | $Q_{52}$ | Me | COOMe | OMe | OMe | CH |
| 1994 | $Q_{52}$ | Me | COOEt | Me | OMe | CH |
| 1995 | $Q_{52}$ | Me | COOEt | OMe | OMe | CH |
| 1996 | $Q_{52}$ | H | H | Me | OMe | CH |
| 1997 | $Q_{52}$ | H | H | OMe | OMe | CH |
| 1998 | Me | H | $Q_{52}$ | Me | OMe | CH |
| 1999 | Me | H | $Q_{52}$ | OMe | OMe | CH |
| 2000 | $Q_{53}$ | H | COOMe | Me | OMe | CH |
| 2001 | $Q_{53}$ | H | COOMe | OMe | OMe | CH |
| 2002 | $Q_{53}$ | H | COOEt | Me | OMe | CH |
| 2003 | $Q_{53}$ | H | COOEt | OMe | OMe | CH |
| 2004 | $Q_{53}$ | Me | COOMe | Me | OMe | CH |
| 2005 | $Q_{53}$ | Me | COOMe | OMe | OMe | CH |
| 2006 | $Q_{53}$ | Me | COOEt | Me | OMe | CH |
| 2007 | $Q_{53}$ | Me | COOEt | OMe | OMe | CH |
| 2008 | $Q_{53}$ | H | H | Me | OMe | CH |
| 2009 | $Q_{53}$ | H | H | OMe | OMe | CH |
| 2010 | Me | H | $Q_{53}$ | Me | OMe | CH |
| 2011 | Me | H | $Q_{53}$ | OMe | OMe | CH |

-continued

| | | | | | | |
|---|---|---|---|---|---|---|
| 2012 | $Q_{54}$ | H | COOMe | Me | Me | CH |
| 2013 | $Q_{54}$ | H | COOMe | Me | OMe | CH |
| 2014 | $Q_{54}$ | H | COOMe | OMe | OMe | CH |
| 2015 | $Q_{54}$ | H | COOMe | Me | OMe | N |
| 2016 | $Q_{54}$ | H | COOMe | OMe | OMe | N |
| 2017 | $Q_{54}$ | H | COOEt | Me | Me | CH |
| 2018 | $Q_{54}$ | H | COOEt | Me | OMe | CH |
| 2019 | $Q_{54}$ | H | COOEt | OMe | OMe | CH |
| 2020 | $Q_{54}$ | H | COOEt | Me | OMe | N |
| 2021 | $Q_{54}$ | H | COOEt | OMe | OMe | N |
| 2022 | $Q_{54}$ | Me | COOMe | Me | OMe | CH |
| 2023 | $Q_{54}$ | Me | COOMe | OMe | OMe | CH |
| 2024 | $Q_{54}$ | Me | COOMe | Me | OMe | N |
| 2025 | $Q_{54}$ | Me | COOEt | Me | OMe | CH |
| 2026 | $Q_{54}$ | Me | COOEt | OMe | OMe | CH |
| 2027 | $Q_{54}$ | Me | COOEt | Me | OMe | N |
| 2028 | $Q_{54}$ | H | CN | Me | OMe | CH |
| 2029 | $Q_{54}$ | H | CN | OMe | OMe | CH |
| 2030 | $Q_{54}$ | H | CN | Me | OMe | N |
| 2031 | $Q_{54}$ | H | H | Me | OMe | CH |
| 2032 | $Q_{54}$ | H | H | OMe | OMe | CH |
| 2033 | $Q_{54}$ | H | H | Me | OMe | N |
| 2034 | Me | H | $Q_{54}$ | Me | Me | CH |
| 2035 | Me | H | $Q_{54}$ | Me | OMe | CH |
| 2036 | Me | H | $Q_{54}$ | OMe | OMe | CH |
| 2037 | Me | H | $Q_{54}$ | Me | OMe | N |
| 2038 | Me | H | $Q_{54}$ | OMe | OMe | N |
| 2039 | $Q_{55}$ | H | COOMe | Me | Me | CH |
| 2040 | $Q_{55}$ | H | COOMe | Me | OMe | CH |
| 2041 | $Q_{55}$ | H | COOMe | OMe | OMe | CH |
| 2042 | $Q_{55}$ | H | COOMe | Me | OMe | N |
| 2043 | $Q_{55}$ | H | COOMe | OMe | OMe | N |
| 2044 | $Q_{55}$ | H | COOEt | Me | Me | CH |
| 2045 | $Q_{55}$ | H | COOEt | Me | OMe | CH |
| 2046 | $Q_{55}$ | H | COOEt | OMe | OMe | CH |
| 2047 | $Q_{55}$ | H | COOEt | Me | OMe | N |
| 2048 | $Q_{55}$ | H | COOEt | OMe | OMe | N |
| 2049 | $Q_{55}$ | Me | COOMe | Me | OMe | CH |
| 2050 | $Q_{55}$ | Me | COOMe | OMe | OMe | CH |
| 2051 | $Q_{55}$ | Me | COOMe | Me | OMe | N |
| 2052 | $Q_{55}$ | Me | COOEt | Me | OMe | CH |
| 2053 | $Q_{55}$ | Me | COOEt | OMe | OMe | CH |
| 2054 | $Q_{55}$ | Me | COOEt | Me | OMe | N |
| 2055 | $Q_{55}$ | H | CN | Me | OMe | CH |
| 2056 | $Q_{55}$ | H | CN | OMe | OMe | CH |
| 2057 | $Q_{55}$ | H | CN | Me | OMe | N |
| 2058 | $Q_{55}$ | H | H | Me | OMe | CH |
| 2059 | $Q_{55}$ | H | H | OMe | OMe | CH |
| 2060 | $Q_{55}$ | H | H | Me | OMe | N |
| 2061 | Me | H | $Q_{55}$ | Me | Me | CH |
| 2062 | Me | H | $Q_{55}$ | Me | OMe | CH |
| 2063 | Me | H | $Q_{55}$ | OMe | OMe | CH |
| 2064 | Me | H | $Q_{55}$ | Me | OMe | N |
| 2065 | Me | H | $Q_{55}$ | OMe | OMe | N |
| 2066 | $Q_{56}$ | H | COOMe | Me | Me | CH |
| 2067 | $Q_{56}$ | H | COOMe | Me | OMe | CH |
| 2068 | $Q_{56}$ | H | COOMe | OMe | OMe | CH |
| 2069 | $Q_{56}$ | H | COOMe | Me | OMe | N |
| 2070 | $Q_{56}$ | H | COOMe | OMe | OMe | N |
| 2071 | $Q_{56}$ | H | COOEt | Me | Me | CH |
| 2072 | $Q_{56}$ | H | COOEt | Me | OMe | CH |
| 2073 | $Q_{56}$ | H | COOEt | OMe | OMe | CH |
| 2074 | $Q_{56}$ | H | COOEt | Me | OMe | N |
| 2075 | $Q_{56}$ | H | COOEt | OMe | OMe | N |
| 2076 | $Q_{56}$ | Me | COOMe | Me | OMe | CH |
| 2077 | $Q_{56}$ | Me | COOMe | OMe | OMe | CH |
| 2078 | $Q_{56}$ | Me | COOMe | Me | OMe | N |
| 2079 | $Q_{56}$ | Me | COOEt | Me | OMe | CH |
| 2080 | $Q_{56}$ | Me | COOEt | OMe | OMe | CH |
| 2081 | $Q_{56}$ | Me | COOEt | Me | OMe | N |
| 2082 | $Q_{56}$ | H | CN | Me | OMe | CH |
| 2083 | $Q_{56}$ | H | CN | OMe | OMe | CH |
| 2084 | $Q_{56}$ | H | CN | Me | OMe | N |
| 2085 | $Q_{56}$ | H | H | Me | OMe | CH |
| 2086 | $Q_{56}$ | H | H | OMe | OMe | CH |
| 2087 | $Q_{56}$ | H | H | Me | OMe | N |
| 2088 | Me | H | $Q_{56}$ | Me | Me | CH |
| 2089 | Me | H | $Q_{56}$ | Me | OMe | CH |
| 2090 | Me | H | $Q_{56}$ | OMe | OMe | CH |
| 2091 | Me | H | $Q_{56}$ | Me | OMe | N |
| 2092 | Me | H | $Q_{56}$ | OMe | OMe | N |
| 2093 | $Q_{57}$ | H | COOMe | Me | OMe | CH |

-continued

| | | | | | | |
|---|---|---|---|---|---|---|
| 2094 | $Q_{57}$ | H | COOMe | OMe | OMe | CH |
| 2095 | $Q_{57}$ | H | COOEt | Me | OMe | CH |
| 2096 | $Q_{57}$ | H | COOEt | OMe | OMe | CH |
| 2097 | $Q_{57}$ | Me | COOMe | Me | OMe | CH |
| 2098 | $Q_{57}$ | Me | COOMe | OMe | OMe | CH |
| 2099 | $Q_{57}$ | Me | COOEt | Me | OMe | CH |
| 2100 | $Q_{57}$ | Me | COOEt | OMe | OMe | CH |
| 2101 | $Q_{57}$ | H | H | Me | OMe | CH |
| 2102 | $Q_{57}$ | H | H | OMe | OMe | CH |
| 2103 | Me | H | $Q_{57}$ | Me | OMe | CH |
| 2104 | Me | H | $Q_{57}$ | OMe | OMe | CH |
| 2105 | $Q_{58}$ | H | COOMe | Me | OMe | CH |
| 2106 | $Q_{58}$ | H | COOMe | OMe | OMe | CH |
| 2107 | $Q_{58}$ | H | COOEt | Me | OMe | CH |
| 2108 | $Q_{58}$ | H | COOEt | OMe | OMe | CH |
| 2109 | $Q_{58}$ | Me | COOMe | Me | OMe | CH |
| 2110 | $Q_{58}$ | Me | COOMe | OMe | OMe | CH |
| 2111 | $Q_{58}$ | Me | COOEt | Me | OMe | CH |
| 2112 | $Q_{58}$ | Me | COOEt | OMe | OMe | CH |
| 2113 | $Q_{58}$ | H | H | Me | OMe | CH |
| 2114 | $Q_{58}$ | H | H | OMe | OMe | CH |
| 2115 | Me | H | $Q_{58}$ | Me | OMe | CH |
| 2116 | Me | H | $Q_{58}$ | OMe | OMe | CH |
| 2117 | $Q_{59}$ | H | COOMe | Me | Me | CH |
| 2118 | $Q_{59}$ | H | COOMe | Me | OMe | CH |
| 2119 | $Q_{59}$ | H | COOMe | OMe | OMe | CH |
| 2120 | $Q_{59}$ | H | COOMe | Me | Me | N |
| 2121 | $Q_{59}$ | H | COOMe | Me | OMe | N |
| 2122 | $Q_{59}$ | H | COOMe | OMe | OMe | N |
| 2123 | $Q_{59}$ | H | COOMe | Me | $OCHF_2$ | CH |
| 2124 | $Q_{59}$ | H | COOMe | Cl | OMe | CH |
| 2125 | $Q_{59}$ | H | COOEt | Me | Me | CH |
| 2126 | $Q_{59}$ | H | COOEt | Me | OMe | CH |
| 2127 | $Q_{59}$ | H | COOEt | OMe | OMe | CH |
| 2128 | $Q_{59}$ | H | COOEt | Me | Me | N |
| 2129 | $Q_{59}$ | H | COOEt | Me | OMe | N |
| 2130 | $Q_{59}$ | H | COOEt | OMe | OMe | N |
| 2131 | $Q_{59}$ | H | COOEt | Me | $OCHF_2$ | CH |
| 2132 | $Q_{59}$ | H | COOEt | Cl | OMe | CH |
| 2133 | $Q_{59}$ | H | COOPr—n | Me | OMe | CH |
| 2134 | $Q_{59}$ | H | COOPr—n | OMe | OMe | CH |
| 2135 | $Q_{59}$ | H | COOPr—n | Me | OMe | N |
| 2136 | $Q_{59}$ | H | COOPr—i | Me | OMe | CH |
| 2137 | $Q_{59}$ | H | COOPr—i | OMe | OMe | CH |
| 2138 | $Q_{59}$ | H | COOPr—i | Me | OMe | N |
| 2139 | $Q_{59}$ | H | $COOCH_2CH_2Cl$ | Me | OMe | CH |
| 2140 | $Q_{59}$ | H | $COOCH_2CH_2Cl$ | OMe | OMe | CH |
| 2141 | $Q_{59}$ | H | $COOCH_2CH_2Cl$ | Me | OMe | N |
| 2142 | $Q_{59}$ | H | $COOCH_2CH{=}CH_2$ | Me | OMe | CH |
| 2143 | $Q_{59}$ | H | $COOCH_2CH{=}CH_2$ | OMe | OMe | CH |
| 2144 | $Q_{59}$ | H | $COOCH_2CH{=}CH_2$ | Me | OMe | N |
| 2145 | $Q_{59}$ | H | $COOCH_2C{\equiv}CH$ | Me | OMe | CH |
| 2146 | $Q_{59}$ | H | $COOCH_2C{\equiv}CH$ | OMe | OMe | CH |
| 2147 | $Q_{59}$ | H | $COOCH_2C{\equiv}CH$ | Me | OMe | N |
| 2148 | $Q_{59}$ | Me | COOMe | Me | Me | CH |
| 2149 | $Q_{59}$ | Me | COOMe | Me | OMe | CH |
| 2150 | $Q_{59}$ | Me | COOMe | OMe | OMe | CH |
| 2151 | $Q_{59}$ | Me | COOMe | Me | OMe | N |
| 2152 | $Q_{59}$ | Me | COOMe | OMe | OMe | N |
| 2153 | $Q_{59}$ | Me | COOEt | Me | Me | CH |
| 2154 | $Q_{59}$ | Me | COOEt | Me | OMe | CH |
| 2155 | $Q_{59}$ | Me | COOEt | OMe | OMe | CH |
| 2156 | $Q_{59}$ | Me | COOEt | Me | OMe | N |
| 2157 | $Q_{59}$ | Me | COOEt | OMe | OMe | N |
| 2158 | $Q_{59}$ | Cl | COOMe | Me | OMe | CH |
| 2159 | $Q_{59}$ | Cl | COOMe | OMe | OMe | CH |
| 2160 | $Q_{59}$ | Cl | COOMe | Me | OMe | N |
| 2161 | $Q_{59}$ | Cl | COOEt | Me | OMe | CH |
| 2162 | $Q_{59}$ | Cl | COOEt | OMe | OMe | CH |
| 2163 | $Q_{59}$ | Cl | COOEt | Me | OMe | N |
| 2164 | $Q_{59}$ | OMe | COOMe | Me | OMe | CH |
| 2165 | $Q_{59}$ | OMe | COOMe | OMe | OMe | CH |
| 2166 | $Q_{59}$ | OMe | COOMe | Me | OMe | N |
| 2167 | $Q_{59}$ | OMe | COOEt | Me | OMe | CH |
| 2168 | $Q_{59}$ | OMe | COOEt | OMe | OMe | CH |
| 2169 | $Q_{59}$ | OMe | COOEt | Me | OMe | N |
| 2170 | $Q_{59}$ | H | Cl | Me | OMe | CH |
| 2171 | $Q_{59}$ | H | Cl | OMe | OMe | CH |
| 2172 | $Q_{59}$ | H | Cl | Me | OMe | N |
| 2173 | $Q_{59}$ | H | $NO_2$ | Me | OMe | CH |
| 2174 | $Q_{59}$ | H | $NO_2$ | OMe | OMe | CH |
| 2175 | $Q_{59}$ | H | $NO_2$ | Me | OMe | N |

-continued

| | | | | | | |
|---|---|---|---|---|---|---|
| 2176 | $Q_{59}$ | H | $SO_2NMe_2$ | Me | OMe | CH |
| 2177 | $Q_{59}$ | H | $SO_2NMe_2$ | OMe | OMe | CH |
| 2178 | $Q_{59}$ | H | $SO_2NMe_2$ | Me | OMe | N |
| 2179 | $Q_{59}$ | H | CN | Me | OMe | CH |
| 2180 | $Q_{59}$ | H | CN | OMe | OMe | CH |
| 2181 | $Q_{59}$ | H | CN | Me | OMe | N |
| 2182 | $Q_{59}$ | Me | CN | Me | OMe | CH |
| 2183 | $Q_{59}$ | Me | CN | OMe | OMe | CH |
| 2184 | $Q_{59}$ | Me | CN | Me | OMe | N |
| 2185 | $Q_{59}$ | H | Me | Me | OMe | CH |
| 2186 | $Q_{59}$ | H | Me | OMe | OMe | CH |
| 2187 | $Q_{59}$ | H | Me | Me | OMe | N |
| 2188 | $Q_{59}$ | H | Et | Me | OMe | CH |
| 2189 | $Q_{59}$ | H | Et | OMe | OMe | CH |
| 2190 | $Q_{59}$ | H | Et | Me | OMe | N |
| 2191 | $Q_{59}$ | H | H | Me | OMe | CH |
| 2192 | $Q_{59}$ | H | H | OMe | OMe | CH |
| 2193 | $Q_{59}$ | H | H | Me | OMe | N |
| 2194 | $Q_{59}$ | H | COPh | Me | OMe | CH |
| 2195 | $Q_{59}$ | H | COPh | OMe | OMe | CH |
| 2196 | $Q_{59}$ | H | COPh | Me | OMe | N |
| 2197 | Me | $Q_{59}$ | COOMe | Me | OMe | CH |
| 2198 | Me | $Q_{59}$ | COOMe | OMe | OMe | CH |
| 2199 | Me | $Q_{59}$ | COOMe | Me | OMe | N |
| 2200 | H | H | $Q_{59}$ | Me | OMe | CH |
| 2201 | H | H | $Q_{59}$ | OMe | OMe | CH |
| 2202 | H | H | $Q_{59}$ | Me | OMe | N |
| 2203 | Me | H | $Q_{59}$ | Me | Me | CH |
| 2204 | Me | H | $Q_{59}$ | Me | OMe | CH |
| 2205 | Me | H | $Q_{59}$ | OMe | OMe | CH |
| 2206 | Me | H | $Q_{59}$ | Me | OMe | N |
| 2207 | Me | H | $Q_{59}$ | OMe | OMe | N |
| 2208 | Me | Me | $Q_{59}$ | Me | OMe | CH |
| 2209 | Me | Me | $Q_{59}$ | OMe | OMe | CH |
| 2210 | Me | Me | $Q_{59}$ | Me | OMe | N |
| 2211 | $Q_{60}$ | H | COOMe | Me | Me | CH |
| 2212 | $Q_{60}$ | H | COOMe | Me | OMe | CH |
| 2213 | $Q_{60}$ | H | COOMe | OMe | OMe | CH |
| 2214 | $Q_{60}$ | H | COOMe | Me | OMe | N |
| 2215 | $Q_{60}$ | H | COOMe | OMe | OMe | N |
| 2216 | $Q_{60}$ | H | COOEt | Me | Me | CH |
| 2217 | $Q_{60}$ | H | COOEt | Me | OMe | CH |
| 2218 | $Q_{60}$ | H | COOEt | OMe | OMe | CH |
| 2219 | $Q_{60}$ | H | COOEt | Me | OMe | N |
| 2220 | $Q_{60}$ | H | COOEt | OMe | OMe | N |
| 2221 | $Q_{60}$ | Me | COOMe | Me | OMe | CH |
| 2222 | $Q_{60}$ | Me | COOMe | OMe | OMe | CH |
| 2223 | $Q_{60}$ | Me | COOMe | Me | OMe | N |
| 2224 | $Q_{60}$ | Me | COOEt | Me | OMe | CH |
| 2225 | $Q_{60}$ | Me | COOEt | OMe | OMe | CH |
| 2226 | $Q_{60}$ | Me | COOEt | Me | OMe | N |
| 2227 | $Q_{60}$ | H | CN | Me | OMe | CH |
| 2228 | $Q_{60}$ | H | CN | OMe | OMe | CH |
| 2229 | $Q_{60}$ | H | CN | Me | OMe | N |
| 2230 | $Q_{60}$ | H | H | Me | OMe | CH |
| 2231 | $Q_{60}$ | H | H | OMe | OMe | CH |
| 2232 | $Q_{60}$ | H | H | Me | OMe | N |
| 2233 | Me | H | $Q_{60}$ | Me | Me | CH |
| 2234 | Me | H | $Q_{60}$ | Me | OMe | CH |
| 2235 | Me | H | $Q_{60}$ | OMe | OMe | CH |
| 2236 | Me | H | $Q_{60}$ | Me | OMe | N |
| 2237 | Me | H | $Q_{60}$ | OMe | OMe | N |
| 2238 | $Q_{61}$ | H | COOMe | Me | Me | CH |
| 2239 | $Q_{61}$ | H | COOMe | Me | OMe | CH |
| 2240 | $Q_{61}$ | H | COOMe | OMe | OMe | CH |
| 2241 | $Q_{61}$ | H | COOMe | Me | OMe | N |
| 2242 | $Q_{61}$ | H | COOMe | OMe | OMe | N |
| 2243 | $Q_{61}$ | H | COOEt | Me | Me | CH |
| 2244 | $Q_{61}$ | H | COOEt | Me | OMe | CH |
| 2245 | $Q_{61}$ | H | COOEt | OMe | OMe | CH |
| 2246 | $Q_{61}$ | H | COOEt | Me | OMe | N |
| 2247 | $Q_{61}$ | H | COOEt | OMe | OMe | N |
| 2248 | $Q_{61}$ | Me | COOMe | Me | OMe | CH |
| 2249 | $Q_{61}$ | Me | COOMe | OMe | OMe | CH |
| 2250 | $Q_{61}$ | Me | COOMe | Me | OMe | N |
| 2251 | $Q_{61}$ | Me | COOEt | Me | OMe | CH |
| 2252 | $Q_{61}$ | Me | COOEt | OMe | OMe | CH |
| 2253 | $Q_{61}$ | Me | COOEt | Me | OMe | N |
| 2254 | $Q_{61}$ | H | CN | Me | OMe | CH |
| 2255 | $Q_{61}$ | H | CN | OMe | OMe | CH |
| 2256 | $Q_{61}$ | H | CN | Me | OMe | N |
| 2257 | $Q_{61}$ | H | H | Me | OMe | CH |

-continued

| | | | | | | |
|---|---|---|---|---|---|---|
| 2258 | $Q_{61}$ | H | H | OMe | OMe | CH |
| 2259 | $Q_{61}$ | H | H | Me | OMe | N |
| 2260 | Me | H | $Q_{61}$ | Me | Me | CH |
| 2261 | Me | H | $Q_{61}$ | Me | OMe | CH |
| 2262 | Me | H | $Q_{61}$ | OMe | OMe | CH |
| 2263 | Me | H | $Q_{61}$ | Me | OMe | N |
| 2264 | Me | H | $Q_{61}$ | OMe | OMe | N |
| 2265 | $Q_{62}$ | H | COOMe | Me | Me | CH |
| 2266 | $Q_{62}$ | H | COOMe | Me | OMe | CH |
| 2267 | $Q_{62}$ | H | COOMe | OMe | OMe | CH |
| 2268 | $Q_{62}$ | H | COOMe | Me | OMe | N |
| 2269 | $Q_{62}$ | H | COOMe | OMe | OMe | N |
| 2270 | $Q_{62}$ | H | COOEt | Me | Me | CH |
| 2271 | $Q_{62}$ | H | COOEt | Me | OMe | CH |
| 2272 | $Q_{62}$ | H | COOEt | OMe | OMe | CH |
| 2273 | $Q_{62}$ | H | COOEt | Me | OMe | N |
| 2274 | $Q_{62}$ | H | COOEt | OMe | OMe | N |
| 2275 | $Q_{62}$ | Me | COOMe | Me | OMe | CH |
| 2276 | $Q_{62}$ | Me | COOMe | OMe | OMe | CH |
| 2277 | $Q_{62}$ | Me | COOMe | Me | OMe | N |
| 2278 | $Q_{62}$ | Me | COOEt | Me | OMe | CH |
| 2279 | $Q_{62}$ | Me | COOEt | OMe | OMe | CH |
| 2280 | $Q_{62}$ | Me | COOEt | Me | OMe | N |
| 2281 | $Q_{62}$ | H | CN | Me | OMe | CH |
| 2282 | $Q_{62}$ | H | CN | OMe | OMe | CH |
| 2283 | $Q_{62}$ | H | CN | Me | OMe | N |
| 2284 | $Q_{62}$ | H | H | Me | OMe | CH |
| 2285 | $Q_{62}$ | H | H | OMe | OMe | CH |
| 2286 | $Q_{62}$ | H | H | Me | OMe | N |
| 2287 | Me | H | $Q_{62}$ | Me | Me | CH |
| 2288 | Me | H | $Q_{62}$ | Me | OMe | CH |
| 2289 | Me | H | $Q_{62}$ | OMe | OMe | CH |
| 2290 | Me | H | $Q_{62}$ | Me | OMe | N |
| 2291 | Me | H | $Q_{62}$ | OMe | OMe | N |
| 2292 | $Q_{63}$ | H | COOMe | Me | OMe | CH |
| 2293 | $Q_{63}$ | H | COOMe | OMe | OMe | CH |
| 2294 | $Q_{63}$ | H | COOEt | Me | OMe | CH |
| 2295 | $Q_{63}$ | H | COOEt | OMe | OMe | CH |
| 2296 | $Q_{63}$ | Me | COOMe | Me | OMe | CH |
| 2297 | $Q_{63}$ | Me | COOMe | OMe | OMe | CH |
| 2298 | $Q_{63}$ | Me | COOEt | Me | OMe | CH |
| 2299 | $Q_{63}$ | Me | COOEt | OMe | OMe | CH |
| 2300 | $Q_{63}$ | H | H | Me | OMe | CH |
| 2301 | $Q_{63}$ | H | H | OMe | OMe | CH |
| 2302 | Me | H | $Q_{63}$ | Me | OMe | CH |
| 2303 | Me | H | $Q_{63}$ | OMe | OMe | CH |
| 2304 | $Q_{64}$ | H | COOMe | Me | OMe | CH |
| 2305 | $Q_{64}$ | H | COOMe | OMe | OMe | CH |
| 2306 | $Q_{64}$ | H | COOEt | Me | OMe | CH |
| 2307 | $Q_{64}$ | H | COOEt | OMe | OMe | CH |
| 2308 | $Q_{64}$ | Me | COOMe | Me | OMe | CH |
| 2309 | $Q_{64}$ | Me | COOMe | OMe | OMe | CH |
| 2310 | $Q_{64}$ | Me | COOEt | Me | OMe | CH |
| 2311 | $Q_{64}$ | Me | COOEt | OMe | OMe | CH |
| 2312 | $Q_{64}$ | H | H | Me | OMe | CH |
| 2313 | $Q_{64}$ | H | H | OMe | OMe | CH |
| 2314 | Me | H | $Q_{64}$ | Me | OMe | CH |
| 2315 | Me | H | $Q_{64}$ | OMe | OMe | CH |
| 2316 | $Q_{65}$ | H | COOMe | Me | Me | CH |
| 2317 | $Q_{65}$ | H | COOMe | Me | OMe | CH |
| 2318 | $Q_{65}$ | H | COOMe | OMe | OMe | CH |
| 2319 | $Q_{65}$ | H | COOMe | Me | OMe | N |
| 2320 | $Q_{65}$ | H | COOMe | OMe | OMe | N |
| 2321 | $Q_{65}$ | H | COOEt | Me | Me | CH |
| 2322 | $Q_{65}$ | H | COOEt | Me | OMe | CH |
| 2323 | $Q_{65}$ | H | COOEt | OMe | OMe | CH |
| 2324 | $Q_{65}$ | H | COOEt | Me | OMe | N |
| 2325 | $Q_{65}$ | H | COOEt | OMe | OMe | N |
| 2326 | $Q_{65}$ | Me | COOMe | Me | OMe | CH |
| 2327 | $Q_{65}$ | Me | COOMe | OMe | OMe | CH |
| 2328 | $Q_{65}$ | Me | COOMe | Me | OMe | N |
| 2329 | $Q_{65}$ | Me | COOEt | Me | OMe | CH |
| 2330 | $Q_{65}$ | Me | COOEt | OMe | OMe | CH |
| 2331 | $Q_{65}$ | Me | COOEt | Me | OMe | N |
| 2332 | $Q_{65}$ | H | CN | Me | OMe | CH |
| 2333 | $Q_{65}$ | H | CN | OMe | OMe | CH |
| 2334 | $Q_{65}$ | H | CN | Me | OMe | N |
| 2335 | $Q_{65}$ | H | H | Me | OMe | CH |
| 2336 | $Q_{65}$ | H | H | OMe | OMe | CH |
| 2337 | $Q_{65}$ | H | H | Me | OMe | N |
| 2338 | Me | H | $Q_{65}$ | Me | Me | CH |
| 2339 | Me | H | $Q_{65}$ | Me | OMe | CH |

-continued

| | | | | | | |
|---|---|---|---|---|---|---|
| 2340 | Me | H | $Q_{65}$ | OMe | OMe | CH |
| 2341 | Me | H | $Q_{65}$ | Me | OMe | N |
| 2342 | Me | H | $Q_{65}$ | OMe | OMe | N |
| 2343 | $Q_{66}$ | H | COOMe | Me | OMe | CH |
| 2344 | $Q_{66}$ | H | COOMe | OMe | OMe | CH |
| 2345 | $Q_{66}$ | H | COOEt | Me | OMe | CH |
| 2346 | $Q_{66}$ | H | COOEt | OMe | OMe | CH |
| 2347 | $Q_{66}$ | Me | COOMe | Me | OMe | CH |
| 2348 | $Q_{66}$ | Me | COOMe | OMe | OMe | CH |
| 2349 | $Q_{66}$ | Me | COOEt | Me | OMe | CH |
| 2350 | $Q_{66}$ | Me | COOEt | OMe | OMe | CH |
| 2351 | $Q_{66}$ | H | H | Me | OMe | CH |
| 2352 | $Q_{66}$ | H | H | OMe | OMe | CH |
| 2353 | Me | H | $Q_{66}$ | Me | OMe | CH |
| 2354 | Me | H | $Q_{66}$ | OMe | OMe | CH |
| 2355 | $Q_{67}$ | H | COOMe | Me | OMe | CH |
| 2356 | $Q_{67}$ | H | COOMe | OMe | OMe | CH |
| 2357 | $Q_{67}$ | H | COOEt | Me | OMe | CH |
| 2358 | $Q_{67}$ | H | COOEt | OMe | OMe | CH |
| 2359 | $Q_{67}$ | Me | COOMe | Me | OMe | CH |
| 2360 | $Q_{67}$ | Me | COOMe | OMe | OMe | CH |
| 2361 | $Q_{67}$ | Me | COOEt | Me | OMe | CH |
| 2362 | $Q_{67}$ | Me | COOEt | OMe | OMe | CH |
| 2363 | $Q_{67}$ | H | H | Me | OMe | CH |
| 2364 | $Q_{67}$ | H | H | OMe | OMe | CH |
| 2365 | Me | H | $Q_{67}$ | Me | OMe | CH |
| 2366 | Me | H | $Q_{67}$ | OMe | OMe | CH |
| 2367 | $Q_{68}$ | H | COOMe | Me | OMe | CH |
| 2368 | $Q_{68}$ | H | COOMe | OMe | OMe | CH |
| 2369 | $Q_{68}$ | H | COOEt | Me | OMe | CH |
| 2370 | $Q_{68}$ | H | COOEt | OMe | OMe | CH |
| 2371 | $Q_{68}$ | Me | COOMe | Me | OMe | CH |
| 2372 | $Q_{68}$ | Me | COOMe | OMe | OMe | CH |
| 2373 | $Q_{68}$ | Me | COOEt | Me | OMe | CH |
| 2374 | $Q_{68}$ | Me | COOEt | OMe | OMe | CH |
| 2375 | $Q_{68}$ | H | H | Me | OMe | CH |
| 2376 | $Q_{68}$ | H | H | OMe | OMe | CH |
| 2377 | Me | H | $Q_{68}$ | Me | OMe | CH |
| 2378 | Me | H | $Q_{68}$ | Me | OMe | CH |
| 2379 | $Q_{69}$ | H | COOMe | Me | OMe | CH |
| 2380 | $Q_{69}$ | H | COOMe | OMe | OMe | CH |
| 2381 | $Q_{69}$ | H | COOEt | Me | OMe | CH |
| 2382 | $Q_{69}$ | H | COOEt | OMe | OMe | CH |
| 2383 | $Q_{69}$ | Me | COOMe | Me | OMe | CH |
| 2384 | $Q_{69}$ | Me | COOMe | OMe | OMe | CH |
| 2385 | $Q_{69}$ | Me | COOEt | Me | OMe | CH |
| 2386 | $Q_{69}$ | Me | COOEt | OMe | OMe | CH |
| 2387 | $Q_{69}$ | H | H | Me | OMe | CH |
| 2388 | $Q_{69}$ | H | H | OMe | OMe | CH |
| 2389 | Me | H | $Q_{69}$ | Me | OMe | CH |
| 2390 | Me | H | $Q_{69}$ | OMe | OMe | CH |
| 2391 | $Q_{70}$ | H | COOMe | Me | Me | CH |
| 2392 | $Q_{70}$ | H | COOMe | Me | OMe | CH |
| 2393 | $Q_{70}$ | H | COOMe | OMe | OMe | CH |
| 2394 | $Q_{70}$ | H | COOMe | Me | OMe | N |
| 2395 | $Q_{70}$ | H | COOMe | OMe | OMe | N |
| 2396 | $Q_{70}$ | H | COOEt | Me | Me | CH |
| 2397 | $Q_{70}$ | H | COOEt | Me | OMe | CH |
| 2398 | $Q_{70}$ | H | COOEt | OMe | OMe | CH |
| 2399 | $Q_{70}$ | H | COOEt | Me | OMe | N |
| 2400 | $Q_{70}$ | H | COOEt | OMe | OMe | N |
| 2401 | $Q_{70}$ | Me | COOMe | Me | OMe | CH |
| 2402 | $Q_{70}$ | Me | COOMe | OMe | OMe | CH |
| 2403 | $Q_{70}$ | Me | COOMe | Me | OMe | N |
| 2404 | $Q_{70}$ | Me | COOEt | Me | OMe | CH |
| 2405 | $Q_{70}$ | Me | COOEt | OMe | OMe | CH |
| 2406 | $Q_{70}$ | Me | COOEt | Me | OMe | N |
| 2407 | $Q_{70}$ | H | CN | Me | OMe | CH |
| 2408 | $Q_{70}$ | H | CN | OMe | OMe | CH |
| 2409 | $Q_{70}$ | H | CN | Me | OMe | N |
| 2410 | $Q_{70}$ | H | H | Me | OMe | CH |
| 2411 | $Q_{70}$ | H | H | OMe | OMe | CH |
| 2412 | $Q_{70}$ | H | H | Me | OMe | N |
| 2413 | Me | H | $Q_{70}$ | Me | Me | CH |
| 2414 | Me | H | $Q_{70}$ | Me | OMe | CH |
| 2415 | Me | H | $Q_{70}$ | OMe | OMe | CH |
| 2416 | Me | H | $Q_{70}$ | Me | OMe | N |
| 2417 | Me | H | $Q_{70}$ | OMe | OMe | N |
| 2418 | $Q_{71}$ | H | COOMe | Me | OMe | CH |
| 2419 | $Q_{71}$ | H | COOMe | OMe | OMe | CH |
| 2420 | $Q_{71}$ | H | COOEt | Me | OMe | CH |
| 2421 | $Q_{71}$ | H | COOEt | OMe | OMe | CH |

-continued

| | | | | | | |
|---|---|---|---|---|---|---|
| 2422 | $Q_{71}$ | Me | COOMe | Me | OMe | CH |
| 2423 | $Q_{71}$ | Me | COOMe | OMe | OMe | CH |
| 2424 | $Q_{71}$ | Me | COOEt | Me | OMe | CH |
| 2425 | $Q_{71}$ | Me | COOEt | OMe | OMe | CH |
| 2426 | $Q_{71}$ | H | H | Me | OMe | CH |
| 2427 | $Q_{71}$ | H | H | OMe | OMe | CH |
| 2428 | Me | H | $Q_{71}$ | Me | OMe | CH |
| 2429 | Me | H | $Q_{71}$ | OMe | OMe | CH |
| 2430 | $Q_{72}$ | H | COOMe | Me | OMe | CH |
| 2431 | $Q_{72}$ | H | COOMe | OMe | OMe | CH |
| 2432 | $Q_{72}$ | H | COOEt | Me | OMe | CH |
| 2433 | $Q_{72}$ | H | COOEt | OMe | OMe | CH |
| 2434 | $Q_{72}$ | Me | COOMe | Me | OMe | CH |
| 2435 | $Q_{72}$ | Me | COOMe | OMe | OMe | CH |
| 2436 | $Q_{72}$ | Me | COOEt | Me | OMe | CH |
| 2437 | $Q_{72}$ | Me | COOEt | OMe | OMe | CH |
| 2438 | $Q_{72}$ | H | H | Me | OMe | CH |
| 2439 | $Q_{72}$ | H | H | OMe | OMe | CH |
| 2440 | Me | H | $Q_{72}$ | Me | OMe | CH |
| 2441 | Me | H | $Q_{72}$ | OMe | OMe | CH |
| 2442 | $Q_{73}$ | H | COOMe | Me | OMe | CH |
| 2443 | $Q_{73}$ | H | COOMe | OMe | OMe | CH |
| 2444 | $Q_{73}$ | H | COOEt | Me | OMe | CH |
| 2445 | $Q_{73}$ | H | COOEt | OMe | OMe | CH |
| 2446 | $Q_{73}$ | Me | COOMe | Me | OMe | CH |
| 2447 | $Q_{73}$ | Me | COOMe | OMe | OMe | CH |
| 2448 | $Q_{73}$ | Me | COOEt | Me | OMe | CH |
| 2449 | $Q_{73}$ | Me | COOEt | OMe | OMe | CH |
| 2450 | $Q_{73}$ | H | H | Me | OMe | CH |
| 2451 | $Q_{73}$ | H | H | OMe | OMe | CH |
| 2452 | Me | H | $Q_{73}$ | Me | OMe | CH |
| 2453 | Me | H | $Q_{73}$ | OMe | OMe | CH |
| 2454 | $Q_{74}$ | H | COOMe | Me | OMe | CH |
| 2455 | $Q_{74}$ | H | COOMe | OMe | OMe | CH |
| 2456 | $Q_{74}$ | H | COOEt | Me | OMe | CH |
| 2457 | $Q_{74}$ | H | COOEt | OMe | OMe | CH |
| 2458 | $Q_{74}$ | Me | COOMe | Me | OMe | CH |
| 2459 | $Q_{74}$ | Me | COOMe | OMe | OMe | CH |
| 2460 | $Q_{74}$ | Me | COOEt | Me | OMe | CH |
| 2461 | $Q_{74}$ | Me | COOEt | OMe | OMe | CH |
| 2462 | $Q_{74}$ | H | H | Me | OMe | CH |
| 2463 | $Q_{74}$ | H | H | OMe | OMe | CH |
| 2464 | Me | H | $Q_{74}$ | Me | OMe | CH |
| 2465 | Me | H | $Q_{74}$ | OMe | OMe | CH |
| 2466 | $Q_{75}$ | H | COOMe | Me | OMe | CH |
| 2467 | $Q_{75}$ | H | COOMe | OMe | OMe | CH |
| 2468 | $Q_{75}$ | H | COOEt | Me | OMe | CH |
| 2469 | $Q_{75}$ | H | COOEt | OMe | OMe | CH |
| 2470 | $Q_{75}$ | Me | COOMe | Me | OMe | CH |
| 2471 | $Q_{75}$ | Me | COOMe | OMe | OMe | CH |
| 2472 | $Q_{75}$ | Me | COOEt | Me | OMe | CH |
| 2473 | $Q_{75}$ | Me | COOEt | OMe | OMe | CH |
| 2474 | $Q_{75}$ | H | H | Me | OMe | CH |
| 2475 | $Q_{75}$ | H | H | OMe | OMe | CH |
| 2476 | Me | H | $Q_{75}$ | Me | OMe | CH |
| 2477 | Me | H | $Q_{75}$ | OMe | OMe | CH |
| 2478 | $Q_{76}$ | H | COOMe | Me | OMe | CH |
| 2479 | $Q_{76}$ | H | COOMe | OMe | OMe | CH |
| 2480 | $Q_{76}$ | H | COOEt | Me | OMe | CH |
| 2481 | $Q_{76}$ | H | COOEt | OMe | OMe | CH |
| 2482 | $Q_{76}$ | Me | COOMe | Me | OMe | CH |
| 2483 | $Q_{76}$ | Me | COOMe | OMe | OMe | CH |
| 2484 | $Q_{76}$ | Me | COOEt | Me | OMe | CH |
| 2485 | $Q_{76}$ | Me | COOEt | OMe | OMe | CH |
| 2486 | $Q_{76}$ | H | H | Me | OMe | CH |
| 2487 | $Q_{76}$ | H | H | OMe | OMe | CH |
| 2488 | Me | H | $Q_{76}$ | Me | OMe | CH |
| 2489 | Me | H | $Q_{76}$ | OMe | OMe | CH |
| 5347 | $Q_{10}$ | Me | COOMe | Me | Me | CH |
| 5348 | $Q_{77}$ | H | COOMe | Me | OMe | CH |
| 5349 | $Q_{77}$ | H | COOMe | OMe | OMe | CH |
| 5350 | $Q_{77}$ | H | COOEt | Me | OMe | CH |
| 5351 | $Q_{77}$ | H | COOEt | OMe | OMe | CH |
| 5352 | $Q_{77}$ | Me | COOMe | Me | OMe | CH |
| 5353 | $Q_{77}$ | Me | COOMe | OMe | OMe | CH |
| 5354 | $Q_{77}$ | Me | COOEt | Me | OMe | CH |
| 5355 | $Q_{77}$ | Me | COOEt | OMe | OMe | CH |
| 5356 | $Q_{77}$ | H | H | Me | OMe | CH |
| 5357 | $Q_{77}$ | H | H | OMe | OMe | CH |
| 5358 | Me | H | $Q_{77}$ | Me | OMe | CH |
| 5359 | Me | H | $Q_{77}$ | OMe | OMe | CH |
| 5360 | $Q_{78}$ | H | COOMe | Me | Me | CH |

-continued

| | | | | | | |
|---|---|---|---|---|---|---|
| 5361 | $Q_{78}$ | H | COOMe | Me | OMe | CH |
| 5362 | $Q_{78}$ | H | COOMe | OMe | OMe | CH |
| 5363 | $Q_{78}$ | H | COOMe | Me | Me | N |
| 5364 | $Q_{78}$ | H | COOMe | Me | OMe | N |
| 5365 | $Q_{78}$ | H | COOMe | OMe | OMe | N |
| 5366 | $Q_{78}$ | H | COOMe | Me | $OCHF_2$ | CH |
| 5367 | $Q_{78}$ | H | COOMe | Cl | OMe | CH |
| 5368 | $Q_{78}$ | H | COOEt | Me | Me | CH |
| 5369 | $Q_{78}$ | H | COOEt | Me | OMe | CH |
| 5370 | $Q_{78}$ | H | COOEt | OMe | OMe | CH |
| 5371 | $Q_{78}$ | H | COOEt | Me | Me | N |
| 5372 | $Q_{78}$ | H | COOEt | Me | OMe | N |
| 5373 | $Q_{78}$ | H | COOEt | OMe | OMe | N |
| 5374 | $Q_{78}$ | H | COOEt | Me | $OCHF_2$ | CH |
| 5375 | $Q_{78}$ | H | COOEt | Cl | OMe | CH |
| 5376 | $Q_{78}$ | H | COOPr—n | Me | OMe | CH |
| 5377 | $Q_{78}$ | H | COOPr—n | OMe | OMe | CH |
| 5378 | $Q_{78}$ | H | COOPr—n | Me | OMe | N |
| 5379 | $Q_{78}$ | H | COOPr—i | Me | OMe | CH |
| 5380 | $Q_{78}$ | H | COOPr—i | OMe | OMe | CH |
| 5381 | $Q_{78}$ | H | COOPr—i | Me | OMe | N |
| 5382 | $Q_{78}$ | H | $COOCH_2CH_2Cl$ | Me | OMe | CH |
| 5383 | $Q_{78}$ | H | $COOCH_2CH_2Cl$ | OMe | OMe | CH |
| 5384 | $Q_{78}$ | H | $COOCH_2CH_2Cl$ | Me | OMe | N |
| 5385 | $Q_{78}$ | H | $COOCH_2CH{=}CH_2$ | Me | OMe | CH |
| 5386 | $Q_{78}$ | H | $COOCH_2CH{=}CH_2$ | OMe | OMe | CH |
| 5387 | $Q_{78}$ | H | $COOCH_2CH{=}CH_2$ | Me | OMe | N |
| 5388 | $Q_{78}$ | H | $COOCH_2C{\equiv}CH$ | Me | OMe | CH |
| 5389 | $Q_{78}$ | H | $COOCH_2C{\equiv}CH$ | OMe | OMe | CH |
| 5390 | $Q_{78}$ | H | $COOCH_2C{\equiv}CH$ | Me | OMe | N |
| 5391 | $Q_{78}$ | Me | COOMe | Me | Me | CH |
| 5392 | $Q_{78}$ | Me | COOMe | Me | OMe | CH |
| 5393 | $Q_{78}$ | Me | COOMe | OMe | OMe | CH |
| 5394 | $Q_{78}$ | Me | COOMe | Me | OMe | N |
| 5395 | $Q_{78}$ | Me | COOMe | OMe | OMe | N |
| 5396 | $Q_{78}$ | Me | COOEt | Me | Me | CH |
| 5397 | $Q_{78}$ | Me | COOEt | Me | OMe | CH |
| 5398 | $Q_{78}$ | Me | COOEt | OMe | OMe | CH |
| 5399 | $Q_{78}$ | Me | COOEt | Me | OMe | N |
| 5400 | $Q_{78}$ | Me | COOEt | OMe | OMe | N |
| 5401 | $Q_{78}$ | Cl | COOMe | Me | OMe | CH |
| 5402 | $Q_{78}$ | Cl | COOMe | OMe | OMe | CH |
| 5403 | $Q_{78}$ | Cl | COOMe | Me | OMe | N |
| 5404 | $Q_{78}$ | Cl | COOEt | Me | OMe | CH |
| 5405 | $Q_{78}$ | Cl | COOEt | OMe | OMe | CH |
| 5406 | $Q_{78}$ | Cl | COOEt | Me | OMe | N |
| 5407 | $Q_{78}$ | OMe | COOMe | Me | OMe | CH |
| 5408 | $Q_{78}$ | OMe | COOMe | OMe | OMe | CH |
| 5409 | $Q_{78}$ | OMe | COOMe | Me | OMe | N |
| 5410 | $Q_{78}$ | OMe | COOEt | Me | OMe | CH |
| 5411 | $Q_{78}$ | OMe | COOEt | OMe | OMe | CH |
| 5412 | $Q_{78}$ | OMe | COOEt | Me | OMe | N |
| 5413 | $Q_{78}$ | H | Cl | Me | OMe | CH |
| 5414 | $Q_{78}$ | H | Cl | OMe | OMe | CH |
| 5415 | $Q_{78}$ | H | Cl | Me | OMe | N |
| 5416 | $Q_{78}$ | H | $NO_2$ | Me | OMe | CH |
| 5417 | $Q_{78}$ | H | $NO_2$ | OMe | OMe | CH |
| 5418 | $Q_{78}$ | H | $NO_2$ | Me | OMe | N |
| 5419 | $Q_{78}$ | H | $SO_2NMe_2$ | Me | OMe | CH |
| 5420 | $Q_{78}$ | H | $SO_2NMe_2$ | OMe | OMe | CH |
| 5421 | $Q_{78}$ | H | $SO_2NMe_2$ | Me | OMe | N |
| 5422 | $Q_{78}$ | H | CN | Me | OMe | CH |
| 5423 | $Q_{78}$ | H | CN | OMe | OMe | CH |
| 5424 | $Q_{78}$ | H | CN | Me | OMe | N |
| 5425 | $Q_{78}$ | Me | CN | Me | OMe | CH |
| 5426 | $Q_{78}$ | Me | CN | OMe | OMe | CH |
| 5427 | $Q_{78}$ | Me | CN | Me | OMe | N |
| 5428 | $Q_{78}$ | H | Me | Me | OMe | CH |
| 5429 | $Q_{78}$ | H | Me | OMe | OMe | CH |
| 5430 | $Q_{78}$ | H | Me | Me | OMe | N |
| 5431 | $Q_{78}$ | H | Et | Me | OMe | CH |
| 5432 | $Q_{78}$ | H | Et | OMe | OMe | CH |
| 5433 | $Q_{78}$ | H | Et | Me | OMe | N |
| 5434 | $Q_{78}$ | H | H | Me | OMe | CH |
| 5435 | $Q_{78}$ | H | H | OMe | OMe | CH |
| 5436 | $Q_{78}$ | H | H | Me | OMe | N |
| 5437 | $Q_{78}$ | H | COPh | Me | OMe | CH |
| 5438 | $Q_{78}$ | H | COPh | OMe | OMe | CH |
| 5439 | $Q_{78}$ | H | COPh | Me | OMe | N |
| 5440 | Me | $Q_{78}$ | COOMe | Me | OMe | CH |
| 5441 | Me | $Q_{78}$ | COOMe | OMe | OMe | CH |
| 5442 | Me | $Q_{78}$ | COOMe | Me | OMe | N |

-continued

| | | | | | | |
|---|---|---|---|---|---|---|
| 5443 | H | H | $Q_{78}$ | Me | OMe | CH |
| 5444 | H | H | $Q_{78}$ | OMe | OMe | CH |
| 5445 | H | H | $Q_{78}$ | Me | OMe | N |
| 5446 | Me | H | $Q_{78}$ | Me | Me | CH |
| 5447 | Me | H | $Q_{78}$ | Me | OMe | CH |
| 5448 | Me | H | $Q_{78}$ | OMe | OMe | CH |
| 5449 | Me | H | $Q_{78}$ | Me | OMe | N |
| 5450 | Me | H | $Q_{78}$ | OMe | OMe | N |
| 5451 | Me | Me | $Q_{78}$ | Me | OMe | CH |
| 5452 | Me | Me | $Q_{78}$ | OMe | OMe | CH |
| 5453 | Me | Me | $Q_{78}$ | Me | OMe | N |
| 5454 | $Q_{79}$ | H | COOMe | Me | Me | CH |
| 5455 | $Q_{79}$ | H | COOMe | Me | OMe | CH |
| 5456 | $Q_{79}$ | H | COOMe | OMe | OMe | CH |
| 5457 | $Q_{79}$ | H | COOMe | Me | Me | N |
| 5458 | $Q_{79}$ | H | COOMe | Me | OMe | N |
| 5459 | $Q_{79}$ | H | COOMe | OMe | OMe | N |
| 5460 | $Q_{79}$ | H | COOMe | Me | $OCHF_2$ | CH |
| 5461 | $Q_{79}$ | H | COOMe | Cl | OMe | CH |
| 5462 | $Q_{79}$ | H | COOEt | Me | Me | CH |
| 5463 | $Q_{79}$ | H | COOEt | Me | OMe | CH |
| 5464 | $Q_{79}$ | H | COOEt | OMe | OMe | CH |
| 5465 | $Q_{79}$ | H | COOEt | Me | Me | N |
| 5466 | $Q_{79}$ | H | COOEt | Me | OMe | N |
| 5467 | $Q_{79}$ | H | COOEt | OMe | OMe | N |
| 5468 | $Q_{79}$ | H | COOEt | Me | $OCHF_2$ | CH |
| 5469 | $Q_{79}$ | H | COOEt | Cl | OMe | CH |
| 5470 | $Q_{79}$ | H | COOPr—n | Me | OMe | CH |
| 5471 | $Q_{79}$ | H | COOPr—n | OMe | OMe | CH |
| 5472 | $Q_{79}$ | H | COOPr—n | Me | OMe | N |
| 5473 | $Q_{79}$ | H | COOPr—i | Me | OMe | CH |
| 5474 | $Q_{79}$ | H | COOPr—i | OMe | OMe | CH |
| 5475 | $Q_{79}$ | H | COOPr—i | Me | OMe | N |
| 5476 | $Q_{79}$ | H | $COOCH_2CH_2Cl$ | Me | OMe | CH |
| 5477 | $Q_{79}$ | H | $COOCH_2CH_2Cl$ | OMe | OMe | CH |
| 5478 | $Q_{79}$ | H | $COOCH_2CH_2Cl$ | Me | OMe | N |
| 5479 | $Q_{79}$ | H | $COOCH_2CH{=}CH_2$ | Me | OMe | CH |
| 5480 | $Q_{79}$ | H | $COOCH_2CH{=}CH_2$ | OMe | OMe | CH |
| 5481 | $Q_{79}$ | H | $COOCH_2CH{=}CH_2$ | Me | OMe | N |
| 5482 | $Q_{79}$ | H | $COOCH_2C{\equiv}CH$ | Me | OMe | CH |
| 5483 | $Q_{79}$ | H | $COOCH_2C{\equiv}CH$ | OMe | OMe | CH |
| 5484 | $Q_{79}$ | H | $COOCH_2C{\equiv}CH$ | Me | OMe | N |
| 5485 | $Q_{79}$ | Me | COOMe | Me | Me | CH |
| 5486 | $Q_{79}$ | Me | COOMe | Me | OMe | CH |
| 5487 | $Q_{79}$ | Me | COOMe | OMe | OMe | CH |
| 5488 | $Q_{79}$ | Me | COOMe | Me | OMe | N |
| 5489 | $Q_{79}$ | Me | COOMe | OMe | OMe | N |
| 5490 | $Q_{79}$ | Me | COOEt | Me | Me | CH |
| 5491 | $Q_{79}$ | Me | COOEt | Me | OMe | CH |
| 5492 | $Q_{79}$ | Me | COOEt | OMe | OMe | CH |
| 5493 | $Q_{79}$ | Me | COOEt | Me | OMe | N |
| 5494 | $Q_{79}$ | Me | COOEt | OMe | OMe | N |
| 5495 | $Q_{79}$ | Cl | COOMe | Me | OMe | CH |
| 5496 | $Q_{79}$ | Cl | COOMe | OMe | OMe | CH |
| 5497 | $Q_{79}$ | Cl | COOMe | Me | OMe | N |
| 5498 | $Q_{79}$ | Cl | COOEt | Me | OMe | CH |
| 5499 | $Q_{79}$ | Cl | COOEt | OMe | OMe | CH |
| 5500 | $Q_{79}$ | Cl | COOEt | Me | OMe | N |
| 5501 | $Q_{79}$ | OMe | COOMe | Me | OMe | CH |
| 5502 | $Q_{79}$ | OMe | COOMe | OMe | OMe | CH |
| 5503 | $Q_{79}$ | OMe | COOMe | Me | OMe | N |
| 5504 | $Q_{79}$ | OMe | COOEt | Me | OMe | CH |
| 5505 | $Q_{79}$ | OMe | COOEt | OMe | OMe | CH |
| 5506 | $Q_{79}$ | OMe | COOEt | Me | OMe | N |
| 5507 | $Q_{79}$ | H | Cl | Me | OMe | CH |
| 5508 | $Q_{79}$ | H | Cl | OMe | OMe | CH |
| 5509 | $Q_{79}$ | H | Cl | Me | OMe | N |
| 5510 | $Q_{79}$ | H | $NO_2$ | Me | OMe | CH |
| 5511 | $Q_{79}$ | H | $NO_2$ | OMe | OMe | CH |
| 5512 | $Q_{79}$ | H | $NO_2$ | Me | OMe | N |
| 5513 | $Q_{79}$ | H | $SO_2NMe_2$ | Me | OMe | CH |
| 5514 | $Q_{79}$ | H | $SO_2NMe_2$ | OMe | OMe | CH |
| 5515 | $Q_{79}$ | H | $SO_2NMe_2$ | Me | OMe | N |
| 5516 | $Q_{79}$ | H | CN | Me | OMe | CH |
| 5517 | $Q_{79}$ | H | CN | OMe | OMe | CH |
| 5518 | $Q_{79}$ | H | CN | Me | OMe | N |
| 5519 | $Q_{79}$ | Me | CN | Me | OMe | CH |
| 5520 | $Q_{79}$ | Me | CN | OMe | OMe | CH |
| 5521 | $Q_{79}$ | Me | CN | Me | OMe | N |
| 5522 | $Q_{79}$ | H | Me | Me | OMe | CH |
| 5523 | $Q_{79}$ | H | Me | OMe | OMe | CH |
| 5524 | $Q_{79}$ | H | Me | Me | OMe | N |

-continued

| | | | | | | |
|---|---|---|---|---|---|---|
| 5525 | $Q_{79}$ | H | Et | Me | OMe | CH |
| 5526 | $Q_{79}$ | H | Et | OMe | OMe | CH |
| 5527 | $Q_{79}$ | H | Et | Me | OMe | N |
| 5528 | $Q_{79}$ | H | H | Me | OMe | CH |
| 5529 | $Q_{79}$ | H | H | OMe | OMe | CH |
| 5530 | $Q_{79}$ | H | H | Me | OMe | N |
| 5531 | $Q_{79}$ | H | COPh | Me | OMe | CH |
| 5532 | $Q_{79}$ | H | COPh | OMe | OMe | CH |
| 5533 | $Q_{79}$ | H | COPh | Me | OMe | N |
| 5534 | Me | $Q_{79}$ | COOMe | Me | OMe | CH |
| 5535 | Me | $Q_{79}$ | COOMe | OMe | OMe | CH |
| 5536 | Me | $Q_{79}$ | COOMe | Me | OMe | N |
| 5537 | H | H | $Q_{79}$ | Me | OMe | CH |
| 5538 | H | H | $Q_{79}$ | OMe | OMe | CH |
| 5539 | H | H | $Q_{79}$ | Me | OMe | N |
| 5540 | Me | H | $Q_{79}$ | Me | Me | CH |
| 5541 | Me | H | $Q_{79}$ | Me | OMe | CH |
| 5542 | Me | H | $Q_{79}$ | OMe | OMe | CH |
| 5543 | Me | H | $Q_{79}$ | Me | OMe | N |
| 5544 | Me | H | $Q_{79}$ | OMe | OMe | N |
| 5545 | Me | Me | $Q_{79}$ | Me | OMe | CH |
| 5546 | Me | Me | $Q_{79}$ | OMe | OMe | CH |
| 5547 | Me | Me | $Q_{79}$ | Me | OMe | N |
| 5548 | $Q_{80}$ | H | COOMe | Me | Me | CH |
| 5549 | $Q_{80}$ | H | COOMe | Me | OMe | CH |
| 5550 | $Q_{80}$ | H | COOMe | OMe | OMe | CH |
| 5551 | $Q_{80}$ | H | COOMe | Me | OMe | N |
| 5552 | $Q_{80}$ | H | COOMe | OMe | OMe | N |
| 5553 | $Q_{80}$ | H | COOEt | Me | Me | CH |
| 5554 | $Q_{80}$ | H | COOEt | Me | OMe | CH |
| 5555 | $Q_{80}$ | H | COOEt | OMe | OMe | CH |
| 5556 | $Q_{80}$ | H | COOEt | Me | OMe | N |
| 5557 | $Q_{80}$ | H | COOEt | OMe | OMe | N |
| 5558 | $Q_{80}$ | Me | COOMe | Me | OMe | CH |
| 5559 | $Q_{80}$ | Me | COOMe | OMe | OMe | CH |
| 5560 | $Q_{80}$ | Me | COOMe | Me | OMe | N |
| 5561 | $Q_{80}$ | Me | COOEt | Me | OMe | CH |
| 5562 | $Q_{80}$ | Me | COOEt | OMe | OMe | CH |
| 5563 | $Q_{80}$ | Me | COOEt | Me | OMe | N |
| 5564 | $Q_{80}$ | H | CN | Me | OMe | CH |
| 5565 | $Q_{80}$ | H | CN | OMe | OMe | CH |
| 5566 | $Q_{80}$ | H | CN | Me | OMe | N |
| 5567 | $Q_{80}$ | H | H | Me | OMe | CH |
| 5568 | $Q_{80}$ | H | H | OMe | OMe | CH |
| 5569 | $Q_{80}$ | H | H | Me | OMe | N |
| 5570 | Me | H | $Q_{80}$ | Me | Me | CH |
| 5571 | Me | H | $Q_{80}$ | Me | OMe | CH |
| 5572 | Me | H | $Q_{80}$ | OMe | OMe | CH |
| 5573 | Me | H | $Q_{80}$ | Me | OMe | N |
| 5574 | Me | H | $Q_{80}$ | OMe | OMe | N |
| 5575 | $Q_{81}$ | H | COOMe | Me | OMe | CH |
| 5576 | $Q_{81}$ | H | COOMe | OMe | OMe | CH |
| 5577 | $Q_{81}$ | H | COOEt | Me | OMe | CH |
| 5578 | $Q_{81}$ | H | COOEt | OMe | OMe | CH |
| 5579 | $Q_{81}$ | Me | COOMe | Me | OMe | CH |
| 5580 | $Q_{81}$ | Me | COOMe | OMe | OMe | CH |
| 5581 | $Q_{81}$ | Me | COOEt | Me | OMe | CH |
| 5582 | $Q_{81}$ | Me | COOEt | OMe | OMe | CH |
| 5583 | $Q_{81}$ | H | H | Me | OMe | CH |
| 5584 | $Q_{81}$ | H | H | OMe | OMe | CH |
| 5585 | Me | H | $Q_{81}$ | Me | OMe | CH |
| 5586 | Me | H | $Q_{81}$ | OMe | OMe | CH |
| 5587 | $Q_{82}$ | H | COOMe | Me | OMe | CH |
| 5588 | $Q_{82}$ | H | COOMe | OMe | OMe | CH |
| 5589 | $Q_{82}$ | H | COOEt | Me | OMe | CH |
| 5590 | $Q_{82}$ | H | COOEt | OMe | OMe | CH |
| 5591 | $Q_{82}$ | Me | COOMe | Me | OMe | CH |
| 5592 | $Q_{82}$ | Me | COOMe | OMe | OMe | CH |
| 5593 | $Q_{82}$ | Me | COOEt | Me | OMe | CH |
| 5594 | $Q_{82}$ | Me | COOEt | OMe | OMe | CH |
| 5595 | $Q_{82}$ | H | H | Me | OMe | CH |
| 5596 | $Q_{82}$ | H | H | OMe | OMe | CH |
| 5597 | Me | H | $Q_{82}$ | Me | OMe | CH |
| 5598 | Me | H | $Q_{82}$ | OMe | OMe | CH |
| 5599 | $Q_{83}$ | H | COOMe | Me | OMe | CH |
| 5600 | $Q_{83}$ | H | COOMe | OMe | OMe | CH |
| 5601 | $Q_{83}$ | H | COOEt | Me | OMe | CH |
| 5602 | $Q_{83}$ | H | COOEt | OMe | OMe | CH |
| 5603 | $Q_{83}$ | Me | COOMe | Me | OMe | CH |
| 5604 | $Q_{83}$ | Me | COOMe | OMe | OMe | CH |
| 5605 | $Q_{83}$ | Me | COOEt | Me | OMe | CH |
| 5606 | $Q_{83}$ | Me | COOEt | OMe | OMe | CH |

-continued
| | | | | | | |
|---|---|---|---|---|---|---|
| 5607 | $Q_{83}$ | H | H | Me | OMe | CH |
| 5608 | $Q_{83}$ | H | H | OMe | OMe | CH |
| 5609 | Me | H | $Q_{83}$ | Me | OMe | CH |
| 5610 | Me | H | $Q_{83}$ | OMe | OMe | CH |
In the above, $Q_1$ to $Q_{83}$ each represent the following heterocyclic group.
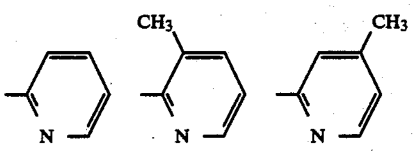
$Q_1$ $Q_2$ $Q_3$
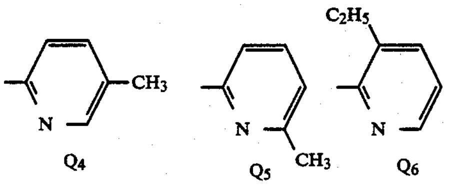
$Q_4$ $Q_5$ $Q_6$
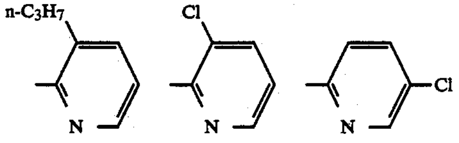
$Q_7$ $Q_8$ $Q_9$
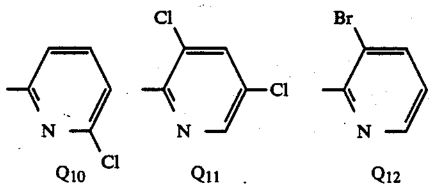
$Q_{10}$ $Q_{11}$ $Q_{12}$
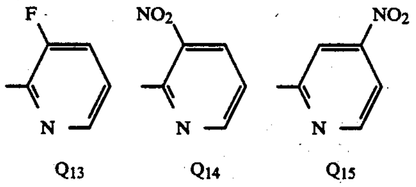
$Q_{13}$ $Q_{14}$ $Q_{15}$
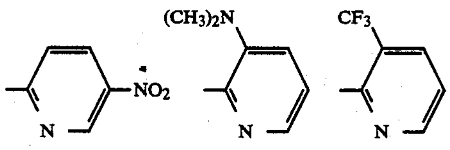
$Q_{16}$ $Q_{17}$ $Q_{18}$
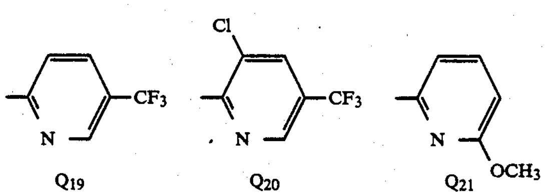
$Q_{19}$ $Q_{20}$ $Q_{21}$
-continued
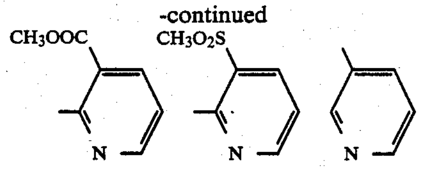
$Q_{22}$ $Q_{23}$ $Q_{24}$
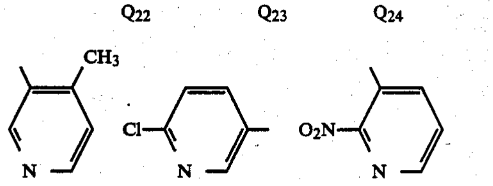
$Q_{25}$ $Q_{26}$ $Q_{27}$
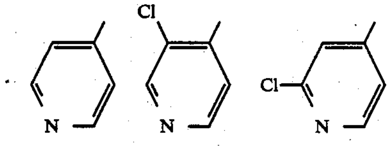
$Q_{28}$ $Q_{29}$ $Q_{30}$
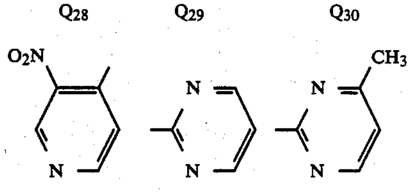
$Q_{31}$ $Q_{32}$ $Q_{33}$
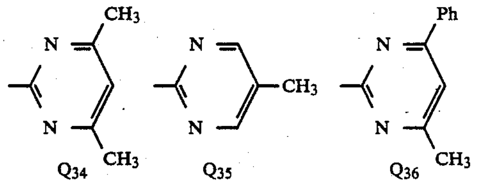
$Q_{34}$ $Q_{35}$ $Q_{36}$
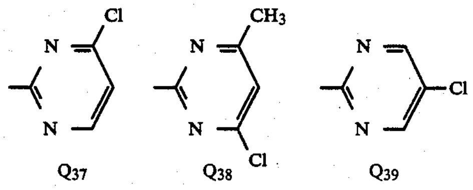
$Q_{37}$ $Q_{38}$ $Q_{39}$
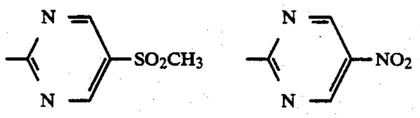
$Q_{40}$ $Q_{41}$
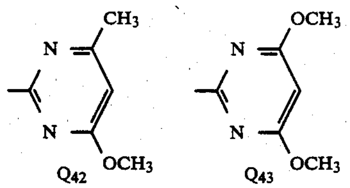
$Q_{42}$ $Q_{43}$ -continued
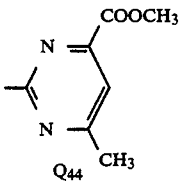
$Q_{44}$
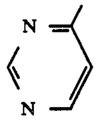
$Q_{45}$
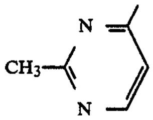
$Q_{46}$
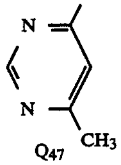
$Q_{47}$
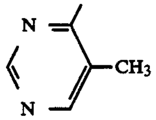
$Q_{48}$
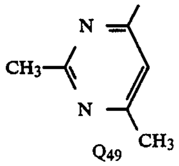
$Q_{49}$
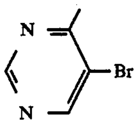
$Q_{50}$
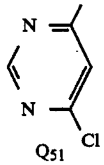
$Q_{51}$
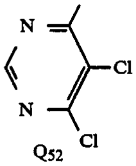
$Q_{52}$
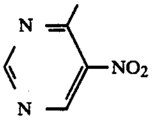
$Q_{53}$
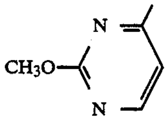
$Q_{54}$
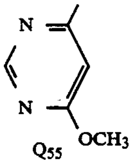
$Q_{55}$
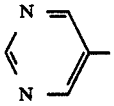
$Q_{56}$
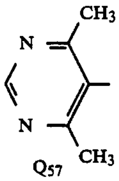
$Q_{57}$
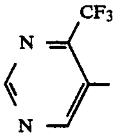
$Q_{58}$
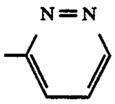
$Q_{59}$
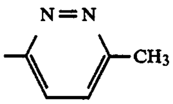
$Q_{60}$
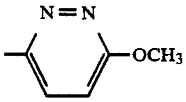
$Q_{61}$
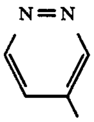
$Q_{62}$
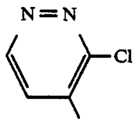
$Q_{63}$
-continued
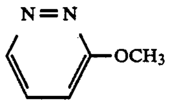
$Q_{64}$
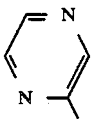
$Q_{65}$
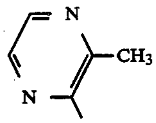
$Q_{66}$
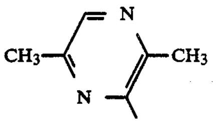
$Q_{67}$
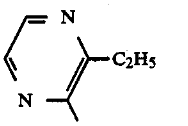
$Q_{68}$
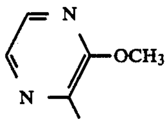
$Q_{69}$
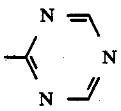
$Q_{70}$
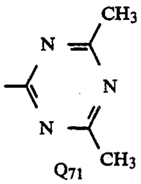
$Q_{71}$
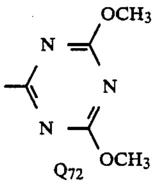
$Q_{72}$
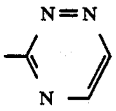
$Q_{73}$
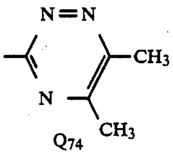
$Q_{74}$
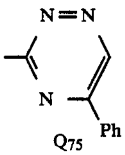
$Q_{75}$
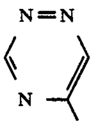
$Q_{76}$
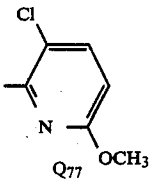
$Q_{77}$
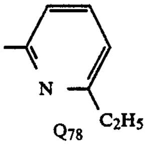
$Q_{78}$
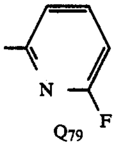
$Q_{79}$
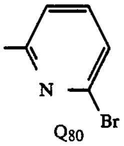
$Q_{80}$
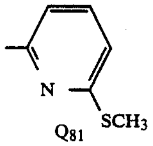
$Q_{81}$
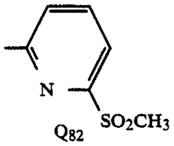
$Q_{82}$
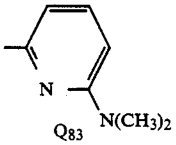
$Q_{83}$

TABLE 2

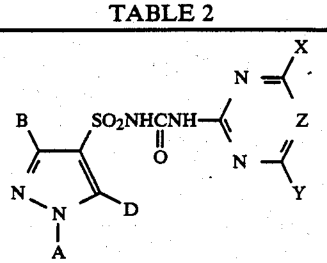

| No. | A | B | D | X | Y | Z |
|---|---|---|---|---|---|---|
| 2490 | $Q_1$ | H | H | Me | Me | CH |
| 2491 | $Q_1$ | H | H | Me | OMe | CH |
| 2492 | $Q_1$ | H | H | OMe | OMe | CH |
| 2493 | $Q_1$ | H | H | Me | OMe | N |
| 2494 | $Q_1$ | H | H | OMe | OMe | N |
| 2495 | $Q_1$ | Me | H | Me | Me | CH |
| 2496 | $Q_1$ | Me | H | Me | OMe | CH |
| 2497 | $Q_1$ | Me | H | OMe | OMe | CH |
| 2498 | $Q_1$ | Me | H | Me | OMe | N |
| 2499 | $Q_1$ | Me | H | OMe | OMe | N |
| 2500 | $Q_1$ | H | Me | Me | Me | CH |
| 2501 | $Q_1$ | H | Me | Me | OMe | CH |
| 2502 | $Q_1$ | H | Me | OMe | OMe | CH |
| 2503 | $Q_1$ | H | Me | Me | OMe | N |
| 2504 | $Q_1$ | H | Me | OMe | OMe | N |
| 2505 | $Q_1$ | Me | Cl | Me | Me | CH |
| 2506 | $Q_1$ | Me | Cl | Me | OMe | CH |
| 2507 | $Q_1$ | Me | Cl | OMe | OMe | CH |
| 2508 | $Q_1$ | Me | Cl | Me | OMe | N |
| 2509 | $Q_1$ | Me | Cl | OMe | OMe | N |
| 2510 | $Q_1$ | Me | OMe | Me | Me | CH |
| 2511 | $Q_1$ | Me | OMe | Me | OMe | CH |
| 2512 | $Q_1$ | Me | OMe | OMe | OMe | CH |
| 2513 | $Q_1$ | Me | OMe | Me | OMe | N |
| 2514 | $Q_1$ | Me | OMe | OMe | OMe | N |
| 2515 | $Q_1$ | Cl | H | Me | Me | CH |
| 2516 | $Q_1$ | Cl | H | Me | OMe | CH |
| 2517 | $Q_1$ | Cl | H | OMe | OMe | CH |
| 2518 | $Q_1$ | Cl | H | Me | OMe | N |
| 2519 | $Q_1$ | Cl | H | OMe | OMe | N |
| 2520 | $Q_1$ | Br | H | Me | Me | CH |
| 2521 | $Q_1$ | Br | H | Me | OMe | CH |
| 2522 | $Q_1$ | Br | H | OMe | OMe | N |
| 2523 | $Q_1$ | $CF_3$ | H | Me | OMe | CH |
| 2524 | $Q_1$ | $CF_3$ | H | OMe | OMe | CH |
| 2525 | $Q_1$ | $CF_3$ | H | Me | Me | CH |
| 2526 | $Q_1$ | $CF_3$ | H | Me | OMe | N |
| 2527 | $Q_1$ | $CF_3$ | H | OMe | OMe | N |
| 2528 | $Q_1$ | H | $CF_3$ | Me | OMe | CH |
| 2529 | $Q_1$ | H | $CF_3$ | OMe | OMe | CH |
| 2530 | $Q_1$ | H | $CF_3$ | OMe | OMe | CH |
| 2531 | $Q_1$ | H | $CF_3$ | Me | OMe | N |
| 2532 | $Q_1$ | H | $CF_3$ | OMe | OMe | N |
| 2533 | $Q_1$ | $CF_3$ | $CH_3$ | Me | Me | CH |
| 2534 | $Q_1$ | $CF_3$ | $CH_3$ | Me | OMe | CH |
| 2535 | $Q_1$ | $CF_3$ | $CH_3$ | OMe | OMe | CH |
| 2536 | $Q_1$ | $CF_3$ | $CH_3$ | Me | OMe | N |
| 2537 | $Q_1$ | $CF_3$ | $CH_3$ | OMe | OMe | N |
| 2538 | $Q_1$ | $CH_3$ | $CF_3$ | Me | Me | CH |
| 2539 | $Q_1$ | $CH_3$ | $CF_3$ | Me | OMe | CH |
| 2540 | $Q_1$ | $CH_3$ | $CF_3$ | OMe | OMe | CH |
| 2541 | $Q_1$ | $CH_3$ | $CF_3$ | Me | OMe | N |
| 2542 | $Q_1$ | $CH_3$ | $CF_3$ | OMe | OMe | N |
| 2543 | $Q_1$ | H | COOMe | Me | Me | CH |
| 2544 | $Q_1$ | H | COOMe | Me | OMe | CH |
| 2545 | $Q_1$ | H | COOMe | OMe | OMe | CH |
| 2546 | $Q_1$ | H | COOMe | Me | OMe | N |
| 2547 | $Q_1$ | H | COOMe | OMe | OMe | N |
| 2548 | $Q_1$ | Me | COOMe | Me | Me | CH |
| 2549 | $Q_1$ | Me | COOMe | Me | OMe | CH |
| 2550 | $Q_1$ | Me | COOMe | OMe | OMe | CH |
| 2551 | $Q_1$ | Me | COOMe | Me | OMe | N |
| 2552 | $Q_1$ | Me | COOMe | OMe | OMe | N |
| 2553 | $Q_1$ | Me | COOMe | Me | Cl | CH |
| 2554 | $Q_1$ | Me | COOMe | Me | $CH_2OMe$ | CH |
| 2555 | $Q_1$ | Me | COOMe | Me | $OCHF_2$ | CH |

TABLE 2-continued

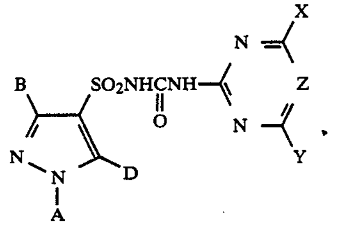

| No. | A | B | D | X | Y | Z |
|---|---|---|---|---|---|---|
| 2556 | $Q_1$ | Me | COOMe | Me | 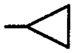 | CH |
| 2557 | $Q_1$ | Me | COOMe | OMe | OMe | CCl |
| 2558 | $Q_1$ | Me | COOMe | Me | $NMe_2$ | N |
| 2559 | $Q_1$ | Me | COOMe | Me | Me | N |
| 2560 | $Q_1$ | Me | COOH | Me | Me | CH |
| 2561 | $Q_1$ | Me | COOH | Me | OMe | CH |
| 2562 | $Q_1$ | Me | COOH | OMe | OMe | CH |
| 2563 | $Q_1$ | Me | COOH | Me | OMe | N |
| 2564 | $Q_1$ | Me | COOH | OMe | OMe | N |
| 2565 | $Q_1$ | Me | COOEt | Me | Me | CH |
| 2566 | $Q_1$ | Me | COOEt | Me | OMe | CH |
| 2567 | $Q_1$ | Me | COOEt | OMe | OMe | CH |
| 2568 | $Q_1$ | Me | COOEt | Me | OMe | N |
| 2569 | $Q_1$ | Me | COOEt | OMe | OMe | N |
| 2570 | $Q_1$ | Me | COOPr—n | Me | Me | CH |
| 2571 | $Q_1$ | Me | COOPr—n | Me | OMe | CH |
| 2572 | $Q_1$ | Me | COOPr—n | OMe | OMe | CH |
| 2573 | $Q_1$ | Me | COOPr—n | Me | OMe | N |
| 2574 | $Q_1$ | Me | COOPr—n | OMe | OMe | N |
| 2575 | $Q_1$ | Me | COOPr—i | Me | Me | CH |
| 2576 | $Q_1$ | Me | COOPr—i | Me | OMe | CH |
| 2577 | $Q_1$ | Me | COOPr—i | OMe | OMe | CH |
| 2578 | $Q_1$ | Me | COOPr—i | Me | OMe | N |
| 2579 | $Q_1$ | Me | COOPr—i | OMe | OMe | N |
| 2580 | $Q_1$ | Me | $COOCH_2CH=CH_2$ | Me | Me | CH |
| 2581 | $Q_1$ | Me | $COOCH_2CH=CH_2$ | Me | OMe | CH |
| 2582 | $Q_1$ | Me | $COOCH_2CH=CH_2$ | OMe | OMe | CH |
| 2583 | $Q_1$ | Me | $COOCH_2CH=CH_2$ | Me | OMe | N |
| 2584 | $Q_1$ | Me | $COOCH_2CH=CH_2$ | OMe | OMe | N |
| 2585 | $Q_1$ | Me | $COOCH_2C\equiv CH$ | Me | Me | CH |
| 2586 | $Q_1$ | Me | $COOCH_2C\equiv CH$ | Me | OMe | CH |
| 2587 | $Q_1$ | Me | $COOCH_2C\equiv CH$ | OMe | OMe | CH |
| 2588 | $Q_1$ | Me | $COOCH_2C\equiv CH$ | Me | OMe | N |
| 2589 | $Q_1$ | Me | $COOCH_2C\equiv CH$ | OMe | OMe | N |
| 2590 | $Q_1$ | Cl | COOMe | Me | OMe | CH |
| 2591 | $Q_1$ | Cl | COOMe | OMe | OMe | CH |
| 2592 | $Q_1$ | Cl | COOMe | Me | OMe | N |
| 2593 | $Q_1$ | Et | COOMe | Me | OMe | CH |
| 2594 | $Q_1$ | Et | COOMe | OMe | OMe | CH |
| 2595 | $Q_1$ | Et | COOMe | Me | OMe | N |
| 2596 | $Q_1$ | Me | $CONMe_2$ | Me | OMe | CH |
| 2597 | $Q_1$ | Me | $CONMe_2$ | OMe | OMe | CH |
| 2598 | $Q_1$ | Me | $CONMe_2$ | Me | OMe | N |
| 2599 | $Q_1$ | Me | SMe | Me | OMe | CH |
| 2600 | $Q_1$ | Me | SMe | OMe | OMe | CH |
| 2601 | $Q_1$ | Me | SMe | Me | OMe | N |
| 2602 | $Q_1$ | Me | SOMe | Me | OMe | CH |
| 2603 | $Q_1$ | Me | SOMe | OMe | OMe | CH |
| 2604 | $Q_1$ | Me | SOMe | Me | OMe | N |
| 2605 | $Q_1$ | Me | $SO_2Me$ | Me | OMe | CH |
| 2606 | $Q_1$ | Me | $SO_2Me$ | OMe | OMe | CH |
| 2607 | $Q_1$ | Me | $SO_2Me$ | Me | OMe | N |
| 2608 | $Q_1$ | Me | $SO_2Et$ | Me | OMe | CH |
| 2609 | $Q_1$ | Me | $SO_2Et$ | OMe | OMe | CH |
| 2610 | $Q_1$ | Me | $SO_2Et$ | Me | OMe | N |
| 2611 | $Q_1$ | Me | $SO_2Pr$—n | Me | Me | CH |
| 2612 | $Q_1$ | Me | $SO_2Pr$—n | Me | OMe | CH |
| 2613 | $Q_1$ | Me | $SO_2Pr$—n | OMe | OMe | CH |
| 2614 | $Q_1$ | Me | $SO_2Pr$—n | Me | OMe | N |
| 2615 | $Q_1$ | Me | $SO_2Pr$—n | OMe | OMe | N |
| 2616 | $Q_1$ | Me | $SO_2Ph$ | Me | OMe | CH |
| 2617 | $Q_1$ | Me | $SO_2Ph$ | OMe | OMe | CH |
| 2618 | $Q_1$ | Me | $SO_2Ph$ | Me | OMe | N |
| 2619 | $Q_1$ | Me | $SO_2CH_2CF_3$ | Me | OMe | CH |
| 2620 | $Q_1$ | Me | $SO_2CH_2CF_3$ | OMe | OMe | CH |
| 2621 | $Q_1$ | Me | $SO_2CH_2CF_3$ | Me | OMe | N |

TABLE 2-continued

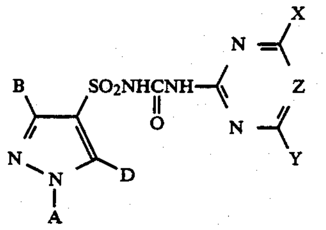

| No. | A | B | D | X | Y | Z |
|---|---|---|---|---|---|---|
| 2622 | $Q_1$ | Me | $SO_3CH_3$ | Me | OMe | CH |
| 2623 | $Q_1$ | Me | $SO_3CH_3$ | OMe | OMe | CH |
| 2624 | $Q_1$ | Me | $SO_3CH_3$ | Me | OMe | N |
| 2625 | $Q_1$ | Me | $SO_3CH_2CH{=}CH_2$ | Me | OMe | CH |
| 2626 | $Q_1$ | Me | $SO_3CH_2CH{=}CH_2$ | OMe | OMe | CH |
| 2627 | $Q_1$ | Me | $SO_3CH_2CH{=}CH_2$ | Me | OMe | N |
| 2628 | $Q_1$ | Me | $SO_3CH_2C{\equiv}CH$ | Me | OMe | CH |
| 2629 | $Q_1$ | Me | $SO_3CH_2C{\equiv}CH$ | OMe | OMe | CH |
| 2630 | $Q_1$ | Me | $SO_3CH_2C{\equiv}CH$ | Me | OMe | N |
| 2631 | $Q_1$ | Me | $SO_3CH_2C{\equiv}CH$ | Me | OMe | CH |
| 2632 | $Q_1$ | Me | $SO_2NMe_2$ | OMe | OMe | CH |
| 2633 | $Q_1$ | Me | $SO_2NMe_2$ | Me | OMe | N |
| 2634 | $Q_1$ | Me | CN | Me | OMe | CH |
| 2635 | $Q_1$ | Me | CN | OMe | OMe | CH |
| 2636 | $Q_1$ | Me | CN | Me | OMe | N |
| 2637 | $Q_1$ | Me | OH | Me | OMe | CH |
| 2638 | $Q_1$ | Me | OH | OMe | OMe | CH |
| 2639 | $Q_1$ | Me | OH | Me | OMe | N |
| 2640 | $Q_1$ | Ph | COOMe | Me | Me | CH |
| 2641 | $Q_1$ | Ph | COOMe | Me | OMe | CH |
| 2642 | $Q_1$ | Ph | COOMe | OMe | OMe | CH |
| 2643 | $Q_1$ | Ph | COOMe | Me | OMe | N |
| 2644 | $Q_1$ | Ph | COOMe | OMe | OMe | N |
| 2645 | $Q_1$ | Me | Ph | Me | OMe | CH |
| 2646 | $Q_1$ | Me | Ph | OMe | OMe | CH |
| 2647 | $Q_1$ | Me | Ph | Me | OMe | N |
| 2648 | $Q_1$ | COOMe | Me | Me | Me | CH |
| 2649 | $Q_1$ | COOMe | Me | Me | OMe | CH |
| 2650 | $Q_1$ | COOMe | Me | OMe | OMe | CH |
| 2651 | $Q_1$ | COOMe | Me | Me | OMe | N |
| 2652 | $Q_1$ | COOMe | Me | OMe | OMe | N |
| 2653 | H | $Q_1$ | Me | Me | Me | CH |
| 2654 | H | $Q_1$ | Me | Me | OMe | CH |
| 2655 | H | $Q_1$ | Me | OMe | OMe | CH |
| 2656 | H | $Q_1$ | Me | Me | OMe | N |
| 2657 | H | $Q_1$ | Me | OMe | OMe | N |
| 2658 | H | $Q_1$ | Cl | Me | Me | CH |
| 2659 | H | $Q_1$ | Cl | Me | OMe | CH |
| 2660 | H | $Q_1$ | Cl | OMe | OMe | CH |
| 2661 | H | $Q_1$ | Cl | Me | OMe | N |
| 2662 | H | $Q_1$ | Cl | OMe | OMe | N |
| 2663 | H | $Q_1$ | OMe | Me | Me | CH |
| 2664 | H | $Q_1$ | OMe | Me | OMe | CH |
| 2665 | H | $Q_1$ | OMe | OMe | OMe | CH |
| 2666 | H | $Q_1$ | OMe | Me | OMe | N |
| 2667 | H | $Q_1$ | OMe | OMe | OMe | N |
| 2668 | H | $Q_1$ | COOMe | Me | Me | CH |
| 2669 | H | $Q_1$ | COOMe | Me | OMe | CH |
| 2670 | H | $Q_1$ | COOMe | OMe | OMe | CH |
| 2671 | H | $Q_1$ | COOMe | Me | OMe | N |
| 2672 | H | $Q_1$ | COOMe | OMe | OMe | N |
| 2673 | H | $Q_1$ | $SO_2Me$ | Me | Me | CH |
| 2674 | H | $Q_1$ | $SO_2Me$ | Me | OMe | CH |
| 2675 | H | $Q_1$ | $SO_2Me$ | OMe | OMe | CH |
| 2676 | H | $Q_1$ | $SO_2Me$ | Me | OMe | N |
| 2677 | H | $Q_1$ | $SO_2Me$ | OMe | OMe | N |
| 2678 | Me | $Q_1$ | Me | Me | Me | CH |
| 2679 | Me | $Q_1$ | Me | Me | OMe | CH |
| 2680 | Me | $Q_1$ | Me | OMe | OMe | CH |
| 2681 | Me | $Q_1$ | Me | Me | OMe | N |
| 2682 | Me | $Q_1$ | Me | OMe | OMe | N |
| 2683 | Me | $Q_1$ | Cl | Me | Me | CH |
| 2684 | Me | $Q_1$ | Cl | Me | OMe | CH |
| 2685 | Me | $Q_1$ | Cl | OMe | OMe | CH |
| 2686 | Me | $Q_1$ | Cl | Me | OMe | N |
| 2687 | Me | $Q_1$ | Cl | OMe | OMe | N |
| 2688 | Me | $Q_1$ | OMe | Me | Me | CH |
| 2689 | Me | $Q_1$ | OMe | Me | OMe | CH |
| 2690 | Me | $Q_1$ | OMe | OMe | OMe | CH |

TABLE 2-continued

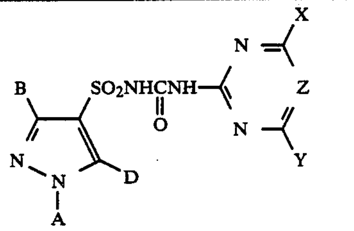

| No. | A | B | D | X | Y | Z |
|---|---|---|---|---|---|---|
| 2691 | Me | $Q_1$ | OMe | Me | OMe | N |
| 2692 | Me | $Q_1$ | OMe | OMe | OMe | N |
| 2693 | Me | $Q_1$ | COOMe | Me | Me | CH |
| 2694 | Me | $Q_1$ | COOMe | Me | OMe | CH |
| 2695 | Me | $Q_1$ | COOMe | OMe | OMe | CH |
| 2696 | Me | $Q_1$ | COOMe | Me | OMe | N |
| 2697 | Me | $Q_1$ | COOMe | OMe | OMe | N |
| 2698 | Me | $Q_1$ | COOEt | Me | OMe | CH |
| 2699 | Me | $Q_1$ | COOEt | OMe | OMe | CH |
| 2700 | Me | $Q_1$ | COOEt | Me | OMe | N |
| 2701 | Me | $Q_1$ | SMe | Me | OMe | CH |
| 2702 | Me | $Q_1$ | SMe | OMe | OMe | CH |
| 2703 | Me | $Q_1$ | SMe | Me | OMe | N |
| 2704 | Me | $Q_1$ | $SO_2Me$ | Me | OMe | CH |
| 2705 | Me | $Q_1$ | $SO_2Me$ | OMe | OMe | CH |
| 2706 | Me | $Q_1$ | $SO_2Me$ | Me | OMe | N |
| 2707 | Me | $Q_1$ | $SO_2Et$ | Me | OMe | CH |
| 2708 | Me | $Q_1$ | $SO_2Et$ | OMe | OMe | CH |
| 2709 | Me | $Q_1$ | $SO_2Et$ | Me | OMe | N |
| 2710 | Me | $Q_1$ | $SO_2Pr$—n | Me | OMe | CH |
| 2711 | Me | $Q_1$ | $SO_2Pr$—n | OMe | OMe | CH |
| 2712 | Me | $Q_1$ | $SO_2Pr$—n | Me | OMe | N |
| 2713 | Me | $Q_1$ | $SO_2Pr$—i | Me | OMe | CH |
| 2714 | Me | $Q_1$ | $SO_2Pr$—i | OMe | OMe | CH |
| 2715 | Me | $Q_1$ | $SO_2Pr$—i | Me | OMe | N |
| 2716 | Me | $Q_1$ | Br | Me | Me | CH |
| 2717 | Me | $Q_1$ | Br | Me | OMe | CH |
| 2718 | Me | $Q_1$ | Br | OMe | OMe | CH |
| 2719 | Me | $Q_1$ | Br | Me | OMe | N |
| 2720 | Me | $Q_1$ | Br | OMe | OMe | N |
| 2721 | Me | $Q_1$ | $SO_2NMe_2$ | Me | Me | CH |
| 2722 | Me | $Q_1$ | $SO_2NMe_2$ | Me | OMe | CH |
| 2723 | Me | $Q_1$ | $SO_2NMe_2$ | OMe | OMe | CH |
| 2724 | Me | $Q_1$ | $SO_2NMe_2$ | Me | OMe | N |
| 2725 | Me | $Q_1$ | $SO_2NMe_2$ | OMe | OMe | N |
| 2726 | Me | $Q_1$ | Ph | Me | Me | CH |
| 2727 | Me | $Q_1$ | Ph | Me | OMe | CH |
| 2728 | Me | $Q_1$ | Ph | OMe | OMe | CH |
| 2729 | Me | $Q_1$ | Ph | Me | OMe | N |
| 2730 | Me | $Q_1$ | Ph | OMe | OMe | N |
| 2731 | Me | $Q_1$ | Ph—2-Cl | Me | OMe | CH |
| 2732 | Me | $Q_1$ | Ph—2-Cl | OMe | OMe | CH |
| 2733 | Me | $Q_1$ | Ph—2-Cl | Me | OMe | N |
| 2734 | Me | $Q_1$ | Ph—2-Me | Me | OMe | CH |
| 2735 | Me | $Q_1$ | Ph—2-Me | OMe | OMe | CH |
| 2736 | Me | $Q_1$ | Ph—2-Me | Me | OMe | N |
| 2737 | Me | $Q_1$ | Ph—2-$NO_2$ | Me | OMe | CH |
| 2738 | Me | $Q_1$ | Ph—2-$NO_2$ | OMe | OMe | CH |
| 2739 | Me | $Q_1$ | Ph—2-$NO_2$ | Me | OMe | N |
| 2740 | Me | $Q_1$ | Ph—4-Cl | Me | OMe | CH |
| 2741 | Me | $Q_1$ | Ph—4-Cl | OMe | OMe | CH |
| 2742 | Me | $Q_1$ | Ph—4-Cl | Me | OMe | N |
| 2743 | Et | $Q_1$ | Me | Me | OMe | CH |
| 2744 | Et | $Q_1$ | Me | OMe | OMe | CH |
| 2745 | Et | $Q_1$ | Me | Me | OMe | N |
| 2746 | $CH_2CH{=}CH_2$ | $Q_1$ | Me | Me | OMe | CH |
| 2747 | $CH_2CH{=}CH_2$ | $Q_1$ | Me | OMe | OMe | CH |
| 2748 | $CH_2CH{=}CH_2$ | $Q_1$ | Me | Me | OMe | N |
| 2749 | $CH_2C{\equiv}CH$ | $Q_1$ | Me | Me | OMe | CH |
| 2750 | $CH_2C{\equiv}CH$ | $Q_1$ | Me | OMe | OMe | CH |
| 2751 | $CH_2C{\equiv}CH$ | $Q_1$ | Me | Me | OMe | N |
| 2752 | $CH_2CN$ | $Q_1$ | Me | Me | OMe | CH |
| 2753 | $CH_2CN$ | $Q_1$ | Me | OMe | OMe | CH |
| 2754 | $CH_2CN$ | $Q_1$ | Me | Me | OMe | N |
| 2755 | $CH_2OMe$ | $Q_1$ | Me | Me | OMe | CH |
| 2756 | $CH_2OMe$ | $Q_1$ | Me | OMe | OMe | CH |
| 2757 | $CH_2OMe$ | $Q_1$ | Me | Me | OMe | N |
| 2758 | Ph | $Q_1$ | Me | Me | OME | CH |
| 2759 | Ph | $Q_1$ | Me | OMe | OMe | CH |

TABLE 2-continued

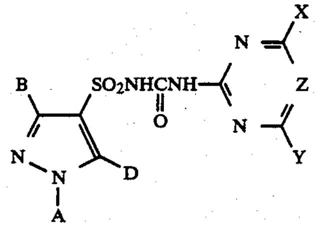

| No. | A | B | D | X | Y | Z |
|---|---|---|---|---|---|---|
| 2760 | Ph | $Q_1$ | Me | Me | OMe | N |
| 2761 | Me | Me | $Q_1$ | Me | Me | CH |
| 2762 | Me | Me | $Q_1$ | Me | OMe | CH |
| 2763 | Me | Me | $Q_1$ | OMe | OMe | CH |
| 2764 | Me | Me | $Q_1$ | Me | OMe | N |
| 2765 | Me | Me | $Q_1$ | OMe | OMe | N |
| 2766 | Me | Cl | $Q_1$ | Me | Me | CH |
| 2767 | Me | Cl | $Q_1$ | Me | OMe | CH |
| 2768 | Me | Cl | $Q_1$ | OMe | OMe | CH |
| 2769 | Me | Cl | $Q_1$ | Me | OMe | N |
| 2770 | Me | Cl | $Q_1$ | OMe | OMe | N |
| 2771 | Me | OMe | $Q_1$ | Me | OMe | CH |
| 2772 | Me | OMe | $Q_1$ | OMe | OMe | CH |
| 2773 | Me | OMe | $Q_1$ | Me | OMe | N |
| 2774 | Me | COOMe | $Q_1$ | Me | Me | CH |
| 2775 | Me | COOMe | $Q_1$ | Me | OMe | CH |
| 2776 | Me | COOMe | $Q_1$ | OMe | OMe | CH |
| 2777 | Me | COOMe | $Q_1$ | Me | OMe | N |
| 2778 | Me | COOMe | $Q_1$ | OMe | OMe | N |
| 2779 | Me | SMe | $Q_1$ | Me | OMe | CH |
| 2780 | Me | SMe | $Q_1$ | OMe | OMe | CH |
| 2781 | Me | SMe | $Q_1$ | Me | OMe | N |
| 2782 | Me | $SO_2Me$ | $Q_1$ | Me | OMe | CH |
| 2783 | Me | $SO_2Me$ | $Q_1$ | OMe | OMe | CH |
| 2784 | Me | $SO_2Me$ | $Q_1$ | Me | OMe | N |
| 2785 | Me | Ph | $Q_1$ | Me | Me | CH |
| 2786 | Me | Ph | $Q_1$ | Me | OMe | CH |
| 2787 | Me | Ph | $Q_1$ | OMe | OMe | CH |
| 2788 | Me | Ph | $Q_1$ | Me | OMe | N |
| 2789 | Me | Ph | $Q_1$ | OMe | OMe | N |
| 2790 | Me | Ph—2-Cl | $Q_1$ | Me | OMe | CH |
| 2791 | Me | Ph—2-Cl | $Q_1$ | OMe | OMe | CH |
| 2792 | Me | Ph—2-Cl | $Q_1$ | Me | OMe | N |
| 2793 | Ph | Me | $Q_1$ | Me | OMe | CH |
| 2794 | Ph | Me | $Q_1$ | OMe | OMe | CH |
| 2795 | Ph | Me | $Q_1$ | Me | OMe | N |
| 2796 | $Q_2$ | Me | Cl | Me | Me | CH |
| 2797 | $Q_2$ | Me | Cl | Me | OMe | CH |
| 2798 | $Q_2$ | Me | Cl | OMe | OMe | CH |
| 2799 | $Q_2$ | Me | Cl | Me | OMe | N |
| 2800 | $Q_2$ | Me | Cl | OMe | OMe | N |
| 2801 | $Q_2$ | Me | OMe | Me | OMe | CH |
| 2802 | $Q_2$ | Me | OMe | OMe | OMe | CH |
| 2803 | $Q_2$ | Me | OMe | Me | OMe | N |
| 2804 | $Q_2$ | $CF_3$ | Me | Me | OMe | CH |
| 2805 | $Q_2$ | $CF_3$ | Me | OMe | OMe | CH |
| 2806 | $Q_2$ | $CF_3$ | Me | Me | OMe | N |
| 2807 | $Q_2$ | Me | COOMe | Me | Me | CH |
| 2808 | $Q_2$ | Me | COOMe | Me | OMe | CH |
| 2809 | $Q_2$ | Me | COOMe | OMe | OMe | CH |
| 2810 | $Q_2$ | Me | COOMe | Me | OMe | N |
| 2811 | $Q_2$ | Me | COOMe | OMe | OMe | N |
| 2812 | $Q_2$ | Me | COOMe | Me | $OCHF_2$ | CH |
| 2813 | $Q_2$ | Me | COOMe | Me | 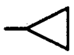 | CH |
| 2814 | $Q_2$ | Me | $SO_2Me$ | Me | OMe | CH |
| 2815 | $Q_2$ | Me | $SO_2Me$ | OMe | OMe | CH |
| 2816 | $Q_2$ | Me | $SO_2Me$ | Me | OMe | N |
| 2817 | H | $Q_2$ | Me | Me | OMe | CH |
| 2818 | H | $Q_2$ | Me | OMe | OMe | CH |
| 2819 | H | $Q_2$ | Me | Me | OMe | N |
| 2820 | Me | $Q_2$ | Me | Me | OMe | CH |
| 2821 | Me | $Q_2$ | Me | OMe | OMe | CH |
| 2822 | Me | $Q_2$ | Me | Me | OMe | N |
| 2823 | Me | $Q_2$ | Cl | Me | OMe | CH |
| 2824 | Me | $Q_2$ | Cl | OMe | OMe | CH |

TABLE 2-continued

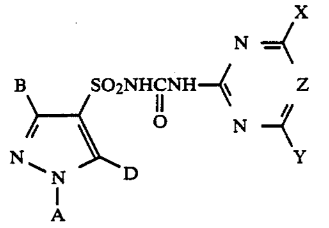

| No. | A | B | D | X | Y | Z |
|---|---|---|---|---|---|---|
| 2825 | Me | $Q_2$ | Cl | Me | OMe | N |
| 2826 | Me | $Q_2$ | COOMe | Me | OMe | CH |
| 2827 | Me | $Q_2$ | COOMe | OMe | OMe | CH |
| 2828 | Me | $Q_2$ | COOMe | Me | OMe | N |
| 2829 | Me | $Q_2$ | Ph | Me | OMe | CH |
| 2830 | Me | $Q_2$ | Ph | OMe | OMe | CH |
| 2831 | Me | $Q_2$ | Ph | Me | OMe | N |
| 2832 | Me | Me | $Q_2$ | Me | OMe | CH |
| 2833 | Me | Me | $Q_2$ | OMe | OMe | CH |
| 2834 | Me | Me | $Q_2$ | Me | OMe | N |
| 2835 | $Q_3$ | Me | COOMe | Me | Me | CH |
| 2836 | $Q_3$ | Me | COOMe | Me | OMe | CH |
| 2837 | $Q_3$ | Me | COOMe | OMe | OMe | CH |
| 2838 | $Q_3$ | Me | COOMe | Me | OMe | N |
| 2839 | $Q_3$ | Me | COOMe | OMe | OMe | N |
| 2840 | Me | $Q_3$ | Me | Me | OMe | CH |
| 2841 | Me | $Q_3$ | Me | OMe | OMe | CH |
| 2842 | Me | $Q_3$ | Me | Me | OMe | N |
| 2843 | Me | Me | $Q_3$ | Me | OMe | CH |
| 2844 | Me | Me | $Q_3$ | OMe | OMe | CH |
| 2845 | Me | Me | $Q_3$ | Me | OMe | N |
| 2846 | $Q_4$ | Me | COOMe | Me | Me | CH |
| 2847 | $Q_4$ | Me | COOMe | Me | OMe | CH |
| 2848 | $Q_4$ | Me | COOMe | OMe | OMe | CH |
| 2849 | $Q_4$ | Me | COOMe | Me | OMe | N |
| 2850 | $Q_4$ | Me | COOMe | OMe | OMe | N |
| 2851 | Me | $Q_4$ | Me | Me | OMe | CH |
| 2852 | Me | $Q_4$ | Me | OMe | OMe | CH |
| 2853 | Me | $Q_4$ | Me | Me | OMe | N |
| 2854 | Me | Me | $Q_4$ | OMe | OMe | CH |
| 2855 | Me | Me | $Q_4$ | Me | OMe | CH |
| 2856 | Me | Me | $Q_4$ | Me | OMe | N |
| 2857 | $Q_5$ | Me | Cl | Me | Me | CH |
| 2858 | $Q_5$ | Me | Cl | Me | OMe | CH |
| 2859 | $Q_5$ | Me | Cl | OMe | OMe | CH |
| 2860 | $Q_5$ | Me | Cl | Me | OMe | N |
| 2861 | $Q_5$ | Me | Cl | OMe | OMe | N |
| 2862 | $Q_5$ | Me | OMe | Me | OMe | CH |
| 2863 | $Q_5$ | Me | OMe | OMe | OMe | CH |
| 2864 | $Q_5$ | Me | OMe | Me | OMe | N |
| 2865 | $Q_5$ | $CF_3$ | Me | Me | OMe | CH |
| 2866 | $Q_5$ | $CF_3$ | Me | OMe | OMe | CH |
| 2867 | $Q_5$ | $CF_3$ | Me | Me | OMe | N |
| 2868 | $Q_5$ | Me | COOMe | Me | Me | CH |
| 2869 | $Q_5$ | Me | COOMe | Me | OMe | CH |
| 2870 | $Q_5$ | Me | COOMe | OMe | OMe | CH |
| 2871 | $Q_5$ | Me | COOMe | Me | OMe | N |
| 2872 | $Q_5$ | Me | COOMe | OMe | OMe | N |
| 2873 | $Q_5$ | Me | COOMe | Me | $OCHF_2$ | CH |
| 2874 | $Q_5$ | Me | COOMe | Me | 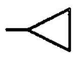 | CH |
| 2875 | $Q_5$ | Me | $SO_2Me$ | Me | OMe | CH |
| 2876 | $Q_5$ | Me | $SO_2Me$ | OMe | OMe | CH |
| 2877 | $Q_5$ | Me | $SO_2Me$ | Me | OMe | N |
| 2878 | H | $Q_5$ | Me | Me | OMe | CH |
| 2879 | H | $Q_5$ | Me | OMe | OMe | CH |
| 2880 | H | $Q_5$ | Me | Me | OMe | N |
| 2881 | Me | $Q_5$ | Me | Me | OMe | CH |
| 2882 | Me | $Q_5$ | Me | OMe | OMe | CH |
| 2883 | Me | $Q_5$ | Me | Me | OMe | N |
| 2884 | Me | $Q_5$ | Cl | Me | OMe | CH |
| 2885 | Me | $Q_5$ | Cl | OMe | OMe | CH |
| 2886 | Me | $Q_5$ | Cl | Me | OMe | N |
| 2887 | Me | $Q_5$ | COOMe | Me | OMe | CH |
| 2888 | Me | $Q_5$ | COOMe | OMe | OMe | CH |
| 2889 | Me | $Q_5$ | COOMe | Me | OMe | N |

TABLE 2-continued

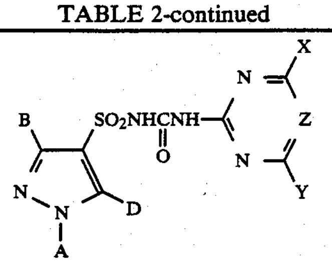

| No. | A | B | D | X | Y | Z |
|---|---|---|---|---|---|---|
| 2890 | Me | $Q_5$ | Ph | Me | OMe | CH |
| 2891 | Me | $Q_5$ | Ph | OMe | OMe | CH |
| 2892 | Me | $Q_5$ | Ph | Me | OMe | N |
| 2893 | Me | Me | $Q_5$ | Me | OMe | CH |
| 2894 | Me | Me | $Q_5$ | OMe | OMe | CH |
| 2895 | Me | Me | $Q_5$ | Me | OMe | N |
| 2896 | $Q_6$ | Me | COOMe | Me | Me | CH |
| 2897 | $Q_6$ | Me | COOMe | Me | OMe | CH |
| 2898 | $Q_6$ | Me | COOMe | OMe | OMe | CH |
| 2899 | $Q_6$ | Me | COOMe | Me | OMe | N |
| 2900 | $Q_6$ | Me | COOMe | OMe | OMe | N |
| 2901 | Me | $Q_6$ | Me | Me | OMe | CH |
| 2902 | Me | $Q_6$ | Me | OMe | OMe | CH |
| 2903 | Me | $Q_6$ | Me | Me | OMe | N |
| 2904 | Me | Me | $Q_6$ | Me | OMe | CH |
| 2905 | Me | Me | $Q_6$ | OMe | OMe | CH |
| 2906 | Me | Me | $Q_6$ | Me | OMe | N |
| 2907 | $Q_7$ | Me | COOMe | Me | OMe | CH |
| 2908 | $Q_7$ | Me | COOMe | OMe | OMe | CH |
| 2909 | $Q_7$ | Me | COOMe | Me | OMe | N |
| 2910 | Me | Me | $Q_7$ | OMe | OMe | CH |
| 2911 | Me | Me | $Q_7$ | Me | OMe | N |
| 2912 | $Q_8$ | Me | Cl | Me | Me | CH |
| 2913 | $Q_8$ | Me | Cl | Me | OMe | CH |
| 2914 | $Q_8$ | Me | Cl | OMe | OMe | CH |
| 2915 | $Q_8$ | Me | Cl | Me | OMe | N |
| 2916 | $Q_8$ | Me | Cl | OMe | OMe | N |
| 2917 | $Q_8$ | Me | OMe | Me | OMe | CH |
| 2918 | $Q_8$ | Me | OMe | OMe | OMe | CH |
| 2919 | $Q_8$ | Me | OMe | Me | OMe | N |
| 2920 | $Q_8$ | $CF_3$ | Me | Me | OMe | CH |
| 2921 | $Q_8$ | $CF_3$ | Me | OMe | OMe | CH |
| 2922 | $Q_8$ | $CF_3$ | Me | Me | OMe | N |
| 2923 | $Q_8$ | Me | COOMe | Me | Me | CH |
| 2924 | $Q_8$ | Me | COOMe | Me | OMe | CH |
| 2925 | $Q_8$ | Me | COOMe | OMe | OMe | CH |
| 2926 | $Q_8$ | Me | COOMe | Me | OMe | N |
| 2927 | $Q_8$ | Me | COOMe | OMe | OMe | N |
| 2928 | $Q_8$ | Me | COOMe | Me | $OCHF_2$ | CH |
| 2929 | $Q_8$ | Me | COOMe | Me | 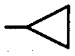 | CH |
| 2930 | $Q_8$ | Me | $SO_2Me$ | Me | OMe | CH |
| 2931 | $Q_8$ | Me | $SO_2Me$ | OMe | OMe | CH |
| 2932 | $Q_8$ | Me | $SO_2Me$ | Me | OMe | N |
| 2933 | H | $Q_8$ | Me | Me | OMe | CH |
| 2934 | H | $Q_8$ | Me | OMe | OMe | CH |
| 2935 | H | $Q_8$ | Me | Me | OMe | N |
| 2936 | Me | $Q_8$ | Me | Me | OMe | CH |
| 2937 | Me | $Q_8$ | Me | OMe | OMe | CH |
| 2938 | Me | $Q_8$ | Me | Me | OMe | N |
| 2939 | Me | $Q_8$ | Cl | Me | OMe | CH |
| 2940 | Me | $Q_8$ | Cl | OMe | OMe | CH |
| 2941 | Me | $Q_8$ | Cl | Me | OMe | N |
| 2942 | Me | $Q_8$ | COOMe | Me | OMe | CH |
| 2943 | Me | $Q_8$ | COOMe | OMe | OMe | CH |
| 2944 | Me | $Q_8$ | COOMe | Me | OMe | N |
| 2945 | Me | $Q_8$ | Ph | Me | OMe | CH |
| 2946 | Me | $Q_8$ | Ph | OMe | OMe | CH |
| 2947 | Me | $Q_8$ | Ph | Me | OMe | N |
| 2948 | Me | Me | $Q_8$ | Me | OMe | CH |
| 2949 | Me | Me | $Q_8$ | OMe | OMe | CH |
| 2950 | Me | Me | $Q_8$ | Me | OMe | N |
| 2951 | $Q_9$ | Me | COOMe | Me | Me | CH |
| 2952 | $Q_9$ | Me | COOMe | Me | OMe | CH |
| 2953 | $Q_9$ | Me | COOMe | OMe | OMe | CH |
| 2954 | $Q_9$ | Me | COOMe | Me | OMe | N |

TABLE 2-continued

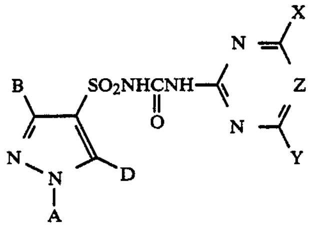

| No. | A | B | D | X | Y | Z |
|---|---|---|---|---|---|---|
| 2955 | $Q_9$ | Me | COOMe | OMe | OMe | N |
| 2956 | Me | $Q_9$ | Me | Me | OMe | CH |
| 2957 | Me | $Q_9$ | Me | OMe | OMe | CH |
| 2958 | Me | $Q_9$ | Me | Me | OMe | N |
| 2959 | Me | Me | $Q_9$ | Me | OMe | CH |
| 2960 | Me | Me | $Q_9$ | OMe | OMe | CH |
| 2961 | Me | Me | $Q_9$ | Me | OMe | N |
| 2962 | $Q_{10}$ | Me | COOMe | Me | Me | CH |
| 2963 | $Q_{10}$ | Me | COOMe | Me | OMe | CH |
| 2964 | $Q_{10}$ | Me | COOMe | OMe | OMe | CH |
| 2965 | $Q_{10}$ | Me | COOMe | Me | OMe | N |
| 2966 | $Q_{10}$ | Me | COOMe | OMe | OMe | N |
| 2967 | Me | $Q_{10}$ | Me | Me | OMe | CH |
| 2968 | Me | $Q_{10}$ | Me | OMe | OMe | CH |
| 2969 | Me | $Q_{10}$ | Me | Me | OMe | N |
| 2970 | Me | Me | $Q_{10}$ | Me | OMe | CH |
| 2971 | Me | Me | $Q_{10}$ | OMe | OMe | CH |
| 2972 | Me | Me | $Q_{10}$ | Me | OMe | N |
| 2973 | $Q_{11}$ | Me | COOMe | Me | Me | CH |
| 2974 | $Q_{11}$ | Me | COOMe | Me | OMe | CH |
| 2975 | $Q_{11}$ | Me | COOMe | OMe | OMe | CH |
| 2976 | $Q_{11}$ | Me | COOMe | Me | OMe | N |
| 2977 | $Q_{11}$ | Me | COOMe | OMe | OMe | N |
| 2978 | Me | $Q_{11}$ | Me | Me | OMe | CH |
| 2979 | Me | $Q_{11}$ | Me | OMe | OMe | CH |
| 2980 | Me | $Q_{11}$ | Me | Me | OMe | N |
| 2981 | Me | Me | $Q_{11}$ | Me | OMe | CH |
| 2982 | Me | Me | $Q_{11}$ | OMe | OMe | CH |
| 2983 | Me | Me | $Q_{11}$ | Me | OMe | N |
| 2984 | $Q_{12}$ | Me | COOMe | Me | Me | CH |
| 2985 | $Q_{12}$ | Me | COOMe | Me | OMe | CH |
| 2986 | $Q_{12}$ | Me | COOMe | OMe | OMe | CH |
| 2987 | $Q_{12}$ | Me | COOMe | Me | OMe | N |
| 2988 | $Q_{12}$ | Me | COOMe | OMe | OMe | N |
| 2989 | Me | $Q_{12}$ | Me | Me | OMe | CH |
| 2990 | Me | $Q_{12}$ | Me | OMe | OMe | CH |
| 2991 | Me | $Q_{12}$ | Me | Me | OMe | N |
| 2992 | Me | Me | $Q_{12}$ | Me | OMe | CH |
| 2993 | Me | Me | $Q_{12}$ | OMe | OMe | CH |
| 2994 | Me | Me | $Q_{12}$ | Me | OMe | N |
| 2995 | $Q_{13}$ | Me | COOMe | Me | OMe | CH |
| 2996 | $Q_{13}$ | Me | COOMe | OMe | OMe | CH |
| 2997 | $Q_{13}$ | Me | COOMe | Me | OMe | N |
| 2998 | Me | Me | $Q_{13}$ | OMe | OMe | CH |
| 2999 | Me | Me | $Q_{13}$ | Me | OMe | N |
| 3000 | $Q_{14}$ | Me | COOMe | Me | Me | CH |
| 3001 | $Q_{14}$ | Me | COOMe | Me | OMe | CH |
| 3002 | $Q_{14}$ | Me | COOMe | OMe | OMe | CH |
| 3003 | $Q_{14}$ | Me | COOMe | Me | OMe | N |
| 3004 | $Q_{14}$ | Me | COOMe | OMe | OMe | N |
| 3005 | Me | $Q_{14}$ | Me | Me | OMe | CH |
| 3006 | Me | $Q_{14}$ | Me | OMe | OMe | CH |
| 3007 | Me | $Q_{14}$ | Me | Me | OMe | N |
| 3008 | Me | Me | $Q_{14}$ | Me | OMe | CH |
| 3009 | Me | Me | $Q_{14}$ | OMe | OMe | CH |
| 3010 | Me | Me | $Q_{14}$ | Me | OMe | N |
| 3011 | $Q_{15}$ | Me | COOMe | Me | Me | CH |
| 3012 | $Q_{15}$ | Me | COOMe | Me | OMe | CH |
| 3013 | $Q_{15}$ | Me | COOMe | OMe | OMe | CH |
| 3014 | $Q_{15}$ | Me | COOMe | Me | OMe | N |
| 3015 | $Q_{15}$ | Me | COOMe | OMe | OMe | N |
| 3016 | Me | $Q_{15}$ | Me | Me | OMe | CH |
| 3017 | Me | $Q_{15}$ | Me | OMe | OMe | CH |
| 3018 | Me | $Q_{15}$ | Me | Me | OMe | N |
| 3019 | Me | Me | $Q_{15}$ | Me | OMe | CH |
| 3020 | Me | Me | $Q_{15}$ | OMe | OMe | CH |
| 3021 | Me | Me | $Q_{15}$ | Me | OMe | N |
| 3022 | $Q_{16}$ | Me | COOMe | Me | Me | CH |
| 3023 | $Q_{16}$ | Me | COOMe | Me | OMe | CH |

TABLE 2-continued

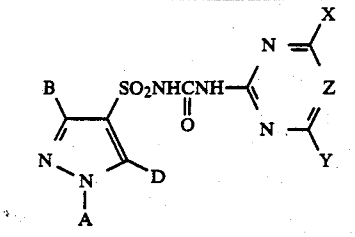

| No. | A | B | D | X | Y | Z |
|---|---|---|---|---|---|---|
| 3024 | $Q_{16}$ | Me | COOMe | OMe | OMe | CH |
| 3025 | $Q_{16}$ | Me | COOMe | Me | OMe | N |
| 3026 | $Q_{16}$ | Me | COOMe | OMe | OMe | N |
| 3027 | Me | $Q_{16}$ | Me | Me | OMe | CH |
| 3028 | Me | $Q_{16}$ | Me | OMe | OMe | CH |
| 3029 | Me | $Q_{16}$ | Me | Me | OMe | N |
| 3030 | Me | Me | $Q_{16}$ | Me | OMe | CH |
| 3031 | Me | Me | $Q_{16}$ | OMe | OMe | CH |
| 3032 | Me | Me | $Q_{16}$ | Me | OMe | N |
| 3033 | $Q_{17}$ | Me | COMe | Me | OMe | CH |
| 3034 | $Q_{17}$ | Me | COOMe | OMe | OMe | CH |
| 3035 | $Q_{17}$ | Me | COOMe | Me | OMe | N |
| 3036 | Me | Me | $Q_{17}$ | OMe | OMe | CH |
| 3037 | Me | Me | $Q_{17}$ | Me | OMe | N |
| 3038 | $Q_{18}$ | Me | COOMe | Me | Me | CH |
| 3039 | $Q_{18}$ | Me | COOMe | Me | OMe | CH |
| 3040 | $Q_{18}$ | Me | COOMe | OMe | OMe | CH |
| 3041 | $Q_{18}$ | Me | COOMe | Me | OMe | N |
| 3042 | $Q_{18}$ | Me | COOMe | OMe | OMe | N |
| 3043 | Me | $Q_{18}$ | Me | Me | OMe | CH |
| 3044 | Me | $Q_{18}$ | Me | OMe | OMe | CH |
| 3045 | Me | $Q_{18}$ | Me | Me | OMe | N |
| 3046 | Me | Me | $Q_{18}$ | Me | OMe | CH |
| 3047 | Me | Me | $Q_{18}$ | OMe | OMe | CH |
| 3048 | Me | Me | $Q_{18}$ | Me | OMe | N |
| 3049 | $Q_{19}$ | Me | COOMe | Me | Me | CH |
| 3050 | $Q_{19}$ | Me | COOMe | Me | OMe | CH |
| 3051 | $Q_{19}$ | Me | COOMe | OMe | OMe | CH |
| 3052 | $Q_{19}$ | Me | COOMe | Me | OMe | N |
| 3053 | $Q_{19}$ | Me | COOMe | OMe | OMe | N |
| 3054 | Me | $Q_{19}$ | Me | Me | OMe | CH |
| 3055 | Me | $Q_{19}$ | Me | OMe | OMe | CH |
| 3056 | Me | $Q_{19}$ | Me | Me | OMe | N |
| 3057 | Me | Me | $Q_{19}$ | Me | OMe | CH |
| 3058 | Me | Me | $Q_{19}$ | OMe | OMe | CH |
| 3059 | Me | Me | $Q_{19}$ | Me | OMe | N |
| 3060 | $Q_{20}$ | Me | COOMe | Me | Me | CH |
| 3061 | $Q_{20}$ | Me | COOMe | Me | OMe | CH |
| 3062 | $Q_{20}$ | Me | COOMe | OMe | OMe | CH |
| 3063 | $Q_{20}$ | Me | COOMe | Me | OMe | N |
| 3064 | $Q_{20}$ | Me | COOMe | OMe | OMe | N |
| 3065 | Me | $Q_{20}$ | Me | Me | OMe | CH |
| 3066 | Me | $Q_{20}$ | Me | OMe | OMe | CH |
| 3067 | Me | $Q_{20}$ | Me | Me | OMe | N |
| 3068 | Me | Me | $Q_{20}$ | Me | OMe | CH |
| 3069 | Me | Me | $Q_{20}$ | OMe | OMe | CH |
| 3070 | Me | Me | $Q_{20}$ | Me | OMe | N |
| 3071 | $Q_{21}$ | Me | COOMe | Me | Me | CH |
| 3072 | $Q_{21}$ | Me | COOMe | Me | OMe | CH |
| 3073 | $Q_{21}$ | Me | COOMe | OMe | OMe | CH |
| 3074 | $Q_{21}$ | Me | COOMe | Me | OMe | N |
| 3075 | $Q_{21}$ | Me | COOMe | OMe | OMe | N |
| 3076 | Me | $Q_{21}$ | Me | Me | OMe | CH |
| 3077 | Me | $Q_{21}$ | Me | OMe | OMe | CH |
| 3078 | Me | $Q_{21}$ | Me | Me | OMe | N |
| 3079 | Me | Me | $Q_{21}$ | Me | OMe | CH |
| 3080 | Me | Me | $Q_{21}$ | OMe | OMe | CH |
| 3081 | Me | Me | $Q_{21}$ | Me | OMe | N |
| 3082 | $Q_{22}$ | Me | COOMe | Me | Me | CH |
| 3083 | $Q_{22}$ | Me | COOMe | Me | OMe | CH |
| 3084 | $Q_{22}$ | Me | COOMe | OMe | OMe | CH |
| 3085 | $Q_{22}$ | Me | COOMe | Me | OMe | N |
| 3086 | $Q_{22}$ | Me | COOMe | OMe | OMe | N |
| 3087 | Me | $Q_{22}$ | Me | Me | OMe | CH |
| 3088 | Me | $Q_{22}$ | Me | OMe | OMe | CH |
| 3089 | Me | $Q_{22}$ | Me | Me | OMe | N |
| 3090 | Me | Me | $Q_{22}$ | Me | OMe | CH |
| 3091 | Me | Me | $Q_{22}$ | OMe | OMe | CH |
| 3092 | Me | Me | $Q_{22}$ | Me | OMe | N |

TABLE 2-continued

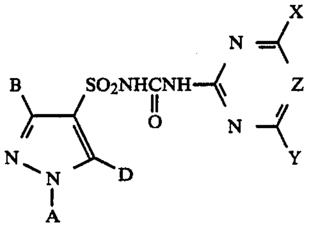

| No. | A | B | D | X | Y | Z |
|---|---|---|---|---|---|---|
| 3093 | $Q_{23}$ | Me | COOMe | Me | OMe | CH |
| 3094 | $Q_{23}$ | Me | COOMe | OMe | OMe | CH |
| 3095 | $Q_{23}$ | Me | COOMe | Me | OMe | N |
| 3096 | Me | Me | $Q_{23}$ | OMe | OMe | CH |
| 3097 | Me | Me | $Q_{23}$ | Me | OMe | N |
| 3098 | $Q_{24}$ | Me | COOMe | Me | Me | CH |
| 3099 | $Q_{24}$ | Me | COOMe | Me | OMe | CH |
| 3100 | $Q_{24}$ | Me | COOMe | OMe | OMe | CH |
| 3101 | $Q_{242}$ | Me | COOMe | Me | OMe | N |
| 3102 | $Q_{24}$ | Me | COOMe | OMe | OMe | N |
| 3103 | Me | $Q_{24}$ | Me | Me | OMe | CH |
| 3104 | Me | $Q_{24}$ | Me | OMe | OMe | CH |
| 3105 | Me | $Q_{24}$ | Me | Me | OMe | N |
| 3106 | Me | Me | $Q_{24}$ | Me | OMe | CH |
| 3107 | Me | Me | $Q_{24}$ | OMe | OMe | CH |
| 3108 | Me | Me | $Q_{24}$ | Me | OMe | N |
| 3109 | $Q_{25}$ | Me | COOMe | Me | Me | CH |
| 3110 | $Q_{25}$ | Me | COOMe | Me | OMe | CH |
| 3111 | $Q_{25}$ | Me | COOMe | OMe | OMe | CH |
| 3112 | $Q_{25}$ | Me | COOMe | Me | OMe | N |
| 3113 | $Q_{25}$ | Me | COOMe | OMe | OMe | N |
| 3114 | Me | $Q_{25}$ | Me | Me | OMe | CH |
| 3115 | Me | $Q_{25}$ | Me | OMe | OMe | CH |
| 3116 | Me | $Q_{25}$ | Me | Me | OMe | N |
| 3117 | Me | Me | $Q_{25}$ | Me | OMe | CH |
| 3118 | Me | Me | $Q_{25}$ | OMe | OMe | CH |
| 3119 | Me | Me | $Q_{25}$ | Me | OMe | N |
| 3120 | $Q_{26}$ | Me | COOMe | Me | OMe | CH |
| 3121 | $Q_{26}$ | Me | COOMe | OMe | OMe | CH |
| 3122 | $Q_{26}$ | Me | COOMe | Me | OMe | N |
| 3123 | Me | Me | $Q_{26}$ | OMe | OMe | CH |
| 3124 | Me | Me | $Q_{26}$ | Me | OMe | N |
| 3125 | $Q_{27}$ | Me | COOMe | Me | OMe | CH |
| 3126 | $Q_{27}$ | Me | COOMe | OMe | OMe | CH |
| 3127 | $Q_{27}$ | Me | COOMe | Me | OMe | N |
| 3128 | Me | Me | $Q_{27}$ | OMe | OMe | CH |
| 3129 | Me | Me | $Q_{27}$ | Me | OMe | N |
| 3130 | $Q_{28}$ | Me | COOMe | Me | Me | CH |
| 3131 | $Q_{28}$ | Me | COOMe | Me | OMe | CH |
| 3132 | $Q_{28}$ | Me | COOMe | OMe | OMe | CH |
| 3133 | $Q_{28}$ | Me | COOMe | Me | OMe | N |
| 3134 | $Q_{28}$ | Me | COOMe | OMe | OMe | N |
| 3135 | Me | $Q_{28}$ | Me | Me | OMe | CH |
| 3136 | Me | $Q_{28}$ | Me | OMe | OMe | CH |
| 3137 | Me | $Q_{28}$ | Me | Me | OMe | N |
| 3138 | Me | Me | $Q_{28}$ | Me | OMe | CH |
| 3139 | Me | Me | $Q_{28}$ | OMe | OMe | CH |
| 3140 | Me | Me | $Q_{28}$ | Me | OMe | N |
| 3141 | $Q_{29}$ | Me | COOMe | Me | OMe | CH |
| 3142 | $Q_{29}$ | Me | COOMe | OMe | OMe | CH |
| 3143 | $Q_{29}$ | Me | COOMe | Me | OMe | N |
| 3144 | Me | Me | $Q_{29}$ | OMe | OMe | CH |
| 3145 | Me | Me | $Q_{29}$ | Me | OMe | N |
| 3146 | $Q_{30}$ | Me | COOMe | Me | OMe | CH |
| 3147 | $Q_{30}$ | Me | COOMe | OMe | OMe | CH |
| 3148 | $Q_{30}$ | Me | COOMe | Me | OMe | N |
| 3149 | Me | Me | $Q_{30}$ | OMe | OMe | CH |
| 3150 | Me | Me | $Q_{30}$ | Me | OMe | N |
| 3151 | $Q_{31}$ | Me | COOMe | Me | OMe | CH |
| 3152 | $Q_{31}$ | Me | COOMe | OMe | OMe | CH |
| 3153 | $Q_{31}$ | Me | COOMe | Me | OMe | N |
| 3154 | Me | Me | $Q_{31}$ | OMe | OMe | CH |
| 3155 | Me | Me | $Q_{31}$ | Me | OMe | N |
| 3156 | $Q_{32}$ | Me | Cl | Me | Me | CH |
| 3157 | $Q_{32}$ | Me | Cl | Me | OMe | CH |
| 3158 | $Q_{32}$ | Me | Cl | OMe | OMe | N |
| 3159 | $Q_{32}$ | Me | Cl | Me | OMe | N |
| 3160 | $Q_{32}$ | Me | Cl | OMe | OMe | N |
| 3161 | $Q_{32}$ | Me | OMe | Me | OMe | CH |

TABLE 2-continued

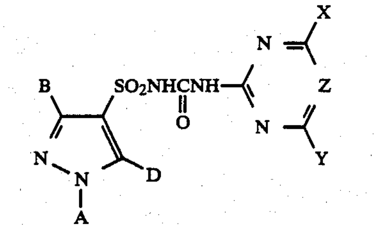

| No. | A | B | D | X | Y | Z |
|---|---|---|---|---|---|---|
| 3162 | $Q_{32}$ | Me | OMe | OMe | OMe | CH |
| 3163 | $Q_{32}$ | Me | OMe | Me | OMe | N |
| 3164 | $Q_{32}$ | $CF_3$ | Me | Me | OMe | CH |
| 3165 | $Q_{32}$ | $CF_3$ | Me | OMe | OMe | CH |
| 3166 | $Q_{32}$ | $CF_3$ | Me | Me | OMe | N |
| 3167 | $Q_{32}$ | Me | COOMe | Me | Me | CH |
| 3168 | $Q_{32}$ | Me | COOMe | Me | OMe | CH |
| 3169 | $Q_{32}$ | Me | COOMe | OMe | OMe | CH |
| 3170 | $Q_{32}$ | Me | COOMe | Me | OMe | N |
| 3171 | $Q_{32}$ | Me | COOMe | OMe | OMe | N |
| 3172 | $Q_{32}$ | Me | COOMe | Me | $OCHF_2$ | CH |
| 3173 | $Q_{32}$ | Me | COOMe | Me | 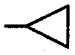 | CH |
| 3174 | $Q_{32}$ | Me | $SO_2Me$ | Me | OMe | CH |
| 3175 | $Q_{32}$ | Me | $SO_2Me$ | OMe | OMe | CH |
| 3176 | $Q_{32}$ | Me | $SO_2Me$ | Me | OMe | N |
| 3177 | H | $Q_{32}$ | Me | Me | OMe | CH |
| 3178 | H | $Q_{32}$ | Me | OMe | OMe | CH |
| 3179 | H | $Q_{32}$ | Me | Me | OMe | N |
| 3180 | Me | $Q_{32}$ | Me | Me | OMe | CH |
| 3181 | Me | $Q_{32}$ | Me | OMe | OMe | CH |
| 3182 | Me | $Q_{32}$ | Me | Me | OMe | N |
| 3183 | Me | $Q_{32}$ | Cl | Me | OMe | CH |
| 3184 | Me | $Q_{32}$ | Cl | OMe | OMe | CH |
| 3185 | Me | $Q_{32}$ | Cl | Me | OMe | N |
| 3186 | Me | $Q_{32}$ | COOMe | Me | OMe | CH |
| 3187 | Me | $Q_{32}$ | COOMe | OMe | OMe | CH |
| 3188 | Me | $Q_{32}$ | COOMe | Me | OMe | N |
| 3189 | Me | $Q_{32}$ | Ph | Me | OMe | CH |
| 3190 | Me | $Q_{32}$ | Ph | OMe | OMe | CH |
| 3191 | Me | $Q_{32}$ | Ph | Me | OMe | N |
| 3192 | Me | Me | $Q_{32}$ | Me | OMe | CH |
| 3193 | Me | Me | $Q_{32}$ | OMe | OMe | CH |
| 3194 | Me | Me | $Q_{32}$ | Me | OMe | N |
| 3195 | $Q_{33}$ | Me | COOMe | Me | Me | CH |
| 3196 | $Q_{33}$ | Me | COOMe | Me | OMe | CH |
| 3197 | $Q_{33}$ | Me | COOMe | OMe | OMe | CH |
| 3198 | $Q_{33}$ | Me | COOMe | Me | OMe | N |
| 3199 | $Q_{33}$ | Me | COOMe | OMe | OMe | N |
| 3200 | Me | $Q_{33}$ | Me | Me | OMe | CH |
| 3201 | Me | $Q_{33}$ | Me | OMe | OMe | CH |
| 3202 | Me | $Q_{33}$ | Me | Me | OMe | N |
| 3203 | Me | Me | $Q_{33}$ | Me | OMe | CH |
| 3204 | Me | Me | $Q_{33}$ | OMe | OMe | CH |
| 3205 | Me | Me | $Q_{33}$ | Me | OMe | N |
| 3206 | $Q_{34}$ | Me | COOMe | Me | Me | CH |
| 3207 | $Q_{34}$ | Me | COOMe | Me | OMe | CH |
| 3208 | $Q_{34}$ | Me | COOMe | OMe | OMe | CH |
| 3209 | $Q_{34}$ | Me | COOMe | Me | OMe | N |
| 3210 | $Q_{34}$ | Me | COOMe | OMe | OMe | N |
| 3211 | Me | $Q_{34}$ | Me | Me | OMe | CH |
| 3212 | Me | $Q_{34}$ | Me | Me | OMe | CH |
| 3213 | Me | $Q_{34}$ | Me | Me | OMe | N |
| 3214 | Me | Me | $Q_{34}$ | Me | OMe | CH |
| 3215 | Me | Me | $Q_{34}$ | OMe | OMe | CH |
| 3216 | Me | Me | $Q_{34}$ | Me | OMe | N |
| 3217 | $Q_{35}$ | Me | COOMe | Me | Me | CH |
| 3218 | $Q_{35}$ | Me | COOMe | Me | OMe | CH |
| 3219 | $Q_{35}$ | Me | COOMe | OMe | OMe | CH |
| 3220 | $Q_{35}$ | Me | COOMe | Me | OMe | N |
| 3221 | $Q_{35}$ | Me | COOMe | OMe | OMe | N |
| 3222 | Me | $Q_{35}$ | Me | Me | OMe | CH |
| 3223 | Me | $Q_{35}$ | Me | OMe | OMe | CH |
| 3224 | Me | $Q_{35}$ | Me | Me | OMe | N |
| 3225 | Me | Me | $Q_{35}$ | Me | OMe | CH |
| 3226 | Me | Me | $Q_{35}$ | OMe | OMe | CH |

TABLE 2-continued

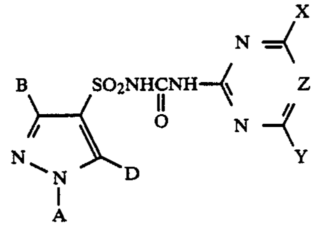

| No. | A | B | D | X | Y | Z |
|---|---|---|---|---|---|---|
| 3227 | Me | Me | $Q_{35}$ | Me | OMe | N |
| 3228 | $Q_{36}$ | Me | COOMe | Me | OMe | CH |
| 3229 | $Q_{36}$ | Me | COOMe | OMe | OMe | CH |
| 3230 | $Q_{36}$ | Me | COOMe | Me | OMe | N |
| 3231 | Me | Me | $Q_{36}$ | OMe | OMe | CH |
| 3232 | Me | Me | $Q_{36}$ | Me | OMe | N |
| 3233 | $Q_{37}$ | Me | COOMe | Me | Me | CH |
| 3234 | $Q_{37}$ | Me | COOMe | Me | OMe | CH |
| 3235 | $Q_{37}$ | Me | COOMe | OMe | OMe | CH |
| 3236 | $Q_{37}$ | Me | COOMe | Me | OMe | N |
| 3237 | $Q_{37}$ | Me | COOMe | OMe | OMe | N |
| 3238 | Me | $Q_{37}$ | Me | Me | OMe | CH |
| 3239 | Me | $Q_{37}$ | Me | OMe | OMe | CH |
| 3240 | Me | $Q_{37}$ | Me | Me | OMe | N |
| 3241 | Me | Me | $Q_{37}$ | Me | OMe | CH |
| 3242 | Me | Me | $Q_{37}$ | OMe | OMe | CH |
| 3243 | Me | Me | $Q_{37}$ | Me | OMe | N |
| 3244 | $Q_{38}$ | Me | COOMe | Me | Me | CH |
| 3245 | $Q_{38}$ | Me | COOMe | Me | OMe | CH |
| 3246 | $Q_{38}$ | Me | COOMe | OMe | OMe | CH |
| 3247 | $Q_{38}$ | Me | COOMe | Me | OMe | N |
| 3248 | $Q_{38}$ | Me | COOMe | OMe | OMe | N |
| 3249 | Me | $Q_{38}$ | Me | Me | OMe | CH |
| 3250 | Me | $Q_{38}$ | Me | OMe | OMe | CH |
| 3251 | Me | $Q_{38}$ | Me | Me | OMe | N |
| 3152 | Me | Me | $Q_{38}$ | Me | OMe | CH |
| 3253 | Me | Me | $Q_{38}$ | OMe | OMe | CH |
| 3254 | Me | Me | $Q_{38}$ | Me | OMe | N |
| 3255 | $Q_{39}$ | Me | COOMe | Me | Me | CH |
| 3256 | $Q_{39}$ | Me | COOMe | Me | OMe | CH |
| 3257 | $Q_{39}$ | Me | COOMe | OMe | OMe | CH |
| 3258 | $Q_{39}$ | Me | COOMe | Me | OMe | N |
| 3259 | $Q_{39}$ | Me | COOMe | OMe | OMe | N |
| 3260 | Me | $Q_{39}$ | Me | Me | OMe | CH |
| 3261 | Me | $Q_{39}$ | Me | OMe | OMe | CH |
| 3262 | Me | $Q_{39}$ | Me | Me | OMe | N |
| 3263 | Me | Me | $Q_{39}$ | Me | OMe | CH |
| 3264 | Me | Me | $Q_{39}$ | OMe | OMe | CH |
| 3265 | Me | Me | $Q_{39}$ | Me | OMe | N |
| 3266 | $Q_{40}$ | Me | COOMe | Me | OMe | CH |
| 3267 | $Q_{40}$ | Me | COOMe | OMe | OMe | CH |
| 3268 | $Q_{40}$ | Me | COOMe | Me | OMe | N |
| 3269 | Me | Me | $Q_{40}$ | OMe | OMe | CH |
| 3270 | Me | Me | $Q_{40}$ | Me | OMe | N |
| 3271 | $Q_{41}$ | Me | COOMe | Me | Me | CH |
| 3272 | $Q_{41}$ | Me | COOMe | Me | OMe | CH |
| 3273 | $Q_{41}$ | Me | COOMe | OMe | OMe | CH |
| 3274 | $Q_{41}$ | Me | COOMe | Me | OMe | N |
| 3275 | $Q_{41}$ | Me | COOMe | OMe | OMe | N |
| 3276 | Me | $Q_{41}$ | Me | Me | OMe | CH |
| 3277 | Me | $Q_{41}$ | Me | OMe | OMe | CH |
| 3278 | Me | $Q_{41}$ | Me | Me | OMe | N |
| 3279 | Me | Me | $Q_{41}$ | Me | OMe | CH |
| 3280 | Me | Me | $Q_{41}$ | OMe | OMe | CH |
| 3281 | Me | Me | $Q_{41}$ | Me | OMe | N |
| 3282 | $Q_{42}$ | Me | COOMe | Me | Me | CH |
| 3283 | $Q_{42}$ | Me | COOMe | Me | OMe | CH |
| 3284 | $Q_{42}$ | Me | COOMe | OMe | OMe | CH |
| 3285 | $Q_{42}$ | Me | COOMe | Me | OMe | N |
| 3286 | $Q_{42}$ | Me | COOMe | OMe | OMe | N |
| 3287 | Me | $Q_{42}$ | Me | Me | OMe | CH |
| 3288 | Me | $Q_{42}$ | Me | OMe | OMe | CH |
| 3289 | Me | $Q_{42}$ | Me | Me | OMe | N |
| 3290 | Me | Me | $Q_{42}$ | Me | OMe | CH |
| 3291 | Me | Me | $Q_{42}$ | OMe | OMe | CH |
| 3292 | Me | Me | $Q_{42}$ | Me | OMe | N |
| 3293 | $Q_{43}$ | Me | COOMe | Me | Me | CH |
| 3294 | $Q_{43}$ | Me | COOMe | Me | OMe | CH |
| 3295 | $Q_{43}$ | Me | COOMe | OMe | OMe | CH |

TABLE 2-continued

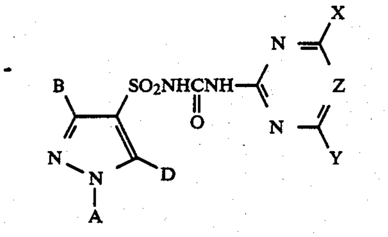

| No. | A | B | D | X | Y | Z |
|---|---|---|---|---|---|---|
| 3296 | $Q_{43}$ | Me | COOMe | Me | OMe | N |
| 3297 | $Q_{43}$ | Me | COOMe | OMe | OMe | N |
| 3298 | Me | $Q_{43}$ | Me | Me | OMe | CH |
| 3299 | Me | $Q_{43}$ | Me | OMe | OMe | CH |
| 3300 | Me | $Q_{43}$ | Me | Me | OMe | N |
| 3301 | Me | Me | $Q_{43}$ | Me | OMe | CH |
| 3302 | Me | Me | $Q_{43}$ | OMe | OMe | CH |
| 3303 | Me | Me | $Q_{43}$ | Me | OMe | N |
| 3304 | $Q_{44}$ | Me | COOMe | Me | OMe | CH |
| 3305 | $Q_{44}$ | Me | COOMe | OMe | OMe | CH |
| 3306 | $Q_{44}$ | Me | COOMe | Me | OMe | N |
| 3307 | Me | Me | $Q_{44}$ | OMe | OMe | CH |
| 3308 | Me | Me | $Q_{44}$ | Me | OMe | N |
| 3309 | $Q_{45}$ | Me | Cl | Me | Me | CH |
| 3310 | $Q_{45}$ | Me | Cl | Me | OMe | CH |
| 3311 | $Q_{45}$ | Me | Cl | OMe | OMe | CH |
| 3312 | $Q_{45}$ | Me | Cl | Me | OMe | N |
| 3313 | $Q_{45}$ | Me | Cl | OMe | OMe | N |
| 3314 | $Q_{45}$ | Me | OMe | Me | OMe | CH |
| 3315 | $Q_{45}$ | Me | OMe | OMe | OMe | CH |
| 3316 | $Q_{45}$ | Me | OMe | Me | OMe | N |
| 3317 | $Q_{45}$ | $CF_3$ | Me | Me | OMe | CH |
| 3318 | $Q_{45}$ | $CF_3$ | Me | OMe | OMe | CH |
| 3319 | $Q_{45}$ | $CF_3$ | Me | Me | OMe | N |
| 3320 | $Q_{45}$ | Me | COOMe | Me | Me | CH |
| 3321 | $Q_{45}$ | Me | COOMe | Me | OMe | CH |
| 3322 | $Q_{45}$ | Me | COOMe | OMe | OMe | CH |
| 3323 | $Q_{45}$ | Me | COOMe | Me | OMe | N |
| 3324 | $Q_{45}$ | Me | COOMe | OMe | OMe | N |
| 3325 | $Q_{45}$ | Me | COOMe | Me | $OCHF_2$ | CH |
| 3326 | $Q_{45}$ | Me | COOMe | Me | 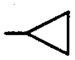 | CH |
| 3327 | $Q_{45}$ | Me | $SO_2Me$ | Me | OMe | CH |
| 3328 | $Q_{45}$ | Me | $SO_2Me$ | OMe | OMe | CH |
| 3329 | $Q_{45}$ | Me | $SO_2Me$ | Me | OMe | N |
| 3330 | H | $Q_{45}$ | Me | Me | OMe | CH |
| 3331 | H | $Q_{45}$ | Me | OMe | OMe | CH |
| 3332 | H | $Q_{45}$ | Me | Me | OMe | N |
| 3333 | Me | $Q_{45}$ | Me | Me | OMe | CH |
| 3334 | Me | $Q_{45}$ | Me | OMe | OMe | CH |
| 3335 | Me | $Q_{45}$ | Me | Me | OMe | N |
| 3336 | Me | $Q_{45}$ | Cl | Me | OMe | CH |
| 3337 | Me | $Q_{45}$ | Cl | OMe | OMe | CH |
| 3338 | Me | $Q_{45}$ | Cl | Me | OMe | N |
| 3339 | Me | $Q_{45}$ | COOMe | Me | OMe | CH |
| 3340 | Me | $Q_{45}$ | COOMe | OMe | OMe | CH |
| 3341 | Me | $Q_{45}$ | COOMe | Me | OMe | N |
| 3342 | Me | $Q_{45}$ | Ph | Me | OMe | CH |
| 3343 | Me | $Q_{45}$ | Ph | OMe | OMe | CH |
| 3344 | Me | $Q_{45}$ | Ph | Me | OMe | N |
| 3345 | Me | Me | $Q_{45}$ | Me | OMe | CH |
| 3346 | Me | Me | $Q_{45}$ | OMe | OMe | CH |
| 3347 | Me | Me | $Q_{45}$ | Me | OMe | N |
| 3348 | $Q_{46}$ | Me | COOMe | Me | Me | CH |
| 3349 | $Q_{46}$ | Me | COOMe | Me | OMe | CH |
| 3350 | $Q_{46}$ | Me | COOMe | OMe | OMe | CH |
| 3351 | $Q_{46}$ | Me | COOMe | Me | OMe | N |
| 3352 | $Q_{46}$ | Me | COOMe | OMe | OMe | N |
| 3353 | Me | $Q_{46}$ | Me | Me | OMe | CH |
| 3354 | Me | $Q_{46}$ | Me | OMe | OMe | CH |
| 3355 | Me | $Q_{46}$ | Me | Me | OMe | N |
| 3356 | Me | Me | $Q_{46}$ | Me | OMe | CH |
| 3357 | Me | Me | $Q_{46}$ | OMe | OMe | CH |
| 3358 | Me | Me | $Q_{46}$ | Me | OMe | N |
| 3359 | $Q_{47}$ | Me | COOMe | Me | Me | CH |
| 3360 | $Q_{47}$ | Me | COOMe | Me | OMe | CH |

TABLE 2-continued

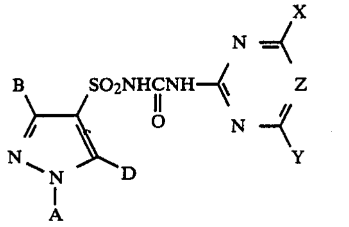

| No. | A | B | D | X | Y | Z |
|---|---|---|---|---|---|---|
| 3361 | $Q_{47}$ | Me | COOMe | OMe | OMe | CH |
| 3362 | $Q_{47}$ | Me | COOMe | Me | OMe | N |
| 3363 | $Q_{47}$ | Me | COOMe | OMe | OMe | N |
| 3364 | Me | $Q_{47}$ | Me | Me | OMe | CH |
| 3365 | Me | $Q_{47}$ | Me | OMe | OMe | CH |
| 3366 | Me | $Q_{47}$ | Me | Me | OMe | N |
| 3367 | Me | Me | $Q_{47}$ | Me | OMe | CH |
| 3368 | Me | Me | $Q_{47}$ | OMe | OMe | CH |
| 3369 | Me | Me | $Q_{47}$ | Me | OMe | N |
| 3370 | $Q_{48}$ | Me | COOMe | Me | Me | CH |
| 3371 | $Q_{48}$ | Me | COOMe | Me | OMe | CH |
| 3372 | $Q_{48}$ | Me | COOMe | OMe | OMe | CH |
| 3373 | $Q_{48}$ | Me | COOMe | Me | OMe | N |
| 3374 | $Q_{48}$ | Me | COOMe | OMe | OMe | N |
| 3375 | Me | $Q_{48}$ | Me | Me | OMe | CH |
| 3376 | Me | $Q_{48}$ | Me | OMe | OMe | CH |
| 3377 | Me | $Q_{48}$ | Me | Me | OMe | CH |
| 3378 | Me | Me | $Q_{48}$ | Me | OMe | CH |
| 3379 | Me | Me | $Q_{48}$ | OMe | OMe | CH |
| 3380 | Me | Me | $Q_{48}$ | Me | OMe | N |
| 3381 | $Q_{49}$ | Me | COOMe | Me | Me | CH |
| 3382 | $Q_{49}$ | Me | COOMe | Me | OMe | CH |
| 3383 | $Q_{49}$ | Me | COOMe | OMe | OMe | CH |
| 3384 | $Q_{49}$ | Me | COOMe | Me | OMe | N |
| 3385 | $Q_{49}$ | Me | COOMe | OMe | OMe | N |
| 3386 | Me | $Q_{49}$ | Me | Me | OMe | CH |
| 3387 | Me | $Q_{49}$ | Me | OMe | OMe | CH |
| 3388 | Me | $Q_{49}$ | Me | Me | OMe | N |
| 3389 | Me | Me | $Q_{49}$ | Me | OMe | CH |
| 3390 | Me | Me | $Q_{49}$ | OMe | OMe | CH |
| 3391 | Me | Me | $Q_{49}$ | Me | OMe | N |
| 3392 | $Q_{50}$ | Me | COOMe | Me | Me | CH |
| 3393 | $Q_{50}$ | Me | COOMe | Me | OMe | CH |
| 3394 | $Q_{50}$ | Me | COOMe | OMe | OMe | CH |
| 3395 | $Q_{50}$ | Me | COOMe | Me | OMe | N |
| 3396 | $Q_{50}$ | Me | COOMe | OMe | OMe | N |
| 3397 | Me | $Q_{50}$ | Me | Me | OMe | CH |
| 3398 | Me | $Q_{50}$ | Me | OMe | OMe | CH |
| 3399 | Me | $Q_{50}$ | Me | Me | OMe | N |
| 3400 | Me | Me | $Q_{50}$ | Me | OMe | CH |
| 3401 | Me | Me | $Q_{50}$ | OMe | OMe | CH |
| 3402 | Me | Me | $Q_{50}$ | Me | OMe | N |
| 3403 | $Q_{51}$ | Me | COOMe | Me | Me | CH |
| 3404 | $Q_{51}$ | Me | COOMe | Me | OMe | CH |
| 3405 | $Q_{51}$ | Me | COOMe | OMe | OMe | CH |
| 3406 | $Q_{51}$ | Me | COOMe | Me | OMe | N |
| 3407 | $Q_{51}$ | Me | COOMe | OMe | OMe | N |
| 3408 | Me | $Q_{51}$ | Me | Me | OMe | CH |
| 3409 | Me | $Q_{51}$ | Me | OMe | OMe | CH |
| 3410 | Me | $Q_{51}$ | Me | Me | OMe | N |
| 3411 | Me | Me | $Q_{51}$ | Me | OMe | CH |
| 3412 | Me | Me | $Q_{51}$ | OMe | OMe | CH |
| 3413 | Me | Me | $Q_{51}$ | Me | OMe | N |
| 3414 | $Q_{52}$ | Me | COOMe | Me | OMe | CH |
| 3415 | $Q_{52}$ | Me | COOMe | OMe | OMe | CH |
| 3416 | $Q_{52}$ | Me | COOMe | Me | OMe | N |
| 3417 | Me | Me | $Q_{52}$ | OMe | OMe | CH |
| 3418 | Me | Me | $Q_{52}$ | Me | OMe | N |
| 3419 | $Q_{53}$ | Me | COOMe | Me | OMe | CH |
| 3420 | $Q_{53}$ | Me | COOMe | OMe | OMe | CH |
| 3421 | $Q_{53}$ | Me | COOMe | Me | OMe | N |
| 3422 | Me | Me | $Q_{53}$ | OMe | OMe | CH |
| 3423 | Me | Me | $Q_{53}$ | Me | OMe | N |
| 3424 | $Q_{54}$ | Me | COOMe | Me | Me | CH |
| 3425 | $Q_{54}$ | Me | COOMe | Me | OMe | CH |
| 3426 | $Q_{54}$ | Me | COOMe | OMe | OMe | CH |
| 3427 | $Q_{54}$ | Me | COOMe | Me | OMe | N |
| 3428 | $Q_{54}$ | Me | COOMe | OMe | OMe | N |
| 3429 | Me | $Q_{54}$ | Me | Me | OMe | CH |

TABLE 2-continued

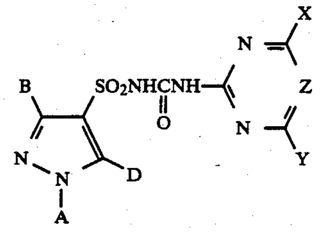

| No. | A | B | D | X | Y | Z |
|---|---|---|---|---|---|---|
| 3430 | Me | $Q_{54}$ | Me | OMe | OMe | CH |
| 3431 | Me | $Q_{54}$ | Me | Me | OMe | N |
| 3432 | Me | Me | $Q_{54}$ | Me | OMe | CH |
| 3433 | Me | Me | $Q_{54}$ | OMe | OMe | CH |
| 3434 | Me | Me | $Q_{54}$ | Me | OMe | N |
| 3435 | $Q_{55}$ | Me | COOMe | Me | Me | CH |
| 3436 | $Q_{55}$ | Me | COOMe | Me | OMe | CH |
| 3437 | $Q_{55}$ | Me | COOMe | OMe | OMe | CH |
| 3438 | $Q_{55}$ | Me | COOMe | Me | OMe | N |
| 3439 | $Q_{55}$ | Me | COOMe | OMe | OMe | N |
| 3440 | Me | $Q_{55}$ | Me | Me | OMe | CH |
| 3441 | Me | $Q_{55}$ | Me | OMe | OMe | CH |
| 3442 | Me | $Q_{55}$ | Me | Me | OMe | N |
| 3443 | Me | Me | $Q_{55}$ | Me | OMe | CH |
| 3444 | Me | Me | $Q_{55}$ | OMe | OMe | CH |
| 3445 | Me | Me | $Q_{55}$ | Me | OMe | N |
| 3446 | $Q_{56}$ | Me | COOMe | Me | Me | CH |
| 3447 | $Q_{56}$ | Me | COOMe | Me | OMe | CH |
| 3448 | $Q_{56}$ | Me | COOMe | OMe | OMe | CH |
| 3449 | $Q_{56}$ | Me | COOMe | Me | OMe | N |
| 3450 | $Q_{56}$ | Me | COOMe | OMe | OMe | N |
| 3451 | Me | $Q_{56}$ | Me | Me | OMe | CH |
| 3452 | Me | $Q_{56}$ | Me | OMe | OMe | CH |
| 3453 | Me | $Q_{56}$ | Me | Me | OMe | N |
| 3454 | Me | Me | $Q_{56}$ | Me | OMe | CH |
| 3455 | Me | Me | $Q_{56}$ | OMe | OMe | CH |
| 3456 | Me | Me | $Q_{56}$ | Me | OMe | N |
| 3457 | $Q_{57}$ | Me | COOMe | Me | OMe | CH |
| 3458 | $Q_{57}$ | Me | COOMe | OMe | OMe | CH |
| 3459 | $Q_{57}$ | Me | COOMe | Me | OMe | N |
| 3460 | Me | Me | $Q_{57}$ | OMe | OMe | CH |
| 3461 | Me | Me | $Q_{57}$ | Me | OMe | N |
| 3462 | $Q_{58}$ | Me | COOMe | Me | OMe | CH |
| 3463 | $Q_{58}$ | Me | COOMe | OMe | OMe | CH |
| 3464 | $Q_{58}$ | Me | COOMe | Me | OMe | N |
| 3465 | Me | Me | $Q_{58}$ | OMe | OMe | CH |
| 3466 | Me | Me | $Q_{58}$ | Me | OMe | N |
| 3467 | $Q_{59}$ | Me | Cl | Me | Me | CH |
| 3468 | $Q_{59}$ | Me | Cl | Me | OMe | CH |
| 3469 | $Q_{59}$ | Me | Cl | OMe | OMe | CH |
| 3470 | $Q_{59}$ | Me | Cl | Me | OMe | N |
| 3471 | $Q_{59}$ | Me | Cl | OMe | OMe | N |
| 3472 | $Q_{59}$ | Me | OMe | Me | OMe | CH |
| 3473 | $Q_{59}$ | Me | OMe | OMe | OMe | CH |
| 3474 | $Q_{59}$ | Me | OMe | Me | OMe | N |
| 3475 | $Q_{59}$ | $CF_3$ | Me | Me | OMe | CH |
| 3476 | $Q_{59}$ | $CF_3$ | Me | OMe | OMe | CH |
| 3477 | $Q_{59}$ | $CF_3$ | Me | Me | OMe | N |
| 3478 | $Q_{59}$ | Me | COOMe | Me | Me | CH |
| 3479 | $Q_{59}$ | Me | COOMe | Me | OMe | CH |
| 3480 | $Q_{59}$ | Me | COOMe | OMe | OMe | CH |
| 3481 | $Q_{59}$ | Me | COOMe | Me | OMe | N |
| 3482 | $Q_{59}$ | Me | COOMe | OMe | OMe | N |
| 3483 | $Q_{59}$ | Me | COOMe | Me | $OCHF_2$ | CH |
| 3484 | $Q_{59}$ | Me | COOMe | Me | 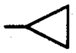 | CH |
| 3485 | $Q_{59}$ | Me | $SO_2Me$ | Me | OMe | CH |
| 3486 | $Q_{59}$ | Me | $SO_2Me$ | OMe | OMe | CH |
| 3487 | $Q_{59}$ | Me | $SO_2Me$ | Me | OMe | N |
| 3488 | H | $Q_{59}$ | Me | Me | OMe | CH |
| 3489 | H | $Q_{59}$ | Me | OMe | OMe | CH |
| 3490 | H | $Q_{59}$ | Me | Me | OMe | N |
| 3491 | Me | $Q_{59}$ | Me | Me | OMe | CH |
| 3492 | Me | $Q_{59}$ | Me | OMe | OMe | CH |
| 3493 | Me | $Q_{59}$ | Me | Me | OMe | N |
| 3494 | Me | $Q_{59}$ | Cl | Me | OMe | CH |

TABLE 2-continued

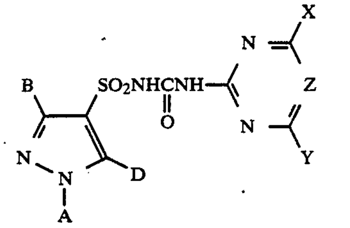

| No. | A | B | D | X | Y | Z |
|---|---|---|---|---|---|---|
| 3495 | Me | $Q_{59}$ | Cl | OMe | OMe | CH |
| 3496 | Me | $Q_{59}$ | Cl | Me | OMe | N |
| 3497 | Me | $Q_{59}$ | COOMe | Me | OMe | CH |
| 3498 | Me | $Q_{59}$ | COOMe | OMe | OMe | CH |
| 3499 | Me | $Q_{59}$ | COOMe | Me | OMe | N |
| 3500 | Me | $Q_{59}$ | Ph | Me | OMe | CH |
| 3501 | Me | $Q_{59}$ | Ph | OMe | OMe | CH |
| 3502 | Me | $Q_{59}$ | Ph | Me | OMe | N |
| 3503 | Me | Me | $Q_{59}$ | Me | OMe | CH |
| 3504 | Me | Me | $Q_{59}$ | OMe | OMe | CH |
| 3505 | Me | Me | $Q_{59}$ | Me | OMe | N |
| 3506 | $Q_{60}$ | Me | COOMe | Me | Me | CH |
| 3507 | $Q_{60}$ | Me | COOMe | Me | OMe | CH |
| 3508 | $Q_{60}$ | Me | COOMe | OMe | OMe | CH |
| 3509 | $Q_{60}$ | Me | COOMe | Me | OMe | N |
| 3510 | $Q_{60}$ | Me | COOMe | OMe | OMe | N |
| 3511 | Me | $Q_{60}$ | Me | Me | OMe | CH |
| 3512 | Me | $Q_{60}$ | Me | OMe | OMe | CH |
| 3513 | Me | $Q_{60}$ | Me | Me | OMe | N |
| 3514 | Me | Me | $Q_{60}$ | Me | OMe | CH |
| 3515 | Me | Me | $Q_{60}$ | OMe | OMe | CH |
| 3516 | Me | Me | $Q_{60}$ | Me | OMe | N |
| 3517 | $Q_{61}$ | Me | COOMe | Me | Me | CH |
| 3518 | $Q_{61}$ | Me | COOMe | Me | OMe | CH |
| 3519 | $Q_{61}$ | Me | COOMe | OMe | OMe | CH |
| 3520 | $Q_{61}$ | Me | COOMe | Me | OMe | N |
| 3521 | $Q_{61}$ | Me | COOMe | OMe | OMe | N |
| 3522 | Me | $Q_{61}$ | Me | Me | OMe | CH |
| 3523 | Me | $Q_{61}$ | Me | OMe | OMe | CH |
| 3524 | Me | $Q_{61}$ | Me | Me | OMe | N |
| 3525 | Me | Me | $Q_{61}$ | Me | OMe | CH |
| 3526 | Me | Me | $Q_{61}$ | OMe | OMe | CH |
| 3527 | Me | Me | $Q_{61}$ | Me | OMe | N |
| 3528 | $Q_{62}$ | Me | COOMe | Me | Me | CH |
| 3529 | $Q_{62}$ | Me | COOMe | Me | OMe | CH |
| 3530 | $Q_{62}$ | Me | COOMe | OMe | OMe | CH |
| 3531 | $Q_{62}$ | Me | COOMe | Me | OMe | N |
| 3532 | $Q_{62}$ | Me | COOMe | OMe | OMe | N |
| 3533 | Me | $Q_{62}$ | Me | Me | OMe | CH |
| 3534 | Me | $Q_{62}$ | Me | OMe | OMe | CH |
| 3535 | Me | $Q_{62}$ | Me | Me | OMe | N |
| 3536 | Me | Me | $Q_{62}$ | Me | OMe | CH |
| 3537 | Me | Me | $Q_{62}$ | OMe | OMe | CH |
| 3538 | Me | Me | $Q_{62}$ | Me | OMe | N |
| 3539 | $Q_{63}$ | Me | COOMe | Me | OMe | CH |
| 3540 | $Q_{63}$ | Me | COOMe | OMe | OMe | CH |
| 3541 | $Q_{63}$ | Me | COOMe | Me | OMe | N |
| 3542 | Me | Me | $Q_{63}$ | OMe | OMe | CH |
| 3543 | Me | Me | $Q_{63}$ | Me | OMe | N |
| 3544 | $Q_{64}$ | Me | COOMe | Me | OMe | CH |
| 3545 | $Q_{64}$ | Me | COOMe | OMe | OMe | CH |
| 3546 | $Q_{64}$ | Me | COOMe | Me | OMe | N |
| 3547 | Me | Me | $Q_{64}$ | OMe | OMe | CH |
| 3548 | Me | Me | $Q_{64}$ | Me | OMe | N |
| 3549 | $Q_{65}$ | Me | COOMe | Me | Me | CH |
| 3550 | $Q_{65}$ | Me | COOMe | Me | OMe | CH |
| 3551 | $Q_{65}$ | Me | COOMe | OMe | OMe | CH |
| 3552 | $Q_{65}$ | Me | COOMe | Me | OMe | N |
| 3553 | $Q_{65}$ | Me | COOMe | OMe | OMe | N |
| 3554 | Me | $Q_{65}$ | Me | Me | OMe | CH |
| 3555 | Me | $Q_{65}$ | Me | OMe | OMe | CH |
| 3556 | Me | $Q_{65}$ | Me | Me | OMe | N |
| 3557 | Me | Me | $Q_{65}$ | Me | OMe | CH |
| 3558 | Me | Me | $Q_{65}$ | OMe | OMe | CH |
| 3559 | Me | Me | $Q_{65}$ | Me | OMe | N |
| 3560 | $Q_{66}$ | Me | COOMe | Me | OMe | CH |
| 3561 | $Q_{66}$ | Me | COOMe | OMe | OMe | CH |
| 3562 | $Q_{66}$ | Me | COOMe | Me | OMe | N |
| 3563 | Me | Me | $Q_{66}$ | OMe | OMe | CH |

TABLE 2-continued

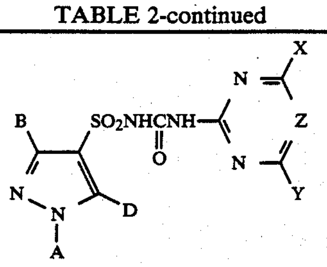

| No. | A | B | D | X | Y | Z |
|---|---|---|---|---|---|---|
| 3564 | Me | Me | $Q_{66}$ | Me | OMe | N |
| 3565 | $Q_{67}$ | Me | COOMe | Me | OMe | CH |
| 3566 | $Q_{67}$ | Me | COOMe | OMe | OMe | CH |
| 3567 | $Q_{67}$ | Me | COOMe | Me | OMe | N |
| 3568 | Me | Me | $Q_{67}$ | OMe | OMe | CH |
| 3569 | Me | Me | $Q_{67}$ | Me | OMe | N |
| 3570 | $Q_{68}$ | Me | COOMe | Me | OMe | CH |
| 3571 | $Q_{68}$ | Me | COOMe | OMe | OMe | CH |
| 3572 | $Q_{68}$ | Me | COOMe | Me | OMe | N |
| 3573 | Me | Me | $Q_{68}$ | OMe | OMe | CH |
| 3574 | Me | Me | $Q_{68}$ | Me | OMe | N |
| 3575 | $Q_{69}$ | Me | COOMe | Me | OMe | CH |
| 3576 | $Q_{69}$ | Me | COOMe | OMe | OMe | CH |
| 3577 | $Q_{69}$ | Me | COOMe | Me | OMe | N |
| 3578 | Me | Me | $Q_{69}$ | OMe | OMe | CH |
| 3579 | Me | Me | $Q_{69}$ | Me | OMe | N |
| 3580 | $Q_{70}$ | Me | COOMe | Me | Me | CH |
| 3581 | $Q_{70}$ | Me | COOMe | Me | OMe | CH |
| 3582 | $Q_{70}$ | Me | COOMe | OMe | OMe | CH |
| 3583 | $Q_{70}$ | Me | COOMe | Me | OMe | N |
| 3584 | $Q_{70}$ | Me | COOMe | OMe | OMe | N |
| 3585 | Me | $Q_{70}$ | Me | Me | OMe | CH |
| 3586 | Me | $Q_{70}$ | Me | OMe | OMe | CH |
| 3587 | Me | $Q_{70}$ | Me | Me | OMe | N |
| 3588 | Me | Me | $Q_{70}$ | Me | OMe | CH |
| 3589 | Me | Me | $Q_{70}$ | OMe | OMe | CH |
| 3590 | Me | Me | $Q_{70}$ | Me | OMe | N |
| 3591 | $Q_{71}$ | Me | COOMe | Me | OMe | CH |
| 3592 | $Q_{71}$ | Me | COOMe | OMe | OMe | CH |
| 3593 | $Q_{71}$ | Me | COOMe | Me | OMe | CH |
| 3594 | Me | Me | $Q_{71}$ | OMe | OMe | CH |
| 3595 | Me | Me | $Q_{71}$ | Me | OMe | N |
| 3596 | $Q_{72}$ | Me | COOMe | Me | OMe | CH |
| 3597 | $Q_{72}$ | Me | COOMe | OMe | OMe | CH |
| 3598 | $Q_{72}$ | Me | COOMe | Me | OMe | N |
| 3599 | Me | Me | $Q_{72}$ | OMe | OMe | CH |
| 3600 | Me | Me | $Q_{72}$ | Me | OMe | N |
| 3601 | $Q_{73}$ | Me | COOMe | Me | OMe | CH |
| 3602 | $Q_{73}$ | Me | COOMe | OMe | OMe | CH |
| 3603 | $Q_{73}$ | Me | COOMe | Me | OMe | N |
| 3604 | Me | Me | $Q_{73}$ | OMe | OMe | CH |
| 3605 | Me | Me | $Q_{73}$ | Me | OMe | N |
| 3606 | $Q_{74}$ | Me | COOMe | Me | OMe | CH |
| 3607 | $Q_{74}$ | Me | COOMe | OMe | OMe | CH |
| 3608 | $Q_{74}$ | Me | COOMe | Me | OMe | N |
| 3609 | Me | Me | $Q_{74}$ | OMe | OMe | CH |
| 3610 | Me | Me | $Q_{74}$ | Me | OMe | N |
| 3611 | $Q_{75}$ | Me | COOMe | Me | OMe | CH |
| 3612 | $Q_{75}$ | Me | COOMe | OMe | OMe | CH |
| 3613 | $Q_{75}$ | Me | COOMe | Me | OMe | N |
| 3614 | Me | Me | $Q_{75}$ | OMe | OMe | CH |
| 3615 | Me | Me | $Q_{75}$ | Me | OMe | N |
| 3616 | $Q_{76}$ | Me | COOMe | Me | OMe | CH |
| 3617 | $Q_{76}$ | Me | COOMe | OMe | OMe | CH |
| 3618 | $Q_{76}$ | Me | COOMe | Me | OMe | N |
| 3619 | Me | Me | $Q_{76}$ | OMe | OMe | CH |
| 3620 | Me | Me | $Q_{76}$ | Me | OMe | N |
| 3621 | $Q_1$ | Me | Me | Me | Me | CH |
| 3622 | $Q_1$ | Me | Me | Me | OMe | CH |
| 3623 | $Q_1$ | Me | Me | OMe | OMe | CH |
| 3624 | $Q_1$ | Me | Me | Me | OMe | N |
| 3625 | $Q_1$ | Me | Me | OMe | OMe | N |
| 3626 | $Q_2$ | Me | Me | Me | Me | CH |
| 3627 | $Q_2$ | Me | Me | Me | OMe | CH |
| 3628 | $Q_2$ | Me | Me | OMe | OMe | CH |
| 3629 | $Q_2$ | Me | Me | Me | OMe | N |
| 3630 | $Q_2$ | Me | Me | OMe | OMe | N |
| 3631 | $Q_3$ | Me | Me | Me | Me | CH |
| 3632 | $Q_3$ | Me | Me | Me | OMe | CH |

TABLE 2-continued

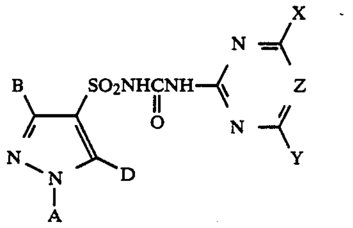

| No. | A | B | D | X | Y | Z |
|---|---|---|---|---|---|---|
| 3633 | $Q_3$ | Me | Me | OMe | OMe | CH |
| 3634 | $Q_3$ | Me | Me | Me | OMe | N |
| 3635 | $Q_3$ | Me | Me | OMe | OMe | N |
| 3636 | $Q_4$ | Me | Me | Me | Me | CH |
| 3637 | $Q_4$ | Me | Me | Me | OMe | CH |
| 3638 | $Q_4$ | Me | Me | OMe | OMe | CH |
| 3639 | $Q_4$ | Me | Me | Me | OMe | N |
| 3640 | $Q_4$ | Me | Me | OMe | OMe | N |
| 3641 | $Q_5$ | Me | Me | Me | Me | CH |
| 3642 | $Q_5$ | Me | Me | Me | OMe | CH |
| 3643 | $Q_5$ | Me | Me | OMe | OMe | CH |
| 3644 | $Q_5$ | Me | Me | Me | OMe | N |
| 3645 | $Q_5$ | Me | Me | OMe | OMe | N |
| 3646 | $Q_6$ | Me | Me | Me | Me | CH |
| 3647 | $Q_6$ | Me | Me | Me | OMe | CH |
| 3648 | $Q_6$ | Me | Me | OMe | OMe | CH |
| 3649 | $Q_6$ | Me | Me | Me | OMe | N |
| 3650 | $Q_6$ | Me | Me | OMe | OMe | N |
| 3651 | $Q_7$ | Me | Me | Me | OMe | CH |
| 3652 | $Q_7$ | Me | Me | OMe | OMe | CH |
| 3653 | $Q_7$ | Me | Me | Me | OMe | N |
| 3654 | $Q_8$ | Me | Me | Me | Me | CH |
| 3655 | $Q_8$ | Me | Me | Me | OMe | CH |
| 3656 | $Q_8$ | Me | Me | OMe | OMe | CH |
| 3657 | $Q_8$ | Me | Me | Me | OMe | N |
| 3658 | $Q_8$ | Me | Me | OMe | OMe | N |
| 3659 | $Q_9$ | Me | Me | Me | Me | CH |
| 3660 | $Q_9$ | Me | Me | Me | OMe | CH |
| 3661 | $Q_9$ | Me | Me | OMe | OMe | CH |
| 3662 | $Q_9$ | Me | Me | Me | OMe | N |
| 3663 | $Q_9$ | Me | Me | OMe | OMe | N |
| 3664 | $Q_{10}$ | Me | Me | Me | Me | CH |
| 3665 | $Q_{10}$ | Me | Me | Me | OMe | CH |
| 3666 | $Q_{10}$ | Me | Me | OMe | OMe | CH |
| 3667 | $Q_{10}$ | Me | Me | Me | OMe | N |
| 3668 | $Q_{10}$ | Me | Me | OMe | OMe | N |
| 3669 | $Q_{11}$ | Me | Me | Me | Me | CH |
| 3670 | $Q_{11}$ | Me | Me | Me | OMe | CH |
| 3671 | $Q_{11}$ | Me | Me | OMe | OMe | CH |
| 3672 | $Q_{11}$ | Me | Me | Me | OMe | N |
| 3673 | $Q_{11}$ | Me | Me | OMe | OMe | N |
| 3674 | $Q_{12}$ | Me | Me | Me | Me | CH |
| 3675 | $Q_{12}$ | Me | Me | Me | OMe | CH |
| 3676 | $Q_{12}$ | Me | Me | OMe | OMe | CH |
| 3677 | $Q_{12}$ | Me | Me | Me | OMe | N |
| 3678 | $Q_{12}$ | Me | Me | OMe | OMe | N |
| 3679 | $Q_{13}$ | Me | Me | Me | OMe | CH |
| 3680 | $Q_{13}$ | Me | Me | OMe | OMe | CH |
| 3681 | $Q_{13}$ | Me | Me | Me | OMe | N |
| 3682 | $Q_{14}$ | Me | Me | Me | Me | CH |
| 3683 | $Q_{14}$ | Me | Me | Me | OMe | CH |
| 3684 | $Q_{14}$ | Me | Me | OMe | OMe | CH |
| 3685 | $Q_{14}$ | Me | Me | Me | OMe | N |
| 3686 | $Q_{14}$ | Me | Me | OMe | OMe | N |
| 3687 | $Q_{15}$ | Me | Me | Me | Me | CH |
| 3688 | $Q_{15}$ | Me | Me | Me | OMe | CH |
| 3689 | $Q_{15}$ | Me | Me | OMe | OMe | CH |
| 3690 | $Q_{15}$ | Me | Me | Me | OMe | N |
| 3691 | $Q_{15}$ | Me | Me | OMe | OMe | N |
| 3692 | $Q_{16}$ | Me | Me | Me | Me | CH |
| 3693 | $Q_{16}$ | Me | Me | Me | OMe | CH |
| 3694 | $Q_{16}$ | Me | Me | OMe | OMe | CH |
| 3695 | $Q_{16}$ | Me | Me | Me | OMe | N |
| 3696 | $Q_{16}$ | Me | Me | OMe | OMe | N |
| 3697 | $Q_{17}$ | Me | Me | Me | OMe | CH |
| 3698 | $Q_{17}$ | Me | Me | OMe | OMe | CH |
| 3699 | $Q_{17}$ | Me | Me | Me | OMe | N |
| 3700 | $Q_{18}$ | Me | Me | Me | Me | CH |
| 3701 | $Q_{18}$ | Me | Me | Me | OMe | CH |

TABLE 2-continued

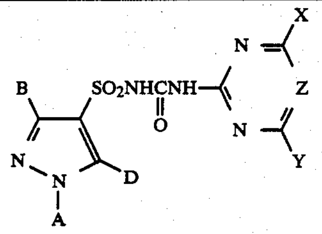

| No. | A | B | D | X | Y | Z |
|---|---|---|---|---|---|---|
| 3702 | $Q_{18}$ | Me | Me | OMe | OMe | CH |
| 3703 | $Q_{18}$ | Me | Me | Me | OMe | N |
| 3704 | $Q_{18}$ | Me | Me | OMe | OMe | N |
| 3705 | $Q_{19}$ | Me | Me | Me | Me | CH |
| 3706 | $Q_{19}$ | Me | Me | Me | OMe | CH |
| 3707 | $Q_{19}$ | Me | Me | OMe | OMe | CH |
| 3708 | $Q_{19}$ | Me | Me | Me | OMe | N |
| 3709 | $Q_{19}$ | Me | Me | OMe | OMe | N |
| 3710 | $Q_{20}$ | Me | Me | Me | Me | CH |
| 3711 | $Q_{20}$ | Me | Me | Me | OMe | CH |
| 3712 | $Q_{20}$ | Me | Me | OMe | OMe | CH |
| 3713 | $Q_{20}$ | Me | Me | Me | OMe | N |
| 3714 | $Q_{20}$ | Me | Me | OMe | OMe | N |
| 3715 | $Q_{21}$ | Me | Me | Me | Me | CH |
| 3716 | $Q_{21}$ | Me | Me | Me | OMe | CH |
| 3717 | $Q_{21}$ | Me | Me | OMe | OMe | CH |
| 3718 | $Q_{21}$ | Me | Me | Me | OMe | N |
| 3719 | $Q_{21}$ | Me | Me | OMe | OMe | N |
| 3720 | $Q_{22}$ | Me | Me | Me | Me | CH |
| 3721 | $Q_{22}$ | Me | Me | Me | OMe | CH |
| 3722 | $Q_{22}$ | Me | Me | OMe | OMe | CH |
| 3723 | $Q_{22}$ | Me | Me | Me | OMe | N |
| 3724 | $Q_{22}$ | Me | Me | OMe | OMe | N |
| 3725 | $Q_{23}$ | Me | Me | Me | OMe | CH |
| 3726 | $Q_{23}$ | Me | Me | OMe | OMe | CH |
| 3727 | $Q_{23}$ | Me | Me | Me | OMe | N |
| 3728 | $Q_{24}$ | Me | Me | Me | Me | CH |
| 3729 | $Q_{24}$ | Me | Me | Me | OMe | CH |
| 3730 | $Q_{24}$ | Me | Me | OMe | OMe | CH |
| 3731 | $Q_{24}$ | Me | Me | Me | OMe | N |
| 3732 | $Q_{24}$ | Me | Me | OMe | OMe | N |
| 3733 | $Q_{25}$ | Me | Me | Me | Me | CH |
| 3734 | $Q_{25}$ | Me | Me | Me | OMe | CH |
| 3735 | $Q_{25}$ | Me | Me | OMe | OMe | CH |
| 3736 | $Q_{25}$ | Me | Me | Me | OMe | N |
| 3737 | $Q_{25}$ | Me | Me | OMe | OMe | N |
| 3738 | $Q_{26}$ | Me | Me | Me | OMe | CH |
| 3739 | $Q_{26}$ | Me | Me | OMe | OMe | CH |
| 3740 | $Q_{26}$ | Me | Me | Me | OMe | N |
| 3741 | $Q_{27}$ | Me | Me | Me | OMe | CH |
| 3742 | $Q_{27}$ | Me | Me | OMe | OMe | CH |
| 3743 | $Q_{27}$ | Me | Me | Me | OMe | N |
| 3744 | $Q_{28}$ | Me | Me | Me | Me | CH |
| 3745 | $Q_{28}$ | Me | Me | Me | OMe | CH |
| 3746 | $Q_{28}$ | Me | Me | OMe | OMe | CH |
| 3747 | $Q_{28}$ | Me | Me | Me | OMe | N |
| 3748 | $Q_{28}$ | Me | Me | OMe | OMe | N |
| 3749 | $Q_{29}$ | Me | Me | Me | OMe | CH |
| 3750 | $Q_{29}$ | Me | Me | OMe | OMe | CH |
| 3751 | $Q_{29}$ | Me | Me | Me | OMe | N |
| 3752 | $Q_{30}$ | Me | Me | Me | OMe | CH |
| 3753 | $Q_{30}$ | Me | Me | OMe | OMe | CH |
| 3754 | $Q_{30}$ | Me | Me | Me | OMe | N |
| 3755 | $Q_{31}$ | Me | Me | Me | OMe | CH |
| 3756 | $Q_{31}$ | Me | Me | OMe | OMe | CH |
| 3757 | $Q_{31}$ | Me | Me | Me | OMe | N |
| 3758 | $Q_{32}$ | Me | Me | Me | Me | CH |
| 3759 | $Q_{32}$ | Me | Me | Me | OMe | CH |
| 3760 | $Q_{32}$ | Me | Me | OMe | OMe | CH |
| 3761 | $Q_{32}$ | Me | Me | Me | OMe | N |
| 3762 | $Q_{32}$ | Me | Me | OMe | OMe | N |
| 3763 | $Q_{33}$ | Me | Me | Me | Me | CH |
| 3764 | $Q_{33}$ | Me | Me | Me | OMe | CH |
| 3765 | $Q_{33}$ | Me | Me | OMe | OMe | CH |
| 3766 | $Q_{33}$ | Me | Me | Me | OMe | N |
| 3767 | $Q_{33}$ | Me | Me | OMe | OMe | N |
| 3768 | $Q_{34}$ | Me | Me | Me | Me | CH |
| 3769 | $Q_{34}$ | Me | Me | Me | OMe | CH |
| 3770 | $Q_{34}$ | Me | Me | OMe | OMe | CH |

TABLE 2-continued

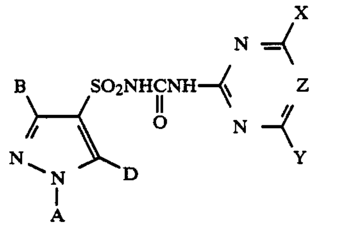

| No. | A | B | D | X | Y | Z |
|---|---|---|---|---|---|---|
| 3771 | $Q_{34}$ | Me | Me | Me | OMe | N |
| 3772 | $Q_{34}$ | Me | Me | OMe | OMe | N |
| 3773 | $Q_{35}$ | Me | Me | Me | Me | CH |
| 3774 | $Q_{35}$ | Me | Me | Me | OMe | CH |
| 3775 | $Q_{35}$ | Me | Me | OMe | OMe | CH |
| 3776 | $Q_{35}$ | Me | Me | Me | OMe | N |
| 3777 | $Q_{35}$ | Me | Me | OMe | OMe | N |
| 3778 | $Q_{36}$ | Me | Me | Me | OMe | CH |
| 3779 | $Q_{36}$ | Me | Me | OMe | OMe | CH |
| 3780 | $Q_{36}$ | Me | Me | Me | OMe | N |
| 3781 | $Q_{37}$ | Me | Me | Me | Me | CH |
| 3782 | $Q_{37}$ | Me | Me | Me | OMe | CH |
| 3783 | $Q_{37}$ | Me | Me | OMe | OMe | CH |
| 3784 | $Q_{37}$ | Me | Me | Me | OMe | N |
| 3785 | $Q_{37}$ | Me | Me | OMe | OMe | N |
| 3786 | $Q_{38}$ | Me | Me | Me | Me | CH |
| 3787 | $Q_{38}$ | Me | Me | Me | OMe | CH |
| 3788 | $Q_{38}$ | Me | Me | OMe | OMe | CH |
| 3789 | $Q_{38}$ | Me | Me | Me | OMe | N |
| 3790 | $Q_{38}$ | Me | Me | OMe | OMe | N |
| 3791 | $Q_{39}$ | Me | Me | Me | Me | CH |
| 3792 | $Q_{39}$ | Me | Me | Me | OMe | CH |
| 3793 | $Q_{39}$ | Me | Me | OMe | OMe | CH |
| 3794 | $Q_{39}$ | Me | Me | Me | OMe | N |
| 3795 | $Q_{39}$ | Me | Me | OMe | OMe | N |
| 3796 | $Q_{40}$ | Me | Me | Me | OMe | CH |
| 3797 | $Q_{40}$ | Me | Me | OMe | OMe | CH |
| 3798 | $Q_{40}$ | Me | Me | Me | OMe | N |
| 3799 | $Q_{41}$ | Me | Me | Me | Me | CH |
| 3800 | $Q_{41}$ | Me | Me | Me | OMe | CH |
| 3801 | $Q_{41}$ | Me | Me | OMe | OMe | CH |
| 3802 | $Q_{41}$ | Me | Me | Me | OMe | N |
| 3803 | $Q_{41}$ | Me | Me | OMe | OMe | N |
| 3804 | $Q_{42}$ | Me | Me | Me | Me | CH |
| 3805 | $Q_{42}$ | Me | Me | Me | OMe | CH |
| 3806 | $Q_{42}$ | Me | Me | OMe | OMe | CH |
| 3807 | $Q_{42}$ | Me | Me | Me | OMe | N |
| 3808 | $Q_{42}$ | Me | Me | OMe | OMe | N |
| 3809 | $Q_{43}$ | Me | Me | Me | Me | CH |
| 3810 | $Q_{43}$ | Me | Me | Me | OMe | CH |
| 3811 | $Q_{43}$ | Me | Me | OMe | OMe | CH |
| 3812 | $Q_{43}$ | Me | Me | Me | OMe | N |
| 3813 | $Q_{43}$ | Me | Me | OMe | OMe | N |
| 3814 | $Q_{44}$ | Me | Me | Me | OMe | CH |
| 3815 | $Q_{44}$ | Me | Me | OMe | OMe | CH |
| 3816 | $Q_{44}$ | Me | Me | Me | OMe | N |
| 3817 | $Q_{45}$ | Me | Me | Me | Me | CH |
| 3818 | $Q_{45}$ | Me | Me | Me | OMe | CH |
| 3819 | $Q_{45}$ | Me | Me | OMe | OMe | CH |
| 3820 | $Q_{45}$ | Me | Me | Me | OMe | N |
| 3821 | $Q_{45}$ | Me | Me | OMe | OMe | N |
| 3822 | $Q_{46}$ | Me | Me | Me | Me | CH |
| 3823 | $Q_{46}$ | Me | Me | Me | OMe | CH |
| 3824 | $Q_{46}$ | Me | Me | OMe | OMe | CH |
| 3825 | $Q_{46}$ | Me | Me | Me | OMe | N |
| 3826 | $Q_{46}$ | Me | Me | OMe | OMe | N |
| 3827 | $Q_{47}$ | Me | Me | Me | Me | CH |
| 3828 | $Q_{47}$ | Me | Me | Me | OMe | CH |
| 3829 | $Q_{47}$ | Me | Me | OMe | OMe | CH |
| 3830 | $Q_{47}$ | Me | Me | Me | OMe | N |
| 3831 | $Q_{47}$ | Me | Me | OMe | OMe | N |
| 3832 | $Q_{48}$ | Me | Me | Me | Me | CH |
| 3833 | $Q_{48}$ | Me | Me | Me | OMe | CH |
| 3834 | $Q_{48}$ | Me | Me | OMe | OMe | CH |
| 3835 | $Q_{48}$ | Me | Me | Me | OMe | N |
| 3836 | $Q_{48}$ | Me | Me | OMe | OMe | N |
| 3837 | $Q_{49}$ | Me | Me | Me | Me | CH |
| 3838 | $Q_{49}$ | Me | Me | Me | OMe | CH |
| 3839 | $Q_{49}$ | Me | Me | OMe | OMe | CH |

TABLE 2-continued

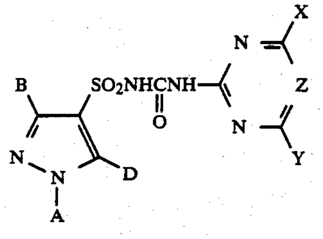

| No. | A | B | D | X | Y | Z |
|---|---|---|---|---|---|---|
| 3840 | $Q_{49}$ | Me | Me | Me | OMe | N |
| 3841 | $Q_{49}$ | Me | Me | OMe | OMe | N |
| 3842 | $Q_{50}$ | Me | Me | Me | Me | CH |
| 3843 | $Q_{50}$ | Me | Me | Me | OMe | CH |
| 3844 | $Q_{50}$ | Me | Me | OMe | OMe | CH |
| 3845 | $Q_{50}$ | Me | Me | Me | OMe | N |
| 3846 | $Q_{50}$ | Me | Me | OMe | OMe | N |
| 3847 | $Q_{51}$ | Me | Me | Me | Me | CH |
| 3848 | $Q_{51}$ | Me | Me | Me | OMe | CH |
| 3849 | $Q_{51}$ | Me | Me | OMe | OMe | CH |
| 3850 | $Q_{51}$ | Me | Me | Me | OMe | N |
| 3851 | $Q_{51}$ | Me | Me | OMe | OMe | N |
| 3852 | $Q_{52}$ | Me | Me | Me | OMe | CH |
| 3853 | $Q_{52}$ | Me | Me | OMe | OMe | CH |
| 3854 | $Q_{52}$ | Me | Me | Me | OMe | N |
| 3855 | $Q_{53}$ | Me | Me | Me | OMe | CH |
| 3856 | $Q_{53}$ | Me | Me | OMe | OMe | CH |
| 3857 | $Q_{53}$ | Me | Me | Me | OMe | N |
| 3858 | $Q_{54}$ | Me | Me | Me | Me | CH |
| 3859 | $Q_{54}$ | Me | Me | Me | OMe | CH |
| 3860 | $Q_{54}$ | Me | Me | OMe | OMe | CH |
| 3861 | $Q_{54}$ | Me | Me | Me | OMe | N |
| 3862 | $Q_{54}$ | Me | Me | OMe | OMe | N |
| 3863 | $Q_{55}$ | Me | Me | Me | Me | CH |
| 3864 | $Q_{55}$ | Me | Me | Me | OMe | CH |
| 3865 | $Q_{55}$ | Me | Me | OMe | OMe | CH |
| 3866 | $Q_{55}$ | Me | Me | Me | OMe | N |
| 3867 | $Q_{55}$ | Me | Me | OMe | OMe | N |
| 3868 | $Q_{56}$ | Me | Me | Me | Me | CH |
| 3869 | $Q_{56}$ | Me | Me | Me | OMe | CH |
| 3870 | $Q_{56}$ | Me | Me | OMe | OMe | CH |
| 3871 | $Q_{56}$ | Me | Me | Me | OMe | N |
| 3872 | $Q_{56}$ | Me | Me | OMe | OMe | N |
| 3873 | $Q_{57}$ | Me | Me | Me | OMe | CH |
| 3874 | $Q_{57}$ | Me | Me | OMe | OMe | CH |
| 3875 | $Q_{57}$ | Me | Me | Me | OMe | N |
| 3876 | $Q_{58}$ | Me | Me | Me | OMe | CH |
| 3877 | $Q_{58}$ | Me | Me | OMe | OMe | CH |
| 3878 | $Q_{58}$ | Me | Me | Me | OMe | N |
| 3879 | $Q_{59}$ | Me | Me | Me | Me | CH |
| 3880 | $Q_{59}$ | Me | Me | Me | OMe | CH |
| 3881 | $Q_{59}$ | Me | Me | OMe | OMe | CH |
| 3882 | $Q_{59}$ | Me | Me | Me | OMe | N |
| 3883 | $Q_{59}$ | Me | Me | OMe | OMe | N |
| 3884 | $Q_{60}$ | Me | Me | Me | Me | CH |
| 3885 | $Q_{60}$ | Me | Me | OMe | OMe | CH |
| 3886 | $Q_{60}$ | Me | Me | OMe | OMe | CH |
| 3887 | $Q_{60}$ | Me | Me | Me | OMe | N |
| 3888 | $Q_{60}$ | Me | Me | OMe | OMe | N |
| 3889 | $Q_{61}$ | Me | Me | Me | Me | CH |
| 3890 | $Q_{61}$ | Me | Me | Me | OMe | CH |
| 3891 | $Q_{61}$ | Me | Me | OMe | OMe | CH |
| 3892 | $Q_{61}$ | Me | Me | Me | OMe | N |
| 3893 | $Q_{61}$ | Me | Me | OMe | OMe | N |
| 3894 | $Q_{62}$ | Me | Me | Me | Me | CH |
| 3895 | $Q_{62}$ | Me | Me | OMe | OMe | CH |
| 3896 | $Q_{62}$ | Me | Me | OMe | OMe | CH |
| 3897 | $Q_{62}$ | Me | Me | Me | OMe | N |
| 3898 | $Q_{62}$ | Me | Me | OMe | OMe | N |
| 3899 | $Q_{63}$ | Me | Me | OMe | OMe | CH |
| 3900 | $Q_{63}$ | Me | Me | OMe | OMe | CH |
| 3901 | $Q_{63}$ | Me | Me | Me | OMe | N |
| 3902 | $Q_{64}$ | Me | Me | Me | OMe | CH |
| 3903 | $Q_{64}$ | Me | Me | OMe | OMe | CH |
| 3904 | $Q_{64}$ | Me | Me | Me | OMe | N |
| 3905 | $Q_{65}$ | Me | Me | Me | Me | CH |
| 3906 | $Q_{65}$ | Me | Me | Me | OMe | CH |
| 3907 | $Q_{65}$ | Me | Me | OMe | OMe | CH |
| 3908 | $Q_{65}$ | Me | Me | Me | OMe | N |

TABLE 2-continued

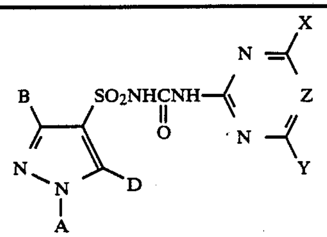

| No. | A | B | D | X | Y | Z |
|---|---|---|---|---|---|---|
| 3909 | $Q_{65}$ | Me | Me | OMe | OMe | N |
| 3910 | $Q_{66}$ | Me | Me | Me | OMe | CH |
| 3911 | $Q_{66}$ | Me | Me | OMe | OMe | CH |
| 3912 | $Q_{66}$ | Me | Me | Me | OMe | N |
| 3913 | $Q_{67}$ | Me | Me | OMe | OMe | CH |
| 3914 | $Q_{67}$ | Me | Me | OMe | OMe | CH |
| 3915 | $Q_{67}$ | Me | Me | Me | OMe | N |
| 3916 | $Q_{68}$ | Me | Me | Me | OMe | CH |
| 3917 | $Q_{68}$ | Me | Me | OMe | OMe | CH |
| 3918 | $Q_{68}$ | Me | Me | Me | OMe | N |
| 3919 | $Q_{69}$ | Me | Me | Me | OMe | CH |
| 3920 | $Q_{69}$ | Me | Me | OMe | OMe | CH |
| 3921 | $Q_{69}$ | Me | Me | Me | OMe | N |
| 3922 | $Q_{70}$ | Me | Me | Me | Me | CH |
| 3923 | $Q_{70}$ | Me | Me | Me | OMe | CH |
| 3924 | $Q_{70}$ | Me | Me | OMe | OMe | CH |
| 3925 | $Q_{70}$ | Me | Me | Me | OMe | N |
| 3926 | $Q_{70}$ | Me | Me | OMe | OMe | N |
| 3927 | $Q_{71}$ | Me | Me | Me | OMe | CH |
| 3928 | $Q_{81}$ | Me | Me | OMe | OMe | CH |
| 3929 | $Q_{71}$ | Me | Me | Me | OMe | N |
| 3930 | $Q_{72}$ | Me | Me | Me | OMe | CH |
| 3931 | $Q_{72}$ | Me | Me | OMe | OMe | CH |
| 3932 | $Q_{72}$ | Me | Me | Me | OMe | N |
| 3933 | $Q_{73}$ | Me | Me | Me | OMe | CH |
| 3934 | $Q_{73}$ | Me | Me | OMe | OMe | CH |
| 3935 | $Q_{73}$ | Me | Me | Me | OMe | N |
| 3936 | $Q_{74}$ | Me | Me | Me | OMe | CH |
| 3937 | $Q_{74}$ | Me | Me | OMe | OMe | CH |
| 3938 | $Q_{74}$ | Me | Me | Me | OMe | N |
| 3939 | $Q_{75}$ | Me | Me | Me | OMe | CH |
| 3940 | $Q_{75}$ | Me | Me | OMe | OMe | CH |
| 3941 | $Q_{75}$ | Me | Me | Me | OMe | N |
| 3942 | $Q_{76}$ | Me | Me | Me | OMe | CH |
| 3943 | $Q_{76}$ | Me | Me | OMe | OMe | CH |
| 3944 | $Q_{76}$ | Me | Me | Me | OMe | N |
| 3945 | Me | $Q_3$ | COOMe | Me | OMe | CH |
| 3946 | Me | $Q_3$ | COOMe | OMe | OMe | CH |
| 3946 | Me | $Q_3$ | COOMe | OMe | OMe | CH |
| 3946 | Me | $Q_3$ | COOMe | OMe | OMe | CH |
| 3947 | Me | $Q_3$ | COOMe | Me | OMe | N |
| 3948 | Me | $Q_4$ | COOMe | Me | OMe | CH |
| 3949 | Me | $Q_4$ | COOMe | OMe | OMe | CH |
| 3950 | Me | $Q_4$ | COOMe | Me | OMe | N |
| 3951 | Me | $Q_6$ | COOMe | Me | OMe | CH |
| 3952 | Me | $Q_6$ | COOMe | OMe | OMe | CH |
| 3953 | Me | $Q_6$ | COOMe | Me | OMe | N |
| 3954 | Me | $Q_9$ | COOMe | Me | OMe | CH |
| 3955 | Me | $Q_9$ | COOMe | OMe | OMe | CH |
| 3956 | Me | $Q_9$ | COOMe | Me | OMe | N |
| 3957 | Me | $Q_{10}$ | COOMe | Me | OMe | CH |
| 3958 | Me | $Q_{10}$ | COOMe | OMe | OMe | CH |
| 3959 | Me | $Q_{10}$ | COOMe | Me | OMe | N |
| 3960 | Me | $Q_{11}$ | COOMe | Me | OMe | CH |
| 3961 | Me | $Q_{11}$ | COOMe | OMe | OMe | CH |
| 3962 | Me | $Q_{11}$ | COOMe | Me | OMe | N |
| 3963 | Me | $Q_{12}$ | COOMe | Me | OMe | CH |
| 3964 | Me | $Q_{12}$ | COOMe | OMe | OMe | CH |
| 3965 | Me | $Q_{12}$ | COOMe | Me | OMe | N |
| 3966 | Me | $Q_{14}$ | COOMe | Me | OMe | CH |
| 3967 | Me | $Q_{14}$ | COOMe | OMe | OMe | CH |
| 3968 | Me | $Q_{14}$ | COOMe | Me | OMe | N |
| 3969 | Me | $Q_{15}$ | COOMe | Me | OMe | CH |
| 3970 | Me | $Q_{15}$ | COOMe | OMe | OMe | CH |
| 3971 | Me | $Q_{15}$ | COOMe | Me | OMe | N |
| 3972 | Me | $Q_{16}$ | COOMe | Me | OMe | CH |
| 3973 | Me | $Q_{16}$ | COOMe | OMe | OMe | CH |
| 3974 | Me | $Q_{16}$ | COOMe | Me | OMe | N |
| 3975 | Me | $Q_{18}$ | COOMe | Me | OMe | CH |

TABLE 2-continued

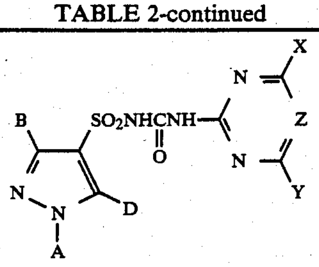

| No. | A | B | D | X | Y | Z |
|---|---|---|---|---|---|---|
| 3976 | Me | $Q_{18}$ | COOMe | OMe | OMe | CH |
| 3977 | Me | $Q_{18}$ | COOMe | Me | OMe | N |
| 3978 | Me | $Q_{19}$ | COOMe | Me | OMe | CH |
| 3979 | Me | $Q_{19}$ | COOMe | OMe | OMe | CH |
| 3980 | Me | $Q_{19}$ | COOMe | Me | OMe | N |
| 3981 | Me | $Q_{20}$ | COOMe | Me | OMe | CH |
| 3982 | Me | $Q_{20}$ | COOMe | OMe | OMe | CH |
| 3983 | Me | $Q_{20}$ | COOMe | Me | OMe | N |
| 3984 | Me | $Q_{21}$ | COOMe | Me | OMe | CH |
| 3985 | Me | $Q_{21}$ | COOMe | OMe | OMe | CH |
| 3986 | Me | $Q_{21}$ | COOMe | Me | OMe | N |
| 3987 | Me | $Q_{22}$ | COOMe | Me | OMe | CH |
| 3988 | Me | $Q_{22}$ | COOMe | OMe | OMe | CH |
| 3989 | Me | $Q_{22}$ | COOMe | Me | OMe | N |
| 3990 | Me | $Q_{24}$ | COOMe | Me | OMe | CH |
| 3991 | Me | $Q_{24}$ | COOMe | OMe | OMe | CH |
| 3992 | Me | $Q_{24}$ | COOMe | Me | OMe | N |
| 3993 | Me | $Q_{25}$ | COOMe | Me | OMe | CH |
| 3994 | Me | $Q_{25}$ | COOMe | OMe | OMe | CH |
| 3995 | Me | $Q_{25}$ | COOMe | Me | OMe | N |
| 3996 | Me | $Q_{28}$ | COOMe | Me | OMe | CH |
| 3997 | Me | $Q_{28}$ | COOMe | OMe | OMe | CH |
| 3998 | Me | $Q_{28}$ | COOMe | Me | OMe | N |
| 3999 | Me | $Q_{33}$ | COOMe | Me | OMe | CH |
| 4000 | Me | $Q_{33}$ | COOMe | OMe | OMe | CH |
| 4001 | Me | $Q_{33}$ | COOMe | Me | OMe | N |
| 4002 | Me | $Q_{34}$ | COOMe | Me | OMe | CH |
| 4003 | Me | $Q_{34}$ | COOMe | OMe | OMe | CH |
| 4004 | Me | $Q_{34}$ | COOMe | Me | OMe | N |
| 4005 | Me | $Q_{35}$ | COOMe | Me | OMe | CH |
| 4006 | Me | $Q_{35}$ | COOMe | OMe | OMe | CH |
| 4007 | Me | $Q_{35}$ | COOMe | Me | OMe | N |
| 4008 | Me | $Q_{37}$ | COOMe | Me | OMe | CH |
| 4009 | Me | $Q_{37}$ | COOMe | OMe | OMe | CH |
| 4010 | Me | $Q_{37}$ | COOMe | Me | OMe | N |
| 4011 | Me | $Q_{38}$ | COOMe | Me | OMe | CH |
| 4012 | Me | $Q_{38}$ | COOMe | OMe | OMe | CH |
| 4013 | Me | $Q_{38}$ | COOMe | Me | OMe | N |
| 4014 | Me | $Q_{39}$ | COOMe | Me | OMe | CH |
| 4015 | Me | $Q_{39}$ | COOMe | OMe | OMe | CH |
| 4016 | Me | $Q_{39}$ | COOMe | Me | OMe | N |
| 4017 | Me | $Q_{41}$ | COOMe | Me | OMe | CH |
| 4018 | Me | $Q_{41}$ | COOMe | OMe | OMe | CH |
| 4019 | Me | $Q_{41}$ | COOMe | Me | OMe | N |
| 4020 | Me | $Q_{42}$ | COOMe | Me | OMe | CH |
| 4021 | Me | $Q_{42}$ | COOMe | OMe | OMe | CH |
| 4022 | Me | $Q_{42}$ | COOMe | Me | OMe | N |
| 4023 | Me | $Q_{43}$ | COOMe | Me | OMe | CH |
| 4024 | Me | $Q_{43}$ | COOMe | OMe | OMe | CH |
| 4025 | Me | $Q_{43}$ | COOMe | Me | OMe | N |
| 4026 | Me | $Q_{46}$ | COOMe | Me | OMe | CH |
| 4027 | Me | $Q_{46}$ | COOMe | OMe | OMe | CH |
| 4028 | Me | $Q_{46}$ | COOMe | Me | OMe | N |
| 4029 | Me | $Q_{47}$ | COOMe | Me | OMe | CH |
| 4030 | Me | $Q_{47}$ | COOMe | OMe | OMe | CH |
| 4031 | Me | $Q_{47}$ | COOMe | Me | OMe | N |
| 4032 | Me | $Q_{48}$ | COOMe | Me | OMe | CH |
| 4033 | Me | $Q_{48}$ | COOMe | OMe | OMe | CH |
| 4034 | Me | $Q_{48}$ | COOMe | Me | OMe | N |
| 4035 | Me | $Q_{49}$ | COOMe | Me | OMe | CH |
| 4036 | Me | $Q_{49}$ | COOMe | OMe | OMe | CH |
| 4037 | Me | $Q_{49}$ | COOMe | Me | OMe | N |
| 4038 | Me | $Q_{50}$ | COOMe | Me | OMe | CH |
| 4039 | Me | $Q_{50}$ | COOMe | OMe | OMe | CH |
| 4040 | Me | $Q_{50}$ | COOMe | Me | OMe | N |
| 4041 | Me | $Q_{51}$ | COOMe | Me | OMe | CH |
| 4042 | Me | $Q_{51}$ | COOMe | OMe | OMe | CH |
| 4043 | Me | $Q_{51}$ | COOMe | Me | OMe | N |
| 4044 | Me | $Q_{54}$ | COOMe | OMe | OMe | CH |

TABLE 2-continued

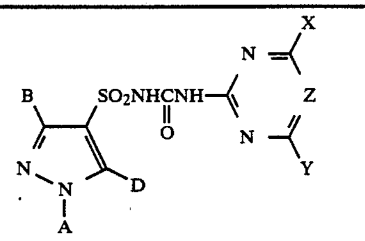

| No. | A | B | D | X | Y | Z |
|---|---|---|---|---|---|---|
| 4045 | Me | $Q_{54}$ | COOMe | OMe | OMe | CH |
| 4046 | Me | $Q_{54}$ | COOMe | Me | OMe | N |
| 4047 | Me | $Q_{55}$ | COOMe | Me | OMe | CH |
| 4048 | Me | $Q_{55}$ | COOMe | OMe | OMe | CH |
| 4049 | Me | $Q_{55}$ | COOMe | Me | OMe | N |
| 4050 | Me | $Q_{56}$ | COOMe | Me | OMe | CH |
| 4051 | Me | $Q_{56}$ | COOMe | OMe | OMe | CH |
| 4052 | Me | $Q_{56}$ | COOMe | Me | OMe | N |
| 4053 | Me | $Q_{60}$ | COOMe | Me | OMe | CH |
| 4054 | Me | $Q_{60}$ | COOMe | OMe | OMe | CH |
| 4055 | Me | $Q_{60}$ | COOMe | Me | OMe | N |
| 4056 | Me | $Q_{61}$ | COOMe | Me | OMe | CH |
| 4057 | Me | $Q_{61}$ | COOMe | OMe | OMe | CH |
| 4058 | Me | $Q_{61}$ | COOMe | Me | OMe | N |
| 4059 | Me | $Q_{62}$ | COOMe | Me | OMe | CH |
| 4060 | Me | $Q_{62}$ | COOMe | OMe | OMe | CH |
| 4061 | Me | $Q_{62}$ | COOMe | Me | OMe | N |
| 4062 | Me | $Q_{65}$ | COOMe | Me | OMe | CH |
| 4063 | Me | $Q_{65}$ | COOMe | OMe | OMe | CH |
| 4064 | Me | $Q_{65}$ | COOMe | Me | OMe | N |
| 4065 | Me | $Q_{70}$ | COOMe | Me | OMe | CH |
| 4066 | Me | $Q_{70}$ | COOMe | OMe | OMe | CH |
| 4067 | Me | $Q_{70}$ | COOMe | Me | OMe | N |
| 4068 | Me | $Q_{7}$ | Me | OMe | OMe | CH |
| 4069 | Me | $Q_{7}$ | Me | Me | OMe | N |
| 4070 | Me | $Q_{13}$ | Me | OMe | OMe | CH |
| 4071 | Me | $Q_{13}$ | Me | Me | OMe | N |
| 4072 | Me | $Q_{17}$ | Me | OMe | OMe | CH |
| 4073 | Me | $Q_{17}$ | Me | Me | OMe | N |
| 4074 | Me | $Q_{23}$ | Me | OMe | OMe | CH |
| 4075 | Me | $Q_{23}$ | Me | Me | OMe | N |
| 4076 | Me | $Q_{26}$ | Me | OMe | OMe | CH |
| 4077 | Me | $Q_{26}$ | Me | Me | OMe | N |
| 4078 | Me | $Q_{27}$ | Me | OMe | OMe | CH |
| 4079 | Me | $Q_{27}$ | Me | Me | OMe | N |
| 4080 | Me | $Q_{29}$ | Me | OMe | OMe | CH |
| 4081 | Me | $Q_{29}$ | Me | Me | OMe | N |
| 4082 | Me | $Q_{30}$ | Me | OMe | OMe | CH |
| 4083 | Me | $Q_{30}$ | Me | Me | OMe | N |
| 4084 | Me | $Q_{31}$ | Me | OMe | OMe | CH |
| 4085 | Me | $Q_{31}$ | Me | Me | OMe | N |
| 4086 | Me | $Q_{36}$ | Me | OMe | OMe | CH |
| 4087 | Me | $Q_{36}$ | Me | Me | OMe | N |
| 4088 | Me | $Q_{40}$ | Me | OMe | OMe | CH |
| 4089 | Me | $Q_{40}$ | Me | Me | OMe | N |
| 4090 | Me | $Q_{44}$ | Me | OMe | OMe | CH |
| 4091 | Me | $Q_{44}$ | Me | Me | OMe | N |
| 4092 | Me | $Q_{52}$ | Me | OMe | OMe | CH |
| 4093 | Me | $Q_{52}$ | Me | Me | OMe | N |
| 4094 | Me | $Q_{53}$ | Me | OMe | OMe | CH |
| 4095 | Me | $Q_{53}$ | Me | Me | OMe | N |
| 4096 | Me | $Q_{57}$ | Me | OMe | OMe | CH |
| 4097 | Me | $Q_{57}$ | Me | Me | OMe | N |
| 4098 | Me | $Q_{58}$ | Me | OMe | OMe | CH |
| 4099 | Me | $Q_{58}$ | Me | Me | OMe | N |
| 4100 | Me | $Q_{63}$ | Me | OMe | OMe | CH |
| 4101 | Me | $Q_{63}$ | Me | Me | OMe | N |
| 4102 | Me | $Q_{64}$ | Me | OMe | OMe | CH |
| 4103 | Me | $Q_{64}$ | Me | Me | OMe | N |
| 4104 | Me | $Q_{66}$ | Me | OMe | OMe | CH |
| 4105 | Me | $Q_{66}$ | Me | Me | OMe | N |
| 4106 | Me | $Q_{67}$ | Me | OMe | OMe | CH |
| 4107 | Me | $Q_{67}$ | Me | Me | OMe | N |
| 4108 | Me | $Q_{68}$ | Me | OMe | OMe | CH |
| 4109 | Me | $Q_{68}$ | Me | Me | OMe | N |
| 4110 | Me | $Q_{69}$ | Me | OMe | OMe | CH |
| 4111 | Me | $Q_{69}$ | Me | Me | OMe | N |
| 4112 | Me | $Q_{71}$ | Me | OMe | OMe | CH |
| 4113 | Me | $Q_{71}$ | Me | Me | OMe | N |

TABLE 2-continued

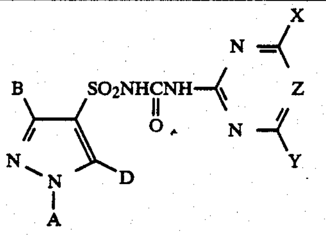

| No. | A | B | D | X | Y | Z |
|---|---|---|---|---|---|---|
| 4114 | Me | $Q_{72}$ | Me | OMe | OMe | CH |
| 4115 | Me | $Q_{72}$ | Me | Me | OMe | N |
| 4116 | Me | $Q_{73}$ | Me | OMe | OMe | CH |
| 4117 | Me | $Q_{73}$ | Me | Me | OMe | N |
| 4118 | Me | $Q_{74}$ | Me | OMe | OMe | CH |
| 4119 | Me | $Q_{74}$ | Me | Me | OMe | N |
| 4120 | Me | $Q_{75}$ | Me | OMe | OMe | CH |
| 4121 | Me | $Q_{75}$ | Me | Me | OMe | N |
| 4122 | Me | $Q_{76}$ | Me | OMe | OMe | CH |
| 4123 | Me | $Q_{76}$ | Me | Me | OMe | N |
| 5611 | $Q_{77}$ | Me | COOMe | Me | OMe | CH |
| 5612 | $Q_{77}$ | Me | COOMe | OMe | OMe | CH |
| 5613 | $Q_{77}$ | Me | COOMe | Me | OMe | N |
| 5614 | Me | Me | $Q_{77}$ | OMe | OMe | CH |
| 5615 | Me | Me | $Q_{77}$ | Me | OMe | N |
| 5616 | $Q_{78}$ | Me | Cl | Me | Me | CH |
| 5617 | $Q_{78}$ | Me | Cl | Me | OMe | CH |
| 5618 | $Q_{78}$ | Me | Cl | OMe | OMe | CH |
| 5619 | $Q_{78}$ | Me | Cl | Me | OMe | N |
| 5620 | $Q_{78}$ | Me | Cl | OMe | OMe | N |
| 5621 | $Q_{78}$ | Me | OMe | Me | OMe | CH |
| 5622 | $Q_{78}$ | Me | OMe | OMe | OMe | CH |
| 5623 | $Q_{78}$ | Me | OMe | Me | OMe | N |
| 5624 | $Q_{78}$ | $CF_3$ | Me | Me | OMe | CH |
| 5625 | $Q_{78}$ | $CF_3$ | Me | OMe | OMe | CH |
| 5626 | $Q_{78}$ | $CF_3$ | Me | Me | OMe | N |
| 5627 | $Q_{78}$ | Me | COOMe | Me | Me | CH |
| 5628 | $Q_{78}$ | Me | COOMe | Me | OMe | CH |
| 5629 | $Q_{78}$ | Me | COOMe | OMe | OMe | CH |
| 5630 | $Q_{78}$ | Me | COOMe | Me | OMe | N |
| 5631 | $Q_{78}$ | Me | COOMe | OMe | OMe | N |
| 5632 | $Q_{78}$ | Me | COOMe | Me | $OCHF_2$ | CH |
| 5633 | $Q_{78}$ | Me | COOMe | Me | 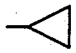 | CH |
| 5634 | $Q_{78}$ | Me | $SO_2Me$ | Me | OMe | CH |
| 5635 | $Q_{78}$ | Me | $SO_2Me$ | OMe | OMe | CH |
| 5636 | $Q_{78}$ | Me | $SO_2Me$ | Me | OMe | N |
| 5637 | H | $Q_{78}$ | Me | Me | OMe | CH |
| 5638 | H | $Q_{78}$ | Me | OMe | OMe | CH |
| 5639 | H | $Q_{78}$ | Me | Me | OMe | N |
| 5640 | Me | $Q_{78}$ | Me | Me | OMe | CH |
| 5641 | Me | $Q_{78}$ | Me | OMe | OMe | CH |
| 5642 | Me | $Q_{78}$ | Me | Me | OMe | N |
| 5643 | Me | $Q_{78}$ | Cl | Me | OMe | CH |
| 5644 | Me | $Q_{78}$ | Cl | OMe | OMe | CH |
| 5645 | Me | $Q_{78}$ | Cl | Me | OMe | N |
| 5646 | Me | $Q_{78}$ | COOMe | Me | OMe | CH |
| 5647 | Me | $Q_{78}$ | COOMe | OMe | OMe | CH |
| 5648 | Me | $Q_{78}$ | COOMe | Me | OMe | N |
| 5649 | Me | $Q_{78}$ | Ph | Me | OMe | CH |
| 5650 | Me | $Q_{78}$ | Ph | OMe | OMe | CH |
| 5651 | Me | $Q_{78}$ | Ph | Me | OMe | N |
| 5652 | Me | Me | $Q_{78}$ | Me | OMe | CH |
| 5653 | Me | Me | $Q_{78}$ | OMe | OMe | CH |
| 5654 | Me | Me | $Q_{78}$ | Me | OMe | N |
| 5655 | $Q_{79}$ | Me | Cl | Me | Me | CH |
| 5656 | $Q_{79}$ | Me | Cl | Me | OMe | CH |
| 5657 | $Q_{79}$ | Me | Cl | OMe | OMe | CH |
| 5658 | $Q_{79}$ | Me | Cl | Me | OMe | N |
| 5659 | $Q_{79}$ | Me | Cl | OMe | OMe | N |
| 5660 | $Q_{79}$ | Me | OMe | Me | OMe | CH |
| 5661 | $Q_{79}$ | Me | OMe | OMe | OMe | CH |
| 5662 | $Q_{79}$ | Me | OMe | Me | OMe | N |
| 5663 | $Q_{79}$ | $CF_3$ | Me | Me | OMe | CH |
| 5664 | $Q_{79}$ | $CF_3$ | Me | OMe | OMe | CH |
| 5665 | $Q_{79}$ | $CF_3$ | Me | Me | OMe | N |

TABLE 2-continued

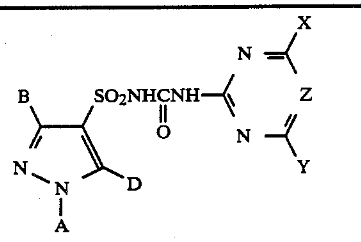

| No. | A | B | D | X | Y | Z |
|---|---|---|---|---|---|---|
| 5666 | $Q_{79}$ | Me | COOMe | Me | Me | CH |
| 5667 | $Q_{79}$ | Me | COOMe | Me | OMe | CH |
| 5668 | $Q_{79}$ | Me | COOMe | OMe | OMe | CH |
| 5669 | $Q_{79}$ | Me | COOMe | Me | OMe | N |
| 5670 | $Q_{79}$ | Me | COOMe | OMe | OMe | N |
| 5671 | $Q_{79}$ | Me | COOMe | Me | $OCHF_2$ | CH |
| 5672 | $Q_{79}$ | Me | COOMe | Me | 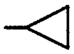 | CH |
| 5673 | $Q_{79}$ | Me | $SO_2Me$ | Me | OMe | CH |
| 5674 | $Q_{79}$ | Me | $SO_2Me$ | OMe | OMe | CH |
| 5675 | $Q_{79}$ | Me | $SO_2Me$ | Me | OMe | N |
| 5676 | H | $Q_{79}$ | Me | Me | OMe | CH |
| 5677 | H | $Q_{79}$ | Me | OMe | OMe | CH |
| 5678 | H | $Q_{79}$ | Me | Me | OMe | N |
| 5679 | Me | $Q_{79}$ | Me | Me | OMe | CH |
| 5680 | Me | $Q_{79}$ | Me | OMe | OMe | CH |
| 5681 | Me | $Q_{79}$ | Me | Me | OMe | N |
| 5682 | Me | $Q_{79}$ | Cl | Me | OMe | CH |
| 5683 | Me | $Q_{79}$ | Cl | OMe | OMe | CH |
| 5684 | Me | $Q_{79}$ | Cl | Me | OMe | N |
| 5685 | Me | $Q_{79}$ | COOMe | Me | OMe | CH |
| 5686 | Me | $Q_{79}$ | COOMe | OMe | OMe | CH |
| 5687 | Me | $Q_{79}$ | COOMe | Me | OMe | N |
| 5688 | Me | $Q_{79}$ | Ph | Me | OMe | CH· |
| 5689 | Me | $Q_{79}$ | Ph | OMe | OMe | CH |
| 5690 | Me | $Q_{79}$ | Ph | Me | OMe | N |
| 5691 | Me | Me | $Q_{79}$ | Me | OMe | CH |
| 5692 | Me | Me | $Q_{79}$ | OMe | OMe | CH |
| 5693 | Me | Me | $Q_{79}$ | Me | OMe | N |
| 5694 | $Q_{80}$ | Me | COOMe | Me | Me | CH |
| 5695 | $Q_{80}$ | Me | COOMe | Me | OMe | CH |
| 5696 | $Q_{80}$ | Me | COOMe | OMe | OMe | CH |
| 5697 | $Q_{80}$ | Me | COOMe | Me | OMe | N |
| 5698 | $Q_{80}$ | Me | COOMe | OMe | OMe | N |
| 5699 | Me | $Q_{80}$ | Me | Me | OMe | CH |
| 5700 | Me | $Q_{80}$ | Me | OMe | OMe | CH |
| 5701 | Me | $Q_{80}$ | Me | Me | OMe | N |
| 5702 | Me | Me | $Q_{80}$ | Me | OMe | CH |
| 5703 | Me | Me | $Q_{80}$ | OMe | OMe | CH |
| 5704 | Me | Me | $Q_{80}$ | Me | OMe | N |
| 5705 | $Q_{81}$ | Me | COOMe | Me | OMe | CH |
| 5706 | $Q_{81}$ | Me | COOMe | OMe | OMe | CH |
| 5707 | $Q_{81}$ | Me | COOMe | Me | OMe | N |
| 5708 | Me | Me | $Q_{81}$ | OMe | OMe | CH |
| 5709 | Me | Me | $Q_{81}$ | Me | OMe | N |
| 5710 | $Q_{82}$ | Me | COOMe | Me | OMe | CH |
| 5711 | $Q_{82}$ | Me | COOMe | OMe | OMe | CH |
| 5712 | $Q_{82}$ | Me | COOMe | Me | OMe | N |
| 5713 | Me | Me | $Q_{83}$ | OMe | OMe | CH |
| 5714 | Me | Me | $Q_{83}$ | Me | OMe | N |
| 5715 | $Q_{83}$ | Me | COOMe | Me | OMe | CH |
| 5716 | $Q_{83}$ | Me | COOMe | OME | OME | CH |
| 5717 | $Q_{83}$ | Me | COOMe | Me | OMe | N |
| 5718 | Me | Me | $Q_{83}$ | OMe | OMe | CH |
| 5719 | Me | Me | $Q_{83}$ | Me | OMe | N |

In the above, $Q_1$ to $Q_{83}$ are as defined above.

TABLE 3

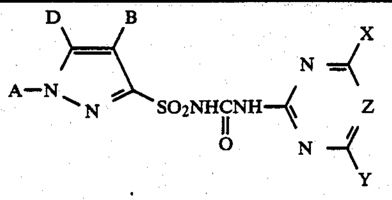

| No. | A | B | D | X | Y | Z |
|---|---|---|---|---|---|---|
| 4124 | $Q_1$ | H | H | Me | Me | CH |
| 4125 | $Q_1$ | H | H | Me | OMe | CH |
| 4126 | $Q_1$ | H | H | OMe | OMe | CH |
| 4127 | $Q_1$ | H | H | Me | OMe | N |
| 4128 | $Q_1$ | H | H | OMe | OMe | N |
| 4129 | $Q_1$ | H | H | Me | $OCHF_2$ | CH |
| 4130 | $Q_1$ | H | H | Cl | OMe | CH |
| 4131 | $Q_1$ | H | H | Me | Me | N |
| 4132 | $Q_1$ | Me | H | Me | Me | CH |
| 4133 | $Q_1$ | Me | H | Me | OMe | CH |
| 4134 | $Q_1$ | Me | H | OMe | OMe | CH |
| 4135 | $Q_1$ | Me | H | Me | OMe | N |
| 4136 | $Q_1$ | Me | H | OMe | OMe | N |
| 4137 | $Q_1$ | Me | H | Me | $OCHF_2$ | CH |
| 4138 | $Q_1$ | Me | H | Cl | OMe | CH |
| 4139 | $Q_1$ | Me | H | Me | Me | N |
| 4140 | $Q_1$ | Et | H | Me | Me | CH |
| 4141 | $Q_1$ | Et | H | Me | OMe | CH |
| 4142 | $Q_1$ | Et | H | OMe | OMe | CH |
| 4143 | $Q_1$ | Et | H | Me | OMe | N |
| 4144 | $Q_1$ | Et | H | OMe | OMe | N |
| 4145 | $Q_1$ | Cl | H | Me | Me | CH |
| 4146 | $Q_1$ | Cl | H | Me | OMe | CH |
| 4147 | $Q_1$ | Cl | H | OMe | OMe | CH |
| 4148 | $Q_1$ | Cl | H | Me | OMe | N |
| 4149 | $Q_1$ | Cl | H | OMe | OMe | N |
| 4150 | $Q_1$ | Br | H | Me | Me | CH |
| 4151 | $Q_1$ | Br | H | Me | OMe | CH |
| 4152 | $Q_1$ | Br | H | OMe | OMe | CH |
| 4153 | $Q_1$ | Br | H | Me | OMe | N |
| 4154 | $Q_1$ | Br | H | OMe | OMe | N |
| 4155 | $Q_1$ | Br | H | Me | $OCHF_2$ | CH |
| 4156 | $Q_1$ | Br | H | Cl | OMe | CH |
| 4157 | $Q_1$ | Br | H | Me | Me | N |
| 4158 | $Q_1$ | $NO_2$ | H | Me | Me | CH |
| 4159 | $Q_1$ | $NO_2$ | H | Me | OMe | CH |
| 4160 | $Q_1$ | $NO_2$ | H | OMe | OMe | CH |
| 4161 | $Q_1$ | $NO_2$ | H | Me | OMe | N |
| 4162 | $Q_1$ | $NO_2$ | H | OMe | OMe | N |
| 4163 | $Q_1$ | COOMe | H | Me | Me | CH |
| 4164 | $Q_1$ | COOMe | H | Me | OMe | CH |
| 4165 | $Q_1$ | COOMe | H | OMe | OMe | CH |
| 4166 | $Q_1$ | COOMe | H | Me | OMe | N |
| 4167 | $Q_1$ | COOMe | H | OMe | OMe | N |
| 4168 | $Q_1$ | COOEt | H | Me | Me | CH |
| 4169 | $Q_1$ | COOEt | H | Me | OMe | CH |
| 4170 | $Q_1$ | COOEt | H | OMe | OMe | CH |
| 4171 | $Q_1$ | COOEt | H | Me | OMe | N |
| 4172 | $Q_1$ | COOEt | H | OMe | OMe | N |
| 4173 | $Q_1$ | $SO_2NMe_2$ | H | Me | Me | CH |
| 4174 | $Q_1$ | $SO_2NMe_2$ | H | Me | OMe | CH |
| 4175 | $Q_1$ | $SO_2NMe_2$ | H | OMe | OMe | CH |
| 4176 | $Q_1$ | $SO_2NMe_2$ | H | Me | OMe | N |
| 4177 | $Q_1$ | $SO_2NMe_2$ | H | OMe | OMe | N |
| 4178 | $Q_1$ | Me | Me | Me | OMe | CH |
| 4179 | $Q_1$ | Me | Me | OMe | OMe | CH |
| 4180 | $Q_1$ | Me | Me | Me | OMe | N |
| 4181 | $Q_1$ | Cl | Me | Me | OMe | CH |
| 4182 | $Q_1$ | Cl | Me | OMe | OMe | CH |
| 4183 | $Q_1$ | Cl | Me | Me | OMe | N |
| 4184 | $Q_1$ | Br | Me | Me | OMe | CH |
| 4185 | $Q_1$ | Br | Me | OMe | OMe | CH |
| 4186 | $Q_1$ | Br | Me | Me | OMe | N |
| 4187 | $Q_1$ | COOMe | Me | Me | OMe | CH |
| 4188 | $Q_1$ | COOMe | Me | OMe | OMe | CH |
| 4189 | $Q_1$ | COOMe | Me | Me | OMe | N |
| 4190 | Me | $Q_1$ | H | Me | Me | CH |
| 4191 | Me | $Q_1$ | H | Me | OMe | CH |
| 4192 | Me | $Q_1$ | H | OMe | OMe | CH |
| 4193 | Me | $Q_1$ | H | Me | OMe | N |
| 4194 | Me | $Q_1$ | H | OMe | OMe | N |

TABLE 3-continued

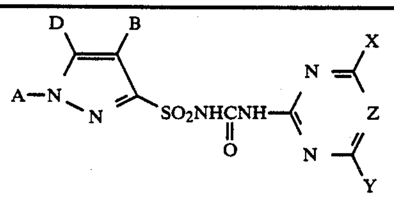

| No. | A | B | D | X | Y | Z |
|---|---|---|---|---|---|---|
| 4195 | Et | $Q_1$ | H | Me | OMe | CH |
| 4196 | Et | $Q_1$ | H | OMe | OMe | CH |
| 4197 | Et | $Q_1$ | H | Me | OMe | N |
| 4198 | $CH_2CH=CH_2$ | $Q_1$ | H | Me | OMe | CH |
| 4199 | $CH_2CH=CH_2$ | $Q_1$ | H | OMe | OMe | CH |
| 4200 | $CH_2CH=CH_2$ | $Q_1$ | H | Me | OMe | N |
| 4201 | $CH_2C\equiv CH$ | $Q_1$ | H | Me | OMe | CH |
| 4202 | $CH_2C\equiv CH$ | $Q_1$ | H | OMe | OMe | CH |
| 4203 | $CH_2C\equiv CH$ | $Q_1$ | H | Me | OMe | N |
| 4204 | $CH_2CN$ | $Q_1$ | H | Me | OMe | CH |
| 4205 | $CH_2CN$ | $Q_1$ | H | OMe | OMe | CH |
| 4206 | $CH_2CN$ | $Q_1$ | H | Me | OMe | N |
| 4207 | $CH_2COOMe$ | $Q_1$ | H | Me | OMe | CH |
| 4208 | $CH_2COOMe$ | $Q_1$ | H | OMe | OMe | CH |
| 4209 | $CH_2COOMe$ | $Q_1$ | H | Me | OMe | N |
| 4210 | COMe | $Q_1$ | H | Me | OMe | CH |
| 4211 | COMe | $Q_1$ | H | OMe | OMe | CH |
| 4212 | COMe | $Q_1$ | H | Me | OMe | N |
| 4213 | $SO_2NMe_2$ | $Q_1$ | H | Me | OMe | CH |
| 4214 | $SO_2NMe_2$ | $Q_1$ | H | OMe | OMe | CH |
| 4215 | $SO_2NMe_2$ | $Q_1$ | H | Me | OMe | N |
| 4216 | $SO_2Me$ | $Q_1$ | H | Me | OMe | CH |
| 4217 | $SO_2Me$ | $Q_1$ | H | OMe | OMe | CH |
| 4218 | $SO_2Me$ | $Q_1$ | H | Me | OMe | N |
| 4219 | Me | $Q_1$ | Me | Me | Me | CH |
| 4220 | Me | $Q_1$ | Me | Me | OMe | CH |
| 4221 | Me | $Q_1$ | Me | OMe | OMe | CH |
| 4222 | Me | $Q_1$ | Me | Me | OMe | N |
| 4223 | Me | $Q_1$ | Me | OMe | OMe | N |
| 4224 | Me | H | $Q_1$ | Me | Me | CH |
| 4225 | Me | H | $Q_1$ | Me | OMe | CH |
| 4226 | Me | H | $Q_1$ | OMe | OMe | CH |
| 4227 | Me | H | $Q_1$ | Me | OMe | N |
| 4228 | Me | H | $Q_1$ | OMe | OMe | N |
| 4229 | Me | Me | $Q_1$ | Me | OMe | CH |
| 4230 | Me | Me | $Q_1$ | OMe | OMe | CH |
| 4231 | Me | Me | $Q_1$ | Me | OMe | N |
| 4232 | Me | Cl | $Q_1$ | Me | OMe | CH |
| 4233 | Me | Cl | $Q_1$ | OMe | OMe | CH |
| 4234 | Me | Cl | $Q_1$ | Me | OMe | N |
| 4235 | Me | Br | $Q_1$ | Me | OMe | CH |
| 4236 | Me | Br | $Q_1$ | OMe | OMe | CH |
| 4237 | Me | Br | $Q_1$ | Me | OMe | N |
| 4238 | Me | $NO_2$ | $Q_1$ | Me | OMe | CH |
| 4239 | Me | $NO_2$ | $Q_1$ | OMe | OMe | CH |
| 4240 | Me | $NO_2$ | $Q_1$ | Me | OMe | N |
| 4241 | Et | H | $Q_1$ | Me | OMe | CH |
| 4242 | Et | H | $Q_1$ | OMe | OMe | CH |
| 4243 | Et | H | $Q_1$ | Me | OMe | N |
| 4244 | $Q_2$ | H | H | Me | OMe | CH |
| 4245 | $Q_2$ | H | H | OMe | OMe | CH |
| 4246 | $Q_2$ | H | H | Me | OMe | N |
| 4247 | $Q_2$ | Me | H | Me | OMe | CH |
| 4248 | $Q_2$ | Me | H | OMe | OMe | CH |
| 4249 | $Q_2$ | Me | H | Me | OMe | N |
| 4250 | $Q_2$ | Cl | H | Me | OMe | CH |
| 4251 | $Q_2$ | Cl | H | OMe | OMe | CH |
| 4252 | $Q_2$ | Cl | H | Me | OMe | N |
| 4253 | $Q_2$ | Br | H | Me | OMe | CH |
| 4254 | $Q_2$ | Br | H | OMe | OMe | CH |
| 4255 | $Q_2$ | Br | H | Me | OMe | N |
| 4256 | $Q_2$ | COOMe | H | Me | OMe | CH |
| 4257 | $Q_2$ | COOMe | H | OMe | OMe | CH |
| 4258 | $Q_2$ | COOMe | H | Me | OMe | N |
| 4259 | $Q_2$ | COOEt | H | Me | OMe | CH |
| 4260 | $Q_2$ | COOEt | H | OMe | OMe | CH |
| 4261 | $Q_2$ | COOEt | H | Me | OMe | N |
| 4262 | Me | $Q_2$ | H | Me | Me | CH |
| 4263 | Me | $Q_2$ | H | Me | OMe | CH |
| 4264 | Me | $Q_2$ | H | OMe | OMe | CH |
| 4265 | Me | $Q_2$ | H | Me | OMe | N |

TABLE 3-continued

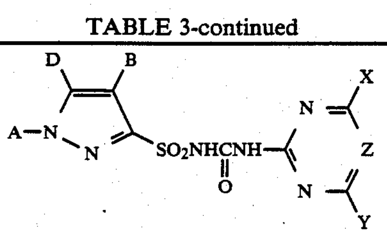

| No. | A | B | D | X | Y | Z |
|---|---|---|---|---|---|---|
| 4266 | Me | $Q_2$ | H | OMe | OMe | N |
| 4267 | COMe | $Q_2$ | H | Me | OMe | CH |
| 4268 | COMe | $Q_2$ | H | OMe | OMe | CH |
| 4269 | COMe | $Q_2$ | H | Me | OMe | N |
| 4270 | $Q_3$ | H | H | Me | OMe | CH |
| 4271 | $Q_3$ | H | H | OMe | OMe | CH |
| 4272 | $Q_3$ | H | H | Me | OMe | N |
| 4273 | $Q_3$ | Cl | H | Me | OMe | CH |
| 4274 | $Q_3$ | Cl | H | OMe | OMe | CH |
| 4275 | $Q_3$ | Cl | H | Me | OMe | N |
| 4276 | $Q_3$ | COOMe | H | Me | OMe | CH |
| 4277 | $Q_3$ | COOMe | H | OMe | OMe | CH |
| 4278 | $Q_3$ | COOMe | H | Me | OMe | N |
| 4279 | Me | $Q_3$ | H | Me | OMe | CH |
| 4280 | Me | $Q_3$ | H | OMe | OMe | CH |
| 4281 | Me | $Q_3$ | H | Me | OMe | N |
| 4282 | $Q_4$ | H | H | Me | OMe | CH |
| 4283 | $Q_4$ | H | H | OMe | OMe | CH |
| 4284 | $Q_4$ | H | H | Me | OMe | N |
| 4285 | $Q_4$ | Cl | H | Me | OMe | CH |
| 4286 | $Q_4$ | Cl | H | OMe | OMe | CH |
| 4287 | $Q_4$ | Cl | H | Me | OMe | N |
| 4288 | $Q_4$ | COOMe | H | Me | OMe | CH |
| 4289 | $Q_4$ | COOMe | H | OMe | OMe | CH |
| 4290 | $Q_4$ | COOMe | H | Me | OMe | N |
| 4291 | Me | $Q_4$ | H | Me | OMe | CH |
| 4292 | Me | $Q_4$ | H | OMe | OMe | CH |
| 4293 | Me | $Q_4$ | H | Me | OMe | N |
| 4294 | $Q_5$ | H | H | Me | OMe | CH |
| 4295 | $Q_5$ | H | H | OMe | OMe | CH |
| 4296 | $Q_5$ | H | H | Me | OMe | N |
| 4297 | $Q_5$ | Me | H | Me | OMe | CH |
| 4298 | $Q_5$ | Me | H | OMe | OMe | CH |
| 4299 | $Q_5$ | Me | H | Me | OMe | N |
| 4300 | $Q_5$ | Cl | H | Me | OMe | CH |
| 4301 | $Q_5$ | Cl | H | OMe | OMe | CH |
| 4302 | $Q_5$ | Cl | H | Me | OMe | N |
| 4303 | $Q_5$ | Br | H | Me | OMe | CH |
| 4304 | $Q_5$ | Br | H | OMe | OMe | CH |
| 4305 | $Q_5$ | Br | H | Me | OMe | N |
| 4306 | $Q_5$ | COOMe | H | Me | OMe | CH |
| 4307 | $Q_5$ | COOMe | H | OMe | OMe | CH |
| 4308 | $Q_5$ | COOMe | H | Me | OMe | N |
| 4309 | $Q_5$ | COOEt | H | Me | OMe | CH |
| 4310 | $Q_5$ | COOEt | H | OMe | OMe | CH |
| 4311 | $Q_5$ | COOEt | H | Me | OMe | N |
| 4312 | Me | $Q_5$ | H | Me | Me | CH |
| 4313 | Me | $Q_5$ | H | Me | OMe | CH |
| 4314 | Me | $Q_5$ | H | OMe | OMe | CH |
| 4315 | Me | $Q_5$ | H | Me | OMe | N |
| 4316 | Me | $Q_5$ | H | OMe | OMe | N |
| 4317 | COMe | $Q_5$ | H | Me | OMe | CH |
| 4318 | COMe | $Q_5$ | H | OMe | OMe | CH |
| 4319 | COMe | $Q_5$ | H | Me | OMe | N |
| 4320 | $Q_6$ | H | H | Me | OMe | CH |
| 4321 | $Q_6$ | H | H | OMe | OMe | CH |
| 4322 | $Q_6$ | H | H | Me | OMe | N |
| 4323 | $Q_6$ | Cl | H | Me | OMe | CH |
| 4324 | $Q_6$ | Cl | H | OMe | OMe | CH |
| 4325 | $Q_6$ | Cl | H | Me | OMe | N |
| 4326 | $Q_6$ | COOMe | H | Me | OMe | CH |
| 4327 | $Q_6$ | COOMe | H | OMe | OMe | CH |
| 4328 | $Q_6$ | COOMe | H | Me | OMe | N |
| 4329 | Me | $Q_6$ | H | Me | OMe | CH |
| 4330 | Me | $Q_6$ | H | OMe | OMe | CH |
| 4331 | Me | $Q_6$ | H | Me | OMe | N |
| 4332 | $Q_7$ | Cl | H | Me | OMe | CH |
| 4333 | $Q_7$ | Cl | H | OMe | OMe | CH |
| 4334 | $Q_7$ | Cl | H | Me | OMe | N |
| 4335 | $Q_7$ | COOMe | H | Me | OMe | CH |
| 4336 | $Q_7$ | COOMe | H | OMe | OMe | CH |

TABLE 3-continued

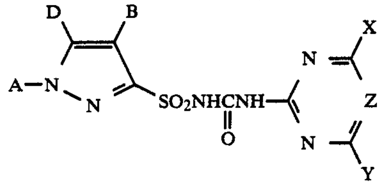

| No. | A | B | D | X | Y | Z |
|---|---|---|---|---|---|---|
| 4337 | $Q_7$ | COOMe | H | Me | OMe | N |
| 4338 | Me | $Q_7$ | H | Me | OMe | CH |
| 4339 | Me | $Q_7$ | H | OMe | OMe | CH |
| 4340 | Me | $Q_7$ | H | Me | OMe | N |
| 4341 | $Q_8$ | H | H | Me | OMe | CH |
| 4342 | $Q_8$ | H | H | OMe | OMe | CH |
| 4343 | $Q_8$ | H | H | Me | OMe | N |
| 4344 | $Q_8$ | Me | H | Me | OMe | CH |
| 4345 | $Q_8$ | Me | H | OMe | OMe | CH |
| 4346 | $Q_8$ | Me | H | Me | OMe | N |
| 4347 | $Q_8$ | Cl | H | Me | OMe | CH |
| 4348 | $Q_8$ | Cl | H | OMe | OMe | CH |
| 4349 | $Q_8$ | Cl | H | Me | OMe | N |
| 4350 | $Q_8$ | Br | H | Me | OMe | CH |
| 4351 | $Q_8$ | Br | H | OMe | OMe | CH |
| 4352 | $Q_8$ | Br | H | Me | OMe | N |
| 4353 | $Q_8$ | COOMe | H | Me | OMe | CH |
| 4354 | $Q_8$ | COOMe | H | OMe | OMe | CH |
| 4355 | $Q_8$ | COOMe | H | Me | OMe | N |
| 4356 | $Q_8$ | COOEt | H | Me | OMe | CH |
| 4357 | $Q_8$ | COOEt | H | OMe | OMe | CH |
| 4358 | $Q_8$ | COOEt | H | Me | OMe | N |
| 4359 | Me | $Q_8$ | H | Me | Me | CH |
| 4360 | Me | $Q_8$ | H | Me | OMe | CH |
| 4361 | Me | $Q_8$ | H | OMe | OMe | CH |
| 4362 | Me | $Q_8$ | H | Me | OMe | N |
| 4363 | Me | $Q_8$ | H | OMe | OMe | N |
| 4364 | COMe | $Q_8$ | H | Me | OMe | CH |
| 4365 | COMe | $Q_8$ | H | OMe | OMe | CH |
| 4366 | COMe | $Q_8$ | H | Me | OMe | N |
| 4367 | $Q_9$ | H | H | Me | OMe | CH |
| 4368 | $Q_9$ | H | H | OMe | OMe | CH |
| 4369 | $Q_9$ | H | H | Me | OMe | N |
| 4370 | $Q_9$ | Cl | H | Me | OMe | CH |
| 4371 | $Q_9$ | Cl | H | OMe | OMe | CH |
| 4372 | $Q_9$ | Cl | H | Me | OMe | N |
| 4373 | $Q_9$ | COOMe | H | Me | OMe | CH |
| 4374 | $Q_9$ | COOMe | H | OMe | OMe | CH |
| 4375 | $Q_9$ | COOMe | H | Me | OMe | N |
| 4376 | Me | $Q_9$ | H | Me | OMe | CH |
| 4377 | Me | $Q_9$ | H | OMe | OMe | CH |
| 4378 | Me | $Q_9$ | H | Me | OMe | N |
| 4379 | $Q_{10}$ | H | H | Me | OMe | CH |
| 4380 | $Q_{10}$ | H | H | OMe | OMe | CH |
| 4381 | $Q_{10}$ | H | H | Me | OMe | N |
| 4382 | $Q_{10}$ | Cl | H | Me | OMe | CH |
| 4383 | $Q_{10}$ | Cl | H | OMe | OMe | CH |
| 4384 | $Q_{10}$ | Cl | H | Me | OMe | N |
| 4385 | $Q_{10}$ | COOMe | H | Me | OMe | CH |
| 4386 | $Q_{10}$ | COOMe | H | OMe | OMe | CH |
| 4387 | $Q_{10}$ | COOMe | H | Me | OMe | N |
| 4388 | Me | $Q_{10}$ | H | Me | OMe | CH |
| 4389 | Me | $Q_{10}$ | H | OMe | OMe | CH |
| 4390 | Me | $Q_{10}$ | H | Me | OMe | N |
| 4391 | $Q_{11}$ | H | H | Me | OMe | CH |
| 4392 | $Q_{11}$ | H | H | OMe | OMe | CH |
| 4393 | $Q_{11}$ | H | H | Me | OMe | N |
| 4394 | $Q_{11}$ | Cl | H | Me | OMe | CH |
| 4395 | $Q_{11}$ | Cl | H | OMe | OMe | CH |
| 4396 | $Q_{11}$ | Cl | H | Me | OMe | N |
| 4397 | $Q_{11}$ | COOMe | H | Me | OMe | CH |
| 4398 | $Q_{11}$ | COOMe | H | OMe | OMe | CH |
| 4399 | $Q_{11}$ | COOMe | H | Me | OMe | N |
| 4400 | Me | $Q_{11}$ | H | Me | OMe | CH |
| 4401 | Me | $Q_{11}$ | H | OMe | OMe | CH |
| 4402 | Me | $Q_{11}$ | H | Me | OMe | N |
| 4403 | $Q_{12}$ | H | H | Me | OMe | CH |
| 4404 | $Q_{12}$ | H | H | OMe | OMe | CH |
| 4405 | $Q_{12}$ | H | H | Me | OMe | N |
| 4406 | $Q_{12}$ | Cl | H | Me | OMe | CH |
| 4407 | $Q_{12}$ | Cl | H | OMe | OMe | CH |

TABLE 3-continued

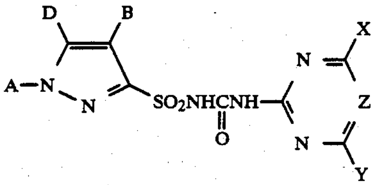

| No. | A | B | D | X | Y | Z |
|---|---|---|---|---|---|---|
| 4408 | $Q_{12}$ | Cl | H | Me | OMe | N |
| 4409 | $Q_{12}$ | COOMe | H | Me | OMe | CH |
| 4410 | $Q_{12}$ | COOMe | H | OMe | OMe | CH |
| 4411 | $Q_{12}$ | COOMe | H | Me | OMe | N |
| 4412 | Me | $Q_{12}$ | H | Me | OMe | CH |
| 4413 | Me | $Q_{12}$ | H | OMe | OMe | CH |
| 4414 | Me | $Q_{12}$ | H | Me | OMe | N |
| 4415 | $Q_{13}$ | Cl | H | Me | OMe | CH |
| 4416 | $Q_{13}$ | Cl | H | OMe | OMe | CH |
| 4417 | $Q_{13}$ | Cl | H | Me | OMe | N |
| 4418 | $Q_{13}$ | COOMe | H | Me | OMe | CH |
| 4419 | $Q_{13}$ | COOMe | H | OMe | OMe | CH |
| 4420 | $Q_{13}$ | COOMe | H | Me | OMe | N |
| 4421 | Me | $Q_{13}$ | H | Me | OMe | CH |
| 4422 | Me | $Q_{13}$ | H | OMe | OMe | CH |
| 4423 | Me | $Q_{13}$ | H | Me | OMe | N |
| 4424 | $Q_{14}$ | H | H | Me | OMe | CH |
| 4425 | $Q_{14}$ | H | H | OMe | OMe | CH |
| 4426 | $Q_{14}$ | H | H | Me | OMe | N |
| 4427 | $Q_{14}$ | Cl | H | Me | OMe | CH |
| 4428 | $Q_{14}$ | Cl | H | OMe | OMe | CH |
| 4429 | $Q_{14}$ | Cl | H | Me | OMe | N |
| 4430 | $Q_{14}$ | COOMe | H | Me | OMe | CH |
| 4431 | $Q_{14}$ | COOMe | H | OMe | OMe | CH |
| 4432 | $Q_{14}$ | COOMe | H | Me | OMe | N |
| 4433 | Me | $Q_{14}$ | H | Me | OMe | CH |
| 4434 | Me | $Q_{14}$ | H | OMe | OMe | CH |
| 4435 | Me | $Q_{14}$ | H | Me | OMe | N |
| 4436 | $Q_{15}$ | H | H | Me | OMe | CH |
| 4437 | $Q_{15}$ | H | H | OMe | OMe | CH |
| 4438 | $Q_{15}$ | H | H | Me | OMe | N |
| 4439 | $Q_{15}$ | Cl | H | Me | OMe | CH |
| 4440 | $Q_{15}$ | Cl | H | OMe | OMe | CH |
| 4441 | $Q_{15}$ | Cl | H | Me | OMe | N |
| 4442 | $Q_{15}$ | COOMe | H | Me | OMe | CH |
| 4443 | $Q_{15}$ | COOMe | H | OMe | OMe | CH |
| 4444 | $Q_{15}$ | COOMe | H | Me | OMe | N |
| 4445 | Me | $Q_{15}$ | H | Me | OMe | CH |
| 4446 | Me | $Q_{15}$ | H | OMe | OMe | CH |
| 4447 | Me | $Q_{15}$ | H | Me | OMe | N |
| 4448 | $Q_{16}$ | H | H | Me | OMe | CH |
| 4449 | $Q_{16}$ | H | H | OMe | OMe | CH |
| 4450 | $Q_{16}$ | H | H | Me | OMe | N |
| 4451 | $Q_{16}$ | Cl | H | Me | OMe | CH |
| 4452 | $Q_{16}$ | Cl | H | OMe | OMe | CH |
| 4453 | $Q_{16}$ | Cl | H | Me | OMe | N |
| 4454 | $Q_{16}$ | COOMe | H | Me | OMe | CH |
| 4455 | $Q_{16}$ | COOMe | H | OMe | OMe | CH |
| 4456 | $Q_{16}$ | COOMe | H | Me | OMe | N |
| 4457 | Me | $Q_{16}$ | H | Me | OMe | CH |
| 4458 | Me | $Q_{16}$ | H | OMe | OMe | CH |
| 4459 | Me | $Q_{16}$ | H | Me | OMe | N |
| 4460 | $Q_{17}$ | Cl | H | Me | OMe | CH |
| 4461 | $Q_{17}$ | Cl | H | OMe | OMe | CH |
| 4462 | $Q_{17}$ | Cl | H | Me | OMe | N |
| 4463 | $Q_{17}$ | COOMe | H | Me | OMe | CH |
| 4464 | $Q_{17}$ | COOMe | H | OMe | OMe | CH |
| 4465 | $Q_{17}$ | COOMe | H | Me | OMe | N |
| 4466 | Me | $Q_{17}$ | H | Me | OMe | CH |
| 4467 | Me | $Q_{17}$ | H | OMe | OMe | CH |
| 4468 | Me | $Q_{17}$ | H | Me | OMe | N |
| 4469 | $Q_{18}$ | H | H | Me | OMe | CH |
| 4470 | $Q_{18}$ | H | H | OMe | OMe | CH |
| 4471 | $Q_{18}$ | H | H | Me | OMe | N |
| 4472 | $Q_{18}$ | Cl | H | Me | OMe | CH |
| 4473 | $Q_{18}$ | Cl | H | OMe | OMe | CH |
| 4474 | $Q_{18}$ | Cl | H | Me | OMe | N |
| 4475 | $Q_{18}$ | COOMe | H | Me | OMe | CH |
| 4476 | $Q_{18}$ | COOMe | H | OMe | OMe | CH |
| 4477 | $Q_{18}$ | COOMe | H | Me | OMe | N |
| 4478 | Me | $Q_{18}$ | H | Me | OMe | CH |

TABLE 3-continued

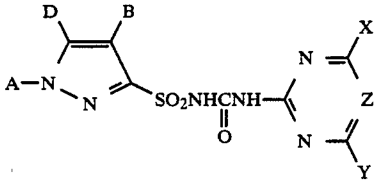

| No. | A | B | D | X | Y | Z |
|---|---|---|---|---|---|---|
| 4479 | Me | $Q_{18}$ | H | OMe | OMe | CH |
| 4480 | Me | $Q_{18}$ | H | Me | OMe | N |
| 4481 | $Q_{19}$ | H | H | Me | OMe | CH |
| 4482 | $Q_{19}$ | H | H | OMe | OMe | CH |
| 4483 | $Q_{19}$ | H | H | Me | OMe | N |
| 4484 | $Q_{19}$ | Cl | H | Me | OMe | CH |
| 4485 | $Q_{19}$ | Cl | H | OMe | OMe | CH |
| 4486 | $Q_{19}$ | Cl | H | Me | OMe | N |
| 4487 | $Q_{19}$ | COOMe | H | Me | OMe | CH |
| 4488 | $Q_{19}$ | COOMe | H | OMe | OMe | CH |
| 4489 | $Q_{19}$ | COOMe | H | Me | OMe | N |
| 4490 | Me | $Q_{19}$ | H | Me | OMe | CH |
| 4491 | Me | $Q_{19}$ | H | OMe | OMe | CH |
| 4492 | Me | $Q_{19}$ | H | Me | OMe | N |
| 4493 | $Q_{20}$ | H | H | Me | OMe | CH |
| 4494 | $Q_{20}$ | H | H | OMe | OMe | CH |
| 4495 | $Q_{20}$ | H | H | Me | OMe | N |
| 4496 | $Q_{20}$ | Cl | H | Me | OMe | CH |
| 4497 | $Q_{20}$ | Cl | H | OMe | OMe | CH |
| 4498 | $Q_{20}$ | Cl | H | Me | OMe | N |
| 4499 | $Q_{20}$ | COOMe | H | Me | OMe | CH |
| 4500 | $Q_{20}$ | COOMe | H | OMe | OMe | CH |
| 4501 | $Q_{20}$ | COOMe | H | Me | OMe | N |
| 4502 | Me | $Q_{20}$ | H | Me | OMe | CH |
| 4503 | Me | $Q_{20}$ | H | OMe | OMe | CH |
| 4504 | Me | $Q_{20}$ | H | Me | OMe | N |
| 4505 | $Q_{21}$ | H | H | Me | OMe | CH |
| 4506 | $Q_{21}$ | H | H | OMe | OMe | CH |
| 4507 | $Q_{21}$ | H | H | Me | OMe | N |
| 4508 | $Q_{21}$ | Cl | H | Me | OMe | CH |
| 4509 | $Q_{21}$ | Cl | H | OMe | OMe | CH |
| 4510 | $Q_{21}$ | Cl | H | Me | OMe | N |
| 4511 | $Q_{21}$ | COOMe | H | Me | OMe | CH |
| 4512 | $Q_{21}$ | COOMe | H | OMe | OMe | CH |
| 4513 | $Q_{21}$ | COOMe | H | Me | OMe | N |
| 4514 | Me | $Q_{21}$ | H | Me | OMe | CH |
| 4515 | Me | $Q_{21}$ | H | OMe | OMe | CH |
| 4516 | Me | $Q_{21}$ | H | Me | OMe | N |
| 4517 | $Q_{22}$ | H | H | Me | OMe | CH |
| 4518 | $Q_{22}$ | H | H | OMe | OMe | CH |
| 4519 | $Q_{22}$ | H | H | Me | OMe | N |
| 4520 | $Q_{22}$ | Cl | H | Me | OMe | CH |
| 4521 | $Q_{22}$ | Cl | H | OMe | OMe | CH |
| 4522 | $Q_{22}$ | Cl | H | Me | OMe | N |
| 4523 | $Q_{22}$ | COOMe | H | Me | OMe | CH |
| 4524 | $Q_{22}$ | COOMe | H | OMe | OMe | CH |
| 4525 | $Q_{22}$ | COOMe | H | Me | OMe | N |
| 4526 | Me | $Q_{22}$ | H | Me | OMe | CH |
| 4527 | Me | $Q_{22}$ | H | OMe | OMe | CH |
| 4528 | Me | $Q_{22}$ | H | Me | OMe | N |
| 4529 | $Q_{23}$ | Cl | H | Me | OMe | CH |
| 4530 | $Q_{23}$ | Cl | H | OMe | OMe | CH |
| 4531 | $Q_{23}$ | Cl | H | Me | OMe | N |
| 4532 | $Q_{23}$ | COOMe | H | Me | OMe | CH |
| 4533 | $Q_{23}$ | COOMe | H | OMe | OMe | CH |
| 4534 | $Q_{23}$ | COOMe | H | Me | OMe | N |
| 4535 | Me | $Q_{23}$ | H | Me | OMe | CH |
| 4536 | Me | $Q_{23}$ | H | OMe | OMe | CH |
| 4537 | Me | $Q_{23}$ | H | Me | OMe | N |
| 4532 | $Q_{24}$ | H | H | Me | OMe | CH |
| 4533 | $Q_{24}$ | H | H | OMe | OMe | CH |
| 4534 | $Q_{24}$ | H | H | Me | OMe | N |
| 4535 | $Q_{24}$ | Cl | H | Me | OMe | CH |
| 4536 | $Q_{24}$ | Cl | H | OMe | OMe | CH |
| 4537 | $Q_{24}$ | Cl | H | Me | OMe | N |
| 4538 | $Q_{24}$ | COOMe | H | Me | OMe | CH |
| 4539 | $Q_{24}$ | COOMe | H | OMe | OMe | CH |
| 4540 | $Q_{24}$ | COOMe | H | Me | OMe | N |
| 4541 | Me | $Q_{24}$ | H | Me | OMe | CH |
| 4542 | Me | $Q_{24}$ | H | OMe | OMe | CH |
| 4543 | Me | $Q_{24}$ | H | Me | OMe | N |

TABLE 3-continued

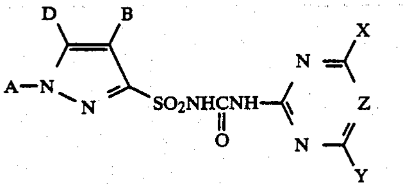

| No. | A | B | D | X | Y | Z |
|---|---|---|---|---|---|---|
| 4544 | $Q_{25}$ | H | H | Me | OMe | CH |
| 4545 | $Q_{25}$ | H | H | OMe | OMe | CH |
| 4546 | $Q_{25}$ | H | H | Me | OMe | N |
| 4547 | $Q_{25}$ | Cl | H | Me | OMe | CH |
| 4548 | $Q_{25}$ | Cl | H | OMe | OMe | CH |
| 4549 | $Q_{25}$ | Cl | H | Me | OMe | N |
| 4550 | $Q_{25}$ | COOMe | H | Me | OMe | CH |
| 4551 | $Q_{25}$ | COOMe | H | OMe | OMe | CH |
| 4552 | $Q_{25}$ | COOMe | H | Me | OMe | N |
| 4553 | Me | $Q_{25}$ | H | Me | OMe | CH |
| 4554 | Me | $Q_{25}$ | H | OMe | OMe | CH |
| 4555 | Me | $Q_{25}$ | H | Me | OMe | N |
| 4556 | $Q_{26}$ | Cl | H | Me | OMe | CH |
| 4557 | $Q_{26}$ | Cl | H | OMe | OMe | CH |
| 4558 | $Q_{26}$ | Cl | H | Me | OMe | N |
| 4559 | $Q_{26}$ | COOMe | H | Me | OMe | CH |
| 4560 | $Q_{26}$ | COOMe | H | OMe | OMe | CH |
| 4561 | $Q_{26}$ | COOMe | H | Me | OMe | N |
| 4562 | Me | $Q_{26}$ | H | Me | OMe | CH |
| 4563 | Me | $Q_{26}$ | H | OMe | OMe | CH |
| 4564 | Me | $Q_{26}$ | H | Me | OMe | N |
| 4565 | $Q_{27}$ | Cl | H | Me | OMe | CH |
| 4566 | $Q_{27}$ | Cl | H | OMe | OMe | CH |
| 4567 | $Q_{27}$ | Cl | H | Me | OMe | N |
| 4568 | $Q_{27}$ | COOMe | H | Me | OMe | CH |
| 4569 | $Q_{27}$ | COOMe | H | OMe | OMe | CH |
| 4570 | $Q_{27}$ | COOMe | H | Me | OMe | N |
| 4571 | Me | $Q_{27}$ | H | Me | OMe | CH |
| 4572 | Me | $Q_{27}$ | H | OMe | OMe | CH |
| 4573 | Me | $Q_{27}$ | H | Me | OMe | N |
| 4574 | $Q_{28}$ | H | H | Me | OMe | CH |
| 4575 | $Q_{28}$ | H | H | OMe | OMe | CH |
| 4576 | $Q_{28}$ | H | H | Me | OMe | N |
| 4577 | $Q_{28}$ | Cl | H | Me | OMe | CH |
| 4578 | $Q_{28}$ | Cl | H | OMe | OMe | CH |
| 4579 | $Q_{28}$ | Cl | H | Me | OMe | N |
| 4580 | $Q_{28}$ | COOMe | H | Me | OMe | CH |
| 4581 | $Q_{28}$ | COOMe | H | OMe | OMe | CH |
| 4582 | $Q_{28}$ | COOMe | H | Me | OMe | N |
| 4583 | Me | $Q_{28}$ | H | Me | OMe | CH |
| 4584 | Me | $Q_{28}$ | H | OMe | OMe | CH |
| 4585 | Me | $Q_{28}$ | H | Me | OMe | N |
| 4586 | $Q_{29}$ | Cl | H | Me | OMe | CH |
| 4587 | $Q_{29}$ | Cl | H | OMe | OMe | CH |
| 4588 | $Q_{29}$ | Cl | H | Me | OMe | N |
| 4589 | $Q_{29}$ | COOMe | H | Me | OMe | CH |
| 4590 | $Q_{29}$ | COOMe | H | OMe | OMe | CH |
| 4591 | $Q_{29}$ | COOMe | H | Me | OMe | N |
| 4592 | Me | $Q_{29}$ | H | Me | OMe | CH |
| 4593 | Me | $Q_{29}$ | H | OMe | OMe | CH |
| 4594 | Me | $Q_{29}$ | H | Me | OMe | N |
| 4595 | $Q_{30}$ | Cl | H | Me | OMe | CH |
| 4596 | $Q_{30}$ | Cl | H | OMe | OMe | CH |
| 4597 | $Q_{30}$ | Cl | H | Me | OMe | N |
| 4598 | $Q_{30}$ | COOMe | H | Me | OMe | CH |
| 4599 | $Q_{30}$ | COOMe | H | OMe | OMe | CH |
| 4600 | $Q_{30}$ | COOMe | H | Me | OMe | N |
| 4601 | Me | $Q_{30}$ | H | Me | OMe | CH |
| 4602 | Me | $Q_{30}$ | H | OMe | OMe | CH |
| 4603 | Me | $Q_{30}$ | H | Me | OMe | N |
| 4604 | $Q_{31}$ | Cl | H | Me | OMe | CH |
| 4605 | $Q_{31}$ | Cl | H | OMe | OMe | CH |
| 4606 | $Q_{31}$ | Cl | H | Me | OMe | N |
| 4607 | $Q_{31}$ | COOMe | H | Me | OMe | CH |
| 4608 | $Q_{31}$ | COOMe | H | OMe | OMe | CH |
| 4609 | $Q_{31}$ | COOMe | H | Me | OMe | N |
| 4610 | Me | $Q_{31}$ | H | Me | OMe | CH |
| 4611 | Me | $Q_{31}$ | H | OMe | OMe | CH |
| 4612 | Me | $Q_{31}$ | H | Me | OMe | N |
| 4613 | $Q_{32}$ | H | H | Me | OMe | CH |
| 4614 | $Q_{32}$ | H | H | OMe | OMe | CH |

TABLE 3-continued

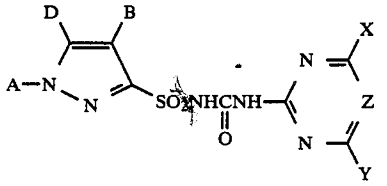

| No. | A | B | D | X | Y | Z |
|---|---|---|---|---|---|---|
| 4615 | $Q_{32}$ | H | H | Me | OMe | N |
| 4616 | $Q_{32}$ | Me | H | Me | OMe | CH |
| 4617 | $Q_{32}$ | Me | H | OMe | OMe | CH |
| 4618 | $Q_{32}$ | Me | H | Me | OMe | N |
| 4619 | $Q_{32}$ | Cl | H | Me | OMe | CH |
| 4620 | $Q_{32}$ | Cl | H | OMe | OMe | CH |
| 4621 | $Q_{32}$ | Cl | H | Me | OMe | N |
| 4622 | $Q_{32}$ | Br | H | Me | OMe | CH |
| 4623 | $Q_{32}$ | Br | H | OMe | OMe | CH |
| 4624 | $Q_{32}$ | Br | H | Me | OMe | N |
| 4625 | $Q_{32}$ | COOMe | H | Me | OMe | CH |
| 4626 | $Q_{32}$ | COOMe | H | OMe | OMe | CH |
| 4627 | $Q_{32}$ | COOMe | H | Me | OMe | N |
| 4628 | $Q_{32}$ | COOEt | H | Me | OMe | CH |
| 4629 | $Q_{32}$ | COOEt | H | OMe | OMe | CH |
| 4630 | $Q_{32}$ | COOEt | H | Me | OMe | N |
| 4631 | Me | $Q_{32}$ | H | Me | Me | CH |
| 4632 | Me | $Q_{32}$ | H | Me | OMe | CH |
| 4633 | Me | $Q_{32}$ | H | OMe | OMe | CH |
| 4634 | Me | $Q_{32}$ | H | Me | OMe | N |
| 4635 | Me | $Q_{32}$ | H | OMe | OMe | N |
| 4636 | COMe | $Q_{32}$ | H | Me | OMe | CH |
| 4637 | COMe | $Q_{32}$ | H | OMe | OMe | CH |
| 4638 | COMe | $Q_{32}$ | H | Me | OMe | N |
| 4639 | $Q_{33}$ | H | H | Me | OMe | CH |
| 4640 | $Q_{33}$ | H | H | OMe | OMe | CH |
| 4641 | $Q_{33}$ | H | H | Me | OMe | N |
| 4642 | $Q_{33}$ | Cl | H | Me | OMe | CH |
| 4643 | $Q_{33}$ | Cl | H | OMe | OMe | CH |
| 4644 | $Q_{33}$ | Cl | H | Me | OMe | N |
| 4645 | $Q_{33}$ | COOMe | H | Me | OMe | CH |
| 4646 | $Q_{33}$ | COOMe | H | OMe | OMe | CH |
| 4647 | $Q_{33}$ | COOMe | H | Me | OMe | N |
| 4648 | Me | $Q_{33}$ | H | Me | OMe | CH |
| 4649 | Me | $Q_{33}$ | H | OMe | OMe | CH |
| 4650 | Me | $Q_{33}$ | H | Me | OMe | N |
| 4651 | $Q_{34}$ | H | H | Me | OMe | CH |
| 4652 | $Q_{34}$ | H | H | OMe | OMe | CH |
| 4653 | $Q_{34}$ | H | H | Me | OMe | N |
| 4654 | $Q_{34}$ | Cl | H | Me | OMe | CH |
| 4655 | $Q_{34}$ | Cl | H | OMe | OMe | CH |
| 4656 | $Q_{34}$ | Cl | H | Me | OMe | N |
| 4657 | $Q_{34}$ | COOMe | H | Me | OMe | CH |
| 4658 | $Q_{34}$ | COOMe | H | OMe | OMe | CH |
| 4659 | $Q_{34}$ | COOMe | H | Me | OMe | N |
| 4660 | Me | $Q_{34}$ | H | Me | OMe | CH |
| 4661 | Me | $Q_{34}$ | H | OMe | OMe | CH |
| 4662 | Me | $Q_{34}$ | H | Me | OMe | N |
| 4663 | $Q_{35}$ | H | H | Me | OMe | CH |
| 4664 | $Q_{35}$ | H | H | OMe | OMe | CH |
| 4665 | $Q_{35}$ | H | H | Me | OMe | N |
| 4666 | $Q_{35}$ | Cl | H | Me | OMe | CH |
| 4667 | $Q_{35}$ | Cl | H | OMe | OMe | CH |
| 4668 | $Q_{35}$ | Cl | H | Me | OMe | N |
| 4669 | $Q_{35}$ | COOMe | H | Me | OMe | CH |
| 4670 | $Q_{35}$ | COOMe | H | OMe | OMe | CH |
| 4671 | $Q_{35}$ | COOMe | H | Me | OMe | N |
| 4672 | Me | $Q_{35}$ | H | Me | OMe | CH |
| 4673 | Me | $Q_{35}$ | H | OMe | OMe | CH |
| 4674 | Me | $Q_{35}$ | H | Me | OMe | N |
| 4675 | $Q_{36}$ | Cl | H | Me | OMe | CH |
| 4676 | $Q_{36}$ | Cl | H | OMe | OMe | CH |
| 4677 | $Q_{36}$ | Cl | H | Me | OMe | N |
| 4678 | $Q_{36}$ | COOMe | H | Me | OMe | CH |
| 4679 | $Q_{36}$ | COOMe | H | OMe | OMe | CH |
| 4680 | $Q_{36}$ | COOMe | H | Me | OMe | N |
| 4681 | Me | $Q_{36}$ | H | Me | OMe | CH |
| 4682 | Me | $Q_{36}$ | H | OMe | OMe | CH |
| 4683 | Me | $Q_{36}$ | H | Me | OMe | N |
| 4684 | $Q_{37}$ | H | H | Me | OMe | CH |
| 4685 | $Q_{37}$ | H | H | OMe | OMe | CH |

TABLE 3-continued

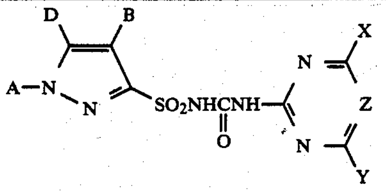

| No. | A | B | D | X | Y | Z |
|---|---|---|---|---|---|---|
| 4686 | $Q_{37}$ | H | H | Me | OMe | N |
| 4687 | $Q_{37}$ | Cl | H | Me | OMe | CH |
| 4688 | $Q_{37}$ | Cl | H | OMe | OMe | CH |
| 4689 | $Q_{37}$ | Cl | H | Me | OMe | N |
| 4690 | $Q_{37}$ | COOMe | H | Me | OMe | CH |
| 4691 | $Q_{37}$ | COOMe | H | OMe | OMe | CH |
| 4692 | $Q_{37}$ | COOMe | H | Me | OMe | N |
| 4693 | Me | $Q_{37}$ | H | Me | OMe | CH |
| 4694 | Me | $Q_{37}$ | H | OMe | OMe | CH |
| 4695 | Me | $Q_{37}$ | H | Me | OMe | N |
| 4696 | $Q_{38}$ | H | H | Me | OMe | CH |
| 4697 | $Q_{38}$ | H | H | OMe | OMe | CH |
| 4698 | $Q_{38}$ | H | H | Me | OMe | N |
| 4699 | $Q_{38}$ | Cl | H | Me | OMe | CH |
| 4700 | $Q_{38}$ | Cl | H | OMe | OMe | CH |
| 4701 | $Q_{38}$ | Cl | H | Me | OMe | N |
| 4702 | $Q_{38}$ | COOMe | H | Me | OMe | CH |
| 4703 | $Q_{38}$ | COOMe | H | OMe | OMe | CH |
| 4704 | $Q_{38}$ | COOMe | H | Me | OMe | N |
| 4705 | Me | $Q_{38}$ | H | Me | OMe | CH |
| 4706 | Me | $Q_{38}$ | H | OMe | OMe | CH |
| 4707 | Me | $Q_{38}$ | H | Me | OMe | N |
| 4708 | $Q_{39}$ | H | H | Me | OMe | CH |
| 4709 | $Q_{39}$ | H | OMe | OMe | CH | |
| 4710 | $Q_{39}$ | H | H | Me | OMe | N |
| 4711 | $Q_{39}$ | Cl | H | Me | OMe | CH |
| 4712 | $Q_{39}$ | Cl | H | OMe | OMe | CH |
| 4713 | $Q_{39}$ | Cl | H | Me | OMe | N |
| 4714 | $Q_{39}$ | COOMe | H | Me | OMe | CH |
| 4715 | $Q_{39}$ | COOMe | H | OMe | OMe | CH |
| 4716 | $Q_{39}$ | COOMe | H | Me | OMe | N |
| 4717 | Me | $Q_{39}$ | H | Me | OMe | CH |
| 4718 | Me | $Q_{39}$ | H | OMe | OMe | CH |
| 4719 | Me | $Q_{39}$ | H | Me | OMe | N |
| 4720 | $Q_{40}$ | Cl | H | Me | OMe | CH |
| 4721 | $Q_{40}$ | Cl | H | OMe | OMe | CH |
| 4722 | $Q_{40}$ | Cl | H | Me | OMe | N |
| 4723 | $Q_{40}$ | COOMe | H | Me | OMe | CH |
| 4724 | $Q_{40}$ | COOMe | H | OMe | OMe | CH |
| 4725 | $Q_{40}$ | COOMe | H | Me | OMe | N |
| 4726 | Me | $Q_{40}$ | H | Me | OMe | CH |
| 4727 | Me | $Q_{40}$ | H | OMe | OMe | CH |
| 4728 | Me | $Q_{40}$ | H | Me | OMe | N |
| 4729 | $Q_{41}$ | H | H | Me | OMe | CH |
| 4730 | $Q_{41}$ | H | H | OMe | OMe | CH |
| 4731 | $Q_{41}$ | H | H | Me | OMe | N |
| 4732 | $Q_{41}$ | Cl | H | Me | OMe | CH |
| 4733 | $Q_{41}$ | Cl | H | OMe | OMe | CH |
| 4734 | $Q_{41}$ | Cl | H | Me | OMe | N |
| 4735 | $Q_{41}$ | COOMe | H | Me | OMe | CH |
| 4736 | $Q_{41}$ | COOMe | H | OMe | OMe | CH |
| 4737 | $Q_{41}$ | COOMe | H | Me | OMe | N |
| 4738 | Me | $Q_{41}$ | H | Me | OMe | CH |
| 4739 | Me | $Q_{41}$ | H | OMe | OMe | CH |
| 4740 | Me | $Q_{41}$ | H | Me | OMe | N |
| 4741 | $Q_{42}$ | H | H | Me | OMe | CH |
| 4742 | $Q_{42}$ | H | H | OMe | OMe | CH |
| 4743 | $Q_{42}$ | H | H | Me | OMe | N |
| 4744 | $Q_{42}$ | Cl | H | OMe | OMe | CH |
| 4745 | $Q_{42}$ | Cl | H | OMe | OMe | CH |
| 4746 | $Q_{42}$ | Cl | H | Me | OMe | N |
| 4747 | $Q_{42}$ | COOMe | H | Me | OMe | CH |
| 4748 | $Q_{42}$ | COOMe | H | OMe | OMe | CH |
| 4749 | $Q_{42}$ | COOMe | H | Me | OMe | N |
| 4750 | Me | $Q_{42}$ | H | Me | OMe | CH |
| 4751 | Me | $Q_{42}$ | H | OMe | OMe | CH |
| 4752 | Me | $Q_{42}$ | H | Me | OMe | N |
| 4753 | $Q_{43}$ | H | H | Me | OMe | CH |
| 4754 | $Q_{43}$ | H | H | OMe | OMe | CH |
| 4755 | $Q_{43}$ | H | H | Me | OMe | N |
| 4756 | $Q_{43}$ | Cl | H | Me | OMe | CH |

TABLE 3-continued

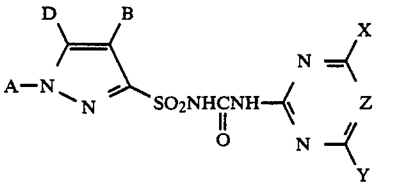

| No. | A | B | D | X | Y | Z |
|---|---|---|---|---|---|---|
| 4757 | $Q_{43}$ | Cl | H | OMe | OMe | CH |
| 4758 | $Q_{43}$ | Cl | H | Me | OMe | N |
| 4759 | $Q_{43}$ | COOMe | H | Me | OMe | CH |
| 4760 | $Q_{43}$ | COOMe | H | OMe | OMe | CH |
| 4761 | $Q_{43}$ | COOMe | H | Me | OMe | N |
| 4762 | Me | $Q_{43}$ | H | Me | OMe | CH |
| 4763 | Me | $Q_{43}$ | H | OMe | OMe | CH |
| 4764 | Me | $Q_{43}$ | H | Me | OMe | N |
| 4765 | $Q_{44}$ | Cl | H | Me | OMe | CH |
| 4766 | $Q_{44}$ | Cl | H | OMe | OMe | CH |
| 4767 | $Q_{44}$ | Cl | H | Me | OMe | N |
| 4768 | $Q_{44}$ | COOMe | H | Me | OMe | CH |
| 4769 | $Q_{44}$ | COOMe | H | OMe | OMe | CH |
| 4770 | $Q_{44}$ | COOMe | H | Me | OMe | N |
| 4771 | Me | $Q_{44}$ | H | Me | OMe | CH |
| 4772 | Me | $Q_{44}$ | H | OMe | OMe | CH |
| 4773 | Me | $Q_{44}$ | H | Me | OMe | N |
| 4774 | $Q_{45}$ | H | H | Me | OMe | CH |
| 4775 | $Q_{45}$ | H | H | OMe | OMe | CH |
| 4776 | $Q_{45}$ | H | H | Me | OMe | N |
| 4777 | $Q_{45}$ | Me | H | Me | OMe | CH |
| 4778 | $Q_{45}$ | Me | H | OMe | OMe | CH |
| 4779 | $Q_{45}$ | Me | H | Me | OMe | N |
| 4780 | $Q_{45}$ | Cl | H | Me | OMe | CH |
| 4781 | $Q_{45}$ | Cl | H | OMe | OMe | CH |
| 4782 | $Q_{45}$ | Cl | H | Me | OMe | N |
| 4783 | $Q_{45}$ | Br | H | Me | OMe | CH |
| 4784 | $Q_{45}$ | Br | H | OMe | OMe | CH |
| 4785 | $Q_{45}$ | Br | H | Me | OMe | N |
| 4786 | $Q_{45}$ | COOMe | H | Me | OMe | CH |
| 4787 | $Q_{45}$ | COOMe | H | OMe | OMe | CH |
| 4788 | $Q_{45}$ | COOMe | H | Me | OMe | N |
| 4789 | $Q_{45}$ | COOEt | H | Me | OMe | CH |
| 4790 | $Q_{45}$ | COOEt | H | OMe | OMe | CH |
| 4791 | $Q_{45}$ | COOEt | H | Me | OMe | N |
| 4792 | Me | $Q_{45}$ | H | Me | Me | CH |
| 4793 | Me | $Q_{45}$ | H | Me | OMe | CH |
| 4794 | Me | $Q_{45}$ | H | OMe | OMe | CH |
| 4795 | Me | $Q_{45}$ | H | Me | OMe | N |
| 4796 | Me | $Q_{45}$ | H | OMe | OMe | N |
| 4797 | COOMe | $Q_{45}$ | H | Me | OMe | CH |
| 4798 | COOMe | $Q_{45}$ | H | OMe | OMe | CH |
| 4799 | COOMe | $Q_{45}$ | H | Me | OMe | N |
| 4800 | $Q_{46}$ | H | H | Me | OMe | CH |
| 4801 | $Q_{46}$ | H | H | OMe | OMe | CH |
| 4802 | $Q_{46}$ | H | H | Me | OMe | N |
| 4803 | $Q_{46}$ | Cl | H | Me | OMe | CH |
| 4804 | $Q_{46}$ | Cl | H | OMe | OMe | CH |
| 4805 | $Q_{46}$ | Cl | H | Me | OMe | N |
| 4806 | $Q_{46}$ | COOMe | H | Me | OMe | CH |
| 4807 | $Q_{46}$ | COOMe | H | OMe | OMe | CH |
| 4808 | $Q_{46}$ | COOMe | H | Me | OMe | N |
| 4809 | Me | $Q_{46}$ | H | Me | OMe | CH |
| 4810 | Me | $Q_{46}$ | H | Me | OMe | CH |
| 4811 | Me | $Q_{46}$ | H | Me | OMe | N |
| 4812 | $Q_{47}$ | H | H | Me | OMe | CH |
| 4813 | $Q_{47}$ | H | H | OMe | OMe | CH |
| 4814 | $Q_{47}$ | H | H | Me | OMe | N |
| 4815 | $Q_{47}$ | Cl | H | Me | OMe | CH |
| 4816 | $Q_{47}$ | Cl | H | OMe | OMe | CH |
| 4817 | $Q_{47}$ | Cl | H | Me | OMe | N |
| 4818 | $Q_{47}$ | COOMe | H | Me | OMe | CH |
| 4819 | $Q_{47}$ | COOMe | H | OMe | OMe | CH |
| 4820 | $Q_{47}$ | COOMe | H | Me | OMe | N |
| 4821 | Me | $Q_{47}$ | H | Me | OMe | CH |
| 4822 | Me | $Q_{47}$ | H | OMe | OMe | CH |
| 4823 | Me | $Q_{47}$ | H | Me | OMe | N |
| 4824 | $Q_{48}$ | H | Me | OMe | CH | |
| 4825 | $Q_{48}$ | H | OMe | OMe | CH | |
| 4826 | $Q_{48}$ | H | Me | OMe | N | |
| 4827 | $Q_{48}$ | Cl | Me | OMe | CH | |

TABLE 3-continued

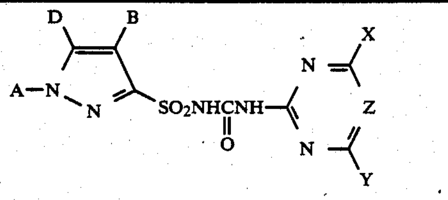

| No. | A | B | D | X | Y | Z |
|---|---|---|---|---|---|---|
| 4828 | $Q_{48}$ | Cl | OMe | OMe | CH | |
| 4829 | $Q_{48}$ | H | Me | OMe | N | |
| 4830 | $Q_{48}$ | COOMe | Me | OMe | CH | |
| 4831 | $Q_{48}$ | COOMe | OMe | OMe | CH | |
| 4832 | $Q_{48}$ | COOMe | Me | OMe | N | |
| 4833 | Me | $Q_{48}$ | H | Me | OMe | CH |
| 4834 | Me | $Q_{48}$ | H | OMe | OMe | CH |
| 4835 | Me | $Q_{48}$ | H | Me | OMe | N |
| 4836 | $Q_{49}$ | H | H | Me | OMe | CH |
| 4837 | $Q_{49}$ | H | H | OMe | OMe | CH |
| 4838 | $Q_{49}$ | H | H | Me | OMe | N |
| 4839 | $Q_{49}$ | Cl | H | Me | OMe | CH |
| 4840 | $Q_{49}$ | Cl | H | OMe | OMe | CH |
| 4841 | $Q_{49}$ | Cl | H | Me | OMe | N |
| 4842 | $Q_{49}$ | COOMe | H | Me | OMe | CH |
| 4843 | $Q_{49}$ | COOMe | H | OMe | OMe | CH |
| 4844 | $Q_{49}$ | COOMe | H | Me | OMe | N |
| 4845 | Me | $Q_{49}$ | H | Me | OMe | CH |
| 4846 | Me | $Q_{49}$ | H | OMe | OMe | CH |
| 4847 | Me | $Q_{49}$ | H | Me | OMe | N |
| 4848 | $Q_{50}$ | H | H | Me | OMe | CH |
| 4849 | $Q_{50}$ | H | H | OMe | OMe | CH |
| 4850 | $Q_{50}$ | H | H | Me | OMe | N |
| 4851 | $Q_{50}$ | Cl | H | Me | OMe | CH |
| 4852 | $Q_{50}$ | Cl | H | OMe | OMe | CH |
| 4853 | $Q_{50}$ | Cl | H | Me | OMe | N |
| 4854 | $Q_{50}$ | COOMe | H | Me | OMe | CH |
| 4855 | $Q_{50}$ | COOMe | H | OMe | OMe | CH |
| 4856 | $Q_{50}$ | COOMe | H | Me | OMe | N |
| 4857 | Me | $Q_{50}$ | H | Me | OMe | CH |
| 4858 | Me | $Q_{50}$ | H | OMe | OMe | CH |
| 4859 | Me | $Q_{50}$ | H | Me | OMe | N |
| 4860 | $Q_{51}$ | H | H | Me | OMe | CH |
| 4861 | $Q_{51}$ | H | H | OMe | OMe | CH |
| 4862 | $Q_{51}$ | H | H | Me | OMe | N |
| 4863 | $Q_{51}$ | Cl | H | Me | OMe | CH |
| 4864 | $Q_{51}$ | Cl | H | OMe | OMe | CH |
| 4865 | $Q_{51}$ | Cl | H | Me | OMe | N |
| 4866 | $Q_{51}$ | COOMe | H | Me | OMe | CH |
| 4867 | $Q_{51}$ | COOMe | H | OMe | OMe | CH |
| 4868 | $Q_{51}$ | COOMe | H | Me | OMe | N |
| 4869 | Me | $Q_{51}$ | H | Me | OMe | CH |
| 4870 | Me | $Q_{51}$ | H | OMe | OMe | CH |
| 4871 | Me | $Q_{51}$ | H | Me | OMe | N |
| 4872 | $Q_{52}$ | Cl | H | Me | OMe | CH |
| 4873 | $Q_{52}$ | Cl | H | OMe | OMe | CH |
| 4874 | $Q_{52}$ | Cl | H | Me | OMe | N |
| 4875 | $Q_{52}$ | COOMe | H | Me | OMe | CH |
| 4876 | $Q_{52}$ | COOMe | H | OMe | OMe | CH |
| 4877 | $Q_{52}$ | COOMe | H | Me | OMe | N |
| 4878 | Me | $Q_{52}$ | H | Me | OMe | CH |
| 4879 | Me | $Q_{52}$ | H | OMe | OMe | CH |
| 4880 | Me | $Q_{52}$ | H | Me | OMe | N |
| 4881 | $Q_{53}$ | Cl | H | Me | OMe | CH |
| 4882 | $Q_{53}$ | Cl | H | OMe | OMe | CH |
| 4883 | $Q_{53}$ | Cl | H | Me | OMe | N |
| 4884 | $Q_{53}$ | COOMe | H | Me | OMe | CH |
| 4885 | $Q_{53}$ | COOMe | H | OMe | OMe | CH |
| 4886 | $Q_{53}$ | COOMe | H | Me | OMe | N |
| 4887 | Me | $Q_{53}$ | H | Me | OMe | CH |
| 4888 | Me | $Q_{53}$ | H | OMe | OMe | CH |
| 4889 | Me | $Q_{53}$ | H | Me | OMe | N |
| 4890 | $Q_{54}$ | H | H | Me | OMe | CH |
| 4891 | $Q_{54}$ | H | H | OMe | OMe | CH |
| 4892 | $Q_{54}$ | H | H | Me | OMe | N |
| 4893 | $Q_{54}$ | Cl | H | Me | OMe | CH |
| 4894 | $Q_{54}$ | Cl | H | OMe | OMe | CH |
| 4895 | $Q_{54}$ | Cl | H | Me | OMe | N |
| 4896 | $Q_{54}$ | COOMe | H | Me | OMe | CH |
| 4897 | $Q_{54}$ | COOMe | H | OMe | OMe | CH |
| 4898 | $Q_{54}$ | COOMe | H | Me | OMe | N |

TABLE 3-continued

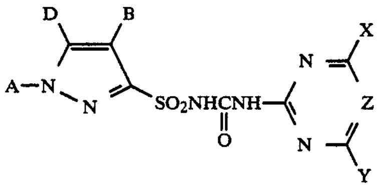

| No. | A | B | D | X | Y | Z |
|---|---|---|---|---|---|---|
| 4899 | Me | $Q_{54}$ | H | Me | OMe | CH |
| 4900 | Me | $Q_{54}$ | H | OMe | OMe | CH |
| 4901 | Me | $Q_{54}$ | H | Me | OMe | N |
| 4902 | $Q_{55}$ | H | H | Me | OMe | CH |
| 4903 | $Q_{55}$ | H | H | OMe | OMe | CH |
| 4904 | $Q_{55}$ | H | H | Me | OMe | N |
| 4905 | $Q_{55}$ | Cl | H | Me | OMe | CH |
| 4906 | $Q_{55}$ | Cl | H | OMe | OMe | CH |
| 4907 | $Q_{55}$ | Cl | H | Me | OMe | N |
| 4908 | $Q_{55}$ | COOMe | H | Me | OMe | CH |
| 4909 | $Q_{55}$ | COOMe | H | OMe | OMe | CH |
| 4910 | $Q_{55}$ | COOMe | H | Me | OMe | N |
| 4911 | Me | $Q_{55}$ | H | Me | OMe | CH |
| 4912 | Me | $Q_{55}$ | H | OMe | OMe | CH |
| 4913 | Me | $Q_{55}$ | H | Me | OMe | N |
| 4914 | $Q_{56}$ | H | H | Me | OMe | CH |
| 4915 | $Q_{56}$ | H | H | OMe | OMe | CH |
| 4916 | $Q_{56}$ | H | H | Me | OMe | N |
| 4917 | $Q_{56}$ | Cl | H | Me | OMe | CH |
| 4918 | $Q_{56}$ | Cl | H | OMe | OMe | CH |
| 4919 | $Q_{56}$ | Cl | H | Me | OMe | N |
| 4920 | $Q_{56}$ | COOMe | H | Me | OMe | CH |
| 4921 | $Q_{56}$ | COOMe | H | OMe | OMe | CH |
| 4922 | $Q_{56}$ | COOMe | H | Me | OMe | N |
| 4923 | Me | $Q_{56}$ | H | Me | OMe | CH |
| 4924 | Me | $Q_{56}$ | H | OMe | OMe | CH |
| 4925 | Me | $Q_{56}$ | H | Me | OMe | N |
| 4926 | $Q_{57}$ | Cl | H | Me | OMe | CH |
| 4927 | $Q_{57}$ | Cl | H | OMe | OMe | CH |
| 4928 | $Q_{57}$ | Cl | H | Me | OMe | N |
| 4929 | $Q_{57}$ | COOMe | H | Me | OMe | CH |
| 4930 | $Q_{57}$ | COOMe | H | OMe | OMe | CH |
| 4931 | $Q_{57}$ | COOMe | H | Me | OMe | N |
| 4932 | Me | $Q_{57}$ | H | Me | OMe | CH |
| 4933 | Me | $Q_{57}$ | H | OMe | OMe | CH |
| 4934 | Me | $Q_{57}$ | H | Me | OMe | N |
| 4935 | $Q_{58}$ | Cl | H | Me | OMe | CH |
| 4936 | $Q_{58}$ | Cl | H | OMe | OMe | CH |
| 4937 | $Q_{58}$ | Cl | H | Me | OMe | N |
| 4938 | $Q_{58}$ | COOMe | H | Me | OMe | CH |
| 4939 | $Q_{58}$ | COOMe | H | OMe | OMe | CH |
| 4940 | $Q_{58}$ | COOMe | H | Me | OMe | N |
| 4941 | Me | $Q_{58}$ | H | Me | OMe | CH |
| 4942 | Me | $Q_{58}$ | H | OMe | OMe | CH |
| 4943 | Me | $Q_{58}$ | H | Me | OMe | N |
| 4944 | $Q_{59}$ | H | H | Me | OMe | CH |
| 4945 | $Q_{59}$ | H | H | OMe | OMe | CH |
| 4946 | $Q_{59}$ | H | H | Me | OMe | N |
| 4947 | $Q_{59}$ | Me | H | Me | OMe | CH |
| 4948 | $Q_{59}$ | Me | H | OMe | OMe | CH |
| 4949 | $Q_{59}$ | Me | H | Me | OMe | N |
| 4950 | $Q_{59}$ | Cl | H | Me | OMe | CH |
| 4951 | $Q_{59}$ | Cl | H | OMe | OMe | CH |
| 4952 | $Q_{59}$ | Cl | H | Me | OMe | N |
| 4953 | $Q_{59}$ | Br | H | Me | OMe | CH |
| 4954 | $Q_{59}$ | Br | H | OMe | OMe | CH |
| 4955 | $Q_{59}$ | Br | H | Me | OMe | N |
| 4956 | $Q_{59}$ | COOMe | H | Me | OMe | CH |
| 4957 | $Q_{59}$ | COOMe | H | Me | OMe | N |
| 4958 | $Q_{59}$ | COOMe | H | Me | OMe | N |
| 4959 | $Q_{59}$ | COOEt | H | Me | OMe | CH |
| 4960 | $Q_{59}$ | COOEt | H | OMe | OMe | CH |
| 4961 | $Q_{59}$ | COOEt | H | Me | OMe | N |
| 4962 | Me | $Q_{59}$ | H | Me | Me | CH |
| 4963 | Me | $Q_{59}$ | H | Me | OMe | CH |
| 4964 | Me | $Q_{59}$ | H | OMe | OMe | CH |
| 4965 | Me | $Q_{59}$ | H | Me | OMe | N |
| 4966 | Me | $Q_{59}$ | H | Me | OMe | N |
| 4967 | COMe | $Q_{59}$ | H | Me | OMe | CH |
| 4968 | COMe | $Q_{59}$ | H | OMe | OMe | CH |
| 4969 | COMe | $Q_{59}$ | H | Me | OMe | N |

TABLE 3-continued

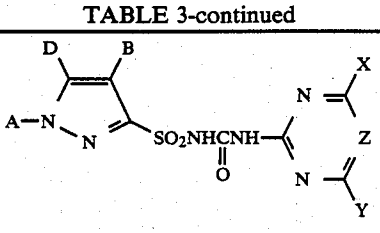

| No. | A | B | D | X | Y | Z |
|---|---|---|---|---|---|---|
| 4970 | $Q_{60}$ | H | H | Me | OMe | CH |
| 4971 | $Q_{60}$ | H | H | OMe | OMe | CH |
| 4972 | $Q_{60}$ | H | H | Me | OMe | N |
| 4973 | $Q_{60}$ | Cl | H | Me | OMe | CH |
| 4974 | $Q_{60}$ | Cl | H | OMe | OMe | CH |
| 4975 | $Q_{60}$ | Cl | H | Me | OMe | N |
| 4976 | $Q_{60}$ | COOMe | H | Me | OMe | CH |
| 4977 | $Q_{60}$ | COOMe | H | OMe | OMe | CH |
| 4978 | $Q_{60}$ | COOMe | H | Me | OMe | N |
| 4979 | Me | $Q_{60}$ | H | Me | OMe | CH |
| 4980 | Me | $Q_{60}$ | H | OMe | OMe | CH |
| 4981 | Me | $Q_{60}$ | H | Me | OMe | N |
| 4970 | $Q_{61}$ | H | H | Me | OMe | CH |
| 4971 | $Q_{61}$ | H | H | OMe | OMe | CH |
| 4972 | $Q_{61}$ | H | H | Me | OMe | N |
| 4973 | $Q_{61}$ | Cl | H | Me | OMe | CH |
| 4974 | $Q_{61}$ | Cl | H | OMe | OMe | CH |
| 4975 | $Q_{61}$ | Cl | H | Me | OMe | N |
| 4976 | $Q_{61}$ | COOMe | H | Me | OMe | CH |
| 4977 | $Q_{61}$ | COOMe | H | OMe | OMe | CH |
| 4978 | $Q_{61}$ | COOMe | H | Me | OMe | N |
| 4979 | Me | $Q_{61}$ | H | Me | OMe | CH |
| 4980 | Me | $Q_{61}$ | H | OMe | OMe | CH |
| 4981 | Me | $Q_{61}$ | H | Me | OMe | N |
| 4982 | $Q_{62}$ | H | H | Me | OMe | CH |
| 4983 | $Q_{62}$ | H | H | OMe | OMe | CH |
| 4984 | $Q_{62}$ | H | H | Me | OMe | N |
| 4985 | $Q_{62}$ | Cl | H | Me | OMe | CH |
| 4986 | $Q_{62}$ | Cl | H | OMe | OMe | CH |
| 4987 | $Q_{62}$ | Cl | H | Me | OMe | N |
| 4988 | $Q_{62}$ | COOMe | H | Me | OMe | CH |
| 4989 | $Q_{62}$ | COOMe | H | OMe | OMe | CH |
| 4990 | $Q_{62}$ | COOMe | H | Me | OMe | N |
| 4991 | Me | $Q_{62}$ | H | Me | OMe | CH |
| 4992 | Me | $Q_{62}$ | H | OMe | OMe | CH |
| 4993 | Me | $Q_{62}$ | H | Me | OMe | N |
| 4994 | $Q_{63}$ | Cl | H | Me | OMe | CH |
| 4995 | $Q_{63}$ | Cl | H | OMe | OMe | CH |
| 4996 | $Q_{63}$ | Cl | H | Me | OMe | N |
| 4997 | $Q_{63}$ | COOMe | H | Me | OMe | CH |
| 4998 | $Q_{63}$ | COOMe | H | OMe | OMe | CH |
| 4999 | $Q_{63}$ | COOMe | H | Me | OMe | N |
| 5000 | Me | $Q_{63}$ | H | Me | OMe | CH |
| 5001 | Me | $Q_{63}$ | H | OMe | OMe | CH |
| 5002 | Me | $Q_{63}$ | H | Me | OMe | N |
| 5003 | $Q_{64}$ | Cl | H | Me | OMe | CH |
| 5004 | $Q_{64}$ | Cl | H | OMe | OMe | CH |
| 5005 | $Q_{64}$ | Cl | H | Me | OMe | N |
| 5006 | $Q_{64}$ | COOMe | H | Me | OMe | CH |
| 5007 | $Q_{64}$ | COOMe | H | OMe | OMe | CH |
| 5008 | $Q_{64}$ | COOMe | H | Me | OMe | N |
| 5009 | Me | $Q_{64}$ | H | Me | OMe | CH |
| 5010 | Me | $Q_{64}$ | H | OMe | OMe | CH |
| 5011 | Me | $Q_{64}$ | H | Me | OMe | N |
| 5012 | $Q_{65}$ | H | H | Me | OMe | CH |
| 5013 | $Q_{65}$ | H | H | OMe | OMe | CH |
| 5014 | $Q_{65}$ | H | H | Me | OMe | N |
| 5015 | $Q_{65}$ | Cl | H | Me | OMe | CH |
| 5016 | $Q_{65}$ | Cl | H | OMe | OMe | CH |
| 5017 | $Q_{65}$ | Cl | H | Me | OMe | N |
| 5018 | $Q_{65}$ | COOMe | H | Me | OMe | CH |
| 5019 | $Q_{65}$ | COOMe | H | OMe | OMe | CH |
| 5020 | $Q_{65}$ | COOMe | H | Me | OMe | N |
| 5021 | Me | $Q_{65}$ | H | Me | OMe | CH |
| 5022 | Me | $Q_{65}$ | H | OMe | OMe | CH |
| 5023 | Me | $Q_{65}$ | H | Me | OMe | N |
| 5024 | $Q_{66}$ | Cl | H | Me | OMe | CH |
| 5025 | $Q_{66}$ | Cl | H | OMe | OMe | CH |
| 5026 | $Q_{66}$ | Cl | H | Me | OMe | N |
| 5027 | $Q_{66}$ | COOMe | H | Me | OMe | CH |
| 5028 | $Q_{66}$ | COOMe | H | OMe | OMe | CH |

TABLE 3-continued

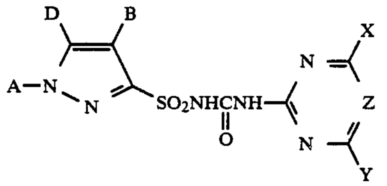

| No. | A | B | D | X | Y | Z |
|---|---|---|---|---|---|---|
| 5029 | $Q_{66}$ | COOMe | H | Me | OMe | N |
| 5030 | Me | $Q_{66}$ | H | Me | OMe | CH |
| 5031 | Me | $Q_{66}$ | H | OMe | OMe | CH |
| 5032 | Me | $Q_{66}$ | H | Me | OMe | N |
| 5033 | $Q_{67}$ | Cl | H | Me | OMe | CH |
| 5034 | $Q_{67}$ | Cl | H | OMe | OMe | CH |
| 5035 | $Q_{67}$ | Cl | H | Me | OMe | N |
| 5036 | $Q_{67}$ | COOMe | H | Me | OMe | CH |
| 5037 | $Q_{67}$ | COOMe | H | OMe | OMe | CH |
| 5038 | $Q_{67}$ | COOMe | H | Me | OMe | N |
| 5039 | Me | $Q_{67}$ | H | Me | OMe | CH |
| 5040 | Me | $Q_{67}$ | H | OMe | OMe | CH |
| 5041 | Me | $Q_{67}$ | H | Me | OMe | N |
| 5042 | $Q_{68}$ | Cl | H | Me | OMe | CH |
| 5043 | $Q_{68}$ | Cl | H | OMe | OMe | CH |
| 5044 | $Q_{68}$ | Cl | H | Me | OMe | N |
| 5045 | $Q_{68}$ | COOMe | H | Me | OMe | CH |
| 5046 | $Q_{68}$ | COOMe | H | OMe | OMe | CH |
| 5047 | $Q_{68}$ | COOMe | H | Me | OMe | N |
| 5048 | Me | $Q_{68}$ | H | Me | OMe | CH |
| 5049 | Me | $Q_{68}$ | H | OMe | OMe | CH |
| 5050 | Me | $Q_{68}$ | H | Me | OMe | N |
| 5051 | $Q_{69}$ | Cl | H | Me | OMe | CH |
| 5052 | $Q_{69}$ | Cl | h | OEM | OMe | CH |
| 5053 | $Q_{69}$ | CL | H | Me | OMe | N |
| 5054 | $Q_{69}$ | COOMe | H | OMe | OMe | CH |
| 5055 | $Q_{69}$ | COOMe | H | OMe | OMe | CH |
| 5056 | $Q_{69}$ | COOMe | H | Me | OMe | N |
| 5057 | Me | $Q_{69}$ | H | Me | OMe | CH |
| 5058 | Me | $Q_{69}$ | H | OMe | OMe | CH |
| 5059 | Me | $Q_{69}$ | H | Me | OMe | N |
| 5060 | $Q_{70}$ | H | H | Me | OMe | CH |
| 5061 | $Q_{70}$ | H | H | OMe | OMe | CH |
| 5062 | $Q_{70}$ | H | H | Me | OMe | N |
| 5063 | $Q_{70}$ | Cl | H | Me | OMe | CH |
| 5064 | $Q_{70}$ | Cl | H | OMe | OMe | CH |
| 5065 | $Q_{70}$ | Cl | H | Me | OMe | N |
| 5066 | $Q_{70}$ | COOMe | H | Me | OMe | CH |
| 5067 | $Q_{70}$ | COOMe | H | OMe | OMe | CH |
| 5068 | $Q_{70}$ | COOMe | H | Me | OMe | N |
| 5069 | Me | $Q_{70}$ | H | Me | OMe | CH |
| 5070 | Me | $Q_{70}$ | H | OMe | OMe | CH |
| 5071 | Me | $Q_{70}$ | H | Me | OMe | N |
| 5072 | $Q_{71}$ | Cl | H | Me | OMe | CH |
| 5073 | $Q_{71}$ | Cl | H | OMe | OMe | CH |
| 5074 | $Q_{71}$ | Cl | H | Me | OMe | N |
| 5075 | $Q_{71}$ | COOMe | H | Me | OMe | CH |
| 5076 | $Q_{71}$ | COOMe | H | OMe | OMe | CH |
| 5077 | $Q_{71}$ | COOMe | H | Me | OMe | N |
| 5078 | Me | $Q_{71}$ | H | Me | OMe | CH |
| 5079 | Me | $Q_{71}$ | H | OMe | OMe | CH |
| 5080 | Me | $Q_{71}$ | H | Me | OMe | N |
| 5081 | $Q_{72}$ | Cl | H | Me | OMe | CH |
| 5082 | $Q_{72}$ | Cl | H | OMe | OMe | CH |
| 5083 | $Q_{72}$ | Cl | H | Me | OMe | N |
| 5084 | $Q_{72}$ | COOMe | H | Me | OMe | CH |
| 5085 | $Q_{72}$ | COOMe | H | OMe | OMe | CH |
| 5086 | $Q_{72}$ | COOMe | H | Me | OMe | N |
| 5087 | Me | $Q_{72}$ | H | Me | OMe | CH |
| 5088 | Me | $Q_{72}$ | H | OMe | OMe | CH |
| 5089 | Me | $Q_{72}$ | H | Me | OMe | N |
| 5090 | $Q_{73}$ | Cl | H | Me | OMe | CH |
| 5091 | $Q_{73}$ | Cl | H | OMe | OMe | CH |
| 5092 | $Q_{73}$ | Cl | H | Me | OMe | N |
| 5093 | $Q_{73}$ | COOMe | H | Me | OMe | CH |
| 5094 | $Q_{73}$ | COOMe | H | OMe | OMe | CH |
| 5095 | $Q_{73}$ | COOMe | H | Me | OMe | N |
| 5096 | Me | $Q_{73}$ | H | Me | OMe | CH |
| 5097 | Me | $Q_{73}$ | H | OMe | OMe | CH |
| 5098 | Me | $Q_{73}$ | H | Me | OMe | N |
| 5099 | $Q_{74}$ | Cl | H | Me | OMe | CH |

TABLE 3-continued

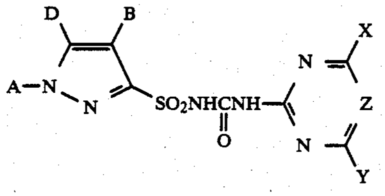

| No. | A | B | D | X | Y | Z |
|---|---|---|---|---|---|---|
| 5100 | $Q_{74}$ | Cl | H | OMe | OMe | CH |
| 5101 | $Q_{74}$ | Cl | H | Me | OMe | N |
| 5102 | $Q_{74}$ | COOMe | H | Me | OMe | CH |
| 5103 | $Q_{74}$ | COOMe | H | OMe | OMe | CH |
| 5104 | $Q_{74}$ | COOMe | H | Me | OMe | N |
| 5105 | Me | $Q_{74}$ | H | Me | OMe | CH |
| 5106 | Me | $Q_{74}$ | H | OMe | OMe | CH |
| 5107 | Me | $Q_{74}$ | H | Me | OMe | N |
| 5108 | $Q_{75}$ | Cl | H | Me | OMe | CH |
| 5109 | $Q_{75}$ | Cl | H | OMe | OMe | CH |
| 5110 | $Q_{75}$ | Cl | H | Me | OMe | N |
| 5111 | $Q_{75}$ | CL | H | Me | OMe | N |
| 5112 | $Q_{75}$ | COOMe | H | OMe | OMe | CH |
| 5113 | $Q_{75}$ | COOMe | H | Me | OMe | N |
| 5114 | Me | $Q_{75}$ | H | Me | OMe | CH |
| 5115 | Me | $Q_{75}$ | H | OMe | OMe | CH |
| 5116 | Me | $Q_{75}$ | H | Me | OMe | N |
| 5117 | 76 | Cl | H | Me | OMe | CH |
| 5118 | $Q_{76}$ | Cl | H | OMe OMe | CH | |
| 5119 | $Q_{76}$ | Cl | H | Me | OMe | N |
| 5120 | $Q_{76}$ | COOMe | H | Me | OMe | CH |
| 5121 | $Q_{76}$ | COOMe | H | OMe | OMe | CH |
| 5122 | $Q_{76}$ | COOMe | H | Me | OMe | N |
| 5123 | Me | $Q_{76}$ | H | Me | OMe | CH |
| 5124 | Me | $Q_{76}$ | H | OMe | OMe | CH |
| 5125 | Me | $Q_{76}$ | H | Me | OMe | N |
| 5720 | $Q_{77}$ | Cl | H | Me | OMe | CH |
| 5721 | $Q_{77}$ | Cl | H | OMe | OMe | CH |
| 5722 | $Q_{77}$ | Cl | H | Me | OMe | N |
| 5723 | $Q_{77}$ | COOMe | H | Me | OMe | CH |
| 5724 | $Q_{77}$ | COOMe | H | OMe | OMe | CH |
| 5725 | $Q_{77}$ | COOMe | H | Me | OMe | N |
| 5726 | Me | $Q_{77}$ | H | Me | OMe | CH |
| 5727 | Me | $Q_{77}$ | H | OMe | OMe | CH |
| 5728 | Me | $Q_{77}$ | H | Me | OMe | N |
| 5729 | $Q_{78}$ | H | H | Me | OMe | CH |
| 5730 | $Q_{78}$ | H | H | OMe | OMe | CH |
| 5731 | $Q_{78}$ | H | H | Me | OMe | N |
| 5732 | $Q_{78}$ | Me | H | Me | OMe | CH |
| 5733 | $Q_{78}$ | Me | H | OMe | OMe | CH |
| 5734 | $Q_{78}$ | Me | H | Me | OMe | N |
| 5735 | $Q_{78}$ | Cl | H | Me | OMe | CH |
| 5736 | $Q_{78}$ | Cl | H | OMe | OMe | CH |
| 5737 | $Q_{78}$ | Cl | H | Me | OMe | N |
| 5738 | $Q_{78}$ | Br | H | Me | OMe | CH |
| 5739 | $Q_{78}$ | Br | H | OMe | OMe | CH |
| 5740 | $Q_{78}$ | Br | H | Me | OMe | N |
| 5741 | $Q_{78}$ | COOMe | H | Me | OMe | CH |
| 5742 | $Q_{78}$ | COOMe | H | OMe | OMe | CH |
| 5743 | $Q_{78}$ | COOMe | H | Me | OMe | N |
| 5744 | $Q_{78}$ | COOEt | H | Me | OMe | CH |
| 5745 | $Q_{78}$ | COOEt | H | OMe | OMe | CH |
| 5746 | $Q_{78}$ | COOEt | H | Me | OMe | N |
| 5747 | Me | $Q_{78}$ | H | Me | Me | CH |
| 5748 | Me | $Q_{78}$ | H | Me | OMe | CH |
| 5749 | Me | $Q_{78}$ | H | OMe | OMe | CH |
| 5750 | Me | $Q_{78}$ | H | Me | OMe | N |
| 5751 | Me | $Q_{78}$ | H | OMe | OMe | N |
| 5752 | COOMe | $Q_{78}$ | H | Me | OMe | CH |
| 5753 | COOMe | $Q_{78}$ | H | OMe | OMe | CH |
| 5754 | COOMe | $Q_{78}$ | H | Me | OMe | N |
| 5755 | $Q_{79}$ | H | H | Me | OMe | CH |
| 5756 | $Q_{79}$ | H | H | OMe | OMe | CH |
| 5757 | $Q_{79}$ | H | H | Me | OMe | N |
| 5758 | $Q_{79}$ | Me | H | Me | OMe | CH |
| 5759 | $Q_{79}$ | Me | H | OMe | OMe | CH |
| 5760 | $Q_{79}$ | Me | H | Me | OMe | N |
| 5761 | $Q_{79}$ | Cl | H | Me | OMe | CH |
| 5762 | $Q_{79}$ | Cl | H | OMe | OMe | CH |
| 5763 | $Q_{79}$ | Cl | H | Me | OMe | N |
| 5764 | $Q_{79}$ | Br | H | Me | OMe | CH |

TABLE 3-continued

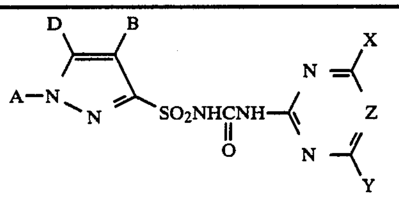

| No. | A | B | D | X | Y | Z |
|---|---|---|---|---|---|---|
| 5765 | $Q_{79}$ | Br | H | OMe | OMe | CH |
| 5766 | $Q_{79}$ | Br | H | Me | OMe | N |
| 5767 | $Q_{79}$ | COOMe | H | Me | OMe | CH |
| 5768 | $Q_{79}$ | COOMe | H | OMe | OMe | CH |
| 5769 | $Q_{79}$ | COOMe | H | Me | OMe | N |
| 5770 | $Q_{79}$ | COOEt | H | Me | OMe | CH |
| 5771 | $Q_{79}$ | COOEt | H | OMe | OMe | CH |
| 5772 | $Q_{79}$ | COOEt | H | Me | OMe | N |
| 5773 | Me | $Q_{79}$ | H | Me | Me | CH |
| 5774 | Me | $Q_{79}$ | H | Me | OMe | CH |
| 5775 | Me | $Q_{79}$ | H | OMe | OMe | CH |
| 5776 | Me | $Q_{79}$ | H | Me | OMe | N |
| 5777 | Me | $Q_{79}$ | H | OMe | OMe | N |
| 5778 | COOMe | $Q_{79}$ | H | Me | OMe | CH |
| 5779 | COOMe | $Q_{79}$ | H | OMe | OMe | CH |
| 5780 | COOMe | $Q_{79}$ | H | Me | OMe | N |
| 5781 | $Q_{80}$ | H | H | Me | OMe | CH |
| 5782 | $Q_{80}$ | H | H | OMe | OMe | CH |
| 5783 | $Q_{80}$ | H | H | Me | OMe | N |
| 5784 | $Q_{80}$ | Cl | H | Me | OMe | CH |
| 5785 | $Q_{80}$ | Cl | H | OMe | OMe | CH |
| 5786 | $Q_{80}$ | Cl | H | Me | OMe | N |
| 5787 | $Q_{80}$ | COOMe | H | Me | OMe | CH |
| 5788 | $Q_{80}$ | COOMe | H | OMe | OMe | CH |
| 5789 | $Q_{80}$ | COOMe | H | Me | OMe | N |
| 5790 | Me | $Q_{80}$ | H | Me | OMe | CH |
| 5791 | Me | $Q_{80}$ | H | OMe | OMe | CH |
| 5792 | Me | $Q_{80}$ | H | Me | OMe | N |
| 5793 | $Q_{81}$ | Cl | H | Me | OMe | CH |
| 5794 | $Q_{81}$ | Cl | H | OMe | OMe | CH |
| 5795 | $Q_{81}$ | Cl | H | Me | OMe | N |
| 5796 | $Q_{81}$ | COOMe | H | Me | OMe | CH |
| 5797 | $Q_{81}$ | COOMe | H | OMe | OMe | CH |
| 5798 | $Q_{81}$ | COOMe | H | Me | OMe | N |
| 5799 | Me | $Q_{81}$ | H | Me | OMe | CH |
| 5800 | Me | $Q_{81}$ | H | OMe | OMe | CH |
| 5801 | Me | $Q_{81}$ | H | Me | OMe | N |
| 5802 | $Q_{82}$ | Cl | H | Me | OMe | CH |
| 5803 | $Q_{82}$ | Cl | H | OMe | OMe | CH |
| 5804 | $Q_{82}$ | Cl | H | Me | OMe | N |
| 5805 | $Q_{82}$ | COOMe | H | OMe | OMe | CH |
| 5806 | $Q_{82}$ | COOMe | H | OMe | OMe | CH |
| 5807 | $Q_{82}$ | COOMe | H | Me | OMe | N |
| 5808 | Me | $Q_{82}$ | H | Me | OMe | CH |
| 5809 | Me | $Q_{82}$ | H | OMe | OMe | CH |
| 5810 | Me | $Q_{82}$ | H | Me | OMe | N |
| 5811 | $Q_{83}$ | Cl | H | Me | OMe | CH |
| 5812 | $Q_{83}$ | Cl | H | OMe | OMe | CH |
| 5813 | $Q_{83}$ | Cl | H | Me | OMe | N |
| 5814 | $Q_{83}$ | COOMe | H | Me | OMe | CH |
| 5815 | $Q_{83}$ | COOMe | H | OMe | OMe | CH |
| 5816 | $Q_{83}$ | COOMe | H | Me | OMe | N |
| 5817 | Me | $Q_{83}$ | H | Me | OMe | CH |
| 5818 | Me | $Q_{83}$ | H | OMe | OMe | CH |
| 5819 | Me | $Q_{83}$ | H | Me | OMe | N |
| 6551 | $Q_{16}$ | COOEt | H | OMe | OMe | CH |
| 4677 | $Q_{36}$ | Cl | H | Me | OMe | N |
| 4678 | $Q_{36}$ | COOMe | H | Me | OMe | CH |
| 4679 | $Q_{36}$ | COOMe | H | OMe | OMe | CH |
| 4680 | $Q_{36}$ | COOMe | H | Me | OMe | N |
| 4681 | Me | $Q_{36}$ | H | Me | OMe | CH |
| 4682 | Me | $Q_{36}$ | H | OMe | OMe | CH |
| 4683 | Me | $Q_{36}$ | H | Me | OMe | N |
| 4684 | $Q_{37}$ | H | H | Me | OMe | CH |
| 4685 | $Q_{37}$ | H | H | OMe | OMe | CH |
| 4686 | $Q_{37}$ | H | H | Me | OMe | N |
| 4687 | $Q_{37}$ | Cl | H | Me | OMe | CH |
| 4688 | $Q_{37}$ | Cl | H | OMe | OMe | CH |
| 4689 | $Q_{37}$ | Cl | H | Me | OMe | N |
| 4690 | $Q_{37}$ | COOMe | H | Me | OMe | CH |
| 4691 | $Q_{37}$ | COOMe | H | OMe | OMe | CH |

TABLE 3-continued

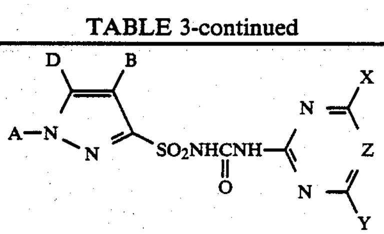

| No. | A | B | D | X | Y | Z |
|---|---|---|---|---|---|---|
| 4692 | $Q_{37}$ | COOMe | H | Me | OMe | N |
| 4693 | Me | $Q_{37}$ | H | Me | OMe | CH |
| 4694 | Me | $Q_{37}$ | H | OMe | OMe | CH |
| 4695 | Me | $Q_{37}$ | H | Me | OMe | N |
| 4696 | $Q_{38}$ | H | H | Me | OMe | CH |
| 4697 | $Q_{38}$ | H | H | OMe | OMe | CH |
| 4698 | $Q_{38}$ | H | H | Me | OMe | N |
| 4699 | $Q_{38}$ | Cl | H | Me | OMe | CH |
| 4700 | $Q_{38}$ | Cl | H | OMe | OMe | CH |
| 4701 | $Q_{38}$ | Cl | H | Me | OMe | N |
| 4702 | $Q_{38}$ | COOMe | H | Me | OMe | CH |
| 4703 | $Q_{38}$ | COOMe | H | OMe | OMe | CH |
| 4704 | $Q_{38}$ | COOMe | H | Me | OMe | N |
| 4705 | Me | $Q_{38}$ | H | Me | OMe | CH |
| 4706 | Me | $Q_{38}$ | H | OMe | OMe | CH |
| 4707 | Me | $Q_{38}$ | H | Me | OMe | N |
| 4708 | $Q_{39}$ | H | H | Me | OMe | CH |
| 4709 | $Q_{39}$ | H | OMe | OMe | CH | |
| 4710 | $Q_{39}$ | H | H | Me | OMe | N |
| 4711 | $Q_{39}$ | Cl | H | Me | OMe | CH |
| 4712 | $Q_{39}$ | Cl | H | OMe | OMe | CH |
| 4713 | $Q_{39}$ | Cl | H | Me | OMe | N |
| 4714 | $Q_{39}$ | COOMe | H | Me | OMe | CH |
| 4715 | $Q_{39}$ | COOMe | H | OMe | OMe | CH |
| 4716 | $Q_{39}$ | COOMe | H | Me | OMe | N |
| 4717 | Me | $Q_{39}$ | H | Me | OMe | CH |
| 4718 | Me | $Q_{39}$ | H | OMe | OMe | CH |
| 4719 | Me | $Q_{39}$ | H | Me | OMe | N |
| 4720 | $Q_{40}$ | Cl | H | Me | OMe | CH |
| 4721 | $Q_{40}$ | Cl | H | OMe | OMe | CH |
| 4722 | $Q_{40}$ | Cl | H | Me | OMe | N |
| 4723 | $Q_{40}$ | COOMe | H | Me | OMe | CH |
| 4724 | $Q_{40}$ | COOMe | H | OMe | OMe | CH |
| 4725 | $Q_{40}$ | COOMe | H | Me | OMe | N |
| 4726 | Me | $Q_{40}$ | H | Me | OMe | CH |
| 4727 | Me | $Q_{40}$ | H | OMe | OMe | CH |
| 4728 | Me | $Q_{40}$ | H | Me | OMe | N |
| 4729 | $Q_{41}$ | H | H | Me | OMe | CH |
| 4730 | $Q_{41}$ | H | H | OMe | OMe | CH |
| 4731 | $Q_{41}$ | H | H | Me | OMe | N |
| 4732 | $Q_{41}$ | Cl | H | Me | OMe | CH |
| 4733 | $Q_{41}$ | Cl | H | OMe | OMe | CH |
| 4734 | $Q_{41}$ | Cl | H | Me | OMe | N |
| 4735 | $Q_{41}$ | COOMe | H | Me | OMe | CH |
| 4736 | $Q_{41}$ | COOMe | H | OMe | OMe | CH |
| 4737 | $Q_{41}$ | COOMe | H | Me | OMe | N |
| 4738 | Me | $Q_{41}$ | H | Me | OMe | CH |
| 4739 | Me | $Q_{41}$ | H | OMe | OMe | CH |
| 4740 | Me | $Q_{41}$ | H | Me | OMe | N |
| 4741 | $Q_{42}$ | H | H | Me | OMe | CH |
| 4742 | $Q_{42}$ | H | H | OMe | OMe | CH |
| 4743 | $Q_{42}$ | H | H | Me | OMe | N |
| 4744 | $Q_{42}$ | Cl | H | OMe | OMe | CH |
| 4745 | $Q_{42}$ | Cl | H | OMe | OMe | CH |
| 4746 | $Q_{42}$ | Cl | H | Me | OMe | N |
| 4747 | $Q_{42}$ | COOMe | H | Me | OMe | CH |
| 4748 | $Q_{42}$ | COOMe | H | OMe | OMe | CH |
| 4749 | $Q_{42}$ | COOMe | H | Me | OMe | N |
| 4750 | Me | $Q_{42}$ | H | Me | OMe | CH |
| 4751 | Me | $Q_{42}$ | H | OMe | OMe | CH |
| 4752 | Me | $Q_{42}$ | H | Me | OMe | N |
| 4753 | $Q_{43}$ | H | H | Me | OMe | CH |
| 4754 | $Q_{43}$ | H | H | OMe | OMe | CH |
| 4755 | $Q_{43}$ | H | H | Me | OMe | N |
| 4756 | $Q_{43}$ | Cl | H | Me | OMe | CH |
| 4757 | $Q_{43}$ | Cl | H | OMe | OMe | CH |
| 4758 | $Q_{43}$ | Cl | H | Me | OMe | N |
| 4759 | $Q_{43}$ | COOMe | H | Me | OMe | CH |
| 4760 | $Q_{43}$ | COOMe | H | OMe | OMe | CH |
| 4761 | $Q_{43}$ | COOMe | H | Me | OMe | N |
| 4762 | Me | $Q_{43}$ | H | Me | OMe | CH |

TABLE 3-continued

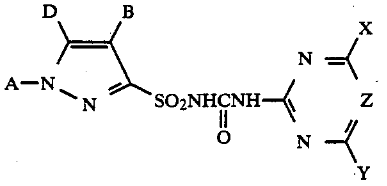

| No. | A | B | D | X | Y | Z |
|---|---|---|---|---|---|---|
| 4763 | Me | $Q_{43}$ | H | OMe | OMe | CH |
| 4764 | Me | $Q_{43}$ | H | Me | OMe | N |
| 4765 | $Q_{44}$ | Cl | H | Me | OMe | CH |
| 4766 | $Q_{44}$ | Cl | H | OMe | OMe | CH |
| 4767 | $Q_{44}$ | Cl | H | Me | OMe | N |
| 4768 | $Q_{44}$ | COOMe | H | Me | OMe | CH |
| 4769 | $Q_{44}$ | COOMe | H | OMe | OMe | CH |
| 4770 | $Q_{44}$ | COOMe | H | Me | OMe | N |
| 4771 | Me | $Q_{44}$ | H | Me | OMe | CH |
| 4772 | Me | $Q_{44}$ | H | OMe | OMe | CH |
| 4773 | Me | $Q_{44}$ | H | Me | OMe | N |
| 4774 | $Q_{45}$ | H | H | Me | OMe | CH |
| 4775 | $Q_{45}$ | H | H | OMe | OMe | CH |
| 4776 | $Q_{45}$ | H | H | Me | OMe | N |
| 4777 | $Q_{45}$ | Me | H | Me | OMe | CH |
| 4778 | $Q_{45}$ | Me | H | OMe | OMe | CH |
| 4779 | $Q_{45}$ | Me | H | Me | OMe | N |
| 4780 | $Q_{45}$ | Cl | H | Me | OMe | CH |
| 4781 | $Q_{45}$ | Cl | H | OMe | OMe | CH |
| 4782 | $Q_{45}$ | Cl | H | Me | OMe | N |
| 4783 | $Q_{45}$ | Br | H | Me | OMe | CH |
| 4784 | $Q_{45}$ | Br | H | OMe | OMe | CH |
| 4785 | $Q_{45}$ | Br | H | Me | OMe | N |
| 4786 | $Q_{45}$ | COOMe | H | Me | OMe | CH |
| 4787 | $Q_{45}$ | COOMe | H | OMe | OMe | CH |
| 4788 | $Q_{45}$ | COOMe | H | Me | OMe | N |
| 4789 | $Q_{45}$ | COOEt | H | Me | OMe | CH |
| 4790 | $Q_{45}$ | COOEt | H | OMe | OMe | CH |
| 4791 | $Q_{45}$ | COOEt | H | Me | OMe | N |
| 4792 | Me | $Q_{45}$ | H | Me | Me | CH |
| 4793 | Me | $Q_{45}$ | H | Me | OMe | CH |
| 4794 | Me | $Q_{45}$ | H | OMe | OMe | CH |
| 4795 | Me | $Q_{45}$ | H | Me | OMe | N |
| 4796 | Me | $Q_{45}$ | H | OMe | OMe | N |
| 4797 | COOMe | $Q_{45}$ | H | Me | OMe | CH |
| 4798 | COOMe | $Q_{45}$ | H | OMe | OMe | CH |
| 4799 | COOMe | $Q_{45}$ | H | Me | OMe | N |
| 4800 | $Q_{46}$ | H | H | Me | OMe | CH |
| 4801 | $Q_{46}$ | H | H | OMe | OMe | CH |
| 4802 | $Q_{46}$ | H | H | Me | OMe | N |
| 4803 | $Q_{46}$ | Cl | H | Me | OMe | CH |
| 4804 | $Q_{46}$ | Cl | H | OMe | OMe | CH |
| 4805 | $Q_{46}$ | Cl | H | Me | OMe | N |
| 4806 | $Q_{46}$ | COOMe | H | Me | OMe | CH |
| 4807 | $Q_{46}$ | COOMe | H | OMe | OMe | CH |
| 4808 | $Q_{46}$ | COOMe | H | Me | OMe | N |
| 4809 | Me | $Q_{46}$ | H | Me | OMe | CH |
| 4810 | Me | $Q_{46}$ | H | Me | OMe | CH |
| 4811 | Me | $Q_{46}$ | H | Me | OMe | N |
| 4812 | $Q_{47}$ | H | H | Me | OMe | CH |
| 4813 | $Q_{47}$ | H | H | OMe | OMe | CH |
| 4814 | $Q_{47}$ | H | H | Me | OMe | N |
| 4815 | $Q_{47}$ | Cl | H | Me | OMe | CH |
| 4816 | $Q_{47}$ | Cl | H | OMe | OMe | CH |
| 4817 | $Q_{47}$ | Cl | H | Me | OMe | N |
| 4818 | $Q_{47}$ | COOMe | H | Me | OMe | CH |
| 4819 | $Q_{47}$ | COOMe | H | OMe | OMe | CH |
| 4820 | $Q_{47}$ | COOMe | H | Me | OMe | N |
| 4821 | Me | $Q_{47}$ | H | Me | OMe | CH |
| 4822 | Me | $Q_{47}$ | H | OMe | OMe | CH |
| 4823 | Me | $Q_{47}$ | H | Me | OMe | N |
| 4824 | $Q_{48}$ | H | Me | OMe | CH | |
| 4825 | $Q_{48}$ | H | OMe | OMe | CH | |
| 4826 | $Q_{48}$ | H | Me | OMe | N | |
| 4827 | $Q_{48}$ | Cl | Me | OMe | CH | |
| 4828 | $Q_{48}$ | Cl | OMe | OMe | CH | |
| 4829 | $Q_{48}$ | H | Me | OMe | N | |
| 4830 | $Q_{48}$ | COOMe | Me | OMe | CH | |
| 4831 | $Q_{48}$ | COOMe | OMe | OMe | CH | |
| 4832 | $Q_{48}$ | COOMe | Me | OMe | N | |
| 4833 | Me | $Q_{48}$ | H | Me | OMe | CH |

TABLE 3-continued

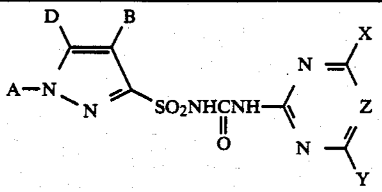

| No. | A | B | D | X | Y | Z |
|---|---|---|---|---|---|---|
| 4834 | Me | $Q_{48}$ | H | OMe | OMe | CH |
| 4835 | Me | $Q_{48}$ | H | Me | OMe | N |
| 4836 | $Q_{49}$ | H | H | Me | OMe | CH |
| 4837 | $Q_{49}$ | H | H | OMe | OMe | CH |
| 4838 | $Q_{49}$ | H | H | Me | OMe | N |
| 4839 | $Q_{49}$ | Cl | H | Me | OMe | CH |
| 4840 | $Q_{49}$ | Cl | H | OMe | OMe | CH |
| 4841 | $Q_{49}$ | Cl | H | Me | OMe | N |
| 4842 | $Q_{49}$ | COOMe | H | Me | OMe | CH |
| 4843 | $Q_{49}$ | COOMe | H | OMe | OMe | CH |
| 4844 | $Q_{49}$ | COOMe | H | Me | OMe | N |
| 4845 | Me | $Q_{49}$ | H | Me | OMe | CH |
| 4846 | Me | $Q_{49}$ | H | OMe | OMe | CH |
| 4847 | Me | $Q_{49}$ | H | Me | OMe | N |
| 4848 | $Q_{50}$ | H | H | Me | OMe | CH |
| 4849 | $Q_{50}$ | H | H | OMe | OMe | CH |
| 4850 | $Q_{50}$ | H | H | Me | OMe | N |
| 4851 | $Q_{50}$ | Cl | H | Me | OMe | CH |
| 4852 | $Q_{50}$ | Cl | H | OMe | OMe | CH |
| 4853 | $Q_{50}$ | Cl | H | Me | OMe | N |
| 4854 | $Q_{50}$ | COOMe | H | Me | OMe | CH |
| 4855 | $Q_{50}$ | COOMe | H | OMe | OMe | CH |
| 4856 | $Q_{50}$ | COOMe | H | Me | OMe | N |
| 4857 | Me | $Q_{50}$ | H | Me | OMe | CH |
| 4858 | Me | $Q_{50}$ | H | OMe | OMe | CH |
| 4859 | Me | $Q_{50}$ | H | Me | OMe | N |
| 4860 | $Q_{51}$ | H | H | Me | OMe | CH |
| 4861 | $Q_{51}$ | H | H | OMe | OMe | CH |
| 4862 | $Q_{51}$ | H | H | Me | OMe | N |
| 4863 | $Q_{51}$ | Cl | H | Me | OMe | CH |
| 4864 | $Q_{51}$ | Cl | H | OMe | OMe | CH |
| 4865 | $Q_{51}$ | Cl | H | Me | OMe | N |
| 4866 | $Q_{51}$ | COOMe | H | Me | OMe | CH |
| 4867 | $Q_{51}$ | COOMe | H | OMe | OMe | CH |
| 4868 | $Q_{51}$ | COOMe | H | Me | OMe | N |
| 4869 | Me | $Q_{51}$ | H | Me | OMe | CH |
| 4870 | Me | $Q_{51}$ | H | OMe | OMe | CH |
| 4871 | Me | $Q_{51}$ | H | Me | OMe | N |
| 4872 | $Q_{52}$ | Cl | H | Me | OMe | CH |
| 4873 | $Q_{52}$ | Cl | H | OMe | OMe | CH |
| 4874 | $Q_{52}$ | Cl | H | Me | OMe | N |
| 4875 | $Q_{52}$ | COOMe | H | Me | OMe | CH |
| 4876 | $Q_{52}$ | COOMe | H | OMe | OMe | CH |
| 4877 | $Q_{52}$ | COOMe | H | Me | OMe | N |
| 4878 | Me | $Q_{52}$ | H | Me | OMe | CH |
| 4879 | Me | $Q_{52}$ | H | OMe | OMe | CH |
| 4880 | Me | $Q_{52}$ | H | Me | OMe | N |
| 4881 | $Q_{53}$ | Cl | H | Me | OMe | CH |
| 4882 | $Q_{53}$ | Cl | H | OMe | OMe | CH |
| 4883 | $Q_{53}$ | Cl | H | Me | OMe | N |
| 4884 | $Q_{53}$ | COOMe | H | Me | OMe | CH |
| 4885 | $Q_{53}$ | COOMe | H | OMe | OMe | CH |
| 4886 | $Q_{53}$ | COOMe | H | Me | OMe | N |
| 4887 | Me | $Q_{53}$ | H | Me | OMe | CH |
| 4888 | Me | $Q_{53}$ | H | OMe | OMe | CH |
| 4889 | Me | $Q_{53}$ | H | Me | OMe | N |
| 4890 | $Q_{54}$ | H | H | Me | OMe | CH |
| 4891 | $Q_{54}$ | H | H | OMe | OMe | CH |
| 4892 | $Q_{54}$ | H | H | Me | OMe | N |
| 4893 | $Q_{54}$ | Cl | H | Me | OMe | CH |
| 4894 | $Q_{54}$ | Cl | H | OMe | OMe | CH |
| 4895 | $Q_{54}$ | Cl | H | Me | OMe | N |
| 4896 | $Q_{54}$ | COOMe | H | Me | OMe | CH |
| 4897 | $Q_{54}$ | COOMe | H | OMe | OMe | CH |
| 4898 | $Q_{54}$ | COOMe | H | Me | OMe | N |
| 4899 | Me | $Q_{54}$ | H | Me | OMe | CH |
| 4900 | Me | $Q_{54}$ | H | OMe | OMe | CH |
| 4901 | Me | $Q_{54}$ | H | Me | OMe | N |
| 4902 | $Q_{55}$ | H | H | Me | OMe | CH |
| 4903 | $Q_{55}$ | H | H | OMe | OMe | CH |
| 4904 | $Q_{55}$ | H | H | Me | OMe | N |

TABLE 3-continued

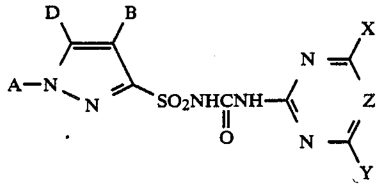

| No. | A | B | D | X | Y | Z |
|---|---|---|---|---|---|---|
| 4905 | $Q_{55}$ | Cl | H | Me | OMe | CH |
| 4906 | $Q_{55}$ | Cl | H | OMe | OMe | CH |
| 4907 | $Q_{55}$ | Cl | H | Me | OMe | N |
| 4908 | $Q_{55}$ | COOMe | H | Me | OMe | CH |
| 4909 | $Q_{55}$ | COOMe | H | OMe | OMe | CH |
| 4910 | $Q_{55}$ | COOMe | H | Me | OMe | N |
| 4911 | Me | $Q_{55}$ | H | Me | OMe | CH |
| 4912 | Me | $Q_{55}$ | H | OMe | OMe | CH |
| 4913 | Me | $Q_{55}$ | H | Me | OMe | N |
| 4914 | $Q_{56}$ | H | H | Me | OMe | CH |
| 4915 | $Q_{56}$ | H | H | OMe | OMe | CH |
| 4916 | $Q_{56}$ | H | H | Me | OMe | N |
| 4917 | $Q_{56}$ | Cl | H | Me | OMe | CH |
| 4918 | $Q_{56}$ | Cl | H | OMe | OMe | CH |
| 4919 | $Q_{56}$ | Cl | H | Me | OMe | N |
| 4920 | $Q_{56}$ | COOMe | H | Me | OMe | CH |
| 4921 | $Q_{56}$ | COOMe | H | OMe | OMe | CH |
| 4922 | $Q_{56}$ | COOMe | H | Me | OMe | N |
| 4923 | Me | $Q_{56}$ | H | Me | OMe | CH |
| 4924 | Me | $Q_{56}$ | H | OMe | OMe | CH |
| 4925 | Me | $Q_{56}$ | H | Me | OMe | N |
| 4926 | $Q_{57}$ | Cl | H | Me | OMe | CH |
| 4927 | $Q_{57}$ | Cl | H | OMe | OMe | CH |
| 4928 | $Q_{57}$ | Cl | H | Me | OMe | N |
| 4929 | $Q_{57}$ | COOMe | H | Me | OMe | CH |
| 4930 | $Q_{57}$ | COOMe | H | OMe | OMe | CH |
| 4931 | $Q_{57}$ | COOMe | H | Me | OMe | N |
| 4932 | Me | $Q_{57}$ | H | Me | OMe | CH |
| 4933 | Me | $Q_{57}$ | H | OMe | OMe | CH |
| 4934 | Me | $Q_{57}$ | H | Me | OMe | N |
| 4935 | $Q_{58}$ | Cl | H | Me | OMe | CH |
| 4936 | $Q_{58}$ | Cl | H | OMe | OMe | CH |
| 4937 | $Q_{58}$ | Cl | H | Me | OMe | N |
| 4938 | $Q_{58}$ | COOMe | H | Me | OMe | CH |
| 4939 | $Q_{58}$ | COOMe | H | OMe | OMe | CH |
| 4940 | $Q_{58}$ | COOMe | H | Me | OMe | N |
| 4941 | Me | $Q_{58}$ | H | Me | OMe | CH |
| 4942 | Me | $Q_{58}$ | H | OMe | OMe | CH |
| 4943 | Me | $Q_{58}$ | H | Me | OMe | N |
| 4944 | $Q_{59}$ | H | H | Me | OMe | CH |
| 4945 | $Q_{59}$ | H | H | OMe | OMe | CH |
| 4946 | $Q_{59}$ | H | H | Me | OMe | N |
| 4947 | $Q_{59}$ | Me | H | Me | OMe | CH |
| 4948 | $Q_{59}$ | Me | H | OMe | OMe | CH |
| 4949 | $Q_{59}$ | Me | H | Me | OMe | N |
| 4950 | $Q_{59}$ | Cl | H | Me | OMe | CH |
| 4951 | $Q_{59}$ | Cl | H | OMe | OMe | CH |
| 4952 | $Q_{59}$ | Cl | H | Me | OMe | N |
| 4953 | $Q_{59}$ | Br | H | Me | OMe | CH |
| 4954 | $Q_{59}$ | Br | H | OMe | OMe | CH |
| 4955 | $Q_{59}$ | Br | H | Me | OMe | N |
| 4956 | $Q_{59}$ | COOMe | H | Me | OMe | CH |
| 4957 | $Q_{59}$ | COOMe | H | Me | OMe | N |
| 4958 | $Q_{59}$ | COOMe | H | Me | OMe | N |
| 4959 | $Q_{59}$ | COOEt | H | Me | OMe | CH |
| 4960 | $Q_{59}$ | COOEt | H | OMe | OMe | CH |
| 4961 | $Q_{59}$ | COOEt | H | Me | OMe | N |
| 4962 | Me | $Q_{59}$ | H | Me | Me | CH |
| 4963 | Me | $Q_{59}$ | H | Me | OMe | CH |
| 4964 | Me | $Q_{59}$ | H | OMe | OMe | CH |
| 4965 | Me | $Q_{59}$ | H | Me | OMe | N |
| 4966 | Me | $Q_{59}$ | H | Me | OMe | N |
| 4967 | COMe | $Q_{59}$ | H | Me | OMe | CH |
| 4968 | COMe | $Q_{59}$ | H | OMe | OMe | CH |
| 4969 | COMe | $Q_{59}$ | H | Me | OMe | N |
| 4970 | $Q_{60}$ | H | H | Me | OMe | CH |
| 4971 | $Q_{60}$ | H | H | OMe | OMe | CH |
| 4972 | $Q_{60}$ | H | H | Me | OMe | N |
| 4973 | $Q_{60}$ | Cl | H | Me | OMe | CH |
| 4974 | $Q_{60}$ | Cl | H | OMe | OMe | CH |
| 4975 | $Q_{60}$ | Cl | H | Me | OMe | N |

TABLE 3-continued

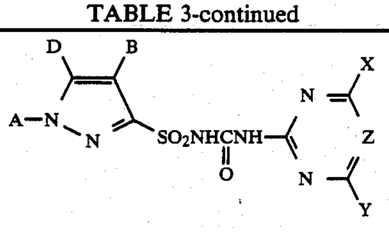

| No. | A | B | D | X | Y | Z |
|---|---|---|---|---|---|---|
| 4976 | $Q_{60}$ | COOMe | H | Me | OMe | CH |
| 4977 | $Q_{60}$ | COOMe | H | OMe | OMe | CH |
| 4978 | $Q_{60}$ | COOMe | H | Me | OMe | N |
| 4979 | Me | $Q_{60}$ | H | Me | OMe | CH |
| 4980 | Me | $Q_{60}$ | H | OMe | OMe | CH |
| 4981 | Me | $Q_{60}$ | H | Me | OMe | N |
| 4970 | $Q_{61}$ | H | H | Me | OMe | CH |
| 4971 | $Q_{61}$ | H | H | OMe | OMe | CH |
| 4972 | $Q_{61}$ | H | H | Me | OMe | N |
| 4973 | $Q_{61}$ | Cl | H | Me | OMe | CH |
| 4974 | $Q_{61}$ | Cl | H | OMe | OMe | CH |
| 4975 | $Q_{61}$ | Cl | H | Me | OMe | N |
| 4976 | $Q_{61}$ | COOMe | H | Me | OMe | CH |
| 4977 | $Q_{61}$ | COOMe | H | OMe | OMe | CH |
| 4978 | $Q_{61}$ | COOMe | H | Me | OMe | N |
| 4979 | Me | $Q_{61}$ | H | Me | OMe | CH |
| 4980 | Me | $Q_{61}$ | H | OMe | OMe | CH |
| 4981 | Me | $Q_{61}$ | H | Me | OMe | N |
| 4982 | $Q_{62}$ | H | H | Me | OMe | CH |
| 4983 | $Q_{62}$ | H | H | OMe | OMe | CH |
| 4984 | $Q_{62}$ | H | H | Me | OMe | N |
| 4985 | $Q_{62}$ | Cl | H | Me | OMe | CH |
| 4986 | $Q_{62}$ | Cl | H | OMe | OMe | CH |
| 4987 | $Q_{62}$ | Cl | H | Me | OMe | N |
| 4988 | $Q_{62}$ | COOMe | H | Me | OMe | CH |
| 4989 | $Q_{62}$ | COOMe | H | OMe | OMe | CH |
| 4990 | $Q_{62}$ | COOMe | H | Me | OMe | N |
| 4991 | Me | $Q_{62}$ | H | Me | OMe | CH |
| 4992 | Me | $Q_{62}$ | H | OMe | OMe | CH |
| 4993 | Me | $Q_{62}$ | H | Me | OMe | N |
| 4994 | $Q_{63}$ | Cl | H | Me | OMe | CH |
| 4995 | $Q_{63}$ | Cl | H | OMe | OMe | CH |
| 4996 | $Q_{63}$ | Cl | H | Me | OMe | N |
| 4997 | $Q_{63}$ | COOMe | H | Me | OMe | CH |
| 4998 | $Q_{63}$ | COOMe | H | OMe | OMe | CH |
| 4999 | $Q_{63}$ | COOMe | H | Me | OMe | N |
| 5000 | Me | $Q_{63}$ | H | Me | OMe | CH |
| 5001 | Me | $Q_{63}$ | H | OMe | OMe | CH |
| 5002 | Me | $Q_{63}$ | H | Me | OMe | N |
| 5003 | $Q_{64}$ | Cl | H | Me | OMe | CH |
| 5004 | $Q_{64}$ | Cl | H | OMe | OMe | CH |
| 5005 | $Q_{64}$ | Cl | H | Me | OMe | N |
| 5006 | $Q_{64}$ | COOMe | H | Me | OMe | CH |
| 5007 | $Q_{64}$ | COOMe | H | OMe | OMe | CH |
| 5008 | $Q_{64}$ | COOMe | H | Me | OMe | N |
| 5009 | Me | $Q_{64}$ | H | Me | OMe | CH |
| 5010 | Me | $Q_{64}$ | H | OMe | OMe | CH |
| 5011 | Me | $Q_{64}$ | H | Me | OMe | N |
| 5012 | $Q_{65}$ | H | H | Me | OMe | CH |
| 5013 | $Q_{65}$ | H | H | OMe | OMe | CH |
| 5014 | $Q_{65}$ | H | H | Me | OMe | N |
| 5015 | $Q_{65}$ | Cl | H | Me | OMe | CH |
| 5016 | $Q_{65}$ | Cl | H | OMe | OMe | CH |
| 5017 | $Q_{65}$ | Cl | H | Me | OMe | N |
| 5018 | $Q_{65}$ | COOMe | H | Me | OMe | CH |
| 5019 | $Q_{65}$ | COOMe | H | OMe | OMe | CH |
| 5020 | $Q_{65}$ | COOMe | H | Me | OMe | N |
| 5021 | Me | $Q_{65}$ | H | Me | OMe | CH |
| 5022 | Me | $Q_{65}$ | H | OMe | OMe | CH |
| 5023 | Me | $Q_{65}$ | H | Me | OMe | N |
| 5024 | $Q_{66}$ | Cl | H | Me | OMe | CH |
| 5025 | $Q_{66}$ | Cl | H | OMe | OMe | CH |
| 5026 | $Q_{66}$ | Cl | H | Me | OMe | N |
| 5027 | $Q_{66}$ | COOMe | H | Me | OMe | CH |
| 5028 | $Q_{66}$ | COOMe | H | OMe | OMe | CH |
| 5029 | $Q_{66}$ | COOMe | H | Me | OMe | N |
| 5030 | Me | $Q_{66}$ | H | Me | OMe | CH |
| 5031 | Me | $Q_{66}$ | H | OMe | OMe | CH |
| 5032 | Me | $Q_{66}$ | H | Me | OMe | N |
| 5033 | $Q_{67}$ | Cl | H | Me | OMe | CH |
| 5034 | $Q_{67}$ | Cl | H | OMe | OMe | CH |

TABLE 3-continued

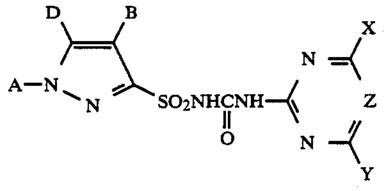

| No. | A | B | D | X | Y | Z |
|---|---|---|---|---|---|---|
| 5035 | $Q_{67}$ | Cl | H | Me | OMe | N |
| 5036 | $Q_{67}$ | COOMe | H | Me | OMe | CH |
| 5037 | $Q_{67}$ | COOMe | H | OMe | OMe | CH |
| 5038 | $Q_{67}$ | COOMe | H | Me | OMe | N |
| 5039 | Me | $Q_{67}$ | H | Me | OMe | CH |
| 5040 | Me | $Q_{67}$ | H | OMe | OMe | CH |
| 5041 | Me | $Q_{67}$ | H | Me | OMe | N |
| 5042 | $Q_{68}$ | Cl | H | Me | OMe | CH |
| 5043 | $Q_{68}$ | Cl | H | OMe | OMe | CH |
| 5044 | $Q_{68}$ | Cl | H | Me | OMe | N |
| 5045 | $Q_{68}$ | COOMe | H | Me | OMe | CH |
| 5046 | $Q_{68}$ | COOMe | H | OMe | OMe | CH |
| 5047 | $Q_{68}$ | COOMe | H | Me | OMe | N |
| 5048 | Me | $Q_{68}$ | H | Me | OMe | CH |
| 5049 | Me | $Q_{68}$ | H | OMe | OMe | CH |
| 5050 | Me | $Q_{68}$ | H | Me | OMe | N |
| 5051 | $Q_{69}$ | Cl | H | Me | OMe | CH |
| 5052 | $Q_{69}$ | Cl | h | OEM | OMe | CH |
| 5053 | $Q_{69}$ | CL | H | Me | OMe | N |
| 5054 | $Q_{69}$ | COOMe | H | OMe | OMe | CH |
| 5055 | $Q_{69}$ | COOMe | H | OMe | OMe | CH |
| 5056 | $Q_{69}$ | COOMe | H | Me | OMe | N |
| 5057 | Me | $Q_{69}$ | H | Me | OMe | CH |
| 5058 | Me | $Q_{69}$ | H | OMe | OMe | CH |
| 5059 | Me | $Q_{69}$ | H | Me | OMe | N |
| 5060 | $Q_{70}$ | H | H | Me | OMe | CH |
| 5061 | $Q_{70}$ | H | H | OMe | OMe | CH |
| 5062 | $Q_{70}$ | H | H | Me | OMe | N |
| 5063 | $Q_{70}$ | Cl | H | Me | OMe | CH |
| 5064 | $Q_{70}$ | Cl | H | OMe | OMe | CH |
| 5065 | $Q_{70}$ | Cl | H | Me | OMe | N |
| 5066 | $Q_{70}$ | COOMe | H | Me | OMe | CH |
| 5067 | $Q_{70}$ | COOMe | H | OMe | OMe | CH |
| 5068 | $Q_{70}$ | COOMe | H | Me | OMe | N |
| 5069 | Me | $Q_{70}$ | H | Me | OMe | CH |
| 5070 | Me | $Q_{70}$ | H | OMe | OMe | CH |
| 5071 | Me | $Q_{70}$ | H | Me | OMe | N |
| 5072 | $Q_{71}$ | Cl | H | Me | OMe | CH |
| 5073 | $Q_{71}$ | Cl | H | OMe | OMe | CH |
| 5074 | $Q_{71}$ | Cl | H | Me | OMe | N |
| 5075 | $Q_{71}$ | COOMe | H | Me | OMe | CH |
| 5076 | $Q_{71}$ | COOMe | H | OMe | OMe | CH |
| 5077 | $Q_{71}$ | COOMe | H | Me | OMe | N |
| 5078 | Me | $Q_{71}$ | H | Me | OMe | CH |
| 5079 | Me | $Q_{71}$ | H | OMe | OMe | CH |
| 5080 | Me | $Q_{71}$ | H | Me | OMe | N |
| 5081 | $Q_{72}$ | Cl | H | Me | OMe | CH |
| 5082 | $Q_{72}$ | Cl | H | OMe | OMe | CH |
| 5083 | $Q_{72}$ | Cl | H | Me | OMe | N |
| 5084 | $Q_{72}$ | COOMe | H | Me | OMe | CH |
| 5085 | $Q_{72}$ | COOMe | H | OMe | OMe | CH |
| 5086 | $Q_{72}$ | COOMe | H | Me | OMe | N |
| 5087 | Me | $Q_{72}$ | H | Me | OMe | CH |
| 5088 | Me | $Q_{72}$ | H | OMe | OMe | CH |
| 5089 | Me | $Q_{72}$ | H | Me | OMe | N |
| 5090 | $Q_{73}$ | Cl | H | Me | OMe | CH |
| 5091 | $Q_{73}$ | Cl | H | OMe | OMe | CH |
| 5092 | $Q_{73}$ | Cl | H | Me | OMe | N |
| 5093 | $Q_{73}$ | COOMe | H | Me | OMe | CH |
| 5094 | $Q_{73}$ | COOMe | H | OMe | OMe | CH |
| 5095 | $Q_{73}$ | COOMe | H | Me | OMe | N |
| 5096 | Me | $Q_{73}$ | H | Me | OMe | CH |
| 5097 | Me | $Q_{73}$ | H | OMe | OMe | CH |
| 5098 | Me | $Q_{73}$ | H | Me | OMe | N |
| 5099 | $Q_{74}$ | Cl | H | Me | OMe | CH |
| 5100 | $Q_{74}$ | Cl | H | OMe | OMe | CH |
| 5101 | $Q_{74}$ | Cl | H | Me | OMe | N |
| 5102 | $Q_{74}$ | COOMe | H | Me | OMe | CH |
| 5103 | $Q_{74}$ | COOMe | H | OMe | OMe | CH |
| 5104 | $Q_{74}$ | COOMe | H | Me | OMe | N |
| 5105 | Me | $Q_{74}$ | H | Me | OMe | CH |

TABLE 3-continued

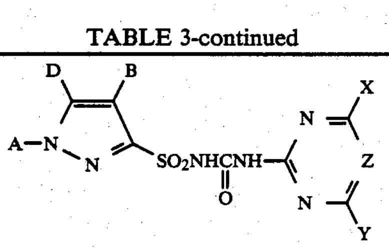

| No. | A | B | D | X | Y | Z |
|---|---|---|---|---|---|---|
| 5106 | Me | $Q_{74}$ | H | OMe | OMe | CH |
| 5107 | Me | $Q_{74}$ | H | Me | OMe | N |
| 5108 | $Q_{75}$ | Cl | H | Me | OMe | CH |
| 5109 | $Q_{75}$ | Cl | H | OMe | OMe | CH |
| 5110 | $Q_{75}$ | Cl | H | Me | OMe | N |
| 5111 | $Q_{75}$ | CL | H | Me | OMe | N |
| 5112 | $Q_{75}$ | COOMe | H | OMe | OMe | CH |
| 5113 | $Q_{75}$ | COOMe | H | Me | OMe | N |
| 5114 | Me | $Q_{75}$ | H | Me | OMe | CH |
| 5115 | Me | $Q_{75}$ | H | OMe | OMe | CH |
| 5116 | Me | $Q_{75}$ | H | Me | OMe | N |
| 5117 | 76 | Cl | H | Me | OMe | CH |
| 5118 | $Q_{76}$ | Cl | H | OMe OMe | CH | |
| 5119 | $Q_{76}$ | Cl | H | Me | OMe | N |
| 5120 | $Q_{76}$ | COOMe | H | Me | OMe | CH |
| 5121 | $Q_{76}$ | COOMe | H | OMe | OMe | CH |
| 5122 | $Q_{76}$ | COOMe | H | Me | OMe | N |
| 5123 | Me | $Q_{76}$ | H | Me | OMe | CH |
| 5124 | Me | $Q_{76}$ | H | OMe | OMe | CH |
| 5125 | Me | $Q_{76}$ | H | Me | OMe | N |
| 5720 | $Q_{77}$ | Cl | H | Me | OMe | CH |
| 5721 | $Q_{77}$ | Cl | H | OMe | OMe | CH |
| 5722 | $Q_{77}$ | Cl | H | Me | OMe | N |
| 5723 | $Q_{77}$ | COOMe | H | Me | OMe | CH |
| 5724 | $Q_{77}$ | COOMe | H | OMe | OMe | CH |
| 5725 | $Q_{77}$ | COOMe | H | Me | OMe | N |
| 5726 | Me | $Q_{77}$ | H | Me | OMe | CH |
| 5727 | Me | $Q_{77}$ | H | OMe | OMe | CH |
| 5728 | Me | $Q_{77}$ | H | Me | OMe | N |
| 5729 | $Q_{78}$ | H | H | Me | OMe | CH |
| 5730 | $Q_{78}$ | H | H | OMe | OMe | CH |
| 5731 | $Q_{78}$ | H | H | Me | OMe | N |
| 5732 | $Q_{78}$ | Me | H | Me | OMe | CH |
| 5733 | $Q_{78}$ | Me | H | OMe | OMe | CH |
| 5734 | $Q_{78}$ | Me | H | Me | OMe | N |
| 5735 | $Q_{78}$ | Cl | H | Me | OMe | CH |
| 5736 | $Q_{78}$ | Cl | H | OMe | OMe | CH |
| 5737 | $Q_{78}$ | Cl | H | Me | OMe | N |
| 5738 | $Q_{78}$ | Br | H | Me | OMe | CH |
| 5739 | $Q_{78}$ | Br | H | OMe | OMe | CH |
| 5740 | $Q_{78}$ | Br | H | Me | OMe | N |
| 5741 | $Q_{78}$ | COOMe | H | Me | OMe | CH |
| 5742 | $Q_{78}$ | COOMe | H | OMe | OMe | CH |
| 5743 | $Q_{78}$ | COOMe | H | Me | OMe | N |
| 5744 | $Q_{78}$ | COOEt | H | Me | OMe | CH |
| 5745 | $Q_{78}$ | COOEt | H | OMe | OMe | CH |
| 5746 | $Q_{78}$ | COOEt | H | Me | OMe | N |
| 5747 | Me | $Q_{78}$ | H | Me | Me | CH |
| 5748 | Me | $Q_{78}$ | H | Me | OMe | CH |
| 5749 | Me | $Q_{78}$ | H | OMe | OMe | CH |
| 5750 | Me | $Q_{78}$ | H | Me | OMe | N |
| 5751 | Me | $Q_{78}$ | H | OMe | OMe | N |
| 5752 | COOMe | $Q_{78}$ | H | Me | OMe | CH |
| 5753 | COOMe | $Q_{78}$ | H | OMe | OMe | CH |
| 5754 | COOMe | $Q_{78}$ | H | Me | OMe | N |
| 5755 | $Q_{79}$ | H | H | Me | OMe | CH |
| 5756 | $Q_{79}$ | H | H | OMe | OMe | CH |
| 5757 | $Q_{79}$ | H | H | Me | OMe | N |
| 5758 | $Q_{79}$ | Me | H | Me | OMe | CH |
| 5759 | $Q_{79}$ | Me | H | OMe | OMe | CH |
| 5760 | $Q_{79}$ | Me | H | Me | OMe | N |
| 5761 | $Q_{79}$ | Cl | H | Me | OMe | CH |
| 5762 | $Q_{79}$ | Cl | H | OMe | OMe | CH |
| 5763 | $Q_{79}$ | Cl | H | Me | OMe | N |
| 5764 | $Q_{79}$ | Br | H | Me | OMe | CH |
| 5765 | $Q_{79}$ | Br | H | OMe | OMe | CH |
| 5766 | $Q_{79}$ | Br | H | Me | OMe | N |
| 5767 | $Q_{79}$ | COOMe | H | Me | OMe | CH |
| 5768 | $Q_{79}$ | COOMe | H | OMe | OMe | CH |
| 5769 | $Q_{79}$ | COOMe | H | Me | OMe | N |
| 5770 | $Q_{79}$ | COOEt | H | Me | OMe | CH |

TABLE 3-continued

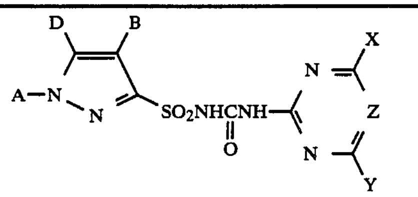

| No. | A | B | D | X | Y | Z |
|---|---|---|---|---|---|---|
| 5771 | $Q_{79}$ | COOEt | H | OMe | OMe | CH |
| 5772 | $Q_{79}$ | COOEt | H | Me | OMe | N |
| 5773 | Me | $Q_{79}$ | H | Me | Me | CH |
| 5774 | Me | $Q_{79}$ | H | Me | OMe | CH |
| 5775 | Me | $Q_{79}$ | H | OMe | OMe | CH |
| 5776 | Me | $Q_{79}$ | H | Me | OMe | N |
| 5777 | Me | $Q_{79}$ | H | OMe | OMe | N |
| 5778 | COOMe | $Q_{79}$ | H | Me | OMe | CH |
| 5779 | COOMe | $Q_{79}$ | H | OMe | OMe | CH |
| 5780 | COOMe | $Q_{79}$ | H | Me | OMe | N |
| 5781 | $Q_{80}$ | H | H | Me | OMe | CH |
| 5782 | $Q_{80}$ | H | H | OMe | OMe | CH |
| 5783 | $Q_{80}$ | H | H | Me | OMe | N |
| 5784 | $Q_{80}$ | Cl | H | Me | OMe | CH |
| 5785 | $Q_{80}$ | Cl | H | OMe | OMe | CH |
| 5786 | $Q_{80}$ | Cl | H | Me | OMe | N |
| 5787 | $Q_{80}$ | COOMe | H | Me | OMe | CH |
| 5788 | $Q_{80}$ | COOMe | H | OMe | OMe | CH |
| 5789 | $Q_{80}$ | COOMe | H | Me | OMe | N |
| 5790 | Me | $Q_{80}$ | H | Me | OMe | CH |
| 5791 | Me | $Q_{80}$ | H | OMe | OMe | CH |
| 5792 | Me | $Q_{80}$ | H | Me | OMe | N |
| 5793 | $Q_{81}$ | Cl | H | Me | OMe | CH |
| 5794 | $Q_{81}$ | Cl | H | OMe | OMe | CH |
| 5795 | $Q_{81}$ | Cl | H | Me | OMe | N |
| 5796 | $Q_{81}$ | COOMe | H | Me | OMe | CH |
| 5797 | $Q_{81}$ | COOMe | H | OMe | OMe | CH |
| 5798 | $Q_{81}$ | COOMe | H | Me | OMe | N |
| 5799 | Me | $Q_{81}$ | H | Me | OMe | CH |
| 5800 | Me | $Q_{81}$ | H | OMe | OMe | CH |
| 5801 | Me | $Q_{81}$ | H | Me | OMe | N |
| 5802 | $Q_{82}$ | Cl | H | Me | OMe | CH |
| 5803 | $Q_{82}$ | Cl | H | OMe | OMe | CH |
| 5804 | $Q_{82}$ | Cl | H | Me | OMe | N |
| 5805 | $Q_{82}$ | COOMe | H | OMe | OMe | CH |
| 5806 | $Q_{82}$ | COOMe | H | OMe | OMe | CH |
| 5807 | $Q_{82}$ | COOMe | H | Me | OMe | N |
| 5808 | Me | $Q_{82}$ | H | Me | OMe | CH |
| 5809 | Me | $Q_{82}$ | H | OMe | OMe | CH |
| 5810 | Me | $Q_{82}$ | H | Me | OMe | N |
| 5811 | $Q_{83}$ | Cl | H | Me | OMe | CH |
| 5812 | $Q_{83}$ | Cl | H | OMe | OMe | CH |
| 5813 | $Q_{83}$ | Cl | H | Me | OMe | N |
| 5814 | $Q_{83}$ | COOMe | H | Me | OMe | CH |
| 5815 | $Q_{83}$ | COOMe | H | OMe | OMe | CH |
| 5816 | $Q_{83}$ | COOMe | H | Me | OMe | N |
| 5817 | Me | $Q_{83}$ | H | Me | OMe | CH |
| 5818 | Me | $Q_{83}$ | H | OMe | OMe | CH |
| 5819 | Me | $Q_{83}$ | H | Me | OMe | N |
| 6551 | $Q_{16}$ | COOEt | H | OMe | OMe | CH |

In the above, $Q_1$ to $Q_{83}$ are as defined above.

TABLE 4

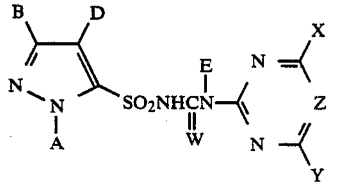

| No. | A | B | D | E | W | X | Y | Z |
|---|---|---|---|---|---|---|---|---|
| 5126 | $Q_1$ | H | COOMe | H | S | Me | OMe | CH |
| 5127 | $Q_1$ | H | COOMe | H | S | OMe | OMe | CH |
| 5128 | $Q_1$ | H | COOEt | H | S | Me | OMe | CH |
| 5129 | $Q_1$ | H | COOEt | H | S | OMe | OMe | CH |

TABLE 4-continued

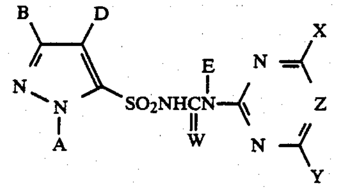

| No. | A | B | D | E | W | X | Y | Z |
|---|---|---|---|---|---|---|---|---|
| 5130 | $Q_1$ | H | COOEt | H | S | Me | OMe | N |
| 5131 | $Q_1$ | H | COOMe | Me | O | Me | OMe | CH |
| 5132 | $Q_1$ | H | COOMe | Me | O | OMe | OMe | CH |
| 5133 | $Q_1$ | H | COOEt | Me | O | Me | OMe | CH |
| 5134 | $Q_1$ | H | COOEt | Me | O | OMe | OMe | CH |
| 5135 | $Q_1$ | H | COOEt | Me | O | Me | OMe | N |
| 5136 | $Q_1$ | H | COOMe | OMe | O | Me | OMe | CH |
| 5137 | $Q_1$ | H | COOMe | OMe | O | OMe | OMe | CH |
| 5138 | $Q_1$ | H | COOEt | OMe | O | Me | OMe | CH |
| 5139 | $Q_1$ | H | COOEt | OMe | O | OMe | OMe | CH |
| 5140 | $Q_1$ | H | COOEt | OMe | O | Me | OMe | N |
| 5141 | $Q_1$ | H | COOMe | $CH_2CH{=}CH_2$ | O | Me | OMe | CH |
| 5142 | $Q_1$ | H | COOMe | $CH_2CH{=}CH_2$ | O | OMe | OMe | CH |
| 5143 | $Q_1$ | H | COOEt | $CH_2CH{=}CH_2$ | O | Me | OMe | CH |
| 5144 | $Q_1$ | H | COOEt | $CH_2CH{=}CH_2$ | O | OMe | OMe | CH |
| 5145 | $Q_1$ | H | COOEt | $CH_2CH{=}CH_2$ | O | Me | OMe | N |
| 5146 | $Q_1$ | H | COOMe | $CH_2C{\equiv}CH$ | O | Me | OMe | CH |
| 5147 | $Q_1$ | H | COOMe | $CH_2C{\equiv}CH$ | O | OMe | OMe | CH |
| 5148 | $Q_1$ | H | COOEt | $CH_2C{\equiv}CH$ | O | Me | OMe | CH |
| 5149 | $Q_1$ | H | COOEt | $CH_2C{\equiv}CH$ | O | OMe | OMe | CH |
| 5150 | $Q_1$ | H | COOEt | $CH_2C{\equiv}CH$ | O | Me | OMe | N |
| 5151 | $Q_2$ | H | COOMe | H | S | Me | OMe | CH |
| 5152 | $Q_2$ | H | COOMe | H | S | OMe | OMe | CH |
| 5153 | $Q_2$ | H | COOEt | H | S | Me | OMe | CH |
| 5154 | $Q_2$ | H | COOEt | H | S | OMe | OMe | CH |
| 5155 | $Q_2$ | H | COOMe | Me | O | Me | OMe | CH |
| 5156 | $Q_2$ | H | COOMe | Me | O | OMe | OMe | CH |
| 5157 | $Q_2$ | H | COOEt | Me | O | OMe | OMe | CH |
| 5158 | $Q_2$ | H | COOMe | OMe | O | Me | OMe | CH |
| 5159 | $Q_2$ | H | COOMe | OMe | O | OMe | OMe | CH |
| 5160 | $Q_2$ | H | COOEt | OMe | O | OMe | OMe | CH |
| 5161 | $Q_2$ | H | COOMe | $CH_2CH{=}CH_2$ | O | Me | OMe | CH |
| 5162 | $Q_2$ | H | COOMe | $CH_2CH{=}CH_2$ | O | OMe | OMe | CH |
| 5163 | $Q_2$ | H | COOEt | $CH_2CH{=}CH_2$ | O | OMe | OMe | CH |
| 5164 | $Q_2$ | H | COOMe | $CH_2C{\equiv}CH$ | O | Me | OMe | CH |
| 5165 | $Q_2$ | H | COOMe | $CH_2C{\equiv}CH$ | O | OMe | OMe | CH |
| 5166 | $Q_2$ | H | COOEt | $CH_2C{\equiv}CH$ | O | OMe | OMe | CH |
| 5167 | $Q_8$ | H | COOMe | H | S | Me | OMe | CH |
| 5168 | $Q_8$ | H | COOMe | H | S | OMe | OMe | CH |
| 5169 | $Q_8$ | H | COOEt | H | S | Me | OMe | CH |
| 5170 | $Q_8$ | H | COOEt | H | S | OMe | OMe | CH |
| 5171 | $Q_8$ | H | COOMe | Me | O | Me | OMe | CH |
| 5172 | $Q_8$ | H | COOMe | Me | O | OMe | OMe | CH |
| 5173 | $Q_8$ | H | COOEt | Me | O | OMe | OMe | CH |
| 5174 | $Q_8$ | H | COOMe | OMe | O | Me | OMe | CH |
| 5175 | $Q_8$ | H | COOMe | OMe | O | OMe | OMe | CH |
| 5176 | $Q_8$ | H | COOEt | OMe | O | OMe | OMe | CH |
| 5177 | $Q_8$ | H | COOMe | $CH_2CH{=}CH_2$ | O | Me | OMe | CH |
| 5178 | $Q_8$ | H | COOMe | $CH_2CH{=}CH_2$ | O | OMe | OMe | CH |
| 5179 | $Q_8$ | H | COOEt | $CH_2CH{=}CH_2$ | O | OMe | OMe | CH |
| 5180 | $Q_8$ | H | COOMe | $CH_2C{\equiv}CH$ | O | Me | OMe | CH |
| 5181 | $Q_8$ | H | COOMe | $CH_2C{\equiv}CH$ | O | OMe | OMe | CH |
| 5182 | $Q_8$ | H | COOEt | $CH_2C{\equiv}CH$ | O | OMe | OMe | CH |
| 5183 | $Q_{32}$ | H | COOMe | H | S | Me | OMe | CH |
| 5184 | $Q_{32}$ | H | COOMe | H | S | OMe | OMe | CH |
| 5185 | $Q_{32}$ | H | COOEt | H | S | Me | OMe | CH |
| 5186 | $Q_{32}$ | H | COOEt | H | S | OMe | OMe | CH |
| 5187 | $Q_{32}$ | H | COOMe | Me | O | Me | OMe | CH |
| 5188 | $Q_{32}$ | H | COOMe | Me | O | OMe | OMe | CH |
| 5189 | $Q_{32}$ | H | COOEt | Me | O | OMe | OMe | CH |
| 5190 | $Q_{32}$ | H | COOMe | OMe | O | Me | OMe | CH |
| 5191 | $Q_{32}$ | H | COOMe | OMe | O | OMe | OMe | CH |
| 5192 | $Q_{32}$ | H | COOEt | OMe | O | OMe | OMe | CH |
| 5193 | $Q_{32}$ | H | COOMe | $CH_2CH{=}CH_2$ | O | Me | OMe | CH |
| 5194 | $Q_{32}$ | H | COOMe | $CH_2CH{=}CH_2$ | O | OMe | OMe | CH |
| 5195 | $Q_{32}$ | H | COOEt | $CH_2CH{=}CH_2$ | O | OMe | OMe | CH |
| 5196 | $Q_{32}$ | H | COOMe | $CH_2C{\equiv}CH$ | O | Me | OMe | CH |
| 5197 | $Q_{32}$ | H | COOMe | $CH_2C{\equiv}CH$ | O | OMe | OMe | CH |
| 5198 | $Q_{32}$ | H | COOEt | $CH_2C{\equiv}CH$ | O | OMe | OMe | CH |
| 5199 | $Q_{45}$ | H | COOMe | H | S | Me | OMe | CH |
| 5200 | $Q_{45}$ | H | COOMe | H | S | OMe | OMe | CH |

TABLE 4-continued

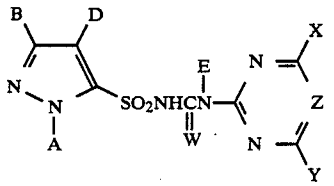

| No. | A | B | D | E | W | X | Y | Z |
|---|---|---|---|---|---|---|---|---|
| 5201 | $Q_{45}$ | H | COOEt | H | S | Me | OMe | CH |
| 5202 | $Q_{45}$ | H | COOEt | H | S | OMe | OMe | CH |
| 5203 | $Q_{45}$ | H | COOMe | Me | O | Me | OMe | CH |
| 5204 | $Q_{45}$ | H | COOMe | Me | O | OMe | OMe | CH |
| 5205 | $Q_{45}$ | H | COOEt | Me | O | OMe | OMe | CH |
| 5206 | $Q_{45}$ | H | COOMe | OMe | O | Me | OMe | CH |
| 5207 | $Q_{45}$ | H | COOMe | OMe | O | OMe | OMe | CH |
| 5208 | $Q_{45}$ | H | COOEt | OMe | O | OMe | OMe | CH |
| 5209 | $Q_{45}$ | H | COOMe | $CH_2CH{=}CH_2$ | O | Me | OMe | CH |
| 5210 | $Q_{45}$ | H | COOMe | $CH_2CH{=}CH_2$ | O | OMe | OMe | CH |
| 5211 | $Q_{45}$ | H | COOEt | $CH_2CH{=}CH_2$ | O | OMe | OMe | CH |
| 5212 | $Q_{45}$ | H | COOMe | $CH_2C{\equiv}CH$ | O | Me | OMe | CH |
| 5213 | $Q_{45}$ | H | COOMe | $CH_2C{\equiv}CH$ | O | OMe | OMe | CH |
| 5214 | $Q_{45}$ | H | COOEt | $CH_2C{\equiv}CH$ | O | OMe | OMe | CH |
| 5215 | $Q_{59}$ | H | COOMe | H | S | Me | OMe | CH |
| 5216 | $Q_{59}$ | H | COOMe | H | S | OMe | OMe | CH |
| 5217 | $Q_{59}$ | H | COOEt | H | S | Me | OMe | CH |
| 5218 | $Q_{59}$ | H | COOEt | H | S | OMe | OMe | CH |
| 5219 | $Q_{59}$ | H | COOMe | Me | O | Me | OMe | CH |
| 5220 | $Q_{59}$ | H | COOMe | Me | O | OMe | OMe | CH |
| 5221 | $Q_{59}$ | H | COOEt | Me | O | OMe | OMe | CH |
| 5222 | $Q_{59}$ | H | COOMe | OMe | O | Me | OMe | CH |
| 5223 | $Q_{59}$ | H | COOMe | OMe | O | OMe | OMe | CH |
| 5224 | $Q_{59}$ | H | COOEt | OMe | O | OMe | OMe | CH |
| 5225 | $Q_{59}$ | H | COOMe | $CH_2CH{=}CH_2$ | O | Me | OMe | CH |
| 5226 | $Q_{59}$ | H | COOMe | $CH_2CH{=}CH_2$ | O | OMe | OMe | CH |
| 5227 | $Q_{59}$ | H | COOEt | $CH_2CH{=}CH_2$ | O | OMe | OMe | CH |
| 5228 | $Q_{59}$ | H | COOMe | $CH_2C{\equiv}CH$ | O | Me | OMe | CH |
| 5229 | $Q_{59}$ | H | COOMe | $CH_2C{\equiv}CH$ | O | OMe | OMe | CH |
| 5230 | $Q_{59}$ | H | COOEt | $CH_2C{\equiv}CH$ | O | OMe | OMe | CH |
| 5231 | Me | H | $Q_1$ | H | S | Me | OMe | CH |
| 5232 | Me | H | $Q_1$ | H | S | OMe | OMe | CH |
| 5233 | Me | H | $Q_1$ | H | S | Me | OMe | CH |
| 5234 | Me | H | $Q_1$ | H | S | OMe | OMe | CH |
| 5235 | Me | H | $Q_1$ | H | S | Me | OMe | N |
| 5236 | Me | H | $Q_1$ | Me | O | Me | OMe | CH |
| 5237 | Me | H | $Q_1$ | Me | O | OMe | OMe | CH |
| 5238 | Me | H | $Q_1$ | Me | O | Me | OMe | CH |
| 5239 | Me | H | $Q_1$ | Me | O | OMe | OMe | CH |
| 5240 | Me | H | $Q_1$ | Me | O | Me | OMe | N |
| 5241 | Me | H | $Q_1$ | OMe | O | Me | OMe | CH |
| 5242 | Me | H | $Q_1$ | OMe | O | OMe | OMe | CH |
| 5243 | Me | H | $Q_1$ | OMe | O | Me | OMe | CH |
| 5244 | Me | H | $Q_1$ | OMe | O | OMe | OMe | CH |
| 5245 | Me | H | $Q_1$ | OMe | O | Me | OMe | N |
| 5246 | Me | H | $Q_1$ | $CH_2CH{=}CH_2$ | O | Me | OMe | CH |
| 5247 | Me | H | $Q_1$ | $CH_2CH{=}CH_2$ | O | OMe | OMe | CH |
| 5248 | Me | H | $Q_1$ | $CH_2CH{=}CH_2$ | O | Me | OMe | CH |
| 5249 | Me | H | $Q_1$ | $CH_2CH{=}CH_2$ | O | OMe | OMe | CH |
| 5250 | Me | H | $Q_1$ | $CH_2CH{=}CH_2$ | O | Me | OMe | N |
| 5251 | Me | H | $Q_1$ | $CH_2C{\equiv}CH$ | O | Me | OMe | CH |
| 5252 | Me | H | $Q_1$ | $CH_2C{\equiv}CH$ | O | OMe | OMe | CH |
| 5253 | Me | H | $Q_1$ | $CH_2C{\equiv}CH$ | O | Me | OMe | CH |
| 5254 | Me | H | $Q_1$ | $CH_2C{\equiv}CH$ | O | OMe | OMe | CH |
| 5255 | Me | H | $Q_1$ | $CH_2C{\equiv}CH$ | O | Me | OMe | N |
| 5820 | $Q_5$ | H | COOMe | H | S | Me | OMe | CH |
| 5821 | $Q_5$ | H | COOMe | H | S | OMe | OMe | CH |
| 5822 | $Q_5$ | H | COOEt | H | S | Me | OMe | CH |
| 5823 | $Q_5$ | H | COOEt | H | S | OMe | OMe | CH |
| 5824 | $Q_5$ | H | COOMe | Me | O | Me | OMe | CH |
| 5825 | $Q_5$ | H | COOMe | Me | O | OMe | OMe | CH |
| 5826 | $Q_5$ | H | COOEt | Me | O | OMe | OMe | CH |
| 5827 | $Q_5$ | H | COOMe | OMe | O | Me | OMe | CH |
| 5828 | $Q_5$ | H | COOMe | OMe | O | OMe | OMe | CH |
| 5829 | $Q_5$ | H | COOEt | OMe | O | OMe | OMe | CH |
| 5830 | $Q_5$ | H | COOMe | $CH_2CH{=}CH_2$ | O | Me | OMe | CH |
| 5831 | $Q_5$ | H | COOMe | $CH_2CH{=}CH_2$ | O | OMe | OMe | CH |
| 5832 | $Q_5$ | H | COOEt | $CH_2CH{=}CH_2$ | O | OMe | OMe | CH |
| 5833 | $Q_5$ | H | COOMe | $CH_2C{\equiv}CH$ | O | Me | OMe | CH |
| 5834 | $Q_5$ | H | COOMe | $CH_2C{\equiv}CH$ | O | OMe | OMe | CH |
| 5835 | $Q_5$ | H | COOEt | $CH_2C{\equiv}CH$ | O | OMe | OMe | CH |

TABLE 4-continued

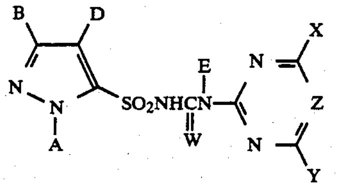

| No. | A | B | D | E | W | X | Y | Z |
|---|---|---|---|---|---|---|---|---|
| 5836 | $Q_{10}$ | H | COOMe | H | S | Me | OMe | CH |
| 5837 | $Q_{10}$ | H | COOMe | H | S | OMe | OMe | CH |
| 5838 | $Q_{10}$ | H | COOEt | H | S | Me | OMe | CH |
| 5839 | $Q_{10}$ | H | COOEt | H | S | OMe | OMe | CH |
| 5840 | $Q_{10}$ | H | COOMe | Me | O | Me | OMe | CH |
| 5841 | $Q_{10}$ | H | COOMe | Me | O | OMe | OMe | CH |
| 5842 | $Q_{10}$ | H | COOEt | Me | O | OMe | OMe | CH |
| 5843 | $Q_{10}$ | H | COOMe | OMe | O | Me | OMe | CH |
| 5844 | $Q_{10}$ | H | COOMe | OMe | O | OMe | OMe | CH |
| 5845 | $Q_{10}$ | H | COOEt | OMe | O | OMe | OMe | CH |
| 5846 | $Q_{10}$ | H | COOMe | $CH_2CH{=}CH_2$ | O | Me | OMe | CH |
| 5847 | $Q_{10}$ | H | COOMe | $CH_2CH{=}CH_2$ | O | OMe | OMe | CH |
| 5848 | $Q_{10}$ | H | COOEt | $CH_2CH{=}CH_2$ | O | OMe | OMe | CH |
| 5849 | $Q_{10}$ | H | COOMe | $CH_2C{\equiv}CH$ | O | Me | OMe | CH |
| 5850 | $Q_{10}$ | H | COOMe | $CH_2C{\equiv}CH$ | O | OMe | OMe | CH |
| 5851 | $Q_{10}$ | H | COOEt | $CH_2C{\equiv}CH$ | O | OMe | OMe | CH |
| 5852 | $Q_{78}$ | H | COOMe | H | S | Me | OMe | CH |
| 5853 | $Q_{78}$ | H | COOMe | H | S | OMe | OMe | CH |
| 5854 | $Q_{78}$ | H | COOEt | H | S | Me | OMe | CH |
| 5855 | $Q_{78}$ | H | COOEt | H | S | OMe | OMe | CH |
| 5856 | $Q_{78}$ | H | COOMe | Me | O | Me | OMe | CH |
| 5857 | $Q_{78}$ | H | COOMe | Me | O | OMe | OMe | CH |
| 5858 | $Q_{78}$ | H | COOEt | Me | O | OMe | OMe | CH |
| 5859 | $Q_{78}$ | H | COOMe | OMe | O | Me | OMe | CH |
| 5860 | $Q_{78}$ | H | COOMe | OMe | O | OMe | OMe | CH |
| 5861 | $Q_{78}$ | H | COOEt | OMe | O | OMe | OMe | CH |
| 5862 | $Q_{78}$ | H | COOMe | $CH_2CH{=}CH_2$ | O | Me | OMe | CH |
| 5863 | $Q_{78}$ | H | COOMe | $CH_2CH{=}CH_2$ | O | OMe | OMe | CH |
| 5864 | $Q_{78}$ | H | COOEt | $CH_2CH{=}CH_2$ | O | OMe | OMe | CH |
| 5865 | $Q_{78}$ | H | COOMe | $CH_2C{\equiv}CH$ | O | Me | OMe | CH |
| 5866 | $Q_{78}$ | H | COOMe | $CH_2C{\equiv}CH$ | O | OMe | OMe | CH |
| 5867 | $Q_{78}$ | H | COOEt | $CH_2C{\equiv}CH$ | O | OMe | OMe | CH |
| 5868 | $Q_{79}$ | H | COOMe | H | S | Me | OMe | CH |
| 5869 | $Q_{79}$ | H | COOMe | H | S | OMe | OMe | CH |
| 5870 | $Q_{79}$ | H | COOEt | H | S | Me | OMe | CH |
| 5871 | $Q_{79}$ | H | COOEt | H | S | OMe | OMe | CH |
| 5872 | $Q_{79}$ | H | COOMe | Me | O | Me | OMe | CH |
| 5873 | $Q_{79}$ | H | COOMe | Me | O | OMe | OMe | CH |
| 5874 | $Q_{79}$ | H | COOEt | Me | O | OMe | OMe | CH |
| 5875 | $Q_{79}$ | H | COOMe | OMe | O | Me | OMe | CH |
| 5876 | $Q_{79}$ | H | COOMe | OMe | O | OMe | OMe | CH |
| 5877 | $Q_{79}$ | H | COOEt | OMe | O | OMe | OMe | CH |
| 5878 | $Q_{79}$ | H | COOMe | $CH_2CH{=}CH_2$ | O | Me | OMe | CH |
| 5879 | $Q_{79}$ | H | COOMe | $CH_2CH{=}CH_2$ | O | OMe | OMe | CH |
| 5880 | $Q_{79}$ | H | COOEt | $CH_2CH{=}CH_2$ | O | OMe | OMe | CH |
| 5881 | $Q_{79}$ | H | COOMe | $CH_2C{\equiv}CH$ | O | Me | OMe | CH |
| 5882 | $Q_{79}$ | H | COOMe | $CH_2C{\equiv}CH$ | O | OMe | OMe | CH |
| 5883 | $Q_{79}$ | H | COOEt | $CH_2C{\equiv}CH$ | O | OMe | OMe | CH |

In the above, $Q_1$ to $Q_{79}$ are as defined above.

TABLE 5

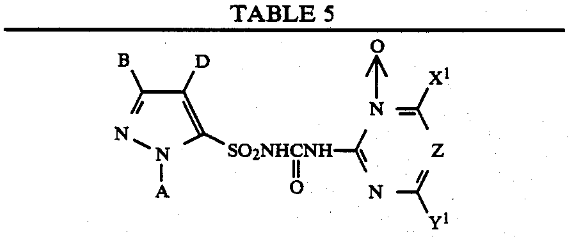

| No. | A | B | D | $X^1$ | $Y^1$ | Z |
|---|---|---|---|---|---|---|
| 5256 | $Q_1$ | H | COOMe | Me | Me | CH |
| 5257 | $Q_1$ | H | COOMe | Me | OMe | CH |
| 5258 | $Q_1$ | H | COOEt | Me | Me | CH |
| 5259 | $Q_1$ | H | COOEt | Me | OMe | CH |
| 5260 | $Q_1$ | H | COOEt | Me | Me | N |
| 5261 | $Q_2$ | H | COOMe | Me | Me | CH |

TABLE 5-continued

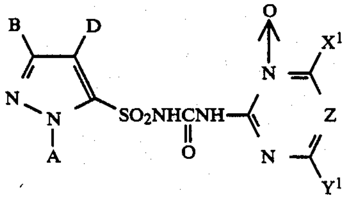

| No. | A | B | D | $X^1$ | $Y^1$ | Z |
|---|---|---|---|---|---|---|
| 5262 | $Q_2$ | H | COOMe | Me | OMe | CH |
| 5263 | $Q_8$ | H | COOMe | Me | Me | CH |
| 5264 | $Q_8$ | H | COOMe | Me | OMe | CH |
| 5265 | $Q_{32}$ | H | COOMe | Me | Me | CH |
| 5266 | $Q_{32}$ | H | COOMe | Me | OMe | CH |
| 5267 | $Q_{45}$ | H | COOMe | Me | Me | CH |
| 5268 | $Q_{45}$ | H | COOMe | Me | OMe | CH |

TABLE 5-continued

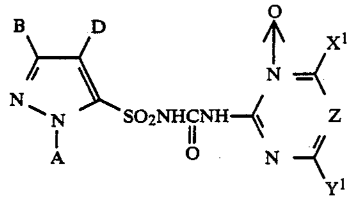

| No. | A | B | D | $X^1$ | $Y^1$ | Z |
|---|---|---|---|---|---|---|
| 5269 | $Q_{59}$ | H | COOMe | Me | Me | CH |
| 5270 | $Q_{59}$ | H | COOMe | Me | OMe | CH |
| 5271 | Me | H | $Q_1$ | Me | Me | CH |
| 5272 | Me | H | $Q_1$ | Me | OMe | CH |
| 5273 | Me | H | $Q_1$ | Me | Me | N |
| 5884 | $Q_5$ | H | COOMe | Me | Me | CH |
| 5885 | $Q_5$ | H | COOMe | Me | OMe | CH |
| 5886 | $Q_{10}$ | H | COOMe | Me | Me | CH |
| 5887 | $Q_{10}$ | H | COOMe | Me | OMe | CH |
| 5888 | $Q_{78}$ | H | COOMe | Me | Me | CH |
| 5889 | $Q_{78}$ | H | COOMe | Me | OMe | CH |
| 5890 | $Q_{79}$ | H | COOMe | Me | Me | CH |
| 5891 | $Q_{79}$ | H | COOMe | Me | OMe | CH |

In the above, $Q_1$ to $Q_{79}$ are as defined above.

TABLE 6

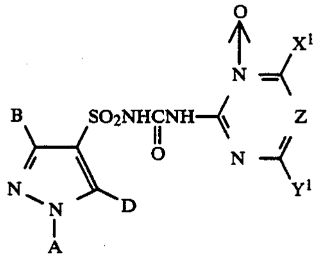

| No. | A | B | D | $X^1$ | $Y^1$ | Z |
|---|---|---|---|---|---|---|
| 5274 | $Q_1$ | Me | Me | Me | Me | CH |
| 5275 | $Q_1$ | Me | Me | Me | OMe | CH |
| 5276 | $Q_1$ | Me | COOMe | Me | Me | CH |
| 5277 | $Q_1$ | Me | COOMe | Me | OMe | CH |
| 5278 | $Q_1$ | Me | COOMe | Me | Me | N |
| 5279 | $Q_2$ | Me | COOMe | Me | Me | CH |
| 5280 | $Q_2$ | Me | COOMe | Me | OMe | CH |
| 5281 | $Q_8$ | Me | COOMe | Me | Me | CH |
| 5282 | $Q_8$ | Me | COOMe | Me | OMe | CH |
| 5283 | $Q_{32}$ | Me | COOMe | Me | Me | CH |
| 5284 | $Q_{32}$ | Me | COOMe | Me | OMe | CH |
| 5285 | $Q_{45}$ | Me | COOMe | Me | Me | CH |
| 5286 | $Q_{45}$ | Me | COOMe | Me | OMe | CH |
| 5287 | $Q_{59}$ | Me | COOMe | Me | Me | CH |
| 5288 | $Q_{59}$ | Me | COOMe | Me | OMe | CH |

In the above, $Q_1$ to $Q_{59}$ are as defined above.

TABLE 7

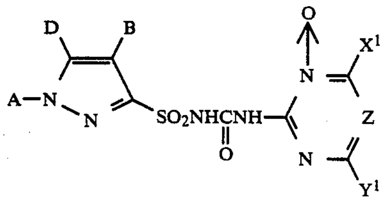

| No. | A | B | D | $X^1$ | $Y^1$ | Z |
|---|---|---|---|---|---|---|
| 5289 | $Q_1$ | Cl | H | Me | Me | CH |
| 5290 | $Q_1$ | Cl | H | Me | OMe | CH |
| 5291 | $Q_1$ | COOMe | H | Me | Me | CH |
| 5292 | $Q_1$ | COOMe | H | Me | OMe | CH |
| 5293 | Me | $Q_1$ | H | Me | Me | CH |

TABLE 7-continued

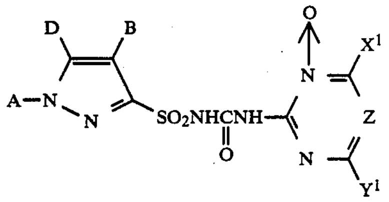

| No. | A | B | D | $X^1$ | $Y^1$ | Z |
|---|---|---|---|---|---|---|
| 5294 | Me | $Q_1$ | H | Me | OMe | CH |
| 5295 | $Q_2$ | Cl | H | Me | Me | CH |
| 5296 | $Q_2$ | Cl | H | Me | OMe | CH |
| 5297 | $Q_8$ | Cl | H | Me | Me | CH |
| 5298 | $Q_8$ | Cl | H | Me | OMe | CH |
| 5299 | $Q_{45}$ | Cl | H | Me | Me | CH |
| 5300 | $Q_{45}$ | Cl | H | Me | OMe | CH |

In the above, $Q_1$ to $Q_{45}$ are as defined above.

TABLE 8

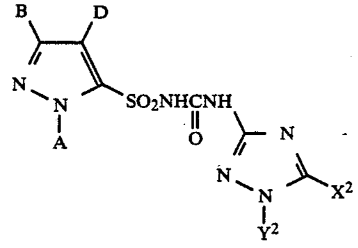

| No. | A | B | D | $X^2$ | $Y^2$ |
|---|---|---|---|---|---|
| 5301 | $Q_1$ | H | COOMe | Me | Me |
| 5302 | $Q_1$ | H | COOMe | OMe | Me |
| 5303 | $Q_1$ | H | COOMe | SMe | Me |
| 5304 | $Q_1$ | H | COOEt | Me | Me |
| 5305 | $Q_1$ | H | COOEt | OMe | Me |
| 5306 | $Q_1$ | H | COOEt | SMe | Me |
| 5307 | $Q_2$ | H | COOMe | Me | Me |
| 5308 | $Q_2$ | H | COOMe | OMe | Me |
| 5309 | $Q_8$ | H | COOMe | Me | Me |
| 5310 | $Q_8$ | H | COOMe | OMe | Me |
| 5311 | $Q_{32}$ | H | COOMe | Me | Me |
| 5312 | $Q_{32}$ | H | COOMe | OMe | Me |
| 5313 | $Q_{45}$ | H | COOMe | Me | Me |
| 5314 | $Q_{45}$ | H | COOMe | OMe | Me |
| 5315 | $Q_{59}$ | H | COOMe | Me | Me |
| 5316 | $Q_{59}$ | H | COOMe | OMe | Me |
| 5317 | Me | H | $Q_1$ | Me | Me |
| 5318 | Me | H | $Q_1$ | OMe | Me |
| 5319 | Me | H | $Q_1$ | SMe | Me |
| 5892 | $Q_5$ | H | COOMe | Me | Me |
| 5893 | $Q_5$ | H | COOMe | OMe | Me |
| 5894 | $Q_{10}$ | H | COOMe | Me | Me |
| 5895 | $Q_{10}$ | H | COOMe | OMe | Me |
| 5896 | $Q_{78}$ | H | COOMe | Me | Me |
| 5897 | $Q_{78}$ | H | COOMe | OMe | Me |
| 5898 | $Q_{79}$ | H | COOMe | Me | Me |
| 5899 | $Q_{79}$ | H | COOMe | OMe | Me |

In the above, $Q_1$ to $Q_{79}$ are as defined above.

TABLE 9

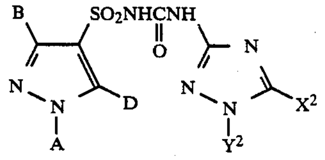

| No. | A | B | D | $X^2$ | $Y^2$ |
|---|---|---|---|---|---|
| 5320 | $Q_1$ | Me | Me | Me | Me |
| 5321 | $Q_1$ | Me | Me | OMe | Me |

TABLE 9-continued

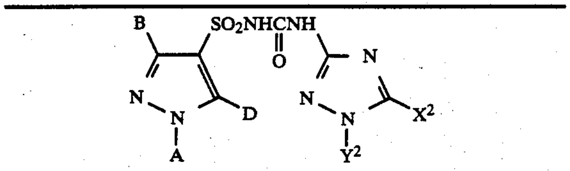

| No. | A | B | D | $X^2$ | $Y^2$ |
|---|---|---|---|---|---|
| 5322 | $Q_1$ | Me | COOMe | Me | Me |
| 5323 | $Q_1$ | Me | COOMe | OMe | Me |
| 5324 | $Q_1$ | Me | COOMe | SMe | Me |
| 5325 | $Q_2$ | Me | COOMe | Me | Me |
| 5326 | $Q_2$ | Me | COOMe | OMe | Me |
| 5327 | $Q_8$ | Me | COOMe | Me | Me |
| 5328 | $Q_8$ | Me | COOMe | OMe | Me |
| 5329 | $Q_{32}$ | Me | COOMe | Me | Me |
| 5330 | $Q_{32}$ | Me | COOMe | OMe | Me |
| 5331 | $Q_{45}$ | Me | COOMe | Me | Me |
| 5332 | $Q_{45}$ | Me | COOMe | OMe | Me |
| 5333 | $Q_{59}$ | Me | COOMe | Me | Me |
| 5334 | $Q_{59}$ | Me | COOMe | OMe | Me |

In the above, $Q_1$ to $Q_{59}$ are as defined above.

TABLE 10

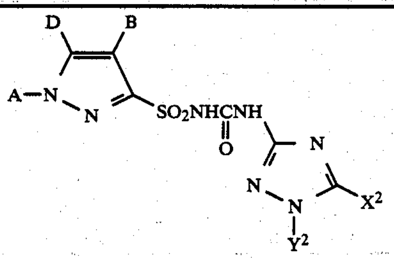

| No. | A | B | D | $X^2$ | $Y^2$ |
|---|---|---|---|---|---|
| 5335 | $Q_1$ | Cl | H | Me | Me |
| 5336 | $Q_1$ | Cl | H | OMe | Me |
| 5337 | $Q_1$ | COOMe | H | Me | Me |
| 5338 | $Q_1$ | COOMe | H | OMe | Me |
| 5339 | Me | $Q_1$ | H | Me | Me |
| 5340 | Me | $Q_1$ | H | OMe | Me |
| 5341 | $Q_2$ | Cl | H | Me | Me |
| 5342 | $Q_2$ | Cl | H | OMe | Me |
| 5343 | $Q_8$ | Cl | H | Me | Me |
| 5344 | $Q_8$ | Cl | H | OMe | Me |
| 5345 | $Q_{45}$ | Cl | H | Me | Me |
| 5346 | $Q_{45}$ | Cl | H | OMe | Me |

In the above, $Q_1$ to $Q_{45}$ are as defined above.

TABLE 11

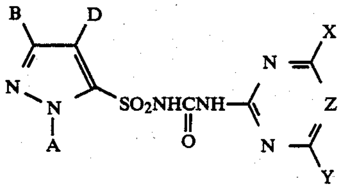

| No. | A | B | D | X | Y | Z |
|---|---|---|---|---|---|---|
| 5900 | $CH_2Q_1$ | H | COOMe | Me | Me | CH |
| 5901 | $CH_2Q_1$ | H | COOMe | Me | OMe | CH |
| 5902 | $CH_2Q_1$ | H | COOMe | OMe | OMe | CH |
| 5903 | $CH_2Q_1$ | H | COOMe | Me | Me | N |
| 5904 | $CH_2Q_1$ | H | COOMe | Me | OMe | N |
| 5905 | $CH_2Q_1$ | H | COOMe | OMe | OMe | N |
| 5906 | $CH_2Q_1$ | H | COOMe | Me | $OCHF_2$ | CH |
| 5907 | $CH_2Q_1$ | H | COOMe | Cl | OMe | CH |
| 5908 | $CH_2Q_1$ | H | COOEt | Me | Me | CH |
| 5909 | $CH_2Q_1$ | H | COOEt | Me | OMe | CH |
| 5910 | $CH_2Q_1$ | H | COOEt | OMe | OMe | CH |
| 5911 | $CH_2Q_1$ | H | COOEt | Me | Me | N |
| 5912 | $CH_2Q_1$ | H | COOEt | Me | OMe | N |
| 5913 | $CH_2Q_1$ | H | COOEt | OMe | OMe | N |
| 5914 | $CH_2Q_1$ | H | COOEt | Me | $OCHF_2$ | CH |
| 5915 | $CH_2Q_1$ | H | COOEt | Cl | OMe | CH |
| 5916 | $CH_2Q_1$ | H | COOPr—n | Me | OMe | CH |
| 5917 | $CH_2Q_1$ | H | COOPr—n | OMe | OMe | CH |
| 5918 | $CH_2Q_1$ | H | COOPr—n | Me | OMe | N |
| 5919 | $CH_2Q_1$ | H | COOPr—i | Me | OMe | CH |
| 5920 | $CH_2Q_1$ | H | COOPr—i | OMe | OMe | CH |
| 5921 | $CH_2Q_1$ | H | COOPr—i | Me | OMe | N |
| 5922 | $CH_2Q_1$ | H | $COOCH_2CH_2Cl$ | Me | OMe | CH |
| 5923 | $CH_2Q_1$ | H | $COOCH_2CH_2Cl$ | OMe | OMe | CH |
| 5924 | $CH_2Q_1$ | H | $COOCH_2CH_2Cl$ | Me | OMe | N |
| 5925 | $CH_2Q_1$ | H | $COOCH_2CH{=}CH_2$ | Me | OMe | CH |
| 5926 | $CH_2Q_1$ | H | $COOCH_2CH{=}CH_2$ | OMe | OMe | CH |
| 5927 | $CH_2Q_1$ | H | $COOCH_2CH{=}CH_2$ | Me | OMe | N |
| 5928 | $CH_2Q_1$ | H | $COOCH_2C\equiv CH$ | Me | OMe | CH |
| 5929 | $CH_2Q_1$ | H | $COOCH_2C\equiv CH$ | OMe | OMe | CH |
| 5930 | $CH_2Q_1$ | H | $COOCH_2C\equiv CH$ | Me | OMe | N |
| 5931 | $CH_2Q_1$ | Me | COOMe | Me | Me | CH |
| 5932 | $CH_2Q_1$ | Me | COOMe | Me | OMe | CH |
| 5933 | $CH_2Q_1$ | Me | COOMe | OMe | OMe | CH |
| 5934 | $CH_2Q_1$ | Me | COOMe | Me | OMe | N |
| 5935 | $CH_2Q_1$ | Me | COOMe | OMe | OMe | N |
| 5936 | $CH_2Q_1$ | Me | COOEt | Me | Me | CH |
| 5937 | $CH_2Q_1$ | Me | COOEt | Me | OMe | CH |
| 5938 | $CH_2Q_1$ | Me | COOEt | OMe | OMe | CH |
| 5939 | $CH_2Q_1$ | Me | COOEt | Me | OMe | N |

TABLE 11-continued

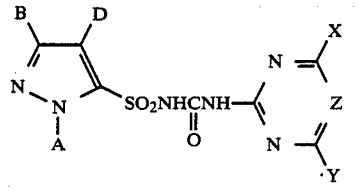

| No. | A | B | D | X | Y | Z |
|---|---|---|---|---|---|---|
| 5940 | $CH_2Q_1$ | Me | COOEt | OMe | OMe | N |
| 5941 | $CH_2Q_1$ | Cl | COOMe | Me | OMe | CH |
| 5942 | $CH_2Q_1$ | Cl | COOMe | OMe | OMe | CH |
| 5943 | $CH_2Q_1$ | Cl | COOMe | Me | OMe | N |
| 5944 | $CH_2Q_1$ | Cl | COOEt | Me | OMe | CH |
| 5945 | $CH_2Q_1$ | Cl | COOEt | OMe | OMe | CH |
| 5946 | $CH_2Q_1$ | Cl | COOEt | Me | OMe | N |
| 5947 | $CH_2Q_1$ | OMe | COOMe | Me | OMe | CH |
| 5948 | $CH_2Q_1$ | OMe | COOMe | OMe | OMe | CH |
| 5949 | $CH_2Q_1$ | OMe | COOMe | Me | OMe | N |
| 5950 | $CH_2Q_1$ | OMe | COOEt | Me | OMe | CH |
| 5951 | $CH_2Q_1$ | OMe | COOEt | OMe | OMe | CH |
| 5952 | $CH_2Q_1$ | OMe | COOEt | Me | OMe | N |
| 5953 | $CH_2Q_1$ | H | Cl | Me | OMe | CH |
| 5954 | $CH_2Q_1$ | H | Cl | OMe | OMe | CH |
| 5955 | $CH_2Q_1$ | H | Cl | Me | OMe | N |
| 5956 | $CH_2Q_1$ | H | $NO_2$ | Me | OMe | CH |
| 5957 | $CH_2Q_1$ | H | $NO_2$ | OMe | OMe | CH |
| 5958 | $CH_2Q_1$ | H | $NO_2$ | Me | OMe | N |
| 5959 | $CH_2Q_1$ | H | $SO_2NMe_2$ | Me | OMe | CH |
| 5960 | $CH_2Q_1$ | H | $SO_2NMe_2$ | OMe | OMe | CH |
| 5961 | $CH_2Q_1$ | H | $SO_2NMe_2$ | Me | OMe | N |
| 5962 | $CH_2Q_1$ | H | CN | Me | OMe | CH |
| 5963 | $CH_2Q_1$ | H | CN | OMe | OMe | CH |
| 5964 | $CH_2Q_1$ | H | CN | Me | OMe | N |
| 5965 | $CH_2Q_1$ | Me | CN | Me | OMe | CH |
| 5966 | $CH_2Q_1$ | Me | CN | OMe | OMe | CH |
| 5967 | $CH_2Q_1$ | Me | CN | Me | OMe | N |
| 5968 | $CH_2Q_1$ | H | Me | Me | OMe | CH |
| 5969 | $CH_2Q_1$ | H | Me | OMe | OMe | CH |
| 5970 | $CH_2Q_1$ | H | Me | Me | OMe | N |
| 5971 | $CH_2Q_1$ | H | Et | Me | OMe | CH |
| 5972 | $CH_2Q_1$ | H | Et | OMe | OMe | CH |
| 5973 | $CH_2Q_1$ | H | Et | Me | OMe | N |
| 5974 | $CH_2Q_1$ | H | H | Me | OMe | CH |
| 5975 | $CH_2Q_1$ | H | H | OMe | OMe | CH |
| 5976 | $CH_2Q_1$ | H | H | Me | OMe | N |
| 5977 | $CH_2Q_1$ | H | COPh | Me | OMe | CH |
| 5978 | $CH_2Q_1$ | H | COPh | OMe | OMe | CH |
| 5979 | $CH_2Q_1$ | H | COPh | Me | OMe | N |
| 5980 | Me | $CH_2Q_1$ | COOMe | Me | OMe | CH |
| 5981 | Me | $CH_2Q_1$ | COOMe | OMe | OMe | CH |
| 5982 | Me | $CH_2Q_1$ | COOMe | Me | OMe | N |
| 5983 | H | H | $CH_2Q_1$ | Me | OMe | CH |
| 5984 | H | H | $CH_2Q_1$ | OMe | OMe | CH |
| 5985 | H | H | $CH_2Q_1$ | Me | OMe | N |
| 5986 | Me | H | $CH_2Q_1$ | Me | Me | CH |
| 5987 | Me | H | $CH_2Q_1$ | Me | OMe | CH |
| 5988 | Me | H | $CH_2Q_1$ | OMe | OMe | CH |
| 5989 | Me | H | $CH_2Q_1$ | Me | OMe | N |
| 5990 | Me | H | $CH_2Q_1$ | OMe | OMe | N |
| 5991 | Me | Me | $CH_2Q_1$ | Me | OMe | CH |
| 5992 | Me | Me | $CH_2Q_1$ | OMe | OMe | CH |
| 5993 | Me | Me | $CH_2Q_1$ | Me | OMe | N |
| 5994 | $CHMeQ_1$ | H | COOMe | Me | OMe | CH |
| 5995 | $CHMeQ_1$ | H | COOMe | OMe | OMe | CH |
| 5996 | $CHMeQ_1$ | H | COOEt | Me | OMe | CH |
| 5997 | $CHMeQ_1$ | H | COOEt | OMe | OMe | CH |
| 5998 | $CHMeQ_1$ | Me | COOMe | Me | OMe | CH |
| 5999 | $CHMeQ_1$ | Me | COOMe | OMe | OMe | CH |
| 6000 | $CHMeQ_1$ | Me | COOEt | Me | OMe | CH |
| 6001 | $CHMeQ_1$ | Me | COOEt | OMe | OMe | CH |
| 6002 | $CHMeQ_1$ | H | H | Me | OMe | CH |
| 6003 | $CHMeQ_1$ | H | H | OMe | OMe | CH |
| 6004 | Me | H | $CHMeQ_1$ | Me | OMe | CH |
| 6005 | Me | H | $CHMeQ_1$ | OMe | OMe | CH |
| 6006 | $CH_2Q_{24}$ | H | COOMe | Me | Me | CH |
| 6007 | $CH_2Q_{24}$ | H | COOMe | Me | OMe | CH |
| 6008 | $CH_2Q_{24}$ | H | COOMe | OMe | OMe | CH |
| 6009 | $CH_2Q_{24}$ | H | COOMe | Me | OMe | N |
| 6010 | $CH_2Q_{24}$ | H | COOMe | OMe | OMe | N |

TABLE 11-continued

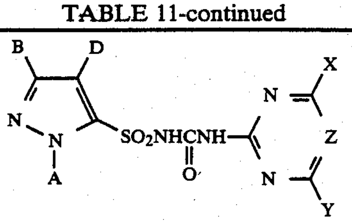

| No. | A | B | D | X | Y | Z |
|---|---|---|---|---|---|---|
| 6011 | $CH_2Q_{24}$ | H | COOEt | Me | Me | CH |
| 6012 | $CH_2Q_{24}$ | H | COOEt | Me | OMe | CH |
| 6013 | $CH_2Q_{24}$ | H | COOEt | OMe | OMe | CH |
| 6014 | $CH_2Q_{24}$ | H | COOEt | Me | OMe | N |
| 6015 | $CH_2Q_{24}$ | H | COOEt | OMe | OMe | N |
| 6016 | $CH_2Q_{24}$ | Me | COOMe | Me | OMe | CH |
| 6017 | $CH_2Q_{24}$ | Me | COOMe | OMe | OMe | CH |
| 6018 | $CH_2Q_{24}$ | Me | COOMe | Me | OMe | N |
| 6019 | $CH_2Q_{24}$ | Me | COOEt | Me | OMe | CH |
| 6020 | $CH_2Q_{24}$ | Me | COOEt | OMe | OMe | CH |
| 6021 | $CH_2Q_{24}$ | Me | COOEt | Me | OMe | N |
| 6022 | $CH_2Q_{24}$ | H | CN | Me | OMe | CH |
| 6023 | $CH_2Q_{24}$ | H | CN | OMe | OMe | CH |
| 6024 | $CH_2Q_{24}$ | H | CN | Me | OMe | N |
| 6025 | $CH_2Q_{24}$ | H | H | Me | OMe | CH |
| 6026 | $CH_2Q_{24}$ | H | H | OMe | OMe | CH |
| 6027 | $CH_2Q_{24}$ | H | H | Me | OMe | N |
| 6028 | Me | H | $CH_2Q_{24}$ | Me | Me | CH |
| 6029 | Me | H | $CH_2Q_{24}$ | Me | OMe | CH |
| 6030 | Me | H | $CH_2Q_{24}$ | OMe | OMe | CH |
| 6031 | Me | H | $CH_2Q_{24}$ | Me | OMe | N |
| 6032 | Me | H | $CH_2Q_{24}$ | OMe | OMe | N |
| 6033 | $CH_2Q_{28}$ | H | COOMe | Me | Me | CH |
| 6034 | $CH_2Q_{28}$ | H | COOMe | Me | OMe | CH |
| 6035 | $CH_2Q_{28}$ | H | COOMe | OMe | OMe | CH |
| 6036 | $CH_2Q_{28}$ | H | COOMe | Me | OMe | N |
| 6037 | $CH_2Q_{28}$ | H | COOMe | OMe | OMe | N |
| 6038 | $CH_2Q_{28}$ | H | COOEt | Me | Me | CH |
| 6039 | $CH_2Q_{28}$ | H | COOEt | Me | OMe | CH |
| 6040 | $CH_2Q_{28}$ | H | COOEt | OMe | OMe | CH |
| 6041 | $CH_2Q_{28}$ | H | COOEt | Me | OMe | N |
| 6042 | $CH_2Q_{28}$ | H | COOEt | OMe | OMe | N |
| 6043 | $CH_2Q_{28}$ | Me | COOMe | Me | OMe | CH |
| 6044 | $CH_2Q_{28}$ | Me | COOMe | OMe | OMe | CH |
| 6045 | $CH_2Q_{28}$ | Me | COOMe | Me | OMe | N |
| 6046 | $CH_2Q_{28}$ | Me | COOEt | Me | OMe | CH |
| 6047 | $CH_2Q_{28}$ | Me | COOEt | OMe | OMe | CH |
| 6048 | $CH_2Q_{28}$ | Me | COOEt | Me | OMe | N |
| 6049 | $CH_2Q_{28}$ | H | CN | Me | OMe | CH |
| 6050 | $CH_2Q_{28}$ | H | CN | OMe | OMe | CH |
| 6051 | $CH_2Q_{28}$ | H | CN | Me | OMe | N |
| 6052 | $CH_2Q_{28}$ | H | H | Me | OMe | CH |
| 6053 | $CH_2Q_{28}$ | H | H | OMe | OMe | CH |
| 6054 | $CH_2Q_{28}$ | H | H | Me | OMe | N |
| 6055 | Me | H | $CH_2Q_{28}$ | Me | Me | CH |
| 6056 | Me | H | $CH_2Q_{28}$ | Me | OMe | CH |
| 6057 | Me | H | $CH_2Q_{28}$ | OMe | OMe | CH |
| 6058 | Me | H | $CH_2Q_{28}$ | Me | OMe | N |
| 6059 | Me | H | $CH_2Q_{28}$ | OMe | OMe | N |
| 6060 | $CH_2Q_{32}$ | H | COOMe | Me | Me | CH |
| 6061 | $CH_2Q_{32}$ | H | COOMe | Me | OMe | CH |
| 6062 | $CH_2Q_{32}$ | H | COOMe | OMe | OMe | CH |
| 6063 | $CH_2Q_{32}$ | H | COOMe | Me | OMe | N |
| 6064 | $CH_2Q_{32}$ | H | COOMe | OMe | OMe | N |
| 6065 | $CH_2Q_{32}$ | H | COOEt | Me | Me | CH |
| 6066 | $CH_2Q_{32}$ | H | COOEt | Me | OMe | CH |
| 6067 | $CH_2Q_{32}$ | H | COOEt | OMe | OMe | CH |
| 6068 | $CH_2Q_{32}$ | H | COOEt | Me | OMe | N |
| 6069 | $CH_2Q_{32}$ | H | COOEt | OMe | OMe | N |
| 6070 | $CH_2Q_{32}$ | Me | COOMe | Me | OMe | CH |
| 6071 | $CH_2Q_{32}$ | Me | COOMe | OMe | OMe | CH |
| 6072 | $CH_2Q_{32}$ | Me | COOMe | Me | OMe | N |
| 6073 | $CH_2Q_{32}$ | Me | COOEt | Me | OMe | CH |
| 6074 | $CH_2Q_{32}$ | Me | COOEt | OMe | OMe | CH |
| 6075 | $CH_2Q_{32}$ | Me | COOEt | Me | OMe | N |
| 6076 | $CH_2Q_{32}$ | H | CN | Me | OMe | CH |
| 6077 | $CH_2Q_{32}$ | H | CN | OMe | OMe | CH |
| 6078 | $CH_2Q_{32}$ | H | CN | Me | OMe | N |
| 6079 | $CH_2Q_{32}$ | H | H | Me | OMe | CH |
| 6080 | $CH_2Q_{32}$ | H | H | OMe | OMe | CH |
| 6081 | $CH_2Q_{32}$ | H | H | Me | OMe | N |

TABLE 11-continued

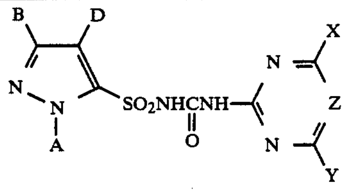

| No. | A | B | D | X | Y | Z |
|---|---|---|---|---|---|---|
| 6082 | Me | H | $CH_2Q_{32}$ | Me | Me | CH |
| 6083 | Me | H | $CH_2Q_{32}$ | Me | OMe | CH |
| 6084 | Me | H | $CH_2Q_{32}$ | OMe | OMe | CH |
| 6085 | Me | H | $CH_2Q_{32}$ | Me | OMe | N |
| 6086 | Me | H | $CH_2Q_{32}$ | OMe | OMe | N |
| 6087 | $CH_2CH_2Q_1$ | H | COOMe | Me | Me | CH |
| 6088 | $CH_2CH_2Q_1$ | H | COOMe | Me | OMe | CH |
| 6089 | $CH_2CH_2Q_1$ | H | COOMe | OMe | OMe | CH |
| 6090 | $CH_2CH_2Q_1$ | H | COOMe | Me | OMe | N |
| 6091 | $CH_2CH_2Q_1$ | H | COOMe | OMe | OMe | N |
| 6092 | $CH_2CH_2Q_1$ | H | COOEt | Me | Me | CH |
| 6093 | $CH_2CH_2Q_1$ | H | COOEt | Me | OMe | CH |
| 6094 | $CH_2CH_2Q_1$ | H | COOEt | OMe | OMe | CH |
| 6095 | $CH_2CH_2Q_1$ | H | COOEt | Me | OMe | N |
| 6096 | $CH_2CH_2Q_1$ | H | COOEt | OMe | OMe | N |
| 6097 | $CH_2CH_2Q_1$ | Me | COOMe | Me | OMe | CH |
| 6098 | $CH_2CH_2Q_1$ | Me | COOMe | OMe | OMe | CH |
| 6099 | $CH_2CH_2Q_1$ | Me | COOMe | Me | OMe | N |
| 6100 | $CH_2CH_2Q_1$ | Me | COOEt | Me | OMe | CH |
| 6101 | $CH_2CH_2Q_1$ | Me | COOEt | OMe | OMe | CH |
| 6102 | $CH_2CH_2Q_1$ | Me | COOEt | Me | OMe | N |
| 6103 | $CH_2CH_2Q_1$ | H | CN | Me | OMe | CH |
| 6104 | $CH_2CH_2Q_1$ | H | CN | OMe | OMe | CH |
| 6105 | $CH_2CH_2Q_1$ | H | CN | Me | OMe | N |
| 6106 | $CH_2CH_2Q_1$ | H | H | Me | OMe | CH |
| 6107 | $CH_2CH_2Q_1$ | H | H | OMe | OMe | CH |
| 6108 | $CH_2CH_2Q_1$ | H | H | Me | OMe | N |
| 6109 | Me | H | $CH_2CH_2Q_1$ | Me | Me | CH |
| 6110 | Me | H | $CH_2CH_2Q_1$ | Me | OMe | CH |
| 6111 | Me | H | $CH_2CH_2Q_1$ | OMe | OMe | CH |
| 6112 | Me | H | $CH_2CH_2Q_1$ | Me | OMe | N |
| 6113 | Me | H | $CH_2CH_2Q_1$ | OMe | OMe | N |

In the above, $Q_1$ to $Q_{32}$ are as defined above.

TABLE 12

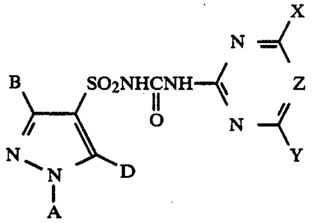

| No. | A | B | D | X | Y | Z |
|---|---|---|---|---|---|---|
| 6114 | $CH_2Q_1$ | Me | Cl | Me | Me | CH |
| 6115 | $CH_2Q_1$ | Me | Cl | Me | OMe | CH |
| 6116 | $CH_2Q_1$ | Me | Cl | OMe | OMe | CH |
| 6117 | $CH_2Q_1$ | Me | Cl | Me | OMe | N |
| 6118 | $CH_2Q_1$ | Me | Cl | OMe | OMe | N |
| 6119 | $CH_2Q_1$ | Me | OMe | Me | OMe | CH |
| 6120 | $CH_2Q_1$ | Me | OMe | OMe | OMe | CH |
| 6121 | $CH_2Q_1$ | Me | OMe | Me | OMe | N |
| 6122 | $CH_2Q_1$ | $CF_3$ | Me | Me | OMe | CH |
| 6123 | $CH_2Q_1$ | $CF_3$ | Me | OMe | OMe | CH |
| 6124 | $CH_2Q_1$ | $CF_3$ | Me | Me | OMe | N |
| 6125 | $CH_2Q_1$ | Me | COOMe | Me | Me | CH |
| 6126 | $CH_2Q_1$ | Me | COOMe | Me | OMe | CH |
| 6127 | $CH_2Q_1$ | Me | COOMe | OMe | OMe | CH |
| 6128 | $CH_2Q_1$ | Me | COOMe | Me | OMe | N |
| 6129 | $CH_2Q_1$ | Me | COOMe | OMe | OMe | N |
| 6130 | $CH_2Q_1$ | Me | COOMe | Me | $OCHF_2$ | CH |

TABLE 12-continued

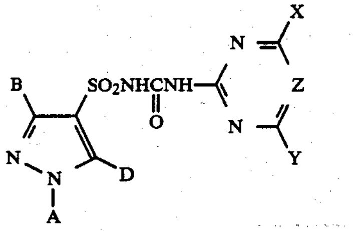

| No. | A | B | D | X | Y | Z |
|---|---|---|---|---|---|---|
| 6131 | $CH_2Q_1$ | Me | COOMe | Me | 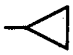 | CH |
| 6132 | $CH_2Q_1$ | Me | $SO_2Me$ | Me | OMe | CH |
| 6133 | $CH_2Q_1$ | Me | $SO_2Me$ | OMe | OMe | CH |
| 6134 | $CH_2Q_1$ | Me | $SO_2Me$ | Me | OMe | N |
| 6135 | H | $CH_2Q_1$ | Me | Me | OMe | CH |
| 6136 | H | $CH_2Q_1$ | Me | OMe | OMe | CH |
| 6137 | H | $CH_2Q_1$ | Me | Me | OMe | N |
| 6138 | Me | $CH_2Q_1$ | Me | Me | OMe | CH |
| 6139 | Me | $CH_2Q_1$ | Me | OMe | OMe | CH |
| 6140 | Me | $CH_2Q_1$ | Me | Me | OMe | N |
| 6141 | Me | $CH_2Q_1$ | Cl | Me | OMe | CH |
| 6142 | Me | $CH_2Q_1$ | Cl | OMe | OMe | CH |
| 6143 | Me | $CH_2Q_1$ | Cl | Me | OMe | N |
| 6144 | Me | $CH_2Q_1$ | COOMe | Me | OMe | CH |
| 6145 | Me | $CH_2Q_1$ | COOMe | OMe | OMe | CH |
| 6146 | Me | $CH_2Q_1$ | COOMe | Me | OMe | N |
| 6147 | Me | $CH_2Q_1$ | Ph | Me | OMe | CH |
| 6148 | Me | $CH_2Q_1$ | Ph | OMe | OMe | CH |
| 6149 | Me | $CH_2Q_1$ | Ph | Me | OMe | N |
| 6150 | Me | Me | $CH_2Q_1$ | Me | OMe | CH |
| 6151 | Me | Me | $CH_2Q_1$ | OMe | OMe | CH |
| 6152 | Me | Me | $CH_2Q_1$ | Me | OMe | N |
| 6153 | $CHMeQ_1$ | Me | COOMe | Me | OMe | CH |
| 6154 | $CHMeQ_1$ | Me | COOMe | OMe | OMe | CH |
| 6155 | $CHMeQ_1$ | Me | COOMe | Me | OMe | N |
| 6156 | Me | Me | $CHMeQ_1$ | OMe | OMe | CH |
| 6157 | Me | Me | $CHMeQ_1$ | Me | OMe | N |
| 6158 | $CH_2Q_{24}$ | Me | COOMe | Me | Me | CH |
| 6159 | $CH_2Q_{24}$ | Me | COOMe | Me | OMe | CH |
| 6160 | $CH_2Q_{24}$ | Me | COOMe | OMe | OMe | CH |
| 6161 | $CH_2Q_{24}$ | Me | COOMe | Me | OMe | N |
| 6162 | $CH_2Q_{24}$ | Me | COOMe | OMe | OMe | N |
| 6163 | Me | $CH_2Q_{24}$ | Me | Me | OMe | CH |
| 6164 | Me | $CH_2Q_{24}$ | Me | OMe | OMe | CH |
| 6165 | Me | $CH_2Q_{24}$ | Me | Me | OMe | N |
| 6166 | Me | Me | $CH_2Q_{24}$ | Me | OMe | CH |
| 6167 | Me | Me | $CH_2Q_{24}$ | OMe | OMe | CH |
| 6168 | Me | Me | $CH_2Q_{24}$ | Me | OMe | N |
| 6169 | $CH_2Q_{28}$ | Me | COOMe | Me | Me | CH |
| 6170 | $CH_2Q_{28}$ | Me | COOMe | Me | OMe | CH |
| 6171 | $CH_2Q_{28}$ | Me | COOMe | OMe | OMe | CH |
| 6172 | $CH_2Q_{28}$ | Me | COOMe | Me | OMe | N |
| 6173 | $CH_2Q_{28}$ | Me | COOMe | OMe | OMe | N |
| 6174 | Me | $CH_2Q_{28}$ | Me | Me | OMe | CH |
| 6175 | Me | $CH_2Q_{28}$ | Me | OMe | OMe | CH |
| 6176 | Me | $CH_2Q_{28}$ | Me | Me | OMe | N |
| 6177 | Me | Me | $CH_2Q_{28}$ | Me | OMe | CH |
| 6178 | Me | Me | $CH_2Q_{28}$ | OMe | OMe | CH |
| 6179 | Me | Me | $CH_2Q_{28}$ | Me | OMe | N |
| 6180 | $CH_2Q_{32}$ | Me | COOMe | Me | Me | CH |
| 6181 | $CH_2Q_{32}$ | Me | COOMe | Me | OMe | CH |
| 6182 | $CH_2Q_{32}$ | Me | COOMe | OMe | OMe | CH |
| 6183 | $CH_2Q_{32}$ | Me | COOMe | Me | OMe | N |
| 6184 | $CH_2Q_{32}$ | Me | COOMe | OMe | OMe | N |
| 6185 | Me | $CH_2Q_{32}$ | Me | Me | OMe | CH |
| 6186 | Me | $CH_2Q_{32}$ | Me | OMe | OMe | CH |
| 6187 | Me | $CH_2Q_{32}$ | Me | Me | OMe | N |
| 6188 | Me | Me | $CH_2Q_{32}$ | Me | OMe | CH |
| 6189 | Me | Me | $CH_2Q_{32}$ | OMe | OMe | CH |
| 6190 | Me | Me | $CH_2Q_{32}$ | Me | OMe | N |
| 6191 | $CH_2CH_2Q_1$ | Me | COOMe | Me | Me | CH |
| 6192 | $CH_2CH_2Q_1$ | Me | COOMe | Me | OMe | CH |
| 6193 | $CH_2CH_2Q_1$ | Me | COOMe | OMe | OMe | CH |
| 6194 | $CH_2CH_2Q_1$ | Me | COOMe | Me | OMe | N |
| 6195 | $CH_2CH_2Q_1$ | Me | COOMe | OMe | OMe | N |
| 6196 | Me | $CH_2CH_2Q_1$ | Me | Me | OMe | CH |

TABLE 12-continued

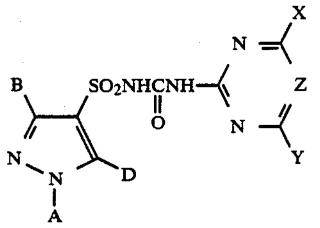

| No. | A | B | D | X | Y | Z |
|---|---|---|---|---|---|---|
| 6197 | Me | $CH_2CH_2Q_1$ | Me | OMe | OMe | CH |
| 6198 | Me | $CH_2CH_2Q_1$ | Me | Me | OMe | N |
| 6199 | Me | Me | $CH_2CH_2Q_1$ | Me | OMe | CH |
| 6200 | Me | Me | $CH_2CH_2Q_1$ | OMe | OMe | CH |
| 6201 | Me | Me | $CH_2CH_2Q_1$ | Me | OMe | N |

In the above, $Q_1$ to $Q_{32}$ are as defined above.

TABLE 13

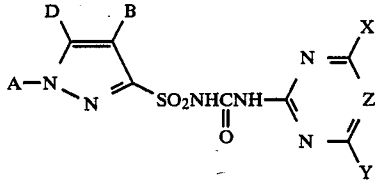

| No. | A | B | D | X | Y | Z |
|---|---|---|---|---|---|---|
| 6202 | $CH_2Q_1$ | H | H | Me | OMe | CH |
| 6203 | $CH_2Q_1$ | H | H | OMe | OMe | CH |
| 6204 | $CH_2Q_1$ | H | H | Me | OMe | N |
| 6205 | $CH_2Q_1$ | Me | H | Me | OMe | CH |
| 6206 | $CH_2Q_1$ | Me | H | OMe | OMe | CH |
| 6207 | $CH_2Q_1$ | Me | H | Me | OMe | N |
| 6208 | $CH_2Q_1$ | Cl | H | Me | OMe | CH |
| 6209 | $CH_2Q_1$ | Cl | H | OMe | OMe | CH |
| 6210 | $CH_2Q_1$ | Cl | H | Me | OMe | N |
| 6211 | $CH_2Q_1$ | Br | H | Me | OMe | CH |
| 6212 | $CH_2Q_1$ | Br | H | OMe | OMe | CH |
| 6213 | $CH_2Q_1$ | Br | H | Me | OMe | N |
| 6214 | $CH_2Q_1$ | COOMe | H | Me | OMe | CH |
| 6215 | $CH_2Q_1$ | COOMe | H | OMe | OMe | CH |
| 6216 | $CH_2Q_1$ | COOMe | H | Me | OMe | N |
| 6217 | $CH_2Q_1$ | COOEt | H | Me | OMe | CH |
| 6218 | $CH_2Q_1$ | COOEt | H | OMe | OMe | CH |
| 6219 | $CH_2Q_1$ | COOEt | H | Me | OMe | N |
| 6220 | Me | $CH_2Q_1$ | H | Me | Me | CH |
| 6221 | Me | $CH_2Q_1$ | H | Me | OMe | CH |
| 6222 | Me | $CH_2Q_1$ | H | OMe | OMe | CH |
| 6223 | Me | $CH_2Q_1$ | H | Me | OMe | N |
| 6224 | Me | $CH_2Q_1$ | H | OMe | OMe | N |
| 6225 | COMe | $CH_2Q_1$ | H | Me | OMe | CH |
| 6226 | COMe | $CH_2Q_1$ | H | OMe | OMe | CH |
| 6227 | COMe | $CH_2Q_1$ | H | Me | OMe | N |
| 6228 | $CHMeQ_1$ | Cl | H | Me | OMe | CH |
| 6229 | $CHMeQ_1$ | Cl | H | OMe | OMe | CH |
| 6230 | $CHMeQ_1$ | Cl | H | Me | OMe | N |
| 6231 | $CHMeQ_1$ | COOMe | H | Me | OMe | CH |
| 6232 | $CHMeQ_1$ | COOMe | H | OMe | OMe | CH |
| 6233 | $CHMeQ_1$ | COOMe | H | Me | OMe | N |
| 6234 | Me | $CHMeQ_1$ | H | Me | OMe | CH |
| 6235 | Me | $CHMeQ_1$ | H | OMe | OMe | CH |
| 6236 | Me | $CHMeQ_1$ | H | Me | OMe | N |
| 6237 | $CH_2Q_{24}$ | H | H | Me | OMe | CH |
| 6238 | $CH_2Q_{24}$ | H | H | OMe | OMe | CH |
| 6239 | $CH_2Q_{24}$ | H | H | Me | OMe | N |
| 6240 | $CH_2Q_{24}$ | Cl | H | Me | OMe | CH |
| 6241 | $CH_2Q_{24}$ | Cl | H | OMe | OMe | CH |
| 6242 | $CH_2Q_{24}$ | Cl | H | Me | OMe | N |
| 6243 | $CH_2Q_{24}$ | COOMe | H | Me | OMe | CH |

TABLE 13-continued

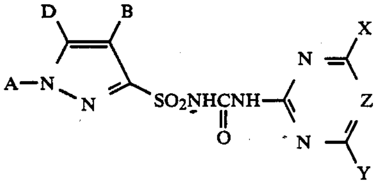

| No. | A | B | D | X | Y | Z |
|---|---|---|---|---|---|---|
| 6244 | $CH_2Q_{24}$ | COOMe | H | OMe | OMe | CH |
| 6245 | $CH_2Q_{24}$ | COOMe | H | Me | OMe | N |
| 6246 | Me | $CH_2Q_{24}$ | H | Me | OMe | CH |
| 6247 | Me | $CH_2Q_{24}$ | H | OMe | OMe | CH |
| 6248 | Me | $CH_2Q_{24}$ | H | Me | OMe | N |
| 6249 | $CH_2Q_{28}$ | H | H | Me | OMe | CH |
| 6250 | $CH_2Q_{28}$ | H | H | OMe | OMe | CH |
| 6251 | $CH_2Q_{28}$ | H | H | Me | OMe | N |
| 6252 | $CH_2Q_{28}$ | Cl | H | Me | OMe | CH |
| 6253 | $CH_2Q_{28}$ | Cl | H | OMe | OMe | CH |
| 6254 | $CH_2Q_{28}$ | Cl | H | Me | OMe | N |
| 6255 | $CH_2Q_{28}$ | COOMe | H | Me | OMe | CH |
| 6256 | $CH_2Q_{28}$ | COOMe | H | OMe | OMe | CH |
| 6257 | $CH_2Q_{28}$ | COOMe | H | Me | OMe | N |
| 6258 | Me | $CH_2Q_{28}$ | H | Me | OMe | CH |
| 6259 | Me | $CH_2Q_{28}$ | H | OMe | OMe | CH |
| 6260 | Me | $CH_2Q_{28}$ | H | Me | OMe | N |
| 6261 | $CH_2Q_{32}$ | H | H | Me | OMe | CH |
| 6262 | $CH_2Q_{32}$ | H | H | OMe | OMe | CH |
| 6263 | $CH_2Q_{32}$ | H | H | Me | OMe | N |
| 6264 | $CH_2Q_{32}$ | Cl | H | Me | OMe | CH |
| 6265 | $CH_2Q_{32}$ | Cl | H | OMe | OMe | CH |
| 6266 | $CH_2Q_{32}$ | Cl | H | Me | OMe | N |
| 6267 | $CH_2Q_{32}$ | COOMe | H | Me | OMe | CH |
| 6268 | $CH_2Q_{32}$ | COOMe | H | OMe | OMe | CH |
| 6269 | $CH_2Q_{32}$ | COOMe | H | Me | OMe | N |
| 6270 | Me | $CH_2Q_{32}$ | H | Me | OMe | CH |
| 6271 | Me | $CH_2Q_{32}$ | H | OMe | OMe | CH |
| 6272 | Me | $CH_2Q_{32}$ | H | Me | OMe | N |
| 6273 | $CH_2CH_2Q_1$ | H | H | Me | OMe | CH |
| 6274 | $CH_2CH_2Q_1$ | H | H | OMe | OMe | CH |
| 6275 | $CH_2CH_2Q_1$ | H | H | Me | OMe | N |
| 6276 | $CH_2CH_2Q_1$ | Cl | H | Me | OMe | CH |
| 6277 | $CH_2CH_2Q_1$ | Cl | H | OMe | OMe | CH |
| 6278 | $CH_2CH_2Q_1$ | Cl | H | Me | OMe | N |
| 6279 | $CH_2CH_2Q_1$ | COOMe | H | Me | OMe | CH |
| 6280 | $CH_2CH_2Q_1$ | COOMe | H | OMe | OMe | CH |
| 6281 | $CH_2CH_2Q_1$ | COOMe | H | Me | OMe | N |
| 6282 | Me | $CH_2CH_2Q_1$ | H | Me | OMe | CH |
| 6283 | Me | $CH_2CH_2Q_1$ | H | OMe | OMe | CH |
| 6284 | Me | $CH_2CH_2Q_1$ | H | Me | OMe | N |

In the above, $Q_1$ to $Q_{32}$ are as defined above.

TABLE 14

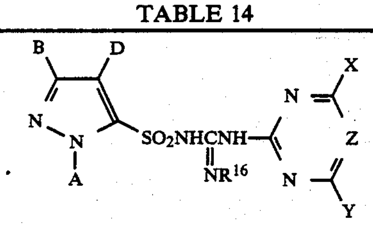

| No. | A | B | D | $R^{16}$ | X | Y | Z |
|---|---|---|---|---|---|---|---|
| 6285 | $Q_1$ | H | COOMe | H | Me | OMe | CH |
| 6286 | $Q_1$ | H | COOMe | H | OMe | OMe | CH |
| 6287 | $Q_1$ | H | COOEt | H | Me | OMe | CH |
| 6288 | $Q_1$ | H | COOEt | H | OMe | OMe | CH |
| 6289 | $Q_1$ | Me | COOMe | H | Me | OMe | CH |
| 6290 | $Q_1$ | Me | COOMe | H | OMe | OMe | CH |
| 6291 | $Q_1$ | Me | COOEt | H | Me | OMe | CH |
| 6292 | $Q_1$ | Me | COOEt | H | OMe | OMe | CH |
| 6293 | $Q_1$ | H | H | H | Me | OMe | CH |
| 6294 | $Q_1$ | H | H | H | OMe | OMe | CH |
| 6295 | Me | H | $Q_1$ | H | Me | OMe | CH |
| 6296 | Me | H | $Q_1$ | H | OMe | OMe | CH |
| 6297 | $Q_1$ | H | COOMe | Me | Me | Me | CH |
| 6298 | $Q_1$ | H | COOMe | Me | Me | OMe | CH |
| 6299 | $Q_1$ | H | COOMe | Me | OMe | OMe | CH |
| 6300 | $Q_1$ | H | COOMe | Me | Me | OMe | N |
| 6301 | $Q_1$ | H | COOMe | Me | OMe | OMe | N |
| 6302 | $Q_1$ | H | COOEt | Me | Me | Me | CH |
| 6303 | $Q_1$ | H | COOEt | Me | Me | OMe | CH |
| 6304 | $Q_1$ | H | COOEt | Me | OMe | OMe | CH |
| 6305 | $Q_1$ | H | COOEt | Me | Me | OMe | N |
| 6306 | $Q_1$ | H | COOEt | Me | OMe | OMe | N |
| 6307 | $Q_1$ | Me | COOMe | Me | Me | OMe | CH |
| 6308 | $Q_1$ | Me | COOMe | Me | OMe | OMe | CH |
| 6309 | $Q_1$ | Me | COOMe | Me | Me | OMe | N |
| 6310 | $Q_1$ | Me | COOEt | Me | Me | OMe | CH |
| 6311 | $Q_1$ | Me | COOEt | Me | OMe | OMe | CH |
| 6312 | $Q_1$ | Me | COOEt | Me | Me | OMe | N |
| 6313 | $Q_1$ | H | CN | Me | Me | OMe | CH |
| 6314 | $Q_1$ | H | CN | Me | OMe | OMe | CH |
| 6315 | $Q_1$ | H | CN | Me | Me | OMe | N |
| 6316 | $Q_1$ | H | H | Me | Me | OMe | CH |
| 6317 | $Q_1$ | H | H | Me | OMe | OMe | CH |
| 6318 | $Q_1$ | H | H | Me | Me | OMe | N |
| 6319 | Me | H | $Q_1$ | Me | Me | Me | CH |
| 6320 | Me | H | $Q_1$ | Me | Me | OMe | CH |
| 6321 | Me | H | $Q_1$ | Me | OMe | OMe | CH |
| 6322 | Me | H | $Q_1$ | Me | Me | OMe | N |
| 6323 | Me | H | $Q_1$ | Me | OMe | OMe | N |
| 6324 | $Q_1$ | H | COOMe | Et | Me | OMe | CH |
| 6325 | $Q_1$ | H | COOMe | Et | OMe | OMe | CH |
| 6326 | $Q_1$ | H | COOEt | Et | Me | OMe | CH |
| 6327 | $Q_1$ | H | COOEt | Et | OMe | OMe | CH |
| 6328 | $Q_1$ | Me | COOMe | Et | Me | OMe | CH |
| 6329 | $Q_1$ | Me | COOMe | Et | OMe | OMe | CH |
| 6330 | $Q_1$ | Me | COOEt | Et | Me | OMe | CH |
| 6331 | $Q_1$ | Me | COOEt | Et | OMe | OMe | CH |
| 6332 | $Q_1$ | H | H | Et | Me | OMe | CH |
| 6333 | $Q_1$ | H | H | Et | OMe | OMe | CH |
| 6334 | Me | H | $Q_1$ | Et | Me | OMe | CH |
| 6335 | Me | H | $Q_1$ | Et | OMe | OMe | CH |
| 6336 | $Q_1$ | H | COOMe | OMe | Me | Me | CH |
| 6337 | $Q_1$ | H | COOMe | OMe | Me | OMe | CH |
| 6338 | $Q_1$ | H | COOMe | OMe | OMe | OMe | CH |
| 6339 | $Q_1$ | H | COOMe | OMe | Me | Me | N |
| 6340 | $Q_1$ | H | COOMe | OMe | Me | OMe | N |
| 6341 | $Q_1$ | H | COOMe | OMe | OMe | OMe | N |
| 6342 | $Q_1$ | H | COOMe | OMe | Me | $OCHF_2$ | CH |
| 6343 | $Q_1$ | H | COOMe | OMe | Cl | OMe | CH |
| 6344 | $Q_1$ | H | COOEt | OMe | Me | Me | CH |
| 6345 | $Q_1$ | H | COOEt | OMe | Me | OMe | CH |
| 6346 | $Q_1$ | H | COOEt | OMe | OMe | OMe | CH |
| 6347 | $Q_1$ | H | COOEt | OMe | Me | Me | N |
| 6348 | $Q_1$ | H | COOEt | OMe | Me | OMe | N |
| 6349 | $Q_1$ | H | COOEt | OMe | OMe | OMe | N |
| 6350 | $Q_1$ | H | COOEt | OMe | Me | $OCHF_2$ | CH |
| 6351 | $Q_1$ | H | COOEt | OMe | Cl | OMe | CH |
| 6352 | $Q_1$ | H | COOPr—n | OMe | Me | OMe | CH |
| 6353 | $Q_1$ | H | COOPr—n | OMe | OMe | OMe | CH |
| 6354 | $Q_1$ | H | COOPr—n | OMe | Me | OMe | N |
| 6355 | $Q_1$ | H | COOPr—i | OMe | Me | OMe | CH |

TABLE 14-continued

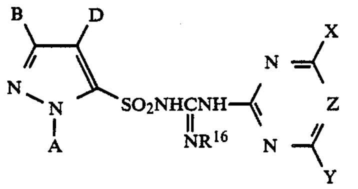

| No. | A | B | D | $R^{16}$ | X | Y | Z |
|---|---|---|---|---|---|---|---|
| 6356 | $Q_1$ | H | COOPr—i | OMe | OMe | OMe | CH |
| 6357 | $Q_1$ | H | COOPr—i | OMe | Me | OMe | N |
| 6358 | $Q_1$ | H | $COOCH_2CH_2Cl$ | OMe | Me | OMe | CH |
| 6359 | $Q_1$ | H | $COOCH_2CH_2Cl$ | OMe | OMe | OMe | CH |
| 6360 | $Q_1$ | H | $COOCH_2CH_2Cl$ | OMe | Me | OMe | N |
| 6361 | $Q_1$ | H | $COOCH_2CH{=}CH_2$ | OMe | Me | OMe | CH |
| 6362 | $Q_1$ | H | $COOCH_2CH{=}CH_2$ | OMe | OMe | OMe | CH |
| 6363 | $Q_1$ | H | $COOCH_2CH{=}CH_2$ | OMe | Me | OMe | N |
| 6364 | $Q_1$ | H | $COOCH_2C{\equiv}CH$ | OMe | Me | OMe | CH |
| 6365 | $Q_1$ | H | $COOCH_2C{\equiv}CH$ | OMe | OMe | OMe | CH |
| 6366 | $Q_1$ | H | $COOCH_2C{\equiv}CH$ | OMe | Me | OMe | N |
| 6367 | $Q_1$ | Me | COOMe | OMe | Me | Me | CH |
| 6368 | $Q_1$ | Me | COOMe | OMe | Me | OMe | CH |
| 6359 | $Q_1$ | Me | COOMe | OMe | OMe | OMe | CH |
| 6370 | $Q_1$ | Me | COOMe | OMe | Me | OMe | N |
| 6371 | $Q_1$ | Me | COOMe | OMe | OMe | OMe | N |
| 6372 | $Q_1$ | Me | COOEt | OMe | Me | Me | CH |
| 6373 | $Q_1$ | Me | COOEt | OMe | Me | OMe | CH |
| 6374 | $Q_1$ | Me | COOEt | OMe | OMe | OMe | CH |
| 6375 | $Q_1$ | Me | COOEt | OMe | Me | OMe | N |
| 6376 | $Q_1$ | Me | COOEt | OMe | OMe | OMe | N |
| 6377 | $Q_1$ | Cl | COOMe | OMe | Me | OMe | CH |
| 6378 | $Q_1$ | Cl | COOMe | OMe | OMe | OMe | CH |
| 6379 | $Q_1$ | Cl | COOMe | OMe | Me | OMe | N |
| 6380 | $Q_1$ | Cl | COOEt | OMe | Me | OMe | CH |
| 6381 | $Q_1$ | Cl | COOEt | OMe | OMe | OMe | CH |
| 6382 | $Q_1$ | Cl | COOEt | OMe | Me | OMe | N |
| 6383 | $Q_1$ | OMe | COOMe | OMe | Me | OMe | CH |
| 6384 | $Q_1$ | OMe | COOMe | OMe | OMe | OMe | CH |
| 6385 | $Q_1$ | OMe | COOMe | OMe | Me | OMe | N |
| 6386 | $Q_1$ | OMe | COOEt | OMe | Me | OMe | CH |
| 6387 | $Q_1$ | OMe | COOEt | OMe | OMe | OMe | CH |
| 6388 | $Q_1$ | OMe | COOEt | OMe | Me | OMe | N |
| 6389 | $Q_1$ | H | Cl | OMe | Me | OMe | CH |
| 6390 | $Q_1$ | H | Cl | OMe | OMe | OMe | CH |
| 6391 | $Q_1$ | H | Cl | OMe | Me | OMe | N |
| 6392 | $Q_1$ | H | $NO_2$ | OMe | Me | OMe | CH |
| 6393 | $Q_1$ | H | $NO_2$ | OMe | OMe | OMe | CH |
| 6394 | $Q_1$ | H | $NO_2$ | OMe | Me | OMe | N |
| 6395 | $Q_1$ | H | $SO_2NMe_2$ | OMe | Me | OMe | CH |
| 6396 | $Q_1$ | H | $SO_2NMe_2$ | OMe | OMe | OMe | CH |
| 6397 | $Q_1$ | H | $SO_2NMe_2$ | OMe | Me | OMe | N |
| 6398 | $Q_1$ | H | CN | OMe | Me | OMe | CH |
| 6399 | $Q_1$ | H | CN | OMe | OMe | OMe | CH |
| 6400 | $Q_1$ | H | CN | OMe | Me | OMe | N |
| 6401 | $Q_1$ | Me | CN | OMe | Me | OMe | CH |
| 6402 | $Q_1$ | Me | CN | OMe | OMe | OMe | CH |
| 6403 | $Q_1$ | Me | CN | OMe | Me | OMe | N |
| 6404 | $Q_1$ | H | Me | OMe | Me | OMe | CH |
| 6405 | $Q_1$ | H | Me | OMe | OMe | OMe | CH |
| 6406 | $Q_1$ | H | Me | OMe | Me | OMe | N |
| 6407 | $Q_1$ | H | Et | OMe | Me | OMe | CH |
| 6408 | $Q_1$ | H | Et | OMe | OMe | OMe | CH |
| 6409 | $Q_1$ | H | Et | OMe | Me | OMe | N |
| 6410 | $Q_1$ | H | H | OMe | Me | OMe | CH |
| 6411 | $Q_1$ | H | H | OMe | OMe | OMe | CH |
| 6412 | $Q_1$ | H | H | OMe | Me | OMe | N |
| 6413 | $Q_1$ | H | COPh | OMe | Me | OMe | CH |
| 6414 | $Q_1$ | H | COPh | OMe | OMe | OMe | CH |
| 6415 | $Q_1$ | H | COPh | OMe | Me | OMe | N |
| 6416 | Me | $Q_1$ | COOMe | OMe | Me | OMe | CH |
| 6417 | Me | $Q_1$ | COOMe | OMe | OMe | OMe | CH |
| 6418 | Me | $Q_1$ | COOMe | OMe | Me | OMe | N |
| 6419 | H | H | $Q_1$ | OMe | Me | OMe | CH |
| 6420 | H | H | $Q_1$ | OMe | OMe | OMe | CH |
| 6421 | H | H | $Q_1$ | OMe | Me | OMe | N |
| 6422 | Me | H | $Q_1$ | OMe | Me | Me | CH |
| 6423 | Me | H | $Q_1$ | OMe | Me | OMe | CH |
| 6424 | Me | H | $Q_1$ | OMe | OMe | OMe | CH |
| 6425 | Me | H | $Q_1$ | OMe | Me | OMe | N |
| 6426 | Me | H | $Q_1$ | OMe | OMe | OMe | N |

TABLE 14-continued

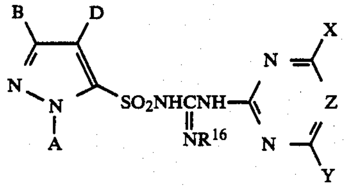

| No. | A | B | D | $R^{16}$ | X | Y | Z |
|---|---|---|---|---|---|---|---|
| 6427 | Me | Me | $Q_1$ | OMe | Me | OMe | CH |
| 6428 | Me | Me | $Q_1$ | OMe | OMe | OMe | CH |
| 6429 | Me | Me | $Q_1$ | OMe | Me | OMe | N |
| 6430 | $Q_1$ | H | COOMe | OEt | Me | OMe | CH |
| 6431 | $Q_1$ | H | COOMe | OEt | OMe | OMe | CH |
| 6432 | $Q_1$ | H | COOEt | OEt | Me | OMe | CH |
| 6433 | $Q_1$ | H | COOEt | OEt | OMe | OMe | CH |
| 6434 | $Q_1$ | Me | COOMe | OEt | Me | OMe | CH |
| 6435 | $Q_1$ | Me | COOMe | OEt | OMe | OMe | CH |
| 6436 | $Q_1$ | Me | COOEt | OEt | Me | OMe | CH |
| 6437 | $Q_1$ | Me | COOEt | OEt | OMe | OMe | CH |
| 6438 | $Q_1$ | H | H | OEt | Me | OMe | CH |
| 6439 | $Q_1$ | H | H | OEt | OMe | OMe | CH |
| 6440 | Me | H | $Q_1$ | OEt | Me | OMe | CH |
| 6441 | Me | H | $Q_1$ | OEt | OMe | OMe | CH |
| 6442 | $Q_2$ | H | COOMe | OMe | Me | Me | CH |
| 6443 | $Q_2$ | H | COOMe | OMe | Me | OMe | CH |
| 6444 | $Q_2$ | H | COOMe | OMe | OMe | OMe | CH |
| 6445 | $Q_2$ | H | COOMe | OMe | Me | OMe | N |
| 6446 | $Q_2$ | H | COOMe | OMe | OMe | OMe | N |
| 6447 | $Q_2$ | H | COOEt | OMe | Me | Me | CH |
| 6448 | $Q_2$ | H | COOEt | OMe | Me | OMe | CH |
| 6449 | $Q_2$ | H | COOEt | OMe | OMe | OMe | CH |
| 6450 | $Q_2$ | H | COOEt | OMe | Me | OMe | N |
| 6451 | $Q_2$ | H | COOEt | OMe | OMe | OMe | N |
| 6452 | $Q_2$ | Me | COOMe | OMe | Me | OMe | CH |
| 6453 | $Q_2$ | Me | COOMe | OMe | OMe | OMe | CH |
| 6454 | $Q_2$ | Me | COOMe | OMe | Me | OMe | N |
| 6455 | $Q_2$ | Me | COOEt | OMe | Me | OMe | CH |
| 6456 | $Q_2$ | Me | COOEt | OMe | OMe | OMe | CH |
| 6457 | $Q_2$ | Me | COOEt | OMe | Me | OMe | N |
| 6458 | $Q_2$ | H | CN | OMe | Me | OMe | CH |
| 6459 | $Q_2$ | H | CN | OMe | OMe | OMe | CH |
| 6460 | $Q_2$ | H | CN | OMe | Me | OMe | N |
| 6461 | $Q_2$ | H | H | OMe | Me | OMe | CH |
| 6462 | $Q_2$ | H | H | OMe | OMe | OMe | CH |
| 6463 | $Q_2$ | H | H | OMe | Me | OMe | N |
| 6464 | Me | H | $Q_2$ | OMe | Me | Me | CH |
| 6465 | Me | H | $Q_2$ | OMe | Me | OMe | CH |
| 6466 | Me | H | $Q_2$ | OMe | OMe | OMe | CH |
| 6467 | Me | H | $Q_2$ | OMe | Me | OMe | N |
| 6468 | Me | H | $Q_2$ | OMe | OMe | OMe | N |
| 6469 | $Q_5$ | H | COOMe | OMe | Me | Me | CH |
| 6470 | $Q_5$ | H | COOMe | OMe | Me | OMe | CH |
| 6471 | $Q_5$ | H | COOMe | OMe | OMe | OMe | CH |
| 6472 | $Q_5$ | H | COOMe | OMe | Me | OMe | N |
| 6473 | $Q_5$ | H | COOMe | OMe | OMe | OMe | N |
| 6474 | $Q_5$ | H | COOEt | OMe | Me | Me | CH |
| 6475 | $Q_5$ | H | COOEt | OMe | Me | OMe | CH |
| 6476 | $Q_5$ | H | COOEt | OMe | OMe | OMe | CH |
| 6477 | $Q_5$ | H | COOEt | OMe | Me | OMe | N |
| 6478 | $Q_5$ | H | COOEt | OMe | OMe | OMe | N |
| 6479 | $Q_5$ | Me | COOMe | OMe | Me | OMe | CH |
| 6480 | $Q_5$ | Me | COOMe | OMe | OMe | OMe | CH |
| 6481 | $Q_5$ | Me | COOMe | OMe | Me | OMe | N |
| 6482 | $Q_5$ | Me | COOEt | OMe | Me | OMe | CH |
| 6483 | $Q_5$ | Me | COOEt | OMe | OMe | OMe | CH |
| 6484 | $Q_5$ | Me | COOEt | OMe | Me | OMe | N |
| 6485 | $Q_5$ | H | CN | OMe | Me | OMe | CH |
| 6486 | $Q_5$ | H | CN | OMe | OMe | OMe | CH |
| 6487 | $Q_5$ | H | CN | OMe | Me | OMe | N |
| 6488 | $Q_5$ | H | H | OMe | Me | OMe | CH |
| 6489 | $Q_5$ | H | H | OMe | OMe | OMe | CH |
| 6490 | $Q_5$ | H | H | OMe | Me | OMe | N |
| 6491 | Me | H | $Q_5$ | OMe | Me | Me | CH |
| 6492 | Me | H | $Q_5$ | OMe | Me | OMe | CH |
| 6493 | Me | H | $Q_5$ | OMe | OMe | OMe | CH |
| 6494 | Me | H | $Q_5$ | OMe | Me | OMe | N |
| 6495 | Me | H | $Q_5$ | OMe | OMe | OMe | N |
| 6496 | $Q_{10}$ | H | COOMe | OMe | Me | Me | CH |
| 6497 | $Q_{10}$ | H | COOMe | OMe | Me | OMe | CH |

TABLE 14-continued

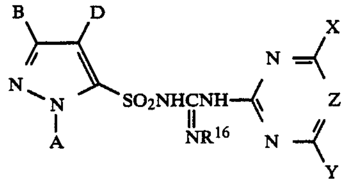

| No. | A | B | D | $R^{16}$ | X | Y | Z |
|---|---|---|---|---|---|---|---|
| 6498 | $Q_{10}$ | H | COOMe | OMe | OMe | OMe | CH |
| 6499 | $Q_{10}$ | H | COOMe | OMe | Me | OMe | N |
| 6500 | $Q_{10}$ | H | COOMe | OMe | OMe | OMe | N |
| 6501 | $Q_{10}$ | H | COOEt | OMe | Me | Me | CH |
| 6502 | $Q_{10}$ | H | COOEt | OMe | Me | OMe | CH |
| 6503 | $Q_{10}$ | H | COOEt | OMe | OMe | OMe | CH |
| 6504 | $Q_{10}$ | H | COOEt | OMe | Me | OMe | N |
| 6505 | $Q_{10}$ | H | COOEt | OMe | OMe | OMe | N |
| 6506 | $Q_{10}$ | Me | COOMe | OMe | Me | OMe | CH |
| 6507 | $Q_{10}$ | Me | COOMe | OMe | OMe | OMe | CH |
| 6508 | $Q_{10}$ | Me | COOMe | OMe | Me | OMe | N |
| 6509 | $Q_{10}$ | Me | COOEt | OMe | Me | OMe | CH |
| 6510 | $Q_{10}$ | Me | COOEt | OMe | OMe | OMe | CH |
| 6511 | $Q_{10}$ | Me | COOEt | OMe | Me | OMe | N |
| 6512 | $Q_{10}$ | H | CN | OMe | Me | OMe | CH |
| 6513 | $Q_{10}$ | H | CN | OMe | OMe | OMe | CH |
| 6514 | $Q_{10}$ | H | CN | OMe | Me | OMe | N |
| 6515 | $Q_{10}$ | H | H | OMe | Me | OMe | CH |
| 6516 | $Q_{10}$ | H | H | OMe | OMe | OMe | CH |
| 6517 | $Q_{10}$ | H | H | OMe | Me | OMe | N |
| 6518 | Me | H | $Q_{10}$ | OMe | Me | Me | CH |
| 6519 | Me | H | $Q_{10}$ | OMe | Me | OMe | CH |
| 6520 | Me | H | $Q_{10}$ | OMe | OMe | OMe | CH |
| 6521 | Me | H | $Q_{10}$ | OMe | Me | OMe | N |
| 6522 | Me | H | $Q_{10}$ | OMe | OMe | OMe | N |
| 6523 | $Q_{32}$ | H | COOMe | OMe | Me | Me | CH |
| 6524 | $Q_{32}$ | H | COOMe | OMe | Me | OMe | CH |
| 6525 | $Q_{32}$ | H | COOMe | OMe | OMe | OMe | CH |
| 6526 | $Q_{32}$ | H | COOMe | OMe | Me | OMe | N |
| 6527 | $Q_{32}$ | H | COOMe | OMe | OMe | OMe | N |
| 6528 | $Q_{32}$ | H | COOEt | OMe | Me | Me | CH |
| 6529 | $Q_{32}$ | H | COOEt | OMe | Me | OMe | CH |
| 6530 | $Q_{32}$ | H | COOEt | OMe | OMe | OMe | CH |
| 6531 | $Q_{32}$ | H | COOEt | OMe | Me | OMe | N |
| 6532 | $Q_{32}$ | H | COOEt | OMe | OMe | OMe | N |
| 6533 | $Q_{32}$ | Me | COOMe | OMe | Me | OMe | CH |
| 6534 | $Q_{32}$ | Me | COOMe | OMe | OMe | OMe | CH |
| 6535 | $Q_{32}$ | Me | COOMe | OMe | Me | OMe | N |
| 6536 | $Q_{32}$ | Me | COOEt | OMe | Me | OMe | CH |
| 6537 | $Q_{32}$ | Me | COOEt | OMe | OMe | OMe | CH |
| 6538 | $Q_{32}$ | Me | COOEt | OMe | Me | OMe | N |
| 6539 | $Q_{32}$ | H | CN | OMe | Me | OMe | CH |
| 6540 | $Q_{32}$ | H | CN | OMe | OMe | OMe | CH |
| 6541 | $Q_{32}$ | H | CN | OMe | Me | OMe | N |
| 6542 | $Q_{32}$ | H | H | OMe | Me | OMe | CH |
| 6543 | $Q_{32}$ | H | H | OMe | OMe | OMe | CH |
| 6544 | $Q_{32}$ | H | H | OMe | Me | OMe | N |
| 6545 | Me | H | $Q_{32}$ | OMe | Me | Me | CH |
| 6546 | Me | H | $Q_{32}$ | OMe | Me | OMe | CH |
| 6547 | Me | H | $Q_{32}$ | OMe | OMe | OMe | CH |
| 6548 | Me | H | $Q_{32}$ | OMe | Me | Me | N |
| 6549 | Me | H | $Q_{32}$ | OMe | Me | OMe | N |
| 6550 | Me | H | $Q_{32}$ | OMe | OMe | OMe | N |

In the above, $Q_1$ to $Q_{32}$ are as defined above.

TABLE 15

| Comp. No. | m.p. (°C.) |
|---|---|
| 1 | 159～160 |
| 2 | 166～166.5 |
| 3 | 182～183 |
| 31 | 166～167 |
| 47 | 154～157 |
| 48 | 143～145 |
| 49 | 140～142 |
| 50 | 137～140 |
| 51 | 133～136 |
| 52 | 141～145 |
| 53 | 147～152 |

TABLE 15-continued

| Comp. No. | m.p. (°C.) |
|---|---|
| 54 | 146～149 |
| 55 | 175～179 |
| 62 | 136～139 |
| 75 | 106～108 |
| 76 | 138～141 |
| 77 | 144～147 |
| 90 | 123～130 |
| 137 | 102～104 |
| 138 | 124～126 |
| 139 | 150～152 |
| 140 | 93～96 |
| 408 | 172～174 |

TABLE 15-continued

| Comp. No. | m.p. (°C.) |
|---|---|
| 481 | 182~185 |
| 490 | 152~156 |
| 491 | 167~170 |
| 492 | 165~168 |
| 497 | 174~177 |
| 917 | 123~124 |
| 918 | 178~179 |
| 919 | 194~195 |
| 1369 | 162~165 |
| 2127 | 110~115 |
| 3621 | 168~170 |
| 3622 | 180~182 |
| 3623 | 196~199 |
| 3624 | 174~175 |
| 3625 | 176~178 |
| 4151 | 173~176 |
| 4152 | 216~218 |
| 5258 | 139~142 |
| 5305 | 102~105 |
| 132 | 129~132 |
| 134 | 129~132 |
| 100 | 127~129 |
| 105 | 149~152 |
| 581 | 135~140 |
| 583 | 167~171 |
| 638 | 90~95 |
| 640 | 181~184 |
| 771 | 152~155 |
| 772 | 169~173 |
| 773 | 151~154 |
| 862 | 161~163 |
| 863 | 176~178 |
| 864 | 191~193 |
| 885 | 170~171 |
| 886 | 140~141 |
| 887 | 174~175 |
| 892 | 154~157 |
| 1359 | 159~161 |
| 1361 | 180~181 |
| 895 | 128~131 |
| 896 | 131~134 |
| 969 | 178.5~179.5 |
| 2323 | 138~140 |
| 1453 | 155~157 |
| 1455 | 165~167 |
| 2548 | 205~207 |
| 2549 | 167~171 |
| 2550 | 169~172 |
| 2551 | 163~165 |
| 2552 | 183~185 |
| 2553 | 204~207 |
| 5347 | 113~116 |
| 288 | 197~199 |
| 630 | 163~166 |
| 632 | 173~175 |
| 663 | 98~100 |
| 666 | 108~111 |
| 668 | 100~103 |
| 5349 | 162~166 |
| 5370 | 143~146 |
| 5462 | 100~103 |
| 5463 | 114~117 |
| 5464 | 145~147 |
| 5554 | 119~121 |
| 5555 | 165~168 |
| 5602 | 134~137 |
| 6218 | 95~96 |
| 605 | 125-128 |
| 661 | 110-113 |
| 1071 | 160-161 |
| 1073 | 152-153 |
| 5454 | 156-159 |
| 5456 | 192-194 |
| 6211 | 115-118 |
| 2763 | 136-139 |
| 6551 | 202-204 |
| 110 | 159-161 |
| 121 | 131-132 |
| 126 | 135-137 |
| 1485 | 158-161 |
| 1487 | 177-180 |

TABLE 15-continued

| Comp. No. | m.p. (°C.) |
|---|---|
| 662 | 113-114 |

In application of the compounds of this invention as herbicides, they can be applied by mixing with suitable carriers such as solid carriers, including for example clay, talc, bentonite, diatomaceous earth and others or liquid carriers, including for example water, alcohols (methanol, ethanol and the like), aromatic hydrocarbons (benzene, toluene, xylene and the like), chlorinated hydrocarbons, ethers, ketones, esters (ethyl acetate, etc.), acid amides (dimethylformamide, etc.) and others. They can be provided for practical use with addition of any desired additive selected from an emulsifier, a dispersing agent, a suspending agent, a wetting agent, a spreader and a stablizer and in any desired form such as a soluble concentrate, an emulsifiable concentrate, a wettable powder, a dust, a granule, a suspension concentrate, etc.

In the following, there are shown examples of formulations of herbicides containing the compounds of this invention as active ingredients, but they are not limitative of this invention. In the exemplary formulations shown below, "parts" mean "parts by weight".

| Exemplary Formulation 1: Wettable powder | |
|---|---|
| Compound No. 3 of this invention | 50 parts |
| Ziegleit A<br>(kaolin type clay; trade name; produced by Ziegleit Kogyo Co., Ltd.) | 46 parts |
| Solpol 5039<br>(mixture of nonionic surfactant and anionic surfactant; trade name; produced by Toho Kagaku Co., Ltd.) | 2 parts |
| Carplex (anticaking agent)<br>(white carbon; trade name, produced by Shionogi Seiyaku Co., Ltd.) | 2 parts |

All of the above components are mixed and pulverized homogeneously to prepare a wettable powder.

| Exemplary Formulation 2: Wettable powder | |
|---|---|
| Compound No. 49 of this invention | 45 parts |
| Ziegleit A<br>(kaolin type clay; trade name; produced by Ziegleit Kogyo Co., Ltd.) | 51 parts |
| Solpol 5039<br>(mixture of nonionic surfactant and anionic surfactant; trade name; produced by Toho Kagaku Co., Ltd.) | 2 parts |
| Carplex (anticaking agent)<br>(white carbon; trade name; produced by Shionogi Seiyaku Co., Ltd.) | 4 parts |

The above components are mixed and pulverized homogeneously to prepare a wettable powder.

| Exemplary Formulation 3: Emulsifiable concentrate | |
|---|---|
| Compound No. 49 of this invention | 2 parts |
| Xylene | 78 parts |
| Dimethylformamide | 15 parts |
| Solpol 2680<br>(mixture of nonionic surfactant and anionic surfactant; trade name; produced by Toho Kagaku Co., Ltd.) | 5 parts |

The above components are homogeneously mixed to prepare an emulsifiable concentrate. In use, the above emulsifiable concentrate is diluted to 10 to 10,000 times and sprayed in an amount of the active ingredient of 0.005 to 10 kg per hectare.

| Exemplary Formulation 4: Suspension concentrate | |
|---|---|
| Compound No. 1369 of this invention | 25 parts |
| Agrisol S-710 | 10 parts |
| (nonionic surfactant;trade name; produced by Kao-Atlas Co., Ltd.) | |
| Runox 1000 C | 0.5 part |
| (anionic surfactant; trade name; produced by Toho Kagaku Co., Ltd.) | |
| 1% Rodopol water | 20 parts |
| (thickener; trade name; produced by Rohne Poulainc) | |
| Water | 44.5 parts |

The above components are mixed homogeneously to provide a suspnsion concentrate preparation.

| Exemplary Formulation 5: Granule | |
|---|---|
| Compound No. 3 of this invention | 0.1 part |
| Bentonite | 55 parts |
| Talc | 44.9 parts |

All of the above components are mixed and pulverized homogeneously, then a little amount of water is added and the whole is stirred, kneaded and granulated by excluding granulator, then dried to prepare a granule.

| Exemplary Formulation 6: Granule | |
|---|---|
| Compound No. 408 of this invention | 0.5 part |
| Bentonite | 55.0 parts |
| Talc | 44.5 parts |

All of the above components are mixed and pulverized homogenerously, then a little amount of water is added and the whole is stirred, kneaded and granulated by excluding granulator, then dried to prepare a granule.

| Exemplary Formulation 7: Wettable powder | |
|---|---|
| Compound No. 1 of this invention | 10 parts |
| Ziegleit PFP | 83 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi Seiyaku Co., Ltd.) | |

The above components are mixed and pulverized homogeneously to prepare a wettable powder.

| Exemplary Formulation 8: Wettable powder | |
|---|---|
| Compound No. 132 of this invention | 20 parts |
| Ziegleit PFP | 73 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi Seiyaku Co., Ltd.) | |

-continued

The above components are mixed and pulverized homogeneously to prepare a wettable powder.

| Exemplary Formulation 9: Wettable powder | |
|---|---|
| Compound No. 638 of this invention | 30 parts |
| Ziegleit PFP | 63 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi Seiyaku Co., Ltd.) | |

The above components are mixed and pulverized homogeneously to prepare a wettable powder.

| Exemplary Formulation 10: Wettable powder | |
|---|---|
| Compound No. 771 of this invention | 40 parts |
| Ziegleit PFP | 53 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi Seiyaku Co., Ltd.) | |

The above components are mixed and pulverized homogeneously to prepare a wettable powder.

| Exemplary Formulation 11: Wettable powder | |
|---|---|
| Compound No. 885 of this invention | 50 parts |
| Ziegleit PFP | 43 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi Seiyaku Co., Ltd.) | |

The above components are mixed and pulverized homogeneously to prepare a wettable powder.

| Exemplary Formulation 12: Wettable powder | |
|---|---|
| Compound No. 887 of this invention | 50 parts |
| Ziegleit PFP | 43 parts |
| (kaolin type clay; trade name; produced by Ziegleit Kogyo Co., Ltd.) | |
| Solpol 5039 | 5 parts |
| (mixture of nonionic surfactant and anionic surfactant; trade name; produced by Toho Kagaku Co., Ltd.) | |
| Carplex (anticaking agent) | 2 parts |
| (white carbon; trade name; produced by Shionogi | |

-continued

| Exemplary Formulation 12: Wettable powder | |
|---|---|
| Seiyaku Co., Ltd.) | |

The above components are mixed and pulverized homogeneously to prepare a wettable powder.

| Exemplary Formulation 13: Wettable powder | |
|---|---|
| Compound No. 896 of this invention | 60 parts |
| Ziegleit PFP (kaolin type clay; trade name; produced by Ziegleit Kogyo Co., Ltd.) | 33 parts |
| Solpol 5039 (mixture of nonionic surfactant and anionic surfactant; trade name; produced by Toho Kagaku Co., Ltd.) | 5 parts |
| Carplex (anticaking agent) (white carbon; trade name; produced by Shionogi Seiyaku Co., Ltd.) | 2 parts |

The above components are mixed and pulverized homogeneously to prepare a wettable powder.

| Exemplary Formulation 14: Wettable powder | |
|---|---|
| Compound No. 1359 of this invention | 70 parts |
| Ziegleit PFP (kaolin type clay; trade name; produced by Ziegleit Kogyo Co., Ltd.) | 23 parts |
| Solpol 5039 (mixture of nonionic surfactant and anionic surfactant; trade name; produced by Toho Kagaku Co., Ltd.) | 5 parts |
| Carplex (anticaking agent) (white carbon; trade name; produced by Shionogi Seiyaku Co., Ltd.) | 2 parts |

The above components are mixed and pulverized homogeneously to prepare a wettable powder.

| Exemplary Formulation 15: Wettable powder | |
|---|---|
| Compound No. 1455 of this invention | 80 parts |
| Ziegleit PFP (kaolin type clay; trade name; produced by Ziegleit Kogyo Co., Ltd.) | 13 parts |
| Solpol 5039 (mixture of nonionic surfactant and anionic surfactant; trade name; produced by Toho Kagaku Co., Ltd.) | 5 parts |
| Carplex (anticaking agent) (white carbon; trade name; produced by Shionogi Seiyaku Co., Ltd.) | 2 parts |

The above components are mixed and pulverized homogeneously to prepare a wettable powder.

| Exemplary Formulation 16: Emulsifiable concentrate | |
|---|---|
| Compound No. 863 of this invention | 1 part |
| Xylene | 79 parts |
| Dimethylformamide | 15 parts |
| Solpol 2680 (mixture of nonionic surfactant and anionic surfactant; trade name; produced by Toho Kagaku Co., Ltd.) | 5 parts |

The above components are homogeneously mixed to prepare an emulsifiable concentrate. In use, the above emulsifiable concentrate is diluted to 10 to 10,000 times and sprayed in an amount of the active ingredient of 0.005 to 10 kg per hectare.

| Exemplary Formulation 17: Emulsifiable concentrate | |
|---|---|
| Compound No. 886 of this invention | 1.5 parts |
| Xylene | 78.5 parts |
| Dimethylformamide | 15 parts |
| Solpol 2680 (mixture of nonionic surfactant and anionic surfactant; trade name; produced by Toho Kagaku Co., Ltd.) | 5 parts |

The above components are homogeneously mixed to prepare an emulsifiable concentrate. In use, the above emulsifiable concentrate is diluted to 10 to 10,000 times and sprayed in an amount of the active ingredient of 0.005 to 10 kg per hectare.

| Exemplary Formulation 18: Emulsifiable concentrate | |
|---|---|
| Compound No. 5347 of this invention | 2 parts |
| Xylene | 78 parts |
| Dimethylformamide | 15 parts |
| Solpol 2680 (mixture of nonionic surfactant and anionic surfactant; trade name; produced by Toho Kagaku Co., Ltd.) | 5 parts |

The above components are homogeneously mixed to prepare an emulsifiable concentrate. In use, the above emulsifiable concentrate is diluted to 10 to 10,000 times and sprayed in an amount of the active ingredient of 0.005 to 10 kg per hectare.

| Exemplary Formulation 19: Suspension concentrate | |
|---|---|
| Compound No. 583 of this invention | 10 parts |
| Agrisol B-710 (nonionic surfactant; trade name; produced by Kao-Atlas Co., Ltd.) | 10 parts |
| Runox 1000 C (anionic surfactant; trade name; produced by Toho Kagaku Co., Ltd.) | 0.5 part |
| 1% Rodopol water (thickener; trade name; produced by Rohne Poulainc) | 20 parts |
| Water | 59.5 parts |

The above components are mixed homogeneously to provide a suspnsion concentrate preparation.

| Exemplary Formulation 20: Suspension concentrate | |
|---|---|
| Compound No. 640 of this invention | 20 parts |
| Agrisol B-710 (nonionic surfactant; trade name; produced by Kao-Atlas Co., Ltd.) | 10 parts |
| Runox 1000 C (anionic surfactant; trade name; produced by Toho Kagaku Co., Ltd.) | 0.5 part |
| 1% Rodopol water (thickener; trade name; produced by Rohne Poulainc) | 20 parts |
| Water | 49.5 parts |

The above components are mixed homogeneously to provide a suspnsion concentrate preparation.

| Exemplary Formulation 21: Suspension concentrate | |
|---|---|
| Compound No. 1361 of this invention | 30 parts |
| Agrisol B-710 (nonionic surfactant; trade name; produced by Kao-Atlas Co., Ltd.) | 10 parts |
| Runox 1000 C | 0.5 part |

-continued

| Exemplary Formulation 21: Suspension concentrate | |
|---|---|
| (anionic surfactant; trade name; produced by Toho Kagaku Co., Ltd.) | |
| 1% Rodopol water | 20 parts |
| (thickener; trade name; produced by Rohne Poulainc) | |
| Water | 39.5 parts |

The above components are mixed homogeneously to provide a suspnsion concentrate preparation.

| Exemplary Formulation 22: Suspension concentrate | |
|---|---|
| Compound No. 1453 of this invention | 40 parts |
| Agrisol B-710 | 10 parts |
| (nonionic surfactant; trade name; produced by Kao-Atlas Co., Ltd.) | |
| Runox 1000 C | 0.5 part |
| (anionic surfactant; trade name; produced by Toho Kagaku Co., Ltd.) | |
| 1% Rodopol water | 20 parts |
| (thickener; trade name; produced by Rohne Poulainc) | |
| Water | 29.5 parts |

The above components are mixed homogeneously to provide a suspnsion concentrate preparation.

| Exemplary Formulation 23: Suspension concentrate | |
|---|---|
| Compound No. 2323 of this invention | 60 parts |
| Agrisol B-710 | 10 parts |
| (nonionic surfactant; trade name; produced by Kao-Atlas Co., Ltd.) | |
| Runox 1000 C | 0.5 part |
| (anionic surfactant; trade name; produced by Toho Kagaku Co., Ltd.) | |
| 1% Rodopol water | 10 parts |
| (thickener; trade name; produced by Rohne Poulainc) | |
| Water | 19.5 parts |

The above components are mixed homogeneously to provide a suspnsion concentrate preparation.

| Exemplary Formulation 24: Granule | |
|---|---|
| Compound No. 885 of this invention | 0.05 part |
| Bentonite | 55.0 parts |
| Talc | 44.95 parts |

All of the above components are mixed and pulverized homogeneously, then a little amount of water is added and the whole is stirred, kneaded and granulated by excluding granulator, then dried to prepare a granule.

| Exemplary Formulation 25: Granule | |
|---|---|
| Compound No. 886 of this invention | 0.2 part |
| Bentonite | 55.0 parts |
| Talc | 44.8 parts |

All of the above components are mixed and pulverized homogeneously, then a little amount of water is added and the whole is stirred, kneaded and granulated by excluding granulator, then dried to prepare a granule.

| Exemplary Formulation 26: Granule | |
|---|---|
| Compound No. 887 of this invention | 1.0 part |
| Bentonite | 55.0 parts |
| Talc | 44.0 parts |

All of the above components are mixed and pulverized homogeneously, then a little amount of water is added and the whole is stirred, kneaded and granulated by excluding granulator, then dried to prepare a granule.

If desired, the compound of this invention may be applied as a mixture with other kinds of herbicides, various insecticides, sterilizers or adjuvants during preparation or spraying In particular, when applied in beet fields, useful ones include phenmedipham, desmedipham, lenacil, pyrazone., ethofumesate and so on.

As the other kinds of herbicides mentioned above, there may be included those as described in Farm Chemicals Handbook, 70th Edition (1984).

The compounds of this invention can also be applied, in addition to the agricultural and horticultural fields such as farm fields, paddy fields, fruit gardens and the like, to athletic grounds, vacant lands, belts along railroads and others. The amounts of the herbicide to be applied, which may differ depending on the scenes to be applied, the time of application, the application method, the kinds of the objective grasses and the crops harvested, may generally range suitably from about 0.25 to about 10 kg per hectare. When applied to beets in particular, it may range suitably from 0.25 to 500 g/ha, preferably from 0.5 to 250 g/ha.

The following test examples are set forth for illustration of the utility of the compounds of this invention as herbicides.

TEST EXAMPLE 1

Herbicidal Effect Test by Soil Treatment

In a plastic box of 15 cm length, 22 cm width and 6 cm depth, there was placed a sterilized deluvium soil, and seeds of (A) rice (*Oryza sativa*), (B) barnyardgrass (*Echinochloa crusgalli*), (C) large crabgrass (*Digitaria adscendens*), (D) annual sedge (*Cyperus microiria*), (E) black nightshade (*Solanum nigrum* L.), (F) hairly galinosoga (*Galinosoga ciliata*), (G) rorippa ssp. (*Rorippa atrovirens*), (H) corn (*Zea mays*), (I) wheat (*Triticum vulgare*), (J) soybean (*Glysine max*), (K) cotton (Gossypium) and (L) sugar beet (*Beta vulgaris*) were sown mixedly. After covering soil to about 1.5 cm over the seeds, herbicides were sprayed evenly on the soil surface to predetermined proportions of the active ingredient. In spraying, the wettable powder as shown in the foregoing exemplary formulations was diluted with water and sprayed over the entire surface by means of a small sprayer. Four weeks after spraying, the herbicidal effect on crops including rice, etc. and the various weeds were examined according to the judgement criteria shown below. The results are shown in Table 16.

Some of the compounds of this invention show the selectivity on certain crops.

| Judgement criteria: |
|---|
| 5. . . Growth control rates of more than 90% (almost completely withered) |
| 4. . . Growth control rates of 70 to 90% |
| 3. . . Growth control rates of 40 to 70% |

-continued

| Judgement criteria: |
|---|
| 2. . . Growth control rates of 20 to 40% |
| 1. . . Growth control rates of 5 to 20% |
| 0. . . Growth control rates of less than 5% (substantially no effect) |

The above growth control rates are determined by measuring the top fresh weights of the treated plants and those of the non-treated plants, and calculated from the following formula:

$$\text{Growth controle rate}(\%) = \left(1 - \frac{\text{Top fresh weight of the treated plants}}{\text{Top fresh weight of the non-treated plants}}\right) \times 100$$

TEST EXAMPLE 2

Herbicidal effect test by stem-leaf treatment

In a plastic box of 15 cm length, 22 cm width and 6 cm depth, there was placed a sterilized deluvium soil, seeds of (A) rice (*Oryza sativa*), (B) barnyardgrass (*Echinochloa crusgalli*), (C) large crabgrass (*Digitaria adscendens*), (D) annual sedge (*Cyperus microiria*), (E) black nightshade (*Solanum nigrum* L.), (F) hairly galinosoga (*Galinosoga ciliata*), (G) rorippa ssp. (*Rorippa atrovirens*), (H) corn (*Zea mays*), (I) wheat (*Triticum vulgare*), (J) soybean (*Glysine max*), (K) cotton (Gossypium) and (L) sugar beet (*Beta vulgaris*) were sown in shapes of spots, respectively, followed by covering of soil to about 1.5 cm over the seeds. After respective plants have grown to the second and the third leaf stage, herbicides were sprayed evenly onto the stem-leaf portion at predetermined proportions of the active ingredient.

In spraying, the wettable powder as shown in the foregoing exemplary formulations was diluted with water and sprayed over the entire surface of the stem-leaf portions of various weeds by means of a small sprayer.

Four weeks after spraying, the herbicidal effect on crops including rice, etc. and the various weeds were examined according to the judgement criteria as shown in Test example 1. The results are shown in Table 17.

TEST EXAMPLE 3

Agricultural chemical damage test on sugar beet

In a plastic box of 15 cm length, 22 cm width and 6 cm depth, there was placed a sterilized deluvium soil, and seeds of (L) sugar beet (*Beta vulgaris*), (M) cocklebar (*Xanthium strumarium*), (N) wild mustard (*Sinapis arvensis*), (E) black nightshade (*Solanum nigrum* L.) and (O) cleavers (*Galium aparine*)) were sown in shapes of spots, respectively, followed by covering of soil to about 1.5 cm over the seeds. After respective plants have grown to the second and the third leaf stage, herbicides were sprayed evenly onto the stem-leaf portion at predetermined proportions of the active ingredient.

On 20 days after treatment, the herbicidal effects on weeds and agricultural chemical damages on sugar beet were examined. The results are shown in Table 18.

TEST EXAMPLE 4

Agricultural chemical damage test on wheat

In a plastic box of 15 cm length, 22 cm width and 6 cm depth, there was placed a sterilized deluvium soil, and seeds of (I) wheat (*Triticum vulgare*) and (P) wild oat (*Avena fatua*) were sown in shapes of spots, respectively, followed by covering of soil to about 1.5 cm over the seeds. After respective plants have grown to the third and the fourth leaf stage, herbicides were sprayed evenly onto the stem-leaf portion at predetermined proportions of the active ingredient.

On 20 days after treatment, the herbicidal effects on weeds and agricultural chemical damages on wheat were examined. The results are shown in Table 19.

TABLE 16

| Comp. No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| No. 3 | 0.02 | 5 | 5 | 5 | 5 | 5 | 5 | 5 | 5 | 0 | 5 | 5 | — |
| | 0.04 | 5 | 5 | 5 | 5 | 5 | 5 | 5 | 5 | 1 | 5 | 5 | — |
| No. 31 | 0.16 | 5 | 5 | 4 | 5 | 5 | 5 | 5 | 5 | 0 | 5 | 5 | — |
| No. 49 | 0.02 | 5 | 2 | 1 | 5 | 5 | 5 | 5 | 5 | 5 | 5 | 5 | 0 |
| | 0.04 | 5 | 3 | 3 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 1 |
| No. 53 | 0.16 | 1 | 0 | 1 | 4 | 2 | 5 | 5 | 1 | 0 | 0 | 0 | — |
| | 0.32 | 2 | 1 | 2 | 5 | 3 | 5 | 5 | 2 | 1 | 1 | 1 | — |
| No. 139 | 0.02 | 5 | 2 | 2 | 5 | 5 | 5 | 5 | 5 | 5 | 5 | 5 | 0 |
| | 0.04 | 5 | 4 | 3 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 1 |
| No. 408 | 0.16 | 2 | 4 | 1 | 5 | 3 | 5 | 5 | 5 | 0 | 3 | 3 | — |
| No. 490 | 0.08 | 4 | 4 | 4 | 4 | 5 | 5 | 5 | 3 | 3 | 1 | 1 | — |
| | 0.16 | 5 | 4 | 4 | 4 | 5 | 5 | 5 | 4 | 4 | 1 | 1 | — |
| No.491 | 0.02 | 0 | 3 | 3 | 4 | 4 | 4 | 5 | 4 | 3 | 3 | 3 | — |
| | 0.04 | 4 | 4 | 5 | 4 | 5 | 5 | 5 | 5 | 5 | 5 | 3 | — |
| | 0.08 | 5 | 5 | 5 | 5 | 5 | 5 | 5 | 5 | 5 | 5 | 4 | — |
| No. 492 | 0.02 | 5 | 4 | 2 | 5 | 5 | 5 | 5 | 5 | 5 | 5 | 5 | — |
| | 0.04 | 5 | 5 | 3 | 5 | 5 | 5 | 5 | 5 | 5 | 5 | 5 | — |
| No. 497 | 0.08 | 4 | 4 | 2 | 4 | 5 | 4 | 5 | 3 | 3 | 2 | 1 | — |
| | 0.16 | 5 | 4 | 3 | 4 | 5 | 5 | 5 | 4 | 5 | 3 | 3 | — |
| No. 1369 | 0.02 | 5 | 4 | 4 | 5 | 5 | 5 | 5 | 5 | 5 | 5 | 3 | — |
| | 0.04 | 5 | 5 | 5 | 5 | 5 | 5 | 5 | 5 | 5 | 5 | 5 | — |
| No. 3624 | 0.16 | 5 | 2 | 5 | 4 | 2 | 4 | 5 | 5 | 5 | 1 | 0 | — |
| No. 4151 | 0.04 | 2 | 0 | 3 | 2 | 0 | 0 | 5 | 2 | 0 | 0 | 0 | — |

TABLE 16-continued

| Comp. No. | Amount of active ingre-dient applied kg/ha | (A) | (B) | (C) | (D) | (E) | (F) | (G) | (H) | (I) | (J) | (K) | (L) |
|---|---|---|---|---|---|---|---|---|---|---|---|---|---|
| | 0.08 | 3 | 3 | 4 | 3 | 0 | 0 | 5 | 3 | 0 | 0 | 0 | — |
| | 0.16 | 4 | 4 | 5 | 5 | 0 | 0 | 5 | 4 | 0 | 0 | 0 | — |
| No. 5258 | 0.32 | 0 | 1 | 4 | 2 | 1 | 4 | 3 | 0 | 0 | 0 | 0 | — |
| No. 132 | 0.32 | 5 | 3 | 3 | 4 | 4 | 5 | 4 | 5 | 2 | 5 | 0 | — |
| No. 583 | 0.16 | 5 | 5 | 2 | 5 | 5 | 5 | 5 | 5 | 5 | 5 | 5 | — |
| | 0.32 | 5 | 5 | 3 | 5 | 5 | 5 | 5 | 5 | 5 | 5 | 5 | — |
| No. 638 | 0.04 | 5 | 4 | 5 | 5 | 5 | 5 | 5 | 5 | 5 | 5 | 5 | — |
| | 0.08 | 5 | 5 | 5 | 5 | 5 | 5 | 5 | 5 | 5 | 5 | 5 | — |
| No. 640 | 0.04 | 5 | 5 | 3 | 5 | 5 | 5 | 5 | 5 | 3 | 4 | 3 | 0 |
| | 0.08 | 5 | 5 | 4 | 5 | 5 | 5 | 5 | 5 | 5 | 5 | 5 | 1 |
| No. 771 | 0.04 | 3 | 3 | 3 | 5 | 5 | 5 | 5 | 3 | 3 | 3 | 3 | — |
| | 0.08 | 4 | 4 | 4 | 5 | 5 | 5 | 5 | 4 | 4 | 4 | 4 | — |
| No. 772 | 0.04 | 5 | 5 | 5 | 5 | 5 | 5 | 5 | 5 | 5 | 5 | 5 | — |
| | 0.08 | 5 | 5 | 5 | 5 | 5 | 5 | 5 | 5 | 5 | 5 | 5 | — |
| No. 773 | 0.04 | 5 | 4 | 3 | 5 | 5 | 5 | 5 | 5 | 4 | 4 | 3 | — |
| | 0.08 | 5 | 5 | 4 | 5 | 5 | 5 | 5 | 5 | 5 | 5 | 4 | — |
| No. 862 | 0.08 | 4 | 3 | 2 | 5 | 5 | 5 | 5 | 5 | 2 | 4 | 2 | — |
| | 0.16 | 5 | 4 | 3 | 5 | 5 | 5 | 5 | 5 | 3 | 5 | 3 | — |
| No. 864 | 0.04 | 4 | 4 | 1 | 5 | 5 | 5 | 5 | 3 | 1 | 3 | 0 | — |
| | 0.08 | 5 | 5 | 2 | 5 | 5 | 5 | 5 | 4 | 3 | 4 | 1 | — |
| No. 885 | 0.08 | 5 | 4 | 3 | 5 | 5 | 5 | 5 | 5 | 0 | 5 | 1 | — |
| | 0.16 | 5 | 5 | 5 | 5 | 5 | 5 | 5 | 5 | 0 | 5 | 3 | — |
| No. 887 | 0.08 | 5 | 5 | 2 | 5 | 5 | 5 | 5 | 5 | 0 | 5 | 5 | 0 |
| | 0.16 | 5 | 5 | 3 | 5 | 5 | 5 | 5 | 5 | 0 | 5 | 5 | 0 |
| No. 896 | 0.04 | 5 | 3 | 3 | 5 | 5 | 5 | 5 | 5 | 5 | 4 | 3 | 0 |
| | 0.08 | 5 | 4 | 4 | 5 | 5 | 5 | 5 | 5 | 5 | 5 | 4 | 0 |
| No. 2323 | 0.04 | 5 | 3 | 5 | 5 | 5 | 5 | 5 | 5 | 0 | 1 | 0 | 0 |
| | 0.08 | 5 | 4 | 5 | 5 | 5 | 5 | 5 | 5 | 0 | 2 | 0 | 0 |
| No. 1455 | 0.16 | 5 | 4 | 5 | 5 | 5 | 5 | 5 | 5 | 3 | 5 | 5 | — |
| | 0.32 | 5 | 4 | 5 | 5 | 5 | 5 | 5 | 5 | 4 | 5 | 5 | — |
| No. 100 | 0.02 | 5 | 2 | 1 | 5 | 5 | 5 | 5 | 5 | 5 | 5 | 5 | 0 |
| | 0.04 | 5 | 3 | 3 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 0 |
| No. 105 | 0.02 | 5 | 2 | 1 | 5 | 5 | 5 | 5 | 5 | 5 | 5 | 5 | 0 |
| | 0.04 | 5 | 3 | 3 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 0 |
| No. 630 | 0.02 | 0 | 3 | 2 | 5 | 5 | 5 | 5 | 5 | 0 | 5 | 4 | — |
| | 0.04 | 0 | 5 | 4 | 5 | 5 | 5 | 5 | 5 | 0 | 5 | 4 | — |
| | 0.08 | 2 | 5 | 5 | 5 | 5 | 5 | 5 | 5 | 0 | 5 | 5 | — |
| No. 632 | 0.02 | 0 | 4 | 3 | 5 | 5 | 5 | 5 | 5 | 0 | 5 | 5 | 0 |
| | 0.04 | 0 | 5 | 4 | 5 | 5 | 5 | 5 | 5 | 0 | 5 | 5 | 0 |
| | 0.08 | 2 | 5 | 5 | 5 | 5 | 5 | 5 | 5 | 0 | 5 | 5 | 0 |
| No. 668 | 0.02 | 5 | 4 | 4 | 5 | 5 | 5 | 5 | 5 | 4 | 5 | 5 | 0 |
| | 0.04 | 5 | 5 | 5 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 1 |
| No. 892 | 0.02 | 5 | 4 | 3 | 5 | 5 | 5 | 5 | 5 | 3 | 5 | 5 | 0 |
| | 0.04 | 5 | 5 | 4 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 0 |
| No. 2549 | 0.63 | 5 | 5 | 5 | 5 | 5 | 5 | 5 | 5 | 5 | 5 | 0 | — |
| No. 2550 | 0.63 | 5 | 5 | 5 | 5 | 5 | 5 | 5 | 5 | 5 | 5 | 0 | — |
| No. 2551 | 0.63 | 5 | 5 | 5 | 5 | 5 | 5 | 5 | 5 | 5 | 5 | 0 | — |
| No. 2552 | 0.63 | 5 | 5 | 5 | 5 | 5 | 5 | 5 | 5 | 5 | 5 | 0 | — |
| No. 5370 | 0.02 | 5 | 4 | 2 | 5 | 5 | 5 | 5 | 5 | 4 | 5 | 5 | 0 |
| | 0.04 | 5 | 5 | 4 | 5 | 5 | 5 | 5 | 5 | 5 | 5 | 5 | 0 |
| | 0.08 | 5 | 5 | 5 | 5 | 5 | 5 | 5 | 5 | 5 | 5 | 5 | 0 |

TABLE 17

| Comp. No. | Amount of active ingre-dient applied kg/ha | (A) | (B) | (C) | (D) | (E) | (F) | (G) | (H) | (I) | (J) | (K) | (L) |
|---|---|---|---|---|---|---|---|---|---|---|---|---|---|
| | 0.01 | 5 | 5 | 4 | 5 | 5 | 5 | 5 | 5 | 1 | 5 | 5 | 5 |
| No. 1 | 0.02 | 5 | 5 | 5 | 5 | 5 | 5 | 5 | 5 | 1 | 5 | 5 | 5 |
| | 0.04 | 5 | 5 | 5 | 5 | 5 | 5 | 5 | 5 | 2 | 5 | 5 | 5 |
| No. 2 | 0.04 | 2 | 5 | 2 | 5 | 5 | 5 | 5 | 5 | 0 | 5 | 5 | 5 |
| | 0.08 | 4 | 5 | 3 | 5 | 5 | 5 | 5 | 5 | 0 | 5 | 5 | 5 |
| | 0.01 | 5 | 5 | 1 | 5 | 5 | 5 | 5 | 5 | 0 | 5 | 5 | 0 |
| No. 3 | 0.02 | 5 | 5 | 1 | 5 | 5 | 5 | 5 | 5 | 0 | 5 | 5 | 0 |
| | 0.04 | 5 | 5 | 3 | 5 | 5 | 5 | 5 | 5 | 0 | 5 | 5 | 1 |

TABLE 17-continued

| Comp. No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| | 0.04 | 1 | 5 | 1 | 5 | 5 | 5 | 5 | 5 | 0 | 5 | 5 | 5 |
| No. 31 | 0.08 | 2 | 5 | 1 | 5 | 5 | 5 | 5 | 5 | 0 | 5 | 5 | 5 |
| | 0.01 | 5 | 3 | 2 | 4 | 5 | 5 | 5 | 5 | 0 | 5 | 5 | 0 |
| No. 48 | 0.02 | 5 | 4 | 2 | 5 | 5 | 5 | 5 | 5 | 1 | 5 | 5 | 0 |
| | 0.04 | 5 | 5 | 3 | 5 | 5 | 5 | 5 | 5 | 2 | 5 | 5 | 0 |
| | 0.01 | 5 | 5 | 2 | 5 | 5 | 5 | 5 | 5 | 5 | 5 | 5 | 0 |
| No. 49 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |
| No. 51 | 0.32 | 5 | 5 | 3 | 5 | 5 | 5 | 5 | 5 | 5 | 5 | 5 | 5 |
| | 0.04 | 4 | 3 | 0 | 4 | 5 | 5 | 3 | 4 | 2 | 3 | 3 | 4 |
| No. 52 | 0.08 | 5 | 3 | 0 | 4 | 5 | 5 | 4 | 5 | 2 | 3 | 4 | 5 |
| | 0.16 | 5 | 3 | 0 | 5 | 5 | 5 | 5 | 5 | 2 | 4 | 4 | 5 |
| No. 53 | 0.16 | 3 | 3 | 2 | 5 | 5 | 5 | 5 | 4 | 0 | 0 | 3 | 3 |
| | 0.16 | 1 | 3 | 0 | 5 | 5 | 5 | 5 | 2 | 1 | 3 | 3 | 5 |
| No. 55 | 0.32 | 2 | 4 | 1 | 5 | 5 | 5 | 5 | 3 | 2 | 4 | 4 | 5 |
| | 0.01 | 5 | 3 | 2 | 5 | 5 | 5 | 5 | 5 | 5 | 5 | 5 | 0 |
| No. 138 | 0.02 | 5 | 4 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |
| | 0.01 | 5 | 5 | 2 | 5 | 5 | 5 | 5 | 5 | 5 | 5 | 5 | 0 |
| No. 139 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 1 |
| No. 140 | 0.32 | 5 | 5 | 3 | 5 | 5 | 5 | 5 | 5 | 5 | 5 | 5 | 5 |
| | 0.04 | 0 | 4 | 0 | 5 | 5 | 5 | 5 | 5 | 0 | 5 | 5 | 5 |
| No. 408 | 0.08 | 2 | 5 | 0 | 5 | 5 | 5 | 5 | 5 | 0 | 5 | 5 | 5 |
| | 0.16 | 3 | 5 | 0 | 5 | 5 | 5 | 5 | 5 | 0 | 5 | 5 | 5 |
| | 0.04 | 4 | 0 | 0 | 2 | 5 | 5 | 5 | 3 | 0 | 5 | 5 | 5 |
| No. 481 | 0.08 | 5 | 0 | 0 | 3 | 5 | 5 | 5 | 4 | 0 | 5 | 5 | 5 |
| | 0.16 | 5 | 0 | 0 | 4 | 5 | 5 | 5 | 5 | 0 | 5 | 5 | 5 |
| | 0.08 | 3 | 5 | 2 | 5 | 5 | 5 | 4 | 4 | 1 | 2 | 2 | 4 |
| No. 490 | 0.16 | 4 | 5 | 3 | 5 | 5 | 5 | 5 | 5 | 2 | 3 | 3 | 5 |
| | 0.01 | 4 | 4 | 3 | 3 | 5 | 5 | 5 | 4 | 4 | 5 | 5 | 5 |
| No. 491 | 0.02 | 5 | 4 | 3 | 4 | 5 | 5 | 5 | 5 | 5 | 5 | 5 | 5 |
| | 0.04 | 5 | 5 | 3 | 5 | 5 | 5 | 5 | 5 | 5 | 5 | 5 | 5 |
| | 0.04 | 5 | 5 | 3 | 5 | 5 | 5 | 5 | 5 | 5 | 5 | 5 | 5 |
| No. 492 | 0.08 | 5 | 5 | 3 | 5 | 5 | 5 | 5 | 5 | 5 | 5 | 5 | 5 |
| | 0.08 | 3 | 4 | 2 | 4 | 5 | 5 | 5 | 3 | 2 | 3 | 5 | 5 |
| No. 497 | 0.16 | 4 | 5 | 2 | 5 | 5 | 5 | 5 | 5 | 3 | 5 | 5 | 5 |
| | 0.04 | 5 | 5 | 5 | 5 | 5 | 5 | 5 | 5 | 5 | 5 | 5 | 0 |
| No. 1369 | 0.08 | 5 | 5 | 5 | 5 | 5 | 5 | 5 | 5 | 5 | 5 | 5 | 1 |
| | 0.08 | 2 | 3 | 2 | 2 | 5 | 5 | 4 | 5 | 1 | 4 | 3 | 0 |
| No. 2127 | 0.16 | 3 | 4 | 4 | 5 | 5 | 5 | 5 | 5 | 3 | 5 | 4 | 1 |
| | 0.08 | 5 | 5 | 5 | 3 | 5 | 5 | 5 | 5 | 5 | 2 | 0 | 5 |
| No. 3624 | 0.16 | 5 | 5 | 5 | 4 | 5 | 5 | 5 | 5 | 5 | 3 | 0 | 5 |
| No. 3625 | 0.16 | 4 | 5 | 5 | 3 | 4 | 5 | 4 | 2 | 3 | 2 | 2 | 5 |
| | 0.04 | 3 | 5 | 4 | 5 | 3 | 0 | 5 | 5 | 0 | 4 | 0 | 5 |
| No. 4151 | 0.08 | 4 | 5 | 5 | 5 | 4 | 1 | 5 | 5 | 2 | 5 | 0 | 5 |
| | 0.16 | 5 | 5 | 5 | 5 | 5 | 2 | 5 | 5 | 3 | 5 | 1 | 5 |
| | 0.04 | 0 | 4 | 2 | 4 | 2 | 2 | 5 | 5 | 0 | 3 | 0 | 5 |
| No. 4152 | 0.08 | 2 | 5 | 4 | 5 | 3 | 5 | 5 | 5 | 0 | 4 | 1 | 5 |
| | 0.16 | 4 | 5 | 5 | 5 | 4 | 5 | 5 | 5 | 0 | 5 | 1 | 5 |
| No. 5258 | 0.32 | 2 | 4 | 2 | 4 | 5 | 5 | 4 | 1 | 1 | 3 | 4 | 3 |
| | 0.02 | 5 | 5 | 3 | 5 | 5 | 5 | 5 | 5 | 0 | 5 | 3 | 5 |
| No. 132 | 0.04 | 5 | 5 | 3 | 5 | 5 | 5 | 5 | 5 | 1 | 5 | 4 | 5 |
| | 0.04 | 5 | 5 | 2 | 5 | 5 | 5 | 5 | 5 | 5 | 5 | 5 | 2 |
| No. 583 | 0.08 | 5 | 5 | 3 | 5 | 5 | 5 | 5 | 5 | 5 | 5 | 5 | 4 |
| | 0.04 | 5 | 5 | 3 | 5 | 5 | 5 | 5 | 5 | 1 | 5 | 5 | 5 |
| No. 638 | 0.08 | 5 | 5 | 4 | 5 | 5 | 5 | 5 | 5 | 2 | 5 | 5 | 5 |
| | 0.02 | 5 | 5 | 2 | 5 | 5 | 5 | 5 | 5 | 2 | 5 | 5 | 1 |
| No. 640 | 0.04 | 5 | 5 | 2 | 5 | 5 | 5 | 5 | 5 | 4 | 5 | 5 | 1 |
| | 0.08 | 5 | 5 | 3 | 5 | 5 | 5 | 5 | 5 | 5 | 5 | 5 | 2 |
| | 0.04 | 5 | 5 | 2 | 3 | 5 | 4 | 5 | 3 | 3 | 5 | 4 | 5 |
| No. 771 | 0.08 | 5 | 5 | 3 | 4 | 5 | 5 | 5 | 4 | 4 | 5 | 5 | 5 |
| | 0.04 | 4 | 5 | 2 | 4 | 5 | 5 | 5 | 5 | 4 | 5 | 4 | 5 |
| No. 772 | 0.08 | 5 | 5 | 4 | 5 | 5 | 5 | 5 | 5 | 5 | 5 | 5 | 5 |
| | 0.04 | 3 | 5 | 2 | 4 | 5 | 5 | 5 | 4 | 4 | 5 | 5 | 5 |
| No. 773 | 0.08 | 5 | 5 | 3 | 5 | 5 | 5 | 5 | 5 | 5 | 5 | 5 | 5 |
| | 0.04 | 5 | 5 | 2 | 4 | 5 | 5 | 5 | 4 | 4 | 5 | 4 | 5 |
| No. 862 | 0.08 | 5 | 5 | 3 | 5 | 5 | 5 | 5 | 5 | 4 | 5 | 5 | 5 |
| No. 863 | 0.32 | 5 | 5 | 2 | 4 | 5 | 5 | 4 | 5 | 2 | 5 | 5 | 3 |
| | 0.04 | 4 | 5 | 2 | 4 | 5 | 5 | 5 | 4 | 2 | 4 | 3 | 3 |
| No. 864 | 0.08 | 5 | 5 | 3 | 4 | 5 | 5 | 5 | 4 | 3 | 5 | 5 | 4 |
| | 0.01 | 0 | 5 | 1 | 5 | 5 | 5 | 5 | 3 | 0 | 5 | 5 | 5 |
| No. 885 | 0.02 | 1 | 5 | 2 | 5 | 5 | 5 | 5 | 5 | 0 | 5 | 5 | 5 |
| | 0.04 | 2 | 5 | 3 | 5 | 5 | 5 | 5 | 5 | 0 | 5 | 5 | 5 |
| | 0.16 | 0 | 5 | 1 | 5 | 5 | 4 | 4 | 4 | 0 | 4 | 3 | 1 |

TABLE 17-continued

| Comp. No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| No. 886 | 0.32 | 0 | 5 | 1 | 5 | 5 | 5 | 5 | 5 | 0 | 4 | 5 | 1 |
| | 0.01 | 0 | 5 | 1 | 5 | 5 | 5 | 5 | 5 | 0 | 5 | 5 | 0 |
| No. 887 | 0.02 | 2 | 5 | 1 | 5 | 5 | 5 | 5 | 5 | 0 | 5 | 5 | 1 |
| | 0.04 | 3 | 5 | 2 | 5 | 5 | 5 | 5 | 5 | 0 | 5 | 5 | 1 |
| No. 1359 | 0.63 | 5 | 2 | 1 | 4 | 5 | 5 | 5 | 4 | 0 | 4 | 4 | 4 |
| | 0.04 | 5 | 5 | 3 | 4 | 5 | 5 | 5 | 5 | 0 | 5 | 5 | 0 |
| No. 1361 | 0.08 | 5 | 5 | 4 | 5 | 5 | 5 | 5 | 5 | 0 | 5 | 5 | 1 |
| | 0.02 | 4 | 4 | 2 | 5 | 5 | 5 | 5 | 5 | 0 | 5 | 4 | 0 |
| No. 896 | 0.04 | 5 | 5 | 3 | 5 | 5 | 5 | 5 | 5 | 1 | 5 | 5 | 1 |
| | 0.08 | 5 | 5 | 4 | 5 | 5 | 5 | 5 | 5 | 2 | 5 | 5 | 2 |
| | 0.04 | 5 | 5 | 2 | 5 | 5 | 5 | 5 | 5 | 0 | 4 | 3 | 4 |
| No. 2323 | 0.08 | 5 | 5 | 3 | 5 | 5 | 5 | 5 | 5 | 0 | 5 | 4 | 5 |
| | 0.16 | 5 | 5 | 0 | 5 | 5 | 5 | 5 | 5 | 0 | 5 | 5 | 5 |
| No. 1453 | 0.32 | 5 | 5 | 1 | 5 | 5 | 5 | 5 | 5 | 0 | 5 | 5 | 5 |
| | 0.04 | 5 | 5 | 3 | 5 | 5 | 5 | 5 | 5 | 5 | 5 | 5 | 5 |
| No. 1455 | 0.08 | 5 | 5 | 4 | 5 | 5 | 5 | 5 | 5 | 5 | 5 | 5 | 5 |
| | 0.01 | 5 | 5 | 2 | 5 | 5 | 5 | 5 | 5 | 5 | 5 | 5 | 0 |
| No. 100 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |
| | 0.01 | 5 | 5 | 2 | 5 | 5 | 5 | 5 | 5 | 5 | 5 | 5 | 0 |
| No. 105 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |
| No. 581 | 0.16 | 5 | 3 | 4 | 5 | 5 | 5 | 5 | 5 | 5 | 5 | 5 | 5 |
| | 0.01 | 0 | 4 | 2 | 5 | 5 | 5 | 5 | 5 | 0 | 5 | 5 | 5 |
| No. 630 | 0.02 | 0 | 4 | 2 | 5 | 5 | 5 | 5 | 5 | 0 | 5 | 5 | 5 |
| | 0.04 | 0 | 5 | 3 | 5 | 5 | 5 | 5 | 5 | 0 | 5 | 5 | 5 |
| | 0.01 | 0 | 4 | 2 | 5 | 5 | 5 | 5 | 5 | 0 | 5 | 5 | 0 |
| No. 632 | 0.02 | 0 | 5 | 3 | 5 | 5 | 5 | 5 | 5 | 0 | 5 | 5 | 0 |
| | 0.04 | 0 | 5 | 3 | 5 | 5 | 5 | 5 | 5 | 0 | 5 | 5 | 0 |
| | 0.01 | 5 | 5 | 3 | 5 | 5 | 5 | 5 | 5 | 5 | 5 | 5 | 0 |
| No. 668 | 0.02 | 5 | 5 | 4 | 5 | 5 | 5 | 5 | 5 | 5 | 5 | 5 | 1 |
| | 0.04 | 5 | 5 | 5 | 5 | 5 | 5 | 5 | 5 | 5 | 5 | 5 | 2 |
| | 0.01 | 5 | 5 | 2 | 5 | 5 | 5 | 5 | 5 | 5 | 5 | 5 | 0 |
| No. 892 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |
| No. 2549 | 0.32 | 5 | 5 | 4 | 5 | 5 | 5 | 5 | 5 | 5 | 5 | 1 | 5 |
| No. 2550 | 0.63 | 5 | 5 | 4 | 5 | 5 | 4 | 5 | 5 | 5 | 5 | 0 | 5 |
| No. 2551 | 0.32 | 5 | 5 | 4 | 5 | 5 | 5 | 5 | 5 | 5 | 5 | 1 | 5 |
| No. 2552 | 0.63 | 5 | 4 | 5 | 5 | 4 | 5 | 5 | 5 | 5 | 5 | 0 | 5 |
| | 0.01 | 5 | 4 | 2 | 5 | 5 | 5 | 5 | 5 | 4 | 5 | 5 | 0 |
| No. 5370 | 0.02 | 5 | 5 | 3 | 5 | 5 | 5 | 5 | 5 | 5 | 5 | 5 | 0 |
| | 0.04 | 5 | 5 | 3 | 5 | 5 | 5 | 5 | 5 | 5 | 5 | 5 | 0 |

TABLE 18

| Comp. No. | Amount of active ingredient applied kg/ha | (M) | (E) | (N) | (O) | (L) |
|---|---|---|---|---|---|---|
| | 0.005 | 5 | 5 | 5 | 5 | 0 |
| | 0.01 | 5 | 5 | 5 | 5 | 0 |
| No. 3 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 48 | 0.02 | 5 | 5 | 5 | 5 | 0 |
| | 0.04 | 5 | 5 | 5 | 5 | 0 |
| | 0.08 | 5 | 5 | 5 | 5 | 0 |
| | 0.005 | 5 | 5 | 5 | 5 | 0 |
| | 0.01 | 5 | 5 | 5 | 5 | 0 |
| No. 49 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 138 | 0.02 | 5 | 5 | 5 | 5 | 0 |
| | 0.04 | 5 | 5 | 5 | 5 | 0 |
| | 0.08 | 5 | 5 | 5 | 5 | 0 |
| | 0.005 | 5 | 5 | 5 | 5 | 0 |

TABLE 18-continued

| Comp. No. | Amount of active ingredient applied kg/ha | (M) | (E) | (N) | (O) | (L) |
|---|---|---|---|---|---|---|
| | 0.01 | 5 | 5 | 5 | 5 | 0 |
| No. 139 | 0.02 | 5 | 5 | 5 | 5 | 0 |
| | 0.04 | 5 | 5 | 5 | 5 | 0 |
| | 0.08 | 5 | 5 | 5 | 5 | 0 |
| | 0.01 | 5 | 5 | 5 | 5 | 0 |
| No. 1369 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.04 | 5 | 5 | 5 | 5 | 0 |
| No. 2127 | 0.08 | 5 | 5 | 5 | 5 | 0 |
| | 0.16 | 5 | 5 | 5 | 5 | 1 |
| | 0.005 | 5 | 5 | 5 | 5 | 0 |
| | 0.01 | 5 | 5 | 5 | 5 | 0 |
| No. 100 | 0.02 | 5 | 5 | 5 | 5 | 0 |
| | 0.04 | 5 | 5 | 5 | 5 | 0 |
| | 0.08 | 5 | 5 | 5 | 5 | 0 |
| | 0.005 | 5 | 5 | 5 | 5 | 0 |
| | 0.01 | 5 | 5 | 5 | 5 | 0 |
| No. 105 | 0.02 | 5 | 5 | 5 | 5 | 0 |
| | 0.04 | 5 | 5 | 5 | 5 | 0 |
| | 0.08 | 5 | 5 | 5 | 5 | 0 |

TABLE 18-continued

| Comp. No. | Amount of active ingredient applied kg/ha | (M) | (E) | (N) | (O) | (L) |
|---|---|---|---|---|---|---|
| | 0.005 | 5 | 5 | 5 | 5 | 0 |
| | 0.01 | 5 | 5 | 5 | 5 | 0 |
| No. 134 | 0.02 | 5 | 5 | 5 | 5 | 0 |
| | 0.04 | 5 | 5 | 5 | 5 | 1 |
| | 0.08 | 5 | 5 | 5 | 5 | 2 |
| | 0.005 | 5 | 5 | 5 | 5 | 0 |
| | 0.01 | 5 | 5 | 5 | 5 | 0 |
| No. 630 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 640 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 668 | 0.02 | 5 | 5 | 5 | 5 | 1 |
| | 0.04 | 5 | 5 | 5 | 5 | 2 |
| | 0.08 | 5 | 5 | 5 | 5 | 3 |
| | 0.005 | 5 | 5 | 5 | 5 | 0 |
| | 0.01 | 5 | 5 | 5 | 5 | 0 |
| No. 887 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 892 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 896 | 0.02 | 5 | 5 | 5 | 5 | 0 |
| | 0.04 | 5 | 5 | 5 | 5 | 1 |
| | 0.08 | 5 | 5 | 5 | 5 | 2 |
| | 0.01 | 5 | 5 | 5 | 5 | 0 |
| No. 1361 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |
| | 0.01 | 5 | 5 | 5 | 5 | 0 |
| No. 1455 | 0.02 | 5 | 5 | 5 | 5 | 0 |
| | 0.04 | 5 | 5 | 5 | 5 | 1 |
| | 0.08 | 5 | 5 | 5 | 5 | 2 |
| | 0.01 | 5 | 5 | 5 | 5 | 0 |
| No. 5349 | 0.02 | 5 | 5 | 5 | 5 | 0 |
| | 0.04 | 5 | 5 | 5 | 5 | 0 |
| | 0.08 | 5 | 5 | 5 | 5 | 1 |
| | 0.005 | 5 | 5 | 5 | 5 | 0 |

TABLE 18-continued

| Comp. No. | Amount of active ingredient applied kg/ha | (M) | (E) | (N) | (O) | (L) |
|---|---|---|---|---|---|---|
| | 0.01 | 5 | 5 | 5 | 5 | 0 |
| No. 5370 | 0.02 | 5 | 5 | 5 | 5 | 0 |
| | 0.04 | 5 | 5 | 5 | 5 | 0 |
| | 0.08 | 5 | 5 | 5 | 5 | 1 |

TABLE 19

| Comp. No. | Amount of active ingredient applied kg/ha | (I) | (P) |
|---|---|---|---|
| | 0.01 | 0 | 4 |
| 1 | 0.02 | 0 | 5 |
| | 0.04 | 0 | 5 |
| | 0.01 | 0 | 4 |
| 132 | 0.02 | 0 | 5 |
| | 0.04 | 0 | 5 |

We claim:

1. A process for growing wheat and selectively preventing or controlling the growth of wild oats in the same site in which the wheat is being cultivated which comprises applying to said site an amount of an active compound sufficient to control the growth of wild oats without adversely affecting the growth of the wheat, said active compound being N-[(4,6-dimethylpyrimidin-2-yl)aminocarbonyl]-4-methoxycarbonyl-3-methyl-1-(2-pyridyl)pyrazole-5-sulfonamide or N-[(4,6-dimethylpyrimidin-2-yl)aminocarbonyl]-4-methoxycarbonyl-1-(2-pyridyl)pyrazole-5-sulfonamide.

2. The process of claim 1, wherein said compound is N-[(4,6-dimethylpyrimidin-2-yl)aminocarbonyl]-4-methoxycarbonyl-3-methyl-1-(2-pyridyl)pyrazole-5-sulfonamide.

3. The process of claim 1, wherein said compound is N-[(4,6-dimethylpyrimidin-2-yl)aminocarbonyl]-4-methoxycarbonyl-1-(2-pyridyl)pyrazole-5-sulfonamide.

4. The process of claim 1, wherein said active compound is applied to said site when the wheat is in a leaf stage.

5. The process of claim 2, wherein said active compound is applied to said site when the wheat is in a leaf stage.

6. The process of claim 3, wherein said active compound is applied to said site when the wheat is in a leaf stage.

* * * * *